US007666586B2

(12) United States Patent
Ørntoft et al.

(10) Patent No.: US 7,666,586 B2
(45) Date of Patent: Feb. 23, 2010

(54) GENE EXPRESSION IN BIOLOGICAL CONDITIONS

(75) Inventors: Torben F. Ørntoft, Aabyhøj (DK);
Thomas Thykjaer, Brabrand (DE);
Karin Demtröder, Rønde (DK)

(73) Assignee: Aros Applied Biotechnology APS, Arhus (DK)

( * ) Notice: Subject to any disclaimer, the term of this patent is extended or adjusted under 35 U.S.C. 154(b) by 462 days.

(21) Appl. No.: 10/312,743

(22) PCT Filed: Jul. 2, 2001

(86) PCT No.: PCT/DK01/00463

§ 371 (c)(1),
(2), (4) Date: Mar. 11, 2003

(87) PCT Pub. No.: WO02/02804

PCT Pub. Date: Jan. 10, 2002

(65) Prior Publication Data
US 2004/0038917 A1    Feb. 26, 2004

(30) Foreign Application Priority Data
Jun. 30, 2000   (DK)   ............... 2000 01020

(51) Int. Cl.
*C12Q 1/68*     (2006.01)
*G01N 33/53*     (2006.01)
*G01N 33/534*    (2006.01)
*C12P 19/34*     (2006.01)

(52) U.S. Cl. ................. 435/6; 435/7.2; 435/7.23; 435/91.1; 435/91.2

(58) Field of Classification Search ............ None
See application file for complete search history.

(56) References Cited

U.S. PATENT DOCUMENTS

| 4,769,330 | A | 9/1988 | Paoletti |
| 5,155,020 | A | 10/1992 | Paoletti |
| 5,204,243 | A | 4/1993 | Paoletti |
| 5,225,336 | A | 7/1993 | Paoletti |
| 5,252,348 | A | 10/1993 | Schreier et al. |
| 6,335,170 | B1 * | 1/2002 | Ørntoft ............... 435/6 |

FOREIGN PATENT DOCUMENTS

| WO | WO 95/21944 | 8/1995 |
| WO | WO 96/30389 | 10/1996 |
| WO | WO 97/10365 | 3/1997 |
| WO | WO 98/53319 | 11/1998 |
| WO | WO 99/51772 | 10/1999 |
| WO | WO 00/52204 | 9/2000 |

OTHER PUBLICATIONS

Sanchez-Carbayo, M. Use of High-Throughput DNA Microarrays to Identify Biomarkers for Bladder Cancer, Clinical Chemistry 49(1):23-31, 2003.*
H61361 from Unigene.*
U90268 from Unigene.*
Torben F. Orntoft, et al, "Molecular Alterations in Bladder Cancer", Invited Editorial. Irol. Res. (1998) 26, pp. 223-233.
Marc O. Grimm, et al. "Expression and Progression Pattern of Transitional Cell Carcinoma of the Bladder", The Journal of Urology, vol. 163, No. 4, May 2000, p. 127.
Bergkvist A. et al., "Classification of bladder tumours based on the cellular pattern. Preliminary report of a clinical-pathological study of 300 cases with a minimum follow-up of eight years," *Acta Chir Scand* 1965, 130(4):371-8.
Dubensky T.W. et al., "Direct transfection of viral and plasmid DNA into the liver or spleen of mice," *Proc. Natl. Acad. Sci.* 1984, USA 81: pp. 7529-7533.
Kaneda Y. et al., "Increased expression of DNA cointroduced with nuclear protein in adult rat liver," *Science* 1989, 243:375-378.
Hiebert S.W. et al., "E1 A-dependent trans-activation of the human *MYC* promoter is mediated by the E2F factor," *Proc. Natl. Acad. Sci.* 1989, USA 86: pp. 3594-3598.
Hatzoglou M. et al., "Hepatic gene transfer in animals using retroviruses containing the promoter from the gene for phosphoenolpyruvate carboxykinase," *J. Biol. Chem.* 1990, 265: pp. 17285-17293.
Ferry N. et al., "Retroviral-mediated gene transfer into hepatocytes in vivo," *Proc. Natl. Acad. Sci.* 1991, USA 88: pp. 8377-8381.
Schreier H. et al., "(Patho)physiologic pathways to drug targeting: artificial viral envelopes," *J. Mol. Recognit.*, 1995, 8:59-62.
Schreier H. et al., "Targeting of lipsomes to cells expressing CD4 using glycosylphosphatidylinositol-anchored gp120. Influence of lipsome composition on inreacellular trafficking," *J. Biol. Chem.*, 1994, 269: pp. 9090-9098.
Schreier H. "The new frontier: gene and oligonucleotide therapy," *Pharm. Acta Helv.* 1994, 68: pp. 145-159.
Chander R. and Schreier, H., "Artificial viral envelopes containing recombinant human immunodeficiency virus (HIV) gp160," *Life Sci.*, 1992, 50: pp. 481-489.
Stecenko, A. A. et al., "Fusion of artificial viral envelopes containing respiratory syncytial virus (RSV) attachment (G) and fusion (F) glycoproteins with Hep-2-cells," *Pharm. Pharmacol. Lett.* 1:127-129 (1992).
Sizemore D. R., et al, "Attenuated *Shigella* as a DNA delivery vehicle for DNA-mediated immunization," *Science* 1995, 270:299302.
Zhu, H. et al., "Cellular gene expression altered by human cytomegalovirus: Global monitoring with oligonucleotide arrays," *Proc. Natl Acad USA* 1998, 95: 14470-75.
Morrison TB, et al. "Quantification of low-copy transcripts by continuous SYBR Green I monitoring during amplification," *Biotechniques* 1998, 24 (6):954-962.

* cited by examiner

*Primary Examiner*—Young J Kim
(74) *Attorney, Agent, or Firm*—Edwards Angell Palmer & Dodge LLP; Kathleen Williams

(57) ABSTRACT

The present invention relates to a method of determining the presence or absence of a biological condition in animal tissue, wherein the expression of genes in normal tissue and tissue from the biological condition is examined and correlated to standards. The invention further relates to the treatment of the biological condition and an assay for determining the condition. More particularly the invention concerns gene expression in epithelial tissue, such as urianry bladder under both normal and abnormal conditions.

2 Claims, 137 Drawing Sheets

Fig. 1.1

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
23 LOST PAAAA and Decreased

| Gene name | Probe Set EST | Avg Diff N | Abs Call N | Avg Diff Tag/P | Abs Call Tag/P | Diff Call Tag/IP(vs)/N | B=A | Fold Change Tag/IP(vs)/N |
|---|---|---|---|---|---|---|---|---|
| yx16e10.r1 Homo sapiens cDNA clone 261930 5'. | N24990_s_at | 83 P | | 51 A | | D | | -1,6 |
| yf41e08.r1 Homo sapiens cDNA clone 129446 5' similar to SP:A46661 A46661 LEUKOTRIENE B4 OMEGA-HYDROXYLASE, P-450LTB OMEGA=CYTOCHROME P-450 SUPERFAMILY MEMBER -; similar to gb:J02982 GLYCOPHORIN B PRECURSOR (HUMAN);. | R11267_at | 521 P | | 157 A | | D | | -3,3 |
| yq76e12.s1 Homo sapiens cDNA clone 201742 3' similar to gb:J02982 GLYCOPHORIN B PRECURSOR (HUMAN);. | RC_H52937_at | 1007 P | | 38 A | | D | | -15,2 |
| yrd9e02.s1 Homo sapiens cDNA clone 212474 3'. | RC_H69547_at | 1865 P | | 522 A | | D | | -3,6 |
| yu73c12.s1 Homo sapiens cDNA clone 239446 3'. | RC_H70047_at | 209 P | | -7 A | | D | | -5,5 |
| yx99c11.s1 Homo sapiens cDNA clone 269876 3'. | RC_N24879_at | 352 P | | 1 A | | D | | -6,4 |
| yz38a06.s1 Homo sapiens cDNA clone 285298 3'. | RC_N66312_at | 334 P | | 97 A | | MD | | -7,7 |
| yh26a02.s1 Homo sapiens cDNA clone 130826 3'. | RC_R22189_at | 254 P | | 29 A | | D | | -7,6 |
| yg44f05.s1 Homo sapiens cDNA clone 35270 3'. | RC_R45582_at | 169 P | | -83 A | | D | | -6,2 |
| yg83e10.s1 Homo sapiens cDNA clone 39835 3'. | RC_R53457_at | 813 P | | 68 A | | D | | -12 |
| yi49g10.s1 Homo sapiens cDNA clone 142626 3'. | RC_R70903_at | 224 P | | 107 A | | D | | -2,1 |
| zi68c01.s1 Stratagene colon (#937204) Homo sapiens cDNA clone 509760 3'. | RC_AA054321_s_at | 808 P | | 94 A | | D | | -18,7 |
| zk87c05.s1 Soares pregnant uterus NbHPU Homo sapiens cDNA clone 489800 3 | RC_AA099820_at | 277 P | | 14 A | | D | | -6,5 |
| zl17g05.s1 Soares pregnant uterus NbHPU Homo sapiens cDNA clone 502232 3' | RC_AA127238_at | 104 P | | 39 A | | D | | -7,8 |
| zo64h02.s1 Stratagene pancreas (#937208) Homo sapiens cDNA clone 591699 3'. | RC_AA147224_at | 216 P | | 13 A | | D | | -5,2 |
| zq12e02.s1 Stratagene muscle 937209 Homo sapiens cDNA clone 629498 3'. | RC_AA192765_at | 83 P | | 0 A | | D | | -3,7 |
| zr33d07.s1 Soares NhHMPu S1 Homo sapiens cDNA clone 665197 3'. | RC_AA195718_at | 241 P | | 25 A | | D | | -5,6 |
| zr28b08.s1 Stratagena NT2 neuronal precursor 937230 Homo sapiens cDNA clone 664695 3' similar to gb:L05779 SOLUBLE EPOXIDE HYDROLASE (HUMAN). | RC_AA232114_s_at | 217 P | | 58 A | | MD | | -3,7 |
| zt07h12.s1 NCI_CGAP_GCB1 Homo sapiens cDNA clone IMAGE:712487 3'. | RC_AA281770_at | 81 P | | 25 A | | D | | -3,2 |
| zw59e03.s1 Soares total fetus Nb2HF8 9w Homo sapiens cDNA clone 774364 3' similar to TR:G1199667 G1199667 PROTEIN KINASE C-BINDING PROTEIN ENIGMA ;. | RC_AA430209_at | 96 P | | 2 A | | D | | -6,2 |
| zx31f03.s1 Soares total fetus Nb2HF8 9w Homo sapiens cDNA clone 788093 3'. | RC_AA452410_at | 360 P | | 100 A | | D | | -3,3 |

Fig. 1.2

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
23 LOST PAAAA and Decreased

| Gene name | Sort Score TagIIP(vs)N | Avg Diff T1gIIIP | Abs Call T1gIIIP | Diff Call T1gIIIP(vs)N | B=A | Fold Change T1gIIIP(vs)N | Sort Score T1gIIIP(vs)N | Avg Diff T2gIIImixP | Abs Call T2gIIImixP | Diff Call T2gIIImixP(vs)N |
|---|---|---|---|---|---|---|---|---|---|---|
| yx16e10.r1 Homo sapiens cDNA clone 261930 5'. | -0,09 | -22 | A | D | | ~7,9 | -1,97 | -51 | A | D |
| yf41e08.r1 Homo sapiens cDNA clone 129446 5' similar to SP:A46661 A46661 LEUKOTRIENE B4 OMEGA-HYDROXYLASE, P-450LTB OMEGA=CYTOCHROME P-450 SUPERFAMILY MEMBER..; | -1,58 | 263 | A | D | | -2,2 | -0,71 | 189 | A | D |
| yq76e12.s1 Homo sapiens cDNA clone 201742 3' similar to gb:J02982 GLYCOPHORIN B PRECURSOR (HUMAN); | -10,7 | 106 | A | D | | -6,7 | -5,22 | 134 | A | D |
| yr89e02.s1 Homo sapiens cDNA clone 212474 3'. | -3,44 | 533 | A | D | | -3,5 | -3,31 | 305 | A | D |
| yu73c12.s1 Homo sapiens cDNA clone 239446 3'. | -2,14 | 21 | A | D | | -4,3 | -1,41 | 14 | A | D |
| yx99c11.s1 Homo sapiens cDNA clone 269876 3'. | -2,89 | 27 | A | D | | -7,9 | -4,37 | -51 | A | D |
| yz38a06.s1 Homo sapiens cDNA clone 285298 3'. | -4,23 | -49 | A | D | | -10,2 | -5,66 | 9 | A | D |
| yh26a02.s1 Homo sapiens cDNA clone 130826 3'. | -4,14 | 6 | A | D | | -8,1 | -4,39 | 34 | A | D |
| yg44f05.s1 Homo sapiens cDNA clone 352703'. | -2,07 | 86 | A | D | | -6,5 | -4,43 | -22 | A | D |
| yg83e10.s1 Homo sapiens cDNA clone 39835 3'. | -9,55 | -72 | A | D | | -19,5 | -13,74 | -68 | A | D |
| yi49g10.s1 Homo sapiens cDNA clone 142626 3'. | -0,36 | 104 | A | D | | -2,1 | -0,39 | 79 | A | D |
| zf68c01.s1 Stratagene colon (#937204) Homo sapiens cDNA clone 509760 3'. | -13,25 | 66 | A | D | | -12,2 | -9,67 | -112 | A | D |
| zk87c05.s1 Soares pregnant uterus NbHPU Homo sapiens cDNA clone 489800 3'. | -3,07 | -22 | A | D | | -7,2 | -3,44 | 61 | A | D |
| zl17g05.s1 Soares pregnant uterus NbHPU Homo sapiens cDNA clone 502232 3'. | -2,69 | 4 | A | D | | -8,1 | -2,81 | 30 | A | D |
| zo64h02.s1 Stratagene pancreas (#937208) Homo sapiens cDNA clone 591699 3'. | -2,05 | 43 | A | D | | -4,9 | -1,91 | 19 | A | D |
| zq12e02.s1 Stratagene muscle 937209 Homo sapiens cDNA clone 629498 3'. | -0,83 | -45 | A | D | | -4,5 | -1,08 | 14 | A | D |
| zr33d07.s1 Soares NhHMPu S1 Homo sapiens cDNA clone 665197 3'. | -2,42 | 32 | A | D | | -5,8 | -2,58 | 117 | A | D |
| zi28b08.s1 Stratagene NT2 neuronal precursor 937230 Homo sapiens cDNA clone 654695 3' similar to gb:L05779 SOLUBLE EPOXIDE HYDROLASE (HUMAN); | -0,97 | -70 | A | D | | -7,9 | -3,26 | -2 | A | D |
| zl07h12.s1 NCI_CGAP_GCB1 Homo sapiens cDNA clone IMAGE:712487 3'. | -0,58 | 11 | A | D | | -4,9 | -1,11 | 28 | A | D |
| zw59e03.s1 Soares total fetus Nb2HF8 9w Homo sapiens cDNA clone 774364 3' similar to TR:G1199667.G1199667 PROTEIN KINASE C-BINDING PROTEIN ENIGMA.; | -1,61 | 16 | A | D | | -5,0 | -1,28 | -20 | A | D |
| zx31f03.s1 Soares total fetus Nb2HF8 9w Homo sapiens cDNA clone 788093 3'. | -1,26 | 78 | A | D | | -4,2 | -1,92 | 77 | A | D |

Fig. 1.3

EST Bladderspecific and with sort score 0.5
2424 selected genes with sort score 0.5 changing from N to tumor
4013 genes from EST sub A&B present in Normal bladder, not colon
1068 bladderspecific ESTs with sort score >= 0,5
23 LOST PAAAA and Decreased

| Gene name | B=A | Fold Change T2gllimixP(vs)N | Sort Score T2gllimixP(vs)N | Avg Diff T2gllsolidP | Abs Call T2gllsolidP | Diff Call T2gllsolidP(vs)N | B=A | Fold Change T2gllsolidP(vs)N | Sort Score T2gllsolidP(vs)N |
|---|---|---|---|---|---|---|---|---|---|
| yx16e10.r1 Homo sapiens cDNA clone 261930 5'. | | -6,4 | -1,37 | -65 | A | D | | -5,2 | -0,94 |
| yf41e08.r1 Homo sapiens cDNA clone 129446 5' similar to SP:A46661 A46661 LEUKOTRIENE B4. | | -3,1 | -1,49 | -12 | A | D | | -15,7 | -10,06 |
| OMEGA-HYDROXYLASE, P-450LTB OMEGA=CYTOCHROME P-450 SUPERFAMILY MEMBER.. | | | | | | | | | |
| yq76e12.s1 Homo sapiens cDNA clone 201742 3' similar to gb:J02982 GLYCOPHORIN B PRECURSOR (HUMAN); | | -5,3 | -3,93 | 99 | A | D | | -7,3 | -5,67 |
| yr09e02.s1 Homo sapiens cDNA clone 212474 3'. | | -6,1 | -7,55 | 421 | A | D | | -4,4 | -4,88 |
| yu73c12.s1 Homo sapiens cDNA clone 239446 3'. | | -4,2 | -1,43 | -28 | A | D | | -4,4 | -1,44 |
| yx99c11.s1 Homo sapiens cDNA clone 269876 3'. | | -5,9 | -2,48 | -6 | A | D | | -6,2 | -3,29 |
| yz38a06.s1 Homo sapiens cDNA clone 285298 3'. | | -7,3 | -3,99 | -54 | A | D | | -5,5 | -2,13 |
| yh26a02.s1 Homo sapiens cDNA clone 130826 3'. | | -6,1 | -3,21 | -140 | A | D | | -7,9 | -4,21 |
| yg44l05.s1 Homo sapiens cDNA clone 35270 3'. | | -10,6 | -7,27 | -207 | A | D | | -6,3 | -1,84 |
| yg83e10.s1 Homo sapiens cDNA clone 39835 3'. | | -15,5 | -11,89 | 78 | A | D | | -10,4 | -8,56 |
| yi49g10.s1 Homo sapiens cDNA clone 142626 3'. | | -2,8 | -0,76 | 13 | A | D | | -3,7 | -1,11 |
| zi68c01.s1 Stratagene colon (#937204) Homo sapiens cDNA clone 509760 3'. | | -19,3 | -14,36 | -343 | A | D | | -17,5 | -13,53 |
| zk87c05.s1 Soares pregnant uterus NbHPU Homo sapiens cDNA clone 489800 3'. | | -5,1 | -2,44 | -41 | A | D | | -6,0 | -2,91 |
| zl17g05.s1 Soares pregnant uterus NbHPU Homo sapiens cDNA clone 502232 3'. | | -5,3 | -1,69 | -83 | A | D | | -6,4 | -1,92 |
| zo64h02.s1 Stratagene pancreas (#937208) Homo sapiens cDNA clone 591699 3'. | | -4,2 | -1,48 | 32 | A | D | | -3,6 | -1,13 |
| zq12e02.s1 Stratagene muscle 937209 Homo sapiens cDNA clone 629498 3'. | | -2,8 | -0,47 | -57 | A | D | | -3,6 | -0,65 |
| zr33d07.s1 Soares NhHMPu 31 Homo sapiens cDNA clone 665197 3'. | | -2,2 | -0,41 | 30 | A | D | | -4,3 | -1,56 |
| zr28b08.s1 Stratagene NT2 neuronal precursor 937230 Homo sapiens cDNA clone 664695 3'. | | -5,3 | -1,96 | 42 | A | D | | -4,2 | -1,4 |
| similar to gb:L05779 SOLUBLE EPOXIDE HYDROLASE (HUMAN); | | | | | | | | | |
| zt07h12.s1 NCI_CGAP_GCD1 Homo sapiens cDNA clone IMAGE:712487 3'. | | -3,3 | -0,57 | 16 | A | D | | -2,8 | -0,38 |
| zw59e03.s1 Soares total fetus Nb2HF8 9w Homo sapiens cDNA clone 774364 3' similar to | | -4,4 | -0,89 | 33 | A | D | | -2,3 | -0,28 |
| TR:G1199667 G1199667 PROTEIN KINASE C-BINDING PROTEIN ENIGMA ; | | | | | | | | | |
| zx31l03.s1 Soares total fetus Nb2HF8 9w Homo sapiens cDNA clone 788093 3'. | | -4,3 | -1,98 | 126 | A | D | | -3 | -1,12 |

Fig. 1.4

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
23 LOST PAAAA and Decreased

| Gene name | Probe Set EST | Avg Diff N | Abs Call N | Avg Diff TagIIP | Abs Call TagII P | Diff Call TagIIP(vs)N | B=A | Fold Change TagIIP(vs)N |
|---|---|---|---|---|---|---|---|---|
| aa39g12.s1 NCI_CGAP_GCB1 Homo sapiens cDNA clone IMAGE:815686 3'. | RC_AA485115_at | 488 | P | 319 | A | MD | | -1,5 |
| zk85e12.r1 Soares pregnant uterus NbHPU Homo sapiens cDNA clone 489646 5'. | AA099391_s_at | 106 | P | 17 | A | D | | -6,1 |
| zo16a05.r1 Stratagene colon (#937204) Homo sapiens cDNA clone 587024 5' similar to SW:CATX_BOVIN P05689 CATHEPSIN .. | AA131127_at | 284 | P | 2 | A | D | | ~-18,4 |
| zp02c06.r1 Stratagene ovarian cancer (#937219) Homo sapiens cDNA clone 595210 5' similar to SW:QRI2_YEAST P43124 HYPOTHETICAL 46.1 KD PROTEIN IN PHO2-POL3 INTERGENIC REGION. [1] ;. | AA173505_at | 150 | P | 125 | A | MD | | -1,6 |
| zl39b07.r1 Soares ovary tumor NbHOT Homo sapiens cDNA clone 724693 5'. | AA291786_s_at | 28 | P | -83 | A | D | | ~-7,8 |
| zu53f10.r1 Soares ovary tumor NbHOT Homo sapiens cDNA clone 741739 5'. | AA402971_s_at | 293 | P | 85 | A | D | | -3,4 |

Fig. 1.5

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
23 LOST PAAAA and Decreased

| Gene name | Sort Score TagIIIP(vs)N | Avg Diff T4gIIIP | Abs Call T4gIIIP | Diff Call T4gIIIP(vs)N | B=A | Fold Change T4gIIIP(vs)N | Sort Score T4gIIIP(vs)N | Avg Diff T2gIIImixP | Abs Call T2gIIImixP | Diff Call T2gIIImixP(vs)N |
|---|---|---|---|---|---|---|---|---|---|---|
| aa39g12.s1 NCI_CGAP_GCB1 Homo sapiens cDNA clone IMAGE:815686 3'. | -0,18 | 14 | A | D | | -19,6 | -9,23 | 192 | A | D |
| zk85e12.r1 Soares pregnant uterus NbHPU Homo sapiens cDNA clone 489646 5'. | -1,77 | 10 | A | D | | -5,8 | -1,63 | 4 | A | D |
| zo16a05.r1 Stratagene colon (#937204) Homo sapiens cDNA clone 587024 5' similar to SW:CATX_BOVIN P05689 CATHEPSIN :. | -7,64 | 27 | A | D | | -10,1 | -4,9 | 16 | A | D |
| zp02c06.r1 Stratagene ovarian cancer (#937219) Homo sapiens cDNA clone 595210 5' similar to SW:QRI2_YEAST P43124 HYPOTHETICAL 46.1 KD PROTEIN IN PHO2-POL3 INTERGENIC REGION. [1] ;. | -0,12 | 72 | A | D. | | -2,7 | -0,63 | -1 | A | D |
| zt39b07.r1 Soares ovary tumor NbHOT Homo sapiens cDNA clone 724693 5'. | -0,78 | -105 | A | D | | -7,5 | -0,66 | -126 | A | D |
| zu53f10.r1 Soares ovary tumor NbHOT Homo sapiens cDNA clone 741739 5'. | -1,27 | 50 | A | D | | -5,9 | -2,82 | 71 | A | D |

Fig. 1.6

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
23 LOST PAAAA and Decreased

| Gene name | A=B | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | A=B | Fold Change T2gIIIsolidP(vs)N | Sort Score T2gIIIsolidP(vs)N |
|---|---|---|---|---|---|---|---|---|---|
| aa39g12.s1 NCI_CGAP_GCB1 Homo sapiens cDNA clone IMAGE:815606 3'. | | -2,5 | -0,88 | 110 | A | D | | -3,5 | -1,55 |
| zk85e12.r1 Soares pregnant uterus NbHPU Homo sapiens cDNA clone 489646 5'. | | -4,4 | -1,07 | 29 | A | D | | -2,9 | -0,52 |
| zo16a05.r1 Stratagene colon (#937204) Homo sapiens cDNA clone 587024 5' similar to SW:CATX_BOVIN P05689 CATHEPSIN ;. | | -9,9 | -4,84 | -83 | A | D | | -10,6 | -5,5 |
| zp02c05.r1 Stratagene ovarian cancer (#937219) Homo sapiens cDNA clone 595210 5' similar to SW:QRI2_YEAST P43124 HYPOTHETICAL 46.1 KD PROTEIN IN PHO2-POL3 INTERGENIC REGION. [1];. | | -7,5 | -3,03 | -41 | A | D | | -6,7 | -2,62 |
| zt39b07.r1 Soares ovary tumor NbHOT Homo sapiens cDNA clone 724693 5'. | | -7,0 | -0,53 | -157 | A | D | | -5,6 | -0,71 |
| zu53l10.r1 Soares ovary tumor NbHOT Homo sapiens cDNA clone 741739 5'. | | -4,1 | -1,74 | 118 | A | D | | -2,5 | -0,64 |

Fig. 2.1

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
7 LOST PPAAA and Decreased (NC excluded)

| Gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIIP | Abs Call TagIIIP | Diff Call TagIIIP(vs)N | B=A |
|---|---|---|---|---|---|---|---|---|---|---|---|---|---|
| yw37b04.r1 Homo sapiens cDNA clone 254383 5'. | N75611_s_at | 230 | P | 25 | P | D | | -7,1 | -2,74 | 8 | A | D | |
| yn64a06.s1 Homo sapiens cDNA clone 173170 3'. | RC_H20769_at | 1411 | P | 742 | P | D | | -1,9 | -0,68 | 535 | A | D | |
| yg87f06.s1 Homo sapiens cDNA clone 403364 3'. | RC_R54822_at | 212 | P | 44 | P | D | | -4,5 | -1,68 | 26 | A | D | |
| zl67e01.s1 Stratagene colon (#937204) Homo sapiens cDNA clone 509688 3' similar to TR:G189087 G189087 NONSPECIFIC CROSSREACTING ANTIGEN.; | RC_AA058357_s_at | 389 | P | 224 | P | D | | -2,2 | -0,65 | 58 | A | D | |
| zn53a05.s1 Stratagene muscle 937209 Homo sapiens cDNA clone 561872 3' similar to contains Alu repetitive element; | RC_AA086487_at | 181 | P | 52 | P | D | | -4,3 | -1,6 | -3 | A | D | |
| aa13e06.s1 Soares NhHMPu S1 Homo sapiens cDNA clone 813154 3'. | RC_AA456269_at | 610 | P | 219 | P | D | | -2,8 | -1,21 | 112 | A | D | |
| af14g11.s1 Soares testis NHT Homo sapiens cDNA clone 1031684 3'. | RC_AA609539_at | 48 | P | 24 | P | D | | -2,5 | -0,27 | -8 | A | D | |

Fig. 2.2

EST Bladderspecific and with sort score 0,5
2424 selected genes with sort score 0,5 changing from N to tumor
4013 genes from EST sub A&B present in Normal bladder, not colon
1066 bladderspecific ESTs with sort score >= 0,5
7 LOST PPAAA and Decreased (NC excluded)

| Gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A | Fold Change T2gIIIsolidP(vs)N | Sort Score T2gIIIsolidP(vs)N |
|---|---|---|---|---|---|---|---|---|---|---|---|---|---|---|
| yw37b04.r1 Homo sapiens cDNA clone 254363 5'. | -10,9 | -4,5 | 22 | A | D | | -7,2 | -3,01 | 46 | A | D | | -4,5 | -1,67 |
| yn64a06.s1 Homo sapiens cDNA clone 173170 3'. | -2,6 | -1,63 | 572 | | D | | -2,5 | -1,4 | 545 | A | D | | -2,6 | -1,56 |
| yg87l06.s1 Homo sapiens cDNA clone 40364 3'. | -6,1 | -2,41 | -19 | A | D | | -4,8 | -1,72 | 58 | A | D | | -4,5 | -1,6 |
| zi67e01.s1 Stratagene colon (#9337204) Homo sapiens cDNA clone 509688 3' similar to TR:G189087 G189087 NONSPECIFIC CROSSREACTING ANTIGEN.; | -11,7 | -7,49 | -13 | A | D | | -10,1 | -6,69 | 10 | A | D | | -8,4 | -5,59 |
| zn53a05.s1 Stratagene muscle 937209 Homo sapiens cDNA clone 561872 3' similar to contains Alu repetitive element.; | -5,7 | -2,33 | -6 | A | D | | -4,8 | -1,79 | 62 | A | D | | -3,3 | -1,02 |
| aa13e06.s1 Soares NhHMPu S1 Homo sapiens cDNA clone 813154 3'. | -6,2 | -4,66 | 140 | A | D | | -4,9 | -3,49 | 413 | A | D | | -1,7 | -0,31 |
| af14g11.s1 Soares testis NHT Homo sapiens cDNA clone 1031684 3'. | -3,8 | -0,5 | 10 | A | D | | -2,3 | -0,17 | -26 | A | D | | -2,9 | -0,23 |

Fig. 3.1

EST Bladder candidates of 17742 ESTs
Exclusion of datasets incl AFFX, all NC, all A, 3xNC + M*
2424 genes with absolut value of sort score >= 0,5 changing from N to tumor in at least 1 comparison
1068 bladderspecific ESTs, not present in normal colon mucosa
11 genes lost PPPAA and decreased in all

| gene name | Probe Set EST subA & B | Avg Diff N | Abs Call N | Avg Diff TagIIP | Abs Call TagII P | Diff Call TagIIP(vs)N | B=A |
|---|---|---|---|---|---|---|---|
| Homo sapiens purinergic receptor P2Y5 mRNA, complete cds. | AF000546_at | 59 | P | 7 | P | D | |
| Homo sapiens epoxide hydrolase (EPHX) gene, complete cds | L25880_s_at | 624 | P | 207 | P | D | |
| yx28d06.s1 Homo sapiens cDNA clone 263051 3'. | RC_N20047_at | 391 | P | 137 | P | D | |
| zc37f06.s1 Soares senescent fibroblasts NbHSF Homo sapiens cDNA clone 324515 3'. | RC_W51910_at | 690 | P | 379 | P | D | |
| zh55a02.s1 Soares fetal liver spleen 1NFLS S1 Homo sapiens cDNA clone 415946 3'. | RC_W86375_s_at | 2209 | P | 375 | P | D | |
| H. sapiens partial cDNA sequence; clone c-05e04. | RC_Z38269_at | 1217 | P | 423 | P | D | |
| H. sapiens partial cDNA sequence; clone c-0qb04. | RC_Z38807_s_at | 201 | P | 103 | P | D | |
| zv64a10.s1 Soares total fetus Nb2HF8 9w Homo sapiens cDNA clone 758394 3'. | RC_AA393793_at | 126 | P | 71 | P | D | |
| zw84c05.s1 Soares total fetus Nb2HF8 9w Homo sapiens cDNA clone 783656 3'. | RC_AA446570_at | 131 | P | 50 | P | D | |
| aa03a08.s1 Soares NhHMPu S1 Homo sapiens cDNA clone 812150 3'. | RC_AA456016_at | 99 | P | 29 | P | D | |
| zv17d09.s1 Soares NhHMPu S1 Homo sapiens cDNA clone 753905 3' similar to contains element TAR1 TAR1 repetitive element;. | RC_AA479350_at | 258 | P | 84 | P | MD | |

Fig. 3.2

EST Bladder candidates of 17742 ESTs
Exclusion of datasets incl AFFX, all NC, all A, 3xNC + M*
2424 genes with absolut value of sort score >= 0,5 changing from N to tumor in at least 1 comparison
1068 bladderspecific ESTs, not present in normal colon mucosa
11 genes lost PPPAA and decreased in all

| gene name | Fold Change TagIIP(vs)N | Sort Score TagIIP(vs)N | Avg Diff T1gIIIP | Abs Call T1gIIIP | Diff Call T1gIIIP(vs)N | B=A | Fold Change T1gIIIP(vs)N | Sort Score T1gIIIP(vs)N | Avg Diff T2gIIImixP | Abs Call T2gIIImixP | Diff Call T2gIIImixP(vs)N |
|---|---|---|---|---|---|---|---|---|---|---|---|
| Homo sapiens purinergic receptor P2Y5 mRNA, complete cds. | -4,2 | -0,77 | -8 | P | MD | | -4,3 | -0,74 | -35 | A | D |
| Homo sapiens epoxide hydrolase (EPHX) gene, complete cds | -3 | -1,47 | 218 | P | D | | -2,9 | -1,32 | 178 | A | D |
| yx28d06.s1 Homo sapiens cDNA clone 263051 3'. | -2,8 | -1,01 | 120 | P | D | | -3,3 | -1,33 | 35 | A | D |
| zc37f06.s1 Soares senescent fibroblasts NbHSF Homo sapiens cDNA clone 324515 3'. | -2,4 | -0,89 | 331 | P | D | | -2,8 | -1,29 | 375 | A | D |
| zh55a02.s1 Soares fetal liver spleen 1NFLS S1 Homo sapiens cDNA clone 415945 3'. | -7,5 | -10,36 | 563 | P | D | | -5 | -6,3 | 86 | A | D |
| H. sapiens partial cDNA sequence; clone c-05e04. | -2,5 | -1,26 | 227 | P | D | | -4,7 | -3,96 | 145 | A | D |
| H. sapiens partial cDNA sequence; clone c-0qb04. | -1,9 | -0,28 | 97 | P | MD | | -2,1 | -0,34 | 45 | A | D |
| zv64a10.s1 Soares total fetus Nb2HF8 9w Homo sapiens cDNA clone 758394 3' | -1,8 | -0,16 | 49 | P | D | | -2,6 | -0,46 | 58 | A | D |
| zw64c05.s1 Soares total fetus Nb2HF8 9w Homo sapiens cDNA clone 783656 3'. | -2,6 | -0,5 | 66 | P | D | | -2 | -0,24 | 44 | A | D |
| aa03a08.s1 Soares NhHMPu S1 Homo sapiens cDNA clone 812150 3'. | -3,5 | -0,75 | 22 | P | D | | -4,6 | -1,18 | 30 | A | D |
| zv17d09.s1 Soares NhHMPu S1 Homo sapiens cDNA clone 753905 3' similar to contains element TAR1 TAR1 repetitive element ;. | -2,7 | -0,68 | 69 | P | MD | | -3,3 | -1,02 | 20 | A | D |

Fig. 3.3

EST Bladder candidates of 17742 ESTs
Exclusion of datasets incl AFFX, all NC, all A, 3xNC + M*
2424 genes with absolut value of sort score >= 0,5 changing from N to tumor in at least 1 comparison
1068 bladderspecific ESTs, not present in normal colon mucosa
11 genes lost PPPAA and decreased in all

| gene name | Fold Change T29IImixP(vs)N B=A | Sort Score T29IImixP(vs)N | Avg Diff T29IIsolidP | Abs Call T29IIsolidP | Diff Call T29IIsolidP(vs)N B=A | Fold Change T29IIsolidP(vs)N | Sort Score T29IIsolidP(vs)N | Abs Calls |
|---|---|---|---|---|---|---|---|---|
| Homo sapiens purinergic receptor P2Y5 mRNA, complete cds. | -4,1 | -0,56 | 3 | A | D | -3,2 | -0,54 | PPPAA |
| Homo sapiens epoxide hydrolase (EPHX) gene, complete cds | -3,5 | -1,96 | 318 | A | D | -2 | -0,52 | PPPAA |
| yx28d06.s1 Homo sapiens cDNA clone 263051 3'. | -6,9 | -3,93 | 207 | A | D | -1,6 | -0,19 | PPPAA |
| zc37f06.s1 Soares senescent fibroblasts NbHSF Homo sapiens cDNA clone 324515 3'. | -2,4 | -0,88 | 268 | A | D | -3,5 | -2 | PPPAA |
| zh55a02.s1 Soares fetal liver spleen 1NFLS S1 Homo sapiens cDNA clone 415946 3'. | -26,9 | -22,82 | 186 | A | D | -13,9 | -17,47 | PPPAA |
| H. sapiens partial cDNA sequence; clone c-05e04. | -7,3 | -6,96 | -170 | A | D | -18,6 | -15,52 | PPPAA |
| H. sapiens partial cDNA sequence, clone c-0qb04. | -3,6 | -1,09 | 84 | A | D | -2,4 | -0,49 | PPPAA |
| zv64a10.s1 Soares total fetus Nb2HF8 9w Homo sapiens cDNA clone 756394 3'. | -2,2 | -0,3 | 26 | A | D | -3,3 | -0,73 | PPPAA |
| zw84c05.s1 Soares total fetus Nb2HF8 9w Homo sapiens cDNA clone 783656 3'. | -3 | -0,65 | 43 | A | D | -2,9 | -0,59 | PPPAA |
| aa03a08.s1 Soares NhHMPu S1 Homo sapiens cDNA clone 812150 3'. | -3,3 | -0,67 | 40 | A | D | -2,4 | -0,36 | PPPAA |
| zv17d09.s1 Soares NhHMPu S1 Homo sapiens cDNA clone 753905 3' similar to contains element TAR1 TAR1 repetitive element.:. | -9,1 | -4,29 | 42 | A | D | -7,2 | -3,59 | PPPAA |

Fig. 4.1

EST Bladderspecific and with sort score 0,5
2424 selected genes with sort score 0,5 changing from N to tumor
4013 genes from EST sub A&B present in Normal bladder, not colon
1068 bladderspecific ESTs with sort score >= 0,5
14 LOST PPPPA, NC in TagII were excluded

| Gene name | Probe Set EST | Avg Diff N | Abs Call N | Avg Diff TagII | Abs Call TagII P | Diff Call TagII(vs)N | B=A | Fold Change TagII(vs)N | Sort Score TagII(vs)N | Avg Diff TagIII | Abs Call TagIII | Diff Call TagIII(vs)N | B=A | Fold Change TagIII(vs)N |
|---|---|---|---|---|---|---|---|---|---|---|---|---|---|---|
| yx78e10.s1 Homo sapiens cDNA clone 267882 3'. | RC_N23319_at | 878 | P | 530 | P | D | | -1,7 | -0,33 | 316 | P | D | | -2,4 |
| yg21a08.s1 Homo sapiens cDNA clone 32940 3'. | RC_R43812_at | 297 | P | 317 | P | D | | -1,5 | -0,14 | -112 | P | MD | | -9,5 |
| zc13b12.s1 Soares parathyroid tumor NbHPA Homo sapiens cDNA clone 322175 3' similar to contains LTR2.t3 LTR2 repetitive element.; | RC_W37778_1_at | 1142 | P | 566 | P | MD | | -2 | -0,74 | 1485 | P | NC | | 1,3 |
| ze47b04.s1 Soares retina N2b4HR Homo sapiens cDNA clone 362095 3'. | RC_AA001045_at | 703 | P | 313 | P | D | | -2,2 | -0,78 | 184 | P | D | | -3,3 |
| zl84c04.s1 Stratagene colon (#937204) Homo sapiens cDNA clone 511302 3'. | RC_AA086005_at | 332 | P | 161 | P | D | | -1,9 | -0,29 | 465 | P | NC | | 1,6 |
| zp88f04.s1 Stratagene HeLa cell s3 937216 Homo sapiens cDNA clone 627295 3'. | RC_AA191524_at | 484 | P | 252 | P | MD | | -1,9 | -0,41 | 178 | P | D | | -2,7 |
| zr05e02.s1 Stratagene NT2 neuronal precursor 937230 Homo sapiens cDNA clone 650618 3'. | RC_AA219653_at | 602 | P | 1052 | P | I | | 1,7 | 0,45 | 1383 | P | I | | 2 |
| zs27d03.s1 NCI_CGAP_GCB1 Homo sapiens cDNA clone IMAGE:686405 3'. | RC_AA252765_at | 273 | P | 165 | P | D | | -2 | -0,35 | 254 | P | NC | | -1,3 |
| zt28d03.s1 Soares ovary tumor NbHOT Homo sapiens cDNA clone 714437 3'. | RC_AA293300_s_at | 918 | P | 1826 | P | I | | 2 | 0,91 | 1006 | P | NC | | 1,1 |
| zu57g11.s1 Soares ovary tumor NbHOT Homo sapiens cDNA clone 742146 3' similar to TR:G780241 G780241 AU-BINDING PROTEIN/ENOYL-COA HYDRATASE.; | RC_AA405832_at | 1154 | P | 492 | P | D | | -2,3 | -1,12 | 545 | P | D | | -2,1 |
| H.sapiens gene for cytokeratin 20 | X73501_at | 51 | P | 219 | P | I | | 3,7 | 1,18 | 505 | P | I | | 9,3 |
| zk72d02.r1 Soares pregnant uterus NbHPU Homo sapiens cDNA clone 488355 5'. | AA046768_at | 655 | P | 384 | P | D | | -1,7 | -0,32 | 506 | P | NC | | -1,3 |
| EST186294 Colon carcinoma (HCC) cell line II Homo sapiens cDNA 5' end. | AA314457_at | 509 | P | 198 | P | D | | -2,6 | -0,92 | 482 | P | NC | | -1,1 |
| EST27743 Cerebellum II Homo sapiens cDNA 5' end. | AA324825_at | 234 | P | 383 | P | I | | 1,6 | 0,21 | 423 | P | I | | 1,8 |

Fig. 4.2

EST Bladderspecific and with sort score 0,5
2424 selected genes with sort score 0,5 changing from N to tumor
4013 genes from EST sub.A&B present in Normal bladder, not colon
1068 bladderspecific ESTs with sort score >= 0,5
14 LOST PPPPA, NC in TagII were excluded

| Gene name | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A | Fold Change T2gIIIsolidP(vs)N | Sort Score T2gIIIsolidP(vs)N |
|---|---|---|---|---|---|---|---|---|---|---|---|---|---|
| yx78e10.s1 Homo sapiens cDNA clone 267882 3'. | -0,95 | 275 | P | D | | -2,7 | -1,3 | 203 | A | D | | -3,7 | -2,27 |
| yg21a08.s1 Homo sapiens cDNA clone 32940 3'. | -4,82 | -71 | P | D | | -7,1 | -3,44 | 176 | A | D | | -1,5 | -0,13 |
| zc13b12.s1 Soares parathyroid tumor NbHPA Homo sapiens cDNA clone 322175 3' similar to contains LTR2.t3 LTR2 repetitive element.:. | 0,13 | 1432 | P | I | | 2 | 0,87 | -6 | A | | A=B | -14,2 | -11,73 |
| ze47b04.s1 Soares retina N2b4HR Homo sapiens cDNA clone 362095 3'. | -1,75 | 157 | P | D | | -3,8 | -2,15 | 84 | A | D | | -7,3 | -5,32 |
| zl84c04.s1 Stratagene colon (#937204) Homo sapiens cDNA clone 511302 3'. | 0,19 | 405 | P | NC | | 1,4 | 0,09 | 104 | A | D | | -2,9 | -0,9 |
| zp88f04.s1 Stratagene HeLa cell s3 937216 Homo sapiens cDNA clone 627295 3'. | -1,02 | 168 | P | D | | -2,9 | -1,15 | 94 | A | D | | -5,2 | -3,08 |
| zr05e02.s1 Stratagene NT2 neuronal precursor 937230 Homo sapiens cDNA clone 650618 3'. | 0,76 | 826 | P | NC | | -1,1 | -0,01 | 508 | A | D | | -1,9 | -0,48 |
| zs27d03.s1 NCI_CGAP_GCB1 Homo sapiens cDNA clone IMAGE:686405 3'. | -0,05 | 198 | P | NC | | -1,4 | -0,08 | 50 | A | D | | -5,8 | -2,44 |
| zt28d03.s1 Soares ovary tumor NbHOT Homo sapiens cDNA clone 714437 3'. | 0,02 | 538 | P | D | | -1,7 | -0,41 | 816 | A | D | | -1,4 | -0,15 |
| zu57g11.s1 Soares ovary tumor NbHOT Homo sapiens cDNA clone 742140 3' similar to TR:G780241 G780241 AU-BINDING PROTEIN/ENOYL-COA HYDRATASE.:. | -0,85 | 628 | P | D | | -1,8 | -0,55 | 450 | A | D | | -2,6 | -1,39 |
| H.sapiens gene for cytokeratin 20 | 5,91 | 991 | P | I | | 18,6 | 13,95 | 14 | A | D | | -2,1 | -0,13 |
| zk72d02.r1 Soares pregnant uterus NbHPU Homo sapiens cDNA clone 488355 5'. | -0,08 | 632 | P | NC | | 1,3 | 0,08 | 122 | A | D | | -5,3 | -3,64 |
| EST186294 Colon carcinoma (HCC) cell line II Homo sapiens cDNA 5' end. | -0,01 | 252 | P | D | | -2 | -0,49 | 63 | A | D | | -6,1 | -5,36 |
| EST27743 Cerebellum II Homo sapiens cDNA 5' end. | 0,32 | 232 | P | NC | | 1,3 | 0,05 | 50 | A | D | | -3,5 | -1,04 |

Fig. 5.1

EST Bladder candidates of 17742 ESTs
Exclusion of data sets incl. AFFX, all NC, all A, 3xNC + M*
2424 genes with sort score >= +/- 0.5 changing from N to tumor
12 genes Abs calls PPPPP and DECREASED more than 3 fold

| gene name | Probe Set EST | Avg Diff N | Abs Call N | Avg Diff Tagll P | Abs Call Tagll P | Diff Call Tagll P(vs)N | B=A | Fold Change TagllP(vs)N | Sort Score TagllP(vs)N | Avg Diff T14gllP | Abs Call T14gllP | Diff Call T14gllP(vs)N | B=A | Fold Change T14gllP(vs)N |
|---|---|---|---|---|---|---|---|---|---|---|---|---|---|---|
| Human mRNA for IgG Fc binding protein, complete cds | D84239_at | 2636 P | | 422 P | | D | | -6,1 | -8,72 | 345 P | | D | | -7,4 |
| yv73b09.s1 Soares fetal liver spleen 1NFLS Homo sapiens cDNA clone 248345 3' | RC_N54841_at | 573 P | | 180 P | | D | | -8,2 | -5,75 | 303 P | | D | | -3,3 |
| ya8804.s1 Homo sapiens cDNA clone 68767 3' | RC_T53389_s_at | 6706 P | | 431 P | | D | | -12,6 | -25,85 | 456 P | | D | | -12 |
| ye30d12.s1 Homo sapiens cDNA clone 119255 3' | RC_T98227_at | 1154 P | | 370 P | | D | | -3,1 | -2,1 | 620 P | | D | | -1,9 |
| zr97c07.s1 NCI_CGAP_GCB1 Homo sapiens cDNA clone IMAGE:683628 3' | RC_AA215379_at | 1235 P | | 298 P | | D | | -5,2 | -5,56 | 166 P | | D | | -9,3 |
| zr81e12.s1 Soares NhHMPu S1 Homo sapiens cDNA clone 682126 3' | RC_AA256485_at | 2650 P | | 197 P | | D | | -11,7 | -15,84 | 333 P | | D | | -6,9 |
| zt19f03.s1 Soares ovary tumor NbHOT Homo sapiens cDNA clone 713597 3' similar to TR:E92665 E92665 AP56 ; | RC_AA290679_at | 1847 P | | 625 P | | D | | -3 | -2,39 | 736 P | | D | | -2,5 |
| zw46c01.s1 Soares total fetus Nb2HF8 9w Homo sapiens cDNA clone 773088 3' | RC_AA425309_at | 813 P | | 98 P | | D | | -8,7 | -6,65 | 574 P | | D | | -1,6 |
| zw71d04.s1 Soares testis NHT Homo sapiens cDNA clone 781639 3' | RC_AA429655_at | 803 P | | 161 P | | D | | -4,9 | -3,73 | 222 P | | D | | -3,6 |
| aa90h11.s1 Stratagene fetal retina 937202 Homo sapiens cDNA clone 838629 3' similar to contains Alu repetitive element; | RC_AA456981_at | 396 P | | 145 P | | D | | -3,1 | -1,3 | 190 P | | D | | -2,4 |
| zx70c04.s1 Soares total fetus Nb2HF8 9w Homo sapiens cDNA clone 796806 3' | RC_AA461174_at | 1060 P | | 290 P | | D | | -3,3 | -2,1 | 111 P | | D | | -8,6 |
| zd27g09.r1 Soares fetal heart NbHH19W Homo sapiens cDNA clone 341920 5' | W61377_at | 243 P | | 47 P | | D | | -5,5 | -2,47 | 87 P | | D | | -2,8 |

Fig. 5.2

EST Bladder candidates of 17742 ESTs
Exclusion of data sets incl. AFFX, all NC, all A, 3xNC + M*
2424 genes with sort score >= +/- 0,5 changing from N to tumor
12 genes Abs calls PPPPP and DECREASED more than 3 fold

| gene name | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|
| Human mRNA for IgG Fc binding protein, complete cds | -10,95 | 468 | P | D | | -5,5 | -7,66 | 600 | P | D | |
| yv73b09.s1 Soares fetal liver spleen 1NFLS Homo sapiens cDNA clone 240345 3'. | -1,60 | 292 | P | D | | -4,2 | -2,48 | 294 | P | D | |
| ya08f04.s1 Homo sapiens cDNA clone 68767 3'. | -24,78 | 634 | P | D | | -8,6 | -18,63 | 601 | P | D | |
| ye30r12.s1 Homo sapiens cDNA clone 119255 3'. | -0,58 | 418 | P | D | | -2,8 | -1,63 | 301 | P | D | |
| zr97c07.s1 NCI_CGAP_GCB1 Homo sapiens cDNA clone IMAGE:683628 3'. | -10,6 | 395 | P | D | | -3,9 | -3,6 | 611 | P | D | |
| zr81e12.s1 Soares NhHMPu S1 Homo sapiens cDNA clone 682126 3'. | -9,68 | 526 | P | D | | -4,4 | -5,34 | 312 | P | D | |
| zt19f03.s1 Soares ovary tumor NbHOT Homo sapiens cDNA clone 713597 3' similar to TR:E92665 E92665 AP56 ;. | -1,66 | 346 | P | D | | -6,3 | -6,32 | 765 | P | D | |
| zw46c01.s1 Soares total fetus Nb2HF8 9w Homo sapiens cDNA clone 773088 3'. | -0,31 | 399 | P | D | | -2,4 | -0,95 | 223 | P | D | |
| zw71d04.s1 Soares testis NHT Homo sapiens cDNA clone 781639 3'. | -2,25 | 206 | P | D | | -3,9 | -2,56 | 253 | P | D | |
| aa90h11.s1 Stratagene fetal retina 937202 Homo sapiens cDNA clone 838629 3' similar to contains Alu repetitive element;. | -0,71 | 268 | P | D | | -1,7 | -0,25 | 333 | P | D | |
| zx70c04.s1 Soares total fetus Nb2HF8 9w Homo sapiens cDNA clone 796806 3'. | -7,78 | 310 | P | D | | -3,1 | -1,86 | 121 | P | D | |
| zd27g09.r1 Soares fetal heart NbHH19W Homo sapiens cDNA clone 341920 5'. | -0,76 | 136 | P | D | | -1,9 | -0,3 | 78 | P | D | |

Fig. 5.3

EST Bladder candidates of 17742 ESTs
Exclusion of data sets Incl. AFFX, all NC, all A, 3xNC + M*
2424 genes with sort score >= +/- 0,5 changing from N to tumor
12 genes Abs calls PPPPP and DECREASED more than 3 fold

| gene name | Fold Change T2g||solidP(vs)N | Sort Score T2g||solidP(vs)N | Abs Calls | N | A | B | C | D |
|---|---|---|---|---|---|---|---|---|
| Human mRNA for IgG Fc binding protein, complete cds | -4,3 | -5,38 | PPPPP | 2636 | 422 | 345 | 468 | 600 |
| yv73b09.s1 Soares fetal liver spleen 1NFLS Homo sapiens cDNA clone 248345 3'. | -5 | -3,22 | PPPPP | 573 | 180 | 303 | 292 | 294 |
| ye88f04.s1 Homo sapiens cDNA clone 68767 3'. | -9,1 | -19,58 | PPPPP | 6706 | 431 | 456 | 634 | 601 |
| ye30d12.s1 Homo sapiens cDNA clone 119255 3'. | -3,3 | -3,03 | PPPPP | 1154 | 370 | 620 | 418 | 301 |
| zr97c07.s1 NCI_CGAP_GCB1 Homo sapiens cDNA clone IMAGE:683628 3' | -2,5 | -1,52 | PPPPP | 1235 | 296 | 166 | 395 | 611 |
| zr61e12.s1 Soares NhHMPu S1 Homo sapiens cDNA clone 682126 3'. | -7,4 | -10,4 | PPPPP | 2650 | 197 | 333 | 526 | 312 |
| zt19i03.s1 Soares ovary tumor NbHOT Homo sapiens cDNA clone 713597 3' similar to TR:E92665 E92665 AP56.; | -2,4 | -1,52 | PPPPP | 1847 | 625 | 736 | 346 | 765 |
| zw46c01.s1 Soares total fetus Nb2HF8 9w Homo sapiens cDNA clone 773088 3'. | -4,4 | -3,17 | PPPPP | 813 | 98 | 574 | 399 | 223 |
| zw71d04.s1 Soares testis NHT Homo sapiens cDNA clone 781639 3'. | -3,1 | -1,77 | PPPPP | 803 | 161 | 222 | 206 | 253 |
| aa90h11.s1 Stratagene fetal retina 937202 Homo sapiens cDNA clone 836629 3' similar to contains Alu repetitive element.; | -1,5 | -0,13 | PPPPP | 396 | 145 | 190 | -268 | 333 |
| zx70c04.s1 Soares total fetus Nb2HF8 9w Homo sapiens cDNA clone 796806 3'. | -7,9 | -7,15 | PPPPP | 1060 | 290 | 111 | 310 | 121 |
| zd27g09.r1 Soares fetal heart NbHH19W Homo sapiens cDNA clone 341920 5'. | -2,8 | -0,75 | PPPPP | 243 | 47 | 87 | 136 | 78 |

Fig. 6.1

EST Bladder candidates of 17742 ESTs
Exclusion of data sets incl. AFFX, all NC, all A, 3xNC + M*
2424 genes with sort score >= +/- 0,5 changing from N to tumor
6 genes Abs calls PPPPP and INCREASED

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A | Fold Change T1gIIIP(vs)N | Sort Score T1gIIIP(vs)N | Avg Diff T2gIIImixP | Abs Call T2gIIImixP |
|---|---|---|---|---|---|---|---|---|---|---|---|---|---|---|---|---|---|
| Human threonyl-tRNA synthetase mRNA, complete cds | M63180_at | 188 | P | 275 | P | I | | 1,5 | 0,11 | 392 | P | I | | 2,1 | 0,48 | 439 | P |
| HFBEST-40 Human fetal brain QBoqin2 Homo sapiens cDNA. | N89563_s_at | 1057 | P | 2036 | P | I | | 1,8 | 0,66 | 3957 | P | I | | 3,5 | 4,79 | 3061 | P |
| Human fetal brain cDNA 3'-end GEN-045C11. | RC_D80198_at | 658 | P | 2031 | P | I | | 3 | 2,44 | 1660 | P | I | | 2,4 | 1,39 | 1646 | P |
| H. sapiens partial cDNA sequence; clone c-0kf11. | RC_F01986_f_at | 753 | P | 1376 | P | I | | 1,8 | 0,6 | 1438 | P | I | | 1,9 | 0,7 | 1567 | P |
| yn51g07.s1 Homo sapiens cDNA clone 171996 3'. | RC_H18997_at | 557 | P | 1139 | P | I | | 2 | 0,76 | 1102 | P | I | | 2 | 0,68 | 1039 | P |
| zn76c11.s1 Stratagene NT2 neuronal precursor 937230 Homo sapiens cDNA clone 564116 3' similar to contains Alu repetitive element;. | RC_AA101562_at | -25 | P | 576 | P | | | ~15,4 | 10,54 | 435 | P | | | ~10,6 | 6,44 | 349 | P |

Fig. 6.2

EST Bladder candidates of 17742 ESTs
Exclusion of data sets incl. AFFX, all NC, all A, 3xNC + M*
2424 genes with sort score >= +/- 0,5 changing from N to tumor
6 genes Abs calls PPPPP and INCREASED

| gene name | Diff Call T2gIIImixP(vs)N | B=A | Fold Change T2gIIImixP(vs)N | Sort Score T2gIIImixP(vs)N | Avg Diff T2gIIsolidP | Abs Call T2gIIsolidP | Diff Call T2gIIsolidP(vs)N | B=A | Fold Change T2gIIsolidP(vs)N | Sort Score T2gIIsolidP(vs)N | Abs Calls | N | A | B | C | D |
|---|---|---|---|---|---|---|---|---|---|---|---|---|---|---|---|---|
| Human threonyl-tRNA synthetase mRNA, complete cds | I | | 2,3 | 0,68 | 394 | P | I | | 2,1 | 0,48 | PPPPP | 188 | 275 | 392 | 439 | 394 |
| HFBEST-40 Human fetal brain QBoqin2 Homo sapiens cDNA. | I | | 2,7 | 2,46 | 3134 | P | I | | 2,8 | 2,61 | PPPPP | 1057 | 2036 | 3957 | 3061 | 3134 |
| Human fetal brain cDNA 3'-end GEN-045C11. | I | | 2,4 | 1,31 | 2503 | P | I | | 3,4 | 3,44 | PPPPP | 658 | 2031 | 1660 | 1646 | 2503 |
| H. sapiens partial cDNA sequence; clone c-0xf11. | I | | 2,1 | 0,94 | 1580 | P | I | | 2,1 | 0,97 | PPPPP | 753 | 1376 | 1438 | 1557 | 1580 |
| yn51p07.s1 Homo sapiens cDNA clone 171998 3'. | I | | 1,9 | 0,55 | 1197 | P | I | | 2,1 | 0,9 | PPPPP | 557 | 1139 | 1102 | 1039 | 1197 |
| zn76c11.s1 Stratagene NT2 neuronal precursor 937230 Homo sapiens cDNA clone 564116 3' similar to contains Alu repetitive element;. | I | | ~-8,3 | 4,51 | 529 | P | | | ~-8,9 | 6,05 | PPPPP | -25 | 576 | 435 | 349 | 529 |

Fig. 7.1

EST Bladder candidates of 17742 ESTs
Exclusion of data sets incl. AFFX; all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIIP | Abs Call TagIIIP | Diff Call TagIIIP(vs)N | B=A |
|---|---|---|---|---|---|---|---|---|---|---|---|---|---|
| zo76b01.s1 Stratagene pancreas (#937208) Homo sapiens cDNA clone 592777 3' | RC_AA158234_at | 3924 | P | 1798 | P | NC | | -2.2 | -1.71 | 5083 | P | NC | |
| yo61a11.s1 Homo sapiens cDNA clone 182396 3' | RC_H42123_at | 2240 | P | 2243 | P | NC | | 1.1 | 0.03 | 3225 | P | NC | |
| H. sapiens partial cDNA sequence; clone c-13f02. | RC_Z39200_at | 1943 | P | 550 | P | D | | -3.5 | -3.44 | 499 | P | MD | |
| yx63h03.s1 Soares melanocyte 2NbHM Homo sapiens cDNA clone 266453 3' | RC_N21687_at | 1806 | P | 665 | P | D | | -2.5 | -1.48 | 511 | P | D | |
| Homo sapiens mRNA for uroplakin II. | Y13645_at | 1633 | P | 1476 | P | NC | | -1.1 | -0.03 | 1335 | P | NC | |
| zb86b03.s1 Soares senescent fibroblasts NbHSF Homo sapiens cDNA clone 310445 3' | RC_N98461_at | 1539 | P | 2136 | P | NC | | 1.2 | 0.06 | 917 | P | D | |
| zd99d10.s1 Soares fetal heart NbHH19W Homo sapiens cDNA clone 357619 3' | RC_W92449_at | 1535 | P | 980 | P | NC | | -1.6 | -0.35 | 933 | P | MD | |
| H. sapiens partial cDNA sequence, clone c-13c12. | RC_Z39191_at | 1426 | P | 719 | P | NC | | -1.6 | -0.29 | 888 | P | NC | |
| z129e12.s1 Soares pregnant uterus NbHPU Homo sapiens cDNA clone 503374 3' | RC_AA125808_at | 1404 | P | 1253 | P | NC | | -1.1 | -0.03 | 1985 | P | NC | |
| ya11a06.s1 Homo sapiens cDNA clone 611138 3' | RC_T40767_at | 1341 | P | 921 | P | NC | | -1.2 | -0.03 | 312 | P | D | |
| yb29c05.s1 Homo sapiens cDNA clone 72584 3' | RC_T51972_at | 1340 | P | 1120 | P | NC | | -1.2 | -0.05 | 2625 | P | I | |
| zs58b06.s1 NCI_CGAP_GCB1 Homo sapiens cDNA clone IMAGE:701651 3' | RC_AA286662_at | 1278 | P | 1104 | P | NC | | -1.2 | -0.05 | 963 | P | NC | |
| yw91b09.s1 Homo sapiens cDNA clone 259577 3' | RC_N29764_at | 1276 | P | 1261 | P | NC | | -1 | 0 | 953 | P | NC | |
| zw32b06.r1 Soares ovary tumor NbHOT Homo sapiens cDNA clone 770963 5' | AA428172_f_at | 1267 | P | 1916 | P | NC | | 1.5 | 0.34 | 1463 | P | NC | |
| yj35d05.s1 Homo sapiens cDNA clone 150729 3' | RC_H02265_at | 1247 | P | 1199 | P | NC | | -1 | -0.01 | 854 | P | NC | |
| zb98a11.s1 Soares parathyroid tumor NbHPA Homo sapiens cDNA clone 320828 3' | RC_W44745_at | 1247 | P | 1120 | P | NC | | -1.4 | -0.18 | 1256 | P | NC | |
| yp99c05.s1 Homo sapiens cDNA clone 195560 3' similar to contains MER1 repetitive element. | RC_R91819_at | 1215 | P | 1537 | P | NC | | 1.3 | 0.11 | 1180 | P | NC | |
| zx84d05.r1 Soares ovary tumor NbHOT Homo sapiens cDNA clone 810441 5' | AA464468_at | 1214 | P | 975 | P | NC | | -1.2 | -0.09 | 646 | P | D | |
| zp78e01.s1 Stratagene HeLa cell s3 937216 Homo sapiens cDNA clone 626328 3' similar to TR:G998813 G998813 TIF1. [1]. | RC_AA188647_at | 1202 | P | 994 | P | NC | | -1.2 | -0.07 | 1100 | P | NC | |
| zu57g11.s1 Soares ovary tumor NbHOT Homo sapiens cDNA clone 742148 3' similar to T R:G780241 G780241 AU-BINDING PROTEIN/ENOYL-COA HYDRATASE. | RC_AA405832_at | 1154 | P | 492 | P | D | | -2.3 | -1.12 | 545 | P | D | |

Fig. 7.2

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1g/lIP(vs)N | Sort Score T1g/lIP(vs)N | Avg Diff T2g/llmixP | Abs Call T2g/llmixP | Diff Call T2g/llmixP(vs)N | B=A | Fold Change T2g/llmixP(vs)N | Sort Score T2g/llmixP(vs)N | Avg Diff T2g/llsolidP | Abs Call T2g/llsolidP | Diff Call T2g/llsolidP(vs)N | B=A |
|---|---|---|---|---|---|---|---|---|---|---|---|---|
| zo76b01.s1 Stratagene pancreas (#937208) Homo sapiens cDNA clone 592777 3' | 1,3 | 0,24 | 2974 | P | NC | | -1,3 | -0,24 | -510 | A | D | |
| yo61a11.s1 Homo sapiens cDNA clone 182396 3' | 1,6 | 0,56 | 1762 | P | NC | | 1,1 | 0,04 | 2012 | A | D | |
| H. sapiens partial cDNA sequence; clone c-13f02. | -3,9 | -4,06 | 701 | P | MD | | -2,6 | -1,77 | -148 | A | D | |
| yx53h03.s1 Soares melanocyte 2NbHM Homo sapiens cDNA clone 266453 3' | -3,2 | -2,61 | 485 | P | D | | -3,4 | -2,88 | 315 | A | D | |
| Homo sapiens mRNA for uroplakin II. | -1,1 | -0,03 | 5941 | P | L | | 3,6 | 6,33 | 78 | A | D | |
| zb86b03.s1 Soares senescent fibroblasts NbHSF Homo sapiens cDNA clone 310445 3' | -1,9 | -0,77 | 1250 | P | D | | -1,4 | -0,23 | 384 | A | D | |
| zd99d10.s1 Soares fetal heart NbHH19W Homo sapiens cDNA clone 357619 3' | -1,6 | -0,43 | 1111 | P | NC | | -1,4 | -0,19 | 769 | A | D | |
| H. sapiens partial cDNA sequence; clone c-13c12. | -1,3 | -0,09 | 828 | P | NC | | -1,3 | -0,14 | 303 | A | D | |
| zl29e12.s1 Soares pregnant uterus NbHPU Homo sapiens cDNA clone 503374 3' | 1,4 | 0,25 | 1580 | P | D | | 1,1 | 0,04 | 315 | A | D | |
| ya11a06.s1 Homo sapiens cDNA clone 61138 3' | -4,3 | -3,95 | 227 | P | D | | -5,9 | -6,12 | -645 | A | D | |
| yb28c05.s1 Homo sapiens cDNA clone 72584 3' | 1,9 | 0,93 | 813 | P | D | | -1,8 | -0,59 | 960 | A | D | |
| zs58b06.s1 NCI_CGAP_GCB1 Homo sapiens cDNA clone IMAGE:701651 3' | -1,3 | -0,14 | 1016 | P | NC | | -1,3 | -0,1 | 591 | A | D | |
| yw91b09.s1 Homo sapiens cDNA clone 259577 3' | -1,3 | -0,14 | 494 | P | NC | | -2,6 | -1,48 | 228 | A | D | |
| zw32b06.r1 Soares ovary tumor NbHOT Homo sapiens cDNA clone 770963 5' | 1,2 | 0,05 | 983 | P | D | | -1,3 | -0,11 | 435 | A | D | |
| yj35d05.s1 Homo sapiens cDNA clone 150729 3' | -1,5 | -0,23 | 682 | P | D | | -1,8 | -0,57 | 130 | A | D | |
| zb99a11.s1 Soares parathyroid tumor NbHPA Homo sapiens cDNA clone 320828 3' | 1 | 0 | 2132 | P | NC | | 1,7 | 0,59 | 289 | A | D | |
| yp99c05.s1 Homo sapiens cDNA clone 195560 3' similar to contains MER1 repetitive element;.. | -1 | 0 | 960 | P | NC | | -1,3 | -0,1 | 281 | A | D | |
| zx84d05.r1 Soares ovary tumor NbHOT Homo sapiens cDNA clone 810441 5'. | -1,9 | -0,61 | 338 | P | D | | -4,7 | -4,29 | 434 | A | D | |
| zp78e01.s1 Stratagene HeLa cell s3 937216 Homo sapiens cDNA clone 626328 3' similar to TR:G998813 G998813 TIF1. [1];.. | -1,1 | -0,02 | 839 | P | NC | | -1,4 | -0,21 | 636 | A | D | |
| zu57g11.s1 Soares ovary tumor NbHOT Homo sapiens cDNA clone 742148 3' similar to T | -2,1 | -0,85 | 528 | P | D | | -1,8 | -0,55 | 450 | A | D | |
| R:G780241 G780241 AU-BINDING PROTEIN/ENOYL-COA HYDRATASE. .; | | | | | | | | | | | | |

Fig. 7.3

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIlIsolidP(vs)N | Sort Score T2gIlIsolidP(vs)N | Abs Calls | N | A | B | C | D |
|---|---|---|---|---|---|---|---|---|
| zo76b01.s1 Stratagene pancreas (#937208) Homo sapiens cDNA clone 592777 3' | -65,2 | -52,03 | PPPPA | 3924 | 1796 | 5083 | 2974 | 0 |
| yo61a11.s1 Homo sapiens cDNA clone 182396 3'. | -1,1 | -0,04 | PPPPA | 2240 | 2243 | 3225 | 1762 | 0 |
| H. sapiens partial cDNA sequence; clone c-13302. | -29,1 | -25,33 | PPPPA | 1943 | 550 | 499 | 701 | 0 |
| yx63h03.s1 Soares melanocyte 2NbHM Homo sapiens cDNA clone 266453 3'. | -5,2 | -5,7 | PPPPA | 1806 | 665 | 511 | 485 | 0 |
| Homo sapiens mRNA for uroplakin II. | -20,2 | -18,83 | PPPPA | 1633 | 1476 | 1335 | 5941 | 0 |
| zb86b03.s1 Soares senescent fibroblasts NbHSF Homo sapiens cDNA clone 310445 3' | -4,7 | -4,76 | PPPPA | 1539 | 2136 | 917 | 1250 | 0 |
| zd99d10.s1 Soares fetal heart NbHH19W Homo sapiens cDNA clone 357619 3'. | -2 | -0,83 | PPPPA | 1535 | 980 | 933 | 1111 | 0 |
| H. sapiens partial cDNA sequence; clone c-13c12. | -3,7 | -2,8 | PPPPA | 1426 | 719 | 888 | 628 | 0 |
| zi29e12.s1 Soares pregnant uterus NbHPU Homo sapiens cDNA clone 503374 3'. | -3,7 | -2,88 | PPPPA | 1404 | 1253 | 1985 | 1580 | 0 |
| ya11a06.s1 Homo sapiens cDNA clone 61138 3'. | -24,3 | -20,64 | PPPPA | 1341 | 921 | 312 | 227 | 0 |
| yb29c05.s1 Homo sapiens cDNA clone 72584 3'. | -1,4 | -0,19 | PPPPA | 1340 | 1120 | 2625 | 813 | 0 |
| zs58b06.s1 NCI_CGAP_GCB1 Homo sapiens cDNA clone IMAGE:701651 3'. | -2,2 | -1 | PPPPA | 1278 | 1104 | 963 | 1016 | 0 |
| yw91b09.s1 Homo sapiens cDNA clone 259577 3'. | -5,6 | -5,58 | PPPPA | 1276 | 1281 | 963 | 494 | 0 |
| zw32b06.r1 Soares ovary tumor NbHOT Homo sapiens cDNA clone 770963 5'. | -3 | -2,09 | PPPPA | 1267 | 1916 | 1463 | 983 | 0 |
| yj35005.s1 Homo sapiens cDNA clone 150729 3' | -6 | -4,82 | PPPPA | 1247 | 1199 | 854 | 682 | 0 |
| zo98a11.s1 Soares parathyroid tumor NbHPA Homo sapiens cDNA clone 320828 3'. | -8,9 | -8,37 | PPPPA | 1247 | 1120 | 1256 | 2132 | 0 |
| yp99c05.s1 Homo sapiens cDNA clone 195560 3' similar to contains MER1 repetitive element ;. | -4,3 | -3,79 | PPPPA | 1215 | 1537 | 1180 | 960 | 0 |
| zx84d05.r1 Soares ovary tumor NbHOT Homo sapiens cDNA clone 810441 5'. | -3,8 | -3,09 | PPPPA | 1214 | 975 | 846 | 338 | 0 |
| zp78e01.s1 Stratagene HeLa cell s3 937216 Homo sapiens cDNA clone 626328 3' similar to T TR:G998813 G998813 TIF1. (1) ;. | -1,9 | -0,62 | PPPPA | 1202 | 994 | 1100 | 639 | 0 |
| zu57g11.s1 Soares ovary tumor NbHOT Homo sapiens cDNA clone 742148 3' similar to T R:G780241 G780241 AU-BINDING PROTEIN/ENOYL-COA HYDRATASE. ;. | -2,6 | -1,39 | PPPPA | 1154 | 482 | 545 | 628 | 0 |

Fig. 7.4

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N B=A | Fold Change TagIIP(vs)N | Sort Score TagIIP(vs)N | Avg Diff T4gIIIP | Abs Call T4gIIIP | Diff Call T4gIIIP(vs)N B=A |
|---|---|---|---|---|---|---|---|---|---|---|---|
| zc13b12.s1 Soares parathyroid tumor NbHPA Homo sapiens cDNA clone 322175 3' similar to contains LTR2.t3 LTR2 repetitive element;. | RC_W37778_f_at | 1142 | P | 566 | P | MD | -2 | -0,74 | 1485 | P | NC |
| Homo sapiens breast cancer-specific protein 1 (BCSG1) mRNA, complete cds. | AF010126_at | 1098 | P | 774 | P | NC | -1,4 | -0,19 | 852 | P | NC |
| yx83a05.r1 Homo sapiens cDNA clone 268304 5'. | N36432_at | 1069 | P | 627 | P | D | -2 | -0,7 | 786 | P | NC |
| zr74c04.s1 Soares NhHMPu S1 Homo sapiens cDNA clone 669126 3' similar to gb:S69002 ECOTROPIC VIRUS INTEGRATION 1 SITE PROTEIN (HUMAN);. | RC_AA236533_s_at | 1064 | P | 1530 | P | NC | 1,2 | 0,07 | 883 | P | NC |
| zt55e05.s1 Soares ovary tumor NbHOT Homo sapiens cDNA clone 726272 3'. | RC_AA293163_at | 972 | P | 11180 | P | NC | 1,2 | 0,07 | 756 | P | NC |
| zq60b06.s1 Stratagene neuroepithelium (#937231) Homo sapiens cDNA clone 645971 3'. | RC_AA196790_at | 949 | P | 733 | P | NC | -1,3 | -0,1 | 873 | P | NC |
| zf53g12.s1 Soares NhHMPu S1 Homo sapiens cDNA clone 667174 3'. | RC_AA253220_at | 940 | P | 964 | P | NC | 1 | 0 | 637 | P | NC |
| zn59e02.s1 Stratagene muscle 937209 Homo sapiens cDNA clone 562490 3'. | RC_AA100437_at | 919 | P | 717 | P | NC | -1,3 | -0,09 | 673 | P | NC |
| zt28d03.s1 Soares ovary tumor NbHOT Homo sapiens cDNA clone 714437 3'. | RC_AA293300_s_at | 918 | P | 1828 | P | I | 2 | 0,91 | 1006 | P | NC |
| H. sapiens partial cDNA sequence; clone c-1fig03. | RC_Z39652_at | 911 | P | 1175 | P | NC | 1,4 | 0,2 | 385 | P | NC |
| Human glutathione transferase M2 (GSTM2) mRNA, complete cds | M63509_s_at | 886 | P | 1365 | P | NC | 1,7 | 0,49 | 2970 | P | NC |
| H. sapiens partial cDNA sequence; clone c-1ke11. | RC_Z39842_at | 882 | P | 556 | P | NC | -1,6 | -0,28 | 662 | P | NC |
| yx78e10.s1 Homo sapiens cDNA clone 267882 3'. | RC_N23319_at | 878 | P | 530 | P | D | -1,7 | -0,33 | 316 | P | D |
| zs76d11.s1 NCI_CGAP_GCB1 Homo sapiens cDNA clone IMAGE:703605 3'. | RC_AA278817_at | 835 | P | 687 | P | NC | -1,2 | -0,06 | 307 | P | D |
| Homo sapiens mRNA in the region near the blk gene involved in a-gamma-globulinemia | L20773_at | 822 | P | 913 | P | NC | 1,1 | 0,02 | 700 | P | D |
| yi44h05.s1 Soares placenta Nb2HP Homo sapiens cDNA clone 142137 3'. | RC_R69276_at | 820 | P | 831 | P | NC | 1 | 0 | 767 | P | NC |
| H. sapiens partial cDNA sequence; clone c-15d02. | RC_F02641_at | 775 | P | 488 | P | NC | -1,6 | -0,27 | 550 | P | NC |
| zw03a04.s1 Soares NhHMPu S1 Homo sapiens cDNA clone 768174 3' similar to contains Alu repetitive element;. | RC_AA424791_at | 775 | P | 410 | P | D | -1,9 | -0,5 | 504 | P | D |
| yf63b06.s1 Homo sapiens cDNA clone 267725 3'. | RC_R39869_at | 759 | P | 136 | P | NC | -4,1 | -2,41 | 356 | P | NC |

Fig. 7.5

EST Bladder candidates of 17742 ESTs
Exclusion of data sets Incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| zc13b12.s1 Soares parathyroid tumor NbHPA Homo sapiens cDNA clone 322175 3' similar to contains LTR2,t3 LTR2 repetitive element.: | 1,3 | 0,13 | 1432 | P | I | | 2 | 0,87 | -5 | A | D | |
| Homo sapiens breast cancer-specific protein 1 (BCSG1) mRNA, complete cds. | 1,1 | 0,01 | 284 | P | D | | -2,8 | -1,4 | 32 | A | D | |
| yx83a05.r1 Homo sapiens cDNA clone 268304 5'. | -1,4 | -0,15 | 704 | P | NC | | -1,3 | -0,08 | -238 | A | D | |
| zr74d04.s1 Soares NhHMPu S1 Homo sapiens cDNA clone 669126 3' similar to gb:S68002 ECOTROPIC VIRUS INTEGRATION 1 SITE PROTEIN (HUMAN):. | -1,4 | -0,19 | 745 | P | D | | -1,7 | -0,43 | 112 | A | D | |
| zt55e05.s1 Soares ovary tumor NbHOT Homo sapiens cDNA clone 726272 3'. | -1,3 | -0,1 | 116 | P | D | | -3,3 | -2,26 | -49 | A | D | |
| zg60b06.s1 Stratagene neuroepithelium (#937231) Homo sapiens cDNA clone 645971 3' | -1,1 | -0,02 | 774 | P | NC | | -1,1 | -0,01 | 175 | A | D | |
| zf53g12.s1 Soares NhHMPu S1 Homo sapiens cDNA clone 657174 3'. | -1,5 | -0,21 | 169 | P | D | | -5,5 | -4,74 | 245 | A | D | |
| zn59e02.s1 Stratagene muscle 937209 Homo sapiens cDNA clone 562490 3'. | -1,4 | -0,14 | 707 | P | NC | | -1,3 | -0,1 | 259 | A | D | |
| zt28d03.s1 Soares ovary tumor NbHOT Homo sapiens cDNA clone 714437 3'. | 1,1 | 0,02 | 538 | P | D | | -1,7 | -0,41 | 816 | A | D | |
| H. sapiens partial cDNA sequence; clone c-1fg03. | -1,4 | -0,15 | 268 | P | NC | | -3,4 | -2,19 | -739 | A | D | |
| Human glutathione transferase M2 (GSTM2) mRNA, complete cds | 3,4 | 3,86 | 5604 | P | MI | | 6,3 | 13,61 | 551 | A | D | |
| H. sapiens partial cDNA sequence; clone c-1ke11. | -1,6 | -0,32 | 841 | P | NC | | -1 | -0,01 | 502 | A | D | |
| yx78e10.s1 Homo sapiens cDNA clone 267882 3'. | -2,4 | -0,95 | 275 | P | D | | -2,7 | -1,3 | 203 | A | D | |
| zs78d11.s1 NCI_CGAP_GCB1 Homo sapiens cDNA clone IMAGE:7036605 3'. | -2,7 | -1,34 | 228 | P | D | | -4 | -2,91 | 60 | A | D | |
| Homo sapiens mRNA in the region near the blk gene involved in a-gamma-globulinemia | -1,2 | -0,04 | 819 | P | D | | -1 | 0 | 367 | A | D | |
| yi44h05.s1 Soares placenta Nb2HP Homo sapiens cDNA clone 142137 3'. | -1,1 | -0,01 | 572 | P | NC | | -1,6 | -0,34 | 300 | A | D | |
| H. sapiens partial cDNA sequence; clone c-15d02. | -1,4 | -0,15 | 349 | P | D | | -2,2 | -0,79 | 193 | A | D | |
| zw03a04.s1 Soares NhHMPu S1 Homo sapiens cDNA clone 768174 3' similar to contains Alu repetitive element:. | -1,5 | -0,23 | 571 | P | NC | | -1,4 | -0,13 | 203 | A | D | |
| yf63b06.s1 Homo sapiens cDNA clone 26725 3'. | -2,1 | -0,7 | 502 | P | D | | -1,8 | -0,43 | 159 | A | D | |

Fig. 7.6

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIIIsolidP(vs)N | Sort Score T2gIIIsolidP(vs)N | Abs Calls | N | A | B | C | D |
|---|---|---|---|---|---|---|---|---|
| zc13b12.s1 Soares parathyroid tumor NbHPA Homo sapiens cDNA clone 322175 3' similar to contains LTR2.13 LTR2 repetitive element:. | -14,2 | -11,73 | PPPPA | 1142 | 566 | 1485 | 1432 | 0 |
| Homo sapiens breast cancer-specific protein 1 (BCSG1) mRNA, complete cds: | -19,6 | -13,16 | PPPPA | 1098 | 774 | 852 | 284 | 0 |
| yx83a05.r1 Homo sapiens cDNA clone 268304 5'. | -28,5 | -18,48 | PPPPA | 1069 | 627 | 786 | 704 | 0 |
| zr74c04.s1 Soares NhHMPu S1 Homo sapiens cDNA clone 669126 3' similar to gb:S69002 ECOTROPIC VIRUS INTEGRATION 1 SITE PROTEIN (HUMAN);. | -8,3 | -7,49 | PPPPA | 1064 | 1530 | 883 | 745 | 0 |
| zt55e05.s1 Soares ovary tumor NbHOT Homo sapiens cDNA clone 726272 3'. | -5,1 | -4,51 | PPPPA | 972 | 1180 | 756 | 116 | 0 |
| zq60b06.s1 Stratagene neuroepithelium (#937231) Homo sapiens cDNA clone 645971 3'. | -4,7 | -3,5 | PPPPA | 949 | 733 | 873 | 774 | 0 |
| zr53g12.s1 Soares NhHMPu S1 Homo sapiens cDNA clone 657174 3'. | -4,3 | -3,47 | PPPPA | 940 | 964 | 637 | 169 | 0 |
| zn59e02.s1 Stratagene muscle 937209 Homo sapiens cDNA clone 562490 3'. | -4,9 | -4,14 | PPPPA | 919 | 717 | 673 | 707 | 0 |
| zt28d03.s1 Soares ovary tumor NbHOT Homo sapiens cDNA clone 714437 3'. | -1,4 | -0,15 | PPPPA | 918 | 1828 | 1006 | 538 | 0 |
| H. sapiens partial cDNA sequence; clone c-1fg03. | -24,6 | -18,85 | PPPPA | 911 | 1175 | 385 | 268 | 0 |
| Human glutathione transferase M2 (GSTM2) mRNA, complete cds | -2,2 | -1,04 | PPPPA | 886 | 1365 | 2970 | 5604 | 0 |
| H. sapiens partial cDNA sequence; clone c-1ke11. | -2,1 | -0,91 | PPPPA | 882 | 556 | 662 | 841 | 0 |
| yx78e10.s1 Homo sapiens cDNA clone 267882 3'. | -3,7 | -2,27 | PPPPA | 878 | 530 | 316 | 275 | 0 |
| zs78d11.s1 NCI_CGAP_GCB1 Homo sapiens cDNA clone IMAGE:703605 3'. | -13,3 | -10,27 | PPPPA | 835 | 687 | 307 | 228 | 0 |
| Homo sapiens mRNA in the region near the btk gene involved in a-gamma-globulinemia | -2,1 | -0,69 | PPPPA | 822 | 913 | 700 | 819 | 0 |
| yl44h05.s1 Soares placenta Nb2HP Homo sapiens cDNA clone 142137 3'. | -2,6 | -1,16 | PPPPA | 820 | 831 | 767 | 572 | 0 |
| H. sapiens partial cDNA sequence; clone c-15d02. | -5,1 | -3,87 | PPPPA | 775 | 488 | 550 | 349 | 0 |
| zw03a04.s1 Soares NhHMPu S1 Homo sapiens cDNA clone 768174 3' similar to contains Alu repetitive element;. | -3,8 | -2,49 | PPPPA | 775 | 410 | 504 | 571 | 0 |
| yf63b06.s1 Homo sapiens cDNA clone 26725 3'. | -4,8 | -3,45 | PPPPA | 759 | 136 | 356 | 502 | 0 |

Fig. 7.7

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagII(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A |
|---|---|---|---|---|---|---|---|---|---|---|---|---|---|
| ab15c03.s1 Stratagene lung (#937210) Homo sapiens cDNA clone 840868 3' | RC_AA482224_f_at | 723 P | P | 677 P | P | NC | | -1,1 | -0,01 | 1204 | P | NC | |
| ze76f02.s1 Soares fetal heart NbHH19W Homo sapiens cDNA clone 364923 3' similar to contains Alu repetitive element;contains element LTR4 repetitive element | RC_AA025277_at | 720 P | P | 1531 P | P | I | | 2,1 | 0,99 | 301 | P | D | |
| ab15c03.r1 Stratagene lung (#937210) Homo sapiens cDNA clone 840868 5' | AA482319_f_at | 712 P | P | 676 P | P | NC | | -1,1 | -0,01 | 1112 | P | NC | |
| ze47b04.s1 Soares retina N2b4HR Homo sapiens cDNA clone 362095 3' | RC_AA001045_at | 703 P | P | 313 P | P | D | | -2,2 | -0,78 | 184 | P | D | |
| zo10i03.s1 Stratagene neuroepithelium NT2RAMI 937234 Homo sapiens cDNA clone 567293 3' similar to SW:NI2M_BOVIN Q02369 NADH-UBIQUINONE OXIDOREDUCTASE B22 SUBUNIT | RC_AA130645_s_at | 674 P | P | 708 P | P | NC | | 1 | 0 | 1539 | P | NC | |
| zt37c02.s1 Soares ovary tumor NbHOT Homo sapiens cDNA clone 724514 3' | RC_AA291659_at | 655 P | P | 462 P | P | NC | | -1,6 | -0,26 | 324 | P | MD | |
| zk72d02.r1 Soares pregnant uterus NbHPU Homo sapiens cDNA clone 488355 5' | AA046768_at | 655 P | P | 384 P | P | D | | -1,7 | -0,32 | 506 | P | NC | |
| yl81e01.r1 Homo sapiens cDNA clone 44466 5' | H07011_at | 654 P | P | 635 P | P | NC | | -1,2 | -0,04 | 612 | P | NC | |
| zt54g04.s1 Soares ovary tumor NbHOT Homo sapiens cDNA clone 726198 3' similar to gb:J05158 CARBOXYPEPTIDASE N 83 KD CHAIN (HUMAN); | RC_AA293533_i_at | 630 P | P | 454 P | P | NC | | -1,4 | -0,13 | 382 | P | NC | |
| zn53g10.s1 Stratagene HeLa cell s3 937216 Homo sapiens cDNA clone 562914 3' similar to SW:LCFA_ECOLI P29212 LONG-CHAIN-FATTY-ACID--COA LIGASE | RC_AA100549_at | 629 P | P | 319 P | P | NC | | -2,1 | -0,58 | 971 | P | NC | |
| ze41a07.s1 Soares retina N2b4HR Homo sapiens cDNA clone 361524 3' similar to contains element PTR7 repetitive element | RC_AA017146_at | 628 P | P | 265 P | P | NC | | -2 | -0,47 | 301 | P | NC | |
| zp40g07.s1 Stratagene muscle 937209 Homo sapiens cDNA clone 611964 3' | RC_AA180054_at | 526 P | P | 362 P | P | NC | | -1,7 | -0,33 | 374 | P | D | |
| PMY0335 KG1a Lambda Zap Express cDNA Library Homo sapiens cDNA 5' | AA263032_s_at | 625 P | P | 798 P | P | NC | | 1,3 | 0,09 | 408 | P | NC | |
| zd46f07.r1 Soares fetal heart NbHH19W Homo sapiens cDNA clone 343717 5' | W69310_at | 607 P | P | 641 P | P | NC | | 1,1 | 0,01 | 924 | P | NC | |
| zr05e02.s1 Stratagene NT2 neuronal precursor 937230 Homo sapiens cDNA clone 650618 3' | RC_AA219653_at | 602 P | P | 1052 P | P | I | | 1,7 | 0,45 | 1383 | P | | |
| aa91c07.s1 Stratagene fetal retina 937202 Homo sapiens cDNA clone 838568 3' | RC_AA457235_at | 599 P | P | 1617 P | P | I | | 2,7 | 1,84 | 956 | P | NC | |
| aa16h10.s1 Soares NhHMPu S1 Homo sapiens cDNA clone 813475 3' | RC_AA455967_at | 591 P | P | 369 P | P | NC | | -1,3 | -0,09 | 454 | P | NC | |

Fig. 7.8

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIP(vs)N | Sort Score T1gIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImix(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| ab15c03.s1 Stratagene lung (#937210) Homo sapiens cDNA clone 840868 3'. | 1,4 | 0,21 | 567 | P | NC | | -1,3 | -0,08 | 212 | A | D | |
| ze76t02.s1 Soares fetal heart NbHH19W Homo sapiens cDNA clone 364923 3' similar to contains Alu repetitive element;contains element LTR4 repetitive element.: | -2,6 | -1,15 | 463 | P | NC | | -1,6 | -0,24 | 324 | A | D | |
| ab15c03.r1 Stratagene lung (#937210) Homo sapiens cDNA clone 840868 5'. | 1,6 | 0,3 | 643 | P | NC | | -1,3 | -0,1 | 96 | A | D | |
| ze47b04.s1 Soares retina N2b4HR Homo sapiens cDNA clone 362095 3'. | -3,3 | -1,75 | 157 | P | D | | -3,8 | -2,15 | 84 | A | D | |
| zo10t03.s1 Stratagene neuroepithelium NT2RAMI 937234 Homo sapiens cDNA clone 567293 3' similar to SW:NI2M_BOVIN Q02369 NADH-UBIQUINONE OXIDOREDUCTASE B22 SUBUNIT.: | 1,8 | 0,55 | 1129 | P | NC | | 1,4 | 0,2 | 1275 | A | D | |
| zl37c02.s1 Soares ovary tumor NbHOT Homo sapiens cDNA clone 724514 3'. | -2,4 | -0,92 | 364 | P | D | | -2,1 | -0,67 | 89 | A | D | |
| zk72d02.s1 Soares pregnant uterus NbHPU Homo sapiens cDNA clone 488355 5'. | -1,3 | -0,09 | 832 | P | NC | | 1,3 | 0,08 | 122 | A | D | |
| yjB1e01.r1 Homo sapiens cDNA clone 44465 5'. | -1,2 | -0,05 | 258 | P | D | | -2,9 | -1,41 | 275 | A | D | |
| zt54g04.s1 Soares ovary tumor NbHOT Homo sapiens cDNA clone 726198 3' similar to gb:J05158 CARBOXYPEPTIDASE N 83 KD CHAIN (HUMAN);. | -1,6 | -0,28 | 329 | P | D | | -1,9 | -0,47 | 117 | A | D | |
| zn63g10.s1 Stratagene HeLa cell s3 937216 Homo sapiens cDNA clone 562914 3' similar to SW:LCFA_ECOLI P29212 LONG-CHAIN-FATTY-ACID--COA LIGASE.: | 1,4 | 0,14 | 386 | P | MD | | -1,5 | -0,15 | 41 | A | D | |
| ze41a07.s1 Soares retina N2b4HR Homo sapiens cDNA clone 361524 3' similar to contains element PTR7 repetitive element.: | -1,7 | -0,31 | 388 | P | NC | | -1,4 | -0,1 | 175 | A | D | |
| zp40g07.s1 Stratagene muscle 937209 Homo sapiens cDNA clone 611964 3'. | -1,8 | -0,35 | 429 | P | NC | | -1,5 | -0,21 | 253 | A | D | |
| PMY0335 KG1a Lambda Zap Express cDNA Library Homo sapiens cDNA 5'. | -1,5 | -0,21 | 479 | P | NC | | -1,3 | -0,09 | 230 | A | D | |
| zd46f07.r1 Soares fetal heart NbHH19W Homo sapiens cDNA clone 343717 5'. | 1,5 | 0,24 | 467 | P | NC | | -1,3 | -0,08 | 250 | A | D | |
| zr05e02.s1 Stratagene NT2 neuronal precursor 937230 Homo sapiens cDNA clone 650618 3'. | 2 | 0,76 | 826 | P | NC | | -1,1 | -0,01 | 508 | A | D | |
| aa91c07.s1 Stratagene fetal retina 937202 Homo sapiens cDNA clone 638668 3'. | 1,6 | 0,3 | 779 | P | NC | | 1,1 | 0,03 | 229 | A | D | |
| aa16h10.s1 Soares NhHMPu S1 Homo sapiens cDNA clone 813475 3'. | -1,3 | -0,08 | 249 | P | D | | -2 | -0,46 | 158 | A | D | |

Fig. 7.9

EST Bladder candidates of 17742 ESTs
Exclusion of data sets incl. AFFX, all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg.Diff N

| gene name | Fold Change T2gIIsolidP(vs)N | Sort Score T2gIIsolidP(vs)N | Abs Calls | N | A | B | C | D |
|---|---|---|---|---|---|---|---|---|
| ab15c03.s1 Stratagene lung (#937210) Homo sapiens cDNA clone 840868 3'. | -3,4 | -1,96 | PPPPA | 723 | 677 | 1204 | 667 | 0 |
| ze76f02.s1 Soares fetal heart NbHH19W Homo sapiens cDNA clone 364923 3' similar to contains Alu repetitive element;contains element LTR4 repetitive element ;. | -2,2 | -0,77 | PPPPA | 720 | 1531 | 301 | 463 | 0 |
| ab15c03.r1 Stratagene lung (#937210) Homo sapiens cDNA clone 840868 5'. | -7,4 | -5,76 | PPPPA | 712 | 676 | 1112 | 543 | 0 |
| ze47b04.s1 Soares retina N2b4HR Homo sapiens cDNA clone 362095 3'. | -7,3 | -5,32 | PPPPA | 703 | 313 | 184 | 157 | 0 |
| zo10f03.s1 Stratagene neuroepithelium NT2RAMI 937234 Homo sapiens cDNA clone 567293 3' similar to SW:NI2M_BOVIN Q02369 NADH-UBIQUINONE OXIDOREDUCTASE B22 SUBUNIT ;. | 1,4 | 0,17 | PPPPA | 674 | 708 | 1539 | 1129 | 0 |
| zt37c02.s1 Soares ovary tumor NbHOT Homo sapiens cDNA clone 724514 3'. | -8,6 | -6,92 | PPPPA | 655 | 482 | 324 | 364 | 0 |
| zk72d02.r1 Soares pregnant uterus NbHPU Homo sapiens cDNA clone 488355 5'. | -5,3 | -3,64 | PPPPA | 655 | 384 | 506 | 832 | 0 |
| yl61e01.r1 Homo sapiens cDNA clone 44466 5'. | -2,7 | -1,23 | PPPPA | 654 | 635 | 612 | 258 | 0 |
| zt54g04.s1 Soares ovary tumor NbHOT Homo sapiens cDNA clone 726198 3' similar to gb:J05158 CARBOXYPEPTIDASE N 63 KD CHAIN (HUMAN);. | -5,4 | -3,71 | PPPPA | 630 | 454 | 382 | 329 | 0 |
| zn63g10.s1 Stratagene HeLa cell s3 937216 Homo sapiens cDNA clone 562914 3' similar to SW:LCFA_ECOLI P29212 LONG-CHAIN-FATTY-ACID--COA LIGASE ;. | ~7,9 | -5,25 | PPPPA | 629 | 319 | 971 | 386 | 0 |
| ze41a07.s1 Soares retina N2b4HR Homo sapiens cDNA clone 361524 3' similar to contains element PTR7 repetitive element ;. | -3 | -1,31 | PPPPA | 628 | 265 | 301 | 388 | 0 |
| zp40g07.s1 Stratagene muscle 937209 Homo sapiens cDNA clone 611964 3'. | -2,6 | -1,06 | PPPPA | 626 | 362 | 374 | 429 | 0 |
| PMY0335 KG1a Lambda Zap Express cDNA Library Homo sapiens cDNA 5'. | -3,1 | -1,64 | PPPPA | 625 | 798 | 408 | 479 | 0 |
| zd46f07.r1 Soares fetal heart NbHH19W Homo sapiens cDNA clone 343717 5'. | -2,1 | -0,59 | PPPPA | 607 | 641 | 924 | 467 | 0 |
| zr05e02.s1 Stratagene NT2 neuronal precursor 937230 Homo sapiens cDNA clone 650618 3'. | -1,9 | -0,48 | PPPPA | 602 | 1052 | 1383 | 826 | 0 |
| aa91c07.s1 Stratagene fetal retina 937202 Homo sapiens cDNA clone 838668 3'. | -3 | -1,52 | PPPPA | 599 | 1817 | 956 | 779 | 0 |
| aa16h10.s1 Soares NhHMPu S1 Homo sapiens cDNA clone 813475 3'. | -3,7 | -2,09 | PPPPA | 591 | 369 | 454 | 249 | 0 |

Fig. 7.10

EST Bladder candidates of 17742 ESTs
Exclusion of data sets incl. AFFX, all NC, all A, 3xNC + M*
2424 genes with sort score >= +/- 0.5 changing from N to tumor
235 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagIIP | Diff Call TagIIP(vs)N | B=A | Fold Change TagIIP(vs)N | Sort Score TagIIP(vs)N | Avg Diff TagIIIP | Abs Call TagIIIP | Diff Call TagIIIP(vs)N | B=A |
|---|---|---|---|---|---|---|---|---|---|---|---|---|---|
| yx51a09.r1 Homo sapiens cDNA clone 265240 5'. | N27670_at | 585 | P | 446 | P | NC | | -1.3 | -0.09 | 620 | P | NC | |
| zp65e02.s1 Homo sapiens cDNA clone 297434 3'. | RC_N80152_at | 575 | P | 330 | P | NC | | -1.7 | -0.33 | 353 | P | NC | |
| yi22a10.s1 Homo sapiens cDNA clone 139962 3'. | RC_R64660_at | 574 | P | 370 | P | NC | | -1.6 | -0.21 | 380 | P | NC | |
| zo64g03.s1 Stratagene pancreas (#937208) Homo sapiens cDNA clone 591700 3'. | RC_AA147218_s_at | 573 | P | 483 | P | NC | | -1.2 | -0.04 | 323 | P | NC | |
| HUMGS0007818, Human Gene Signature, 3'-directed cDNA sequence. | C01139_at | 572 | P | 807 | P | NC | | 1.4 | 0.16 | 460 | P | NC | |
| PMY0691 KG1a Lambda Zap Express cDNA Library Homo sapiens cDNA 5'. | AA285284_at | 564 | P | 525 | P | NC | | -1.2 | -0.06 | 226 | P | D | |
| zx44c03.s1 Soares total fetus Nb2HF8 9w Homo sapiens cDNA clone 789316 3'. | RC_AA451685_at | 562 | P | 471 | P | NC | | -1.5 | -0.21 | 589 | P | NC | |
| zx56e01.r1 Soares fetal liver spleen 1NFLS S1 Homo sapiens cDNA clone 445520 5' similar to contains element MER17 repetitive element;. | AA203222_at | 559 | P | 429 | P | NC | | -1.3 | -0.08 | 597 | P | NC | |
| zt52g01.s1 Soares ovary tumor NbHOT Homo sapiens cDNA clone 726000 3' similar to SW:ADG_MOUSE P22892 GAMMA-ADAPTIN;. | RC_AA394071_at | 554 | P | 353 | P | NC | | -1.6 | -0.21 | 144 | P | NC | |
| zv17e07.s1 Soares NhHMPu S1 Homo sapiens cDNA clone 753924 3'. | RC_AA479096_at | 548 | P | 375 | P | NC | | -1.5 | -0.16 | 378 | P | NC | |
| zo34b05.s1 Stratagene colon (#937204) Homo sapiens cDNA clone 588753 3'. | RC_AA156532_at | 540 | P | 436 | P | NC | | 1 | 0 | 486 | P | NC | |
| H. sapiens partial cDNA sequence; clone c-1wg05. | RC_Z40233_at | 516 | P | 971 | P | NC | | 1.9 | 0.55 | 1036 | P | D | |
| seq2490 Homo sapiens cDNA clone 3HFLSK20-87 3'. | RC_T03927_at | 511 | P | 311 | P | NC | | -1.6 | -0.25 | 216 | P | NC | |
| EST185294 Colon carcinoma (HCC) cell line II Homo sapiens cDNA 5' end. | AA314457_at | 509 | P | 198 | P | D | | -2.6 | -0.92 | 482 | P | NC | |
| yy89f05.s1 Homo sapiens cDNA clone 280737 3'. | RC_N50550_at | 492 | P | 378 | P | NC | | -1.3 | -0.08 | 165 | P | NC | |
| zp88f04.s1 Stratagene HeLa cell s3 937216 Homo sapiens cDNA clone 627285 3'. | RC_AA191524_at | 484 | P | 252 | P | MD | | -1.9 | -0.41 | 178 | P | D | |
| yw90b12.s1 Homo sapiens cDNA clone 259487 3'. | RC_N29740_at | 482 | P | 514 | P | NC | | 1.1 | 0.01 | 603 | P | NC | |
| yy75h02.s1 Homo sapiens cDNA clone 279411 3'. | RC_N48715_at | 481 | P | 345 | P | NC | | -1.4 | -0.11 | 318 | P | NC | |
| zx98h04.s1 Soares NhHMPu S1 Homo sapiens cDNA clone 811831 3'. | RC_AA463637_at | 478 | P | 259 | P | NC | | -1.8 | -0.36 | 349 | P | NC | |
| zw38a06.s1 Soares total fetus Nb2HF8 9w Homo sapiens cDNA clone 772306 3'. | RC_AA404487_at | 476 | P | 70 | P | D | | -6.8 | -4.29 | 96 | P | D | |

Fig. 7.11

EST Bladder candidates of 17742 ESTs
Exclusion of data sets Incl. AFFX, all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1g/liP(vs)N | Sort Score T1g/liP(vs)N | Avg Diff T2g/limixP | Abs Call T2g/limixP | Diff Call T2g/limixP(vs)N | B=A | Fold Change T2g/limixP(vs)N | Sort Score T2g/limixP(vs)N | Avg Diff T2g/lisoIldP | Abs Call T2g/lisoIldP | Diff Call T2g/lisoIldP(vs)N | B=A |
|---|---|---|---|---|---|---|---|---|---|---|---|---|
| yx51a09.r1 Homo sapiens cDNA clone 265240 5'. | 1.1 | 0.01 | 727 | P | NC | | 1.2 | 0.07 | 211 | A | D | |
| 2a65e02.s1 Homo sapiens cDNA clone 297434 3' | -1.6 | -0.25 | 213 | P | D | | -3.4 | -1.7 | 133 | A | D | |
| yi22a10.s1 Homo sapiens cDNA clone 139962 3'. | -1.5 | -0.19 | 324 | P | NC | | -1.8 | -0.34 | 61 | A | D | |
| zo64g03.s1 Stratagene pancreas (#937208) Homo sapiens cDNA clone 591700 3'. | -1.8 | -0.35 | 319 | P | D | | -1.8 | -0.36 | 88 | A | D | |
| HUMGS0007818, Human Gene Signature, 3'-directed cDNA sequence. | -1.2 | -0.06 | 678 | P | NC | | 1.2 | 0.04 | 376 | A | D | |
| PMY0691 KG1a Lambda Zap Express cDNA Library Homo sapiens cDNA 5'. | -1.9 | -0.37 | 37 | P | D | | -15.2 | -9.46 | -12 | A | D | |
| zx44c03.s1 Soares total fetus Nb2HF8 9w Homo sapiens cDNA clone 789316 3'. | -1.2 | -0.05 | 512 | P | NC | | -1.4 | -0.14 | 44 | A | D | |
| 2x56g01.r1 Soares fetal liver spleen 1NFLS S1 Homo sapiens cDNA clone 446520 5' similar to contains element MER17 repetitive element. | 1.1 | 0.01 | 420 | P | NC | | -1.3 | -0.1 | 89 | A | D | |
| zt52g01.s1 Soares ovary tumor NbHOT Homo sapiens cDNA clone 726000 3' similar to SW:ADG_MOUSE P22892 GAMMA-ADAPTIN. | -3.9 | -2.13 | 276 | P | NC | | -2.2 | -0.73 | 132 | A | D | |
| 2v17e07.s1 Soares NhHMPu S1 Homo sapiens cDNA clone 753924 3'. | -1.5 | -0.15 | 478 | P | NC | | -1.1 | -0.03 | 254 | A | D | |
| zo34h05.s1 Stratagene colon (#937204) Homo sapiens cDNA clone 588753 3'. | -1.2 | -0.04 | 661 | P | NC | | 1.3 | 0.11 | 195 | A | D | |
| H. sapiens partial cDNA sequence; clone c-1wg05. | 2 | 0.69 | 880 | P | NC | | 1.2 | 0.08 | 177 | A | D | |
| seq2490 Homo sapiens cDNA clone 3HFLSK20-87 3'. | -2.2 | -0.65 | 359 | P | D | | -1.4 | -0.1 | 121 | A | D | |
| EST186294 Colon carcinoma (HCC) cell line II Homo sapiens cDNA 5' end. | -1.1 | -0.01 | 252 | P | NC | | -2 | -0.49 | 63 | A | D | |
| yy89f05.s1 Homo sapiens cDNA clone 280737 3'. | -3 | -1.25 | 508 | P | NC | | 1 | 0 | -129 | A | D | |
| zp88h04.s1 Stratagene HeLa cell s3 937216 Homo sapiens cDNA clone 627295 3'. | -2.7 | -1.02 | 168 | P | D | | -2.9 | -1.15 | 94 | A | D | |
| yw90b12.s1 Homo sapiens cDNA clone 259487 3'. | 1.3 | 0.06 | 385 | P | NC | | -1 | 0 | 154 | A | D | |
| yy75h02.s1 Homo sapiens cDNA clone 279411 3'. | -1.3 | -0.07 | 264 | P | NC | | -1.8 | -0.35 | 49 | A | D | |
| zx98h04.s1 Soares NhHMPu S1 Homo sapiens cDNA clone 811831 3'. | -1.4 | -0.1 | 329 | P | NC | | -1.5 | -0.14 | 38 | A | D | |
| 2w38a06.s1 Soares total fetus Nb2HF8 9w Homo sapiens cDNA clone 772306 3'. | -4.9 | -2.88 | 401 | P | NC | | -1.2 | -0.04 | -74 | A | D | |

Fig. 7.12

EST Bladder candidates of 17742 ESTs
Exclusion of data sets incl. AFFX, all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2g/IIsolidP(vs)N | Sort Score T2g/IIsolidP(vs)N | Abs Calls | N | A | B | C | D |
|---|---|---|---|---|---|---|---|---|
| yx51e09.r1 Homo sapiens cDNA clone 265240 5' | -2.5 | -0.85 | PPPPA | 585 | 446 | 620 | 727 | 0 |
| za65e02.s1 Homo sapiens cDNA clone 297434 3' | -8.4 | -5.92 | PPPPA | 575 | 330 | 353 | 213 | 0 |
| yi22a10.s1 Homo sapiens cDNA clone 1399662 3' | -8.3 | -5.86 | PPPPA | 574 | 370 | 380 | 324 | 0 |
| zo64g03.s1 Stratagene pancreas (#937208) Homo sapiens cDNA clone 591700 3' | -6.5 | -4.47 | PPPPA | 573 | 483 | 323 | 319 | 0 |
| HUMGS0007818, Human Gene Signature, 3'-directed cDNA sequence. | -2 | -0.56 | PPPPA | 572 | 807 | 460 | 678 | 0 |
| PMY0691 KG1a Lambda Zap Express cDNA Library Homo sapiens cDNA 5'. | -11.1 | -5.19 | PPPPA | 564 | 525 | 226 | 37 | 0 |
| zx44c03.s1 Soares total fetus Nb2HF8 9w Homo sapiens cDNA clone 789316 3' | -15.9 | -10.91 | PPPPA | 562 | 471 | 589 | 512 | 0 |
| zx56e01.r1 Soares fetal liver spleen 1NFLS S1 Homo sapiens cDNA clone 446520 5' similar to contains element MER17 repetitive element ;. | -4.9 | -2.67 | PPPPA | 559 | 429 | 597 | 420 | 0 |
| zt52g01.s1 Soares ovary tumor NbHOT Homo sapiens cDNA clone 726000 3' similar to SW:ADG_MOUSE P22892 GAMMA-ADAPTIN ;. | -4.7 | -3.11 | PPPPA | 554 | 363 | 144 | 276 | 0 |
| zv17e07.s1 Soares NhHMPu S1 Homo sapiens cDNA clone 753924 3'. | -2.2 | -0.67 | PPPPA | 548 | 375 | 378 | 478 | 0 |
| zo34b05.s1 Stratagene colon (#937204) Homo sapiens cDNA clone 588753 3'. | -3.1 | -1.5 | PPPPA | 540 | 435 | 486 | 661 | 0 |
| H. sapiens partial cDNA sequence; clone c-1wg05. | -4 | -2.53 | PPPPA | 516 | 971 | 1036 | 880 | 0 |
| seq2490 Homo sapiens cDNA clone 3HFLSK20-87 3'. | -4 | -2.12 | PPPPA | 511 | 311 | 216 | 359 | 0 |
| EST186294 Colon carcinoma (HCC) cell line II Homo sapiens cDNA 5' end. | -8.1 | -5.36 | PPPPA | 509 | 198 | 482 | 252 | 0 |
| yy69f05.s1 Homo sapiens cDNA clone 280737 3'. | -9.9 | -6.48 | PPPPA | 492 | 378 | 165 | 508 | 0 |
| zp88f04.s1 Stratagene HeLa cell s3 937216 Homo sapiens cDNA clone 627295 3' | -5.2 | -3.08 | PPPPA | 484 | 252 | 178 | 168 | 0 |
| yw90b12.s1 Homo sapiens cDNA clone 259487 3'. | -2.5 | -0.75 | PPPPA | 482 | 514 | 603 | 385 | 0 |
| yy75h02.s1 Homo sapiens cDNA clone 279411 3'. | -7.2 | -4.59 | PPPPA | 481 | 345 | 318 | 264 | 0 |
| zx98h04.s1 Soares NhHMPu S1 Homo sapiens cDNA clone 811831 3'. | -10.7 | -6.36 | PPPPA | 476 | 259 | 349 | 329 | 0 |
| zw38a06.s1 Soares total fetus Nb2HF8 9w Homo sapiens cDNA clone 772306 3'. | -13.2 | -7.73 | PPPPA | 476 | 70 | 96 | 401 | 0 |

Fig. 7.13

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T4gIIP | Abs Call T4gIIP | Diff Call T4gIIP(vs)N | B=A |
|---|---|---|---|---|---|---|---|---|---|---|---|---|---|
| ym26a10.s1 Homo sapiens cDNA clone 491155 3'. | RC_H16666_at | 468 | P | 329 | P | NC | | -1,4 | -0,13 | 288 | P | NC | |
| zv24d11.s1 Soares NhHMPu S1 Homo sapiens cDNA clone 754581 3'. | RC_AA406197_at | 468 | P | 346 | P | NC | | -1,4 | -0,11 | 206 | P | D | |
| yl97b11.s1 Homo sapiens cDNA clone 462276 3'. | RC_H09594_at | 466 | P | 369 | P | NC | | -1,3 | -0,06 | 500 | P | NC | |
| zo62h09.s1 Stratagene pancreas (#937208) Homo sapiens cDNA clone 591521 3' similar to SW:PPAP_RAT P20646 PROSTATIC ACID PHOSPHATASE PRECURSOR.; | RC_AA161085_at | 464 | P | 332 | P | NC | | -1,4 | -0,11 | 318 | P | NC | |
| zx15d06.s1 Soares total fetus Nb2HF8 9w Homo sapiens cDNA clone 786539 3'. | RC_AA452131_at | 451 | P | 312 | P | NC | | -1,4 | -0,1 | 322 | P | NC | |
| zt54g04.s1 Soares ovary tumor NbHOT Homo sapiens cDNA clone 726198 3' similar to gb:J05158 CARBOXYPEPTIDASE N 83 KD CHAIN (HUMAN).; | RC_AA293533_f_at | 442 | P | 358 | P | NC | | -1,2 | -0,05 | 299 | P | NC | |
| zt59a08.s1 Soares testis NHT Homo sapiens cDNA clone 726614 3'. | RC_AA398197_at | 442 | P | 362 | P | NC | | -1,2 | -0,05 | 127 | P | D | |
| zx86d04.r1 Soares ovary tumor NbHOT Homo sapiens cDNA clone 810631 5'. | AA464051_s_at | 436 | P | 290 | P | NC | | -1,5 | -0,16 | 189 | P | NC | |
| yb29g01.s1 Homo sapiens cDNA clone 72600 3'. | RC_T51990_at | 432 | P | 427 | P | NC | | -1,3 | -0,06 | 615 | P | NC | |
| zr54a11.s1 Soares NhHMPu S1 Homo sapiens cDNA clone 667195 3'. | RC_AA236356_at | 420 | P | 344 | P | NC | | -1,2 | -0,04 | 371 | P | NC | |
| zd92e04.r1 Soares fetal heart NbHH19W Homo sapiens cDNA clone 356910 5' similar to contains element LTR3 repetitive element.; | W92678_at | 415 | P | 423 | P | NC | | 1 | 0 | 353 | P | NC | |
| yz33d11.s1 Homo sapiens cDNA clone 284853 3' similar to contains Alu repetitive element.; | RC_N63332_at | 413 | P | 415 | P | NC | | 1,3 | 0,08 | -337 | P | D | |
| Human aorta cDNA 5'-end GEN-259H09. | C16281_s_at | 406 | P | 261 | P | D | | -1,6 | -0,18 | 318 | P | NC | |
| zu29h10.s1 Soares ovary tumor NbHOT Homo sapiens cDNA clone 739459 3'. | RC_AA477252_at | 403 | P | 482 | P | NC | | -1,6 | -0,19 | 151 | P | NC | |
| yw20e07.r1 Homo sapiens cDNA clone 252804 5'. | H88035_s_at | 399 | P | 370 | P | NC | | -1,1 | -0,01 | 468 | P | NC | |
| Human mRNA for KIAA0389 gene, complete cds. | AB002387_at | 392 | P | 365 | P | NC | | -1,1 | -0,01 | 409 | P | NC | |
| yg45h12.s1 Homo sapiens cDNA clone 35838 3'. | RC_R45698_at | 392 | P | 279 | P | NC | | -1,2 | -0,03 | 204 | P | D | |
| zr75g11.s1 Soares NhHMPu S1 Homo sapiens cDNA clone 669284 3'. | RC_AA236542_at | 391 | P | 321 | P | NC | | 1,1 | 0,01 | 206 | P | D | |
| EST89388 Small intestine I Homo sapiens cDNA 5' end similar to monoamine oxidase A. | AA376875_at | 378 | P | 204 | P | NC | | -1,3 | -0,07 | 197 | P | D | |

Fig. 7.14

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| ym26a10.s1 Homo sapiens cDNA clone 491155 3'. | -1,6 | -0,23 | 134 | P | D | | -3,5 | -1,64 | 109 | A | D | |
| zv24d11.s1 Soares NhHMPu S1 Homo sapiens cDNA clone 754581 3'. | -1,8 | -0,28 | 220 | P | NC | | -1,7 | -0,22 | 2 | A | D | |
| yl97b11.s1 Homo sapiens cDNA clone 46276 3'. | 1,1 | 0,01 | 363 | P | NC | | -1,3 | -0,07 | 79 | A | D | |
| zo62h09.s1 Stratagene pancreas (#937208) Homo sapiens cDNA clone 591521 3' similar to SW:PPAP_RAT P20646 PROSTATIC ACID PHOSPHATASE PRECURSOR ;. | -1,5 | -0,14 | 621 | P | NC | | 1,3 | 0,1 | 23 | A | D | |
| zx15d06.s1 Soares total fetus Nb2HF8 9w Homo sapiens cDNA clone 786539 3'. | -1,3 | -0,08 | 342 | P | NC | | -1,1 | -0,01 | 117 | A | D | |
| zt54g04.s1 Soares ovary tumor NbHOT Homo sapiens cDNA clone 726198 3' similar to gb:J05158 CARBOXYPEPTIDASE N 83 KD CHAIN (HUMAN);. | -1,5 | -0,15 | 294 | P | D | | -1,5 | -0,16 | 44 | A | D | |
| zt59g08.s1 Soares testis NHT Homo sapiens cDNA clone 726614 3'. | -3,5 | -1,59 | 65 | P | D | | -6,8 | -4,13 | 29 | A | D | |
| zx86d04.r1 Soares ovary tumor NbHOT Homo sapiens cDNA clone 810631 5'. | -2,3 | -0,66 | -151 | P | NC | | -6,3 | -3,15 | -615 | A | D | |
| yb29e01.s1 Homo sapiens cDNA clone 72600 3'. | 1,4 | 0,14 | 440 | P | NC | | -1,3 | -0,08 | 86 | A | D | |
| zr54a11.s1 Soares NhHMPu S1 Homo sapiens cDNA clone 667196 3'. | -1,1 | -0,02 | 508 | P | NC | | 1,1 | 0,01 | 113 | A | D | |
| zd92a04.r1 Soares fetal heart NbHH19W Homo sapiens cDNA clone 356910 5' similar to contains element LTR3 repetitive element ;. | 1,1 | 0,01 | 374 | P | NC | | 1,1 | 0,02 | 75 | A | D | |
| yz33d11.s1 Homo sapiens cDNA clone 234853 3' similar to contains Alu repetitive element;. | -11,8 | -6,88 | 67 | P | D | | -6,1 | -3,55 | 20 | A | D | |
| Human aorta cDNA 5'-end GEN-259H09. | -1,3 | -0,06 | 261 | P | NC | | -1,6 | -0,18 | 61 | A | D | |
| zu29h10.s1 Soares ovary tumor NbHOT Homo sapiens cDNA clone 739459 3'. | -2,7 | -0,9 | 621 | P | D | | 1,1 | 0,01 | 181 | A | D | |
| yw20e07.r1 Homo sapiens cDNA clone 252804 5'. | 1,2 | 0,03 | 201 | P | NC | | -2 | -0,41 | 129 | A | D | |
| Human mRNA for KIAA0389 gene, complete cds. | 1 | 0 | 449 | P | NC | | 1,1 | 0,02 | 34 | A | D | |
| yg45h12.s1 Homo sapiens cDNA clone 356838 3'. | -1,6 | -0,19 | 238 | P | NC | | -1,4 | -0,1 | 95 | A | D | |
| zr75g11.s1 Soares NhHMPu S1 Homo sapiens cDNA clone 669284 3'. | -1,9 | -0,36 | 190 | P | D | | -2,1 | -0,45 | -83 | A | D | |
| EST89386 Small intestine I Homo sapiens cDNA 5' end similar to monoamine oxidase A. | -1,7 | -0,2 | 57 | P | D | | -5,7 | -2,89 | 32 | A | D | |

Fig. 7.15

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIIIsolidP(vs)N | Sort Score T2gIIIsolidP(vs)N | Abs Calls | N | A | B | C | D |
|---|---|---|---|---|---|---|---|---|
| ym26a10.s1 Homo sapiens cDNA clone 49155 3'. | -,4 | -2,03 | PPPPA | 468 | 329 | 288 | 134 | 0 |
| zv24d11.s1 Soares NhHMPu S1 Homo sapiens cDNA clone 754581 3'. | -9,9 | -5,52 | PPPPA | 468 | 346 | 206 | 220 | 0 |
| yl97b11.s1 Homo sapiens cDNA clone 46276 3'. | -5,9 | -3,58 | PPPPA | 466 | 369 | 500 | 363 | 0 |
| zo62h09.s1 Stratagene pancreas (#937206) Homo sapiens cDNA clone 591521 3' similar to SW:PPAP_RAT P20646 PROSTATIC ACID PHOSPHATASE PRECURSOR.; | -11,2 | -6,71 | PPPPA | 464 | 332 | 318 | 621 | 0 |
| zx15d06.s1 Soares total fetus Nb2HF8 9w Homo sapiens cDNA clone 786539 3'. | -3,7 | -1,73 | PPPPA | 451 | 312 | 322 | 342 | 0 |
| zt54g04.s1 Soares ovary tumor NbHOT Homo sapiens cDNA clone 726198 3' similar to gb:J05158 CARBOXYPEPTIDASE N 83 KD CHAIN (HUMAN);. | -10,1 | -6,12 | PPPPA | 442 | 358 | 299 | 294 | 0 |
| zt59a08.s1 Soares testis NHT Homo sapiens cDNA clone 726614 3'. | -10,3 | -6,04 | PPPPA | 442 | 362 | 127 | 65 | 0 |
| zx86d04.r1 Soares ovary tumor NbHOT Homo sapiens cDNA clone 810631 5'. | -14,7 | -7,4 | PPPPA | 436 | 290 | 189 | -151 | 0 |
| yb29e01.s1 Homo sapiens cDNA clone 72600 3'. | -4,9 | -2,63 | PPPPA | 432 | 427 | 615 | 440 | 0 |
| zf54a11.s1 Soares NhHMPu S1 Homo sapiens cDNA clone 667195 3'. | -2,9 | -1,06 | PPPPA | 420 | 344 | 371 | 508 | 0 |
| zd92a04.r1 Soares fetal heart NbHH19W Homo sapiens cDNA clone 356910 5' similar to contains element LTR3 repetitive element.; | -2,9 | -0,78 | PPPPA | 415 | 423 | 353 | 374 | 0 |
| yz33d11.s1 Homo sapiens cDNA clone 284853 3' similar to contains Alu repetitive element.; | -6,6 | -3,87 | PPPPA | 413 | 415 | -337 | 67 | 0 |
| Human aorta cDNA 5'-end GEN-259H09. | -6,6 | -3,84 | PPPPA | 406 | 261 | 318 | 261 | 0 |
| zu29h10.s1 Soares ovary tumor NbHOT Homo sapiens cDNA clone 739459 3'. | -3,3 | -1,63 | PPPPA | 403 | 482 | 151 | 621 | 0 |
| yw20e07.r1 Homo sapiens cDNA clone 252804 5'. | -3,1 | -1,21 | PPPPA | 399 | 370 | 468 | 201 | 0 |
| Human mRNA for KIAA0389 gene, complete cds. | -9,7 | -5,6 | PPPPA | 392 | 365 | 409 | 449 | 0 |
| yg45h12.s1 Homo sapiens cDNA clone 358836 3'. | -3,5 | -1,4 | PPPPA | 392 | 279 | 204 | 238 | 0 |
| zr75g11.s1 Soares NhHMPu S1 Homo sapiens cDNA clone 669284 3'. | -10,3 | -5,89 | PPPPA | 391 | 321 | 206 | 190 | 0 |
| EST89388 Small intestine I Homo sapiens cDNA 5' end similar to monoamine oxidase A. | -9,6 | -5,09 | PPPPA | 378 | 204 | 197 | 57 | 0 |

Fig. 7.16

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N B=A | Fold Change TagIIP(vs)N | Sort Score TagIIP(vs)N | Avg Diff T19IIP | Abs Call T19IIP | Diff Call T19IIP(vs)N B=A |
|---|---|---|---|---|---|---|---|---|---|---|---|
| yg15g06.s1 Homo sapiens cDNA clone 32365 3'. | RC_R43365_at | 376 | P | 162 | P | NC | -2,3 | -0,62 | 97 | P | MD |
| yl83h08.s1 Homo sapiens cDNA clone 44847 3'. | RC_H06746_at | 375 | P | 478 | P | NC | 1,3 | 0,07 | 568 | P | NC |
| zr47f06.s1 Soares NhHMPu S1 Homo sapiens cDNA clone 666553 3'. | RC_AA233837_at | 375 | P | 273 | P | NC | -1,4 | -0,09 | 480 | P | NC |
| z15h06.s1 Soares fetal heart NbHH19W Homo sapiens cDNA clone 377051 3'. | RC_AA057620_at | 374 | P | 159 | P | NC | -2,4 | -0,64 | 102 | P | D |
| zx42e09.s1 Soares total fetus Nb2HF8 9w Homo sapiens cDNA clone 789160 3'. | RC_AA450118_at | 373 | P | 269 | P | NC | -1,4 | -0,1 | 243 | P | NC |
| ae37b10.s1 Gessler Wilms tumor Homo sapiens cDNA clone 897979 3'. | RC_AA598872_at | 373 | P | 260 | P | NC | -1,4 | -0,12 | 367 | P | NC |
| zl52g06.s1 Soares pregnant uterus NbHPU Homo sapiens cDNA clone 505594 3'. | RC_AA147646_s_at | 364 | P | 294 | P | NC | -1,2 | -0,05 | 222 | P | NC |
| zb94b05.s1 Soares parathyroid tumor NbHPA Homo sapiens cDNA clone 320433 3'. | RC_W04698_at | 362 | P | 248 | P | NC | -1,5 | -0,12 | 205 | P | NC |
| yv39c06.s1 Homo sapiens cDNA clone 245098 3'. | RC_N54365_at | 359 | P | 190 | P | NC | -1,9 | -0,34 | 289 | P | NC |
| zr80a08.s1 Soares NhHMPu S1 Homo sapiens cDNA clone 681874 3'. | RC_AA256208_at | 350 | P | 333 | P | NC | -1,1 | 0 | 269 | P | NC |
| zk62g01.r1 Soares pregnant uterus NbHPU Homo sapiens cDNA clone 487440 5'. | AA046593_at | 350 | P | 565 | P | NC | 1,6 | 0,24 | 335 | P | NC |
| zh85g03.s1 Soares fetal liver spleen 1NFLS S1 Homo sapiens cDNA clone 428116 3'. | RC_AA002088_at | 346 | P | 255 | P | NC | -1,4 | -0,08 | 353 | P | NC |
| z81c12.s1 Soares NhHMPu S1 Homo sapiens cDNA clone 682102 3'. | RC_AA256273_at | 342 | P | 131 | P | D | -4,2 | -2,02 | 487 | P | D |
| aa46e04.r1 NCI_CGAP_GCB1 Homo sapiens cDNA clone IMAGE:823998 5'. | AA491114_at | 337 | P | 396 | P | NC | -1 | 0 | 228 | P | NC |
| z155h03.s1 Soares ovary tumor NbHOT Homo sapiens cDNA clone 726293 3'. | RC_AA293719_at | 336 | P | 365 | P | NC | 1,1 | 0,01 | 423 | P | NC |
| z184c04.s1 Stratagene colon (#937204) Homo sapiens cDNA clone 511302 3'. | RC_AA086005_at | 332 | P | 161 | P | D | -1,9 | -0,29 | 465 | P | D |
| zw44a07.s1 Soares total fetus Nb2HF8 9w Homo sapiens cDNA clone 772884 3'. | RC_AA479885_at | 326 | P | 202 | P | NC | -1,6 | -0,18 | 124 | P | D |
| zv70f08.r1 Soares total fetus Nb2HF8 9w Homo sapiens cDNA clone 759015 5' similar to SW:YB72_YEAST P38137 HYPOTHETICAL 60.5 KD PROTEIN IN PDB1-ABD1 INTERGENIC REGION.; | AA442428_at | 326 | P | 212 | P | NC | -1,5 | -0,15 | 487 | P | NC |
| ab35b12.s1 Stratagene HeLa cell s3 937216 Homo sapiens cDNA clone 842879 3'. | RC_AA486410_at | 323 | P | 215 | P | NC | -1,5 | -0,13 | 203 | P | NC |
| yf89f02.r1 Homo sapiens cDNA clone 29565 5'. | R15268_at | 321 | P | 319 | P | NC | 1,1 | 0,01 | 151 | P | D |

Fig. 7.17

EST Bladder candidates of 17742 ESTs
Exclusion of data sets incl. AFFX, all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIsolidP | Abs Call T2gIIsolidP | Diff Call T2gIIsolidP(vs)N | B=A |
|---|---|---|---|---|---|---|---|---|---|---|---|---|
| yg15g06.s1 Homo sapiens cDNA clone 323365 3'. | -3,7 | -1,63 | 107 | P | D | | -3,5 | -1,5 | 8 | A | D | |
| yl83h08.s1 Homo sapiens cDNA clone 44847 3'. | 1,5 | 0,19 | 748 | P | NC | | 2 | 0,58 | 96 | A | D | |
| zr47f05.s1 Soares NhHMPu S1 Homo sapiens cDNA clone 666563 3'. | 1,3 | 0,07 | 456 | P | NC | | 1,2 | 0,05 | 125 | A | D | |
| zf15h06.s1 Soares fetal heart NbHH19W Homo sapiens cDNA clone 377051 3'. | -3,7 | -1,68 | -108 | P | D | | -13,8 | -6,6 | -78 | A | D | |
| zx42e09.s1 Soares total fetus Nb2HF8 9w Homo sapiens cDNA clone 789160 3'. | -1,5 | -0,16 | 449 | P | NC | | 1,2 | 0,04 | 228 | A | D | |
| ae37b10.s1 Gessler Wilms tumor Homo sapiens cDNA clone 897979 3'. | -1 | 0 | 310 | P | NC | | -1,2 | -0,04 | 137 | A | D | |
| zl52g06.s1 Soares pregnant uterus NbHPU Homo sapiens cDNA clone 505594 3'. | -1,6 | -0,21 | 155 | P | D | | -2,4 | -0,63 | 37 | A | D | |
| zb94b05.s1 Soares parathyroid tumor NbHPA Homo sapiens cDNA clone 320433 3'. | -1,8 | -0,27 | 292 | P | NC | | -1,5 | -0,14 | 139 | A | D | |
| yv39c06.s1 Homo sapiens cDNA clone 245098 3'. | -1,2 | -0,05 | 186 | P | D | | -1,9 | -0,36 | 181 | A | D | |
| zr80a08.s1 Soares NhHMPu S1 Homo sapiens cDNA clone 681974 3'. | -1,3 | -0,06 | 261 | P | NC | | -1,3 | -0,08 | 40 | A | D | |
| zk62g01.r1 Soares pregnant uterus NbHPU Homo sapiens cDNA clone 487440 5'. | -1,2 | -0,03 | 372 | P | NC | | -1,1 | 0 | 154 | A | D | |
| zh85g03.s1 Soares fetal liver spleen 1NFLS S1 Homo sapiens cDNA clone 428116 3'. | 1 | 0 | 384 | P | NC | | 1,1 | 0,02 | -14 | A | D | |
| zr81c12.s1 Soares NhHMPu S1 Homo sapiens cDNA clone 682102 3'. | -1,5 | -0,13 | 1612 | P | D | | 1,8 | 0,42 | 530 | A | D | |
| aa46e04.r1 NCI_CGAP_GCB1 Homo sapiens cDNA clone IMAGE:823998 5'. | -1,2 | -0,02 | 286 | P | NC | | -1,5 | -0,15 | 72 | A | D | |
| zt55h03.s1 Soares ovary tumor NbHOT Homo sapiens cDNA clone 726293 3'. | 1,3 | 0,06 | 254 | P | NC | | -1,1 | -0,01 | 14 | A | D | |
| zl84c04.s1 Stratagene colon (#937204) Homo sapiens cDNA clone 511302 3'. | 1,6 | 0,19 | 405 | P | NC | | 1,4 | 0,09 | 104 | A | D | |
| zw44a07.s1 Soares total fetus Nb2HF8 9w Homo sapiens cDNA clone 772884 3'. | -2,6 | -0,77 | 222 | P | D | | -1,5 | -0,12 | 83 | A | D | |
| zv70f08.r1 Soares total fetus Nb2HF8 9w Homo sapiens cDNA clone 759015 5' similar to SW:YB72_YEAST P38137 HYPOTHETICAL 60.5 KD PROTEIN IN PDB1-ABD1 INTERGENIC REGION.; | 1,5 | 0,16 | 257 | P | NC | | -1,3 | -0,05 | 32 | A | D | |
| ab36b12.s1 Stratagene HeLa cell s3 937216 Homo sapiens cDNA clone 842879 3'. | -1,6 | -0,17 | 229 | P | NC | | -1,4 | -0,1 | 85 | A | D | |
| yf89f02.r1 Homo sapiens cDNA clone 29665 5'. | -2,1 | -0,46 | 170 | P | D | | -1,9 | -0,32 | 46 | A | D | |

Fig. 7.18
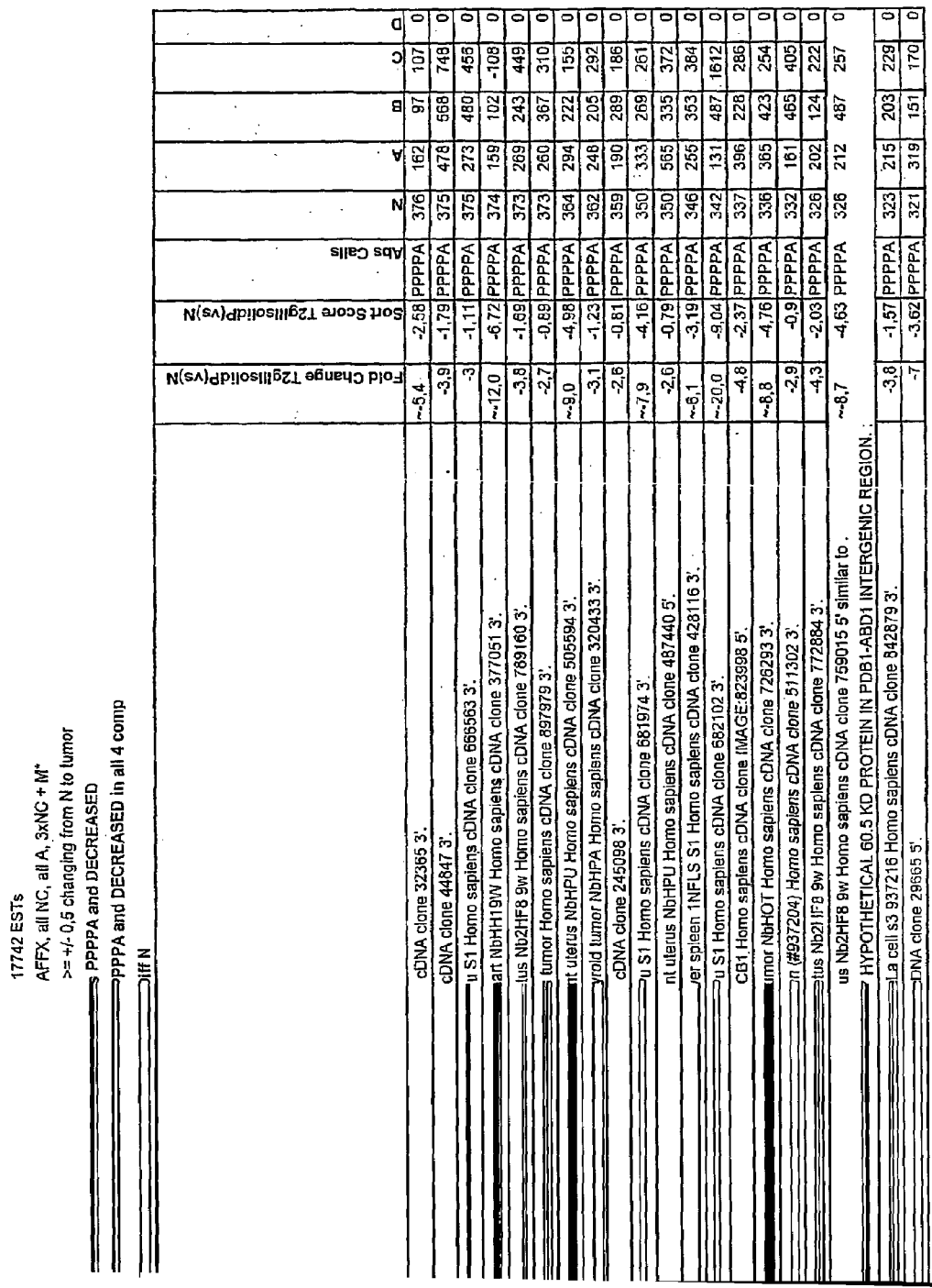

Fig. 7.19

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIP | Abs Call TagIIP | Diff Call TagIIP(vs)N | B=A |
|---|---|---|---|---|---|---|---|---|---|---|---|---|---|
| zw66a10.s1 Soares total fetus Nb2HF8 9w Homo sapiens cDNA clone 7833834 3' similar to TR:G438639 G438639 LAMIN B RECEPTOR. [1]:. | RC_AA443658_at | 319 | P | 154 | P | NC | | -2,1 | -0,42 | 185 | P | NC | |
| ym39b01.s1 Homo sapiens cDNA clone 50559 3'. | RC_H16790_at | 318 | P | 207 | P | D | | -1,5 | -0,15 | 199 | P | D | |
| zx80b07.r1 Soares ovary tumor NbHOT Homo sapiens cDNA clone 810037 5'. | AA465000_s_at | 316 | P | 264 | P | NC | | -1,2 | -0,03 | 219 | P | NC | |
| yy43e04.s1 Homo sapiens cDNA clone 274014 3'. | RC_N38930_at | 315 | P | 251 | P | NC | | -3,2 | -1,15 | 123 | P | NC | |
| Human mRNA for KIAA0323 gene, partial cds. | AB002321_at | 314 | P | 436 | P | NC | | 1,4 | 0,11 | 285 | P | MD | |
| H. sapiens partial cDNA sequence; clone c-0qb09. | RC_Z38810_at | 314 | P | 161 | P | NC | | -1,9 | -0,35 | 48 | P | NC | |
| WUGSC:H_GS188P18.1a gene extracted from Human BAC clone GS188P18 | AC000115_cds1_at | 310 | P | 145 | P | NC | | -2 | -0,35 | 436 | P | NC | |
| zi83b02.s1 Soares NhHMPu S1 Homo sapiens cDNA clone 662251 3'. | RC_AA255464_at | 308 | P | 247 | P | NC | | -1 | 0 | 324 | P | NC | |
| zs31g05.s1 NCI_CGAP_GCB1 Homo sapiens cDNA clone IMAGE:686842 3'. | RC_AA255628_at | 308 | P | 105 | P | NC | | -1,7 | -0,16 | 107 | P | NC | |
| yr91a03.s1 Homo sapiens cDNA clone 212620 3'. | RC_H70554_at | 305 | P | 113 | P | NC | | -2,7 | -0,8 | 339 | P | NC | |
| EST180743 Jurkat T-cells V Homo sapiens cDNA 5' end. | AA309880_at | 301 | P | 348 | P | D | | 1,2 | 0,02 | 253 | P | MD | |
| yg21a08.s1 Soares ovary tumor NbHOT Homo sapiens cDNA clone 32940 3'. | RC_R43812_at | 297 | P | 317 | P | NC | | -1,5 | -0,14 | -112 | P | NC | |
| zv47a04.s1 Soares ovary tumor NbHOT Homo sapiens cDNA clone 756750 3'. | RC_AA426636_at | 297 | P | 291 | P | NC | | -2,3 | -0,54 | 599 | P | NC | |
| yz39f01.s1 Homo sapiens cDNA clone 265433 3'. | RC_N65388_at | 295 | P | 161 | P | NC | | -1,3 | -0,04 | 205 | P | NC | |
| zs85d09.s1 NCI_CGAP_GCB1 Homo sapiens cDNA clone IMAGE:704273 3' similar to TR:G974805 G974805 T0BA11.2.:. | RC_AA279420_at | 295 | P | 430 | P | NC | | 1,5 | 0,14 | 206 | P | NC | |
| zi05c10.s1 Soares fetal liver spleen 1NFLS S1 Homo sapiens cDNA clone 429906 3'. | RC_AA033974_at | 291 | P | 241 | P | NC | | -1,2 | -0,03 | 216 | P | NC | |
| Homo sapiens sodium bicarbonate cotransporter (HNBC1) mRNA, complete cds. | AF007216_at | 289 | P | 49 | P | D | | -4,5 | -1,67 | 77 | P | D | |
| aa56h11.s1 NCI_CGAP_GCB1 Homo sapiens cDNA clone IMAGE:824997 3'. | RC_AA489101_at | 289 | P | 165 | P | NC | | -1,8 | -0,24 | 160 | P | NC | |
| Human aorta cDNA 5'-end GEN-286G10. | D79601_f_at | 285 | P | 217 | P | NC | | -1,2 | -0,02 | 168 | P | D | |
| yw70l05.s1 Homo sapiens cDNA clone 257601 3'. | RC_N30856_at | 285 | P | 132 | P | MD | | -2,2 | -0,45 | 385 | P | NC | |

Fig. 7.20

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1g/IIP(vs)N | Sort Score T1g/IIP(vs)N | Avg Diff T2g/IImixP | Abs Call T2g/IImixP | Diff Call T2g/IImixP(vs)N | B=A | Fold Change T2g/IImixP(vs)N | Sort Score T2g/IImixP(vs)N | Avg Diff T2g/IIsolidP | Abs Call T2g/IIsolidP | Diff Call T2g/IIsolidP(vs)N | B=A |
|---|---|---|---|---|---|---|---|---|---|---|---|---|
| zw86a10.s1 Soares total fetus Nb2HF8 9w Homo sapiens cDNA clone 783834 3' similar to TR:G438639 G438639 LAMIN B RECEPTOR. [1]. | -1,7 | -0,23 | 501 | P | NC | | 1,3 | 0,08 | 189 | A | D | |
| ym39b01.s1 Homo sapiens cDNA clone 50559 3'. | -1,6 | -0,18 | 207 | P | NC | | -1,5 | -0,15 | 116 | A | D | |
| zx80b07.r1 Soares ovary tumor NbHOT Homo sapiens cDNA clone 810037 5'. | -1,3 | -0,07 | 183 | P | NC | | -1,7 | -0,23 | 70 | A | D | |
| yy43e04.s1 Homo sapiens cDNA clone 274014 3'. | -2,6 | -0,72 | 623 | P | NC | | 2 | 0,51 | -17 | A | D | |
| Human mRNA for KIAA0323 gene, partial cds. | -1,1 | -0,01 | -391 | P | NC | | -21,3 | -8,68 | -1391 | A | D | |
| H. sapiens partial cDNA sequence; clone c-0qb09. | -6,6 | -3,35 | 210 | P | NC | | -1,5 | -0,13 | 380 | A | D | |
| WUGSC:H_GS188P18.1a gene extracted from Human BAC clone GS188P18 | 1,7 | 0,27 | 298 | P | NC | | 1,3 | 0,05 | 96 | A | D | |
| zf83b22.s1 Soares NhHMPu S1 Homo sapiens cDNA clone 682251 3'. | 1,1 | 0 | 313 | P | NC | | 1 | 0 | -135 | A | D | |
| zs31g06.s1 NCI_CGAP_GCB1 Homo sapiens cDNA clone IMAGE:686842 3'. | -1,7 | -0,15 | 93 | P | NC | | -1,9 | -0,24 | 24 | A | D | |
| yr91s03.s1 Homo sapiens cDNA clone 212620 3'. | 1,1 | 0,01 | 130 | P | NC | | -2,4 | -0,58 | -21 | A | D | |
| EST180743 Jurkat T-cells V Homo sapiens cDNA 5' end. | -1,2 | -0,03 | 353 | P | NC | | 1,2 | 0,03 | 107 | A | D | |
| yg21a08.s1 Homo sapiens cDNA clone 32940 3'. | -9,5 | -4,82 | -71 | P | D | | -7,1 | -3,44 | 176 | A | D | |
| zv47e04.s1 Soares ovary tumor NbHOT Homo sapiens cDNA clone 756750 3'. | 1,2 | 0,03 | 447 | P | NC | | -1,5 | -0,12 | 165 | A | D | |
| yz39l01.s1 NCI_CGAP_GCB1 Homo sapiens cDNA clone 285433 3'. | -1 | 0 | 227 | P | NC | | -1,3 | -0,06 | 100 | A | D | |
| zs65d09.s1 NCI_CGAP_GCB1 Homo sapiens cDNA clone IMAGE:704273 3' similar to TR:G974805 G974805 T08A11.2.:. | -1,2 | -0,02 | 328 | P | NC | | 1,4 | 0,09 | 72 | A | D | |
| zi05c10.s1 Soares fetal liver spleen 1NFLS S1 Homo sapiens cDNA clone 429906 3'. | -1,3 | -0,07 | 208 | P | NC | | -1,6 | -0,17 | 105 | A | D | |
| Homo sapiens sodium bicarbonate cotransporter (HNBC1) mRNA, complete cds. | -2,8 | -0,75 | 20 | P | D | | -7,6 | -3,27 | 4 | A | D | |
| aa56h11.s1 NCI_CGAP_GCB1 Homo sapiens cDNA clone IMAGE:824997 3'. | -1,8 | -0,27 | 215 | P | NC | | -1,3 | -0,07 | -136 | A | D | |
| Human aorta cDNA 5'-end GEN-286G10. | -1,7 | -0,21 | 136 | P | D | | -1,8 | -0,25 | 60 | A | D | |
| yw70f05.s1 Homo sapiens cDNA clone 2576013'. | 1,4 | 0,09 | 729 | P | I | | 2,6 | 1,09 | -27 | A | D | |

Fig. 7.21

EST Bladder candidates of 17742 ESTs
Exclusion of data sets incl. AFFX, all NC, all A, 3xNC + M*
2424 genes with sort score >= +/- 0.5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIIIsolidP(vs)N | Sort Score T2gIIIsolidP(vs)N | Abs Calls | N | A | B | C | D |
|---|---|---|---|---|---|---|---|---|
| zw86a10.s1 Soares total fetus Nb2HF8 9w Homo sapiens cDNA clone 783834 3' similar to TR:G438639 G438639 LAMIN B RECEPTOR. [1].: | -2,7 | -0,86 | PPPPA | 319 | 154 | 185 | 501 | 0 |
| ym39b01.s1 Homo sapiens cDNA clone 50559 3'. | -2,7 | -0,83 | PPPPA | 318 | 207 | 199 | 207 | 0 |
| zx80b07.r1 Soares ovary tumor NbHOT Homo sapiens cDNA clone 810037 5'. | -4,5 | -2,04 | PPPPA | 316 | 264 | 219 | 183 | 0 |
| yy43e04.s1 Homo sapiens cDNA clone 274014 3'. | -5,8 | -2,77 | PPPPA | 315 | 251 | 123 | 623 | 0 |
| Human mRNA for KIAA0323 gene, partial cds. | -26,5 | -10,28 | PPPPA | 314 | 436 | 285 | -391 | 0 |
| H. sapiens partial cDNA sequence; clone c-0qb09. | -5 | -0,73 | PPPPA | 314 | 161 | 48 | 210 | 0 |
| WUGSC:H_GS188P18.1a gene extracted from Human BAC clone GS188P18 | -2,6 | -2,36 | PPPPA | 310 | 145 | 436 | 298 | 0 |
| zr83b02.s1 Soares NhHMPu S1 Homo sapiens cDNA clone 682251 3'. | -11,8 | -6,07 | PPPPA | 308 | 247 | 324 | 313 | 0 |
| zs31g06.s1 NCI_CGAP_GCB1 Homo sapiens cDNA clone IMAGE:586842 3'. | -4,8 | -1,63 | PPPPA | 308 | 105 | 107 | 93 | 0 |
| yr91a03.s1 Homo sapiens cDNA clone 212520 3'. | -7,7 | -4,15 | PPPPA | 305 | 113 | 339 | 130 | 0 |
| EST180743 Jurkat T-cells V Homo sapiens cDNA 5' end. | -2,8 | -0,86 | PPPPA | 301 | 348 | 253 | 353 | 0 |
| yg21a08.s1 Soares ovary tumor NbHOT Homo sapiens cDNA clone 32940 3'. | -1,5 | -0,13 | PPPPA | 297 | 317 | -112 | -71 | 0 |
| zv47a04.s1 Soares ovary tumor NbHOT Homo sapiens cDNA clone 756750 3'. | -2 | -0,41 | PPPPA | 297 | 291 | 599 | 447 | 0 |
| yz39f01.s1 Homo sapiens cDNA clone 285433 3'. | -3 | -0,95 | PPPPA | 295 | 161 | 205 | 227 | 0 |
| zs85d09.s1 NCI_CGAP_GCB1 Homo sapiens cDNA clone IMAGE:704273 3' similar to TR:G974805 G974805 T08A11.2.: | -3,3 | -1,06 | PPPPA | 295 | 430 | 206 | 328 | 0 |
| zl05c10.s1 Soares fetal liver spleen 1NFLS S1 Homo sapiens cDNA clone 429906 3'. | -3,1 | -1,11 | PPPPA | 291 | 241 | 216 | 208 | 0 |
| Homo sapiens sodium bicarbonate cotransporter (HNBC1) mRNA, complete cds. | -6,2 | -2,59 | PPPPA | 289 | 49 | 77 | 20 | 0 |
| aa56h11.s1 NCI_CGAP_GCB1 Homo sapiens cDNA clone IMAGE:824997 3'. | -11,4 | -5,67 | PPPPA | 289 | 165 | 160 | 215 | 0 |
| Human aorta cDNA 5'-end GEN-286G10. | -4,7 | -2,09 | PPPPA | 285 | 217 | 166 | 136 | 0 |
| yw70f05.s1 Homo sapiens cDNA clone 257601 3'. | -5,0 | -2,02 | PPPPA | 285 | 132 | 385 | 729 | 0 |

Fig. 7.22

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIIP | Abs Call TagIIIP | Diff Call TagIIIP(vs)N | B=A |
|---|---|---|---|---|---|---|---|---|---|---|---|---|---|
| Homo sapiens clk2 mRNA, complete cds | L29218_s_at | 282 | P | 164 | P | NC | | -1,7 | -0,22 | 152 | P | NC | |
| zo67g05.s1 Stratagene pancreas (#937208) Homo sapiens cDNA clone 591994 3' similar to TR:G530823 G530823 EPIDERMAL GROWTH FACTOR RECEPTOR KINASE SUBSTRATE. | RC_AA143726_at | 282 | P | 420 | P | NC | | 1,5 | 0,15 | 296 | P | NC | |
| zl17g05.r1 Soares pregnant uterus NbHPU Homo sapiens cDNA clone 502232 5' | AA126592_at | 280 | P | 226 | P | NC | | -1,2 | -0,04 | 191 | P | NC | |
| H. sapiens partial cDNA sequence; clone c-0xh11. | RC_F02397_s_at | 278 | P | 204 | P | D | | -1,8 | -0,26 | 313 | P | NC | |
| zs27d03.s1 NCI_CGAP_GCB1 Homo sapiens cDNA clone IMAGE:686405 3' | RC_AA252765_at | 273 | P | 165 | P | NC | | -2 | -0,35 | 254 | P | NC | |
| zc36a04.s1 Soares senescent fibroblasts NbHSF Homo sapiens cDNA clone 324366 3' | RC_W46846_at | 271 | P | 309 | P | NC | | 1,3 | 0,06 | 635 | P | NC | |
| zo27a05.s1 Stratagene colon (#937204) Homo sapiens cDNA clone 588080 3'. | RC_AA135185_at | 270 | P | 395 | P | NC | | 1,6 | 0,19 | 201 | P | NC | |
| yf73f10.s1 Homo sapiens cDNA clone 27959 3'. | RC_R40702_at | 260 | P | 455 | P | NC | | 1,7 | 0,29 | 612 | P | NC | |
| yv36d12.s1 Homo sapiens cDNA clone 244823 3'. | RC_N52565_at | 257 | P | 519 | P | I | | 1,7 | 0,29 | 326 | P | I | |
| zc06a02.s1 Soares parathyroid tumor NbHPA Homo sapiens cDNA clone 321482 3'. | RC_W32506_s_at | 253 | P | 341 | P | NC | | 1,1 | 0 | 827 | P | D | |
| zr85c04.s1 Soares NhHMPu S1 Homo sapiens cDNA clone 682470 3'. | RC_AA255539_at | 248 | P | 276 | P | NC | | 1,1 | 0,01 | 144 | P | NC | |
| zx38a10.s1 Soares total fetus Nb2HF8 9w Homo sapiens cDNA clone 788730 3'. | RC_AA449951_at | 246 | P | 233 | P | NC | | -1,1 | 0 | 323 | P | NC | |
| cdhn2404.seq.F Fetal heart, Lambda ZAP Express Homo sapiens cDNA 5'. | AA091278_at | 244 | P | 292 | P | NC | | 1,2 | 0,03 | 206 | P | NC | |
| zs05g08.s1 NCI_CGAP_GCB1 Homo sapiens cDNA clone IMAGE:684350 3'. | RC_AA236037_at | 241 | P | 164 | P | NC | | -1,1 | -0,01 | 402 | P | NC | |
| ll2053.seq.F Fetal heart, Lambda ZAP Express Homo sapiens cDNA 5'. | AA091412_s_at | 239 | P | 413 | P | NC | | 1,4 | 0,11 | 204 | P | NC | |
| zf12b09.s1 Soares fetal heart NbHH19W Homo sapiens cDNA clone 376697 5'. | AA046865_at | 236 | P | 147 | P | D | | -1,6 | -0,15 | 119 | P | D | |
| EST27743 Cerebellum II Homo sapiens cDNA 5' end. | AA324825_at | 234 | P | 383 | P | I | | 1,6 | 0,21 | 423 | P | I | |
| zx79d09.s1 Soares ovary tumor NbHOT Homo sapiens cDNA clone 809969 3'. | RC_AA454840_s_at | 233 | P | 121 | P | NC | | -1,5 | -0,09 | 58 | P | MD | |
| zh49e02.s1 Soares fetal liver spleen 1NFLS S1 Homo sapiens cDNA clone 415370 3'. | RC_W80354_at | 223 | P | 140 | P | NC | | -1,6 | -0,15 | 308 | P | NC | |
| zt65c03.s1 Soares testis NHT Homo sapiens cDNA clone 727204 3'. | RC_AA402484_at | 221 | P | 68 | P | MD | | -3,3 | -1 | 94 | P | D | |
| 15h10 Human retina cDNA randomly primed sublibrary Homo sapiens cDNA. | W26883_at | 220 | P | 210 | P | NC | | -1,2 | -0,03 | 162 | P | NC | |

Fig. 7.23

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N B=A | Fold Change T2gIIImixP(vs)N | Sort Score T2gIIImixP(vs)N | Avg Diff T2gIIsolidP | Abs Call T2gIIsolidP | Diff Call T2gIIsolidP(vs)N B=A |
|---|---|---|---|---|---|---|---|---|---|---|
| Homo sapiens clk2 mRNA, complete cds | -1,9 | -0,28 | 236 | P | NC | -1,2 | -0,03 | 181 | A | D |
| zo67g06.s1 Stratagene pancreas (#937208) Homo sapiens cDNA clone 591994 3' similar to TR:G530823 G530823 EPIDERMAL GROWTH FACTOR RECEPTOR KINASE SUBSTRATE, .. | 1,7 | 0,23 | 210 | P | NC | 1,2 | 0,03 | -143 | A | D |
| zl17g05.r1 Soares pregnant uterus NbHPU Homo sapiens cDNA clone 502232 5' | -1,5 | -0,11 | 171 | P | NC | -1,6 | -0,18 | 94 | A | D |
| H. sapiens partial cDNA sequence; clone c-0xh11. | -1,1 | -0,02 | 231 | P | NC | -1,2 | -0,03 | 99 | A | D |
| zs27d03.s1 NCI_CGAP_GCB1 Homo sapiens cDNA clone IMAGE:686405 3' | -1,3 | -0,05 | 198 | P | NC | -1,4 | -0,08 | 50 | A | D |
| zc36a04.s1 Soares senescent fibroblasts NbHSF Homo sapiens cDNA clone 324366 3' | 2,7 | 1,23 | 505 | P | NC | 2,1 | 0,6 | 169 | A | D |
| zo27a05.s1 Stratagene colon (#937204) Homo sapiens cDNA clone 588080 3' | -1,3 | -0,07 | 156 | P | NC | -1,7 | -0,22 | -7 | A | D |
| yf73l10.s1 Homo sapiens cDNA clone 27969 3' | 1,5 | 0,17 | 331 | P | NC | 1,3 | 0,05 | -6 | A | D |
| yv36d12.s1 Homo sapiens cDNA clone 244823 3'. | 1,3 | 0,05 | 288 | P | NC | 1,1 | 0,01 | 104 | A | D |
| zc06a02.s1 Soares parathyroid tumor NbHPA Homo sapiens cDNA clone 321482 3'. | 3,3 | 1,94 | 438 | P | NC | 1,7 | 0,28 | 134 | A | D |
| zr85c04.s1 Soares NhHMPu S1 Homo sapiens cDNA clone 682470 3' | -1,7 | -0,21 | 302 | P | NC | 1,2 | 0,04 | 93 | A | D |
| zx38a10.s1 Soares total fetus Nb2HF8 9w Homo sapiens cDNA clone 788730 3' | 1,3 | 0,07 | 278 | P | NC | 1,1 | 0,02 | 62 | A | D |
| cchn2404.seq.F Fetal heart, Lambda ZAP Express Homo sapiens cDNA 5' | -1,2 | -0,02 | 232 | P | NC | -1,1 | 0 | 96 | A | D |
| 2s05g08.s1 NCI_CGAP_GCB1 Homo sapiens cDNA clone IMAGE:684350 3' | 1,7 | 0,23 | 203 | P | NC | -1,2 | -0,03 | 20 | A | D |
| ll2053.seq.F Fetal heart, Lambda ZAP Express Homo sapiens cDNA 5'. | -1,2 | -0,02 | 280 | P | NC | -1,1 | -0,01 | 24 | A | D |
| zf12b09.r1 Soares fetal heart NbHH19W Homo sapiens cDNA clone 376697 5'. | -1,9 | -0,28 | 136 | P | NC | -1,7 | -0,2 | 26 | A | D |
| EST27743 Cerebellum II Homo sapiens cDNA 5' end. | 1,8 | 0,32 | 232 | P | NC | 1,3 | 0,05 | 50 | A | D |
| zx79d09.s1 Soares ovary tumor NbHOT Homo sapiens cDNA clone 809969 3'. | -3,1 | -0,8 | 75 | P | NC | -2,4 | -0,45 | 19 | A | D |
| zh49a02.s1 Soares fetal liver spleen 1NFLS S1 Homo sapiens cDNA clone 415370 3' | 1,4 | 0,09 | 214 | P | NC | -1 | 0 | 75 | A | D |
| zl65c03.s1 Soares testis NHT Homo sapiens cDNA clone 727204 3'. | -2,4 | -0,5 | 201 | P | D | -4,2 | -1,54 | 50 | A | D |
| l5h10 Human retina cDNA randomly primed sublibrary Homo sapiens cDNA. | -1,5 | -0,13 | 110 | P | D | -2,3 | -0,47 | 40 | A | D |

Fig. 7.24

EST Bladder candidates of 17742 ESTs
Exclusion of data sets incl. AFFX, all NC, all A, 3xNC + M*
2424 genes with sort score >= +/- 0.5 changing from N to tumor
235 genes LOST Abs calls PPPPA and DECREASED
8 genes LOST Abs calls PPPPA and DECREASED in all 4 comp.
data sorted acc. To Avg Diff N

| gene name | Fold Change T2gII/solidP(vs)N | Sort Score T2gII/solidP(vs)N | Abs Calls | N | A | B | C | D |
|---|---|---|---|---|---|---|---|---|
| Homo sapiens clk2 mRNA, complete cds | -2.3 | -0.58 | PPPPA | 282 | 164 | 152 | 236 | 0 |
| zc67g06.s1 Stratagene pancreas (#937208) Homo sapiens cDNA clone 591994 3' similar to | -5.5 | -1.6 | PPPPA | 282 | 420 | 296 | 210 | 0 |
| TR:G530823 G530823 EPIDERMAL GROWTH FACTOR RECEPTOR KINASE SUBSTRATE.; | | | | | | | | |
| zi17g05.r1 Soares pregnant uterus NbHPU Homo sapiens cDNA clone 502232 5' | -3 | -0.95 | PPPPA | 280 | 226 | 191 | 171 | 0 |
| H. sapiens partial cDNA sequence; clone c-0xh11. | -4.1 | -1.65 | PPPPA | 278 | 204 | 313 | 231 | 0 |
| zs27d03.s1 NCI_CGAP_GCB1 Homo sapiens cDNA clone IMAGE:686405 3' | -5.8 | -2.44 | PPPPA | 273 | 165 | 254 | 198 | 0 |
| zc36a04.s1 Soares senescent fibroblasts NbHSF Homo sapiens cDNA clone 324366 3'. | -1.6 | -0.17 | PPPPA | 271 | 309 | 635 | 505 | 0 |
| zo27a05.s1 Stratagene colon (#937204) Homo sapiens cDNA clone 588080 3'. | -8.5 | -4.09 | PPPPA | 270 | 395 | 201 | 156 | 0 |
| yf73h10.s1 Homo sapiens cDNA clone 27969 3'. | -6.4 | -3.45 | PPPPA | 260 | 455 | 612 | 331 | 0 |
| yv36d12.s1 Homo sapiens cDNA clone 244823 3'. | -2.5 | -0.59 | PPPPA | 257 | 519 | 326 | 288 | 0 |
| zc06a02.s1 Soares parathyroid tumor NbHPA Homo sapiens cDNA clone 321482 3'. | -1.9 | -0.28 | PPPPA | 253 | 341 | 827 | 438 | 0 |
| zr85c04.s1 Soares NhHMPu S1 Homo sapiens cDNA clone 682470 3'. | -2.7 | -0.89 | PPPPA | 248 | 276 | 144 | 302 | 0 |
| zx38a10.s1 Soares total fetus Nb2HF8 9w Homo sapiens cDNA clone 788730 3'. | -4 | -1.48 | PPPPA | 246 | 233 | 323 | 278 | 0 |
| cchn2404.seq.F Fetal heart, Lambda ZAP Express Homo sapiens cDNA 5'. | -2.5 | -0.62 | PPPPA | 244 | 292 | 206 | 232 | 0 |
| zs05g06.s1 NCI_CGAP_GCB1 Homo sapiens cDNA clone IMAGE:684350 3'. | -3 | -0.86 | PPPPA | 241 | 164 | 402 | 203 | 0 |
| jj2053.seq.F Fetal heart, Lambda ZAP Express Homo sapiens cDNA 5'. | -7.7 | -3.45 | PPPPA | 239 | 413 | 204 | 280 | 0 |
| zf12b09.r1 Soares fetal heart NbHH19W Homo sapiens cDNA clone 376697 5'. | -5.8 | -2.52 | PPPPA | 236 | 147 | 119 | 135 | 0 |
| EST27743 Cerebellum II Homo sapiens cDNA 5' end. | -3.5 | -1.04 | PPPPA | 234 | 383 | 423 | 232 | 0 |
| zx79d09.s1 Soares ovary tumor NbHOT Homo sapiens cDNA clone 809909 3'. | -4.9 | -1.69 | PPPPA | 233 | 121 | 58 | 75 | 0 |
| zh49a02.s1 Soares fetal liver spleen 1NFLS S1 Homo sapiens cDNA clone 415370 3'. | -3 | -0.84 | PPPPA | 223 | 140 | 308 | 214 | 0 |
| zi65c03.s1 Soares testis NHT Homo sapiens cDNA clone 727204 3'. | -4.5 | -1.7 | PPPPA | 221 | 68 | 94 | 201 | 0 |
| 15h10 Human retina cDNA randomly primed sublibrary Homo sapiens cDNA. | -5.4 | -2.2 | PPPPA | 220 | 210 | 162 | 110 | 0 |

Fig. 7.25

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIP | Abs Call T1gIIP | Diff Call T1gIIP(vs)N | B=A |
|---|---|---|---|---|---|---|---|---|---|---|---|---|---|
| zs17h07.s1 NCI_CGAP_GCB1 Homo sapiens cDNA clone IMAGE:685501 3'. | RC_AA262485_at | 219 | P | 178 | P | NC | | -1,2 | -0,03 | 115 | P | NC | |
| zw39c01.s1 Soares total fetus Nb2HF8 9w Homo sapiens cDNA clone 772416 3'. | RC_AA405543_at | 219 | P | 244 | P | NC | | 1,1 | 0,01 | 240 | P | NC | |
| yx54c04.s1 Homo sapiens cDNA clone 265542 3'. | RC_N21380_at | 218 | P | 378 | P | NC | | 1,7 | 0,26 | 6 | P | NC | |
| zn77a05.s1 Stratagene NT2 neuronal precursor 937230 Homo sapiens cDNA clone 554176 3'. | RC_AA121360_s_at | 217 | P | 181 | P | NC | | -1,2 | -0,03 | 171 | P | NC | |
| Homo sapiens zinc finger homeodomain protein (ATBF1-A) mRNA, complete cds. | L32832_s_at | 210 | P | 322 | P | NC | | 1,5 | 0,15 | 268 | P | NC | |
| Human fetal-lung cDNA 5'-end sequence. | D31313_s_at | 209 | P | 396 | P | NC | | 1,3 | 0,06 | 163 | P | NC | |
| ym45b05.r1 Homo sapiens cDNA clone 51043 5' similar to contains Alu repetitive element.: | H18718_at | 209 | P | 174 | P | NC | | -1,2 | -0,03 | 203 | P | NC | |
| zf03g09.s1 Soares fetal heart NbHH19W Homo sapiens cDNA clone 375904 3'. | RC_AA037828_at | 207 | P | 103 | P | NC | | -1,6 | -0,15 | 97 | P | NC | |
| yi04c10.s1 Homo sapiens cDNA clone 138258 3'. | RC_R67995_at | 203 | P | 113 | P | NC | | -2,1 | -0,36 | 788 | P | MI | |
| ze92g08.s1 Soares fetal heart NbHH19W Homo sapiens cDNA clone 366494 3'. | RC_AA026417_at | 202 | P | 236 | P | NC | | -1,1 | -0,01 | 167 | P | NC | |
| H. sapiens partial cDNA sequence; clone c-33a10. | RC_F11115_at | 199 | P | 216 | P | NC | | 1,1 | 0,07 | 89 | P | D | |
| yfz1e07.s1 Homo sapiens cDNA clone 127524 3'. | RC_R06871_at | 192 | P | 89 | P | D | | -2,2 | -0,37 | 123 | P | NC | |
| zr12e05.s1 Stratagene hNT neuron (#937233) Homo sapiens cDNA clone 648608 3'. | RC_AA224324_at | 188 | P | 115 | P | NC | | -1,6 | -0,15 | 107 | P | D | |
| zt50c01.s1 Soares ovary tumor NbHOT Homo sapiens cDNA clone 725760 3'. | RC_AA399226_at | 187 | P | 100 | P | MD | | -1,9 | -0,24 | 94 | P | D | |
| yi25l09.r1 Homo sapiens cDNA clone 140297 5' similar to contains Alu repetitive element.: | R66920_at | 184 | P | 208 | P | NC | | 1,1 | 0,01 | 284 | P | NC | |
| zx81a05.s1 Soares ovary tumor NbHOT Homo sapiens cDNA clone 810128 3'. | RC_AA464240_s_at | 182 | P | 70 | P | NC | | -2,6 | -0,56 | 18 | P | NC | |
| zv08g07.r1 Soares NhHMPu S1 Homo sapiens cDNA clone 753084 5'. | AA436536_at | 178 | P | 225 | P | NC | | 1,3 | 0,04 | 267 | P | NC | |
| yz34f07.s1 Homo sapiens cDNA clone 284965 3'. | RC_N71875_at | 176 | P | 147 | P | NC | | -1,2 | -0,03 | 99 | P | NC | |
| zk10b03.s1 Soares pregnant uterus NbHPU Homo sapiens cDNA clone 470093 3' similar to PIR:H45193 H45193 zinc finger protein ZNF65.: | RC_AA029288_at | 176 | P | 76 | P | D | | -2,3 | -0,41 | 142 | P | NC | |
| yl63h11.r1 Homo sapiens cDNA clone 162981 5' similar to SP:GCN5_YEAST Q03330 TRANSCRIPTIONAL ACTIVATOR.: | H27242_at | 175 | P | 223 | P | NC | | 1,3 | 0,04 | 140 | P | NC | |

Fig. 7.26

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| zs17h07.s1 NCI_CGAP_GCB1 Homo sapiens cDNA clone IMAGE:685501 3'. | -1,1 | -0,01 | 207 | P | NC | | -1,1 | 0 | -20 | A | D | |
| zw39c01.s1 Soares total fetus Nb2HF8 9w Homo sapiens cDNA clone 772416 3'. | -1,3 | -0,05 | 233 | P | NC | | 1,1 | 0 | 71 | A | D | |
| yx54c04.s1 Homo sapiens cDNA clone 265542 3'. | -5,4 | -2,16 | 54 | P | NC | | -3,7 | -1,23 | 37 | A | D | |
| zn77a05.s1 Stratagene NT2 neuronal precursor 937230 Homo sapiens cDNA clone 564176 3'. | -1,3 | -0,04 | 184 | P | NC | | -1,2 | -0,02 | 67 | A | D | |
| Homo sapiens zinc finger homeodomain protein (ATBF1-A) mRNA, complete cds. | 1,3 | 0,05 | 200 | P | NC | | -1,4 | -0,1 | -254 | A | D | |
| Human fetal-lung cDNA 5'-end sequence. | -1,3 | -0,04 | 487 | P | NC | | 1,4 | 0,1 | -11 | A | D | |
| ym45b05.r1 Homo sapiens cDNA clone 510043 5' similar to contains Alu repetitive element;. | -1 | 0 | 236 | P | NC | | 1,1 | 0,02 | 75 | A | D | |
| zt03g09.s1 Soares fetal heart NbHH19W Homo sapiens cDNA clone 375904 3'. | -1,8 | -0,18 | 88 | P | NC | | -1,9 | -0,25 | 21 | A | D | |
| yl04c10.s1 Homo sapiens cDNA clone 138258 3'. | 3,9 | 2,56 | 297 | P | NC | | 2 | 0,34 | 132 | A | D | |
| ze92g08.s1 Soares fetal heart NbHH19W Homo sapiens cDNA clone 366494 3'. | -1,2 | -0,03 | 166 | P | NC | | 1 | 0 | 70 | A | D | |
| H. sapiens partial cDNA sequence; clone c-33a10. | -2,2 | -0,41 | 105 | P | NC | | -1,9 | -0,26 | 49 | A | D | |
| yf21e07.s1 Homo sapiens cDNA clone 127524 3'. | -1,6 | -0,12 | 138 | P | D | | -1,7 | -0,19 | 17 | A | D | |
| zr12e05.s1 Stratagene hNT neuron (#937233) Homo sapiens cDNA clone 648608 3'. | -1,8 | -0,2 | 133 | P | NC | | -1,4 | -0,08 | 74 | A | D | |
| zt50c01.s1 Soares ovary tumor NbHOT Homo sapiens cDNA clone 725760 3'. | -2 | -0,29 | 124 | P | NC | | -1,5 | -0,1 | 29 | A | D | |
| yi25f09.r1 Homo sapiens cDNA clone 140297 5' similar to contains Alu repetitive element;. | 1,5 | 0,14 | 159 | P | NC | | 1,2 | 0,03 | -110 | A | D | |
| zx81e05.s1 Soares ovary tumor NbHOT Homo sapiens cDNA clone 810128 3'. | ~9,1 | -3,57 | 39 | P | D | | -4,7 | -1,63 | -156 | A | D | |
| zv06g07.r1 Soares NhHMPu S1 Homo sapiens cDNA clone 753084 5'. | 1,2 | 0,02 | 285 | P | NC | | 1,6 | 0,17 | 15 | A | D | |
| yx34f07.s1 Homo sapiens cDNA clone 284965 3'. | -1,8 | -0,19 | 143 | P | NC | | -1,2 | -0,03 | 17 | A | D | |
| zk10b03.s1 Soares pregnant uterus NbHPU Homo sapiens cDNA clone 470093 3' similar to PIR:H45193 H45193 zinc finger protein ZNF65 ;. | | | 92 | P | NC | | -1,8 | -0,19 | 22 | A | D | |
| yi63h11.r1 Homo sapiens cDNA clone 162981 5' similar to SP:GCN5_YEAST Q03330 TRANSCRIPTIONAL ACTIVATOR ;. | -1,2 | -0,03 | 160 | P | NC | | -1,1 | -0,01 | -32 | A | D | |

Fig. 7.27

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIIIsolidP(vs)N | Sort Score T2gIIIsolidP(vs)N | Abs Calls | N | A | B | C | D |
|---|---|---|---|---|---|---|---|---|
| zs17h07.s1 NCI_CGAP_GCB1 Homo sapiens cDNA clone IMAGE:685501 3' | -4,6 | -1,24 | PPPPA | 219 | 178 | 115 | 207 | 0 |
| zw39c01.s1 Soares total fetus Nb2HF8 9w Homo sapiens cDNA clone 772416 3' | -6,5 | -2,72 | PPPPA | 219 | 244 | 240 | 233 | 0 |
| yx54c04.s1 Homo sapiens cDNA clone 265542 3' | -5,2 | -2,52 | PPPPA | 218 | 378 | 6 | 54 | 0 |
| zn77a05.r1 Stratagene NT2 neuronal precursor 937230 Homo sapiens cDNA clone 564176 3' | -2,7 | -0,62 | PPPPA | 217 | 181 | 171 | 184 | 0 |
| Homo sapiens zinc finger homeodomain protein (ATBF1-A) mRNA, complete cds. | -13,5 | -6,28 | PPPPA | 210 | 322 | 268 | 200 | 0 |
| Human fetal-lung cDNA 5'-end sequence. | -6,4 | -2,58 | PPPPA | 209 | 396 | 163 | 487 | 0 |
| ym45b05.r1 Homo sapiens cDNA clone 51043 5' similar to contains Alu repetitive element:. | -2,8 | -0,7 | PPPPA | 209 | 174 | 203 | 236 | 0 |
| zf03g09.s1 Soares fetal heart NbHH19W Homo sapiens cDNA clone 375904 3'. | -4,7 | -1,59 | PPPPA | 207 | 103 | 97 | 88 | 0 |
| yl04c10.s1 Homo sapiens cDNA clone 138258 3'. | -1,5 | -0,12 | PPPPA | 203 | 113 | 788 | 297 | 0 |
| ze92g08.s1 Soares fetal heart NbHH19W Homo sapiens cDNA clone 366494 3'. | -3,7 | -1,32 | PPPPA | 202 | 236 | 167 | 166 | 0 |
| H. sapiens partial cDNA sequence; clone c-33a10. | -3,2 | -0,86 | PPPPA | 199 | 216 | 89 | 105 | 0 |
| yl21e07.s1 Homo sapiens cDNA clone 127524 3'. | -3,5 | -0,97 | PPPPA | 192 | 89 | 123 | 138 | 0 |
| zr12e05.s1 Stratagene hNT neuron (#937233) Homo sapiens cDNA clone 648608 3' | -2,5 | -0,55 | PPPPA | 188 | 115 | 107 | 133 | 0 |
| zl50c01.s1 Soares ovary tumor NbHOT Homo sapiens cDNA clone 725760 3'. | -4,8 | -1,73 | PPPPA | 187 | 100 | 94 | 124 | 0 |
| yi25f09.r1 Soares ovary tumor NbHOT Homo sapiens cDNA clone 140297 5' similar to contains Alu repetitive element:. | -7,0 | -2,63 | PPPPA | 184 | 208 | 284 | 159 | 0 |
| zx81a05.s1 Soares ovary tumor NbHOT Homo sapiens cDNA clone 810128 3'. | -9,3 | -3,52 | PPPPA | 182 | 70 | 18 | 39 | 0 |
| zv08g07.r1 Soares NhHMPu S1 Homo sapiens cDNA clone 753084 5'. | -4,7 | -1,3 | PPPPA | 178 | 225 | 267 | 285 | 0 |
| yz34f07.s1 Homo sapiens cDNA clone 284965 3'. | -3,4 | -0,88 | PPPPA | 176 | 147 | 99 | 143 | 0 |
| zk10b03.s1 Soares pregnant uterus NbHPU Homo sapiens cDNA clone 470093 3' similar to PIR:H45193 H45193 zinc finger protein ZNF65 :. | -4,6 | -1,52 | PPPPA | 175 | 76 | 142 | 92 | 0 |
| yl63h11.r1 Homo sapiens cDNA clone 162981 5' similar to SP:GCN5_YEAST Q03330 TRANSCRIPTIONAL ACTIVATOR :. | -6,0 | -2,17 | PPPPA | 175 | 223 | 140 | 160 | 0 |

Fig. 7.28

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIIP | Abs Call TagIIIP | Diff Call TagIIIP(vs)N | B=A |
|---|---|---|---|---|---|---|---|---|---|---|---|---|---|
| Human cytochrome P450 PCN3 gene, complete cds | J04813_s_at | 174 P | P | 81 P | P | D | | -2,4 | -0,38 | 108 P | P | D | |
| aa32h08.s1 NCI_CGAP_GCB1-Homo sapiens cDNA clone IMAGE:815007 3'. | RC_AA465093_at | 174 P | P | 136 P | P | NC | | -1,1 | -0,08 | 135 P | P | NC | |
| zs91c05.s1 NCI_CGAP_GCB1 Homo sapiens cDNA clone IMAGE:704840 3'. | RC_AA282791_at | 173 P | P | 250 P | P | NC | | 1,4 | 0,1 | 240 P | P | NC | |
| zx83f04.s1 Soares ovary tumor NbHOT Homo sapiens cDNA clone 810367 3' similar to gb:M38188 OVARIAN GRANULOSA CELL 13.0 KD PROTEIN HGR74 (HUMAN);. | RC_AA464180_at | 172 P | P | 210 P | P | NC | | 1,5 | 0,13 | 159 P | P | NC | |
| zo03d03.s1 Stratagene colon (#937204) Homo sapiens cDNA clone 566597 3'. | RC_AA149987_at | 169 P | P | 219 P | P | NC | | 1,3 | 0,05 | 357 P | P | NC | |
| zr82h09.s1 Soares NhHMPu S1 Homo sapiens cDNA clone 682241 3'. | RC_AA256680_at | 168 P | P | 30 P | P | D | | -6,7 | -2,77 | 97 P | P | D | |
| zl50c12.r1 Soares pregnant uterus NbHPU Homo sapiens cDNA clone 505366 5'. | AA147510_s_at | 166 P | P | 195 P | P | NC | | 1,2 | 0,02 | 229 P | P | NC | |
| yl80c10.r1 Homo sapiens cDNA clone 145554 5'. | R78119_at | 165 P | P | 93 P | P | NC | | -1,8 | -0,19 | 98 P | P | NC | |
| H. sapiens partial cDNA sequence; clone c-0ac03. | RC_Z38407_s_at | 160 P | P | 81 P | P | NC | | -2 | -0,27 | 168 P | P | NC | |
| zs58f12.s1 NCI_CGAP_GCB1 Homo sapiens cDNA clone IMAGE:701711 3'. | RC_AA287107_s_at | 159 P | P | 133 P | P | NC | | -1,2 | -0,02 | 73 P | P | D | |
| zs57e07.s1 NCI_CGAP_GCB1 Homo sapiens cDNA clone IMAGE:701604 3'. | RC_AA287042_at | 157 P | P | 63 P | P | D | | -1,4 | -0,06 | 73 P | P | NC | |
| ab35g04.r1 Stratagene HeLa cell s3 937216 Homo sapiens cDNA clone 842838 5'. | AA489299_at | 157 P | P | 307 P | P | NC | | 1,4 | 0,08 | 156 P | P | NC | |
| aa63f03.r1 NCI_CGAP_GCB1 Homo sapiens cDNA clone IMAGE:825629 5'. | AA504744_at | 157 P | P | 113 P | P | NC | | -1,7 | -0,16 | 176 P | P | NC | |
| zu47g07.s1 Soares ovary tumor NbHOT Homo sapiens cDNA clone 741180 3'. | RC_AA402622_at | 155 P | P | 180 P | P | NC | | 1,2 | 0,02 | 325 P | P | NC | |
| zw55e10.s1 Soares total fetus Nb2HF8 9w Homo sapiens cDNA clone 773994 3'. | RC_AA436628_at | 146 P | P | 66 P | P | D | | -1,9 | -0,19 | 162 P | P | NC | |
| zt02a10.s1 NCI_CGAP_GCB1 Homo sapiens cDNA clone IMAGE:711930 3'. | RC_AA282138_at | 142 P | P | 119 P | P | NC | | -1,2 | -0,02 | 41 P | P | D | |
| zk75a04.r1 Soares pregnant uterus NbHPU Homo sapiens cDNA clone 488622 5'. | AA045870_at | 142 P | P | 124 P | P | NC | | -1,1 | -0,01 | 64 P | P | NC | |
| zv94b04.r1 Soares NhHMPu S1 Homo sapiens cDNA clone 767407 5'. | AA418098_at | 141 P | P | 301 P | P | NC | | 1,1 | 0,01 | 109 P | P | NC | |
| zr65f05.s1 Soares NhHMPu S1 Homo sapiens cDNA clone 668291 3' similar to SW:SPO8_YEAST P41833 TRANSCRIPTIONAL REGULATOR SPO8. [1];. | RC_AA242799_at | 139 P | P | 54 P | P | NC | | -1,5 | -0,11 | 121 P | P | NC | |
| af12f04.s1 Soares testis NHT Homo sapiens cDNA clone 1031455 3'. | RC_AA609210_at | | | | | | | | -0,48 | 145 P | P | NC | |

Fig. 7.29

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| Human cytochrome P450 PCN3 gene, complete cds | -1,8 | -0,17 | 67 | P | D | | -3,6 | -1,09 | -10 | A | D | |
| aa32h08.s1 NCI_CGAP_GCB1 Homo sapiens cDNA clone IMAGE:815007 3' | -1,3 | -0,04 | 134 | P | NC | | -1,4 | -0,06 | 85 | A | D | |
| zs91c05.s1 NCI_CGAP_GCB1 Homo sapiens cDNA clone IMAGE:704840 3' | 1,4 | 0,08 | 210 | P | NC | | 1,2 | 0,03 | 36 | A | D | |
| zx83f04.s1 Soares ovary tumor NbHOT Homo sapiens cDNA clone 810367 3' similar to gb:M38188 OVARIAN GRANULOSA CELL 13.0 KD PROTEIN HGR74 (HUMAN);. | 1,1 | 0,01 | 130 | P | D | | 1 | 0 | -9 | A | D | |
| zo03d03.s1 Stratagene colon (#937204) Homo sapiens cDNA clone 566597 3' | 1,9 | 0,3 | 261 | P | D | | 1,5 | 0,14 | 23 | A | D | |
| zr82h09.s1 Soares NhHMPu S1 Homo sapiens cDNA clone 662241 3' | -1,6 | -0,13 | 76 | P | D | | -2,7 | -0,64 | 33 | A | D | |
| zl50c12.r1 Soares pregnant uterus NbHPU Homo sapiens cDNA clone 505366 5' | 1,4 | 0,08 | 143 | P | NC | | -2 | -0,28 | -138 | A | D | |
| yi80c10.r1 Homo sapiens cDNA clone 145554 5' | -1,4 | -0,06 | 72 | P | D | | -2,7 | -0,65 | -35 | A | D | |
| H. sapiens partial cDNA sequence; clone c-0ac03. | 1,1 | 0 | 83 | P | NC | | -1,9 | -0,24 | 45 | A | D | |
| zs58f12.s1 NCI_CGAP_GCB1 Homo sapiens cDNA clone IMAGE:701711 3' | -2,2 | -0,33 | 81 | P | D | | -2 | -0,25 | 36 | A | D | |
| zs57e07.s1 NCI_CGAP_GCB1 Homo sapiens cDNA clone IMAGE:701604 3' | -1,1 | -0,01 | 123 | P | NC | | -1,2 | -0,02 | 47 | A | D | |
| ab35g04.r1 Stratagene HeLa cell s3 937216 Homo sapiens cDNA clone 842838 5' | -1,4 | -0,09 | 144 | P | D | | -1,1 | -0,01 | -103 | A | D | |
| aa63f03.r1 NCI_CGAP_GCB1 Homo sapiens cDNA clone IMAGE:825629 5' | -1,1 | -0,01 | 187 | P | NC | | 1 | 0 | 20 | A | D | |
| zu47g07.s1 Soares ovary tumor NbHOT Homo sapiens cDNA clone 741180 3' | 2,1 | 0,44 | 120 | P | D | | -5,4 | -1,84 | 91 | A | D | |
| zw55e10.s1 Soares total fetus Nb2HF8 9w Homo sapiens cDNA clone 773994 3' | 1,1 | 0,01 | 169 | P | NC | | 1,2 | 0,02 | 16 | A | D | |
| zt02e10.s1 NCI_CGAP_GCB1 Homo sapiens cDNA clone IMAGE:711930 3' | -3,5 | -0,89 | 46 | P | D | | -2,6 | -0,45 | 30 | A | D | |
| zk75a04.r1 Soares pregnant uterus NbHPU Homo sapiens cDNA clone 488622 5' | -2,1 | -0,29 | 69 | P | D | | -2,3 | -0,39 | 48 | A | D | |
| zv94b04.r1 Soares NhHMPu S1 Homo sapiens cDNA clone 767407 5' | -1,3 | -0,04 | 161 | P | NC | | 1,1 | 0,01 | 16 | A | D | |
| zr65f06.s1 Soares NhHMPu S1 Homo sapiens cDNA clone 668291 3' similar to SW:SPO8_YEAST P41833 TRANSCRIPTIONAL REGULATOR SPO8. [1];. | -3,7 | -0,93 | 50 | P | D | | -2,8 | -0,59 | -129 | A | D | |
| af12f04.s1 Soares testis NHT Homo sapiens cDNA clone 1031455 3' | 1 | 0 | 68 | P | D | | -2,1 | -0,27 | 50 | A | D | |

Fig. 7.30

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2g/IIsolidP(vs)N | Sort Score T2g/IIsolidP(vs)N | Abs Calls | N | A | B | C | D |
|---|---|---|---|---|---|---|---|---|
| Human cytochrome P450 PCN3 gene, complete cds | -4,5 | -1,25 | PPPPA | 174 | 81 | 108 | 67 | 0 |
| aa32h08.s1 NCI_CGAP_GCB1 Homo sapiens cDNA clone IMAGE:815007 3' | -2,6 | -0,55 | PPPPA | 174 | 138 | 135 | 134 | 0 |
| zs91c05.s1 NCI_CGAP_GCB1 Homo sapiens cDNA clone IMAGE:704840 3' | -4,4 | -1,43 | PPPPA | 173 | 250 | 240 | 210 | 0 |
| zx83f04.s1 Soares ovary tumor NbHOT Homo sapiens cDNA clone 810367 3' similar to gb:M38188 OVARIAN GRANULOSA CELL 13.0 KD PROTEIN HGR74 (HUMAN); | -5,4 | -1,87 | PPPPA | 172 | 210 | 159 | 130 | 0 |
| zo03d03.s1 Stratagene colon (#937204) Homo sapiens cDNA clone 566597 3' | -4,6 | -1,49 | PPPPA | 169 | 219 | 357 | 261 | 0 |
| zr82h09.s1 Soares NhHMPu S1 Homo sapiens cDNA clone 682241 3' | -5,2 | -2 | PPPPA | 168 | 30 | 97 | 76 | 0 |
| zt50c12.r1 Soares pregnant uterus NbHPU Homo sapiens cDNA clone 503366 5' | -7,2 | -2,52 | PPPPA | 166 | 195 | 229 | 143 | 0 |
| yi80c10.r1 Homo sapiens cDNA clone 145554 5' | -5,1 | -1,89 | PPPPA | 165 | 93 | 98 | 72 | 0 |
| H. sapiens partial cDNA sequence; clone c-0ac03. | -2,8 | -0,6 | PPPPA | 160 | 81 | 168 | 83 | 0 |
| zs58f12.s1 NCI_CGAP_GCB1 Homo sapiens cDNA clone IMAGE:701711 3' | -4,0 | -1,2 | PPPPA | 159 | 133 | 73 | 81 | 0 |
| zs57e07.s1 NCI_CGAP_GCB1 Homo sapiens cDNA clone IMAGE:701604 3' | -2,9 | -0,65 | PPPPA | 157 | 63 | 73 | 123 | 0 |
| ab35g04.r1 Stratagene HeLa cell s3 937216 Homo sapiens cDNA clone 842838 5' | -7,4 | -2,49 | PPPPA | 157 | 307 | 156 | 144 | 0 |
| ae63f03.r1 NCI_CGAP_GCB1 Homo sapiens cDNA clone IMAGE:825629 5' | -4,6 | -1,43 | PPPPA | 157 | 113 | 176 | 187 | 0 |
| zu47g07.s1 Soares ovary tumor NbHOT Homo sapiens cDNA clone 741180 3' | -5,1 | -1,61 | PPPPA | 155 | 180 | 325 | 120 | 0 |
| zw55e10.s1 Soares total fetus Nb2HF8 9w Homo sapiens cDNA clone 773994 3' | -4,0 | -1,1 | PPPPA | 146 | 66 | 162 | 169 | 0 |
| zt02a10.s1 NCI_CGAP_GCB1 Homo sapiens cDNA clone IMAGE:711930 3' | -3,7 | -0,99 | PPPPA | 142 | 119 | 41 | 46 | 0 |
| zk75g04.r1 Soares pregnant uterus NbHPU Homo sapiens cDNA clone 488622 5' | -2,8 | -0,57 | PPPPA | 142 | 124 | 84 | 69 | 0 |
| zv94b04.r1 Soares NhHMPu S1 Homo sapiens cDNA clone 767407 5' | -5,2 | -1,54 | PPPPA | 142 | 301 | 109 | 161 | 0 |
| zr65f06.s1 Soares NhHMPu S1 Homo sapiens cDNA clone 668291 3' similar to SW:SPO8_YEAST P41833 TRANSCRIPTIONAL REGULATOR SPO8. [1]; | -7,6 | -2,37 | PPPPA | 141 | 63 | 121 | 50 | 0 |
| af12f04.s1 Soares testis NHT Homo sapiens cDNA clone 1031455 3' | -3,8 | -0,99 | PPPPA | 139 | 54 | 145 | 68 | 0 |

Fig. 7.31

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T4gIIIP | Abs Call T4gIIIP | Diff Call T4gIIIP(vs)N | B=A |
|---|---|---|---|---|---|---|---|---|---|---|---|---|---|
| zo13c11.s1 Stratagene colon (#937204) Homo sapiens cDNA clone 586796 3'. | RC_AA133469_at | 138 | P | 561 | P | NC | | 3,3 | 1,46 | 1137 | P | I | |
| yh25b11.r1 Homo sapiens cDNA clone 130749 5'. | R22139_at | 137 | P | 99 | P | NC | | -1,4 | -0,06 | 232 | P | MI | |
| EST178117 Colon carcinoma (Caco-2) cell line II Homo sapiens cDNA 5' end | AA305116_at | 135 | P | 76 | P | NC | | -1,2 | -0,02 | 67 | P | D | |
| zk05c12.s1 Soares pregnant uterus NbHPU Homo sapiens cDNA clone 469554 3'. | RC_AA027954_at | 134 | P | 281 | P | NC | | 1,2 | 0,03 | 255 | P | NC | |
| zk29e11.r1 Soares pregnant uterus NbHPU Homo sapiens cDNA clone 471980 5'. | AA036900_at | 134 | P | 871 | P | NC | | 3 | 1,16 | 841 | P | NC | |
| ze92d07.s1 Soares fetal heart NbHH19W Homo sapiens cDNA clone 366445 3'. | RC_AA026397_at | 133 | P | 43 | P | NC | | -1,6 | -0,14 | 168 | P | D | |
| Human fetal brain cDNA 3'-end GEN-I79C04: | RC_D59981_s_at | 132 | P | 124 | P | NC | | -1,1 | 0 | 99 | P | NC | |
| zs47c07.s1 NCI_CGAP_GCB1 Homo sapiens cDNA clone IMAGE:700620 3'. | RC_AA284143_at | 132 | P | 278 | P | NC | | 1,3 | 0,04 | 194 | P | NC | |
| zb08f12.r1 Soares fetal lung NbHL19W Homo sapiens cDNA clone 301487 5'. | W16686_at | 131 | P | 86 | P | NC | | -1,2 | -0,02 | 161 | P | NC | |
| yw28c11.r1 Homo sapiens cDNA clone 253556 5'. | H89575_s_at | 129 | P | 233 | P | NC | | 1,8 | 0,24 | 351 | P | I | |
| zs07g11.s1 NCI_CGAP_GCB1 Homo sapiens cDNA clone IMAGE:684548 3'. | RC_AA251003_at | 128 | P | 104 | P | NC | | -1,2 | -0,03 | 88 | P | NC | |
| zs84h09.s1 NCI_CGAP_GCB1 Homo sapiens cDNA clone IMAGE:704225 3'. | RC_AA279408_at | 126 | P | 166 | P | NC | | 1,3 | 0,05 | 113 | P | NC | |
| zt07g10.s1 NCI_CGAP_GCB1 Homo sapiens cDNA clone IMAGE:712482 3' similar to TR:G808826 G808826 HYPOTHETICAL 25.7 KD PROTEIN. ; | RC_AA281760_at | 126 | P | 77 | P | NC | | -1,5 | -0,12 | 66 | P | NC | |
| Human mRNA for KIAA0383 gene, partial cds. | AB002381_at | 123 | P | 168 | P | NC | | 1,4 | 0,06 | 102 | P | NC | |
| zx89g08.r1 Soares ovary tumor NbHOT Homo sapiens cDNA clone 810927 5' similar to TR:G608025 G608025 ANKYRIN G. ; | AA459542_s_at | 123 | P | 174 | P | MD | | -1,2 | -0,02 | 247 | P | NC | |
| zl07b12.s1 Soares pregnant uterus NbHPU Homo sapiens cDNA clone 491615 3'. | RC_AA115559_at | 121 | P | 106 | P | NC | | -1,2 | -0,01 | 91 | P | NC | |
| ye36a05.r1 Homo sapiens cDNA clone 119792 5'. | T94506_at | 117 | P | 71 | P | MD | | -2,2 | -0,34 | 51 | P | NC | |
| Human fetal brain cDNA 5'-end GEN-404F02. | D55869_s_at | 115 | P | 145 | P | NC | | 1,3 | 0,03 | 79 | P | NC | |
| Homo sapiens (clone pZ50-19) cleavage stimulation factor 50kDa subunit, complete cds | L02547_at | 115 | P | 106 | P | NC | | -1,1 | -0,01 | 99 | P | NC | |
| Human syntaxin 7 mRNA, complete cds. | U77942_at | 115 | P | 61 | P | NC | | -1,9 | -0,19 | 38 | P | NC | |

Fig. 7.32

EST Bladder candidates of 17742 ESTs
Exclusion of data sets incl. AFFX, all NC, all A, 3xNC + M*
2424 genes with sort score >= +/- 0,5 changing from N to tumor
235 genes LOST Abs calls PPPPA and DECREASED
8 genes LOST Abs calls PPPPA and DECREASED in all 4 comp
data sorted acc. To Avg Diff N

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIsolidP | Abs Call T2gIIsolidP | Diff Call T2gIIsolidP(vs)N | B=A |
|---|---|---|---|---|---|---|---|---|---|---|---|---|
| zo13e11.s1 Stratagene colon (#937204) Homo sapiens cDNA clone 584796 3'. | 9,5 | 8,57 | 2303 | P | I | | 19,6 | 20,68 | 55 | A | D | |
| yh25b11.r1 Homo sapiens cDNA clone 130749 5'. | 1,7 | 0,19 | 237 | P | NC | | 1,7 | 0,21 | 17 | A | D | |
| EST176117 Colon carcinoma (Caco-2) cell line II Homo sapiens cDNA 5' end. | -1,3 | -0,05 | 87 | P | NC | | -1,4 | -0,05 | -113 | A | D | |
| zk05c12.s1 Soares pregnant uterus NbHPU Homo sapiens cDNA clone 469654 3'. | 1,2 | 0,02 | 275 | P | NC | | 1,2 | 0,02 | -8 | A | D | |
| zk29e11.r1 Soares pregnant uterus NbHPU Homo sapiens cDNA clone 471980 5'. | 1,1 | 0,01 | 1005 | P | NC | | 1,5 | 0,2 | 1093 | A | D | |
| ze92a07.s1 Soares fetal heart NbHH19W Homo sapiens cDNA clone 366445 3'. | -1,4 | -0,07 | 97 | P | NC | | -1,5 | -0,08 | 10 | A | D | |
| Human fetal brain cDNA 3'-end GEN-079C04. | -1,3 | -0,05 | 89 | P | NC | | -1,5 | -0,08 | 32 | A | D | |
| zs47c07.s1 NCI_CGAP_GCB1 Homo sapiens cDNA clone IMAGE:700620 3'. | -1,1 | -0,02 | 174 | P | NC | | -1,3 | -0,04 | -79 | A | D | |
| zb08f12.r1 Soares fetal lung NbHL19W Homo sapiens cDNA clone 301487 5'. | 1,5 | 0,1 | 82 | P | NC | | -1,2 | -0,02 | 22 | A | D | |
| yw28c11.r1 Homo sapiens cDNA clone 233556 5'. | 2,7 | 0,87 | 130 | P | NC | | 1 | 0 | 41 | A | D | |
| zs07g11.s1 NCI_CGAP_GCB1 Homo sapiens cDNA clone IMAGE:684548 3'. | -1,5 | -0,07 | 65 | P | D | | -2,1 | -0,3 | 46 | A | D | |
| zs84h09.s1 NCI_CGAP_GCB1 Homo sapiens cDNA clone IMAGE:704225 3'. | -1,1 | -0,01 | 60 | P | D | | -2,1 | -0,28 | 22 | A | D | |
| zt07g10.s1 NCI_CGAP_GCB1 Homo sapiens cDNA clone IMAGE:712482 3' similar to TR:G608826 G608826 HYPOTHETICAL 25.7 KD PROTEIN. ; | -1,3 | -0,04 | 46 | P | D | | -1,9 | -0,18 | -18 | A | D | |
| Human mRNA for KIAA0383 gene, partial cds. | -1 | 0 | 95 | P | NC | | -1,3 | -0,04 | 38 | A | D | |
| zx89d08.r1 Soares ovary tumor NbHOT Homo sapiens cDNA clone 810927 5' similar to TR:G608025 G608025 ANKYRIN G. ; | ~-8,4 | -2,72 | 6 | P | NC | | ~-4,9 | -1,38 | 186 | A | D | |
| zl07b12.s1 Soares pregnant uterus NbHPU Homo sapiens cDNA clone 491615 3'. | -1,3 | -0,04 | 77 | P | NC | | -1,6 | -0,1 | 34 | A | D | |
| ye36a05.r1 Homo sapiens cDNA clone 119792 5'. | -3,1 | -0,74 | 148 | P | NC | | -1 | 0 | 115 | A | D | |
| Human fetal brain cDNA 5'-end GEN-4D4F02. | -1,5 | -0,07 | 71 | P | NC | | -1,6 | -0,11 | 40 | A | D | |
| Homo sapiens (clone pZ50-19) cleavage stimulation factor 50kDa subunit, complete cds. | -1,4 | -0,05 | 96 | P | NC | | -1,3 | -0,04 | 32 | A | D | |
| Human syntaxin 7 mRNA, complete cds. | -3,1 | -0,63 | 73 | P | NC | | -1,6 | -0,1 | 5 | A | D | |

Fig. 7.33

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T2gIIIsolidP(vs)N | Sort Score T2gIIIsolidP(vs)N | Abs Calls | N | A | B | C | D |
|---|---|---|---|---|---|---|---|---|
| zo13e11.s1 Stratagene colon (#937204) Homo sapiens cDNA clone 586796 3' | -2,9 | -0,54 | PPPPA | 138 | 661 | 11137 | 2303 | 0 |
| yh25b11.r1 Homo sapiens cDNA clone 130749 5'. | -4,3 | -1,26 | PPPPA | 137 | 99 | 232 | 237 | 0 |
| EST176117 Colon carcinoma (Caco-2) cell line II Homo sapiens cDNA 5' end. | -4,7 | -0,89 | PPPPA | 135 | 76 | 67 | 87 | 0 |
| zk05c12.s1 Soares pregnant uterus NbHPU Homo sapiens cDNA clone 469654 3' | -3,0 | -0,55 | PPPPA | 134 | 281 | 255 | 275 | 0 |
| zk28e11.r1 Soares pregnant uterus NbHPU Homo sapiens cDNA clone 471980 5'. | -4,1 | -2,15 | PPPPA | 134 | 871 | 841 | 1005 | 0 |
| ze92d07.s1 Soares fetal heart NbHH19W Homo sapiens cDNA clone 366445 3'. | -4,2 | -1,18 | PPPPA | 133 | 43 | 168 | 97 | 0 |
| Human fetal brain cDNA 3'-end GEN-079C04. | -3,0 | -0,56 | PPPPA | 132 | 124 | 99 | 89 | 0 |
| zs47c07.s1 NCI_CGAP_GCB1 Homo sapiens cDNA clone IMAGE:700620 3'. | -6,6 | -2,15 | PPPPA | 132 | 278 | 194 | 174 | 0 |
| zb08f12.r1 Soares fetal lung NbHL19W Homo sapiens cDNA clone 301487 5'. | -3,9 | -1,03 | PPPPA | 131 | 86 | 161 | 82 | 0 |
| yw28c11.r1 Homo sapiens cDNA clone 253556 5'. | -2,9 | -0,6 | PPPPA | 129 | 233 | 351 | 130 | 0 |
| zs07g11.s1 NCI_CGAP_GCB1 Homo sapiens cDNA clone IMAGE:684548 3'. | -2,9 | -0,59 | PPPPA | 128 | 104 | 88 | 65 | 0 |
| zs84h09.s1 NCI_CGAP_GCB1 Homo sapiens cDNA clone IMAGE:704225 3'. | -3,5 | -0,84 | PPPPA | 126 | 166 | 113 | 60 | 0 |
| zt07g10.s1 NCI_CGAP_GCB1 Homo sapiens cDNA clone IMAGE:712482 3' similar to TR:G808826 G808826 HYPOTHETICAL 25.7 KD PROTEIN. ;. | -4,5 | -1,17 | PPPPA | 126 | 77 | 66 | 46 | 0 |
| Human mRNA for KIAA0383 gene, partial cds. | -2,9 | -0,56 | PPPPA | 123 | 168 | 102 | 95 | 0 |
| zx89d08.r1 Soares ovary tumor NbHOT Homo sapiens cDNA clone 510927 5' similar to TR:G608025 G608025 ANKYRIN G. ;. | -5,3 | -1,39 | PPPPA | 123 | 174 | 247 | 6 | 0 |
| zl07b12.s1 Soares pregnant uterus NbHPU Homo sapiens cDNA clone 491615 3'. | -3,1 | -0,67 | PPPPA | 121 | 106 | 91 | 77 | 0 |
| ye36a05.r1 Homo sapiens cDNA clone 119792 5'. | -1,6 | -0,13 | PPPPA | 117 | 71 | 51 | 148 | 0 |
| Human fetal brain cDNA 5'-end GEN-404F02. | -2,8 | -0,54 | PPPPA | 115 | 145 | 79 | 71 | 0 |
| Homo sapiens (clone pZ50-19) cleavage stimulation factor 50kDa subunit, complete cds | -3,2 | -0,71 | PPPPA | 115 | 106 | 99 | 96 | 0 |
| Human syntaxin 7 mRNA, complete cds. | -3,7 | -0,82 | PPPPA | 115 | 61 | 38 | 73 | 0 |

Fig. 7.34

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Probe Set EST | Avg Diff N | Abs Call N | Avg Diff TagIIP | Abs Call Tag II P | Diff-Call TagIIP(vs)N B=A | Fold Change TagIIP(vs)N | Sort Score TagIIP(vs)N | Avg Diff TagIIP | Abs Call TagIIP | Diff Call T19IIP(vs)N B=A |
|---|---|---|---|---|---|---|---|---|---|---|---|
| zw76e03.r1 Soares testis NHT Homo sapiens cDNA clone 782140 5' | AA431505_at | 115 | P | 57 | P | NC | -1,7 | -0,13 | 78 | P | NC |
| zf38c08.s1 Soares NbHMPu S1 Homo sapiens cDNA clone 665678 3' | RC_AA194045_at | 114 | P | 95 | P | NC | -1,2 | -0,02 | 155 | P | NC |
| ze78t05.s1 Soares fetal heart NbHH19W Homo sapiens cDNA clone 365121 3' | RC_AA025104_at | 111 | P | 162 | P | NC | 1,6 | 0,13 | 358 | P | I |
| zr65e09.s1 Soares NhHMPu S1 Homo sapiens cDNA clone 668296 3' | RC_AA242822_at | 110 | P | 105 | P | NC | -1 | 0 | 104 | P | NC |
| zs50f04.s1 NCI_CGAP_GCB1 Homo sapiens cDNA clone IMAGE:700927 3' | AA287388_at | 110 | P | 168 | P | NC | 1,5 | 0,1 | 195 | P | NC |
| hfe0045.seq.F Human fetal heart, Lambda ZAP Express Homo sapiens cDNA 5' | AA247679_at | 110 | P | 131 | P | NC | 1,2 | 0,02 | 100 | P | NC |
| ab41e08.s1 Stratagene HeLa cell s3 937216 Homo sapiens cDNA clone 843398 3' | RC_AA489383_at | 108 | P | 45 | P | MD | -2,4 | -0,35 | 41 | P | NC |
| zu81a08.s1 Soares testis NHT Homo sapiens cDNA clone 744374 3' | RC_AA621188_at | 108 | P | 68 | P | NC | -1,3 | -0,04 | 281 | P | NC |
| ab35a01.s1 Stratagene HeLa cell s3 937216 Homo sapiens cDNA clone 842760 3' | RC_AA486182_at | 105 | P | 102 | P | NC | -1 | 0 | 291 | P | I |
| zv64h10.s1 Soares total fetus Nb2HF8 9w Homo sapiens cDNA clone 758457 3' | RC_AA393876_s_at | 103 | P | 171 | P | NC | 1,7 | 0,15 | 86 | P | NC |
| zi06h12.s1 Soares fetal liver spleen 1NFLS S1 Homo sapiens cDNA clone 430055 3' | RC_AA034189_at | 100 | P | 85 | P | NC | -1,2 | -0,02 | 44 | P | NC |
| ze79b09.s1 Soares fetal heart NbHH19W Homo sapiens cDNA clone 365177 3' | RC_AA024866_at | 99 | P | 56 | P | MD | -1,8 | -0,14 | 39 | P | D |
| zx05h06.s1 Soares total fetus Nb2HF8 9w Homo sapiens cDNA clone 785627 3' | RC_AA450373_at | 99 | P | 126 | P | NC | 1,1 | 0 | 114 | P | NC |
| yz78d07.r1 Homo sapiens cDNA clone 289165 5' | N78483_at | 97 | P | 98 | P | NC | -1 | 0 | 63 | P | NC |
| zs94d07.s1 NCI_CGAP_GCB1 Homo sapiens cDNA clone IMAGE:705133 3' | RC_AA281245_at | 90 | P | 86 | P | NC | -1 | 0 | 63 | P | NC |
| zc45b12.r1 Soares senescent fibroblasts NbHSF Homo sapiens cDNA clone 325247 5' similar to SW:WDNM_RAT P14730 WDNM1 PROTEIN. [2] PIR:S07807 ; | W52431_at | 79 | P | 42 | P | NC | -1,9 | -0,16 | 437 | P | I |
| zw64f01.s1 Soares total fetus Nb2HF8 9w Homo sapiens cDNA clone 783673 3' | RC_AA446597_at | 66 | P | 64 | P | NC | -1,7 | -0,09 | 57 | P | NC |
| zr81h11.s1 Soares NhHMPu S1 Homo sapiens cDNA clone 682149 3' | RC_AA256996_at | 63 | P | 50 | P | NC | -1,5 | -0,07 | 72 | P | NC |
| H.sapiens gene for cytokeratin 20 | X73501_at | 51 | P | 219 | P | I | 3,7 | 1,18 | 505 | P | I |
| zi20g02.s1 Soares ovary tumor NbHOT Homo sapiens cDNA clone 713714 3' similar to TR:E124071 E124071 NAD+-ISOCITRATE DEHYDROGENASE ; | RC_AA287131_at | -160 | P | 266 | P | NC | -17,5 | 7,21 | -229 | P | NC |

Fig. 7.35

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg Diff N

| gene name | Fold Change T1g/IIIP(vs)N | Sort Score T1g/IIIP(vs)N | Avg Diff T2g/IImixP | Abs Call T2g/IImixP | Diff Call T2g/IImixP(vs)N | B=A | Fold Change T2g/IImixP(vs)N | Sort Score T2g/IImixP(vs)N | Avg Diff T2g/IIsolidP | Abs Call T2g/IIsolidP | Diff Call T2g/IIsolidP(vs)N | B=A |
|---|---|---|---|---|---|---|---|---|---|---|---|---|
| zw76e03.r1 Soares testis NHT Homo sapiens cDNA clone 782140 5'. | -1,5 | -0,07 | 53 | P | NC | | -1,8 | -0,16 | 2 | A | D | |
| zr38c08.s1 Soares NhHMPu S1 Homo sapiens cDNA clone 665678 3'. | -1,1 | -0,01 | 100 | P | NC | | -1,1 | -0,01 | 14 | A | D | |
| ze78f05.s1 Soares fetal heart NbHH19W Homo sapiens cDNA clone 365121 3'. | 3,5 | 1,48 | 265 | P | NC | | 2,7 | 0,77 | 1 | A | D | |
| zr65e09.s1 Soares NhHMPu S1 Homo sapiens cDNA clone 668296 3'. | -1,1 | 0 | 52 | P | D | | -2,1 | -0,26 | 40 | A | D | |
| zs50f04.s1 NCI_CGAP_GCB1 Homo sapiens cDNA clone IMAGE:700927 3'. | 1,5 | 0,11 | 108 | P | NC | | -1 | 0 | 5 | A | D | |
| hfe0045.seq.F Human fetal heart, Lambda ZAP Express Homo sapiens cDNA 5'. | -1,1 | -0,01 | 34 | P | NC | | -1,7 | -0,13 | -69 | A | D | |
| ab41e08.s1 Stratagene HeLa cell s3 937216 Homo sapiens cDNA clone 843398 3'. | -2,6 | -0,45 | 109 | P | NC | | 1 | 0 | 19 | A | D | |
| zu81a08.s1 Soares testis NHT Homo sapiens cDNA clone 744374 3'. | 2,6 | 0,7 | 86 | P | NC | | -1 | 0 | 91 | A. | D | |
| ab35a01.s1 Stratagene HeLa cell s3 937216 Homo sapiens cDNA clone 842760 3'. | 2,3 | 0,48 | 255 | P | | | 2,4 | 0,57 | 51 | A | D | |
| zv64h10.s1 Soares total fetus Nb2HF8 9w Homo sapiens cDNA clone 758467 3'. | -1,2 | -0,02 | 61 | P | NC | | -1,7 | -0,12 | 43 | A | D | |
| zi06h12.s1 Soares fetal liver spleen 1NFLS S1 Homo sapiens cDNA clone 430055 3'. | -2,3 | -0,3 | 14 | P | NC | | -3,9 | -0,86 | -126 | A. | D | |
| ze79b09.s1 Soares fetal heart NbHH19W Homo sapiens cDNA clone 365177 3'. | -2,5 | -0,39 | 62 | P | NC | | -1,6 | -0,09 | -17 | A | D | |
| zx05h06.s1 Soares total fetus Nb2HF8 9w Homo sapiens cDNA clone 785627 3'. | -1,1 | -0,01 | 98 | P | NC | | -1 | 0 | 39 | A | D | |
| yz78d07.r1 Homo sapiens cDNA clone 289165 5'. | -1,5 | -0,08 | 29 | P | D | | -3,0 | -0,53 | 31 | A | D | |
| zs94d07.s1 NCI_CGAP_GCB1 Homo sapiens cDNA clone IMAGE:705133 3'. | -1,4 | -0,06 | 49 | P | D | | -1,9 | -0,17 | -1 | A | D | |
| zc45b12.r1 Soares senescent fibroblasts NbHSF Homo sapiens cDNA clone 325247 5' similar to SW:WDNM_RAT P14730 WDNM1 PROTEIN. [2] PIR:S07807.; | ~21,6 | 10,27 | 2228 | P | | | 28,2 | 26,64 | 82 | A | D | |
| zw84f01.s1 Soares total fetus Nb2HF8 9w Homo sapiens cDNA clone 783573 3'. | ~3,3 | -0,55 | 70 | P | D | | -1,5 | -0,07 | 43 | A | D | |
| zr81h11.s1 Soares NhHMPu S1 Homo sapiens cDNA clone 682149 3'. | -1,4 | -0,06 | 68 | P | NC | | -1,1 | -0,01 | 43 | A | D | |
| H.sapiens gene for cytokeratin 20 | 9,3 | 5,91 | 991 | P | | | 18,6 | 13,95 | 14 | A | D | |
| zt20g02.s1 Soares ovary tumor NbHOT Homo sapiens cDNA clone 713714 3' similar to | -0,25 | 308 | P . | NC | | 1,8 | 0,29 | -343 | A | D | | |
| TR:E124071 E124071 NAD+-ISOCITRATE DEHYDROGENASE.; | | | | | | | | | | | | |

Fig. 7.36

EST Bladder candidates of 17742 ESTs
Exclusion of data sets incl. AFFX, all NC, all A, 3xNC + M*
2424 genes with sort score >= +/- 0,5 changing from N to tumor
236 genes LOST Abs calls PPPPA and DECREASED
8 genes LOST Abs calls PPPPA and DECREASED in all 4 comp
data sorted acc. To Avg DiffN

| gene name | Fold Change T2gIIIsolidP(vs)N | Sort Score T2gIIIsolidP(vs)N | Abs Calls | N | A | B | C | D |
|---|---|---|---|---|---|---|---|---|
| zw76e03.r1 Soares testis NHT Homo sapiens cDNA clone 782140 5'. | -3,7 | -0,83 | PPPPA | 115 | 57 | 78 | 53 | 0 |
| zi36c08.s1 Soares NhHMPu S1 Homo sapiens cDNA clone 665678 3'. | -2,7 | -0,61 | PPPPA | 114 | 95 | 155 | 100 | 0 |
| ze78f05.s1 Soares fetal heart NbHH19W Homo sapiens cDNA clone 365121 3'. | -2,1 | -0,21 | PPPPA | 111 | 162 | 358 | 265 | 0 |
| zr65e09.s1 Soares NhHMPu S1 Homo sapiens cDNA clone 668296 3'. | -3,1 | -0,63 | PPPPA | 110 | 105 | 104 | 52 | 0 |
| z550f04.s1 NCI_CGAP_GCB1 Homo sapiens cDNA clone IMAGE:700927 3'. | -4,1 | -0,9 | PPPPA | 110 | 168 | 195 | 108 | 0 |
| hfe0045.seq.F Human fetal heart, Lambda ZAP Express Homo sapiens cDNA 5'. | -4,3 | -1,03 | PPPPA | 110 | 131 | 100 | 34 | 0 |
| ab41e08.s1 Stratagene-HeLa cell s3 937216 Homo sapiens cDNA clone 843398 3'. | -3,2 | -0,61 | PPPPA | 108 | 45 | 41 | 109 | 0 |
| zu81a08.s1 Soares testis NHT Homo sapiens cDNA clone 744374 3'. | -1,9 | -0,24 | PPPPA | 108 | 68 | 281 | 86 | 0 |
| ab35a01.s1 Stratagene-HeLa cell s3 937216 Homo sapiens cDNA clone 842760 3'. | -3,8 | -0,84 | PPPPA | 105 | 102 | 291 | 255 | 0 |
| zv64h10.s1 Soares total fetus Nb2HF8 9w Homo sapiens cDNA clone 758467 3'. | -3,8 | -0,93 | PPPPA | 103 | 171 | 86 | 61 | 0 |
| zi06h12.s1 Soares fetal liver spleen 1NFLS S1 Homo sapiens cDNA clone 430055 3'. | -7,0 | -1,6 | PPPPA | 100 | 85 | 44 | 14 | 0 |
| ze79b09.s1 Soares fetal heart NbHH19W Homo sapiens cDNA clone 365177 3'. | -3,5 | -0,56 | PPPPA | 99 | 56 | 39 | 62 | 0 |
| zx05h06.s1 Soares total fetus Nb2HF8 9w Homo sapiens cDNA clone 785627 3'. | -3,4 | -0,58 | PPPPA | 99 | 126 | 114 | 98 | 0 |
| yz78d07.r1 Homo sapiens cDNA clone 289165 5'. | -2,8 | -0,46 | PPPPA | 97 | 98 | 63 | 29 | 0 |
| zs94d07.s1 NCI_CGAP_GCB1 Homo sapiens cDNA clone IMAGE:705133 3'. | -3,2 | -0,53 | PPPPA | 90 | 86 | 63 | 49 | 0 |
| zc45b12.r1 Soares senescent fibroblasts NbHSF Homo sapiens cDNA clone 325247 5' similar to SW:WDNM_RAT P14730 WDNM1 PROTEIN. [2] PIR:S07807 ;. | -1,4 | -0,06 | PPPPA | 79 | 42 | 437 | 2228 | 0 |
| zw84f01.s1 Soares total fetus Nb2HF8 9w Homo sapiens cDNA clone 783673 3'. | -2,4 | -0,27 | PPPPA | 66 | 64 | 57 | 70 | 0 |
| zr81h11.s1 Soares NhHMPu S1 Homo sapiens cDNA clone 682149 3'. | -3,2 | -0,58 | PPPPA | 63 | 50 | 72 | 88 | 0 |
| H.sapiens gene for cytokeratin 20 | -2,1 | -0,13 | PPPPA | 51 | 219 | 505 | 991 | 0 |
| zt20g02.s1 Soares ovary tumor NbHOT Homo sapiens cDNA clone 713714 3' similar to TR:E124071 E124071 NAD+-ISOCITRATE DEHYDROGENASE ;. | -9,0 | -0,81 | PPPPA | -160 | 266 | -229 | 308 | 0 |

Fig. 8.1

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TrigIIP | Abs Call TrigIIP | Diff Call TrigIIP(vs)N | B=A | Fold Change TrigIIP(vs)N |
|---|---|---|---|---|---|---|---|---|---|---|---|---|---|---|
| Human mRNA for KIAA0372 gene, complete cds. | AB002370_at | 81 P | P | 64 P | P | D | | -1,8 | -0,13 | 89 P | P | NC | | -1,5 |
| Homo sapiens purinergic receptor P2Y5 mRNA, complete cds. | AF000546_at | 59 P | P | 7 P | P | D | | -4,2 | -0,77 | -8 P | P | MD | | -4,3 |
| yo70c03.r1 Homo sapiens cDNA clone 183268 5'. | H43922_at | 162 P | P | 114 P | P | NC | | -1,4 | -0,07 | 117 P | P | NC | | -1,4 |
| yp17b05.r1 Homo sapiens cDNA clone 187665 5' similar to contains Alu repetitive element. | H44269_at | 377 P | P | 415 P | P | NC | | 1,1 | 0,01 | 339 P | P | NC | | 1,1 |
| yw23e08.r1 Homo sapiens cDNA clone 253094 5'. | H88706_s_at | 262 P | P | 183 P | P | NC | | -1,4 | -0,09 | 133 P | P | NC | | -2 |
| Homo sapiens epoxide hydrolase (EPHX) gene, complete cds | L25880_6_at | 624 P | P | 207 P | P | D | | -3 | -1,47 | 218 P | P | D | | -2,9 |
| yw36d01.r1 Homo sapiens cDNA clone 254305 5'. | N81162_at | 335 P | P | 286 P | P | NC | | -1,2 | -0,03 | 157 P | P | D | | -2,1 |
| H. sapiens partial cDNA sequence; clone c-3ec07. | RC_F10381_s_at | 217 P | P | 206 P | P | NC | | 1,1 | 0,01 | 175 P | P | NC | | -1,4 |
| EST00018 HE6W Homo sapiens cDNA clone HE6WCR108 3'. | RC_H54559_at | 317 P | P | 297 P | P | NC | | -1,2 | -0,03 | 180 P | P | NC | | -7,8 |
| yr20g08.s1 Homo sapiens cDNA clone 205886 3' similar to SP:FTDH_RAT P28037 FORMYLTETRAHYDROFOLATE DEHYDROGENASE.; | RC_H58692_s_at | 622 P | P | 591 P | P | NC | | -1,1 | -0,01 | 40 P | P | D | | -13,2 |
| yx28d05.s1 Homo sapiens cDNA clone 263051 3'. | RC_N20047_at | 391 P | P | 137 P | P | D | | -2,8 | -1,01 | 120 P | P | D | | -3,3 |
| yv28e04.s1 Homo sapiens cDNA clone 244062 3'. | RC_N38810_at | 1198 P | P | 799 P | P | NC | | -1,5 | -0,26 | -78 P | P | NC | | -1,9 |
| yg61h01.s1 Homo sapiens cDNA clone 36305 3'. | RC_R46497_at | 197 P | P | 186 P | P | NC | | -1,1 | 0 | 251 P | P | NC | | 1,2 |
| yj76a08.s1 Homo sapiens cDNA clone 154646 3'. | RC_R55001_at | 700 P | P | 791 P | P | NC | | 1,1 | 0,03 | 596 P | P | NC | | -1,6 |
| EST10130 Homo sapiens cDNA 3' end similar to None. | RC_T29986_s_at | 1498 P | P | 1158 P | P | NC | | -1,5 | -0,31 | 1153 P | P | D | | -1,6 |
| EST12901 Homo sapiens cDNA 3' end similar to None. | RC_T30214_at | 359 P | P | 353 P | P | NC | | -1,5 | -0,15 | 381 P | P | NC | | -1,4 |
| ya01c07.s2 Homo sapiens cDNA clone 60204 3'. | RC_T40438_at | 314 P | P | 158 P | P | D | | -1,6 | -0,17 | 93 P | P | NC | | -2,2 |
| zc37f06.s1 Soares senescent fibroblasts NbHSF Homo sapiens cDNA clone 324515 3'. | RC_W51910_at | 690 P | P | 379 P | P | D | | -2,4 | -0,89 | 331 P | P | D | | -2,8 |
| zd71f09.s1 Soares fetal heart NbHH19W Homo sapiens cDNA clone 346121 3'. | RC_W73949_at | 660 P | P | 275 P | P | MD | | -2,4 | -0,9 | 200 P | P | NC | | -2,7 |
| zh55a02.s1 Soares fetal liver spleen 1NFLS S1 Homo sapiens cDNA clone 415946 3'. | RC_W66375_s_at | 2209 P | P | 375 P | P | D | | -7,5 | -10,36 | 563 P | P | D | | -5 |
| H. sapiens partial cDNA sequence; clone c-05e04. | RC_Z38289_at | 1217 P | P | 423 P | P | D | | -2,5 | -1,26 | 227 P | P | D | | -4,7 |
| H. sapiens partial cDNA sequence; clone c-0qb04. | RC_Z38807_s_at | 201 P | P | 103 P | P | D | | -1,9 | -0,28 | 97 P | P | MD | | -2,1 |

Fig. 8.2

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Sort Score T1gIIIP(vs)N | Avg Diff T2gIIImixP | Abs Call T2gIIImixP | Diff Call N(vs)T2gIIImixP | B=A | Fold Change T2gIIImixP(vs)N | Sort Score N(vs)T2gIIImixP | Avg Diff T2gIIsolidP | Abs Call T2gIIsolidP | Diff Call N(vs)T2gIIsolidP | B=A |
|---|---|---|---|---|---|---|---|---|---|---|---|
| Human mRNA for KIAA0372 gene, complete cds. | -0,07 | 32 | A | D | | -3,2 | -0,55 | 34 | A | D | |
| Homo sapiens purinergic receptor P2Y5 mRNA, complete cds. | -0,74 | -35 | A | D | | -4,1 | -0,58 | 3 | A | D | |
| yo70c03.r1 Homo sapiens cDNA clone 183268 5'. | -0,06 | 76 | A | D | | -2,1 | -0,32 | 61 | A | D | |
| yp17b05.r1 Homo sapiens cDNA clone 187665 5' similar to contains Alu repetitive element;. | 0,01 | 444 | A | D | | 1 | 0 | 49 | A | D | |
| yw23e08.r1 Homo sapiens cDNA clone 253094 5'. | -0,33 | 108 | A | D | | -2,4 | -0,57 | 24 | A | D | |
| Homo sapiens epoxide hydrolase (EPHX) gene, complete cds | -1,32 | 178 | A | D | | -3,5 | -1,96 | 318 | A | D | |
| yw36d01.r1 Homo sapiens cDNA clone 254305 5'. | -0,48 | 143 | A | D | | -2,3 | -0,6 | 109 | A | D | |
| H. sapiens partial cDNA sequence; clone c-3ec07. | -0,08 | 73 | A | D | | -3 | -0,88 | 98 | A | D | |
| EST00018 HE6W Homo sapiens cDNA clone HE6WCR108 3'. | -4,24 | 58 | A | D | | -8,3 | -4,52 | 52 | A | D | |
| yr20g08.s1 Homo sapiens cDNA clone 205886 3' similar to SP:FTDH_RAT P28037 FORMYLTETRAHYDROFOLATE DEHYDROGENASE ;. | -8,99 | -149 | A | D | | -13,7 | -9,7 | -103 | A | D | |
| yx28d05.s1 Homo sapiens cDNA clone 263051 3'. | -1,33 | 35 | A | D | | -6,9 | -3,93 | 207 | A | D | |
| yv28e04.s1 Homo sapiens cDNA clone 244062 3'. | -0,59 | 100 | A | D | | -1,8 | -0,68 | 900 | A | D | |
| yg51h01.s1 Homo sapiens cDNA clone 353053'. | 0,02 | 86 | A | D | | -2,5 | -0,57 | 107 | A | D | |
| yj76a08.s1 Homo sapiens cDNA clone 154646 3'. | -0,23 | 350 | A | D | | -3,2 | -1,67 | 133 | A | D | |
| EST10130 Homo sapiens cDNA 3' end similar to None. | -0,39 | 716 | A | D | | -2,7 | -1,77 | 806 | A | D | |
| EST12901 Homo sapiens cDNA 3' end similar to None. | -0,1 | 195 | A | D | | -2,6 | -0,99 | -32 | A | D | |
| ya01c07.s2 Homo sapiens cDNA clone 60204 3'. | -0,41 | 96 | A | D | | -2,7 | -0,73 | 134 | A | D | |
| zc37f06.s1 Soares senescent fibroblasts NbHSF Homo sapiens cDNA clone 324515 3'. | -1,29 | 375 | A | D | | -2,4 | -0,88 | 268 | A | D | |
| zd71f09.s1 Soares fetal heart NbHH19W Homo sapiens cDNA clone 346121 3'. | -1,11 | 133 | A | D | | -5,2 | -3,72 | -28 | A | D | |
| zh55a02.s1 Soares fetal liver spleen 1NFLS S1 Homo sapiens cDNA clone 415946 3'. | -6,3 | 86 | A | D | | -26,9 | -22,82 | 186 | A | D | |
| H. sapiens partial cDNA sequence; clone c-05e04. | -3,96 | 145 | A | D | | -7,3 | -6,96 | -170 | A | D | |
| H. sapiens partial cDNA sequence; clone c-0gb04. | -0,34 | 45 | A | D | | -3,6 | -1,09 | 84 | A | D | |

Fig. 8.3

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Fold Change T2g/IIIsoildP(vs)N | Sort Score T2g/IIIsoildP(vs)N | Abs Calls | N | A | B | C | D |
|---|---|---|---|---|---|---|---|---|
| Human mRNA for KIAA0372 gene, complete cds. | -2,5 | -0,3 | PPPAA | 81 | 64 | 89 | 0 | 0 |
| Homo sapiens purinergic receptor P2Y5 mRNA, complete cds. | -3,2 | -0,54 | PPPAA | 59 | 7 | -8 | 0 | 0 |
| yo70c03.r1 Homo sapiens cDNA clone 163268 5'. | -2,6 | -0,55 | PPPAA | 162 | 114 | 117 | 0 | 0 |
| yp17b05.r1 Homo sapiens cDNA clone 187655 5' similar to contains Alu repetitive element. | -4,5 | -1,7 | PPPAA | 377 | 415 | 339 | 0 | 0 |
| yw23e08.r1 Homo sapiens cDNA clone 253094 5'. | -5,7 | -2,31 | PPPAA | 262 | 186 | 133 | 0 | 0 |
| Homo sapiens epoxide hydrolase (EPHX) gene, complete cds | -2 | -0,52 | PPPAA | 624 | 207 | 218 | 0 | 0 |
| yw36d01.r1 Homo sapiens cDNA clone 254305 5'. | -3,2 | -1,24 | PPPAA | 336 | 286 | 157 | 0 | 0 |
| H. sapiens partial cDNA sequence; clone c-3ec07. | -2,3 | -0,45 | PPPAA | 217 | 206 | 175 | 0 | 0 |
| EST00018 HE6W Homo sapiens cDNA clone HE6WCR108 3'. | -11,3 | -6,04 | PPPAA | 317 | 297 | 180 | 0 | 0 |
| yr20g08.s1 Homo sapiens cDNA clone 205886 3' similar to SP:FTDH_RAT P28037 FORMYLTETRAHYDROFOLATE DEHYDROGENASE.; | -12,1 | -8,78 | PPPAA | 622 | 591 | 40 | 0 | 0 |
| yx28d06.s1 Homo sapiens cDNA clone 263051 3'. | -1,6 | -0,19 | PPPAA | 391 | 137 | 120 | 0 | 0 |
| yv28e04.s1 Homo sapiens cDNA clone 244062 3'. | -8,9 | -8,97 | PPPAA | 1198 | 799 | -78 | 0 | 0 |
| yg51h01.s1 Homo sapiens cDNA clone 36305 3'. | -2 | -0,33 | PPPAA | 197 | 186 | 251 | 0 | 0 |
| yj76a08.s1 Homo sapiens cDNA clone 154646 3'. | -9,0 | -6,51 | PPPAA | 700 | 791 | 596 | 0 | 0 |
| EST10130 Homo sapiens cDNA 3' end similar to None. | -1,9 | -0,66 | PPPAA | 1498 | 1158 | 1153 | 0 | 0 |
| EST12901 Homo sapiens cDNA 3' end similar to None. | -7,3 | -4,24 | PPPAA | 359 | 353 | 381 | 0 | 0 |
| ya01c07.s2 Homo sapiens cDNA clone 60204 3'. | -1,9 | -0,31 | PPPAA | 314 | 158 | 93 | 0 | 0 |
| zc37f06.s1 Soares senescent fibroblasts NbHSF Homo sapiens cDNA clone 324515 3'. | -3,5 | -2 | PPPAA | 690 | 379 | 331 | 0 | 0 |
| zd71f09.s1 Soares fetal heart NbHH19W Homo sapiens cDNA clone 346121 3'. | -10,8 | -8,09 | PPPAA | 660 | 275 | 200 | 0 | 0 |
| zh55a02.s1 Soares fetal liver spleen 1NFLS S1 Homo sapiens cDNA clone 415946 3'. | -13,9 | -17,47 | PPPAA | 2209 | 375 | 563 | 0 | 0 |
| H. sapiens partial cDNA sequence; clone c-05e04. | -18,6 | -15,52 | PPPAA | 1217 | 423 | 227 | 0 | 0 |
| H. sapiens partial cDNA sequence; clone c-0qb04. | -2,4 | -0,49 | PPPAA | 201 | 103 | 97 | 0 | 0 |

Fig. 8.4

EST Bladder candidates of 17742 ESTs
Exclusion of data sets incl. AFFX, all NC, all A, 3xNC + M*
2424 genes with soft score >= +/- 0,5 changing from N to tumor
52 genes LOST Abs calls PPPAA and DECREASED
9 genes LOST Abs calls PPPAA and DECREASED in all 4 comp

| gene name | Probe Set EST | Avg Diff N | Abs Call N | Avg Diff TagIIP | Abs Call TagIIP P | Diff Call TagIIP(vs)N | B=A | Fold Change TagIIP(vs)N | Sort Score TagIIP(vs)N | Avg Diff T19IIP | Abs Call T19IIP | Diff Call T19IIP(vs)N | B=A | Fold Change T19IIP(vs)N |
|---|---|---|---|---|---|---|---|---|---|---|---|---|---|---|
| H. sapiens partial cDNA sequence; clone c-1ed10. | RC_Z39599_at | 312 P | P | 185 P | P | NC | | -1,7 | -0,21 | 201 P | P | NC | | -1,6 |
| ze74h03.s1 Soares fetal heart NbHH19W Homo sapiens cDNA clone 364757 3' similar to contains OFR.t1 OFR repetitive element ;. | RC_AA025351_at | 121 P | P | 85 P | P | NC | | -1,8 | -0,15 | 109 P | P | NC | | -1,4 |
| zl01f04.s1 Soares pregnant uterus NbHPU Homo sapiens cDNA clone 491071 3'. | RC_AA136474_at | 155 P | P | 67 P | P | NC | | -2,3 | -0,39 | 63 P | P | NC | | -2,5 |
| zk99b02.s1 Soares pregnant uterus NbHPU Homo sapiens cDNA clone 490923 3'. | RC_AA136611_at | 88 P | P | 76 P | P | NC | | -1,2 | -0,01 | 31 P | P | D | | -2,9 |
| zr48f07.s1 Soares NhHMPu S1 Homo sapiens cDNA clone 666661 3'. | RC_AA233375_at | 282 P | P | 104 P | P | D | | -2,4 | -0,52 | 228 P | P | NC | | -1,3 |
| zt36c05.s1 Soares ovary tumor NbHOT Homo sapiens cDNA clone 724424 3'. | RC_AA235621_s_at | 417 P | P | 220 P | P | NC | | -1,9 | -0,37 | 176 P | P | D | | -2,4 |
| zr72g02.s1 Soares NhHMPu S1 Homo sapiens cDNA clone 668978 3'. | RC_AA253331_at | 167 P | P | 160 P | P | NC | | -1 | 0 | 166 P | P | NC | | -1 |
| zv64a10.s1 Soares total fetus Nb2HF8 9w Homo sapiens cDNA clone 758394 3'. | RC_AA393793_at | 126 P | P | 71 P | P | D | | -1,8 | -0,16 | 49 P | P | D | | -2,6 |
| zv04a05.s1 Soares ovary tumor NbHOT Homo sapiens cDNA clone 752624 3'. | RC_AA419547_at | 156 P | P | 102 P | P | NC | | -1,5 | -0,1 | 58 P | P | D | | -2,9 |
| zu27d11.s1 Soares NhHMPu S1 Homo sapiens cDNA clone 739221 3'. | RC_AA421100_at | 630 P | P | 495 P | P | NC | | -1,3 | -0,07 | 252 P | P | D | | -2,1 |
| zw87f05.s1 Soares total fetus Nb2HF8 9w Homo sapiens cDNA clone 783971 3'. | RC_AA443277_at | 115 P | P | 63 P | P | NC | | -2,1 | -0,26 | 89 P | P | NC | | -1,3 |
| zw84c05.s1 Soares total fetus Nb2HF8 9w Homo sapiens cDNA clone 783656 3'. | RC_AA446570_at | 131 P | P | 50 P | P | D | | -2,6 | -0,5 | 66 P | P | D | | -2 |
| zw93c01.s1 Soares total fetus Nb2HF8 9w Homo sapiens cDNA clone 784512 3'. | RC_AA447123_at | 189 P | P | 150 P | P | NC | | -1,3 | -0,04 | 55 P | P | D | | -3,4 |
| zx06g09.s1 Soares total fetus Nb2HF8 9w Homo sapiens cDNA clone 785728 3'. | RC_AA449343_at | 102 P | P | 111 P | P | NC | | 1,1 | 0,01 | 72 P | P | D | | -2,8 |
| aa03e08.s1 Soares NhHMPu S1 Homo sapiens cDNA clone 812150 3'. | RC_AA456016_at | 99 P | P | 29 P | P | D | | -3,5 | -0,75 | 22 P | P | MD | | -4,6 |
| zv21f04.s1 Soares NhHMPu S1 Homo sapiens cDNA clone 754303 3'. | RC_AA479299_at | 215 P | P | 402 P | P | I | | 2,2 | 0,6 | 109 P | P | D | | -2 |
| zv17d09.s1 Soares NhHMPu S1 Homo sapiens cDNA clone 753905 3' similar to contains element TAR1 TAR1 repetitive element ;. | RC_AA479350_at | 258 P | | 84 P | P | MD | | -2,7 | -0,68 | 69 P | P | MD | | -3,3 |

Fig. 8.5

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Sort Score T/gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIIsolidP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|
| H. sapiens partial cDNA sequence; clone c-1ed10. | -0,15 | 33 | A | D | | -5,6 | -2,73 | 151 | A | D | |
| ze74h03.s1 Soares fetal heart NbHH19W Homo sapiens cDNA clone 364757 3' similar to contains OFR.t1 OFR repetitive element.; | -0,06 | -19 | A | D | | -6,9 | -1,73 | 25 | A | D | |
| zl01f04.s1 Soares pregnant uterus NbHPU Homo sapiens cDNA clone 491071 3'. | -0,46 | 39 | A | D | | -4,5 | -1,55 | 37 | A | D | |
| zk99b02.s1 Soares pregnant uterus NbHPU Homo sapiens cDNA clone 490923 3'. | -0,49 | 17 | A | D | | -3,5 | -0,68 | 30 | A | D | |
| zr48f07.s1 Soares NhHMPu S1 Homo sapiens cDNA clone 666661 3'. | -0,07 | 89 | A | D | | -3,4 | -1,25 | 106 | A | D | |
| zt36c05.s1 Soares ovary tumor NbHOT Homo sapiens cDNA clone 724424 3'. | -0,69 | 122 | A | D | | -3,4 | -1,49 | 40 | A | D | |
| zr72g02.s1 Soares NhHMPu S1 Homo sapiens cDNA clone 668978 3'. | 0 | 7 | A | D | | -5,6 | -1,73 | 26 | A | D | |
| zv64a10.s1 Soares total fetus Nb2HF8 9w Homo sapiens cDNA clone 758394 3'. | -0,46 | 58 | A | D | | -2,2 | -0,3 | 26 | A | D | |
| zv94a05.s1 Soares NhHMPu S1 Homo sapiens cDNA clone 752624 3'. | -0,7 | 33 | A | D | | -5,1 | -1,79 | 39 | A | D | |
| zu27d11.s1 Soares ovary tumor NbHOT Homo sapiens cDNA clone 739221 3'. | -0,54 | 245 | A | D | | -2,1 | -0,59 | -82 | A | D | |
| zw87f06.s1 Soares total fetus Nb2HF8 9w Homo sapiens cDNA clone 783971 3'. | -0,04 | 21 | A | D | | -3,8 | -0,9 | 18 | A | D | |
| zw84c05.s1 Soares total fetus Nb2HF8 9w Homo sapiens cDNA clone 783656 3'. | -0,24 | 44 | A | D | | -3 | -0,65 | 43 | A | D | |
| zw93c01.s1 Soares total fetus Nb2HF8 9w Homo sapiens cDNA clone 784512 3'. | -1,01 | 74 | A | D | | -2,5 | -0,55 | 78 | A | D | |
| zx05g09.s1 Soares total fetus Nb2HF8 9w Homo sapiens cDNA clone 785728 3'. | -0,67 | 40 | A | D | | -5 | -1,87 | 263 | A | D | |
| aa03a08.s1 Soares NhHMPu S1 Homo sapiens cDNA clone 812150 3'. | -1,18 | 30 | A | D | | -3,3 | -0,67 | 40 | A | D | |
| zv21f04.s1 Soares NhHMPu S1 Homo sapiens cDNA clone 754303 3'. | -0,31 | 48 | A | D | | -4,5 | -1,67 | 8 | A | D | |
| zv17d09.s1 Soares NhHMPu S1 Homo sapiens cDNA clone 753905 3' similar to contains element TAR1 TAR1 repetitive element.; | -1,02 | 20 | A | D | | -9,1 | -4,29 | 42 | A | D | |

Fig. 8.6

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Fold Change T2gIIsolidP(vs)N | Sort Score T2gIIsolidP(vs)N | Abs Calls | N | A | B | C | D |
|---|---|---|---|---|---|---|---|---|
| H. sapiens partial cDNA sequence; clone c-1ed10. | -2,1 | -0,41 | PPPAA | 312 | 185 | 201 | 0 | 0 |
| ze74h03.s1 Soares fetal heart NbHH19W Homo sapiens cDNA clone 364757 3' similar to contains OFR.t1 OFR repetitive element.; | -3,9 | -1,03 | PPPAA | 121 | 85 | 109 | 0 | 0 |
| zi01f04.s1 Soares pregnant uterus NbHPU Homo sapiens cDNA clone 491071 3'. | -3,9 | -1,12 | PPPAA | 155 | 67 | 63 | 0 | 0 |
| zk99b02.s1 Soares pregnant uterus NbHPU Homo sapiens cDNA clone 490923 3'. | -2,4 | -0,32 | PPPAA | 88 | 76 | 31 | 0 | 0 |
| zr48f07.s1 Soares NhHMPu S1 Homo sapiens cDNA clone 666661 3'. | -2,7 | -0,75 | PPPAA | 282 | 104 | 228 | 0 | 0 |
| zt36c05.s1 Soares ovary tumor NbHOT Homo sapiens cDNA clone 724424 3'. | -10,2 | -5,99 | PPPAA | 417 | 220 | 176 | 0 | 0 |
| zr72g02.s1 Soares NhHMPu S1 Homo sapiens cDNA clone 668978 3'. | -4,1 | -1,05 | PPPAA | 167 | 160 | 166 | 0 | 0 |
| zv64a10.s1 Soares total fetus Nb2HF8 9w Homo sapiens cDNA clone 758394 3'. | -3,3 | -0,73 | PPPAA | 126 | 71 | 49 | 0 | 0 |
| zv04a05.s1 Soares NhHMPu S1 Homo sapiens cDNA clone 752624 3'. | -3,8 | -1,11 | PPPAA | 156 | 102 | 58 | 0 | 0 |
| zu27d11.s1 Soares ovary tumor NbHOT Homo sapiens cDNA clone 739221 3'. | -15,8 | -9,78 | PPPAA | 630 | 495 | 252 | 0 | 0 |
| zw87f06.s1 Soares total fetus Nb2HF8 9w Homo sapiens cDNA clone 783971 3'. | -3,4 | -0,72 | PPPAA | 115 | 63 | 89 | 0 | 0 |
| zw64c05.s1 Soares total fetus Nb2HF8 9w Homo sapiens cDNA clone 783656 3'. | -2,9 | -0,59 | PPPAA | 131 | 50 | 66 | 0 | 0 |
| zw93c01.s1 Soares total fetus Nb2HF8 9w Homo sapiens cDNA clone 784512 3'. | -2,4 | -0,49 | PPPAA | 189 | 150 | 55 | 0 | 0 |
| zx06g09.s1 Soares total fetus Nb2HF8 9w Homo sapiens cDNA clone 785728 3'. | -5,3 | -2,01 | PPPAA | 102 | 111 | 72 | 0 | 0 |
| aa03a08.s1 Soares NhHMPu S1 Homo sapiens cDNA clone 812150 3'. | -2,4 | -0,36 | PPPAA | 99 | 29 | 22 | 0 | 0 |
| zv21f04.s1 Soares NhHMPu S1 Homo sapiens cDNA clone 754303 3'. | -6,1 | -2,49 | PPPAA | 215 | 402 | 109 | 0 | 0 |
| zv17d09.s1 Soares NhHMPu S1 Homo sapiens cDNA clone 753905 3' similar to contains element TAR1 TAR1 repetitive element.; | -7,2 | -3,59 | PPPAA | 258 | 84 | 69 | 0 | 0 |

Fig. 8.7

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A | Fold Change T1gIIIP(vs)N |
|---|---|---|---|---|---|---|---|---|---|---|---|---|---|---|
| Human leukemogenic homolog protein (MEIS1) mRNA, complete cds | U85707_at | 91 | P | 90 | P | NC | | -1,2 | -0,02 | 64 | P | NC | | -1,7 |
| Human multispanning membrane protein mRNA, complete cds. /gb=U94831 /ntype=RNA | U94831_at | 206 | P | 253 | P | NC | | 1,2 | 0,04 | 380 | P | NC | | -1,3 |
| 38c8 Human retina cDNA randomly primed sublibrary Homo sapiens cDNA. | W27827_at | 382 | P | 167 | P | NC | | -2,3 | -0,6 | 243 | P | MD | | -1,6 |
| zd85a12.r1 Soares fetal heart NbHH19W Homo sapiens cDNA clone 347422 5'. | W81301_at | 575 | P | 584 | P | NC | | 1 | 0 | 86 | P | D | | -6,3 |
| H.sapiens mRNA for putative progesterone binding protein | Y12711_at | 551 | P | 486 | P | NC | | -1,1 | -0,02 | 673 | P | NC | | 1,2 |
| zm15c08.r1 Stratagene pancreas (#937208) Homo sapiens cDNA clone 525710 5'. | AA074407_at | 67 | P | 59 | P | NC | | -1,3 | -0,04 | 44 | P | NC | | -1,8 |
| yy1646.seq.F Fetal heart, Lambda ZAP Express Homo sapiens cDNA 5'. | AA091017_at | 308 | P | 234 | P | NC | | 1,1 | 0,01 | 447 | P | NC | | 1,5 |
| l7134.seq.F Fetal heart, Lambda ZAP Express Homo sapiens cDNA 5'. | AA104023_at | 328 | P | 326 | P | NC | | -1 | 0 | 201 | P | NC | | -1,6 |
| zo95d05.r1 Stratagene ovarian cancer (#937219) Homo sapiens cDNA clone 594633 5'. | AA171913_at | 398 | P | 442 | P | NC | | 1,5 | 0,14 | 310 | P | NC | | 1 |
| zr32h05.r1 Soares NhHMPu S1 Homo sapiens cDNA clone 665145 5'. | AA195678_at | 95 | P | 88 | P | NC | | -1,1 | -0,01 | 100 | P | NC | | -1,1 |
| zr55e05.r1 Soares NhHMPu S1 Homo sapiens cDNA clone 667328 5'. | AA227678_at | 258 | P | 125 | P | D | | -1,9 | -0,26 | 88 | P | D | | -2,1 |
| csg0306.seq.F Human fetal heart, Lambda ZAP Express Homo sapiens cDNA 5'. | AA247204_at | 232 | P | 431 | P | NC | | -1,3 | -0,05 | 400 | P | NC | | -1,4 |
| zv18b05.r1 Soares NhHMPu S1 Homo sapiens cDNA clone 753969 5'. | AA479995_at | 302 | P | 242 | P | NC | | -1,2 | -0,04 | 185 | P | NC | | -1,9 |

Fig. 8.8

EST Bladder candidates of 17742 ESTs
Exclusion of data sets incl. AFFX, all NC, all A, 3xNC + M*
2424 genes with sort score >= +/- 0.5 changing from N to tumor
52 genes LOST Abs calls PPPAA and DECREASED
9 genes LOST Abs calls PPPAA and DECREASED in all 4 comp

| gene name | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|
| Human leukemogenic homolog protein (MEIS1) mRNA, complete cds | -0,12 | 25 | A | D | | -3,7 | -0,85 | -6 | A | D | |
| Human multispanning membrane protein mRNA, complete cds. /gb=U94831 /ntype=RNA | -0,05 | 246 | A | D | | -2,4 | -0,59 | 305 | A | D | |
| 38c8 Human retina cDNA randomly primed sublibrary Homo sapiens cDNA. | -0,18 | 123 | A | D | | -3,1 | -1,19 | 30 | A | D | |
| zd85a12.r1 Soares fetal heart NbHH19W Homo sapiens cDNA clone 347422 5' | -4,17 | -2 | A | D | | -19,2 | -10,94 | 381 | A | D | |
| H.sapiens mRNA for putative progesterone binding protein | 0,06 | 180 | A | D | | -3,1 | -1,39 | -19 | A | D | |
| zm15c08.r1 Stratagene pancreas (#937208) Homo sapiens cDNA clone 525710 5' | -0,14 | -6 | A | D | | -3,9 | -0,71 | -129 | A | D | |
| yy1646.seq.F Fetal heart, Lambda ZAP Express Homo sapiens cDNA 5' | 0,13 | 32 | A | D | | -6,9 | -2,93 | 338 | A | D | |
| l7134.seq.F Fetal heart, Lambda ZAP Express Homo sapiens cDNA 5' | -0,19 | 71 | A | D | | -4,6 | -2,17 | 65 | A | D | |
| zo95d05.r1 Stratagene ovarian cancer (#937219) Homo sapiens cDNA clone 594633 5' | 0 | -12 | A | D | | -14,2 | -7,01 | -51 | A | D | |
| zr32h05.r1 Soares NhHMPu S1 Homo sapiens cDNA clone 665145 5' | 0 | 35 | A | D | | -3,4 | -0,7 | 41 | A | D | |
| zr55e05.r1 Soares NhHMPu S1 Homo sapiens cDNA clone 667328 5' | -0,37 | 61 | A | D | | -3,5 | -1,11 | 92 | A | D | |
| csg0306.seq.F Human fetal heart, Lambda ZAP Express Homo sapiens cDNA 5' | -0,07 | 337 | A | D | | -2,2 | -0,4 | 134 | A | D | |
| zv18b05.r1 Soares NhHMPu S1 Homo sapiens cDNA clone 753969 5' | -0,37 | 27 | A | D | | -10,1 | -5,07 | 19 | A | D | |

Fig. 8.9

EST Bladder candidates of 17742 ESTs
Exclusion of data sets incl. AFFX, all NC, all A, 3xNC + M*
2424 genes with sort score >= +/- 0,5 changing from N to tumor
52 genes LOST Abs calls PPPAA and DECREASED
9 genes LOST Abs calls PPPAA and DECREASED in all 4 comp

| gene name | Fold Change T2gllsolidP(vs)N | Sort Score T2gIIIsolidP(vs)N | Abs Calls | N | A | B | C | D |
|---|---|---|---|---|---|---|---|---|
| Human leukemogenic homolog protein (MEIS1) mRNA, complete cds | ~3,7 | -0,78 | PPPAA | 91 | 90 | 64 | 0 | 0 |
| Human multispanning membrane protein mRNA, complete cds. /gb=U94831 /ntype=RNA | -2,5 | -0,64 | PPPAA | 206 | 253 | 380 | 0 | 0 |
| 38c8 Human retina cDNA randomly primed sublibrary Homo sapiens cDNA. | -9,6 | -5,45 | PPPAA | 382 | 167 | 243 | 0 | 0 |
| zd85a12.r1 Soares fetal heart NbHH19W Homo sapiens cDNA clone 34/422 5' | -1,7 | -0,35 | PPPAA | 575 | 584 | 86 | 0 | 0 |
| H.sapiens mRNA for putative progesterone binding protein | -14,9 | -9,41 | PPPAA | 551 | 486 | 673 | 0 | 0 |
| zm15c08.r1 Stratagene pancreas (#937208) Homo sapiens cDNA clone 525710 5' | -6,0 | -1 | PPPAA | 67 | 59 | 44 | 0 | 0 |
| yy1646.seq.F Fetal heart, Lambda ZAP Express Homo sapiens cDNA 5'. | 1,1 | 0,01 | PPPAA | 308 | 234 | 447 | 0 | 0 |
| l7134.seq.F Fetal heart, Lambda ZAP Express Homo sapiens cDNA 5'. | -6 | -3,34 | PPPAA | 328 | 326 | 201 | 0 | 0 |
| zo95d05.r1 Stratagene ovarian cancer (#937219) Homo sapiens cDNA clone 594633 5'. | ~11,8 | -6,01 | PPPAA | 398 | 442 | 310 | 0 | 0 |
| zr32h05.r1 Soares NhHMPu S1 Homo sapiens cDNA clone 665145 5'. | -2,8 | -0,46 | PPPAA | 95 | 88 | 100 | 0 | 0 |
| zr55e05.r1 Soares NhHMPu S1 Homo sapiens cDNA clone 667328 5'. | -2,9 | -0,84 | PPPAA | 258 | 125 | 88 | 0 | 0 |
| csg0306.seq.F Human fetal heart, Lambda ZAP Express Homo sapiens cDNA 5'. | -6,2 | -1,75 | PPPAA | 232 | 431 | 400 | 0 | 0 |
| zv18b05.r1 Soares NhHMPu S1 Homo sapiens cDNA clone 753969 5'. | -7,3 | -3,52 | PPPAA | 302 | 242 | 185 | 0 | 0 |

Fig. 9.1

EST Bladder candidates of 17742 ESTs
Exclusion of data sets incl. AFFX, all NC, all A, 3xNC + M*
2424 genes with sort score >= +/- 0,5 changing from N to tumor
42 genes LOST Abs calls PPAAA and DECREASED

| gene name | Probe Set EST | Avg Diff N | Abs Call N | Avg Diff TagIIP | Abs Call TagIIP P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A |
|---|---|---|---|---|---|---|---|---|---|---|---|---|---|
| Human mRNA for KIAA0347 gene, complete cds. | AI3002345_at | 93 | P | 24 | P | D | | -4,4 | -1,13 | 2 | A | D | |
| Homo sapiens breast cancer suppressor candidate 1 (bcsc-1) mRNA, complete cds. | AF002672_at | 98 | P | -7 | P | NC | | -7,5 | -2,13 | -232 | A | D | |
| Human liver arylamine N-acetyltransferase (EC 2.3.1.5) gene | D90041_s_at | 160 | P | 98 | P | NC | | -1,6 | -0,13 | 39 | A | D | |
| yw37b04.r1 Homo sapiens cDNA clone 254383 5'. | N75611_s_at | 230 | P | 25 | P | D | | -7,1 | -2,74 | 8 | A | D | |
| yq52h06.r1 Homo sapiens cDNA clone 199451 5'. | R97361_at | 236 | P | 179 | P | NC | | -1,3 | -0,06 | 93 | A | D | |
| H. sapiens partial cDNA sequence; clone c-3cg10. | RC_F10282_at | 433 | P | 719 | P | NC | | 1,1 | 0,02 | 201 | A | D | |
| yn64a06.s1 Homo sapiens cDNA clone 173170 3'. | RC_H20769_at | 1411 | P | 742 | P | D | | -1,9 | -0,68 | 535 | A | D | |
| yy46c12.s1 Homo sapiens cDNA clone 276598 3' similar to contains L1.11 L1 repetitive element.; | RC_N34871_at | 628 | P | 426 | P | NC | | -1,1 | -0,02 | -149 | A | D | |
| ze11a07.s1 Homo sapiens cDNA clone 292212 3'. | RC_N66159_at | 980 | P | 381 | P | MD | | -2,6 | -1,28 | 72 | A | D | |
| yf35b02.s1 Homo sapiens cDNA clone 128811 3'. | RC_R10075_at | 154 | P | 112 | P | NC | | -1,4 | -0,06 | 19 | A | D | |
| yg87h06.s1 Homo sapiens cDNA clone 40364 3'. | RC_R54822_at | 212 | P | 44 | P | D | | -4,5 | -1,88 | 26 | A | D | |
| zd89b03.s1 Soares fetal heart NbHH19W Homo sapiens cDNA clone 356621 3'. | RC_W84413_at | 247 | P | 868 | P | NC | | 2,9 | 1,48 | 46 | A | D | |
| zk19l06.s1 Soares pregnant uterus NbHPU Homo sapiens cDNA clone 471011 3'. | RC_AA032250_at | 182 | P | 101 | P | NC | | -1,4 | -0,07 | 15 | A | D | |
| zf13f05.s1 Soares fetal heart NbHH19W Homo sapiens cDNA clone 376833 3'. | RC_AA047616_at | 124 | P | 72 | P | NC | | -1,4 | -0,06 | 36 | A- | D | |
| zf50a03.s1 Soares retina N2b4HR Homo sapiens cDNA clone 380332 3'. | RC_AA047864_at | 63 | P | 59 | P | D | | -1,4 | -0,04 | 17 | A | D | |
| zi67e01.s1 Stratagene colon (#937204) Homo sapiens cDNA clone 509688 3' similar to TR:G189087 G189087 NONSPECIFIC CROSSREACTING ANTIGEN.; | RC_AA058357_s_at | 389 | P | 224 | P | D | | -2,2 | -0,65 | 58 | A | D | |
| zn53a05.s1 Stratagene muscle 937209 Homo sapiens cDNA clone 561672 3' similar to contains Alu repetitive element; | RC_AA086487_at | 181 | P | 52 | P | D | | -4,3 | -1,6 | -3 | A | D | |
| zf15b11.s1 Soares pregnant uterus NbHPU Homo sapiens cDNA clone 501981 3'. | RC_AA126561_at | 259 | P | 303 | P | NC | | 1,4 | 0,09 | -37 | A | D | |
| zo71b06.r1 Stratagene pancreas (#937208) Homo sapiens cDNA clone 592307 3'. | RC_AA146619_at | 1174 | P | 1195 | P | NC | | 1 | 0 | 257 | A | D | |
| zo78e05.r1 Stratagene pancreas (#937208) Homo sapiens cDNA clone 593024 3'. | RC_AA159355_at | 338 | P | 534 | P | D | | 1,4 | 0,1 | 52 | A | D | |
| zs16l06.s1 NCI_CGAP_GCB1 Homo sapiens cDNA clone IMAGE:685383 3'. | RC_AA243582_at | 195 | P | 64 | P | D | | -3,1 | -0,82 | -15 | A | D | |
| zs91h04.s1 NCI_CGAP_GCB1 Homo sapiens cDNA clone IMAGE:704867 3'. | RC_AA283066_at | 142 | P | 76 | P | MD | | -1,9 | -0,2 | 32 | A | D | |
| zw50d12.s1 Soares total fetus Nb2HF8 9w Homo sapiens cDNA clone 773495 3'. | RC_AA427924_at | 218 | P | 140 | P | NC | | -1,6 | -0,13 | 93 | A | D | |
| zv53d04.s1 Soares testis NHT Homo sapiens cDNA clone 757351 3'. | RC_AA437118_at | 176 | P | 59 | P | MD | | -3,7 | -1,22 | 33 | A | D | |

Fig. 9.2

EST Bladder candidates of 17742 ESTs
Exclusion of data sets incl. AFFX, all NC, all A, 3xNC + M*
2424 genes with sort score >= +/- 0,5 changing from N to tumor
42 genes LOST Abs calls PPAAA and DECREASED

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N |
|---|---|---|---|---|---|---|---|---|---|---|---|
| Human mRNA for KIAA0347 gene, complete cds. | -6,1 | -1,76 | -18 | A | D | | -5,1 | -1,31 | -12 | A | D |
| Homo sapiens breast cancer suppressor candidate 1 (bcsc-1) mRNA, complete cds. | -17,3 | -4,68 | -210 | A | D | | -11,2 | -2,87 | -161 | A | D |
| Human liver arylamine N-acetyltransferase (EC 2.3.1.5) gene | -4,1 | -1,25 | 60 | A | D | | -2,7 | -0,55 | 98 | A | D |
| yw37b04.r1 Homo sapiens cDNA clone 254383 5'. | -10,9 | -4,5 | 22 | A | D | | -7,2 | -3,01 | 46 | A | D |
| yq52h06.r1 Homo sapiens cDNA clone 199451 5'. | -2,6 | -0,62 | 84 | A | D | | -3,7 | -1,31 | 104 | A | D |
| H. sapiens partial cDNA sequence; clone c-3cg10. | -2,2 | -0,55 | 7 | A | D | | -8,0 | -4,9 | 82 | A | D |
| yn64a06.s1 Homo sapiens cDNA clone 173170 3'. | -2,6 | -1,63 | 572 | A | D | | -2,5 | -1,4 | 545 | A | D |
| yy46c12.s1 Homo sapiens cDNA clone 276598 3' similar to contains L1.t1 L1 repetitive element.; | -16,7 | -11,72 | -212 | A | D | | -12,6 | -9,03 | 139 | A | D |
| za11a07.s1 Homo sapiens cDNA clone 292212 3'. | -13,6 | -11,56 | 19 | A | D | | -18,8 | -13,47 | 86 | A | D |
| yf35b02.s1 Homo sapiens cDNA clone 128811 3'. | -3,8 | -1,04 | 47 | A | D | | -2,8 | -0,57 | 41 | A | D |
| yg87f06.s1 Homo sapiens cDNA clone 40364 3'. | -6,1 | -2,41 | -19 | A | D | | -4,8 | -1,72 | 68 | A | D |
| zd68b03.s1 Soares fetal heart NbIH19W Homo sapiens cDNA clone 356621 3'. | -5,2 | -2,21 | 58 | A | D | | -5,8 | -3,05 | -37 | A | D |
| zk19f06.s1 Soares pregnant uterus NbHPU Homo sapiens cDNA clone 471011 3'. | -5,1 | -1,33 | 97 | A | D | | -1,9 | -0,25 | 58 | A | D |
| zf13f05.s1 Soares fetal heart NbHH19W Homo sapiens cDNA clone 376833 3'. | -3,5 | -0,86 | 28 | A | D | | -3,5 | -0,77 | -13 | A | D |
| zi50a03.s1 Soares retina N2b4HR Homo sapiens cDNA clone 380332 3'. | -3,8 | -0,75 | 38 | A | D | | -2,5 | -0,34 | -67 | A | D |
| zi67e01.s1 Stratagene colon (#937204) Homo sapiens cDNA clone 509688 3' similar to TR:G189087 G189087 NONSPECIFIC CROSSREACTING ANTIGEN.; | -11,7 | -7,49 | -13 | A | D | | -10,1 | -6,69 | 10 | A | D |
| zn53a05.s1 Stratagene muscle 937209 Homo sapiens cDNA clone 561872 3' similar to contains Alu repetitive element;. | -5,7 | -2,33 | -8 | A | D | | -4,8 | -1,79 | 62 | A | D |
| zl15b11.s1 Soares pregnant uterus NbHPU Homo sapiens cDNA clone 501981 3'. | -7,2 | -3,32 | -36 | A | D | | -5,4 | -2,52 | -14 | A | D |
| zo71b06.s1 Stratagene pancreas (#937208) Homo sapiens cDNA clone 592307 3'. | -4,7 | -4,3 | 974 | A | D | | -1,6 | -0,41 | 1912 | A | D |
| zo78e05.s1 Stratagene pancreas (#937208) Homo sapiens cDNA clone 593024 3'. | -6,7 | -3,65 | -1 | A | D | | -6,6 | -3,46 | -40 | A | D |
| zs16f08.s1 NCI_CGAP_GCB1 Homo sapiens cDNA clone IMAGE:685383 3'. | -11,4 | -4,56 | -38 | A | D | | -8,7 | -3,57 | -58 | A | D |
| zs91h04.s1 NCI_CGAP_GCB1 Homo sapiens cDNA clone IMAGE:704887 3'. | -4,4 | -1,34 | 25 | A | D | | -4,9 | -1,52 | 22 | A | D |
| zs92hf12.s1 Soares total fetus Nb2HF8.9w Homo sapiens cDNA clone 773495 3'. | -2,3 | -0,49 | -3 | A | D | | -5,4 | -2,3 | 27 | A | D |
| zv53d04.s1 Soares testis NHT Homo sapiens cDNA clone 757351 3'. | -3,5 | -0,83 | 58 | A | D | | -3 | -0,76 | -62 | A | D |

Fig. 9.3

EST Bladder candidates of 17742 ESTs
Exclusion of data sets incl. AFFX, all NC, all A, 3xNC + M*
2424 genes with sort score >= +/- 0,5 changing from N to tumor
42 genes LOST Abs calls PPAAA and DECREASED

| gene name | B=A | Fold Change T2g/lisolidP(vs)N | Sort Score T2g/lisolidP(vs)N | Abs Calls | N | A | B | C | D |
|---|---|---|---|---|---|---|---|---|---|
| Human mRNA for KIAA0347 gene, complete cds. | | -3,9 | -0,82 | PPAAA | 93 | 24 | 0 | 0 | 0 |
| Homo sapiens breast cancer suppressor candidate 1 (bcsc-1) mRNA, complete cds. | | -8,3 | -1,89 | PPAAA | 98 | -7 | 0 | 0 | 0 |
| Human liver arylamine N-acetyltransferase (EC 2.3.1.5) gene | | -1,2 | PPAAA | 160 | 98 | 0 | 0 | 0 | |
| yw37b04.r1 Homo sapiens cDNA clone 254383 5'. | | -4,5 | -1,67 | PPAAA | 230 | 25 | 0 | 0 | 0 |
| yq52h05.r1 Homo sapiens cDNA clone 199451 5'. | | -2,3 | -0,47 | PPAAA | 238 | 179 | 0 | 0 | 0 |
| H. sapiens partial cDNA sequence; clone c-3cg10. | | -5,3 | -3,02 | PPAAA | 433 | 719 | 0 | 0 | 0 |
| yn64a06.s1 Homo sapiens cDNA clone 173170 3'. | | -2,6 | -1,56 | PPAAA | 1411 | 742 | 0 | 0 | 0 |
| yy46c12.s1 Homo sapiens cDNA clone 276598 3' similar to contains L1.t1 L1 repetitive element.; | | -10,4 | -7,61 | PPAAA | 628 | 426 | 0 | 0 | 0 |
| za11a07.s1 Homo sapiens cDNA clone 292212 3'. | | -18,3 | -15,52 | PPAAA | 980 | 381 | 0 | 0 | 0 |
| yf35b02.s1 Homo sapiens cDNA clone 128811 3'. | | -2,6 | -0,48 | PPAAA | 154 | 112 | 0 | 0 | 0 |
| yg87f06.s1 Homo sapiens cDNA clone 40354 3'. | | -4,5 | -1,6 | PPAAA | 212 | 44 | 0 | 0 | 0 |
| zd89b03.s1 Soares fetal heart NbHH19W Homo sapiens cDNA clone 356621 3'. | | -6,4 | -2,63 | PPAAA | 247 | 868 | 0 | 0 | 0 |
| zk19f05.s1 Soares pregnant uterus NbHPU Homo sapiens cDNA clone 471011 3'. | | -1,7 | -0,15 | PPAAA | 182 | 101 | 0 | 0 | 0 |
| zf13t05.s1 Soares fetal heart NbHH19W Homo sapiens cDNA clone 376833 3'. | | -4,3 | -1,06 | PPAAA | 124 | 72 | 0 | 0 | 0 |
| zf50a03.s1 Soares retina N2b4HR Homo sapiens cDNA clone 380332 3'. | | -4,8 | -0,59 | PPAAA | 63 | 59 | 0 | 0 | 0 |
| zl67e01.s1 Stratagene colon (#937204) Homo sapiens cDNA clone 509688 3' similar to TR:G189087 G189087 NONSPECIFIC CROSSREACTING ANTIGEN.; | | -8,4 | -5,59 | PPAAA | 389 | 224 | 0 | 0 | 0 |
| zn53a05.s1 Stratagene muscle 937209 Homo sapiens cDNA clone 561872 3' similar to contains Alu repetitive element.; | | -3,3 | -1,02 | PPAAA | 181 | 52 | 0 | 0 | 0 |
| zt15b11.s1 Soares pregnant uterus NbHPU Homo sapiens cDNA clone 501981 3'. | | -4,9 | -1,99 | PPAAA | 259 | 303 | 0 | 0 | 0 |
| zo71b06.s1 Stratagene pancreas (#937208) Homo sapiens cDNA clone 592307 3'. | | 1,2 | 0,09 | PPAAA | 1174 | 1195 | 0 | 0 | 0 |
| zo78e05.s1 Stratagene pancreas (#937208) Homo sapiens cDNA clone 593024 3'. | | -6,6 | -3,41 | PPAAA | 338 | 534 | 0 | 0 | 0 |
| zs16f08.s1 NCI_CGAP_GCB1 Homo sapiens cDNA clone IMAGE:685383 3'. | | -7,2 | -2,82 | PPAAA | 195 | 64 | 0 | 0 | 0 |
| zs91h04.s1 NCI_CGAP_GCB1 Homo sapiens cDNA clone IMAGE:704887 3'. | | -3,9 | -1,06 | PPAAA | 142 | 76 | 0 | 0 | 0 |
| zw50d12.s1 Soares total fetus Nb2HF8 9w Homo sapiens cDNA clone 773495 3'. | | -4,9 | -1,56 | PPAAA | 218 | 140 | 0 | 0 | 0 |
| zv53d04.s1 Soares testis NHT Homo sapiens cDNA clone 757351 3'. | | -5,3 | -1,34 | PPAAA | 176 | 59 | 0 | 0 | 0 |

Fig. 9.4

EST Bladder candidates of 17742 ESTs
Exclusion of data sets incl. AFFX, all NC, all A, 3xNC + M*
2424 genes with sort score >= +/- 0.5 changing from N to tumor
42 genes LOST Abs calls PPAAA and DECREASED

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIP | Abs Call TagIIP | Diff Call TagIIP(vs)N | B=A |
|---|---|---|---|---|---|---|---|---|---|---|---|---|---|
| aa13e06.s1 Soares NhHMPu S1 Homo sapiens cDNA clone 8131154 3' | RC_AA456289_at | 610 | P | 219 | P | D | | -2.8 | -1.21 | 112 | A | D | |
| aa11f10.s1 Soares NhHMPu S1 Homo sapiens cDNA clone 812971 3' | RC_AA464603_at | 136 | P | 65 | P | D | | -2.1 | -0.29 | 13 | A | D | |
| zv14d09.s1 Soares NhHMPu S1 Homo sapiens cDNA clone 753617 3' | RC_AA478726_at | 147 | P | 109 | P | MD | | -2.4 | -0.41 | 135 | A | D | |
| zv14g12.s1 Soares NhHMPu S1 Homo sapiens cDNA clone 753670 3' | RC_AA478740_at | 7 | P | 0 | P | NC | | -3.7 | -0.49 | -166 | A | D | |
| zv45a05.s1 Soares ovary tumor NbHOT Homo sapiens cDNA clone 755560 3' | RC_AA481440_at | 471 | P | 334 | P | NC | | -1.4 | -0.12 | 94 | A | D | |
| af14g11.s1 Soares testis NHT Homo sapiens cDNA clone 1031684 3' | RC_AA608539_at | 48 | P | 24 | P | D | | -2.5 | -0.27 | -8 | A | D | |
| af14h01.s1 Soares testis NHT Homo sapiens cDNA clone 1031665 3' | RC_AA609540_at | 149 | P | 52 | P | NC | | -2.9 | -0.63 | 35 | A | D | |
| ae60g06.s1 Stratagene lung carcinoma 937218 Homo sapiens cDNA clone 851322 3' | RC_AA620587_at | 174 | P | 84 | P | NC | | -1.6 | -0.12 | 78 | A | D | |
| zc27a04.r1 Soares senescent fibroblasts NbHSF Homo sapiens cDNA clone 323502 5' | V144317_at | 90 | P | 56 | P | NC | | -1.6 | -0.1 | -4 | A | D | |
| H.sapiens mRNA for acylphosphatase, muscle type (MT) isoenzyme | X84195_at | 79 | P | 69 | P | NC | | -1.1 | -0.01 | 0 | A | D | |
| zp78h07.r1 Stratagene HeLa cell s3 937216 Homo sapiens cDNA clone 626365 5' | AA188921_at | 341 | P | 235 | P | NC | | -1.4 | -0.12 | -9 | A | D | |
| EST47122 Fetal kidney II Homo sapiens cDNA 5' end. | AA341723_at | 619 | P | 332 | P | NC | | -1.5 | -0.16 | 222 | A | D | |
| EST56447 Infant brain Homo sapiens cDNA 5' end similar to similar to S.cerevisiae hypothetical protein YBR201B. | AA349630_at | 475 | P | 556 | P | NC | | -1.1 | -0.02 | 41 | A | D | |
| zv11e04.r1 Soares NhHMPu S1 Homo sapiens cDNA clone 753342 5' | AA410375_at | 125 | P | 104 | P | NC | | -1.2 | -0.02 | 61 | A | D | |
| zv23a01.r1 Soares NhHMPu S1 Homo sapiens cDNA clone 754440 5' | AA410529_s_at | 221 | P | 114 | P | NC | | -1.4 | -0.09 | 96 | A | D | |
| zv57d06.r1 Soares NhHMPu S1 Homo sapiens cDNA clone 774155 5' | AA429793_at | 202 | P | 214 | P | NC | | 1.1 | 0 | 126 | A | D | |
| zv22d07.r1 Soares NhHMPu S1 Homo sapiens cDNA clone 754381 5' | AA436302_at | 989 | P | 1380 | P | NC | | 1.5 | 0.31 | 736 | A | D | |
| zw84c05.r1 Soares total fetus Nb2HF8 9w Homo sapiens cDNA clone 783656 5' | AA446695_at | 92 | P | 68 | P | NC | | -1.7 | -0.13 | 69 | A | D | |

Fig. 9.5

EST Bladder candidates of 17742 ESTs,
Exclusion of data sets incl. AFFX, all NC, all A, 3xNC + M*
2424 genes with sort score >= +/- 0,5 changing from N to tumor
42 genes LOST Abs calls PPAAA and DECREASED

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIisolidP | Abs Call T2gIIisolidP | Diff Call T2gIIisolidP(vs)N |
|---|---|---|---|---|---|---|---|---|---|---|---|
| aa13e06.s1 Soares NhHMPu S1 Homo sapiens cDNA clone 813154 3'. | -6,2 | -4,66 | 140 | A | D | | -4,9 | -3,49 | 413 | A | D |
| aa11f10.s1 Soares NhHMPu S1 Homo sapiens cDNA clone 812971 3'. | -7,2 | -2,43 | 8 | A | D | | -5,3 | -1,67 | 44 | A | D |
| zv14d09.s1 Soares NhHMPu S1 Homo sapiens cDNA clone 753617 3'. | -2,3 | -0,39 | 7 | A | D | | -6,4 | -2,17 | 122 | A | D |
| zv14g12.s1 Soares NhHMPu S1 Homo sapiens cDNA clone 753670 3'. | -12,4 | -2,54 | -245 | A | D | | -11,3 | -1,98 | 35 | A | D |
| zv45a05.s1 Soares ovary tumor NbHOT Homo sapiens cDNA clone 756560 3'. | -3,7 | -1,59 | 115 | A | D | | -3 | -1,1 | 96 | A | D |
| af14g11.s1 Soares testis NHT Homo sapiens cDNA clone 1031684 3'. | -3,8 | -0,5 | 10 | A | D | | -2,3 | -0,17 | -26 | A | D |
| af14h01.s1 Soares testis NHT Homo sapiens cDNA clone 1031665 3'. | -4,2 | -1,28 | 1 | A | D | | -5,9 | -1,99 | 57 | A | D |
| ae60g06.s1 Stratagene lung carcinoma 937218 Homo sapiens cDNA clone 951322 3'. | -2,2 | -0,38 | 41 | A | D | | -3,3 | -0,81 | 99 | A | D |
| zc27a04.r1 Soares senescent fibroblasts NbHSF Homo sapiens cDNA clone 323502 5'. | -5,7 | -1,44 | 15 | A | D | | -3,5 | -0,68 | 22 | A | D |
| H.sapiens mRNA for acylphosphatase, muscle type (MT) isoenzyme | -4,9 | -1,12 | -11 | A | D | | -4,0 | -0,75 | 41 | A | D |
| zp78h07.r1 Stratagene HeLa cell s3 937216 Homo sapiens cDNA clone 626365 5'. | -18,3 | -8,44 | -36 | A | D | | -13,5 | -6,99 | -116 | A | D |
| EST47122 Fetal kidney II Homo sapiens cDNA 5' end. | -2,8 | -1,23 | 317 | A | D | | -2 | -0,49 | 95 | A | D |
| EST56447 Infant brain Homo sapiens cDNA 5' end similar to similar to S.cerevisiae hypothetical protein YBR2018. | -28,8 | -13,25 | 222 | A | D | | -5,5 | -3,81 | 392 | A | D |
| zv11e04.r1 Soares NhHMPu S1 Homo sapiens cDNA clone 753342 5'. | -2 | -0,25 | 48 | A | D | | -2,6 | -0,48 | 15 | A | D |
| zv23a01.r1 Soares NhHMPu S1 Homo sapiens cDNA clone 754440 5'. | -2,3 | -0,47 | 115 | A | D | | -1,9 | -0,28 | -19 | A | D |
| zw57d06.r1 Soares total fetus Nb2HF8 9w Homo sapiens cDNA clone 774155 5'. | -4,5 | -1,63 | 25 | A | D | | -6,9 | -2,82 | 149 | A | D |
| zv22d07.r1 Soares NhHMPu S1 Homo sapiens cDNA clone 754381 5'. | -1,3 | -0,13 | 313 | A | D | | -2,8 | -1,52 | 182 | A | D |
| zw84c05.r1 Soares total fetus Nb2HF8 9w Homo sapiens cDNA clone 783656 5'. | -1,7 | -0,12 | 40 | A | D | | -2,9 | -0,56 | 16 | A | D |

Fig. 9.6

EST Bladder candidates of 17742 ESTs
Exclusion of data sets incl. AFFX, all NC, all A, 3xNC + M*
2424 genes with sort score >= +/- 0.5 changing from N to tumor
42 genes LOST Abs calls PPAAA and DECREASED

| gene name | B=A | Fold Change T2gIIIsolidP(vs)N | Sort Score T2gIIIsolidP(vs)N | Abs Calls | N | A | B | C | D |
|---|---|---|---|---|---|---|---|---|---|
| aa13906.s1 Soares NhHMPu S1 Homo sapiens cDNA clone 8131154 3' | | -1,7 | -0,31 | PPAAA | 610 | 219 | 0 | 0 | 0 |
| aa11f10.s1 Soares NhHMPu S1 Homo sapiens cDNA clone 812971 3' | | -4,0 | -1,07 | PPAAA | 138 | 65 | 0 | 0 | 0 |
| zv14d09.s1 Soares NhHMPu S1 Homo sapiens cDNA clone 753617 3' | | -4,7 | -1,38 | PPAAA | 147 | 109 | 0 | 0 | 0 |
| zv14g12.s1 Soares NhHMPu S1 Homo sapiens cDNA clone 753670 3' | | -6,3 | -1,54 | PPAAA | 7 | 0 | 0 | 0 | 0 |
| zv45a05.s1 Soares ovary tumor NbHOT Homo sapiens cDNA clone 756560 3' | | -3,6 | -1,52 | PPAAA | 471 | 334 | 0 | 0 | 0 |
| af14g11.s1 Soares testis NHT Homo sapiens cDNA clone 1031684 3' | | -2,9 | -0,23 | PPAAA | 48 | 24 | 0 | 0 | 0 |
| af14h01.s1 Soares testis NHT Homo sapiens cDNA clone 1031665 3' | | -4,0 | -1,17 | PPAAA | 149 | 52 | 0 | 0 | 0 |
| ae60g06.s1 Stratagene lung carcinoma 937218 Homo sapiens cDNA clone 951322 3' | | -,2 | -0,32 | PPAAA | 174 | 84 | 0 | 0 | 0 |
| zc27a04.r1 Soares senescent fibroblasts NbHSF Homo sapiens cDNA clone 323502 5' | | -2,7 | -0,38 | PPAAA | 90 | 56 | 0 | 0 | 0 |
| H.sapiens mRNA for acylphosphatase, muscle type (MT) isoenzyme | | -1,9 | -0,17 | PPAAA | 79 | 69 | 0 | 0 | 0 |
| zp78h07.r1 Stratagene HeLa cell s3 937216 Homo sapiens cDNA clone 626365 5' | | -2,9 | -0,97 | PPAAA | 341 | 236 | 0 | 0 | 0 |
| EST47122 Fetal kidney II Homo sapiens cDNA 5' end. | | -6,5 | -4,68 | PPAAA | 619 | 332 | 0 | 0 | 0 |
| EST56447 Infant brain Homo sapiens cDNA 5' end similar to similar to S.cerevisiae hypothetical protein YBR2018. | | -2,5 | -1,02 | PPAAA | 475 | 556 | 0 | 0 | 0 |
| zv11e04.r1 Soares NhHMPu S1 Homo sapiens cDNA clone 753342 5' | | -3,7 | -0,86 | PPAAA | 125 | 104 | 0 | 0 | 0 |
| zv23a01.r1 Soares NhHMPu S1 Homo sapiens cDNA clone 754440 5' | | -6,9 | -2,91 | PPAAA | 221 | 114 | 0 | 0 | 0 |
| zw57d06.r1 Soares total fetus Nb2HF8 9w Homo sapiens cDNA clone 774155 5' | | -2,7 | -0,65 | PPAAA | 202 | 214 | 0 | 0 | 0 |
| zv22d07.r1 Soares NhHMPu S1 Homo sapiens cDNA clone 754381 5' | | -4,8 | -3,76 | PPAAA | 989 | 1380 | 0 | 0 | 0 |
| zw84c05.r1 Soares total fetus Nb2HF8 9w Homo sapiens cDNA clone 763656 5' | | -3,7 | -0,81 | PPAAA | 92 | 68 | 0 | 0 | 0 |

Fig. 10.1

EST Bladder candidates of 17742 ESTs
Exclusion of data sets incl. AFFX, all NC, all A, 3xNC + M*
2424 genes with sort score >= +/- 0,5 changing from N to tumor
12 genes GAINED Abs calls APPPP and INCREASED
4 genes GAINED Abs calls APPPP and INCREASED in all comp

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TagIIP |
|---|---|---|---|---|---|---|---|---|---|---|
| Homo sapiens TTF-I interacting peptide 21 mRNA, partial cds. | AF000561_at | 154 | A | 425 | P | I | * | 3,4 | 1,61 | 315 |
| H. sapiens partial cDNA sequence; clone c-3fc12. | RC_F10453_at | 27 | A | 201 | P | I | * | -4,7 | 1,69 | 198 |
| yn53b04.s1 Homo sapiens cDNA clone 172111 3'. | RC_H20269_at | 162 | A | 361 | P | I | * | 2,9 | 1,25 | 1244 |
| yf14h07.s1 Homo sapiens cDNA clone 126877 3'. | RC_R07210_at | 175 | A | 743 | P | I | * | 4,2 | 2,88 | 512 |
| yj01b08.s1 Homo sapiens cDNA clone 147447 3'. | RC_R81173_at | 142 | A | 607 | P | I | * | 6,6 | 4,92 | 563 |
| yp89d08.s1 Homo sapiens cDNA clone 194607 3' similar to contains Alu repetitive element;. | RC_R87650_at | 45 | A | 122 | P | I | * | -2,6 | 0,47 | 151 |
| H. sapiens partial cDNA sequence; clone c-2ea12. | RC_Z40715_at | 110 | A | 363 | P | I | * | 3,3 | 1,31 | 547 |
| zk17c02.s1 Soares pregnant uterus NbHPU Homo sapiens cDNA clone 470786 3'. | RC_AA031698_at | 71 | A | 143 | P | I | * | 2 | 0,25 | 229 |
| zl05h04.s1 Soares fetal liver spleen 1NFLS S1 Homo sapiens cDNA clone 429943 3'. | RC_AA034069_at | 132 | A | 244 | P | I | * | 1,8 | 0,26 | 417 |
| zk54e03.s1 Soares pregnant uterus NbHPU Homo sapiens cDNA clone 486652 3'. | RC_AA044231_at | 42 | A | 393 | P | I | * | -8,4 | 4,86 | 262 |
| zm79a11.s1 Stratagene neuroepithelium (#937231) Homo sapiens cDNA clone 531836 3'. | RC_AA116036_at | 36 | A | 145 | P | I | * | 4,1 | 1,18 | 355 |
| zn92a08.s1 Stratagene lung carcinoma 937218 Homo sapiens cDNA clone 565622 3'. | RC_AA133250_at | -1 | A | 88 | P | I | * | -2,7 | 0,36 | 101 |

Fig. 10.2

EST Bladder candidates of 17742 ESTs
Exclusion of data sets incl. AFFX, all NC, all A, 3xNC + M*
2424 genes with sort score >= +/- 0.5 changing from N to tumor
12 genes GAINED Abs calls APPPP and INCREASED
4 genes GAINED Abs calls APPPP and INCREASED in all comp

| gene name | Abs Call T1g|||P | Diff Call T1g|||P(vs)N | B=A | Fold Change T1g|||P(vs)N | Sort Score T1g|||P(vs)N | Avg Diff T2g|||mixP | Abs Call T2g|||mixP | Diff Call T2g|||mixP(vs)N | B=A | Fold Change T2g|||mixP(vs)N | Sort Score T2g|||mixP(vs)N | Avg Diff T2g|||soli|dP |
|---|---|---|---|---|---|---|---|---|---|---|---|---|
| Homo sapiens TTF-I interacting peptide 21 mRNA, partial cds. | P | I |  | 2,8 | 1,01 | 337 | P | I |  | 2,7 | 0,95 | 326 |
| H. sapiens partial cDNA sequence; clone c-3fc12. | P | I |  | 2,2 | 0,4 | 46 | P | NC |  | -1,3 | 0,02 | 241 |
| yn53b04.s1 Homo sapiens cDNA clone 172111 3'. | P | I |  | 4,7 | 3,64 | 804 | P | I |  | 4,2 | 2,85 | 1463 |
| yf14h07.s1 Homo sapiens cDNA clone 126877 3'. | P | I |  | 2,9 | 1,23 | 771 | P | I |  | 5,2 | 4,33 | 449 |
| yj01b08.s1 Homo sapiens cDNA clone 147447 3'. | P | I |  | 4 | 2,26 | 442 | P | I |  | 3,1 | 1,3 | 366 |
| yp89d08.s1 Homo sapiens cDNA clone 194607 3' similar to contains Alu repetitive element;. | P | I |  | -3,2 | 0,79 | 205 | P | I |  | -3,6 | 1,15 | 98 |
| H. sapiens partial cDNA sequence; clone c-2ea12. | P | I |  | 5 | 3,12 | 1448 | P | I |  | 13,6 | 14,22 | 1753 |
| zk17c02.s1 Soares pregnant uterus NbHPU Homo sapiens cDNA clone 470786 3' | P | I |  | 2,6 | 0,85 | 185 | P | I |  | 2,8 | 0,7 | 248 |
| zi05h04.s1 Soares fetal liver spleen 1NFLS S1 Homo sapiens cDNA clone 429943 3' | P | I |  | 3,1 | 1,28 | 435 | P | I |  | 3,3 | 1,42 | 138 |
| zk54e03.s1 Soares pregnant uterus NbHPU Homo sapiens cDNA clone 486652 3' | P | I |  | -5,6 | 2,52 | 396 | P | MI |  | -6,8 | 3,95 | 245 |
| zm79a11.s1 Stratagene neuroepithelium (#937231) Homo sapiens cDNA clone 531836 3' | P | I |  | 9,9 | 5,39 | 387 | P | I |  | 10,8 | 6,06 | 360 |
| zn92a08.s1 Stratagene lung carcinoma 937218 Homo sapiens cDNA clone 555622 3'. | P | I |  | -3,1 | 0,53 | 246 | P | I |  | -5,1 | 2,05 | 168 |

Fig. 10.3

EST Bladder candidates of 17742 ESTs
Exclusion of data sets incl. AFFX, all NC, all A, 3xNC + M*
2424 genes with sort score >= +/- 0.5 changing from N to tumor
12 genes GAINED Abs calls APPPP and INCREASED
4 genes GAINED Abs calls APPPP and INCREASED in all comp

| gene name | Abs Call T2gIIsolidP | Diff Call T2gIIsolidP(vs)N | B=A | Fold Change T2gIIsolidP(vs)N | Sort Score T2gIIsolidP(vs)N | Abs Calls | N | A | B | C | D |
|---|---|---|---|---|---|---|---|---|---|---|---|
| Homo sapiens TTF-I interacting peptide 21 mRNA, partial cds. | P | NC | - | 2.7 | 0.92 | APPPP | 0 | 425 | 315 | 337 | 326 |
| H. sapiens partial cDNA sequence; clone c-3fc12. | P | MI | - | ~-1.3 | -0.03 | APPPP | 0 | 201 | 198 | 46 | 241 |
| yn53b04.s1 Homo sapiens cDNA clone 172111 3'. | P | I | - | 4.7 | 3.57 | APPPP | 0 | 361 | 1244 | 804 | 1463 |
| yf14h07.s1 Homo sapiens cDNA clone 126877 3'. | P | NC | - | 2.6 | 0.86 | APPPP | 0 | 743 | 512 | 771 | 449 |
| yj01b08.s1 Homo sapiens cDNA clone 147447 3'. | P | NC | - | 2.6 | 0.79 | APPPP | 0 | 687 | 563 | 442 | 366 |
| yp89d08.s1 Homo sapiens cDNA clone 194607 3' similar to contains Alu repetitive element;. | P | NC | - | ~1.8 | 0.13 | APPPP | 0 | 122 | 151 | 205 | 98 |
| H. sapiens partial cDNA sequence; clone c-2ea12. | P | I | - | 16.2 | 17.52 | APPPP | 0 | 363 | 547 | 1448 | 1753 |
| zk17c02.s1 Soares pregnant uterus NbHPU Homo sapiens cDNA clone 470786 3'. | P | NC | - | ~-2.4 | 0.4 | APPPP | 0 | 143 | 229 | 186 | 248 |
| zi05h04.s1 Soares fetal liver spleen 1NFLS S1 Homo sapiens cDNA clone 429943 3'. | P | I | - | 1 | 0 | APPPP | 0 | 244 | 417 | 435 | 138 |
| zk54e03.s1 Soares pregnant uterus NbHPU Homo sapiens cDNA clone 486652 3'. | P | NC | - | ~-3.9 | 1.41 | APPPP | 0 | 393 | 262 | 396 | 245 |
| zm79a11.s1 Stratagene neuroepithelium (#937231) Homo sapiens cDNA clone 531836 3'. | P | I | - | ~-9.4 | 5.32 | APPPP | 0 | 145 | 355 | 387 | 380 |
| zn92a06.s1 Stratagene lung carcinoma 937218 Homo sapiens cDNA clone 565622 3'. | P | I | - | ~-3.4 | 0.83 | APPPP | 0 | 88 | 101 | 246 | 168 |

Fig. 11.1

EST Bladder candidates of 17742 ESTs
Exclusion of data sets incl. AFFX, all NC, all A, 3xNC + M*
2424 genes with sort score >= +/- 0,5 changing from N to tumor
4 genes GAINED Abs calls AAPPP and INCREASED in all comp
9 genes GAINED Abs calls AAPPP and INCREASED

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort score TagIIP(vs)N | Avg Diff T49IIIP | Abs Call T49IIIP | Diff Call T49IIIP(vs)N | B=A | Fold Change T49IIIP(vs)N | Sort Score T49IIIP(vs)N | Avg Diff T49IIImixP |
|---|---|---|---|---|---|---|---|---|---|---|---|---|---|---|---|---|
| Homo sapiens mRNA for CC chemokine, complete cds. | AB000221_at | 91 | A | 97 | A | NC | * | 1,1 | 0 | 283 | P | I | * | 3,1 | 1,02 | 590 |
| Human fetal brain cDNA 3'-end GEN-097D06. | RC_D60296_at | 51 | A | 28 | A | NC | * | -1,2 | -0,01 | 139 | P | I | * | 2,7 | 0,55 | 64 |
| Human fetal brain cDNA 3'-end GEN-132E11. | RC_D60813_at | 40 | A | 27 | A | NC | * | -1,3 | -0,02 | 137 | P | I | * | -3,2 | 0,73 | 60 |
| yg71a11.s1 Homo sapiens cDNA clone 38542 3' | RC_R49708_s_at | -43 | A | -90 | A | NC | * | ~1,8 | 0,07 | 180 | P | I | * | -7,4 | 2,67 | 55 |
| H. sapiens partial cDNA sequence; clone c-02a08. | RC_Z38182_at | 84 | A | 177 | A | NC | * | 2,1 | 0,33 | 736 | P | I | * | 8,7 | 6,92 | 161 |
| aa38e07.s1 NCI_CGAP_GCB1 Homo sapiens cDNA clone IMAGE:8155556 3'. | RC_AA456821_at | 46 | A | 48 | A | NC | * | 1 | 0 | 109 | P | I | * | 2,3 | 0,34 | 122 |
| ae53d05.s1 Stratagene lung carcinoma 937218 Homo sapiens cDNA clone 950601 3' | RC_AA608545_at | -43 | A | 20 | A | NC | * | 1,1 | 0 | 140 | P | I | * | -7,0 | 2,41 | 182 |
| ae58g12.s1 Stratagene lung carcinoma 937218 Homo sapiens cDNA clone 951142 3' | RC_AA620553_s_at | 97 | A | 68 | A | NC | * | -1,4 | -0,06 | 152 | P | I | * | 3 | 0,98 | 166 |
| cp3067.seq.F Fetal heart, Lambda ZAP Express Homo sapiens cDNA 5'. | AA095119_at | 3 | A | 100 | A | * | * | ~6,8 | 1,47 | 60 | P | I | * | ~6,0 | 1,34 | 137 |

Fig. 11.2

EST Bladder candidates of 17742 ESTs
Exclusion of data sets incl. AFFX, all NC, all A, 3xNC + M*
2424 genes with sort score >= +/- 0,5 changing from N to tumor
4 genes GAINED Abs calls AAPPP and INCREASED in all comp
9 genes GAINED Abs calls AAPPP and INCREASED

| gene name | Abs Call T2gIIImixP | Diff Call T2gIIImixP(vs)N | B=A | Fold Change T2gIIImixP(vs)N | Sort Score T2gIIImixP(vs)N | Avg Diff T2gIIsolidP | Abs Call T2gIIsolidP | Diff Call T2gIIsolidP(vs)N | B=A | Fold Change T2gIIsolidP(vs)N | Sort Score T2gIIsolidP(vs)N | Abs Calls | N | A | B | C | D |
|---|---|---|---|---|---|---|---|---|---|---|---|---|---|---|---|---|---|
| Homo sapiens mRNA for CC chemokine, complete cds. | P | I | * | 6,5 | 4,52 | 1379 | P | I | * | 15,1 | 14,73 | AAPPP | 0 | 0 | 283 | 590 | 1379 |
| Human fetal brain cDNA 3'-end GEN-097D06. | P | NC | * | 1,4 | 0,05 | 111 | P | NC | * | -2,3 | 0,3 | AAPPP | 0 | 0 | 139 | 64 | 111 |
| Human fetal brain cDNA 3'-end GEN-132E11. | P | NC | * | -1,3 | 0,02 | 67 | P | NC | * | -1,4 | 0,03 | AAPPP | 0 | 0 | 137 | 60 | 67 |
| yg71a11.s1 Homo sapiens cDNA clone 38542 3'. | P | NC | * | -2,9 | 0,23 | 51 | P | NC | * | -1,5 | 0,05 | AAPPP | 0 | 0 | 180 | 55 | 51 |
| H. sapiens partial cDNA sequence; clone c-02a08. | P | NC | * | 1,9 | 0,23 | 316 | P | I | * | 3,8 | 1,54 | AAPPP | 0 | 0 | 736 | 161 | 316 |
| aa38e07.s1 NCI_CGAP_GCB1 Homo sapiens cDNA clone IMAGE:815556 3'. | P | I | * | 2,6 | 0,47 | 198 | P | I | * | 4,3 | 1,49 | AAPPP | 0 | 0 | 109 | 122 | 198 |
| ae53d05.s1 Stratagene lung carcinoma 937218 Homo sapiens cDNA clone 950601 3' | P | I | * | -6,5 | 2,49 | 169 | P | I | * | -4,7 | 1,54 | AAPPP | 0 | 0 | 140 | 182 | 169 |
| ae58g12.s1 Stratagene lung carcinoma 937218 Homo sapiens cDNA clone 951142 3'. | P | NC | * | 3 | 1 | 376 | P | I | * | 5,3 | 3,24 | AAPPP | 0 | 0 | 152 | 166 | 376 |
| cp3087.seq.F Fetal heart, Lambda ZAP Express Homo sapiens cDNA 5'. | P | I | * | -6,5 | 2,09 | 196 | P | I | * | -6,5 | 2,52 | AAPPP | 0 | 0 | 80 | 137 | 196 |

Fig. 12.1

EST Bladder candidates of 17742 ESTs
Exclusion of data sets incl. AFFX, all NC, all A, 3xNC + M*
2424 genes with sort score >= +/- 0,5 changing from N to tumor
11 genes GAINED Abs calls AAAPP and INCREASED
3 genes GAINED Abs calls AAAPP and INCREASED in all comp

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A |
|---|---|---|---|---|---|---|---|---|---|---|---|---|---|
| ye73c08.s1 Homo sapiens cDNA clone 123374 3'. | RC_R00083_at | -523 | A | -413 | A | NC | . | -3.3 | 0.25 | -956 | A | NC | . |
| yj80e01.s1 Homo sapiens cDNA clone 155064 3'. | RC_R71391_at | 69 | A | 897 | A | NC | . | 5.3 | 3.71 | 1252 | A | NC | . |
| seq2147 Homo sapiens cDNA clone NHB3MK-9 3'. | RC_T23991_at | 219 | A | 85 | A | NC | . | -1.2 | -0.03 | 123 | A | NC | . |
| yd70t06.s1 Homo sapiens cDNA clone 113603 3' similar to contains Alu repetitive element. | RC_T79196_at | 35 | A | 35 | A | NC | . | -1.0 | 0 | 78 | A | NC | . |
| zo26a09.s1 Stratagene colon (#937204) Homo sapiens cDNA clone 587992 3'. | RC_AA130596_at | 59 | A | 20 | A | NC | . | 1.3 | 0.02 | 62 | A | NC | . |
| zx89d06.s1 Soares ovary tumor NbHOT Homo sapiens cDNA clone 810923 3'. | RC_AA459310_r_at | 775 | A | 42 | A | NC | . | -13.1 | -8.46 | 823 | A | NC | . |
| aa48f12.s1 NCI_CGAP_GCB1 Homo sapiens cDNA clone IMAGE:824207 3'. | RC_AA490965_at | 10 | A | -11 | A | NC | . | -1.7 | -0.04 | 16 | A | NC | . |
| Human DNA binding protein homolog (DRX) mRNA, partial cds | U88047_at | 54 | A | 57 | A | NC | . | 1 | 0 | 90 | A | NC | . |
| Human DSC2 mRNA for desmocollins type 2a and 2b | X56807_at | 23 | A | 7 | A | NC | . | -2.0 | -0.08 | 32 | A | NC | . |
| zi01b10.r1 Soares fetal liver spleen 1NFLS S1 Homo sapiens cDNA clone 429499 5'. | AA011479_at | 27 | A | -158 | A | NC | . | -12.4 | -1.2 | 90 | A | NC | . |
| EST112387 Aorta endothelial cells Homo sapiens cDNA 5' end. | AA296821_at | 31 | A | -10 | A | NC | . | -2.1 | -0.13 | 40 | A | NC | . |

Fig. 12.2

EST Bladder candidates of 17742 ESTs
Exclusion of data sets incl. AFFX, all NC, all A, 3xNC + M*
2424 genes with sort score >= +/- 0,5 changing from N to tumor
11 genes GAINED Abs calls AAAPP and INCREASED
3 genes GAINED Abs calls AAAPP and INCREASED in all comp

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A | Fold Change T2gIIIsolidP(vs)N |
|---|---|---|---|---|---|---|---|---|---|---|---|---|---|
| ya73c08.s1 Homo sapiens cDNA clone 1233374 3'. | ~10,0 | -0,97 | 666 | P | I | * | ~16,0 | 11,46 | 1365 | P | I | * | 8,6 |
| yj80e01.s1 Homo sapiens cDNA clone 155054 3'. | 7,3 | 6,41 | 1043 | P | I | * | 6,4 | 5,08 | 1512 | P | I | * | 9,5 |
| seq2147 Homo sapiens cDNA clone NHB3MK-9 3'. | -1 | 0 | 56 | P | NC | * | -1,1 | -0,01 | 485 | P | I | * | 2,2 |
| yd70l06.s1 Homo sapiens cDNA clone 113603 3' similar to contains Alu repetitive element;. | -1,9 | 0,15 | 473 | P | I | * | -8,2 | 5,25 | 204 | P | I | * | -3,4 |
| zo26a09.s1 Stratagene colon (#937204) Homo sapiens cDNA clone 587992 3'. | 1,5 | 0,08 | 212 | P | MI | * | 3,9 | 1,58 | 174 | P | MI | * | -4,0 |
| zx89d06.s1 Soares ovary tumor NbHOT Homo sapiens cDNA clone 810923 3'. | 1,1 | 0,01 | 1805 | P | MI | * | 2,9 | 2,2 | 2171 | P | MI | * | 3,4 |
| aa48f12.s1 NCI_CGAP_GCB1 Homo sapiens cDNA clone IMAGE:824207 3'. | -1,6 | 0,03 | 71 | P | I | * | -3,3 | 0,56 | 106 | P | MI | * | -3,3 |
| Human DNA binding protein homolog (DRX) mRNA, partial cds | 1,7 | 0,11 | 172 | P | I | * | 3,2 | 0,84 | 130 | P | NC | * | 2,4 |
| Human DSC2 mRNA for desmocollins type 2a and 2b | 1,4 | 0,03 | 44 | P | NC | * | -1,7 | 0,07 | 146 | P | I | * | -4,0 |
| zl01b10.r1 Soares fetal liver spleen 1NFLS S1 Homo sapiens cDNA clone 429499 5' | 3,3 | 0,66 | 585 | P | I | * | -4,3 | 1,2 | 2544 | P | I | * | -22,9 |
| EST112387 Aorta endothelial cells Homo sapiens cDNA 5' end. | 2 | 0,17 | 72 | P | NC | * | -2,3 | 0,27 | 216 | P | I | * | -5,5 |

Fig. 12.3

EST Bladder candidates of 17742 ESTs
Exclusion of data sets incl. AFFX, all NC, all A, 3xNC + M*
2424 genes with sort score >= +/- 0,5 changing from N to tumor
11 genes GAINED Abs calls AAAPP and INCREASED
3 genes GAINED Abs calls AAAPP and INCREASED in all comp

| gene name | Sort Score T2gIIIsolidP(vs)N | Abs Calls | N | A | B | C | D |
|---|---|---|---|---|---|---|---|
| ye73c08.s1 Homo sapiens cDNA clone 123374 3'. | 9,27 | AAAPP | 0 | 0 | 0 | 666 | 1365 |
| yj60e01.s1 Homo sapiens cDNA clone 155064 3'. | 9,45 | AAAPP | 0 | 0 | 0 | 1043 | 1512 |
| seq2147 Homo sapiens cDNA clone NHB3MK-9 3'. | 0,62 | AAAPP | 0 | 0 | 0 | 56 | 485 |
| yd70f06.s1 Homo sapiens cDNA clone 113603 3' similar to contains Alu repetitive element;. | 1 | AAAPP | 0 | 0 | 0 | 473 | 204 |
| zo26a09.s1 Stratagene colon (#937204) Homo sapiens cDNA clone 587992 3'. | 1,53 | AAAPP | 0 | 0 | 0 | 212 | 174 |
| zx89d06.s1 Soares ovary tumor NbHOT Homo sapiens cDNA clone 610923 3'. | 3,47 | AAAPP | 0 | 0 | 0 | 1805 | 2171 |
| aa48f12.s1 NCI_CGAP_GCB1 Homo sapiens cDNA clone IMAGE:824207 3'. | 0,65 | AAAPP | 0 | 0 | 0 | 71 | 106 |
| Human DNA binding protein homolog (DRX) mRNA, partial cds | 0,39 | AAAPP | 0 | 0 | 0 | 172 | 130 |
| Human DSC2 mRNA for desmocollins type 2a and 2b | 1,13 | AAAPP | 0 | 0 | 0 | 44 | 146 |
| zi01b10.r1 Soares fetal liver spleen 1NFLS S1 Homo sapiens cDNA clone 429499 5'. | 15,52 | AAAPP | 0 | 0 | 0 | 585 | 2544 |
| EST112387 Aorta endothelial cells Homo sapiens cDNA 5' end. | 2,24 | AAAPP | 0 | 0 | 0 | 72 | 216 |

Fig. 13.1

EST Bladder candidates of 17742 ESTs
Exclusion of data sets incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIsoIIdP

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff TrigIIP | Abs Call TrigIIP | Diff Call TrigIIP(vs)N | B=A |
|---|---|---|---|---|---|---|---|---|---|---|---|---|---|
| ze92h01.s1 Soares fetal heart NbHH19W Homo sapiens cDNA clone 366481 3'. | RC_AA026418_at | 1 | A | 75 | A | NC | * | -2,5 | 0,27 | -44 | A | NC | * |
| Human fetal brain cDNA 3'-end GEN-070G07. | RC_D59847_at | -187 | A | 482 | A | NC | * | 1,5 | 0,21 | 456 | A | NC | * |
| seq2287 Homo sapiens cDNA clone Cot250F1-b4HB3MA-8.3'. | RC_T24099_at | -507 | A | -303 | A | NC | * | -5,3 | 0,48 | -368 | A | NC | * |
| yh16a10.s1 Homo sapiens cDNA clone 37689 3'. | RC_R55292_at | 40 | A | -38 | A | NC | * | -2,5 | -0,16 | -4 | A | NC | * |
| zd25e10.s1 Soares fetal heart NbHH19W Homo sapiens cDNA clone 341705 3' similar to gb:M33188 OVARIAN GRANULOSA CELL 13,0 KD PROTEIN HGR74 (HUMAN).. | RC_W60582_at | 158 | A | 285 | A |   |   | 1,3 | 0,04 | 406 | A |   |   |
| Human 5-lipoxygenase activating protein (FLAP) gene | M63262_at | 34 | A | -129 | A | MD | * | -10,4 | -1,27 | 157 | A | NC | * |
| yc89405.s1 Homo sapiens cDNA clone 233443 3'. | RC_R38678_at | -114 | A | -124 | A | NC | * | -1,2 | -0,01 | 58 | A | NC | * |
| zd29g01.r1 Soares fetal heart NbHH19W Homo sapiens cDNA clone 342096 5'. | W60268_at | -17 | A | 106 | A | MI | * | -8,2 | 2,36 | -4 | A | NC | * |
| zx80d02.r1 Soares ovary tumor NbHOT Homo sapiens cDNA clone 810051 5' similar to TR:G1020091 G1020091 NEUROPSIN.:contains element LTR3 repetitive element.; | AA465016_at | 47 | A | -5 | A | NC | * | -4,2 | -0,62 | -69 | A | MD | * |
| yd83f04.s1 Homo sapiens cDNA clone 114847 3'. | RC_T79842_at | 246 | A | 442 | A |   |   | 4,2 | 2,08 | 983 | A | I |   |
| zq56g08.s1 Stratagene neuroepithelium (#937231) Homo sapiens cDNA clone 645662 3'. | RC_AA206225_at | 65 | A | 114 | A | NC | * | 1,7 | 0,14 | 28 | A | NC | * |
| zx37g02.s1 Soares total fetus Nb2HF8 9w Homo sapiens cDNA clone 788690 3'. | RC_AA449914_at | 173 | A | 106 | A | NC | * | -1,6 | -0,14 | 184 | A | NC | * |
| H. sapiens partial cDNA sequence; clone c-3bh08. | RC_F10211_at | -6 | A | -2 | A | NC | * | -1,5 | -0,04 | 41 | A | NC | * |
| zw41f05.s1 Soares ovary tumor NbHOT Homo sapiens cDNA clone 756225 3' similar to TR:G498729 G498729 ZINC FINGER PROTEIN.; | RC_AA480109_r_at | 80 | A | 22 | A | MD | * | -5,2 | -1,24 | 58 | A | NC | * |
| zi72a06.s1 Stratagene colon (#937204) Homo sapiens cDNA clone 510130 3'. | RC_AA053102_s_at | 14 | A | -56 | A | NC | * | -1,7 | -0,06 | -66 | A | NC | * |
| zw24b11.s1 Soares ovary tumor NbHOT Homo sapiens cDNA clone 770205,3' similar to contains element TAR1 repetitive element.; | RC_AA434113_at | 110 | A | 58 | A |   |   | -1,9 | -0,19 | 35 | A |   |   |
| zw62c02.s1 Soares total fetus Nb2HF8.9w Homo sapiens cDNA clone 774626 3'. | RC_AA441791_at | 119 | A | 164 | A | NC | * | 1 | 0 | -70 | A | NC | * |
| yz42c02.s1 Homo sapiens cDNA clone 285698 3'. | RC_N67583_at | 68 | A | -38 | A | NC | * | -3,2 | -0,36 | -31 | A | NC | * |
| ye47b12.s1 Homo sapiens cDNA clone 120863 3'. | RC_T96077_at | -179 | A | 109 | A | NC | * | -1,6 | -0,15 | 174 | A | NC | * |
| Human mRNA for KIAA0318 gene, partial cds. | AB002316_at | 34 | A | 53 | A | NC | * | 1,6 | 0,06 | 79 | A | NC | * |
| ze10g07.s1 Soares fetal heart NbHH19W Homo sapiens cDNA clone 358620 3'. | RC_W96222_at | 89 | A | -74 | A | D | * | -4,4 | -0,77 | -42 | A | D | * |
| Human hemopoietic cell protein-tyrosine kinase (HCK) gene, complete cds, clone lambda-a2/1a | M16591_s_at | 35 | A | -25 | A | MD | * | -4,7 | -0,56 | -13 | A | NC | * |
| yz76b12.s1 Homo sapiens cDNA clone 288959 3'. | RC_N58808_at | 138 | A | 76 | A | NC | * | -1,8 | -0,18 | 130 | A | NC | * |

Fig. 13.2

EST Bladder candidates of 177742 ESTs
Exclusion of data sets incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| ze92h01.s1 Soares fetal heart NbHH19W Homo sapiens cDNA clone 356481 3'. | -1,9 | -0,09 | 48 | A | NC | * | -1,8 | 0,08 | 2770 | P | I | . |
| Human fetal brain cDNA 3'-end GEN-070G07. | 2,4 | 0,77 | 286 | A | NC | * | 1,5 | 0,14 | 2179 | P | I | * |
| seq2287 Homo sapiens cDNA clone Cot250F-b4H53MA-8 3'. | -3,9 | 0,32 | -189 | A | NC | * | -4,8 | 0,48 | 2105 | P | I | . |
| yh18a10.s1 Homo sapiens cDNA clone 37669 3'. | -1,8 | -0,08 | 119 | A | NC | * | -2,4 | 0,34 | 1955 | P | I | . |
| zd25e10.s1 Soares fetal heart NbHH19W Homo sapiens cDNA clone 341706 3' similar to | 2 | 0,37 | 291 | A | NC | * | 1,3 | 0,05 | 1474 | P | I | * |
| gb:M38188 OVARIAN GRANULOSA CELL 13.0 KD PROTEIN HGR74 (HUMAN);. | | | | | | | | | | | | |
| Human 5-lipoxygenase activating protein (FLAP) gene | 2 | 0,18 | 29 | A | MD | * | -4,2 | -0,32 | 1296 | P | I | . |
| yo69d05.s1 Homo sapiens cDNA clone 23443 3'. | -1,9 | -0,09 | -10 | A | NC | * | -2,7 | 0,21 | 1235 | P | I | . |
| zd29g01.r1 Soares fetal heart NbHH19W Homo sapiens cDNA clone 342096 5'. | -1,7 | 0,04 | 73 | A | MI | * | -2,9 | 0,43 | 1234 | P | I | . |
| zx60d02.r1 Soares ovary tumor NbHOT Homo sapiens cDNA clone 810051 5' similar to | -6,7 | -1,01 | -41 | A | NC | * | -3,9 | -0,42 | 1047 | P | I | . |
| TR:G1020091 G1020091 NEUROPSIN. ;contains element LTR3 repetitive element;. | | | | | | | | | | | | |
| yd83f04.s1 Homo sapiens cDNA clone 114847 3'. | 3,1 | 1,69 | 687 | A | NC | * | 2 | 0,46 | 1007 | P | I | . |
| zq56g08.s1 Stratagene neuroepithelium (#937231) Homo sapiens cDNA clone 645662 3'. | -1,8 | -0,1 | 26 | A | NC | * | -1,7 | -0,07 | 832 | P | I | . |
| zx37g02.s1 Soares total fetus Nb2HF8.9w Homo sapiens cDNA clone 788690 3'. | 1,1 | 0 | 247 | A | NC | * | 1,4 | 0,09 | 758 | P | I | . |
| H. sapiens partial cDNA sequence, clone c-3bh08. | -1,4 | 0,03 | -28 | A | NC | * | -1,4 | -0,03 | 681 | P | I | . |
| zw41f05.s1 Soares ovary tumor NbHOT Homo sapiens cDNA clone 756225 3' similar to | -1,7 | -0,12 | 61 | A | D | * | -1,3 | -0,03 | 625 | P | I | . |
| TR:G498729 G498729 ZINC FINGER PROTEIN ;. | | | | | | | | | | | | |
| zf72a06.s1 Stratagene colon (#937204) Homo sapiens cDNA clone 510130 3'. | -1,4 | -0,03 | -79 | A | NC | * | -1,7 | -0,06 | 605 | P | I | . |
| zw24b11.s1 Soares ovary tumor NbHOT Homo sapiens cDNA clone 770205 3' similar | -3,2 | -0,67 | 22 | A | NC | * | -1 | 0 | 519 | P | I | . |
| to contains element TAR1 repetitive element ;. | | | | | | | | | | | | |
| zw62c02.s1 Soares total fetus Nb2HF8.9w Homo sapiens cDNA clone 774626 3'. | -2,6 | 0,11 | -150 | A | NC | * | 1,1 | 0 | 519 | P | I | . |
| yz42c02.s1 Homo sapiens cDNA clone 285638 3'. | -4,6 | -1,27 | -139 | A | NC | * | -4,4 | -0,49 | 494 | P | I | . |
| ye47b12.s1 Homo sapiens cDNA clone 120863 3'. | -1 | 0 | 318 | A | NC | * | 1,8 | 0,26 | 492 | P | I | . |
| Human mRNA for KIAA0316 gene, partial cds. | 1,4 | 0,04 | 77 | A | NC | * | 2,2 | 0,25 | 490 | P | I | . |
| ze10g07.s1 Soares fetal heart NbHH19W Homo sapiens cDNA clone 358520 3'. | -3,7 | -0,61 | -51 | A | D | * | -3,3 | -0,44 | 395 | P | I | . |
| Human hemopoietic cell protein-tyrosine kinase (HCK) gene, complete cds, clone lambda-a2/1a | -3,4 | -0,32 | -25 | A | MD | * | -3,0 | -0,21 | 358 | P | I | . |
| yz76b12.s1 Homo sapiens cDNA clone 288069 3'. | -1,1 | 0 | 113 | A | NC | * | -1,9 | -0,23 | 349 | P | I | . |

Fig. 13.3

EST Bladder candidates of 17742 ESTs
Exclusion of data sets Incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Fold Change T2gIIIsolidP(vs)N | Sort Score T2gIIIsolidP(vs)N | Abs Calls | N | A | B | C | D |
|---|---|---|---|---|---|---|---|---|
| ze92h01.s1 Soares fetal heart NbHH19W Homo sapiens cDNA clone 366461 3'. | -42,6 | 36,56 | AAAAP | 0 | 0 | 0 | 0 | 2770 |
| Human fetal brain cDNA 3'-end GEN-070G07. | 11,6 | 15,32 | AAAAP | 0 | 0 | 0 | 0 | 2179 |
| seq287 Homo sapiens cDNA clone Col250Ft-b4HB3MA-6 3'. | -29,3 | 24,83 | AAAAP | 0 | 0 | 0 | 0 | 2105 |
| yh16a10.s1 Homo sapiens cDNA clone 37689 3'. | -26,4 | 25,16 | AAAAP | 0 | 0 | 0 | 0 | 1955 |
| zd25e10.s1 Soares fetal heart NbHH19W Homo sapiens cDNA clone 341706 3' similar to | 8,8 | 9,69 | AAAAP | 0 | 0 | 0 | 0 | 1474 |
| gbM38183 OVARIAN GRANULOSA CELL 13.0 KD PROTEIN HGR74 (HUMAN);. | | | | | | | | |
| Human 5-lipoxygenase activating protein (FLAP) gene | -31,8 | 21,48 | AAAAP | 0 | 0 | 0 | 0 | 1296 |
| yc89d05.s1 Homo sapiens cDNA clone 23443 3'. | -17,3 | 14,43 | AAAAP | 0 | 0 | 0 | 0 | 1235 |
| zd29g01.r1 Soares fetal heart NbHH19W Homo sapiens cDNA clone 342096 5'. | -27,9 | 18,9 | AAAAP | 0 | 0 | 0 | 0 | 1234 |
| zx80d02.r1 Soares ovary tumor NbHOT Homo sapiens cDNA clone 810051 5' similar to | -26,1 | 17,68 | AAAAP | 0 | 0 | 0 | 0 | 1047 |
| TR:G1020091 G1020091 NEUROPSIN. ;contains element LTR3 repetitive element ;. | | | | | | | | |
| yb83f04.s1 Homo sapiens cDNA clone 114847 3'. | 4,3 | 2,44 | AAAAP | 0 | 0 | 0 | 0 | 1007 |
| zq56g08.s1 Stratagene neuroepithelium (#937231) Homo sapiens cDNA clone 645662 3'. | 3,8 | 2,38 | AAAAP | 0 | 0 | 0 | 0 | 832 |
| zx37g02.s1 Soares total fetus Nb2HF8 9w Homo sapiens cDNA clone 788650 3'. | 4,4 | 3,06 | AAAAP | 0 | 0 | 0 | 0 | 758 |
| H. sapiens partial cDNA sequence; clone c-3UI08. | -10,8 | 8,12 | AAAAP | 0 | 0 | 0 | 0 | 681 |
| zv41f05.s1 Soares ovary tumor NbHOT Homo sapiens cDNA clone 755225 3' similar to | 5,6 | 3,36 | AAAAP | 0 | 0 | 0 | 0 | 625 |
| TR:G498729 G498729 ZINC FINGER PROTEIN.;. | | | | | | | | |
| zl72a06.s1 Stratagene colon (#937204) Homo sapiens cDNA clone 510130 3'. | -8,6 | 5,89 | AAAAP | 0 | 0 | 0 | 0 | 605 |
| zw24b11.s1 Soares ovary tumor NbHOT Homo sapiens cDNA clone 770205 3' similar | 4,7 | 2,8 | AAAAP | 0 | 0 | 0 | 0 | 519 |
| to contains element TAR1 repetitive element ;. | | | | | | | | |
| zw62c02.s1 Soares total fetus Nb2HF8 9w Homo sapiens cDNA clone 774626 3'. | 5,2 | 3,24 | AAAAP | 0 | 0 | 0 | 0 | 519 |
| yz42c02.s1 Homo sapiens cDNA clone 285698 3'. | -7,1 | 4,6 | AAAAP | 0 | 0 | 0 | 0 | 494 |
| ye47b12.s1 Homo sapiens cDNA clone 120863 3'. | 2,7 | 1,05 | AAAAP | 0 | 0 | 0 | 0 | 492 |
| Human mRNA for KIAA0316 gene, partial cds. | 6,5 | 5,52 | AAAAP | 0 | 0 | 0 | 0 | 490 |
| ze10g07.s1 Soares fetal heart NbHH19W Homo sapiens cDNA clone 358620 3'. | 4,4 | 2,24 | AAAAP | 0 | 0 | 0 | 0 | 395 |
| Human hemopoietic cell protein-tyrosine kinase (HCK) gene, complete cds, clone lambda-az/1a | -8,9 | 4,91 | AAAAP | 0 | 0 | 0 | 0 | 358 |
| yz76b12.s1 Homo sapiens cDNA clone 268959 3'. | 2,3 | 0,57 | AAAAP | 0 | 0 | 0 | 0 | 349 |

Fig. 13.4

EST Bladder candidates of 17742 ESTs
Exclusion of data sets incl. AFFX, all NC, all A, 3xNC + M*
2424 genes with sort score >= +/- 0.5 changing from N to tumor
57 genes GAINED Abs calls AAAAP and INCREASED
sorted acc. To Avg Diff T2gIIIsolidP

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A |
|---|---|---|---|---|---|---|---|---|---|---|---|---|---|
| H. saplens partial cDNA sequence; clone c-39g09. | RC_F10040_at | 14 | A | 128 | A | NC | . | 1.4 | 0.06 | 28 | A | NC | . |
| zx62b09.s1 Soares total fetus Nb2HF8 9w Homo sapiens cDNA clone 796025 3'. | RC_AA461549_at | 28 | A | 22 | A | NC | . | -1.2 | -0.01 | 32 | A | NC | . |
| zd35d04.s1 Soares fetal heart NbHH19W Homo sapiens cDNA clone 342631 3'. | RC_W66663_at | 121 | A | 137 | A | NC | . | 1.1 | 0.01 | 153 | A | NC | . |
| zn20d05.s1 Stratagene neuroepithelium NT2RAMI 937234 Homo sapiens cDNA clone 547877 3'. | RC_AA084640_at | 150 | A | 233 | A | NC | . | 1.6 | 0.13 | 177 | A | NC | . |
| HUMGS0007850, Human Gene Signature, 3'-directed cDNA sequence. | C01169_at | -11 | A | -11 | A | NC | . | -1.6 | -0.03 | -10 | A | NC | . |
| ab04a05.s1 Stratagene fetal retina 937202 Homo sapiens cDNA clone 839792 3'. | RC_AA491465_at | 16 | A | 15 | A | NC | . | -1.0 | 0 | 14 | A | NC | . |
| zd41c07.s1 Soares fetal heart NbHH19W Homo sapiens cDNA clone 343212 3'. | RC_W67564_s_at | -47 | A | 73 | A | NC | . | -3.5 | 0.45 | 8 | A | NC | . |
| Human beta-1-adrenergic receptor mRNA, complete cds. | J03019_s_at | 64 | A | 103 | A | NC | . | 1.6 | 0.11 | 165 | A | NC | . |
| yu77b06.s1 Homo sapiens cDNA clone 239795 3'. | RC_H80622_at | 46 | A | -42 | A | NC | . | -2.2 | -0.12 | -33 | A | NC | . |
| yy15h06.s1 Homo sapiens cDNA clone 271355 3'. | RC_N34686_at | -9 | A | 8 | A | NC | . | -1.4 | 0.03 | 10 | A | NC | . |
| yg91d08.s1 Homo sapiens cDNA clone 40992 3'. | RC_R66066_s_at | -45 | A | -7 | A | NC | . | -1.9 | 0.08 | -5 | A | NC | . |
| EST71577 Homo sapiens cDNA 3' end similar to None. | RC_T34611_at | 52 | A | 16 | A | NC | . | -1.7 | -0.07 | 37 | A | NC | . |
| zk15e12.s1 Soares pregnant uterus NbHPU Homo sapiens cDNA clone 470638 3'. | RC_AA031373_s_at | 12 | A | -15 | A | D | . | -1.6 | -0.05 | 25 | A | NC | . |
| Human mRNA for sp1-1 proto-oncogene. | X52055_at | 28 | A | -33 | A | NC | . | -2.2 | -0.07 | 37 | A | D | . |
| yz89g12.r1 Homo sapiens cDNA clone 290278 5'. | N77564_at | 16 | A | -38 | A | NC | . | -4.3 | -0.22 | -46 | A | NC | . |
| HUMGS0003713, Human Gene Signature, 3'-directed cDNA sequence. | C01765_at | -10 | A | -1 | A | NC | . | -1.5 | 0.02 | -6 | A | NC | . |
| ae32d03.s1 Gessler Wilms tumor Homo sapiens cDNA clone 897509 3'. | RC_AA496936_at | 20 | A | 5 | A | NC | . | -1.5 | -0.02 | 7 | A | NC | . |
| zk04e03.s1 Soares pregnant uterus NbHPU Homo sapiens cDNA clone 469564 3'. | RC_AA027103_at | 40 | A | -7 | A | NC | . | -1.0 | 0 | 62 | A | NC | . |
| yg32c11.s1 Homo sapiens cDNA clone 34069 3'. | RC_R44131_at | -34 | A | -18 | A | NC | . | -1.3 | 0.02 | -28 | A | NC | . |
| yz48f04.s1 Homo sapiens cDNA clone 286303 3'. | RC_N67727_at | 41 | A | -17 | A | NC | . | -1.9 | -0.08 | -24 | A | NC | . |
| ye52f03.s1 Homo sapiens cDNA clone 121373 3'. | RC_T96677_at | 34 | A | 39 | A | NC | . | -1.1 | 0 | 98 | A | NC | . |
| zo23g05.s1 Stratagene colon (#937204) Homo sapiens cDNA clone 587766 3'. | RC_AA134965_l_at | 15 | A | 34 | A | I | . | -2.6 | 0.22 | 60 | A | NC | . |

Fig. 13.5

EST Bladder candidates of 17742 ESTs
Exclusion of data sets incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| H. sapiens partial cDNA sequence; clone c-39g09. | -1,3 | 0,02 | -13 | A | NC | * | -1,5 | -0,04 | 329 | P | I | * |
| zx62b09.s1 Soares total fetus Nb2HF8 9w Homo sapiens cDNA clone 796025 3'. | 1,1 | 0,01 | 28 | A | NC | * | -1,3 | -0,02 | 325 | P | I | * |
| zd35d04.s1 Soares fetal heart NbHH19W Homo sapiens cDNA clone 342631 3'. | 1,3 | 0,04 | 75 | A | NC | * | -1,6 | -0,11 | 308 | P | I | * |
| zn20d05.s1 Stratagene neuroepithelium NT2RAMI 937234 Homo sapiens cDNA clone 547977 3'. | 1,2 | 0,02 | 157 | A | NC | * | 1 | 0 | 302 | P | I | * |
| HUMGS0007858, Human Gene Signature, 3'-directed cDNA sequence. | -1,5 | -0,02 | -18 | A | NC | * | -1,6 | -0,04 | 287 | P | I | * |
| ab04a05.s1 Stratagene fetal retina 937202 Homo sapiens cDNA clone 639792 3'. | -1,2 | 0,01 | 14 | A | NC | * | -1,2 | 0,01 | 268 | P | I | * |
| zd41c07.s1 Soares fetal heart NbHH19W Homo sapiens cDNA clone 343212 3'. | -2,2 | 0,11 | -68 | A | NC | * | -1,4 | -0,03 | 263 | P | I | * |
| Human beta-1-adrenergic receptor mRNA, complete cds. | 2,6 | 0,53 | 217 | A | NC | * | 3,4 | 1,07 | 246 | P | I | * |
| yu77b06.s1 Homo sapiens cDNA clone 239795 3'. | -2,5 | -0,15 | 15 | A | NC | * | -1,4 | -0,03 | 239 | P | I | * |
| yy15h06.s1 Homo sapiens cDNA clone 271355 3'. | -1,4 | 0,03 | -33 | A | NC | * | -1,4 | -0,03 | 222 | P | I | * |
| yg91d08.s1 Homo sapiens cDNA clone 40992 3'. | -1,9 | 0,09 | -101 | A | NC | * | -1,7 | -0,07 | 201 | P | I | * |
| EST71577 Homo sapiens cDNA 3' end similar to None. | -1,3 | -0,02 | -32 | A | D | * | -2,4 | -0,16 | 198 | P | I | * |
| zk15e12.s1 Soares pregnant uterus NbHPU Homo sapiens cDNA clone 470638 3'. | -1,1 | 0 | 10 | A | NC | * | -1,0 | 0 | 190 | P | I | * |
| Human mRNA for spi-1 proto-oncogene | 1,3 | 0,02 | 28 | A | NC | * | -2,2 | -0,09 | 190 | P | I | * |
| yz89g12.r1 Homo sapiens cDNA clone 290278 5'. | -4,2 | -0,23 | -20 | A | NC | * | -1,2 | -0,01 | 173 | P | I | * |
| HUMGS0003713, Human Gene Signature, 3'-directed cDNA sequence. | -1,2 | 0,01 | -17 | A | NC | * | -1,2 | -0,08 | 167 | P | I | * |
| ae32d03.s1 Gessler Wilms tumor Homo sapiens cDNA clone 897509 3'. | -1,5 | -0,02 | -17 | A | NC | * | -2,0 | 0,04 | 167 | P | I | * |
| zk04e03.s1 Soares pregnant uterus NbHPU Homo sapiens cDNA clone 469564 3'. | 1,5 | 0,05 | 13 | A | NC | * | -1,4 | 0,03 | 166 | P | I | * |
| yg32c11.s1 Homo sapiens cDNA clone 34089 3'. | -1,1 | 0,01 | -12 | A | NC | * | -1,4 | -0,01 | 164 | P | I | * |
| yz48f04.s1 Homo sapiens cDNA clone 286303 3'. | -2,0 | -0,1 | 20 | A | NC | * | -1,2 | 0 | 163 | P | I | * |
| ye52i03.s1 Homo sapiens cDNA clone 121373 3'. | -2,3 | 0,3 | 29 | A | NC | * | -1,1 | -0,01 | 162 | P | I | * |
| zo23g05.s1 Stratagene colon (#937204) Homo sapiens cDNA clone 587768 3'. | -4,0 | 0,81 | 27 | A | NC | * | -2,0 | 0,12 | 161 | P | I | * |

Fig. 13.6

EST Bladder candidates of 17742 ESTs
Exclusion of data sets incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Fold Change T2gIIIsolidP(vs)N | Sort Score T2gIIIsolidP(vs)N | Abs Calls | N | A | B | C | D |
|---|---|---|---|---|---|---|---|---|
| H. sapiens partial cDNA sequence; clone c-39g09. | -6,1 | 3,28 | AAAAP | 0 | 0 | 0 | 0 | 329 |
| zx62b09.s1 Soares total fetus Nb2HF8 9w Homo sapiens cDNA clone 796025 3'. | -8,2 | 4,35 | AAAAP | 0 | 0 | 0 | 0 | 325 |
| zd35d04.s1 Soares fetal heart NbHH19W Homo sapiens cDNA clone 342631 3'. | 2,6 | 0,71 | AAAAP | 0 | 0 | 0 | 0 | 308 |
| zn20d05.s1 Stratagene neuroepithelium NT2RAMI 937234 Homo sapiens cDNA clone 547977 3'. | -3,7 | 1,06 | AAAAP | 0 | 0 | 0 | 0 | 302 |
| HUMGS0007858, Human Gene Signature, 3'-directed cDNA sequence. | -8,0 | 3,96 | AAAAP | 0 | 0 | 0 | 0 | 287 |
| ab04a05.s1 Stratagene fetal retina 937202 Homo sapiens cDNA clone 839792 3'. | -7,1 | 3,4 | AAAAP | 0 | 0 | 0 | 0 | 268 |
| zd41c07.s1 Soares fetal heart NuHH19W Homo sapiens cDNA clone 343212 3'. | -5,4 | 2,28 | AAAAP | 0 | 0 | 0 | 0 | 263 |
| Human beta-1-adrenergic receptor mRNA, complete cds. | 3,9 | 1,43 | AAAAP | 0 | 0 | 0 | 0 | 246 |
| yu77b06.s1 Homo sapiens cDNA clone 239795 3'. | -4,2 | 1,53 | AAAAP | 0 | 0 | 0 | 0 | 239 |
| yy15h06.s1 Homo sapiens cDNA clone 271355 3'. | -4,3 | 1,49 | AAAAP | 0 | 0 | 0 | 0 | 222 |
| yg91d08.s1 Homo sapiens cDNA clone 40992 3'. | -5,5 | 2,26 | AAAAP | 0 | 0 | 0 | 0 | 201 |
| EST71577 Homo sapiens cDNA 3' end similar to None. | -3,1 | 0,83 | AAAAP | 0 | 0 | 0 | 0 | 198 |
| zk16e12.s1 Soares pregnant uterus NbHPU Homo sapiens cDNA clone 470638 3'. | -3,5 | 0,98 | AAAAP | 0 | 0 | 0 | 0 | 190 |
| Human mRNA for spi-1 proto-oncogene | -6,0 | 1,8 | AAAAP | 0 | 0 | 0 | 0 | 190 |
| yz89g12.r1 Homo sapiens cDNA clone 290278 5'. | -4,8 | 1,63 | AAAAP | 0 | 0 | 0 | 0 | 173 |
| HUMGS0003713, Human Gene Signature, 3'-directed cDNA sequence. | -3,8 | 0,78 | AAAAP | 0 | 0 | 0 | 0 | 167 |
| ae32d03.s1 Gessler Wilms tumor Homo sapiens cDNA clone 897509 3'. | -4,8 | 1,56 | AAAAP | 0 | 0 | 0 | 0 | 167 |
| zk04e03.s1 Soares pregnant uterus NbHPU Homo sapiens cDNA clone 469564 3'. | -2,8 | 0,59 | AAAAP | 0 | 0 | 0 | 0 | 166 |
| yg32c11.s1 Homo sapiens cDNA clone 34089 3'. | -3,8 | 0,95 | AAAAP | 0 | 0 | 0 | 0 | 164 |
| yz48f04.s1 Homo sapiens cDNA clone 286303 3'. | -3,1 | 0,79 | AAAAP | 0 | 0 | 0 | 0 | 163 |
| ye52f03.s1 Homo sapiens cDNA clone 121373 3'. | -2,8 | 0,59 | AAAAP | 0 | 0 | 0 | 0 | 162 |
| zo23g05.s1 Stratagene colon (#937204) Homo sapiens cDNA clone 587768 3'. | -4,7 | 1,52 | AAAAP | 0 | 0 | 0 | 0 | 161 |

Fig. 13.7

EST Bladder candidates of 17742 ESTs
Exclusion of data sets Incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T1gIIIP | Abs Call T1gIIIP | Diff Call T1gIIIP(vs)N | B=A |
|---|---|---|---|---|---|---|---|---|---|---|---|---|---|
| yd87610.s1 Homo sapiens cDNA clone 115219 3'. | RC_T86600_at | 43 A | A | 66 A | A | NC | * | -1,5 | 0,05 | 28 A | A | NC | * |
| zf51f03.s1 Soares retina N2b4HR Homo sapiens cDNA clone 380477 3'. | RC_AA054087_at | 77 A | A | 73 A | A | NC | * | | 0 | 33 A | A | NC | * |
| zv76b10.r1 Soares total fetus Nb2HF8 9w Homo sapiens cDNA 5'. | AA444374_at | 113 A | A | 81 A | A | NC | * | 1,6 | 0,1 | 5 A | A | NC | * |
| ys04401.s1 Homo sapiens cDNA clone 213817 3' similar to gb:J04970 CARBOXYPEPTIDASE M PRECURSOR (HUMAN);contains Alu repetitive element;. | RC_H72357_at | -3 A | A | 16 A | A | NC | * | -1,6 | 0,06 | 31 A | A | NC | * |
| ze37611.s1 Soares retina N2b4HR Homo sapiens cDNA clone 361173 3'. | RC_AA017045_at | -6 A | A | 10 A | A | NC | * | -1,9 | 0,05 | 3 A | A | NC | * |
| zi09c03.r1 Soares fetal liver spleen 1NFLS S1 Homo sapiens cDNA clone 430276 5'. | AA010324_at | -10 A | A | -4 A | A | NC | * | -1,3 | 0,01 | 38 A | A | NC | * |
| zs38b09.s1 Soares NhHMPu S1 Homo sapiens cDNA clone 687449 3'. | RC_AA234743_at | 29 A | A | 25 A | A | NC | * | -1,2 | -0,01 | 39 A | A | NC | * |
| zf20d06.s1 Soares fetal heart NbHH19W Homo sapiens cDNA clone 377483 3'. | RC_AA055892_at | 20 A | A | 12 A | A | NC | * | -1,5 | -0,03 | 123 A | A | NC | * |
| zw89g02.s1 Soares total fetus Nb2hF8 9w Homo sapiens cDNA clone 784178 3'. | RC_AA446650_at | 5 A | A | -2 A | A | NC | * | -1,4 | -0,02 | 15 A | A | NC | * |
| ys80e03.r1 Homo sapiens cDNA clone 221116 5'. | H91747_s_at | 10 A | A | 1 A | A | NC | * | -1,3 | -0,01 | -1 A | A | NC | * |
| zu63c08.r1 Soares testis NHT Homo sapiens cDNA clone 742870 5'. | AA401510_s_at | -1 A | A | -7 A | A | NC | * | -1,4 | -0,01 | 10 A | A | NC | * |
| zd31d10.s1 Soares fetal heart NbHH19W Homo sapiens cDNA clone 342259 3'. | RC_W61239_at | -528 A | A | -704 A | A | NC | * | -4,1 | 0,35 | -660 A | A | NC | * |

Fig. 13.8

EST Bladder candidates of 17742 ESTs
Exclusion of data sets Incl. AFFX, all NC, all A, 3xNC + M*
2424 genes with sort score >= +/- 0.5 changing from N to tumor
57 genes GAINED Abs calls AAAAP and INCREASED
sorted acc. To Avg Diff T2gIIIsolidP

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| yd87d10.s1 Homo sapiens cDNA clone 115219 3'. | -1,3 | -0,02 | 5 | A | NC | * | -1,6 | -0,06 | 152 | P | I | * |
| zf51103.s1 Soares retina N2b4HR Homo sapiens cDNA clone 380477 3'. | 1 | 0 | 108 | A | NC | * | 1,4 | 0,06 | 152 | P | I | * |
| zv76b10.r1 Soares total fetus Nb2HF8 9w Homo sapiens cDNA 5'. | -2,3 | 0,08 | 40 | A | NC | * | -3,0 | 0,24 | 152 | P | I | * |
| ys04f01.s1 Homo sapiens cDNA clone 213817 3' similar to gb:J04970 CARBOXYPEPTIDASE M PRECURSOR (HUMAN) ;contains Alu repetitive element;. | -1,7 | 0,06 | 40 | A | NC | * | -1,7 | 0,07 | 143 | P | I | * |
| ze37d11.s1 Soares retina N2b4HR Homo sapiens cDNA clone 361173 3'. | -1,8 | 0,05 | 12 | A | NC | * | -1,7 | 0,05 | 137 | P | I | * |
| zl09c03.r1 Soares fetal liver spleen 1NFLS S1 Homo sapiens cDNA clone 430276 5'. | -2,4 | 0,19 | 63 | A | NC | * | -2,8 | 0,33 | 127 | P | I | * |
| zs36b09.s1 Soares NhHMPu S1 Homo sapiens cDNA clone 687449 3'. | 1,3 | 0,03 | 41 | A | I | * | -1,4 | 0,03 | 100 | P | I | * |
| zt20d06.s1 Soares fetal heart NbHH19W Homo sapiens cDNA clone 377483 3'. | -7,3 | 2,31 | 97 | A | NC | * | -4,3 | 0,93 | 98 | P | I | * |
| zw89g02.s1 Soares total fetus Nb2HF8 9w Homo sapiens cDNA clone 784178 3'. | -1,5 | 0,03 | 28 | A | NC | * | -1,7 | 0,05 | 97 | P | I | * |
| ys80e03.r1 Homo sapiens cDNA clone 222116 5'. | -1,3 | -0,01 | 9 | A | NC | * | -1,0 | 0 | 94 | P | I | * |
| zu63c08.r1 Soares testis NHT Homo sapiens cDNA clone 742670 5'. | -1,6 | 0,03 | -1 | A | NC | * | -1,0 | 0 | 92 | P | I | * |
| zd31d10.s1 Soares fetal heart NbHH19W Homo sapiens cDNA clone 342259 3'. | -3,8 | -0,31 | -544 | A | NC | * | -1,3 | -0,02 | -116 | P | I | * |

Fig. 13.9

EST Bladder candidates of 17742 ESTs
Exclusion of data sets incl. AFFX, all NC, all A, 3xNC + M*
2424 genes with sort score >= +/- 0,5 changing from N to tumor
57 genes GAINED Abs calls AAAAP and INCREASED
sorted acc. To Avg Diff T2gIIIsolidP

| gene name | Fold Change T2gIIIsolidP(vs)N | Sort Score T2gIIIsolidP(vs)N | Abs Calls | N | A | B | C | D |
|---|---|---|---|---|---|---|---|---|
| yd87d10.s1 Homo sapiens cDNA clone 115219 3'. | -3,6 | 1,13 | AAAAP | 0 | 0 | 0 | 0 | 152 |
| zf51f03.s1 Soares retina N2b4HR Homo sapiens cDNA clone 360477 3'. | 2,8 | 0,73 | AAAAP | 0 | 0 | 0 | 0 | 152 |
| zv76b10.r1 Soares total fetus Nb2HF8 9w Homo sapiens cDNA 5'. | -5,2 | 1,64 | AAAAP | 0 | 0 | 0 | 0 | 152 |
| ys04f01.s1 Homo sapiens cDNA clone 213817 3' similar to gb:J04970 CARBOXYPEPTIDASE M PRECURSOR (HUMAN);contains Alu repetitive element;. | -3,1 | 0,6 | AAAAP | 0 | 0 | 0 | 0 | 143 |
| ze37d11.s1 Soares retina N2b4HR Homo sapiens cDNA clone 361173 3'. | -3,5 | 0,66 | AAAAP | 0 | 0 | 0 | 0 | 137 |
| zi09c03.r1 Soares fetal liver spleen 1NFLS S1 Homo sapiens cDNA clone 430276 5'. | -3,9 | 0,95 | AAAAP | 0 | 0 | 0 | 0 | 127 |
| zs38b09.s1 Soares NhHMPu S1 Homo sapiens cDNA clone 687449 3'. | -3,0 | 0,52 | AAAAP | 0 | 0 | 0 | 0 | 100 |
| zf20d06.s1 Soares fetal heart NbHH19W Homo sapiens cDNA clone 377483 3'. | -4,4 | 1,17 | AAAAP | 0 | 0 | 0 | 0 | 98 |
| zw89g02.s1 Soares total fetus Nb2HF8 9w Homo sapiens cDNA clone 764176 3'. | -3,2 | 0,58 | AAAAP | 0 | 0 | 0 | 0 | 97 |
| ys80e03.r1 Homo sapiens cDNA clone 221116 5'. | -3,1 | 0,55 | AAAAP | 0 | 0 | 0 | 0 | 94 |
| zu63c08.r1 Soares testis NHT Homo sapiens cDNA clone 742670 5'. | -3,3 | 0,56 | AAAAP | 0 | 0 | 0 | 0 | 92 |
| zd31d10.s1 Soares fetal heart NbHH19W Homo sapiens cDNA clone 342259 3'. | -6,9 | 0,79 | AAAAP | 0 | 0 | 0 | 0 | -116 |

Fig. 14.1

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mix  Abs calls AAAPA and INCREASED
sorted acc. To Avg Diff T2gIII mix

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T9gIIP | Abs Call T9gIIP |
|---|---|---|---|---|---|---|---|---|---|---|---|
| zx58c10.r1 Soares fetal liver spleen 1NFLS S1 Homo sapiens cDNA clone 446706 5' similar to contains Alu repetitive element. | AA203639_at | 52 | A | -24 | A | MI | * | 3 | 0.7 | 169 | A |
| Human prealbumin gene, complete cds. | M11844_at | 45 | A | 107 | A | NC | * | -1 | 0 | 183 | A |
| zq77f02.s1 Stratagene hNT neuron (#937233) Homo sapiens cDNA clone 647643 3' similar to contains element MSR1 repetitive element.; | RC_AA206042_at | -730 | A | -439 | A | NC | * | -7.1 | 0.68 | -856 | A |
| yz03e04.s1 Homo sapiens cDNA clone 281982 3'. | RC_N51097_at | 187 | A | 246 | A | NC | * | 1.3 | 0.06 | 264 | A |
| yl70f08.s1 Soares infant brain 1NIB Homo sapiens cDNA clone 43327 3'. | RC_H05527_at | 265 | A | 222 | A | NC | * | -1.2 | -0.03 | 335 | A |
| zl05d11.f1 Soares pregnant uterus NbHPU Homo sapiens cDNA clone 491445 5' similar to TR:G895845 G895845 PUTATIVE P64 CLCP PROTEIN. ;. | AA115572_s_at | 52 | A | 55 | A | NC | * | 1.1 | 0 | 85 | A |
| yj14b12.s1 Homo sapiens cDNA clone 148703 3'. | RC_H12863_at | 81 | A | 207 | A | NC | * | 2.6 | 0.58 | 294 | A |
| ab36e04.r1 Stratagene HeLa cell s3 937216 Homo sapiens cDNA clone 842910 5'. | AA489287_at | 33 | A | 100 | A | NC | * | 3 | 0.58 | 90 | A |
| ye49h07.s1 Homo sapiens cDNA clone 121117 3'. | RC_T96383_at | -4 | A | 81 | A | NC | * | -2.8 | 0.34 | 24 | A |
| yq98g12.s1 Homo sapiens cDNA clone 203878 3'. | RC_H56453_at | 11 | A | 99 | A | NC | * | 2.1 | 0.24 | 89 | A |
| zl03h01.s1 Soares pregnant uterus NbHPU Homo sapiens cDNA clone 491281 3'. | RC_AA152194_at | 24 | A | 62 | A | NC | * | 1.3 | 0.03 | 84 | A |
| H. sapiens partial cDNA sequence; clone c-0ed05. | RC_Z38520_at | 13 | A | 49 | A | NC | * | -1.8 | 0.07 | 38 | A |
| yd05g09.s1 Homo sapiens cDNA clone 25061 3' similar to contains Alu repetitive element;. | RC_R38944_at | -19 | A | 47 | A | NC | * | -2.4 | 0.14 | -31 | A |

Fig. 14.2

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mix  Abs calls AAAPA and INCREASED
sorted acc. To Avg Diff T2gIII mix

| gene name | Diff Call T1gIIIP(vs)N | B=A | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImix(vs)N | Sort Score T2gIIImixP(vs)N | Avg Diff T2gIIIsolidP | Abs Call T2gIIIsolidP |
|---|---|---|---|---|---|---|---|---|---|---|---|---|
| zx58c10.r1 Soares fetal liver spleen 1NFLS S1 Homo sapiens cDNA clone 446706 5' similar to contains Alu repetitive element; | MI | * | 3,1 | 0,75 | 573 | P | I | * | 7,5 | 4,29 | 445 | A |
| Human prealbumin gene, complete cds. | NC | * | 1,1 | 0 | 526 | P | I | * | 4,7 | 2,86 | 149 | A |
| zq77i02.s1 Stratagene hNT neuron (#937233) Homo sapiens cDNA clone 647643 3' similar to contains element MSR1 repetitive element.; | NC | * | ~3,6 | -0,29 | 488 | P | I | * | ~23,2 | 13,95 | -1216 | A |
| yz03e04.s1 Homo sapiens cDNA clone 281982 3'. | NC | * | 1,4 | 0,09 | 418 | P | I | * | 2,2 | 0,5 | 317 | A |
| yi70f08.s1 Soares infant brain 1NIB Homo sapiens cDNA clone 43327 3'. | NC | * | 1,3 | 0,05 | 402 | P | I | * | 2,1 | 0,32 | 637 | A |
| zi05d11.r1 Soares pregnant uterus NbHPU Homo sapiens cDNA clone 491445 5' similar to TR:G895845 G895845 PUTATIVE P64 CLCP PROTEIN.; | NC | * | 4,9 | 2,07 | 292 | P | I | * | 8,7 | 5,44 | 235 | A |
| yi14b12.s1 Homo sapiens cDNA clone 148703 3'. | NC | * | 3,6 | 1,39 | 285 | P | I | * | 3,5 | 1,31 | 229 | A |
| ab36e04.r1 Stratagene HeLa cell s3 937216 Homo sapiens cDNA clone 842910 5'. | NC | * | 2,7 | 0,43 | 241 | P | I | * | 10,8 | 5,81 | 116 | A |
| ye49h07.s1 Homo sapiens cDNA clone 121117 3'. | NC | * | ~1,6 | 0,05 | 185 | P | I | * | ~4,1 | 1,26 | 138 | A |
| yq98g12.s1 Homo sapiens cDNA clone 203878 3'. | NC | * | ~2,6 | 0,34 | 170 | P | I | * | ~4,0 | 1,11 | 57 | A |
| zl03h01.s1 Soares pregnant uterus NbHPU Homo sapiens cDNA clone 491281 3'. | NC | * | 1,7 | 0,12 | 167 | P | I | * | ~3,0 | 0,69 | 86 | A |
| H. sapiens partial cDNA sequence; clone c-Oed05. | NC | * | ~1,5 | 0,04 | 134 | P | I | * | ~3,0 | 0,57 | 118 | A |
| yd06g09.s1 Homo sapiens cDNA clone 25061 3' similar to contains Alu repetitive element. | NC | * | ~1,2 | -0,01 | 133 | P | I | * | ~3,5 | 0,73 | 147 | A |

Fig. 14.3

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mix Abs calls AAAPA and INCREASED sorted acc. To Avg Diff T2gIII mix

| gene name | Diff Call T2gIIIsolidP(vs)N | B=A | Fold Change T2gIIIsolidP(vs)N | Sort Score T2gIIIsolidP(vs)N | Abs Calls | N | A | B | C | D |
|---|---|---|---|---|---|---|---|---|---|---|
| zx58c10.r1 Soares fetal liver spleen 1NFLS S1 Homo sapiens cDNA clone 446706 5' similar to contains Alu repetitive element.: | NC | * | 10,5 | 7,12 | AAAPA | 0 | 0 | 0 | 573 | 0 |
| Human prealbumin gene, complete cds. | NC | * | 1 | 0 | AAAPA | 0 | 0 | 0 | 526 | 0 |
| zq77f02.s1 Stratagene hNT neuron (#937233) Homo sapiens cDNA clone 647643 3' similar to contains element MSR1 repetitive element.: | NC | * | ~7,9 | -0,92 | AAAPA | 0 | 0 | 0 | 488 | 0 |
| yz03e04.s1 Soares fetal liver spleen 1NFLS S1 Homo sapiens cDNA clone 281982 3'. | NC | * | 1,7 | 0,22 | AAAPA | 0 | 0 | 0 | 418 | 0 |
| yl70f08.s1 Soares infant brain 1NIB Homo sapiens cDNA clone 43327 3'. | NC | * | 2,4 | 0,88 | AAAPA | 0 | 0 | 0 | 402 | 0 |
| zl05d11.r1 Soares pregnant uterus NbHPU Homo sapiens cDNA clone 491445 5' similar to TR:G895845 G895845 PUTATIVE P64 CLCP PROTEIN.: | NC |   | 4,5 | 1,76 | AAAPA | 0 | 0 | 0 | 292 | 0 |
| yj14b12.s1 Homo sapiens cDNA clone 148703 3'. | NC | * | 2,8 | 0,77 | AAAPA | 0 | 0 | 0 | 285 | 0 |
| ab36e04.r1 Stratagene HeLa cell s3 937216 Homo sapiens cDNA clone 842910 5'. | NC | * | ~4,1 | 1,28 | AAAPA | 0 | 0 | 0 | 241 | 0 |
| ye49h07.s1 Homo sapiens cDNA clone 121117 3'. | NC | * | ~3,0 | 0,56 | AAAPA | 0 | 0 | 0 | 185 | 0 |
| yq98g12.s1 Homo sapiens cDNA clone 203878 3'. | NC | * | ~1,7 | 0,07 | AAAPA | 0 | 0 | 0 | 170 | 0 |
| zl03h01.s1 Soares pregnant uterus NbHPU Homo sapiens cDNA clone 491281 3'. | NC | * | ~1,5 | 0,07 | AAAPA | 0 | 0 | 0 | 167 | 0 |
| H. sapiens partial cDNA sequence; clone c-0ed05. | 1 |   | ~2,5 | 0,34 | AAAPA | 0 | 0 | 0 | 134 | 0 |
| yd06g09.s1 Homo sapiens cDNA clone 25061 3' similar to contains Alu repetitive element.. | NC | * | ~3,4 | 0,71 | AAAPA | 0 | 0 | 0 | 133 | 0 |

Fig. 14.4

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mix Abs calls AAAPA and INCREASED sorted acc. To Avg Diff T2gIII mix

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T9gIIP | Abs Call T9gIIP |
|---|---|---|---|---|---|---|---|---|---|---|---|
| zo16e11.s1 Stratagene colon (#937204) Homo sapiens cDNA clone 587084 3' | RC_AA133926_at | 5 | A | 14 | A | NC | * | -1,2 | 0,01 | 18 | A |
| 7a68f06.s1 Homo sapiens cDNA clone 297731 3' similar to gb:X59244 ZINC FINGER PROTEIN 43 (HUMAN); | RC_N69908_f_at | -54 | A | 19 | A | NC | * | -2,5 | 0,16 | 33 | A |
| zo02c02.s1 Stratagene colon (#937204) Homo sapiens cDNA clone 556498 3' similar to contains Alu repetitive element;. | RC_AA151945_at | 12 | A | 21 | A | NC | * | -1,2 | 0,01 | 49 | A |
| SOX5=Sry-related HMG box gene (alternatively spliced) [human, testis, mRNA, 1473 nt] | S83308_at | 18 | A | 40 | A | NC | * | 2,2 | 0,17 | 53 | A |
| zv11b06.s1 Soares NhHMPu S1 Homo sapiens cDNA clone 753299 3' | RC_AA406570_at | 23 | A | 5 | A | NC | * | -2,4 | 0,09 | -34 | A |
| zl67g04.s1 Stratagene colon (#937204) Homo sapiens cDNA clone 509718 3' similar to contains Alu repetitive element;contains element PTR5 repetitive element;. | RC_AA058314_at | -3 | A | 21 | A | NC | * | -1,5 | 0,04 | 22 | A |
| yr31g12.s1 Homo sapiens cDNA clone 206950 3'. | RC_R98735_at | -1040 | A | 447 | A | NC | * | -13,5 | 8,2 | 327 | A |

Fig. 14.5

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mlx Abs calls AAAPA and INCREASED
sorted acc. To Avg Diff T2gIII mlx

| gene name | Diff Call T1gIIIP(vs)N | B=A | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP |
|---|---|---|---|---|---|---|---|---|---|---|---|---|
| zo16e11.s1 Stratagene colon (#937204) Homo sapiens cDNA clone 587084 3'. | NC | * | ~1,3 | 0,02 | 124 | P | I | * | ~3,0 | 0,53 | 27 | A |
| za68l06.s1 Homo sapiens cDNA clone 297731 3' similar to gb:X59244 ZINC FINGER PROTEIN 43 (HUMAN);. | I | | ~2,8 | 0,19 | 117 | P | I | | ~3,3 | 0,58 | -104 | A |
| zo02c02.s1 Stratagene colon (#937204) Homo sapiens cDNA clone 566498 3' similar to contains Alu repetitive element;. | NC | * | ~1,8 | 0,07 | 106 | P | I | * | ~3,7 | 1,04 | -79 | A |
| SOX5=Sry-related HMG box gene {alternatively spliced} [human, testis, mRNA, 1473 nt]. | NC | * | ~2,7 | 0,33 | 98 | P | I | * | ~3,6 | 0,77 | 111 | A |
| zv11b06.s1 Soares NhHMPu S1 Homo sapiens cDNA clone 753299 3'. | NC | * | ~1,8 | -0,05 | 92 | P | I | * | ~4,6 | 1,03 | -99 | A |
| zi67g04.s1 Stratagene colon (#937204) Homo sapiens cDNA clone 509718 3' similar to contains Alu repetitive element;contains element PTR5 repetitive element ;. | NC | * | ~1,5 | 0,04 | 65 | P | I | * | ~3,8 | 1,01 | 10 | A |
| yr31g12.s1 Homo sapiens cDNA clone 206950 3'. | NC | * | ~10,9 | 5,82 | -244 | P | I | * | ~6,8 | 0,73 | -670 | A |

Fig. 14.6

EST Bladder candidates of 17742 ESTs
Exclusion of data sets incl. AFFX, all NC, all A, 3xNC + M*
2424 genes with sort score >= +/- 0,5 changing from N to tumor
20 genes only in T2gIII mix Abs calls AAAPA and INCREASED
sorted acc. To Avg Diff T2gIII mix

| gene name | Diff Call T2gIIIsolidP(vs)N B=A* | Fold Change T2gIIIsolidP(vs)N | Sort Score T2gIIIsolidP(vs)N | Abs Calls | N | A | B | C | D |
|---|---|---|---|---|---|---|---|---|---|
| zo16e11.s1 Stratagene colon (#937204) Homo sapiens cDNA clone 587084 3'. | NC * | -1,3 | 0,03 | AAAPA | 0 | 0 | 0 | 124 | 0 |
| za68f06.s1 Homo sapiens cDNA clone 297731 3' similar to gb:X59244 ZINC FINGER PROTEIN 43 (HUMAN);. | NC * | -1,7 | -0,08 | AAAPA | 0 | 0 | 0 | 117 | 0 |
| zo02c02.s1 Stratagene colon (#937204) Homo sapiens cDNA clone 566498 3' similar to contains Alu repetitive element;. | NC * | -1,6 | 0,06 | AAAPA | 0 | 0 | 0 | 106 | 0 |
| SOX5=Sry-related HMG-box gene [alternatively spliced] {human, testis, mRNA, 1473 nt] | I * | -3,0 | 0,55 | AAAPA | 0 | 0 | 0 | 98 | 0 |
| zv11b06.s1 Soares NhHMPu S1 Homo sapiens cDNA clone 753299 3'. | NC * | -3,0 | -0,2 | AAAPA | 0 | 0 | 0 | 92 | 0 |
| zi57g04.s1 Stratagene colon (#937204) Homo sapiens cDNA clone 509718 3' similar to contains Alu repetitive element;contains element PTR5 repetitive element;. | NC * | -1,2 | 0,01 | AAAPA | 0 | 0 | 0 | 65 | 0 |
| yf31g12.s1 Homo sapiens cDNA clone 206850 3'. | NC * | -2,6 | -0,21 | AAAPA | 0 | 0 | 0 | -244 | 0 |

Fig. 15.1

EST Bladder candidates of 17742 ESTs
Exclusion of datasets incl AFFX, all NC, all A, 3xNC + M*
2424 genes with absolut value of sort score >= 0,5 changing from N to tumor in at least 1 comparison
14 genes gained only in T1gIIIP Abs Calls AAPAA and increased

| gene name | Probe Set EST subA & B | Avg Diff N | Abs Call N | Avg Diff TagIIP | Abs Call TagII P | Diff Call TagII(vs)N | B=A | Fold Change TagII(vs)N | Sort Score TagII(vs)N |
|---|---|---|---|---|---|---|---|---|---|
| yh81f02.s1 Homo sapiens cDNA clone 136155 3' similar to contains Alu repetitive element. | RC_R33146_at | 28 | A | 28 | A | NC | . | -1,0 | 0 |
| yw65f02.s1 Homo sapiens cDNA clone 257115 3'. | RC_N30806_at | 120 | A | 108 | A | NC | . | -1,1 | 0 |
| zn17a03.s1 Stratagene neuroepithelium NT2RAMI 937234 Homo sapiens cDNA clone 547660 3'. | RC_AA084138_at | 79 | A | 61 | A | NC | . | 1,1 | 0 |
| similar to none. | D82418_at | 18 | A | 48 | A | NC | . | -6,4 | -0,4 |
| zrl3a10.s1 Stratagene hNT neuron (#937233) Homo sapiens cDNA clone 648666 3'. | RC_AA223902_at | 215 | A | 87 | A | NC | . | -1,5 | -0,08 |
| aa65d11.s1 NCI_CGAP_GCB1 Homo sapiens cDNA clone IMAGE:825813 3'. | RC_AA505136_at | -8 | A | 2 | A | NC | . | -2,5 | -0,09 |
| zk05c04.s1 Soares pregnant uterus NbHPU Homo sapiens cDNA clone 469638 3'. | RC_AA027823_at | 50 | A | 69 | A | NC | . | 1,4 | 0,04 |
| yi23g09.s1 Homo sapiens cDNA clone 140128 3'. | RC_R65998_at | -19 | A | 1 | A | NC | . | -1,7 | 0,07 |
| yx59d10.r1 Homo sapiens cDNA clone 266035 5'. | N28843_at | 28 | A | 87 | A | NC | . | 3,1 | 0,57 |
| H. sapiens partial cDNA sequence; clone c-12c11. | RC_F02541_at | 3 | A | -7 | A | NC | . | -1,2 | -0,01 |
| | AA043223_at | 14 | A | 21 | A | NC | . | -1,4 | 0,02 |
| zk55g12.r1 Soares pregnant uterus NbHPU Homo sapiens cDNA clone 486790 5'. | RC_AA424524_at | 23 | A | 25 | A | NC | . | 1,1 | 0 |
| zv90g02.s1 Soares NhHMPu S1 Homo sapiens cDNA clone 767090 3'. | RC_R40166_at | 65 | A | -50 | A | NC | . | 1,1 | 0 |
| yf70a09.s1 Homo sapiens cDNA clone 27448 3'. | D80002_at | -197 | A | 78 | A | NC | . | -27,5 | 1,55 |
| Human mRNA for KIAA0180 gene, partial cds | | | | | | | | | |

Fig. 15.2

EST Bladder candidates of 17742 ESTs
Exclusion of datasets incl AFFX, all NC, all A, 3xNC + M*
2424 genes with absolut value of sort score >= 0,5 changing from N to tumor in at least 1 comparison
14 genes gained only in T1gIIIP Abs Calls AAPAA and increased

| gene name | Avg Diff T1gIIIP | Abs Call T1gIIIP | Diff Call T1gIIIP(vs)N | B=A | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N |
|---|---|---|---|---|---|---|---|---|---|---|---|
| yh81f02.s1 Homo sapiens cDNA clone 136155 3' similar to contains Alu repetitive element. | 956 | P | I | * | ~20,4 | 14,82 | 26 | A | NC | * | ~1,0 |
| yw65f02.s1 Homo sapiens cDNA clone 257115 3'. | 516 | P | I | * | ~8,0 | 4,52 | 87 | A | NC | * | ~1,7 |
| zn17a03.s1 Stratagene neuroepithelium NT2RAMI 937234 Homo sapiens cDNA clone 547660 3'. | 296 | P | I | * | 4,4 | 2,06 | 58 | A | NC | * | 1,4 |
| similar to none. | 241 | P | I | * | -4,3 | 0,96 | -72 | A | NC | * | -4,0 |
| zr13a10.s1 Stratagene hNT neuron (#937233) Homo sapiens cDNA clone 648666 3'. | 239 | P | I | * | 1,3 | 0,05 | -8 | A | NC | * | -3,2 |
| aa65d11.s1 NCI_CGAP_GCB1 Homo sapiens cDNA clone IMAGE:825813 3'. | 201 | P | I | * | -11,4 | 4,62 | 20 | A | NC | * | -1,9 |
| zk05c04.s1 Soares pregnant uterus NbHPU Homo sapiens cDNA clone 469638 3'. | 191 | P | I | * | 3,8 | 1,21 | 112 | A | NC | * | -2,0 |
| yl23g09.s1 Homo sapiens cDNA clone 140128 3'. | 139 | P | I | * | -3,8 | 0,78 | 35 | A | NC | * | -1,9 |
| yx59d10.r1 Homo sapiens cDNA clone 266035 5'. | 136 | P | I | * | 4,8 | 1,48 | 31 | A | NC | * | -1,1 |
| H. sapiens partial cDNA sequence; clone c-12c11. | 118 | P | I | * | -3,4 | 0,7 | 82 | A | NC | * | -2,3 |
| zk55g12.r1 Soares pregnant uterus NbHPU Homo sapiens cDNA clone 486790 5'. | 88 | P | I | * | 3,1 | 0,56 | 44 | A | NC | * | -1,5 |
| zv90g02.s1 Soares NhHMPu S1 Homo sapiens cDNA clone 767090 3'. | 72 | P | I | * | 3,1 | 0,5 | 59 | A | NC | * | -2,2 |
| yf70a09.s1 Homo sapiens cDNA clone 277448 3'. | -38 | P | I | * | 6,4 | 4,13 | -28 | A | NC | * | 1,8 |
| Human mRNA for KIAA0160 gene, partial cds | -131 | P | I | * | -14,9 | 0,91 | -77 | A | NC | * | -5,0 |

Fig. 15.3

EST Bladder candidates of 17742 ESTs
Exclusion of datasets incl AFFX; all NC, all A, 3xNC + M*
2424 genes with absolut value of sort score >= 0,5 changing from N to tumor in at least 1 comparison
14 genes gained only in T1gIIIP Abs Calls AAPAA and increased

| gene name | Sort Score T2gIIImixP(vs)N | Avg Diff T2gIIIsolidP | Abs Call T2gIIIsolidP | Diff Call T2gIIIsolidP(vs)N | B=A | Fold Change T2gIIIsolidP(vs)N | Sort Score T2gIIIsolidP(vs)N | Abs Calls |
|---|---|---|---|---|---|---|---|---|
| yh81f02.s1 Homo sapiens cDNA clone 136155 3' similar to contains Alu repetitive element;. | 0 | 19 | A | NC | * | -1,1 | -0,01 | AAPAA |
| yw65f02.s1 Homo sapiens cDNA clone 257115 3'. | 0,08 | -97 | A | NC | * | -1,2 | -0,01 | AAPAA |
| zn17a03.s1 Stratagene neuroepithelium NT2RAMI 937234 Homo sapiens cDNA clone 547660 3'. similar to none. | 0,06 | 253 | A | NC | * | 4,1 | 1,84 | AAPAA |
| zr13a10.s1 Stratagene hNT neuron (#937233) Homo sapiens cDNA clone 848666 3'. | -0,27 | -103 | A | NC | * | -4,0 | -0,3 | AAPAA |
| aa65d11.s1 NCI_CGAP_GCB1 Homo sapiens cDNA clone IMAGE:825813 3'. | -0,62 | -139 | A | NC | * | -3,7 | -0,36 | AAPAA |
| zk05c04.s1 Soares pregnant uterus NbHPU Homo sapiens cDNA clone 469638 3'. | 0,07 | -64 | A | NC | * | -2,4 | -0,13 | AAPAA |
| yj23g09.s1 Homo sapiens cDNA clone 140128 3'. | 0,22 | 119 | A | NC | * | -1,9 | 0,19 | AAPAA |
| yx59d10.r1 Homo sapiens cDNA clone 265035 5'. | 0,1 | -23 | A | NC | * | -1,3 | 0,02 | AAPAA |
| H. sapiens partial cDNA sequence; clone c-12c11. | 0 | 17 | A | NC | * | -1,3 | -0,02 | AAPAA |
| zk55g12.r1 Soares pregnant uterus NbHPU Homo sapiens cDNA clone 486790 5'. | 0,21 | -17 | A | NC | * | -1,0 | 0 | 0AAPAA |
| zv90g02.s1 Soares NhHMPu S1 Homo sapiens cDNA clone 767090 3'. | 0,05 | 183 | A | NC | * | -4,8 | 1,67 | AAPAA |
| yf70a09.s1 Homo sapiens cDNA clone 27448 3'. | 0,2 | 42 | A | NC | * | -1,6 | 0,01 | AAPAA |
| Human mRNA for KIAA0180 gene, partial cds | 0,15 | 67 | A | NC | * | -2,7 | 0,63 | AAPAA |
|  | 0,35 | -80 | A | NC | * | -3,8 | 0,29 | AAPAA |

Fig. 16.1

EST Bladder candidates of 17742 ESTs
Exclusion of data sets incl. AFFX, all NC, all A, 3xNC + M*
2424 genes with sort score >= +/- 0.5 changing from N to tumor
39 genes in TagII only , Abs calls APAAA and INCREASED
sorted acc. To Avg Diff TagII

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T4gIIP | Abs Call T4gIIIP | Diff Call T4gIIIP(vs)N | B=A |
|---|---|---|---|---|---|---|---|---|---|---|---|---|---|
| H. sapiens partial cDNA sequence; clone c-1pb12. | RC_F03192_at | 484 A | | 2936 | P | I | * | 12,6 | 18 | 1701 | A | NC | * |
| zd87g10.s1 Soares fetal heart NbHH19W Homo sapiens cDNA clone 347682 3'. | RC_W81552_at | -143 A | | 1363 | P | I | * | -19,7 | 13,57 | -26 | A | I | * |
| H. sapiens partial cDNA sequence; clone c-10c01. | RC_F02470_at | 162 A | | 629 | P | I | * | 6 | 5,38 | 325 | A | NC | * |
| zc20b06.s1 Soares senescent fibroblasts NbHSF Homo sapiens cDNA clone 322835 3' similar to PIR:S44218 S44218 testin - mouse [1] . | RC_W44927_at | 314 A | | 497 | P | I | * | 2,3 | 0,85 | 469 A | | NC | * |
| yg46b01.s1 Homo sapiens cDNA clone 35626 3'. | RC_R45292_at | 148 A | | 494 | P | I | * | 3,3 | 1,55 | 207 | A | NC | * |
| yr47b09.s1 Homo sapiens cDNA clone 208409 3' similar to contains Alu repetitive element; contains MER15 repetitive element .; | RC_H62159_at | 250 A | | 490 | P | I | * | 2 | 0,44 | 172 A | | NC | * |
| yf45a10.s2 Homo sapiens cDNA clone 129786 3'. | RC_R17069_at | 140 A | | 471 | P | I | * | 3,4 | 1,54 | 248 | A | NC | * |
| yn30c10.s1 Homo sapiens cDNA clone 49795 3'. | RC_H15259_at | 50 A | | 340 | P | I | * | 8,6 | 5,21 | 152 | A | NC | * |
| 28a6 Human retina cDNA randomly primed sublibrary Homo sapiens cDNA. | W25376_at | 18 A | | 285 | P | I | * | 1,7 | 0,26 | -175 | A | NC | * |
| H.sapiens mRNA for putative carboxylesterase | Y09616_at | 169 A | | 285 | P | I | * | 1,7 | 0,2 | 138 | A | NC | * |
| zw48f02.r1 Soares total fetus Nb2HF8 9w Homo sapiens cDNA clone 773307 5'. | AA425593_at | 75 A | | 285 | P | I | * | 3,8 | 1,47 | -54 | A | NC | * |
| zt08e05.s1 NCI_CGAP_GCB1 Homo sapiens cDNA clone IMAGE:712544 3'. | RC_AA279960_at | -33 A | | 234 | P | I | * | -17,5 | 6,94 | 36 | A | I | * |
| yn62c07.s1 Homo sapiens cDNA clone 163500 3'. | RC_H14089_at | 42 A | | 230 | P | I | * | -5,0 | 2 | 31 | A | NC | * |
| zc17d10.s1 Soares parathyroid tumor NbHPA Homo sapiens cDNA clone 322579 3' similar to PIR:S39983 S39983 eps8 protein - mouse .; | RC_R46079_f_at | -42 A | | 205 | P | I | * | -6,2 | 2,41 | -84 | A | NC | * |
| Human mRNA for retinoic acid receptor-like protein | RC_W15360_at | -43 A | | 199 | P | I | * | -6,1 | 2,32 | 108 A | | NC | * |
| ze75b05.s1 Soares fetal heart NbHH19W Homo sapiens cDNA clone 364765 3' similar to TR:G451330 G451330 STEROL REGULATORY ELEMENT BINDING PROTEIN-2.; | X52773_at | -18 A | | 195 | P | I | * | -14,1 | 5,41 | 70 | A | I | * |
| z031a10.s1 Stratagene colon (#937204) Homo sapiens cDNA clone 588474 3'. | RC_AA053886_s_at | -171 A | | 158 | P | I | * | -7,9 | 2,59 | 11 | A | I | * |
| Homo sapiens mRNA; expressed sequence tag; clone DKFZphsnu1_1b13, 3' read. | RC_AA143493_at | 131 A | | 152 | P | I | * | 2,8 | 0,6 | 59 | A | NC | * |
| H. sapiens partial cDNA sequence. | RC_Z98492_at | -13 A | | 126 | P | I | * | -4,0 | 0,94 | 25 | A | NC | * |
| yh10f08.s1 Homo sapiens cDNA clone 42872 3'. | F15201_at | 30 A | | 121 | P | I | * | 4 | 1,05 | 48 | A | NC | * |
| 30e12 Human retina cDNA randomly primed sublibrary Homo sapiens cDNA. | RC_R61883_at | 10 A | | 121 | P | I | * | -3,8 | 0,83 | 139 | A | NC | * |
| | W26505_at | 34 A | | 117 | P | I | * | 3,4 | 0,8 | 52 | A | MI | * |

Fig. 16.2

EST Bladder candidates of 17742 ESTs
Exclusion of data sets incl. AFFX, all NC, all A, 3xNC + M*
2424 genes with sort score >= +/- 0,5 changing from N to tumor
39 genes in Tagil only, Abs calls APAAA and INCREASED
sorted acc. To Avg Diff TagII

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| H. sapiens partial cDNA sequence; clone c-1pb12. | 2,5 | 1,29 | -41 | A | D | * | -16,6 | -10,38 | 170 | A | D | * |
| zd87g10.s1 Soares fetal heart NbHH19W Homo sapiens cDNA clone 347682 3'. | -3,4 | 0,27 | -86 | A | NC | * | -1,9 | 0,1 | -171 | A | NC | * |
| H. sapiens partial cDNA sequence; clone c-10c01. | 2 | 0,38 | 498 | A | NC | * | 3,1 | 1,33 | 451 | A | NC | * |
| zc20b06.s1 Soares senescent fibroblasts NbHSF Homo sapiens cDNA clone 322835 3' similar to PIR:S44218 S44218 testin - mouse [1]. | 1,5 | 0,16 | 212 | A | NC | * | -1,5 | -0,13 | 653 | A | NC | * |
| yg46b01.s1 Homo sapiens cDNA clone 35626 3'. | 1,4 | 0,08 | 257 | A | NC | * | 1,7 | 0,21 | 86 | A | NC | * |
| yv47o09.s1 Homo sapiens cDNA clone 208409 3' similar to contains Alu repetitive element; contains MER15 repetitive element.;. | 1,1 | 0 | 140 | A | NC | * | -1,1 | -0,01 | 77 | A | NC | * |
| yt45a10.s2 Homo sapiens cDNA clone 129760 3'. | 1,8 | 0,23 | 241 | A | NC | * | 1,7 | 0,2 | 22 | A | NC | * |
| ym30c10.s1 Homo sapiens cDNA clone 49795 3'. | 3,1 | 0,73 | 54 | A | NC | * | -1,1 | 0 | -114 | A | NC | * |
| 29a6 Human retina cDNA randomly primed sublibrary Homo sapiens cDNA. | -4,0 | 0,84 | 248 | A | NC | * | -8,7 | 3,99 | 385 | A | NC | * |
| H.sapiens mRNA for putative carboxylesterase | -1,2 | -0,03 | 106 | A | NC | * | -1,6 | -0,13 | 37 | A | NC | * |
| zw48f02.r1 Soares total fetus Nb2HF8 9w Homo sapiens cDNA clone 773307 5' | -2,5 | -0,33 | 187 | A | NC | * | 3,8 | 1,46 | 72 | A | NC | * |
| zt08e05.s1 NCI_CGAP_GCB1 Homo sapiens cDNA clone IMAGE:712544 3'. | -6,5 | 0,76 | 45 | A | NC | * | -3,7 | 0,38 | -70 | A | NC | * |
| ym62c07.s1 Homo sapiens cDNA clone 163500 3'. | -2,7 | -0,47 | -39 | A | NC | * | -2,3 | -0,15 | 64 | A | NC | * |
| yg49c02.s1 Soares parathyroid tumor NbPA Homo sapiens cDNA clone 36133 3'. | -1,9 | -0,08 | 113 | A | NC | * | -3,6 | 0,64 | -71 | A | NC | * |
| zc17d10.s1 Soares parathyroid tumor NbPA Homo sapiens cDNA clone 322579 3' similar to PIR:S39983 S39983 eps8 protein - mouse.;. | -4,1 | 0,85 | 43 | A | NC | * | -2,4 | 0,16 | -4 | A | NC | * |
| Human mRNA for retinoic acid receptor-like protein | -5,3 | 1,11 | 27 | A | NC | * | -2,5 | 0,12 | -27 | A | NC | * |
| za75b05.s1 Soares fetal heart NbHH19W Homo sapiens cDNA clone 364785 3' similar to TR:G451330 G451330 STEROL REGULATORY ELEMENT BINDING PROTEIN-2.;. | -4,8 | 0,43 | 39 | A | I | * | -4,5 | 0,44 | -25 | A | NC | * |
| zb31a10.s1 Stratagene colon (#937204) Homo sapiens cDNA clone 588474 3'. | -2,2 | -0,32 | 47 | A | NC | * | -2,4 | -0,37 | -23 | A | NC | * |
| Homo sapiens mRNA; expressed sequence tag; clone DKFZphtsnu1_1b13, 3' read. | -1,8 | 0,07 | 53 | A | I | * | -2,0 | 0,11 | 26 | A | NC | * |
| H. sapiens partial cDNA sequence. | -1,9 | -0,06 | 29 | A | NC | * | -1,1 | 0 | 76 | A | NC | * |
| yh10f08.s1 Homo sapiens cDNA clone 42872 3'. | -3,7 | 0,91 | 147 | A | MI | * | -3,3 | 0,72 | 134 | A | NC | * |
| 30e12 Human retina cDNA randomly primed sublibrary Homo sapiens cDNA. | 1,5 | 0,06 | 63 | A | NC | * | 1,9 | 0,14 | 164 | A | NC | * |

Fig. 16.3

EST Bladder candidates of 17742 ESTs
Exclusion of data sets incl. AFFX, all NC, all A, 3xNC + M*
2424 genes with sort score >= +/- 0,5 changing from N to tumor
39 genes in TagII only, Abs calls APAAA and INCREASED
sorted acc. To Avg Diff TagII

| gene name | Fold Change T2gIIsolidP(vs)N | Sort Score T2gIIsolidP(vs)N | Abs Calls | N | A | B | C | D |
|---|---|---|---|---|---|---|---|---|
| H. sapiens partial cDNA sequence; clone c-1pb12. | -9,1 | -5,92 | APAAA | 0 | 2936 | 0 | 0 | 0 |
| zd87g10.s1 Soares fetal heart NbHH19W Homo sapiens cDNA clone 347682 3'. | -1,4 | -0,04 | APAAA | 0 | 1363 | 0 | 0 | 0 |
| H. sapiens partial cDNA sequence; clone c-10c01. | 2,8 | 1,03 | APAAA | 0 | 629 | 0 | 0 | 0 |
| zc20b06.s1 Soares senescent fibroblasts NbHSF Homo sapiens cDNA clone 322835 3' similar to PIR:S44218 S44218 testin - mouse [1].; | 2,1 | 0,61 | APAAA | 0 | 497 | 0 | 0 | 0 |
| yg46b01.s1 Homo sapiens cDNA clone 35626 3'. | -2,0 | -0,62 | APAAA | 0 | 494 | 0 | 0 | 0 |
| yr47b09.s1 Homo sapiens cDNA clone 208409 3' similar to contains Alu repetitive element; contains MER15 repetitive element.; | -3,2 | -1,04 | APAAA | 0 | 490 | 0 | 0 | 0 |
| yt45a10.s2 Homo sapiens cDNA clone 129786 3'. | -1,7 | -0,07 | APAAA | 0 | 471 | 0 | 0 | 0 |
| ym30c10.s1 Homo sapiens cDNA clone 49795 3'. | -1,7 | -0,08 | APAAA | 0 | 340 | 0 | 0 | 0 |
| 29a6 Human retina cDNA randomly primed sublibrary Homo sapiens cDNA. | -10,0 | 5,68 | APAAA | 0 | 285 | 0 | 0 | 0 |
| H. sapiens mRNA for putative carboxylesterase | -4,2 | -1,36 | APAAA | 0 | 285 | 0 | 0 | 0 |
| zw48k02.r1 Soares total fetus Nb2HF8.9w Homo sapiens cDNA clone 773307 5'. | -2,4 | -0,43 | APAAA | 0 | 285 | 0 | 0 | 0 |
| zi08e05.s1 NCI_CGAP_GCB1 Homo sapiens cDNA clone IMAGE:712544 3'. | -1,4 | -0,02 | APAAA | 0 | 234 | 0 | 0 | 0 |
| ym62c07.s1 Homo sapiens cDNA clone 163500 3'. | -1,7 | -0,13 | APAAA | 0 | 230 | 0 | 0 | 0 |
| yg49c02.s1 Homo sapiens cDNA clone 36133 3'. | -1,4 | -0,04 | APAAA | 0 | 205 | 0 | 0 | 0 |
| zc17d10.s1 Soares parathyroid tumor NbHPA Homo sapiens cDNA clone 322579 3' similar to PIR:S39863 S39983 eps8 protein - mouse.; | -1,6 | 0,05 | APAAA | 0 | 199 | 0 | 0 | 0 |
| Human mRNA for retinoic acid receptor-like protein | -1,2 | -0,01 | APAAA | 0 | 195 | 0 | 0 | 0 |
| ze75b05.s1 Soares fetal heart NbHH19W Homo sapiens cDNA clone 364785 3' similar to TR:G451330 G451330 STEROL REGULATORY ELEMENT BINDING PROTEIN-2.; | -3,1 | 0,27 | APAAA | 0 | 158 | 0 | 0 | 0 |
| zo31a10.s1 Stratagene colon (#937204) Homo sapiens cDNA clone 588474 3'. | -3,2 | -0,58 | APAAA | 0 | 152 | 0 | 0 | 0 |
| Homo sapiens mRNA; expressed sequence tag; clone DKFZphsnu1_1b13; 3' read. | -1,5 | 0,05 | APAAA | 0 | 126 | 0 | 0 | 0 |
| H. sapiens partial cDNA sequence. | -1,9 | 0,15 | APAAA | 0 | 121 | 0 | 0 | 0 |
| yn10l08.s1 Homo sapiens cDNA clone 42872 3'. | -2,8 | 0,47 | APAAA | 0 | 121 | 0 | 0 | 0 |
| 30e12 Human retina cDNA randomly primed sublibrary Homo sapiens cDNA. | -4,2 | 1,3 | APAAA | 0 | 117 | 0 | 0 | 0 |

Fig. 16.4

EST Bladder candidates of 17742 ESTs
Exclusion of data sets incl. AFFX, all NC, all /A, 3xNC + M*
2424 genes with sort score >= +/- 0.5 changing from N to tumor
39 genes in TagII only, Abs calls APAAA and INCREASED
sorted acc. To Avg Diff TagII

| gene name | Probe Set EST | Avg Diff N | Abs Call N | Avg Diff TagIIP | Abs Call TagII P | Diff Call TagIIP(vs)N | B=A | Fold Change TagIIP(vs)N | Sort Score TagIIP(vs)N | Avg Diff T4gIIP | Abs Call T4gIIP | Diff Call T4gIIP(vs)N | B=A |
|---|---|---|---|---|---|---|---|---|---|---|---|---|---|
| zn53e03.s1 Stratagene muscle 937209 Homo sapiens cDNA clone 561916 3'. | RC_AA085676_at | 8 | A | 98 | P | I | * | -6,6 | 1,84 | 122 | A | NC | * |
| ze55c07.r1 Soares retina N2b4HR Homo sapiens cDNA clone 362892 5' similar to SW:RB14_RAT P35287 RAS-RELATED PROTEIN RAB-14. [1];: | AA018804_at | -1 | A | 98 | P | I | * | -7,1 | 2,02 | -2 | A | NC | * |
| Human class I histocompatibility antigen-like protein mRNA, complete cds. | U22963_at | 10 | A | 92 | P | I | * | -6,1 | 1,63 | 19 | A | NC | * |
| yf26d08.s1 Homo sapiens cDNA clone 127983 3'. | RC_R09230_at | -52 | A | 88 | P | I | * | -3,9 | 0,64 | 60 | A | I | * |
| yj25g01.s1 Homo sapiens cDNA clone 140304 3'. | RC_R67918_at | -113 | A | 88 | P | I | * | -5,2 | 0,94 | 14 | A | NC | * |
| zu55d04.r1 Soares ovary tumor NbHOT Homo sapiens cDNA clone 741895 5' similar to TR:G397579 G397579 LL5 MRNA.;: | AA402119_at | -124 | A | 79 | P | I | * | -10,4 | 1,13 | -123 | A | NC | * |
| zn42g07.r1 Stratagene endothelial cell 937223 Homo sapiens cDNA clone 550140 5'. | AA082171_at | 20 | A | 74 | P | I | * | 3,1 | 0,5 | 44 | A | NC | * |
| yl89d09.r1 Homo sapiens cDNA clone 146417 5'. | R79750_at | -14 | A | 70 | P | I | * | -6,2 | 1,39 | 7 | A | NC | * |
| zw80d04.s1 Soares testis NHT Homo sapiens cDNA clone 782503 3'. | RC_AA431773_at | -24 | A | 68 | P | I | * | -5,7 | 1 | 115 | A | I | * |
| zs97a07.s1 NCI_CGAP_GCB1 Homo sapiens cDNA clone IMAGE:711540 3'. | RC_AA280670_at | 20 | A | 66 | P | I | * | 3,4 | 0,57 | 4 | A | NC | * |
| EST16378 Aorta endothelial cells, TNF alpha-treated Homo sapiens cDNA 5' end. | AA303711_at | -72 | A | 61 | P | I | * | -14,4 | 2,95 | -123 | A | NC | * |
| zu64g03.r1 Soares testis NHT Homo sapiens cDNA clone 742804 5'. | AA400361_at | -1 | A | 60 | P | I | * | -4,8 | 0,91 | 23 | A | NC | * |
| Homo sapiens MDM2-like p53-binding protein (MDMX) mRNA, complete cds. | AF007111_at | 10 | A | 51 | P | I | * | -5,2 | 1,21 | -4 | A | NC | * |
| aa59c02.r1 NCI_CGAP_GCB1 Homo sapiens cDNA clone IMAGE:825218 5' similar to contains element MIR repetitive element.;: | AA504354_at | -23 | A | 43 | P | I | * | -6,0 | 0,89 | -39 | A | NC | * |
| K1565F Fetal heart, Lambda ZAP Express Homo sapiens cDNA clone K1565 5' similar to EST(YD54C09.R1). | N88108_at | -24 | A | 25 | P | I | * | -6,0 | 0,84 | -8 | A | NC | * |
| aa20e01.s1 Soares NhHMPu S1 Homo sapiens cDNA clone 813816 3'. | RC_AA447769_at | -18 | A | -158 | P | I | * | -11,1 | 3,85 | -159 | A | NC | * |

Fig. 16.5

EST Bladder candidates of 17742 ESTs
Exclusion of data sets incl. AFFX, all NC, all A, 3xNC + M*
2424 genes with sort score >= +/- 0,5 changing from N to tumor
39 genes in TagII only , Abs calls APAAA and INCREASED
sorted acc. To Avg Diff TagII

| gene name | Fold Change T1gIIIP(vs)N | Sort Score T1gIIIP(vs)N | Avg Diff T2gIIImixP | Abs Call T2gIIImixP | Diff Call T2gIIImixP(vs)N | B=A | Fold Change T2gIIImixP(vs)N | Sort Score T2gIIImixP(vs)N | Avg Diff T2gIIIsolidP | Abs Call T2gIIIsolidP | Diff Call T2gIIIsolidP(vs)N | B=A |
|---|---|---|---|---|---|---|---|---|---|---|---|---|
| zn53e03.s1 Stratagene muscle 937209 Homo sapiens cDNA clone 5619163'. | 1,9 | 0,21 | 49 | A | NC | * | -1,5 | 0,08 | 101 | A | NC | * |
| ze55c07.r1 Soares retina N2b4HR Homo sapiens cDNA clone 362892 5' similar to SW:RB14_RAT P35287 RAS-RELATED PROTEIN RAB-14. [1]; | -1,0 | 0 | 46 | A | NC | * | -2,6 | 0,22 | 87 | A | NC | * |
| Human class I histocompatibility antigen-like protein mRNA, complete cds. | -1,4 | 0,02 | -63 | A | NC | * | -2,3 | -0,1 | -115 | A | NC | * |
| yi28d08.s1 Homo sapiens cDNA clone 127983 3' | -3,3 | 0,33 | -4 | A | NC | * | -1,8 | 0,08 | 11 | A | NC | * |
| yi25g01.s1 Homo sapiens cDNA clone 140304 3' | -3,6 | 0,29 | 16 | A | NC | * | -3,1 | 0,26 | 99 | A | NC | * |
| zu55d04.r1 Soares ovary tumor NbHOT Homo sapiens cDNA clone 741895 5' similar to TR:G397579 G397579 LL5 MRNA. ; | -1,0 | 0 | -49 | A | NC | * | -3,5 | 0,22 | -115 | A | NC | * |
| zn42g07.r1 Stratagene endothelial cell 937223 Homo sapiens cDNA clone 550140 5'. | -2,1 | 0,12 | 45 | A | NC | * | -1,6 | 0,05 | 45 | A | NC | * |
| yi89d09.r1 Homo sapiens cDNA clone 146417 5'. | -2,0 | 0,07 | -68 | A | NC | * | -1,8 | -0,05 | -15 | A | NC | * |
| zw80d04.s1 Soares testis NHT Homo sapiens cDNA clone 782503 3'. | -6,6 | 1,71 | 40 | A | NC | * | -2,4 | 0,11 | 50 | A | NC | * |
| zs97a07.s1 NCI_CGAP_GCB1 Homo sapiens cDNA clone IMAGE:711540 3'. | -1,5 | -0,02 | 18 | A | NC | * | -1,5 | 0,03 | -40 | A | D | * |
| EST16378 Aorta endothelial cells, TNF alpha-treated Homo sapiens cDNA 5' end. | -3,5 | -0,18 | -254 | A | NC | * | -7,0 | -0,53 | -540 | A | D | * |
| zu64g03.r1 Soares testis NHT Homo sapiens cDNA clone 742804 5'. | -1,7 | 0,04 | -4 | A | NC | * | -1,1 | 0 | -49 | A | NC | * |
| Homo sapiens MDM2-like p53-binding protein (MDMX) mRNA, complete cds. | -1,2 | 0,01 | 43 | A | NC | * | -2,0 | 0,1 | -7 | A | NC | * |
| aa59c02.r1 NCI_CGAP_GCB1 Homo sapiens cDNA clone IMAGE:825218 5' similar to contains element MIR repetitive element ;; | -1,8 | -0,05 | -39 | A | I | * | -1,7 | -0,05 | -11 | A | NC | * |
| K1565F Fetal heart, Lambda ZAP Express Homo sapiens cDNA clone K1565 5' similar to EST(YD54C09.R1). | -2,5 | 0,1 | 34 | A | NC | * | -3,1 | 0,24 | -65 | A | NC | * |
| aa20e01.s1 Soares NhHMPu S1 Homo sapiens cDNA clone 813816 3'. | -4,4 | 0,64 | -107 | A | NC | * | -5,7 | 1,69 | -804 | A | MD | * |

Fig. 16.6

EST Bladder candidates of 17742 ESTs
Exclusion of data sets incl. AFFX, all NC, all A, 3xNC + M*
2424 genes with sort score >= +/- 0,5 changing from N to tumor
39 genes in TagII only, Abs calls APAAA and INCREASED
sorted acc. To Avg Diff TagII

| gene name | Fold Change T2gIIsolidP(vs)N | Sort Score T2gIIsolidP(vs)N | Abs Calls | N | A | B | C | D |
|---|---|---|---|---|---|---|---|---|
| zn53e03.s1 Stratagene muscle 937209 Homo sapiens cDNA clone 561916 3'. | 1,6 | 0,09 | APAAA | 0 | 98 | 0 | 0 | 0 |
| ze55c07.r1 Soares retina N2b4HR Homo sapiens cDNA clone 362892 5' similar to SW:RB14_RAT P35287 RAS-RELATED PROTEIN RAB-14. [1].; | -1,4 | 0,03 | APAAA | 0 | 98 | 0 | 0 | 0 |
| Human class I histocompatibility antigen-like protein mRNA, complete cds. | -3,5 | -0,26 | APAAA | 0 | 92 | 0 | 0 | 0 |
| yf26d08.s1 Homo sapiens cDNA clone 127983 3'. | -1,9 | 0,1 | APAAA | 0 | 88 | 0 | 0 | 0 |
| yl25g01.s1 Homo sapiens cDNA clone 140304 3'. | -4,0 | 0,61 | APAAA | 0 | 88 | 0 | 0 | 0 |
| zu55d04.r1 Soares ovary tumor NbHOT Homo sapiens cDNA clone 741895 5' similar to TR:G397579 G397579 LL5 MRNA.; | -1,2 | 0,01 | APAAA | 0 | 79 | 0 | 0 | 0 |
| zn42g07.r1 Stratagene endothelial cell 937223 Homo sapiens cDNA clone 550140 5'. | -1,3 | 0,02 | APAAA | 0 | 74 | 0 | 0 | 0 |
| yi89d09.r1 Homo sapiens cDNA clone 145417 5'. | -1,9 | 0,08 | APAAA | 0 | 70 | 0 | 0 | 0 |
| zw80d04.s1 Soares testis NHT Homo sapiens cDNA clone 782503 3'. | -3,7 | 0,83 | APAAA | 0 | 68 | 0 | 0 | 0 |
| zs97a07.s1 NCI_CGAP_GCB1 Homo sapiens cDNA clone IMAGE:711540 3'. | -2,3 | -0,12 | APAAA | 0 | 66 | 0 | 0 | 0 |
| EST16378 Aorta endothelial cells, TNF alpha-treated Homo sapiens cDNA 5' end. | -12,4 | -1,1 | APAAA | 0 | 61 | 0 | 0 | 0 |
| zu64g03.r1 Soares testis NHT Homo sapiens cDNA clone 742804 5'. | -2,2 | -0,11 | APAAA | 0 | 60 | 0 | 0 | 0 |
| Homo sapiens MDM2-like p53-binding protein (MDMX) mRNA, complete cds. | -1,1 | 0 | APAAA | 0 | 51 | 0 | 0 | 0 |
| aa59c02.r1 NCI_CGAP_GCB1 Homo sapiens cDNA clone IMAGE:825218 5' similar to contains element MIR repetitive element.; | -1,1 | 0,01 | APAAA | 0 | 43 | 0 | 0 | 0 |
| K1565F Fetal heart, Lambda ZAP Express Homo sapiens cDNA clone K1565 5' similar to EST(YD54C09.R1). | -1,7 | -0,05 | APAAA | 0 | 25 | 0 | 0 | 0 |
| aa20e01.s1 Soares NhHMPu S1 Homo sapiens cDNA clone 813816 3'. | -11,5 | -1,02 | APAAA | 0 | -158 | 0 | 0 | 0 |

Fig. 17.1

| Chip | Probe Set | Description | Normal Avg Diff | Abs Call |
|---|---|---|---|---|
| Increase in all | | | | |
| subA | RC_AA116036_at | zm79a11.s1 Stratagene neuroepithelium (#937231) Homo sapiens cDNA clone 531836 3'. | 36 | A |
| subB | RC_AA101562_at | zn76c11.s1 Stratagene NT2 neuronal precursor 937230 . | -25 | P |
| subB | RC_H20269_at | yn53b04.s1 Homo sapiens cDNA clone 172111 3'. | 182 | A |
| subB | RC_Z40715_at | H. sapiens partial cDNA sequence; clone c-2ea12. | 110 | A |
| Decrease in all | | | | |
| subA | AA131127_at | zo16a05.r1 Stratagene colon (#937204) Homo sapiens cDNA clone 587024 5' similar to .SW:CATX_BOVIN P05689 CATHEPSIN ; | 284 | P |
| subA | AA372630_s_at | EST84548 Colon adenocarcinoma IV Homo sapiens cDNA 5' end. | 3937 | P |
| subA | AA434329_at | zw24g07.r1 Soares ovary tumor NbHOT Homo sapiens cDNA clone 770268 5' similar to .contains element TAR1 repetitive element ; | 288 | P |
| subA | C01409_s_at | HUMGS00008391, Human Gene Signature, 3'-directed cDNA sequence. | 673 | P |
| subA | RC_AA256485_at | zr81e12.s1 Soares NhHMPu S1 Homo sapiens cDNA clone 682126 3'. | 2650 | P |
| subA | RC_AA290679_at | zt19l03.s1 Soares ovary tumor NbHOT Homo sapiens cDNA clone 713597 3' similar to .TR:E92665 E92665 AP56 ; | 1847 | P |
| subA | RC_AA429655_at | zw71d04.s1 Soares testis NHT Homo sapiens cDNA clone 781839 3'. | 803 | P |
| subA | RC_AA452410_at | zx31f03.s1 Soares total fetus Nb2HF8 9w Homo sapiens cDNA clone 780093 3'. | 380 | P |
| subA | RC_AA461174_at | zx70c04.s1 Soares total fetus Nb2HF8 9w Homo sapiens cDNA clone 796806 3'. | 1060 | P |
| subA | RC_AA491463_at | ze84f10.s1 Soares fetal heart NbHH19W Homo sapiens cDNA clone 365707 3'. | 320 | P |
| subA | RC_AA025434_at | ze84d01.s1 Soares fetal heart NbHH19W Homo sapiens cDNA clone 365665 3' similar to .PIR:A48764 A48764 calpain ; | 1291 | P |
| subA | RC_AA026030_at | zl68c01.s1 Stratagene colon (#937204) Homo sapiens cDNA clone 509760 3'. | 1936 | P |
| subB | RC_AA054321_s_at | zk87c05.s1 Soares pregnant uterus NbHPU Homo sapiens cDNA clone 489800 3'. | 808 | P |
| subB | RC_AA099820_at | zr97c07.s1 NCI_CGAP_GCB1 Homo sapiens cDNA clone IMAGE:683628 3'. | 277 | P |
| subB | RC_AA161043_at | yl98l11.s1 Homo sapiens cDNA clone 46316 3'. | 5134 | P |
| subB | RC_AA215379_at | ym45d10.s1 Homo sapiens cDNA clone 51262 3'. | 1235 | P |
| subB | RC_H09281_at | yq76e12.s1 Homo sapiens cDNA clone 201742 3' similar to gb:. | 1383 | P |
| subB | RC_H18836_at | J02982 GLYCOPHORIN B PRECURSOR (HUMAN); | 2471 | P |
| subB | RC_H52937_at | yr89e02.s1 Homo sapiens cDNA clone 212474 3'. | 1007 | P |
| subB | RC_H69547_at | yv20a05.s1 Homo sapiens cDNA clone 243248 3'. | 1865 | P |
| subB | RC_H95039_at | yx63h03.s1 Soares melanocyte 2NbHM Homo sapiens cDNA clone 266453 3'. | 1117 | P |
| subB | RC_N21687_at | | 1806 | P |
| subB | RC_N54841_at | | 573 | P |
| subB | RC_N59622_at | yz38a06.s1 Homo sapiens cDNA clone 285298 3'. | 307 | P |
| subB | RC_N66312_at | | 334 | P |
| subB | RC_N90717_at | za90a10.s1 Soares fetal lung NbHL19W Homo sapiens cDNA clone 299802 3'. | 523 | P |
| subB | RC_R22189_at | yh28a02.s1 Homo sapiens cDNA clone 130826 3'. | 254 | P |

Fig. 17.2

| Chip | Probe Set | Description | Ta Abs Call | Diff Call | Fold Change | Sort Score |
|---|---|---|---|---|---|---|
| Increase in all | | | | | | |
| subA | RC_AA116036_at | zm79a11.s1 Stratagene neuroepithelium (#937231) Homo sapiens cDNA clone 531836 3'. | P | I | 4,1 | 1,18 |
| subA | RC_AA101562_at | zn76c11.s1 Stratagene NT2 neuronal precursor 937230. | P | I | -15,4 | 10,54 |
| subB | RC_H20269_at | yn53b04.s1 Homo sapiens cDNA clone 172111 3'. | P | I | 2,9 | 1,25 |
| subB | RC_Z40715_at | H. sapiens partial cDNA sequence; clone c-2ea12. | P | I | 3,3 | 1,31 |
| Decrease in all | | | | | | |
| subA | AA131127_at | zo16a05.r1 Stratagene colon (#937204) Homo sapiens cDNA clone 587024 5' similar to SW:CATX_BOVIN P05689 CATHEPSIN ;. | A | D | -18,4 | -7,64 |
| subA | AA372630_s_at | EST84548 Colon adenocarcinoma IV Homo sapiens cDNA 5' end. | P | D | -71,4 | -50,28 |
| subA | AA434329_at | zw24g07.r1 Soares ovary tumor NbHOT Homo sapiens cDNA clone 770268 5' similar to contains element TAR1 repetitive element ;. | A | D | -18,1 | -7,28 |
| subA | C01409_s_at | HUMGS0008391, Human Gene Signature, 3'-directed cDNA sequence. | P | D | -4,5 | -2,73 |
| subA | RC_AA256485_at | zk81e12.s1 Soares NhHMPu S1 Homo sapiens cDNA clone 682126 3'. | P | D | -11,7 | -15,84 |
| subA | RC_AA290679_at | zt119f03.s1 Soares ovary tumor NbHOT Homo sapiens cDNA clone 713597 3' similar to TR:E92665 E92665 AP56 ;. | P | D | -3 | -2,39 |
| subA | RC_AA429655_at | zw71d04.s1 Soares testis NHT Homo sapiens cDNA clone 781639 3'. | P | D | -4,9 | -3,73 |
| subA | RC_AA452410_at | zx31f03.s1 Soares total fetus Nb2HF8 9w Homo sapiens cDNA clone 788093 3'. | A | D | -3,3 | -1,26 |
| subA | RC_AA461174_at | zx70c04.s1 Soares total fetus Nb2HF8 9w Homo sapiens cDNA clone 796806 3'. | P | D | -3,3 | -2,1 |
| subA | RC_AA491463_at | ze84f10.s1 Soares fetal heart NbHH19W Homo sapiens cDNA clone 365707 3'. | P | D | -16,4 | -6,78 |
| subA | RC_AA025434_at | ze84d01.s1 Soares fetal heart NbHH19W Homo sapiens cDNA clone 365665 3' similar to PIR:A48764 A48764 calpain. | A | D | -34,1 | -23,95 |
| subB | RC_AA026030_at | | A | D | -4,4 | -4,64 |
| subB | RC_AA054321_s_at | zl68c01.s1 Stratagene colon (#937204) Homo sapiens cDNA clone 509760 3'. | A | D | -18,7 | -13,25 |
| subB | RC_AAC99820_at | zk87c05.s1 Soares pregnant uterus NbHPU Homo sapiens cDNA clone 489800 3'. | A | D | -6,5 | -3,07 |
| subB | RC_AA161043_at | | P | D | -2,6 | -3,13 |
| subB | RC_AA215379_at | zg97c07.s1 NCI_CGAP_GCB1 Homo sapiens cDNA clone IMAGE:t683628 3'. | P | D | -5,2 | -5,56 |
| subB | RC_H09281_at | yl98f11.s1 Homo sapiens cDNA clone 46315 3'. | P | D | -2,3 | 1,15 |
| subB | RC_H18836_at | ym45d10.s1 Homo sapiens cDNA clone 51282 3'. | A | D | -1,9 | -1,04 |
| subB | RC_H52937_at | yq76e12.s1 Homo sapiens cDNA clone 201742 3' similar to gb: JD2982 GLYCOPHORIN B PRECURSOR (HUMAN) ;. | A | D | -15,2 | -10,7 |
| subB | RC_H69547_at | yr89e02.s1 Homo sapiens cDNA clone 212474 3'. | A | D | -3,6 | -3,44 |
| subB | RC_H95039_at | yv20a05.s1 Homo sapiens cDNA clone 243248 3'. | P | D | -2,7 | -1,59 |
| subB | RC_N21687_at | yx63h03.s1 Soares melanocyte 2NbHM Homo sapiens cDNA clone 266453 3'. | P | D | -2,5 | -1,48 |
| subB | RC_N54841_at | | A | D | -8,2 | -5,75 |
| subB | RC_N59622_at | | A | D | -6,1 | -2,22 |
| subB | RC_N66312_at | yz38a06.s1 Homo sapiens cDNA clone 285298 3'. | A | D | -7,7 | -4,23 |
| subB | RC_N90717_at | za90a10.s1 Soares fetal lung NbHL19W Homo sapiens cDNA clone 299802 3'. | A | D | -15,5 | -9,87 |
| subB | RC_R22189_at | yh26e02.s1 Homo sapiens cDNA clone 130826 3'. | A | D | -7,6 | -4,14 |

Fig. 17.3

| Chip | Probe Set | Description | T1 Abs Call | Diff Call | Fold Change | Sort Score |
|---|---|---|---|---|---|---|
| Increase in all | | | | | | |
| subA | RC_AA116036_at | zm79a11.s1 Stratagene neuroepithelium (#937231) Homo sapiens cDNA clone 531836 3'. | P | I | 9,9 | 5,39 |
| subA | RC_AA101562_at | zn76c11.s1 Stratagene NT2 neuronal precursor 937230. | P | I | -10.6 | 6,44 |
| subB | RC_H20269_at | yn53b04.s1 Homo sapiens cDNA clone 172111 3'. | P | I | 4,7 | 3,64 |
| subB | RC_240715_at | H. sapiens partial cDNA sequence; clone c-2ea12. | P | I | 5 | 3,12 |
| Decrease in all | | | | | | |
| subA | AA131127_at | zo16a05.r1 Stratagene colon (#937204) Homo sapiens cDNA clone 587024 5' similar to .SW:CATX_BOVIN P05689 CATHEPSIN ; | A | D | -10,1 | -4,9 |
| subA | AA372630_s_at | EST84548 Colon adenocarcinoma IV Homo sapiens cDNA 5' end. | A | D | -195.5 | -65,13 |
| subA | AA434329_at | zw24g07.r1 Soares ovary tumor NbHOT Homo sapiens cDNA clone 770268 5' similar to .contains element TAR1 repetitive element ; | A | D | -13,6 | -5,92 |
| subA | C01409_s_at | HUMGS0008391, Human Gene Signature, 3'-directed cDNA sequence. | P | D | -3,2 | -1,57 |
| subA | RC_AA256485_at | zr81e12.s1 Soares NhHMPu S1 Homo sapiens cDNA clone 682126 3'. | P | D | -6,9 | -9,68 |
| subA | RC_AA290679_at | zt19h03.s1 Soares ovary tumor NbHOT Homo sapiens cDNA clone 713597 3' similar to .TR:E92665 E92665 AP56 ; | P | D | -2,5 | -1,66 |
| subA | RC_AA429655_at | zw71d04.s1 Soares testis NHT Homo sapiens cDNA clone 781639 3'. | P | D | -3,6 | -2,25 |
| subA | RC_AA452410_at | zx31f03.s1 Soares total fetus Nb2HF8 9w Homo sapiens cDNA clone 788093 3'. | A | D | -4,2 | -1,92 |
| subA | RC_AA461174_at | zx70c04.s1 Soares total fetus Nb2HF8 9w Homo sapiens cDNA clone 796806 3'. | P | D | -8,6 | -7,78 |
| subA | RC_AA491463_at | ze84f10.s1 Soares fetal heart NbHH19W Homo sapiens cDNA clone 365707 3'. | A | D | -14,2 | -6,24 |
| subA | RC_AA025434_at | ze84d01.s1 Soares fetal heart NbHH19W Homo sapiens cDNA clone 365665 3' similar to .PIR:A48764 A48764 calpain ; | A | D | -41,4 | -27,96 |
| subA | RC_AA026030_at | zl68c01.s1 Stratagene colon (#937204) Homo sapiens cDNA clone 509760 3'. | M | D | -6,4 | -7,7 |
| subB | RC_AA054321_s_at | zk87c05.s1 Soares pregnant uterus NbHPU Homo sapiens cDNA clone 489800 3'. | A | D | -12,2 | -9,67 |
| subB | RC_AA099820_at | zr97c07.s1 NCI_CGAP_GCB1 Homo sapiens cDNA clone IMAGE:683628 3'. | A | D | -7,2 | -3,44 |
| subB | RC_AA161043_at | yl98f11.s1 Homo sapiens cDNA clone 46316 3'. | P | D | -5,5 | -10,7 |
| subB | RC_AA215379_at | ym45d10.s1 Homo sapiens cDNA clone 51262 3'. | P | D | -9,3 | -10,6 |
| subB | RC_H09281_at | yq76e12.s1 Homo sapiens cDNA clone 201742 3' similar to gb:. | P | D | -4,9 | -4,81 |
| subB | RC_H18836_at | J02982 GLYCOPHORIN B PRECURSOR (HUMAN); | P | D | -2,1 | -1,24 |
| subB | RC_H52937_at | yr89e02.s1 Homo sapiens cDNA clone 212474 3'. | A | D | -6,7 | -5,22 |
| subB | RC_H69547_at | yv20a05.s1 Homo sapiens cDNA clone 243248 3'. | A | D | -3,5 | -3,31 |
| subB | RC_H95039_at | yx63h03.s1 Soares melanocyte 2NbHM Homo sapiens cDNA clone 266453 3'. | P | D | -4,5 | -3,99 |
| subB | RC_N21687_at | | P | D | -3,2 | -2,61 |
| subB | RC_N54841_at | | P | D | -3,3 | -1,66 |
| subB | RC_N59622_at | | A | D | -5,4 | -1,9 |
| subB | RC_N66312_at | yz38a06.s1 Homo sapiens cDNA clone 285298 3'. | A | D | -10,2 | -5,66 |
| subB | RC_N90717_at | za90a10.s1 Soares fetal lung NbHL19W Homo sapiens cDNA clone 299802 3'. | A | D | -20,3 | -12,5 |
| subB | RC_R22189_at | yh26a02.s1 Homo sapiens cDNA clone 130826 3'. | A | D | -8,1 | -4,39 |

Fig. 17.4

| Chip | Probe Set | Description | T2 Mix Abs Call | Diff Call | Fold Change | Sort Score |
|---|---|---|---|---|---|---|
| Increase in all | | | | | | |
| subA | RC_AA116036_at | zm79a11.s1 Stratagene neuroepithelium (#937231) Homo sapiens cDNA clone 531836 3'. | P | I | 10,8 | 6,06 |
| subB | RC_AA101562_at | zn76c11.s1 Stratagene NT2 neuronal precursor 937230. | P | I | -8.3 | 4,51 |
| subB | RC_H20269_at | yn53d04.s1 Homo sapiens cDNA clone 172111 3'. | P | I | 4,2 | 2,85 |
| subB | RC_Z40715_at | H. sapiens partial cDNA sequence; clone c-2ea12. | P | I | 13,6 | 14,22 |
| Decrease in all | | | | | | |
| subA | AA131127_at | zo16a05.r1 Stratagene colon (#937204) Homo sapiens cDNA clone 587024 5' similar to .SW:CATX_BOVIN P05689 CATHEPSIN ; | A | D | -9.9 | -4,84 |
| subA | AA372630_s_at | EST84548 Colon adenocarcinoma IV Homo sapiens cDNA 5' end. | A | D | -114,8 | -57,37 |
| subA | AA434329_at | zw24g07.r1 Soares ovary tumor NbHOT Homo sapiens cDNA clone 770268 5' similar to .contains element TAR1 repetitive element ; | P | D | -4 | -1,35 |
| subA | C01409_s_at | HUMGS0008391. Human Gene Signature, 3'-directed cDNA sequence. | A | D | -4,5 | -2,71 |
| subA | RC_AA256485_at | zr81e12.s1 Soares NhHMPu S1 Homo sapiens cDNA clone 682126 3'. | P | D | -4,4 | -5,34 |
| subA | RC_AA290679_at | zt19j03.s1 Soares ovary tumor NbHOT Homo sapiens cDNA clone 713597 3' similar to .TR:E92665 E92665 AP56 ; | P | D | -5,3 | -6,32 |
| subA | RC_AA429655_at | zw71d04.s1 Soares testis NHT Homo sapiens cDNA clone 781639 3'. | P | D | -3,9 | -2,56 |
| subA | RC_AA452410_at | zx31f03.s1 Soares total fetus Nb2HF8 9w Homo sapiens cDNA clone 788093 3'. | A | D | -4,3 | -1,98 |
| subA | RC_AA461174_at | zx70c04.s1 Soares total fetus Nb2HF8 9w Homo sapiens cDNA clone 796806 3'. | P | D | -3,1 | -1,86 |
| subA | RC_AA491463_at | ze84f10.s1 Soares fetal heart NbHH19W Homo sapiens cDNA clone 365707 3'. | A | D | -12,1 | -6,05 |
| subA | RC_AA025434_at | ze84d01.s1 Soares fetal heart NbHH19W Homo sapiens cDNA clone 365665 3' similar to .PIR:A48764 A48764 calpain ; | A | D | -29,6 | -23,21 |
| subB | RC_AA026030_at | zl68c01.s1 Stratagene colon (#937204) Homo sapiens cDNA clone 509760 3'. | A | D | -11,8 | -13,8 |
| subB | RC_AA054321_s_at | zk87c05.s1 Soares pregnant uterus NbHPU Homo sapiens cDNA clone 489800 3' | A | D | -19,3 | -14,36 |
| subB | RC_AA099820_at | | A | D | -5,1 | -2,44 |
| subB | RC_AA161043_at | | P | D | -5,6 | -10,78 |
| subB | RC_AA215379_at | zr97c07.s1 NCI_CGAP_GCB1 Homo sapiens cDNA clone IMAGE:683628 3'. | P | D | -3,9 | -3,6 |
| subB | RC_H09281_at | yl98f11.s1 Homo sapiens cDNA clone 46316 3'. | P | D | -16,6 | -15,67 |
| subB | RC_H18836_at | ym45d10.s1 Homo sapiens cDNA clone 51262 3'. | P | D | -2,4 | -1,89 |
| subB | RC_H52937_at | yq76e12.s1 Homo sapiens cDNA clone 201742 3' similar to gb:. J02982 GLYCOPHORIN B PRECURSOR (HUMAN). | A | D | -5,3 | -3,93 |
| subB | RC_H69547_at | yr89e02.s1 Homo sapiens cDNA clone 212474 3'. | A | D | -6,1 | -7,55 |
| subB | RC_H95039_at | yv20a05.s1 Homo sapiens cDNA clone 243248 3'. | P | D | -5,3 | -4,9 |
| subB | RC_N21687_at | yx63h03.s1 Soares melanocyte 2NbHM Homo sapiens cDNA clone 266453 3'. | P | D | -3,4 | -2,88 |
| subB | RC_N54841_at | | P | D | -4,2 | -2,48 |
| subB | RC_N59622_at | | A | D | -3,3 | -1,11 |
| subB | RC_N66312_at | yz38a06.s1 Homo sapiens cDNA clone 285298 3'. | A | D | -7,3 | -3,99 |
| subB | RC_N90717_at | za90a10.s1 Soares fetal lung NbHL19W Homo sapiens cDNA clone 299802 3'. | A | D | -14,7 | -9,64 |
| subB | RC_R22189_at | yh26a02.s1 Homo sapiens cDNA clone 130826 3'. | A | D | -6.1 | -3,21 |

Fig. 17.5

| Chip | Probe Set | Description | T2 Solid Abs Call | Diff Call | Fold Change | Sort Score |
|---|---|---|---|---|---|---|
| Increase in all | | | | | | |
| subA | RC_AA116036_at | zm79a11.s1 Stratagene neuroepithelium (#937231) Homo sapiens cDNA clone 531836 3'. | P | I | -9.4 | 5.32 |
| subB | RC_AA101562_at | zn76c11.s1 Stratagene NT2 neuronal precursor 937230 . | P | I | -8.9 | 6.05 |
| subB | RC_H20269_at | yn53b04.s1 Homo sapiens cDNA clone 172111 3'. | P | I | 4.7 | 3.57 |
| subB | RC_Z40715_at | H. sapiens partial cDNA sequence; clone c-2ea12. | P | I | 16.2 | 17.52 |
| Decrease in all | | | | | | |
| subA | AA131127_at | zo16a05.r1 Stratagene colon (#937204) Homo sapiens cDNA clone 587024 5' similar to .SW:CATX_BOVIN P05689 CATHEPSIN ; | A | D | -10.6 | -5.5 |
| subA | AA372630_s_at | EST84548 Colon adenocarcinoma IV Homo sapiens cDNA 5' end. | P | D | -11.6 | -20.55 |
| subA | AA434329_at | zw24g07.r1 Soares ovary tumor NbHOT Homo sapiens cDNA clone 770268 5' similar to .contains element TAR1 repetitive element ; | A | D | -7.7 | -3.84 |
| subA | C01409_s_at | HUMGS0008391, Human Gene Signature, 3'-directed cDNA sequence. | P | D | -3 | -1.32 |
| subA | RC_AA256485_at | zr81e12.s1 Soares NhHMPu S1 Homo sapiens cDNA clone 682126 3'. | P | D | -7.4 | -10.4 |
| subA | RC_AA290679_at | zt19f03.s1 Soares ovary tumor NbHOT Homo sapiens cDNA clone 713597 3' similar to .TR:E92665 E92665 AP56 ; | P | D | -2.4 | -1.52 |
| subA | RC_AA429655_at | zw71d04.s1 Soares testis NHT Homo sapiens cDNA clone 781639 3'. | P | D | -3.1 | -1.77 |
| subA | RC_AA452410_at | zx31f03.s1 Soares total fetus Nb2HF8 9w Homo sapiens cDNA clone 788093 3'. | A | D | -3 | -1.12 |
| subA | RC_AA461174_at | zx70c04.s1 Soares total fetus Nb2HF8 9w Homo sapiens cDNA clone 796806 3'. | P | D | -7.9 | -7.15 |
| subA | RC_AA491463_at | ze84f10.s1 Soares fetal heart NbHH19W Homo sapiens cDNA clone 365707 3'. | P | D | -8.3 | -4.25 |
| subA | RC_AA025434_at | ze84d01.s1 Soares fetal heart NbHH19W Homo sapiens cDNA clone 365665 3' similar to .PIR:A48764 A48764 calpain ; | A | D | -27.8 | -23 |
| subA | RC_AA026030_at | zl68c01.s1 Stratagene colon (#937204) Homo sapiens cDNA clone 509760 3'. | M | D | -5.3 | -6.15 |
| subB | RC_AA054321_s_at | zl68c01.s1 Stratagene colon (#937204) Homo sapiens cDNA clone 509760 3'. | A | D | -17.5 | -13.53 |
| subB | RC_AA099820_at | zk87c05.s1 Soares pregnant uterus NbHPU Homo sapiens cDNA clone 489800 3'. | A | D | -6.0 | -2.91 |
| subB | RC_AA161043_at | | P | D | -2.5 | -2.61 |
| subB | RC_AA215379_at | zr97c07.s1 NCI_CGAP_GCB1 Homo sapiens cDNA clone IMAGE:683628 3'. | P | D | -2.5 | -1.52 |
| subB | RC_H09281_at | yl98f11.s1 Homo sapiens cDNA clone 46316 3'. | P | D | -6.2 | -6.55 |
| subB | RC_H18836_at | ym45d10.s1 Homo sapiens cDNA clone 51262 3'. | P | D | -3.5 | -4.38 |
| subB | RC_H52937_at | yq76e12.s1 Homo sapiens cDNA clone 201742 3' similar to gb:. J02982 GLYCOPHORIN B PRECURSOR (HUMAN); | A | D | -7.3 | -5.67 |
| subB | RC_H69547_at | yr89e02.s1 Homo sapiens cDNA clone 212474 3'. | A | D | -4.4 | -4.88 |
| subB | RC_H95039_at | yv20a05.s1 Homo sapiens cDNA clone 243248 3'. | A | D | -3.6 | -2.75 |
| subB | RC_N21687_at | yx63h03.s1 Soares melanocyte 2NbHM Homo sapiens cDNA clone 266453 3'. | P | D | -5.2 | -5.7 |
| subB | RC_N54841_at | | P | D | -5 | -3.22 |
| subB | RC_N59622_at | | P | D | -3.7 | -1.36 |
| subB | RC_N66312_at | yz38a06.s1 Homo sapiens cDNA clone 285298 3'. | A | D | -5.5 | -2.13 |
| subB | RC_N90717_at | za90a10.s1 Soares fetal lung NbHL19W Homo sapiens cDNA clone 299802 3'. | A | D | -13.3 | -9.66 |
| subB | RC_R22189_at | yh26a02.s1 Homo sapiens cDNA clone 130826 3'. | A | D | -7.9 | -4.21 |

Fig. 17.6

| Chip | Probe Set | Description | Normal Avg Diff | Abs Call |
|---|---|---|---|---|
| Decrease in all | | | | |
| subB | RC_R53457_at | yg83e10.s1 Homo sapiens cDNA clone 39835 3'. | 813 | P |
| subB | RC_T53389_s_at | ya88f04.s1 Homo sapiens cDNA clone 68767 3'. | 6706 | P |
| subB | RC_W86375_s_at | | 2209 | P |
| subB | RC_Z38289_at | H. sapiens partial cDNA sequence; clone c-05e04. | 1217 | P |
| Increase in Ta | | | | |
| subA | AA402119_at | zu55d04.r1 Soares ovary tumor NbHOT Homo sapiens cDNA clone 741895 5' similar to ,TR:G397579 G397579 LL5 MRNA, ; | -124 | A |
| subA | RC_AA102581_at | ym62c07.s1 Homo sapiens cDNA clone 163500 3', | -75 | A |
| subB | RC_H14089_at | yg49c02.s1 Homo sapiens cDNA clone 36133 3', | 42 | A |
| subA | RC_R46079_f_at | yi25g01.s1 Homo sapiens cDNA clone 140304 3', | -42 | A |
| subB | RC_R67918_at | | -113 | A |
| subB | RC_W15360_at | similar to ,PIR:S39983 S39983 eps8 protein - mouse ; | -43 | A |
| subA | AA082171_at | zw48f02.r1 Soares total fetus Nb2HF8 9w Homo sapiens cDNA clone 773307 5', | 20 | A |
| subA | AA425593_at | H, sapiens partial cDNA sequence, | 75 | A |
| subA | F15201_at | ym36f02.r1 Homo sapiens cDNA clone 49693 5', | 30 | A |
| subA | H15219_at | yh04b02.r1 Homo sapiens cDNA clone 42052 5', | 28 | P |
| subA | R60368_at | ym86a02.r1 Homo sapiens cDNA clone 165770 5', | 147 | P |
| subA | R86859_at | zk59g01.s1 Soares pregnant uterus NbHPU Homo sapiens cDNA clone 487152 3', | 105 | A |
| subA | RC_AA045342_at | zo98g05.s1 Stratagene ovarian cancer (#937219) Homo sapiens cDNA clone 694968 3', | 56 | P |
| subA | RC_AA171985_at | yc04e08.r1 Homo sapiens cDNA clone 79718 5' similar to contains Alu repetitive element;. | 76 | P |
| subA | T63174_s_at | Human Krit1 mRNA, complete cds, | 211 | P |
| subA | U90268_at | Human mRNA for thrombospondin | 21 | P |
| subA | X14787_at | zq10a10.s1 Stratagene muscle 937209 Homo sapiens cDNA clone 629274 3' similar to ,;TR:G1049074 G1049074 VASOPRESSIN-ACTIVATED CALCIUM-MOBILIZING PROTEIN, | 20 | P |
| subB | RC_AA196091_s_at | | 50 | A |
| subB | RC_F02470_at | H, sapiens partial cDNA sequence; clone c-10c01, | 162 | A |
| subB | RC_F08899_at | H, sapiens partial cDNA sequence; clone c-2uc10, | 146 | P |
| subB | RC_H15259_at | ym30c10.s1 Homo sapiens cDNA clone 48795 3', | 50 | A |
| subB | RC_H52133_at | yo44d04.s1 Homo sapiens cDNA clone 180775 3', | 252 | A |
| subB | RC_R17059_at | yf45a10.s2 Homo sapiens cDNA clone 129786 3', | 140 | A |
| subB | RC_R45292_at | yg46b01.s1 Homo sapiens cDNA clone 35626 3'. | 148 | A |
| Increase in T1 | | | | |
| subA | C01360_at | HUMGS0008341, Human Gene Signature, 3'-directed cDNA sequence, | 47 | M |
| subA | D80002_at | Human mRNA for KIAA0180 gene, partial cds | -197 | A |
| subA | RC_AA149586_at | zl39e03.s1 Soares pregnant uterus NbHPU Homo sapiens cDNA clone 504316 3', | -30 | P |

Fig. 17.7

| Chip | Probe Set | Description | Ta Abs Call | Diff Call | Fold Change | Sort Score |
|---|---|---|---|---|---|---|
| Decrease in all | | | | | | |
| subB | RC_R53457_at | yg83e10.s1 Homo sapiens cDNA clone 39835 3'. | A | D | -12 | -9,55 |
| subB | RC_T53389_s_at | ya88f04.s1 Homo sapiens cDNA clone 68767 3'. | P | D | -12,6 | -25,85 |
| subB | RC_W85375_s_at | | P | D | -7,5 | -10,36 |
| subB | RC_Z38289_at | H. sapiens partial cDNA sequence; clone c-05e04. | P | D | -2,5 | -1,26 |
| Increase in Ta | | | | | | |
| subA | AA402119_at | zu55d04,r1 Soares ovary tumor NbHOT Homo sapiens cDNA clone 741895 5' similar to ,TR:G397579 G397579 LL5 MRNA, ; | P | I | -10,4 | 1,13 |
| subA | AA102581_at | ym62c07,s1 Homo sapiens cDNA clone 163500 3', | P | I | -21,4 | 8,48 |
| subB | RC_H14089_at | | P | I | -5,0 | 2 |
| subB | RC_R46079_f_at | yg49c02,s1 Homo sapiens cDNA clone 36133 3', | P | I | -6,2 | 2,41 |
| subB | RC_R67918_at | yi25g01,s1 Homo sapiens cDNA clone 140304 3', | P | I | -5,2 | 0,94 |
| subB | RC_W15360_at | similar to ,PIR:S39983 S39983 eps8 protein - mouse ; | P | I | -6,1 | 2,32 |
| subA | AA082171_at | zw48f02,r1 Soares total fetus Nb2HF8 9w Homo sapiens cDNA clone 773307 5', | P | I | 3,1 | 0,5 |
| subA | AA425593_at | H, sapiens partial cDNA sequence, | P | I | 3,8 | 1,47 |
| subA | F15201_at | ym30f02,r1 Homo sapiens cDNA clone 48693 5', | P | I | 4 | 1,05 |
| subA | H15219_at | yh04b02,r1 Homo sapiens cDNA clone 42052 5', | P | I | 3,2 | 0,63 |
| subA | R60368_at | ym86a02,r1 Homo sapiens cDNA clone 165770 5', | P | I | 3 | 1,19 |
| subA | R86859_at | zk59g01,s1 Soares pregnant uterus NbHPU Homo sapiens cDNA clone 487152 3', | P | I | 3,7 | 1,63 |
| subA | RC_AA045342_at | zo98g05,s1 Stratagene ovarian cancer (#937219) Homo sapiens cDNA clone 594863 3', | P | I | 3,5 | 0,82 |
| subA | RC_AA171985_at | | P | I | 3,1 | 0,96 |
| subA | T63174_s_at | yc04e08,r1 Homo sapiens cDNA clone 79718 5' similar to contains Alu repetitive element,; | P | I | 3 | 1,46 |
| subA | U90268_at | Human Krit1 mRNA, complete cds, | P | I | 7 | 2,46 |
| subA | X14787_at | Human mRNA for thrombospondin | P | I | 5,8 | 1,76 |
| subB | RC_AA196991_s_at | zq10a10,s1 Stratagene muscle 937209 Homo sapiens cDNA clone 629274 3' similar to :;TR:G1049074 G1049074 VASOPRESSIN-ACTIVATED CALCIUM-MOBILIZING PROTEIN. | P | I | 3,3 | 0,89 |
| subB | RC_F02470_at | H, sapiens partial cDNA sequence; clone c-10c01, | P | I | 6 | 5,38 |
| subB | RC_F08899_at | H, sapiens partial cDNA sequence; clone c-2uc10, | P | I | 3,9 | 1,91 |
| subB | RC_H15259_at | ym30c10,s1 Homo sapiens cDNA clone 49795 3', | P | I | 8,6 | 5,21 |
| subB | RC_H52133_at | yo44d04,s1 Homo sapiens cDNA clone 180775 3', | P | I | 3,9 | 2,95 |
| subB | RC_R17059_at | yf45a10,s2 Homo sapiens cDNA clone 129786 3', | P | I | 3,4 | 1,54 |
| subB | RC_R45292_at | yg46b01,s1 Homo sapiens cDNA clone 35626 3', | P | I | 3,3 | 1,55 |
| Increase in T1 | | | | | | |
| subA | C01360_at | HUMGS0008341, Human Gene Signature, 3'-directed cDNA sequence, | A | NC | -1,7 | -0,1 |
| subA | D80002_at | Human mRNA for KIAA0180 gene, partial cds | A | NC | -27,5 | 1,55 |
| subA | RC_AA149586_at | zl39e03,s1 Soares pregnant uterus NbHPU Homo sapiens cDNA clone 504316 3', | P | NC | 2,5 | 0,34 |

Fig. 17.8

| Chip | Probe Set | Description | T1 Abs Call | Diff Call | Fold Change | Sort Score |
|---|---|---|---|---|---|---|
| Decrease in all | | | | | | |
| subB | RC_R53457_at | yg83e10.s1 Homo sapiens cDNA clone 39835 3'. | A | D | -19,5 | -13,74 |
| subB | RC_T53389_s_at | ya88f04.s1 Homo sapiens cDNA clone 68767 3'. | P | D | -12 | -24,78 |
| subB | RC_W86375_s_at | | P | D | -5 | -6,3 |
| subB | RC_Z38289_at | H. sapiens partial cDNA sequence; clone c-05e04. | P | D | -4,7 | -3,96 |
| Increase in Ta | | | | | | |
| subA | AA402119_at | zu55d04.r1 Soares ovary tumor NbHOT Homo sapiens cDNA clone 741895 5' similar to ,TR:G397579 G397579 LL5 MRNA, ; | A | NC | -1,0 | 0 |
| subA | RC_AA102581_at | ym62c07.s1 Homo sapiens cDNA clone 163500 3'. | A | NC | 4,4 | 1,31 |
| subB | RC_H14089_at | ym62c07.s1 Homo sapiens cDNA clone 163500 3'. | A | NC | -2,7 | -0,47 |
| subB | RC_R48079_f_at | yg49c02.s1 Homo sapiens cDNA clone 36133 3', | A | NC | -1,9 | -0,08 |
| subB | RC_R67918_at | yi25g01.s1 Homo sapiens cDNA clone 140304 3'. | A | NC | -3,6 | 0,29 |
| subB | RC_W15360_at | | A | NC | -4,1 | 0,85 |
| subA | AA082171_at | similar to ,PIR:S39983 S39983 eps8 protein - mouse ; | A | NC | -2,1 | 0,12 |
| subA | AA425593_at | zw48f02.r1 Soares total fetus Nb2HF8 9w Homo sapiens cDNA clone 773307 5', | A | NC | -2,5 | -0,33 |
| subA | F15201_at | H. sapiens partial cDNA sequence, | A | NC | -1,9 | -0,06 |
| subA | H15219_at | ym30f02.r1 Homo sapiens cDNA clone 49693 5', | P | NC | 1,8 | 0,1 |
| subA | R60368_at | yh04b02.r1 Homo sapiens cDNA clone 42052 5'. | P | NC | 1,2 | 0,03 |
| subA | R86859_at | ym86a02.r1 Homo sapiens cDNA clone 165770 5', | A | NC | 1,5 | 0,12 |
| subA | RC_AA045342_at | zk59g01.s1 Soares pregnant uterus NbHPU Homo sapiens cDNA clone 487152 3', | A | NC | 2 | 0,17 |
| subA | RC_AA171985_at | zo98g05.s1 Stratagene ovarian cancer (#937219) Homo sapiens cDNA clone 594968 3'. | P | NC | 1,3 | 0,03 |
| subA | T63174_s_at | yc04e08.r1 Homo sapiens cDNA clone 79718 5' similar to ;contains Alu repetitive element,;, | P | NC | 1,8 | 0,33 |
| subA | U90268_at | Human Krit1 mRNA, complete cds, | A | NC | 1,2 | 0,02 |
| subA | X14787_at | Human mRNA for thrombospondin | A | NC | 1,9 | 0,11 |
| subB | RC_AA196991_s_at | zq10a10.s1 Stratagene muscle 937209 Homo sapiens cDNA clone 629274 3' similar to ,;TR:G1049074 G1049074 VASOPRESSIN-ACTIVATED CALCIUM-MOBILIZING PROTEIN, | P | NC | 2,8 | 0,56 |
| subB | RC_F02470_at | H. sapiens partial cDNA sequence; clone c-10c01, | A | NC | 2 | 0,38 |
| subB | RC_F08899_at | H. sapiens partial cDNA sequence; clone c-2uc10, | P | NC | 1,9 | 0,29 |
| subB | RC_H15259_at | ym30c10.s1 Homo sapiens cDNA clone 49795 3', | A | NC | 3,1 | 0,73 |
| subB | RC_H52133_at | yo44d04.s1 Homo sapiens cDNA clone 180775 3'. | M | NC | 2,4 | 0,81 |
| subB | RC_R17059_at | yf45a10.s2 Homo sapiens cDNA clone 129786 3', | A | NC | 1,8 | 0,23 |
| subB | RC_R45292_at | yg46b01.s1 Homo sapiens cDNA clone 35626 3', | A | NC | 1,4 | 0,08 |
| Increase in T1 | | | | | | |
| subA | I01360_at | HUMGS0008341, Human Gene Signature, 3'-directed cDNA sequence, | P | I | -18,6 | 8,71 |
| subA | D80002_at | Human mRNA for KIAA0180 gene, partial cds | P | I | -14,9 | 0,91 |
| subA | RC_AA149586_at | zl39e03.s1 Soares pregnant uterus NbHPU Homo sapiens cDNA clone 504316 3', | P | I | -9,3 | 3,16 |

Fig. 17.9

| Chip | Probe Set | Description | T2 Mix Abs Call | Diff Call | Fold Change | Sort Score |
|---|---|---|---|---|---|---|
| Decrease in all | | | | | | |
| subB | RC_R53457_at | yg83e10.s1 Homo sapiens cDNA clone 39835 3'. | A | D | -15.5 | -11,89 |
| subB | RC_T53389_s_at | ya88f04.s1 Homo sapiens cDNA clone 68767 3'. | P | D | -8,6 | -18,63 |
| subB | RC_W86375_s_at | | A | D | -26,9 | -22,82 |
| subB | RC_Z38289_at | H. sapiens partial cDNA sequence; clone c-05e04. | A | D | -7,3 | -6,96 |
| Increase in Ta | | | | | | |
| subA | AA402119_at | zu55d04.r1 Soares ovary tumor NbHOT Homo sapiens cDNA clone 741895 5' similar to ;TR:G397579 G397579 LL5 MRNA, ; | A | NC | -3,5 | 0,22 |
| subA | RC_AA102581_at | ym62c07.s1 Homo sapiens cDNA clone 163500 3', | P | NC | 4,1 | 1,33 |
| subB | RC_H14089_at | yg49c02.s1 Homo sapiens cDNA clone 36133 3', | A | NC | -2,3 | -0,15 |
| subA | RC_R46079_f_at | | A | NC | -3,6 | 0,64 |
| subB | RC_R67918_at | yi25g01.s1 Homo sapiens cDNA clone 140304 3', | A | NC | -3,1 | 0,26 |
| subB | RC_W15360_at | similar to ,PIR:S39983 S39983 eps8 protein - mouse ; | A | NC | -2,4 | 0,16 |
| subA | AA082171_at | zw48f02.r1 Soares total fetus Nb2HF8 9w Homo sapiens cDNA clone 773307 5', | A | NC | -1,6 | 0,05 |
| subA | AA425593_at | H, sapiens partial cDNA sequence, | A | NC | 3,8 | 1,46 |
| subA | F15201_at | ym30f02.r1 Homo sapiens cDNA clone 496933 5', | A | NC | -1,1 | 0 |
| subA | H15219_at | yh04b02.r1 Homo sapiens cDNA clone 42052 5', | P | NC | -1,2 | -0,01 |
| subA | R60368_at | ym86a02.r1 Homo sapiens cDNA clone 165770 5', | A | NC | -1,1 | -0,02 |
| subA | R86859_at | zk59g01.s1 Soares pregnant uterus NbHPU Homo sapiens cDNA clone 487152 3' | P | NC | 1,5 | 0,1 |
| subA | RC_AA045342_at | zo98g05.s1 Stratagene ovarian cancer (#937219) Homo sapiens cDNA clone 594968 3', | P | NC | 2,3 | 0,29 |
| subA | RC_AA171985_at | yc04e08.r1 Homo sapiens cDNA clone 79718 5' similar to contains Alu repetitive element;, | P | NC | -1,2 | -0,02 |
| subA | T63174_s_at | Human Krit1 mRNA, complete cds, | P | NC | 1,4 | 0,08 |
| subA | U90268_at | Human mRNA for thrombospondin | P | NC | -2,6 | 0,32 |
| subA | X14787_at | zq10a10.s1 Stratagene muscle 937209 Homo sapiens cDNA clone 629274 3' similar to ; TR:G1049074 G1049074 VASOPRESSIN-ACTIVATED CALCIUM-MOBILIZING PROTEIN, | P | NC | -1,7 | 0,06 |
| subA | RC_AA196991_s_at | | P | NC | -2,9 | 0,66 |
| Increase in T1 | | | | | | |
| subB | RC_F02470_at | H, sapiens partial cDNA sequence; clone c-10c01, | A | NC | 3,1 | 1,33 |
| subB | RC_F08899_at | H, sapiens partial cDNA sequence; clone c-2uc10, | A | NC | 1,1 | 0 |
| subB | RC_H15259_at | ym30c10.s1 Homo sapiens cDNA clone 49795 3', | A | NC | -1,1 | 0 |
| subB | RC_H52133_at | yo44d04.s1 Homo sapiens cDNA clone 180775 3', | A | NC | 2 | 0,48 |
| subB | RC_R17059_at | yf45a10.s2 Homo sapiens cDNA clone 129786 3', | A | NC | 1,7 | 0,2 |
| subB | RC_R45292_at | yg46b01.s1 Homo sapiens cDNA clone 35626 3', | A | NC | 1,7 | 0,21 |
| subA | C01360_at | HUMGS000B341, Human Gene Signature, 3'-directed cDNA sequence, | A | NC | -3,8 | -0,4 |
| subA | D80002_at | Human mRNA for KIAA0180 gene, partial cds | A | NC | -5,0 | 0,35 |
| subA | RC_AA149586_at | zi39e03.s1 Soares pregnant uterus NbHPU Homo sapiens cDNA clone 504316 3', | P | NC | -3,8 | 0,95 |

Fig. 17.10

| Chip | Probe Set | Description | T2 Solid Abs Call | Diff Call | Fold Change | Sort Score |
|---|---|---|---|---|---|---|
| Decrease in all | | | | | | |
| subB | RC_R53457_at | yg83e10.s1 Homo sapiens cDNA clone 398353 3' | A | D | -10,4 | -8,56 |
| subB | RC_T53389_s_at | ye88f04.s1 Homo sapiens cDNA clone 68767 3'. | P | D | -9,1 | -19,58 |
| subB | RC_W86375_s_at | H. sapiens partial cDNA sequence; | A | D | -13,9 | -17,47 |
| subB | RC_Z38289_at | H. sapiens partial cDNA sequence; clone c-05ed4. | A | D | -18,6 | -15,52 |
| Increase in Ta | | | | | | |
| subA | AA402119_at | zu55d04.r1 Soares ovary tumor NbHOT Homo sapiens cDNA clone 741895 5' similar to ,TR:G397579 G397579 LL5 MRNA, ; | A | NC | -1,2 | 0,01 |
| subA | RC_AA102581_at | ym62c07.s1 Homo sapiens cDNA clone 163500 3', | A | NC | -2,3 | 0,26 |
| subB | RC_H14089_at | yg49c02.s1 Homo sapiens cDNA clone 36133 3', | A | NC | -1,7 | -0,13 |
| subB | RC_R46079_f_at | yi25g01.s1 Homo sapiens cDNA clone 140304 3', | A | NC | -1,4 | -0,04 |
| subB | RC_R67918_at |  | A | NC | -4,0 | 0,61 |
| subB | RC_W15360_at | similar to ,PIR:S39983 S39983 eps8 protein - mouse ; | A | NC | -1,6 | 0,05 |
| subA | AA082171_at | zw48f02.r1 Soares total fetus Nb2HF8 9w Homo sapiens cDNA clone 773307 5', | A | NC | -1,3 | 0,02 |
| subA | AA425593_at | H. sapiens partial cDNA sequence, | A | NC | -2,4 | -0,43 |
| subA | F15201_at | ym30f02.r1 Homo sapiens cDNA clone 49693 5', | A | NC | -1,9 | 0,15 |
| subA | H15219_at | yhi04b02.r1 Homo sapiens cDNA clone 42052 5', | A | NC | -1,9 | 0,13 |
| subA | R60368_at |  | P | NC | -1,9 | -0,3 |
| subA | R86859_at | ym86a02.r1 Homo sapiens cDNA clone 165770 5', | P | NC | -3,3 | 0,71 |
| subA | RC_AA045342_at | zk59g01.s1 Soares pregnant uterus NbHPU Homo sapiens cDNA clone 487152 3', | A | NC | 1,3 | 0,03 |
| subA | RC_AA171985_at | zo98g05.s1 Stratagene ovarian cancer (#937219) Homo sapiens cDNA clone 584968 3', | P | NC | -1,1 | -0,01 |
| subA | T63174_s_at | yc04e08.r1 Homo sapiens cDNA clone 79718 5' similar to contains Alu repetitive element;, | P | NC | 1,9 | 0,35 |
| subA | U90268_at | Human Krit1 mRNA, complete cds, | P | NC | 3,2 | 0,91 |
| subA | X14787_at | Human mRNA for thrombospondin | P | NC | -1,1 | 0,01 |
| subA | RC_AA196991_s_at | zq10a10.s1 Stratagene muscle 937209 Homo sapiens cDNA clone 629274 3' similar to ;,TR:G1049074 G1049074 VASOPRESSIN-ACTIVATED CALCIUM-MOBILIZING PROTEIN, | P | NC | -1,8 | 0,14 |
| subA | RC_F02470_at | H. sapiens partial cDNA sequence; clone c-10c01, | A | NC | 2,8 | 1,03 |
| subA | RC_F08899_at | H. sapiens partial cDNA sequence; clone c-2uc10, | P | NC | 1,9 | 0,29 |
| subB | RC_H15259_at | ym30c10.s1 Homo sapiens cDNA clone 49795 3', | A | NC | -1,7 | -0,08 |
| subB | RC_H52133_at | yc44d04.s1 Homo sapiens cDNA clone 180775 3', | A | NC | 3,5 | 2,34 |
| subB | RC_R17059_at | yf45a10.s2 Homo sapiens cDNA clone 129786 3', | A | NC | -1,7 | -0,07 |
| subB | RC_R45292_at | yg46b01.s1 Homo sapiens cDNA clone 35626 3', | A | NC | -2,6 | -0,62 |
| Increase in T1 | | | | | | |
| subA | C01360_at | HUMGS0008341, Human Gene Signature, 3'-directed cDNA sequence, | A | NC | -4,0 | -0,37 |
| subA | D80002_at | Human mRNA for KIAA0180 gene, partial cds | A | NC | -3,8 | 0,29 |
| subA | RC_AA149586_at | zt39e03.s1 Soares pregnant uterus NbHPU Homo sapiens cDNA clone 504316 3', | P | NC | -2,1 | 0,1 |

Fig. 17.11

| Chip | Probe Set | Description | Normal Avg Diff | Abs Call |
|---|---|---|---|---|
| Increase in T1 | | | | |
| subB | RC_H68772_at | yr83f01.s1 Homo sapiens cDNA clone 211897 3'; | -98 | A |
| subB | RC_N30806_at | yw65f02.s1 Homo sapiens cDNA clone 257115 3'; | 120 | A |
| subB | RC_N63143_at | yz37c12.s1 Homo sapiens cDNA clone 285238 3'; | -255 | A |
| subB | RC_R33146_at | yh81f02.s1 Homo sapiens cDNA clone 136155 3' similar to contains Alu repetitive element;; | 28 | A |
| subB | RC_R46206_at | yj53d08.s1 Homo sapiens cDNA clone 152463 3'; | 71 | A |
| subB | RC_R49731_s_at | yg71e10.s1 Homo sapiens cDNA clone 38554 3'; | 30 | A |
| subA | AA043223_at | zk55g12.r1 Soares pregnant uterus NbHPU Homo sapiens cDNA clone 486790 5'; | 14 | A |
| subA | AB002346_at | Human mRNA for KIAA0348 gene, complete cds, | 37 | A |
| subA | D81608_at | Human fetal brain cDNA 5'-end GEN-177B09, | 32 | A |
| subA | M83670_s_at | Human carbonic anhydrase IV mRNA, complete cds | 90 | M |
| subA | N28843_at | yx59d10.r1 Homo sapiens cDNA clone 266035 5'; | 28 | A |
| subA | RC_AA149044_at | zl45d09.s1 Soares pregnant uterus NbHPU Homo sapiens cDNA clone 504881 3'; | 21 | A |
| subA | RC_AA258130_at | zs35f03.s1 NCI_CGAP_GCB1 Homo sapiens cDNA clone IMAGE:687197 3'; | 87 | P |
| subA | RC_AA281743_r_at | zt06h05.s1 NCI_CGAP_GCB1 Homo sapiens cDNA clone IMAGE:712377 3'; | 20 | A |
| subA | RC_AA406338_at | zv10f06.s1 Soares NhHMPu S1 Homo sapiens cDNA clone 753251 3'; | 67 | A |
| subA | RC_AA424524_at | zv90g02.s1 Soares NhHMPu S1 Homo sapiens cDNA clone 767090 3'; | 23 | A |
| subA | RC_AA435340_at | zt80b08.s1 Soares testis NHT Homo sapiens cDNA clone 728631 3'; | 51 | A |
| subA | RC_AA027823_at | zk05c04.s1 Soares pregnant uterus NbHPU Homo sapiens cDNA clone 469638 3'; | 50 | P |
| subB | RC_AA084138_at | zn17a03.s1 Stratagene neuroepithelium NT2RAMI 937234 Homo sapiens cDNA clone 547660 3'; | 79 | A |
| subB | RC_AA135406_at | zo28e08.s1 Stratagene colon (#937204) Homo sapiens cDNA clone 588230 3'; | 106 | A |
| subB | RC_AA149923_at | zl27g11.s1 Soares pregnant uterus NbHPU Homo sapiens cDNA clone 503204 3'; | 86 | A |
| subB | RC_H98653_at | yx12h06.s1 Homo sapiens cDNA clone 261563 3'; | 86 | P |
| subB | RC_N30077_at | yw81g11.s1 Homo sapiens cDNA clone 258692 3'; | 81 | P |
| subB | RC_R40166_at | yf70a09.s1 Homo sapiens cDNA clone 27448 3'; | 65 | A |
| subB | RC_T90374_at | RETROVIRUS-RELATED POL POLYPROTEIN ; | 337 | A |
| subB | RC_Z38182_at | H. sapiens partial cDNA sequence; clone c-02a08, | 84 | A |
| Increase in T2 mix | | | | |
| subA | RC_AA054726_at | zk68e06.s1 Soares pregnant uterus NbHPU Homo sapiens cDNA clone 488002 3'; | 2 | A |
| subB | RC_AA206042_at | similar to contains element MSR1 repetitive element ; | -730 | A |
| subB | RC_R98735_at | yr31g12.s1 Homo sapiens cDNA clone 206950 3'; | -1040 | A |
| subA | AA115572_s_at | zl05d11.r1 Soares pregnant uterus NbHPU Homo sapiens cDNA clone 491445 5' similar to.TR:G895845 G895845 PUTATIVE P64 CLCP PROTEIN.; | 52 | A |
| subA | AA430979_at | PMY0789 KG1a Lambda Zap Express cDNA Library Homo sapiens cDNA 5'; | 56 | P |
| subA | AA489287_at | | 33 | A |

Fig. 17.12

| Chip | Probe Set | Description | Ta Abs Call | Diff Call | Fold Change | Sort Score |
|---|---|---|---|---|---|---|
| Increase in T1 | | | | | | |
| subB | RC_H68772_at | yr83f01.s1 Homo sapiens cDNA clone 211897 3', | A | NC | -1,2 | -0,01 |
| subB | RC_N30806_at | yw65f02.s1 Homo sapiens cDNA clone 257115 3', | A | NC | -1,1 | 0 |
| subB | RC_N63143_at | yz37c12.s1 Homo sapiens cDNA clone 285238 3', | A | NC | -3,9 | 0,32 |
| subB | RC_R33146_at | yh81f02.s1 Homo sapiens cDNA clone 136155 3' similar to contains Alu repetitive element;. | A | NC | -1,0 | 0 |
| subB | RC_R46206_at | yj53d08.s1 Homo sapiens cDNA clone 152463 3', | A | NC | 1,2 | 0,02 |
| subB | RC_R49731_s_at | yg71e10.s1 Homo sapiens cDNA clone 385554 3', | A | NC | -1,5 | -0,04 |
| subA | AA043223_at | zk55g12.r1 Soares pregnant uterus NbHPU Homo sapiens cDNA clone 486790 5', | P | NC | -1,4 | 0,02 |
| subA | AB002346_at | Human mRNA for KIAA0348 gene, complete cds, | P | NC | 2,2 | 0,23 |
| subA | D81608_at | Human fetal brain cDNA 5'-end GEN-177B09, | P | NC | 1,5 | 0,05 |
| subA | M83670_s_at | Human carbonic anhydrase IV mRNA, complete cds | P | NC | 1,2 | 0,02 |
| subA | N28843_at | yx69d10.r1 Homo sapiens cDNA clone 266035 5', | A | NC | 3,1 | 0,57 |
| subA | RC_AA149044_at | zl45d09.s1 Soares pregnant uterus NbHPU Homo sapiens cDNA clone 504881 3', | P | NC | 2,8 | 0,39 |
| subA | RC_AA258130_at | zs35f03.s1 NCI_CGAP_GCB1 Homo sapiens cDNA clone IMAGE:687197 3', | P | NC | -1,1 | -0,01 |
| subA | RC_AA281743_r_at | zt06h05.s1 NCI_CGAP_GCB1 Homo sapiens cDNA clone IMAGE:712377 3', | A | NC | -1,2 | -0,01 |
| subA | RC_AA406338_at | zv10f06.s1 Soares NhHMPu S1 Homo sapiens cDNA clone 753251 3', | P | NC | 1,2 | 0,02 |
| subA | RC_AA424524_at | zv90g02.s1 Soares NhHMPu S1 Homo sapiens cDNA clone 767090 3', | A | NC | 1,1 | 0 |
| subA | RC_AA435840_at | zt80b08.s1 Soares testis NHT Homo sapiens cDNA clone 728631 3', | P | NC | 1,6 | 0,1 |
| subB | RC_AA027823_at | zk05c04.s1 Soares pregnant uterus NbHPU Homo sapiens cDNA clone 469638 3', | A | NC | 1,4 | 0,04 |
| subB | RC_AA084138_at | zm17a03.s1 Soares pregnant uterus NT2RAMI 937234 Homo sapiens cDNA clone 547660 3', | A | NC | 1,1 | 0 |
| subB | RC_AA135406_at | zo28e08.s1 Stratagene colon (#937204) Homo sapiens cDNA clone 588230 3', | P | NC | 1,9 | 0,26 |
| subB | RC_AA148923_at | zl27g11.s1 Soares pregnant uterus NbHPU Homo sapiens cDNA clone 503204 3', | P | NC | 2,5 | 0,55 |
| subB | RC_H98653_at | yx12h06.s1 Homo sapiens cDNA clone 261563 3', | M | NC | 1,7 | 0,13 |
| subB | RC_N30077_at | yw81g11.s1 Homo sapiens cDNA clone 258892 3', | A | NC | 1,1 | 0,01 |
| subB | RC_R40166_at | yw70a09.s1 Homo sapiens cDNA clone 27448 3', | A | NC | 1,1 | 0 |
| subB | RC_190374_at | RETROVIRUS-RELATED POL POLYPROTEIN ; | P | NC | 1,1 | 0,01 |
| subB | RC_Z38182_at | H. sapiens partial cDNA sequence; clone c-02a08, | A | NC | 2,1 | 0,33 |
| Increase in T2 mix | | | | | | |
| subA | RC_AA054726_at | zk68e06.s1 Soares pregnant uterus NbHPU Homo sapiens cDNA clone 488002 3', | A | NC | -2,1 | 0,08 |
| subB | RC_AA206042_at | similar to contains element MSR1 repetitive element ; | A | NC | -7,1 | 0,68 |
| subB | RC_R98735_at | yr31g12.s1 Homo sapiens cDNA clone 206950 3', | A | NC | -13,5 | 8,2 |
| subA | AA115572_s_at | zl05d11.r1 Soares pregnant uterus NbHPU Homo sapiens cDNA clone 491445 5' similar to, TR:G895845 G895845 PUTATIVE P64 CLCP PROTEIN, ; | A | NC | 1,1 | 0 |
| subA | AA430979_at | PMY0789 KG1a Lambda Zap Express cDNA Library Homo sapiens cDNA 5', | P | NC | 1,7 | 0,12 |
| subA | AA489287_at | | A | NC | 3 | 0,58 |

Fig. 17.13

| Chip | Probe Set | Description | T1 Abs Call | Diff Call | Fold Change | Sort Score |
|---|---|---|---|---|---|---|
| Increase in T1 | | | | | | |
| subB | RC_H68772_at | yr83f01.s1 Homo sapiens cDNA clone 211897 3', | P | | -3,8 | 0,31 |
| subB | RC_N30806_at | yw65f02.s1 Homo sapiens cDNA clone 257115 3', | P | | -8,0 | 4,52 |
| subB | RC_N63143_at | yz37c12.s1 Homo sapiens cDNA clone 285238 3', | P | | -4,0 | 0,34 |
| subB | RC_R33146_at | yh81f02.s1 Homo sapiens cDNA clone 136155 3' similar to contains Alu repetitive element;, | P | | -20,4 | 14,82 |
| subB | RC_R46206_at | yj53d08.s1 Homo sapiens cDNA clone 152463 3', | P | | -3,6 | 0,9 |
| subB | RC_R49731_s_at | yg71e10.s1 Homo sapiens cDNA clone 38554 3', | P | | -8,2 | 4,7 |
| subA | AA043223_at | zk55g12.r1 Soares pregnant uterus NbHPU Homo sapiens cDNA clone 486790 5', | P | | 3,1 | 0,56 |
| subA | AB002346_at | Human mRNA for KIAA0348 gene, complete cds, | P | | 3,3 | 0,73 |
| subA | D81608_at | Human fetal brain cDNA 5'-end GEN-177B09, | P | | 9,3 | 4,67 |
| subA | M83670_s_at | Human carbonic anhydrase IV mRNA, complete cds | P | | 3,2 | 1,09 |
| subA | N28843_at | yx59d10.r1 Homo sapiens cDNA clone 266035 5', | P | | 4,8 | 1,48 |
| subA | RC_AA149044_at | zl45d09.s1 Soares pregnant uterus NbHPU Homo sapiens cDNA clone 504881 3', | P | | 11,1 | 4,76 |
| subA | RC_AA258130_at | zs35f03.s1 NCI_CGAP_GCB1 Homo sapiens cDNA clone IMAGE:687197 3', | P | | 3,4 | 1,28 |
| subA | RC_AA281743_r_at | zt06h05.s1 NCI_CGAP_GCB1 Homo sapiens cDNA clone IMAGE:712377 3', | P | | 4 | 0,84 |
| subA | RC_AA406338_at | zv10t06.s1 Soares NhHMPu S1 Homo sapiens cDNA clone 753251 3', | P | | 4,3 | 1,87 |
| subA | RC_AA424524_at | zv90g02.s1 Soares NhHMPu S1 Homo sapiens cDNA clone 767090 3', | P | | 3,1 | 0,5 |
| subA | RC_AA435840_at | zt80b08.s1 Soares testis NHT Homo sapiens cDNA clone 726631 3', | P | | 5,8 | 2,78 |
| subB | RC_AA027823_at | zk05c04.s1 Soares pregnant uterus NbHPU Homo sapiens cDNA clone 469638 3', | P | | 3,8 | 1,21 |
| subB | RC_AA084138_at | zn17a03.s1 Stratagene neuroepithelium NT2RAMI 937234 Homo sapiens cDNA clone 547660 3', | P | | 4,4 | 2,06 |
| subB | RC_AA135406_at | zo28e08.s1 Stratagene colon (#937204) Homo sapiens cDNA clone 588230 3', | P | | 3,3 | 1,29 |
| subB | RC_AA148923_at | zl27g11.s1 Soares pregnant uterus NbHPU Homo sapiens cDNA clone 503204 3', | P | | 8,2 | 5,66 |
| subB | RC_H98653_at | yx12h06.s1 Soares pregnant uterus NbHPU Homo sapiens cDNA clone 261663 3', | P | | 3,6 | 1,43 |
| subB | RC_N30077_at | yw81g11.s1 Soares pregnant uterus NbHPU Homo sapiens cDNA clone 258692 3', | P | | 6,5 | 4,31 |
| subB | RC_R40166_at | yf70a09.s1 Homo sapiens cDNA clone 27448 3', | P | | 6,4 | 4,13 |
| subB | RC_T90374_at | RETROVIRUS-RELATED POL POLYPROTEIN ; | P | | 4,3 | 4,15 |
| subB | RC_Z38182_at | H, sapiens partial cDNA sequence; clone c-02a08, | P | | 8,7 | 6,92 |
| Increase in T2 mix | | | | | | |
| subA | RC_AA054726_at | zk68e06.s1 Soares pregnant uterus NbHPU Homo sapiens cDNA clone 488002 3', | A | NC | -1,6 | 0,03 |
| subB | RC_AA206042_at | similar to contains element MSR1 repetitive element ; | A | NC | -3,6 | -0,29 |
| subB | RC_R98735_at | yr31g12.s1 Homo sapiens cDNA clone 206950 3', | A | NC | -10,9 | 5,82 |
| subA | AA115572_s_at | zl05d11.r1 Soares pregnant uterus NbHPU Homo sapiens cDNA clone 491445 5' similar to ,TR:G895845 G695845 | A | NC | 4,9 | 2,07 |
| subA | AA430979_at | PUTATIVE P64 CLCP PROTEIN, ; | P | NC | 1 | 0 |
| subA | AA489287_at | PMY0789 KG1a Lambda Zap Express cDNA Library Homo sapiens cDNA 5', | A | NC | 2,7 | 0,43 |

Fig. 17.14

| Chip | Probe Set | Description | T2 Mix Abs Call | Diff Call | Fold Change | Sort Score |
|---|---|---|---|---|---|---|
| Increase in T1 | | | | | | |
| subB | RC_H68772_at | yr83f01.s1 Homo sapiens cDNA clone 211897 3', | A | NC | -4,1 | -0,4 |
| subB | RC_N30806_at | yw65f02.s1 Homo sapiens cDNA clone 257115 3', | A | NC | -1,7 | 0,08 |
| subB | RC_N63143_at | yz37c12.s1 Homo sapiens cDNA clone 285238 3'; | A | NC | -1,5 | 0,05 |
| subB | RC_R33146_at | yh81f02.s1 Homo sapiens cDNA clone 136155 3' similar to contains Alu repetitive element;, | A | NC | -1,0 | 0 |
| subB | RC_R46206_at | yj53d08.s1 Homo sapiens cDNA clone 152463 3' | A | NC | 1,9 | 0,22 |
| subB | RC_R49731_s_at | yg71e10.s1 Homo sapiens cDNA clone 38554 3', | P | NC | -1,7 | 0,07 |
| subA | AA043223_at | zk55g12.r1 Soares pregnant uterus NbHPU Homo sapiens cDNA clone 486790 5', | A | NC | -1,5 | 0,05 |
| subA | AB002346_at | Human mRNA for KIAA0348 gene, complete cds, | A | NC | -1,2 | -0,01 |
| subA | D81608_at | Human fetal brain cDNA 5'-end GEN-177B09, | P | NC | 5,3 | 1,86 |
| subA | M83670_s_at | Human carbonic anhydrase IV mRNA, complete cds | M | NC | 1,8 | 0,2 |
| subA | N28843_at | yx59d10.r1 Homo sapiens cDNA clone 266035 5'. | A | NC | -1,1 | 0 |
| subA | RC_AA149044_at | zl45d09.s1 Soares pregnant uterus NbHPU Homo sapiens cDNA clone 504881 3', | M | NC | -3,2 | 0,56 |
| subA | RC_AA258130_at | zs35f03.s1 NCI_CGAP_GCB1 Homo sapiens cDNA clone IMAGE:687197 3', | A | NC | -3,9 | -0,77 |
| subA | RC_AA281743_r_at | zt06h05.s1 NCI_CGAP_GCB1 Homo sapiens cDNA clone IMAGE:712377 3' | P | NC | -2,3 | 0,22 |
| subA | RC_AA406338_at | zv10f06.s1 Soares NhHMPu S1 Homo sapiens cDNA clone 753251 3', | P | NC | 3 | 0,78 |
| subA | RC_AA424524_at | zv90g02.s1 Soares NhHMPu S1 Homo sapiens cDNA clone 767090 3', | P | NC | -2,2 | 0,2 |
| subA | RC_AA435840_at | zt80b08.s1 Soares testis NHT Homo sapiens cDNA clone 728631 3', | A | NC | 3 | 0,71 |
| subB | RC_AA027823_at | zk05c04.s1 Soares pregnant uterus NbHPU Homo sapiens cDNA clone 469638 3', | A | NC | -2,0 | 0,22 |
| subB | RC_AA084138_at | zn17a03.s1 Stratagene neuroepithelium NT2RAMI 937234 Homo sapiens cDNA clone 547660 3'. | A | NC | 1,4 | 0,06 |
| subB | RC_AA135406_at | zo28e08.s1 Stratagene colon (#937204) Homo sapiens cDNA clone 588230 3', | P | NC | 2,5 | 0,59 |
| subB | RC_AA148923_at | zl27g11.s1 Soares pregnant uterus NbHPU Homo sapiens cDNA clone 503204 3', | P | NC | 6,1 | 4 |
| subB | RC_H98653_at | yx12h06.s1 Homo sapiens cDNA clone 261563 3', | A | NC | -1,1 | -0,01 |
| subB | RC_N30077_at | yw81g11.s1 Homo sapiens cDNA clone 258692 3' | P | NC | 2,8 | 0,71 |
| subB | RC_R40166_at | yff70a09.s1 Homo sapiens cDNA clone 27448 3', | A | NC | 1,8 | 0,15 |
| subB | RC_T90374_at | RETROVIRUS-RELATED POL POLYPROTEIN ;, | P | NC | 1,7 | 0,31 |
| subB | RC_Z38182_at | H, sapiens partial cDNA sequence; clone c-02a08,. | P | NC | 1,9 | 0,23 |
| Increase in T2 mix | | | | | | |
| subA | RC_AA054726_at | zk68e06.s1 Soares pregnant uterus NbHPU Homo sapiens cDNA clone 488002 3'. | P | 1 | -3,1 | 0,43 |
| subA | RC_AA206042_at | similar to contains element MSR1 repetitive element ;, | P | 1 | -23,2 | 13,95 |
| subB | RC_R98735_at | yr31g12.s1 Homo sapiens cDNA clone 206950 3', | P | 1 | -6,8 | 0,73 |
| subA | AA115572_s_at | zl05d11.r1 Soares pregnant uterus NbHPU Homo sapiens cDNA clone 491445 5' similar to ,TR:G895845 G895845 PUTATIVE P64 CLCP PROTEIN,; | P | 1 | 8,7 | 5,44 |
| subA | AA430979_at | PMY0789 KG1a Lambda Zap Express cDNA Library Homo sapiens cDNA 5', | P | | 4,6 | 1,88 |
| subA | AA489287_at | | P | | 10,8 | 5,81 |

Fig. 17.15

| Chip | Probe Set | Description | T2 Solid Abs Call | Diff Call | Fold Change | Sort Score |
|---|---|---|---|---|---|---|
| Increase in T1 | | | | | | |
| subB | RC_H68772_at | yr83f01,s1 Homo sapiens cDNA clone 211897 3', | A | NC | -2,0 | -0,12 |
| subB | RC_N30806_at | yw65f02,s1 Homo sapiens cDNA clone 257115 3', | A | NC | -1,2 | -0,01 |
| subB | RC_N63143_at | yz37c12,s1 Homo sapiens cDNA clone 285238 3', | A | NC | -4,4 | -0,47 |
| subB | RC_R33146_at | yh81f02,s1 Homo sapiens cDNA clone 136155 3' similar to contains Alu repetitive element;, | A | NC | -1,1 | -0,01 |
| subB | RC_R46206_at | yj53d08,s1 Homo sapiens cDNA clone 152463 3', | P | NC | -2,2 | 0,24 |
| subB | RC_R49731_s_at | yg71e10,s1 Homo sapiens cDNA clone 38554 3', | A | NC | -1,1 | 0 |
| subA | AA043223_at | zk55g12,r1 Soares pregnant uterus NbHPU Homo sapiens cDNA clone 486790 5', | A | NC | -4,8 | 1,67 |
| subA | AB002346_at | Human mRNA for KIAA0348 gene, complete cds, | P | NC | -2,4 | 0,32 |
| subA | D81608_at | Human fetal brain cDNA 5'-end GEN-177B09, | P | NC | -1,4 | 0,03 |
| subA | M83670_s_at | Human carbonic anhydrase IV mRNA, complete cds | P | NC | 3,3 | 1,2 |
| subA | N28843_at | yx59d10,r1 Homo sapiens cDNA clone 266035 5', | A | NC | -1,3 | -0,02 |
| subA | RC_AA149044_at | zl45d09,s1 Soares pregnant uterus NbHPU Homo sapiens cDNA clone 504881 3', | P | NC | -5,0 | 1,75 |
| subA | RC_AA258130_at | zs35f03,s1 NCI_CGAP_GCB1 Homo sapiens cDNA clone IMAGE:687197 3', | P | NC | -3,4 | -0,55 |
| subA | RC_AA281743_r_at | zt06h05,s1 NCI_CGAP_GCB1 Homo sapiens cDNA clone IMAGE:712377 3', | P | NC | -1,9 | 0,12 |
| subA | RC_AA406338_at | zv10l06,s1 Soares NhHMPu S1 Homo sapiens cDNA clone 753251 3', | A | NC | 1,2 | 0,01 |
| subA | RC_AA424524_at | zv90g02,s1 Soares NhHMPu S1 Homo sapiens cDNA clone 767090 3', | P | NC | -1,6 | 0,04 |
| subA | RC_AA435840_at | zl80b08,s1 Soares testis NHT Homo sapiens cDNA clone 728631 3', | P | NC | 1,6 | 0,09 |
| subB | RC_AA027823_at | zx05c04,s1 Soares pregnant uterus NbHPU Homo sapiens cDNA clone 469638 3', | A | NC | -1,9 | 0,19 |
| subB | RC_AA084138_at | zn17a03,s1 Stratagene neuroepithelium NT2RAMI 937234 Homo sapiens cDNA clone 547660 3', | A | NC | 4,1 | 1,84 |
| subB | RC_AA135406_at | zo28e08,s1 Stratagene colon (#937204) Homo sapiens cDNA clone 588230 3', | P | NC | 2,5 | 0,6 |
| subB | RC_AA148923_at | zi27g11,s1 Soares pregnant uterus NbHPU Homo sapiens cDNA clone 503204 3', | A | NC | 1 | 0 |
| subB | RC_H98653_at | yx12h06,s1 Homo sapiens cDNA clone 261563 3', | P | NC | 1,2 | 0,02 |
| subB | RC_N30077_at | yw81g11,s1 Soares pregnant uterus NbHPU Homo sapiens cDNA clone 258692 3', | A | NC | -2,7 | -0,25 |
| subB | RC_R40166_at | yf70a09,s1 Homo sapiens cDNA clone 27448 3', | P | NC | -2,7 | 0,63 |
| subB | RC_T90374_at | RETROVIRUS-RELATED POL POLYPROTEIN ; | A | NC | 1,5 | 0,14 |
| subB | RC_Z38182_at | H, sapiens partial cDNA sequence; clone c-02a08, | P | NC | 3,8 | 1,54 |
| Increase in T2 mix | | | | | | |
| subA | RC_AA054726_at | zk68e06,s1 Soares pregnant uterus NbHPU Homo sapiens cDNA clone 488002 3', | A | NC | -1,7 | -0,06 |
| subB | RC_AA206042_at | similar to contains element MSR1 repetitive element ; | A | NC | -7,9 | -0,92 |
| subB | RC_R98735_at | yr31g12,s1 Homo sapiens cDNA clone 206950 3', | A | NC | -2,6 | -0,21 |
| subA | AA115572_s_at | zl05d11,r1 Soares pregnant uterus NbHPU Homo sapiens cDNA clone 491445 5' similar to ,TR:G895845 G895845 PUTATIVE P64 CLCP PROTEIN, ; | A | NC | 4,5 | 1,76 |
| subA | AA430979_at | PMY0789 KG1a Lambda Zap Express cDNA Library Homo sapiens cDNA 5', | P | NC | -2,3 | -0,17 |
| subA | AA489287_at | | A | NC | -4,1 | 1,28 |

Fig. 17.16

| Chip | Probe Set | Description | Normal Avg Diff | Abs Call |
|---|---|---|---|---|
| Increase in T2 mix | | | | |
| subA | D82226_s_at | similar to TAT-binding protein-2, | 322 | P |
| subA | H49499_s_at | | 134 | P |
| subA | M11844_at | Human prealbumin gene, complete cds, | 45 | A |
| subA | RC_AA026388_at | ze92c03.s1 Soares fetal heart NbHH19W Homo sapiens cDNA clone 366436 3', | 69 | P |
| subA | RC_AA044601_at | zk55d05.s1 Soares pregnant uterus NbHPU Homo sapiens cDNA clone 486729 3', | 399 | P |
| subA | RC_AA182030_at | | 30 | P |
| subA | RC_AA233451_at | zr30b02.s1 Stratagene NT2 neuronal precursor 937230 Homo sapiens cDNA clone 664875 3', | 49 | M |
| subA | RC_AA236493_at | zr75c10.s1 Soares NhHMPu S1 Homo sapiens cDNA clone 669234 3', | 61 | A |
| subA | RC_AA401098_f_at | zu50g01.s1 Soares ovary tumor NbHOT Homo sapiens cDNA clone 741456 3' similar to contains Alu repetitive element; contains element THR repetitive element ; | 182 | P |
| subA | RC_AA441818_at | zw62f01.s1 Soares total fetus Nb2HF8 9w Homo sapiens cDNA clone 774649 3', | 177 | P |
| subA | RC_AA478109_at | zt89d04.s1 Soares testis NHT Homo sapiens cDNA clone 729511 3', | 35 | A |
| subA | RC_AA481430_at | zv06g11.s1 Soares NhHMPu S1 Homo sapiens cDNA clone 752900 3', | 407 | P |
| subA | RC_AA488878_at | aa55f02.s1 NCI_CGAP_GCB1 Homo sapiens cDNA clone IMAGE:824859 3', | 64 | A |
| subA | RC_AA599032_at | ae41h03.s1 Gessler Wilms tumor Homo sapiens cDNA clone 898421 3', | 135 | A |
| subA | S73288_at | small proline-rich protein SPRK [human, odontogenic keratocysts, mRNA Partial, 317 nt], | 253 | P |
| subA | U87459_at | Human autoimmunogenic cancer/testis antigen NY-ESO-1 mRNA, complete cds | 324 | P |
| subA | U88047_at | Human DNA binding protein homolog (DRX) mRNA, partial cds | 54 | A |
| subB | RC_AA063574_at | ze25f03.s1 Soares fetal heart NbHH19W Homo sapiens cDNA clone 360029 3' similar to gb:X52104 P68 PROTEIN (HUMAN); | 88 | A |
| subB | RC_AA132524_at | zo20c04.s1 Stratagene colon (#937204) Homo sapiens cDNA clone 587430 3' similar to contains Alu repetitive element; | 95 | A |
| subB | RC_F09317_at | H. sapiens partial cDNA sequence; clone c-22h11, | 511 | P |
| subB | RC_H12863_at | yl14b12.s1 Homo sapiens cDNA clone 148703 3', | 81 | A |
| subB | RC_N33927_s_at | yv25e09.s1 Homo sapiens cDNA clone 243784 3', | 277 | P |
| subB | RC_R08189_at | yf18f03.s1 Homo sapiens cDNA clone 127229 3', | 134 | M |
| subB | RC_R39191_s_at | yc89c12.s1 Homo sapiens cDNA clone 23345 3', | 118 | P |
| subB | RC_T82323_at | AS322 Homo sapiens cDNA clone AS322 3', | 142 | P |
| subB | RC_T90746_at | yd41f10.s1 Homo sapiens cDNA clone 110527 3', | 105 | A |
| subB | RC_Z39338_at | H. sapiens partial cDNA sequence; clone c-17f11, | 67 | A |
| Increase in T2 solid | | | | |
| subA | AA011479_at | EST186601 Colon carcinoma (HCC) cell line II Homo sapiens cDNA 5' end, | 27 | A |
| subA | AA314779_at | zn20d05.s1 Stratagene neuroepithelium NT2RAMI 937234 Homo sapiens cDNA clone 547977 3', | 57 | P |
| subA | RC_AA084640_at | | 150 | A |

Fig. 17.17

| Chip | Probe Set | Description | Ta Abs Call | Diff Call | Fold Change | Sort Score |
|---|---|---|---|---|---|---|
| Increase in T2 mix | | | | | | |
| subA | D82226_s_at | similar to TAT-binding protein-2, | P | NC | 1,1 | 0,01 |
| subA | H49499_s_at | | P | NC | 1,5 | 0,1 |
| subA | M11844_at | Human prealbumin gene, complete cds, | A | NC | -1 | 0 |
| subA | RC_AA026388_at | ze92c03.s1 Soares fetal heart NbHH19W Homo sapiens cDNA clone 366436 3', | P | NC | 2 | 0,24 |
| subA | RC_AA044601_at | zk55d05.s1 Soares pregnant uterus NbHPU Homo sapiens cDNA clone 486729 3', | P | NC | -1,1 | -0,01 |
| subA | RC_AA182030_at | | P | NC | 2 | 0,14 |
| subA | RC_AA233451_at | zr30b02.s1 Stratagene NT2 neuronal precursor 937230 Homo sapiens cDNA clone 664875 3', | P | NC | 1,6 | 0,08 |
| subA | RC_AA236493_at | zr75c10.s1 Soares NhHMPu S1 Homo sapiens cDNA clone 669234 3', | P | NC | 1,6 | 0,1 |
| subA | RC_AA401098_f_at | zu50g01.s1 Soares ovary tumor NbHOT Homo sapiens cDNA clone 741456 3' similar to .contains ,Alu repetitive element; contains element THR repetitive element ; | P | NC | 2,1 | 0,44 |
| subA | RC_AA441818_at | zw62f01.s1 Soares total fetus Nb2HF8 9w Homo sapiens cDNA clone 774649 3', | P | NC | 1 | 0 |
| subA | RC_AA478109_at | zt89d04.s1 Soares testis NHT Homo sapiens cDNA clone 729511 3', | A | NC | 1,5 | 0,05 |
| subA | RC_AA481430_at | zv06g11.s1 Soares NhHMPu S1 Homo sapiens cDNA clone 752900 3', | P | NC | 1,4 | 0,12 |
| subA | RC_AA488878_at | aa55f02.s1 NCI_CGAP_GCB1 Homo sapiens cDNA clone IMAGE:824859 3', | P | NC | 1,3 | 0,03 |
| subA | RC_AA599032_at | ae41h03.s1 Gessler Wilms tumor Homo sapiens cDNA clone 898421 3', | M | NC | 1,1 | 0,01 |
| subA | S73288_at | small proline-rich protein SPRK (human, odontogenic keratocysts, mRNA Partial, 317 nt], | P | NC | 1,2 | 0,04 |
| subA | U87459_at | Human autoimmunogenic cancer/testis antigen NY-ESO-1 mRNA, complete cds | P | NC | 1,2 | 0,05 |
| subA | U88047_at | Human DNA binding protein homolog (DRX) mRNA, partial cds | A | NC | 1 | 0 |
| subB | RC_AA063574_at | ze25c03.s1 Soares fetal heart NbHH19W Homo sapiens cDNA clone 360029 3' similar to ,gb:X52104 P68 PROTEIN (HUMAN); | A | NC | 1,5 | 0,08 |
| subB | RC_AA132524_at | zo20c04.s1 Stratagene colon (#937204) Homo sapiens cDNA clone 587430 3' similar to ,contains Alu repetitive element; | P | NC | 2,3 | 0,48 |
| subB | RC_F09317_at | H, sapiens partial cDNA sequence; clone c-2zh11, | P | NC | 1,7 | 0,37 |
| subB | RC_H12863_at | yl14b12.s1 Homo sapiens cDNA clone 148703 3', | A | NC | 2,6 | 0,58 |
| subB | RC_N33927_s_at | yv25e09.s1 Homo sapiens cDNA clone 243784 3', | A | NC | -2 | -0,36 |
| subB | RC_R08189_at | yf18f03.s1 Homo sapiens cDNA clone 127229 3', | P | NC | -1,1 | 0 |
| subB | RC_R39191_s_at | yc89c12.s1 Homo sapiens cDNA clone 233345 3', | P | NC | 2,8 | 0,9 |
| subB | RC_T82323_at | AS322 Homo sapiens cDNA clone AS322 3', | P | NC | -1,1 | -0,01 |
| subB | RC_T90746_at | yd41f10.s1 Homo sapiens cDNA clone 110827 3', | M | NC | 1,7 | 0,18 |
| subB | RC_Z39338_at | H, sapiens partial cDNA sequence; clone c-17f11, | P | NC | 2 | 0,23 |
| Increase in T2 solid | | | | | | |
| subA | AA011479_at | EST186601 Colon carcinoma (HCC) cell line II Homo sapiens cDNA 5' end, | A | NC | -12,4 | -1,2 |
| subA | AA314779_at | zn20d05.s1 Stratagene neuroepithelium NT2RAMI 937234 Homo sapiens cDNA clone 547977 3', | A | NC | -2,1 | -0,18 |
| subA | RC_AA084640_at | | A | NC | 1,6 | 0,13 |

Fig. 17.18

| Chip | Probe Set | Description | T1 Abs Call | Diff Call | Fold Change | Sort Score |
|---|---|---|---|---|---|---|
| Increase in T2 mix | | | | | | |
| subA | D82226_s_at | similar to TAT-binding protein-2, | P | NC | 1,4 | 0,1 |
| subA | H49499_s_at | | P | NC | -1,2 | 0,03 |
| subA | M11844_at | Human prealbumin gene, complete cds, | A | NC | 1,1 | 0 |
| subA | RC_AA026388_at | ze92c03.s1 Soares fetal heart NbHH19W Homo sapiens cDNA clone 368436 3', | P | NC | 2,7 | 0,61 |
| subA | RC_AA044601_at | zk55d05.s1 Soares pregnant uterus NbHPU Homo sapiens cDNA clone 486729 3', | P | NC | 2,5 | 1,27 |
| subA | RC_AA182030_at | | P | NC | 2,3 | 0,27 |
| subA | RC_AA233451_at | zr30b02.s1 Stratagene NT2 neuronal precursor 937230 Homo sapiens cDNA clone 664875 3', | P | NC | 3,4 | 0,93 |
| subA | RC_AA236493_at | zr75c10.s1 Soares NhHMPu S1 Homo sapiens cDNA clone 669234 3', | P | NC | 2,1 | 0,29 |
| subA | RC_AA401098_f_at | zu50g01.s1 Soares ovary tumor NbHOT Homo sapiens cDNA clone 741456 3' similar to contains Alu repetitive element; contains element THR repetitive element; | P | NC | 1,4 | 0,08 |
| subA | RC_AA441818_at | zw62f01.s1 Soares total fetus Nb2HF8.9w Homo sapiens cDNA clone 774649 3', | P | NC | 1 | 0 |
| subA | RC_AA478109_at | zt89d04.s1 Soares testis NHT Homo sapiens cDNA clone 729511 3', | P | NC | 1,7 | 0,1 |
| subA | RC_AA481430_at | zv06g11.s1 Soares NhHMPu S1 Homo sapiens cDNA clone 752900 3', | A | NC | 1,4 | 0,12 |
| subA | RC_AA488878_at | aa55f02.s1 NCI_CGAP_GCB1 Homo sapiens cDNA clone IMAGE:824859 3', | P | NC | 1,7 | 0,13 |
| subA | RC_AA599032_at | ae41h03.s1 Gessler Wilms tumor Homo sapiens cDNA clone 898421 3', | P | NC | 1,7 | 0,2 |
| subA | S73288_at | small proline-rich protein SPRK [human, odontogenic keratocysts, mRNA Partial, 317 nt], | | | 2,2 | 0,68 |
| subA | U87459_at | Human autoimmunogenic cancer/testis antigen NY-ESO-1 mRNA, complete cds | P | NC | 1,2 | 0,03 |
| subA | U88047_at | Human DNA binding protein homolog (DRX) mRNA, partial cds | A | NC | 1,7 | 0,11 |
| subB | RC_AA063574_at | ze25f03.s1 Soares fetal heart NbHH19W Homo sapiens cDNA clone 360029 3' similar to ,gb:X52104 P68 PROTEIN (HUMAN); | P | NC | 2,4 | 0,51 |
| subB | RC_AA132524_at | zo20c04.s1 Stratagene colon (#937204) Homo sapiens cDNA clone 587430 3' similar to ,contains Alu repetitive element; | P | NC | 3,5 | 1,4 |
| subB | RC_F09317_at | H, sapiens partial cDNA sequence; clone c-22h11, | P | NC | 1,8 | 0,42 |
| subB | RC_H12863_at | yl14f12.s1 Homo sapiens cDNA clone 148703 3', | A | NC | 3,6 | 1,39 |
| subB | RC_N33927_s_at | yv25e09.s1 Homo sapiens cDNA clone 243784 3', | P | NC | -1,2 | -0,03 |
| subB | RC_R08189_at | yf18f03.s1 Homo sapiens cDNA clone 127229 3', | P | NC | 1,4 | 0,07 |
| subB | RC_R39191_s_at | yc89c12.s1 Homo sapiens cDNA clone 23345 3', | P | NC | 2,8 | 0,94 |
| subB | RC_T82323_at | AS322 Homo sapiens cDNA clone AS322 3', | P | NC | 1,4 | 0,08 |
| subB | RC_T90746_at | yd41f10.s1 Homo sapiens cDNA clone 110827 3', | P | NC | 2 | 0,29 |
| subB | RC_Z39338_at | H, sapiens partial cDNA sequence; clone c-17f11, | P | NC | 2,8 | 0,65 |
| Increase in T2 solid | | | | | | |
| subA | AA0114479_at | EST186601 Colon carcinoma (HCC) cell line II Homo sapiens cDNA 5' end. | A | NC | 3,3 | 0,66 |
| subA | AA314779_at | | P | NC | 1,4 | 0,07 |
| subA | RC_AA084640_at | zn20d05.s1 Stratagene neuroepithelium NT2RAMI 937234 Homo sapiens cDNA clone 547977 3' | A | NC | 1,2 | 0,02 |

Fig. 17.19

| Chip | Probe Set | Description | T2 Mix Abs Call | Diff Call | Fold Change | Sort Score |
|---|---|---|---|---|---|---|
| Increase in T2 mix | | | | | | |
| subA | D82226_s_at | similar to TAT-binding protein-2, | P | I | 3 | 1,54 |
| subA | H49499_s_at | | P | I | 3,3 | 1,4 |
| subA | M11844_at | Human prealbumin gene, complete cds, | P | I | 4,7 | 2,86 |
| subA | RC_AA026388_at | ze92co3,s1 Soares fetal heart NbHH19W Homo sapiens cDNA clone 366436 3', | P | I | 4,3 | 1,84 |
| subA | RC_AA044601_at | zk55d05,s1 Soares pregnant uterus NbHPU Homo sapiens cDNA clone 486729 3', | P | I | 4,9 | 4,82 |
| subA | RC_AA182030_at | | | | 4,5 | 1,33 |
| subA | RC_AA233451_at | zr30b02,s1 Stratagene NT2 neuronal precursor 937230 Homo sapiens cDNA clone 664875 3', | P | I | 4,5 | 1,75 |
| subA | RC_AA236493_at | zr75c10,s1 Soares NhHMPu S1 Homo sapiens cDNA clone 669234 3', | | | 3 | 0,74 |
| subA | RC_AA401098_f_at | zu50g01,s1 Soares ovary tumor NbHOT Homo sapiens cDNA clone 741456 3' similar to contains ,Alu repetitive element; contains element THR repetitive element ; | P | I | 3,8 | 2,35 |
| subA | RC_AA441818_at | zw62f01,s1 Soares total fetus Nb2HF8 9w Homo sapiens cDNA clone 774649 3', | P | I | 3,1 | 1,14 |
| subA | RC_AA478109_at | zt89d04,s1 Soares testis NHT Homo sapiens cDNA clone 729511 3', | P | I | 3,7 | 0,97 |
| subA | RC_AA481430_at | zv08g11,s1 Soares NhHMPu S1 Homo sapiens cDNA clone 752900 3', | P | I | 5,7 | 6,41 |
| subA | RC_AA488878_at | aa55f02,s1 NCI_CGAP_GCB1 Homo sapiens cDNA clone IMAGE:824859 3', | P | I | 3,3 | 0,99 |
| subA | RC_AA599032_at | ae41h03,s1 Gessler Wilms tumor Homo sapiens cDNA clone 898421 3', | P | I | 3,9 | 1,8 |
| subA | S73288_at | small proline-rich protein SPRK [human, odontogenic keratocysts, mRNA Partial, 317 nt], | P | I | 6,4 | 5,98 |
| subA | U87459_at | Human autoimmunogenic cancer/testis antigen NY-ESO-1 mRNA, complete cds | P | I | 3,7 | 2,98 |
| subA | U88047_at | Human DNA binding protein homolog (DRX) mRNA, partial cds | P | I | 3,2 | 0,84 |
| subB | RC_AA063574_at | ze25f03,s1 Soares fetal heart NbHH19W Homo sapiens cDNA clone 360029 3' similar to ,gb:X52104 P68 PROTEIN (HUMAN); | P | I | 3,7 | 1,56 |
| subB | RC_AA132524_at | zo20c04,s1 Stratagene colon (#937204) Homo sapiens cDNA clone 587430 3' similar to ,contains Alu repetitive element; | P | I | 4,3 | 2,17 |
| subB | RC_F09317_at | H, sapiens partial cDNA sequence; clone c-22h11, | P | I | 3 | 2,18 |
| subB | RC_H12863_at | yi14b12,s1 Homo sapiens cDNA clone 148703 3', | P | I | 3,5 | 1,31 |
| subB | RC_N33927_s_at | yv25e09,s1 Homo sapiens cDNA clone 243784 3', | P | I | 3,1 | 1,58 |
| subB | RC_R08189_at | yf18f03,s1 Homo sapiens cDNA clone 127229 3', | P | I | 4,4 | 2,7 |
| subB | RC_R39191_s_at | yc89c12,s1 Homo sapiens cDNA clone 23345 3', | P | I | 7,8 | 6,99 |
| subB | RC_T82323_at | AS322 Homo sapiens cDNA clone AS322 3', | P | I | 4,1 | 2,37 |
| subB | RC_T90746_at | yd41f10,s1 Homo sapiens cDNA clone 110827 3', | P | I | 3,1 | 1,09 |
| subB | RC_Z39338_at | H, sapiens partial cDNA sequence; clone c-17f11, | P | I | 5,8 | 3,24 |
| Increase in T2 solid | | | | | | |
| subA | AA011479_at | EST186601 Colon carcinoma (HCC) cell line II Homo sapiens cDNA 5' end, | P | NC | -4,3 | 1,2 |
| subA | AA314779_at | zn20d05,s1 Stratagene neuroepithelium NT2RAMI 937234 Homo sapiens cDNA clone 547977 3', | P | NC | 1,7 | 0,12 |
| subA | RC_AA084640_at | | A | NC | 1 | 0 |

Fig. 17.20

| Chip | Probe Set | Description | T2 Solid Abs Call | Diff Call | Fold Change | Sort Score |
|---|---|---|---|---|---|---|
| Increase in T2 mix | | | | | | |
| subA | D82226_s_at | similar to TAT-binding protein-2, | P | NC | 1,4 | 0,12 |
| subA | H49499_s_at | | P | NC | 1,2 | 0,02 |
| subA | M11844_at | Human prealbumin gene, complete cds, | A | NC | 1 | 0 |
| subA | RC_AA026388_at | ze92c03.s1 Soares fetal heart NbHH19W Homo sapiens cDNA clone 366436 3', | A | NC | -1,6 | -0,05 |
| subA | RC_AA044601_at | zk55d05.s1 Soares pregnant uterus NbHPU Homo sapiens cDNA clone 486729 3', | P | NC | 3,8 | 3,41 |
| subA | RC_AA182030_at | | P | NC | -3,5 | 0,85 |
| subA | RC_AA233451_at | zr30b02.s1 Stratagene NT2 neuronal precursor 937230 Homo sapiens cDNA clone 664875 3', | M | NC | 1,1 | 0 |
| subA | RC_AA236493_at | zr75c10.s1 Soares NhHMPu S1 Homo sapiens cDNA clone 669234 3', | A | NC | 1,9 | 0,21 |
| subA | RC_AA401098_f_at | zu50g01.s1 Soares ovary tumor NbHOT Homo sapiens cDNA clone 741456 3' similar to ,contains ,Alu repetitive element; contains element THR repetitive element ; | P | NC | 2,1 | 0,5 |
| subA | RC_AA441818_at | zw62f01.s1 Soares total fetus Nb2HF8 9w Homo sapiens cDNA clone 774649 3', | P | NC | 1,1 | 0,01 |
| subA | RC_AA478109_at | zt89d04.s1 Soares testis NHT Homo sapiens cDNA clone 729511 3', | A | NC | -1,7 | 0,1 |
| subA | RC_AA481430_at | zv06g11.s1 Soares NhHMPu S1 Homo sapiens cDNA clone 752900 3', | P | NC | 1,8 | 0,32 |
| subA | RC_AA488878_at | aa55f02.s1 NCI_CGAP_GCB1 Homo sapiens cDNA clone IMAGE:824859 3', | A | NC | -2,7 | -0,27 |
| subA | RC_AA599032_at | ae41h03.s1 Gessler Wilms tumor Homo sapiens cDNA clone 898421 3', | A | NC | 2,8 | 0,85 |
| subA | S73288_at | small proline-rich protein SPRK [human, odontogenic keratocysts, mRNA Partial, 317 nt]; | P | NC | 2,4 | 0,81 |
| subA | U87459_at | Human autoimmunogenic cancer/testis antigen NY-ESO-1 mRNA, complete cds | M | NC | 1,1 | 0,01 |
| subA | U88047_at | Human DNA binding protein homolog (DRX) mRNA, partial cds | P | NC | 2,4 | 0,39 |
| subA | RC_AA063574_at | ze25f03.s1 Soares fetal heart NbHH19W Homo sapiens cDNA clone 360029 3' similar to ,gb:X52104 P68 PROTEIN (HUMAN); | A | NC | 2,5 | 0,58 |
| subB | RC_AA132524_at | zo20c04.s1 Stratagene colon (#937204) Homo sapiens cDNA clone 587430 3' similar to ,contains Alu repetitive element; | P | NC | 3 | 0,94 |
| subB | RC_F09317_at | H. sapiens partial cDNA sequence; clone c-2zh11, | A | NC | 1,4 | 0,13 |
| subB | RC_H12863_at | yj14b12.s1 Homo sapiens cDNA clone 148703 3', | A | NC | 2,8 | 0,77 |
| subB | RC_N33927_s_at | yv25e09.s1 Homo sapiens cDNA clone 243784 3', | P | NC | 1,8 | 0,31 |
| subB | RC_R08189_at | yf18f03.s1 Homo sapiens cDNA clone 127229 3', | A | NC | -1 | 0 |
| subB | RC_R39191_s_at | yc89c12.s1 Homo sapiens cDNA clone 233345 3', | P | NC | 2 | 0,32 |
| subB | RC_T82323_at | AS322 Homo sapiens cDNA clone AS322 3', | P | NC | 1,6 | 0,17 |
| subB | RC_T90746_at | yd41f10.s1 Homo sapiens cDNA clone 110827 3', | P | NC | 2,2 | 0,4 |
| subB | RC_Z39338_at | H. sapiens partial cDNA sequence; clone c-17f11, | P | NC | -4,7 | 2,24 |
| Increase in T2 solid | | | | | | |
| subA | AA011479_at | EST186601 Colon carcinoma (HCC) cell line II Homo sapiens cDNA 5' end, | P | I | -22,9 | 15,52 |
| subA | AA314779_at | zn20d05.s1 Stratagene neuroepithelium NT2RAMII 937234 Homo sapiens cDNA clone 547977 3', | P | I | -41,3 | 27,3 |
| subA | RC_AA084640_at | | P | I | -3,7 | 1,06 |

Fig. 17.21

| Chip | Probe Set | Description | Normal Avg Diff | Abs Call |
|---|---|---|---|---|
| Increase in T2 solid | | | | |
| subA | RC_AA121534_at | zk89d11.s1 Soares pregnant uterus NbHPU Homo sapiens cDNA clone 490005 3' similar to ,gb:X79535 TUBULIN BETA-2 CHAIN (HUMAN); | -23 | P |
| subA | RC_AA131047_s_at | zo16f05.s1 Stratagene colon (#937204) Homo sapiens cDNA clone 587073 3' | 53 | M |
| subA | RC_AA461549_at | zx62b09.s1 Soares total fetus Nb2HF8 9w Homo sapiens cDNA clone 796025 3' | 28 | A |
| subA | RC_AA491465_at | | 16 | A |
| subA | RC_AA496936_at | ae32d03.s1 Gessler Wilms tumor Homo sapiens cDNA clone 897509 3' | 20 | A |
| subA | RC_AA598689_at | | 24 | A |
| subA | W26392_at | 30g3 Human retina cDNA randomly primed sublibrary Homo sapiens cDNA, | 25 | A |
| subB | RC_AA004887_at | | 37 | A |
| subB | RC_AA135153_at | zo24g02.s1 Stratagene colon (#937204) Homo sapiens cDNA clone 587858 3' | 39 | A |
| subB | RC_AA197311_s_at | zq50e09.s1 Stratagene neuroepithelium (#937231) Homo sapiens cDNA clone G45064 3' similar to ,gb:M24283 INTERCELLULAR ADHESION MOLECULE-1 PRECURSOR (HUMAN); | -233 | A |
| subB | RC_H80622_at | yu77b06.s1 Homo sapiens cDNA clone 239795 3' | 46 | A |
| subB | RC_N64436_at | zaa33a09.s1 Homo sapiens cDNA clone 294328 3' | 54 | M |
| subB | RC_N67583_at | yz42c02.s1 Homo sapiens cDNA clone 285698 3' | 68 | A |
| subB | RC_R38678_at | yc89d05.s1 Homo sapiens cDNA clone 234433'; | -114 | A |
| subB | RC_R56066_s_at | yg91d08.s1 Homo sapiens cDNA clone 40992 3' | -48 | A |
| subB | RC_R59292_at | yh16a10.s1 Homo sapiens cDNA clone 37689 3'; | 40 | A |
| subB | RC_T24099_at | seq2287 Homo sapiens cDNA clone Cot25 0Ft-b4HB3MA-8 3' | -507 | A |
| subA | AA150364_at | zl07b03.r1 Soares pregnant uterus NbHPU Homo sapiens cDNA clone 491597 5' | 89 | P |
| subA | AA174185_at | PTH207 HTCDL1 Homo sapiens cDNA 5'/3'; | 120 | P |
| subA | AA452353_i_at | zx15d05.r1 Soares total fetus Nb2HF8 9w Homo sapiens cDNA clone 786537 5' | 361 | A |
| subA | AB002316_at | Human mRNA for KIAA0318 gene, partial cds, | 34 | A |
| subA | H86858_at | ys72d05.r1 Homo sapiens cDNA clone 220329 5'; | 60 | P |
| subA | M93119_s_at | Human zinc-finger DNA-binding motifs (IA-1) mRNA, complete cds | 62 | P |
| subA | R72037_at | yj86c09.r1 Homo sapiens cDNA clone 155632 5'; | 424 | P |
| subA | RC_AA004274_at | similar to contains element MER22 repetitive element: | 223 | A |
| subA | RC_AA004415_at | zI74e07.s1 Stratagene colon (#937204) Homo sapiens cDNA clone 510372 3' similar to ,contains Alu repetitive element; | 49 | P |
| subA | RC_AA007160_at | | 117 | P |
| subA | RC_AA053660_at | | 274 | A |
| subA | RC_AA252603_at | zs14a11.s1 NCI_CGAP_GCB1 Homo sapiens cDNA clone IMAGE:685148 3' | 59 | P |
| subA | RC_AA411944_at | zu03h01.s1 Soares testis NHT Homo sapiens cDNA clone 730801 3'; | 53 | P |
| subA | RC_AA412700_at | zu12g03.s1 Soares testis NHT Homo sapiens cDNA clone 731668 3'; | 557 | P |
| subA | RC_AA430032_at | zw65l05.s1 Soares testis NHT Homo sapiens cDNA clone 781089 3'; | 285 | P |
| subA | RC_AA430368_at | zw20l06.s1 Soares ovary tumor NbHOT Homo sapiens cDNA clone 769859 3' | 48 | A |

Fig. 17.22

| Chip | Probe Set | Description | Ta Abs Call | Diff Call | Fold Change | Sort Score |
|---|---|---|---|---|---|---|
| Increase in T2 solid | | | | | | |
| subA | RC_AA121534_at | zk89d11.s1 Soares pregnant uterus NbHPU Homo sapiens cDNA clone 490005 3' similar to ,gb:X79535 TUBULIN BETA-2 CHAIN (HUMAN); | A | NC | -3,3 | -0,23 |
| subA | RC_AA131047_s_at | zo16f05.s1 Stratagene colon (#937204) Homo sapiens cDNA clone 587073 3' | A | NC | -1,3 | -0,02 |
| subA | RC_AA461549_at | zx62b09.s1 Soares total fetus Nb2HF8 9w Homo sapiens cDNA clone 796025 3' | A | NC | -1,2 | -0,01 |
| subA | RC_AA491465_at | | A | NC | -1,0 | 0 |
| subA | RC_AA499936_at | ae32d03.s1 Geissler Wilms tumor Homo sapiens cDNA clone 897509 3'; | A | NC | -1,5 | -0,02 |
| subA | RC_AA598689_at | | A | NC | -1 | 0 |
| W26392_at | | 30g3 Human retina cDNA randomly primed sublibrary Homo sapiens cDNA, | A | NC | -1,8 | -0,06 |
| subB | RC_AA004887_at | zo24c02.s1 Stratagene colon (#937204) Homo sapiens cDNA clone 587858 3'; | P | NC | -1,2 | 0,01 |
| subB | RC_AA135153_at | zq50e09.s1 Stratagene neuroepithelium (#937231) Homo sapiens cDNA clone 645064 3' similar to ,gb:M24283 INTERCELLULAR ADHESION MOLECULE-1 PRECURSOR (HUMAN); | P | NC | -2,5 | 0,39 |
| subB | RC_AA197311_s_at | | A | NC | -2,6 | 0,17 |
| subB | RC_H80622_at | yu77b06.s1 Homo sapiens cDNA clone 239795 3'; | A | NC | -2,2 | -0,12 |
| subB | RC_N64436_at | za33a09.s1 Homo sapiens cDNA clone 294328 3'; | A | NC | 1 | 0 |
| subB | RC_N67583_at | yz42c02.s1 Homo sapiens cDNA clone 285698 3'; | A | NC | -3,2 | -0,36 |
| subB | RC_R38678_at | yc89d05.s1 Homo sapiens cDNA clone 23443 3'; | A | NC | -1,2 | -0,01 |
| subB | RC_R56066_s_at | yg91d08.s1 Homo sapiens cDNA clone 40992 3'; | A | NC | -1,9 | 0,08 |
| subB | RC_R59292_at | yh16a10.s1 Homo sapiens cDNA clone 37689 3'; | A | NC | -2,5 | -0,16 |
| subB | RC_T24099_at | seq2287 Homo sapiens cDNA clone Cot25OFt-b4H33MA-8 3'; | A | NC | -5,3 | 0,48 |
| subA | AA150364_at | zi07b03.r1 Soares pregnant uterus NbHPU Homo sapiens cDNA clone 491597 5'; | P | NC | 1,6 | 0,11 |
| subA | AA174185_at | PTH207 HTCDL1 Homo sapiens cDNA 5'/3'; | A | NC | 1,2 | 0,03 |
| subA | AA452353_i_at | zx15d05.r1 Soares total fetus Nb2HF8 9w Homo sapiens cDNA clone 786537 5'; | P | NC | 1,2 | 0,05 |
| subA | AB002316_at | Human mRNA for KIAA0318 gene, partial cds, | A | NC | 1,6 | 0,06 |
| H86858_at | | ys72d05.r1 Homo sapiens cDNA clone 220329 5'; | M | NC | 1,2 | 0,02 |
| M93119_s_at | | Human zinc-finger DNA-binding motifs (IA-1) mRNA, complete cds | P | NC | 1,3 | 0,04 |
| R72037_at | | yj86c09.r1 Homo sapiens cDNA clone 155632 5'; | P | NC | 1,1 | 0 |
| subA | RC_AA004274_at | similar to contains element MER22 repetitive element;, | P | NC | -1,3 | -0,05 |
| subA | RC_AA004415_at | | P | NC | -1,7 | -0,08 |
| subA | RC_AA007160_at | | P | NC | 1,5 | 0,11 |
| subA | RC_AA053660_at | zi74e07.s1 Stratagene colon (#937204) Homo sapiens cDNA clone 510372 3' similar to ,contains Alu repetitive element; | P | NC | -1,5 | -0,09 |
| subA | RC_AA252603_at | zs14a11.s1 NCI_CGAP_GCB1 Homo sapiens cDNA IMAGE:685148 3'; | P | NC | -1,1 | -0,01 |
| subA | RC_AA411944_at | zu03h01.s1 Soares testis NHT Homo sapiens cDNA clone 730801 3'; | P | NC | -1,4 | -0,04 |
| subA | RC_AA412700_at | zu12g03.s1 Soares testis NHT Homo sapiens cDNA clone 731668 3'; | P | NC | -1 | 0 |
| subA | RC_AA430032_at | zw65f05.s1 Soares testis NHT Homo sapiens cDNA clone 781089 3'; | P | NC | -1,4 | -0,08 |
| subA | RC_AA430368_at | zw20f06.s1 Soares ovary tumor NbHOT Homo sapiens cDNA clone 769859 3'; | P | NC | 1,1 | 0,01 |

Fig. 17.23

| Chip | Probe Set | Description | T1 Abs Call | Diff Call | Fold Change | Sort Score |
|---|---|---|---|---|---|---|
| Increase in T2 solid | | | | | | |
| subA | RC_AA121534_at | zk89d11.s1 Soares pregnant uterus NbHPU Homo sapiens cDNA clone 490005 3' similar to .gb:X79535 TUBULIN BETA-2 CHAIN (HUMAN); | A | NC | -2,5 | -0,1 |
| subA | RC_AA131047_s_at | zo16f05,s1 Stratagene colon (#937204) Homo sapiens cDNA clone 587073 3', | A | NC | -1,4 | -0,04 |
| subA | RC_AA461549_at | zx62b09,s1 Soares total fetus Nb2HF8 9w Homo sapiens cDNA clone 796025 3', | A | NC | 1,1 | 0,01 |
| subA | RC_AA491465_at | | A | NC | -1,2 | 0,01 |
| subA | RC_AA496936_at | ae32d03,s1 Gessler Wilms tumor Homo sapiens cDNA clone 897609 3', | A | NC | -1,5 | -0,02 |
| subA | RC_AA598689_at | | P | NC | -1,2 | -0,01 |
| subA | W26392_at | 30g3 Human retina cDNA randomly primed sublibrary Homo sapiens cDNA, | P | NC | 2,2 | 0,2 |
| subB | RC_AA004887_at | zo24g02,s1 Stratagene colon (#937204) Homo sapiens cDNA clone 587858 3', | P | NC | -1,4 | 0,02 |
| subB | RC_AA135153_at | zq50e09,s1 Stratagene neuroepithelium (#937231) Homo sapiens cDNA | P | NC | -2,9 | 0,41 |
| subB | RC_AA197311_s_at | clone 645064 3' similar to .gb:M24283 INTERCELLULAR ADHESION MOLECULE-1 PRECURSOR (HUMAN); | A | NC | -4,0 | -0,33 |
| subB | RC_H80622_at | yu77b06,s1 Homo sapiens cDNA clone 239795 3', | A | NC | -2,5 | -0,15 |
| subB | RC_N64436_at | za33a09,s1 Homo sapiens cDNA clone 294326 3', | A | NC | -2,3 | -0,15 |
| subB | RC_N67583_at | yz42c02,s1 Homo sapiens cDNA clone 285698 3', | A | NC | -4,6 | -1,27 |
| subB | RC_R38678_at | yc89d05,s1 Homo sapiens cDNA clone 23443 3', | A | NC | -1,9 | -0,09 |
| subB | RC_R56066_s_at | yg91d08,s1 Homo sapiens cDNA clone 40992 3', | A | NC | -1,9 | 0,09 |
| subB | RC_R59292_at | yh16a10,s1 Homo sapiens cDNA clone 37689 3', | A | NC | -1,8 | -0,08 |
| subB | RC_T24099_at | seq2287 Homo sapiens cDNA clone Cot25oFl-b4HB3MA-8 3', | A | NC | -3,9 | 0,32 |
| subA | AA150364_at | zl07h03,r1 Soares pregnant uterus NbHPU Homo sapiens cDNA clone 491597 5', | P | NC | 1,2 | 0,02 |
| subA | AA174185_at | PTH207 HTCDL1 Homo sapiens cDNA 5'/3', | P | NC | 1,8 | 0,23 |
| subA | AA452353_i_at | zx1bd05,r1 Soares total fetus Nb2HF8 9w Homo sapiens cDNA clone 786537 5', | A | NC | 1,7 | 0,28 |
| subA | AB002316_at | Human mRNA for KIAA0318 gene, partial cds, | A | NC | 1,4 | 0,04 |
| subA | H86858_at | ys72d05,r1 Homo sapiens cDNA clone 220329 5', | P | NC | 1,6 | 0,15 |
| subA | M93119_s_at | Human zinc-finger DNA-binding motifs (IA-1) mRNA, complete cds | P | NC | 1,7 | 0,13 |
| subA | R72037_at | yj86e09,r1 Homo sapiens cDNA clone 155632 5', | P | NC | 1,2 | 0,06 |
| subA | RC_AA004274_at | similar to contains element MER22 repetitive element;, | P | NC | -1,2 | -0,03 |
| subA | RC_AA004415_at | | P | NC | 1,7 | 0,12 |
| subA | RC_AA007160_at | zl74e07,s1 Stratagene colon (#937204) Homo sapiens cDNA clone 510372 3' similar to ,contains Alu repetitive element; | P | NC | 1 | 0 |
| subA | RC_AA053660_at | | A | NC | -1,3 | -0,04 |
| subA | RC_AA252603_at | zs14a11,s1 NCI_CGAP_GCB1 Homo sapiens cDNA clone IMAGE:685148 3', | P | NC | 1,2 | 0,01 |
| subA | RC_AA411944_at | zu03h01,s1 Soares testis NHT Homo sapiens cDNA clone 730801 3', | P | NC | 1,7 | 0,12 |
| subA | RC_AA412700_at | zu12g03,s1 Soares testis NHT Homo sapiens cDNA clone 731668 3', | P | NC | -1,1 | -0,01 |
| subA | RC_AA430032_at | zw65f05,s1 Soares testis NHT Homo sapiens cDNA clone 781089 3', | P | NC | 1,9 | 0,42 |
| subA | RC_AA430368_at | zw20f06,s1 Soares ovary tumor NbHOT Homo sapiens cDNA clone 769859 3', | A | NC | 1,5 | 0,07 |

Fig. 17.24

| Chip | Probe Set | Description | T2 Mix Abs Call | Diff Call | Fold Change | Sort Score |
|---|---|---|---|---|---|---|
| Increase in T2 solid | | | | | | |
| subA | RC_AA121534_at | zk89d11.s1 Soares pregnant uterus NbHPU Homo sapiens cDNA clone 490005 3' similar to ,gb:X79535 TUBULIN BETA-2 CHAIN (HUMAN); | P | NC | -1,5 | 0,04 |
| subA | RC_AA131047_s_at | zo16f05,s1 Stratagene colon (#937204) Homo sapiens cDNA clone 587073 3', | A | NC | -1,6 | -0,05 |
| subA | RC_AA461549_at | zx62b09,s1 Soares total fetus Nb2HF8 9w Homo sapiens cDNA clone 796025 3', | A | NC | -1,3 | -0,02 |
| subA | RC_AA491465_at |  | A | NC | -1,2 | 0,01 |
| subA | RC_AA496936_at | ae32d03,s1 Gessler Wilms tumor Homo sapiens cDNA clone 897509 3', | A | NC | -2,0 | -0,08 |
| subA | RC_AA598689_at |  | M | NC | -1,7 | 0,07 |
| subB | W26392_at | 30g3 Human retina cDNA randomly primed sublibrary Homo sapiens cDNA, | A | NC | -1,5 | 0,04 |
| subB | RC_AA004887_at |  | P | NC | -2,0 | 0,22 |
| subB | RC_AA135153_at | zo24g02,s1 Stratagene colon (#937204) Homo sapiens cDNA clone 587858 3', | P | NC | -2,3 | 0,33 |
| subB | RC_AA197311_s_at | zq50e09,s1 Stratagene neuroepithelium (#937231) Homo sapiens cDNA clone 645064 3' similar to ,gb:M24283 INTERCELLULAR ADHESION MOLECULE-1 PRECURSOR (HUMAN); | A | NC | -2,3 | 0,15 |
| subB | RC_H80622_at | yu77b06,s1 Homo sapiens cDNA clone 239795 3', | A | NC | -1,4 | -0,03 |
| subB | RC_N64436_at | za33a09,s1 Homo sapiens cDNA clone 294328 3', | A | NC | -2,4 | -0,16 |
| subB | RC_N67683_at | yz42c02,s1 Homo sapiens cDNA clone 285698 3', | A | NC | -4,4 | -0,49 |
| subB | RC_R38678_at | yc89d05,s1 Homo sapiens cDNA clone 23443 3', | A | NC | -2,7 | 0,21 |
| subB | RC_R56066_s_at | yg91d08,s1 Homo sapiens cDNA clone 40992 3', | A | NC | -1,7 | -0,07 |
| subB | RC_R59292_at | yh16a10,s1 Homo sapiens cDNA clone 37689 3', | A | NC | -2,4 | 0,34 |
| subB | RC_T24099_at | seq2287 Homo sapiens cDNA clone Col250Ft-b4HB3MA-8 3', | P | NC | -4,8 | 0,48 |
| subA | AA150364_at | zl07b03,r1 Soares pregnant uterus NbHPU Homo sapiens cDNA clone 491597 5', | M | NC | 1,6 | 0,1 |
| subA | AA174185_at | PTH207 HTCDL1 Homo sapiens cDNA 5'/3', | P | NC | 1,7 | 0,16 |
| subA | AA452353_i_at | zx15d05,r1 Soares total fetus Nb2HF8 9w Homo sapiens cDNA clone 786537 5', | A | NC | 1,7 | 0,33 |
| subA | AB002316_at | Human mRNA for KIAA0318 gene, partial cds, | M | NC | 2,2 | 0,25 |
| subA | H86858_at | ys72d05,r1 Homo sapiens cDNA clone 220329 5', | A | NC | 1,8 | 0,15 |
| subA | M93119_s_at | Human zinc-finger DNA-binding motifs (IA-1) mRNA, complete cds | P | NC | 1,6 | 0,11 |
| subA | R72037_at | yj86c09,r1 Homo sapiens cDNA clone 155632 5', | P | NC | -1,2 | -0,03 |
| subA | RC_AA004274_at | similar to contains element MER22 repetitive element ;, | P | NC | -2,3 | -0,47 |
| subA | RC_AA004415_at |  | P | NC | 2 | 0,22 |
| subA | RC_AA007160_at | zl74e07,s1 Stratagene colon (#937204) Homo sapiens cDNA clone 510372 3' similar to ,contains Alu repetitive element; | P | NC | 1,4 | 0,06 |
| subA | RC_AA053660_at |  | P | NC | -1,2 | -0,03 |
| subA | RC_AA252603_at | zs14a11,s1 NCI_CGAP_GCB1 Homo sapiens cDNA clone IMAGE:685148 3', | P | NC | 1,2 | 0,01 |
| subA | RC_AA411944_at | zu03h01,s1 Soares testis NHT Homo sapiens cDNA clone 730801 3', | P | NC | 1,2 | 0,02 |
| subA | RC_AA412700_at | zu12g03,s1 Soares testis NHT Homo sapiens cDNA clone 731668 3', | P | NC | -1,4 | -0,13 |
| subA | RC_AA430032_at | zw65f05,s1 Soares testis NHT Homo sapiens cDNA clone 781089 3', | P | NC | 1,6 | 0,2 |
| subA | RC_AA430368_at | zw20l06,s1 Soares ovary tumor NbHOT Homo sapiens cDNA clone 769859 3', | A | NC | -1,1 | -0,01 |

Fig. 17.25

| Chip | Probe Set | Description | T2 Solid Abs Call | Diff Call | Fold Change | Sort Score |
|---|---|---|---|---|---|---|
| Increase in T2 solid | | | | | | |
| subA | RC_AA121534_at | zk89d11.s1 Soares pregnant uterus NbHPU Homo sapiens cDNA clone 490005 3' similar to .gb:X79535 TUBULIN BETA-2 CHAIN (HUMAN); | P | I | -9,1 | 4,69 |
| subA | RC_AA131047_s_at | zo16f05.s1 Stratagene colon (#937204) Homo sapiens cDNA clone 587073 3', | P | I | -4,9 | 1,78 |
| subA | RC_AA461549_at | zx62b09.s1 Soares total fetus Nb2HF8 9w Homo sapiens cDNA clone 796025 3', | P | I | -8,2 | 4,35 |
| subA | RC_AA491465_at | | P | I | -7,1 | 3,4 |
| subA | RC_AA496936_at | ae32d03.s1 Gessler Wilms tumor Homo sapiens cDNA clone 897509 3'. | P | I | -4,8 | 1,56 |
| subA | RC_AA598689_at | | P | I | -4,9 | 1,75 |
| subB | W26392_at | 30g3 Human retina cDNA randomly primed sublibrary Homo sapiens cDNA, | P | I | -6,9 | 3,26 |
| subB | RC_AA004887_at | zo24g02.s1 Stratagene colon (#937204) Homo sapiens cDNA clone 587858 3', | P | I | -8,2 | 5,57 |
| subB | RC_AA135153_at | zq50e09.s1 Stratagene neuroepithelium (#937231) Homo sapiens cDNA clone 645064 3' similar to .gb:M24283 INTERCELLULAR ADHESION MOLECULE-1 PRECURSOR (HUMAN); | P | I | -11,8 | 9,42 |
| subB | RC_AA197311_s_at | | | | -4,0 | 0,41 |
| subB | RC_H80622_at | yu77b06.s1 Homo sapiens cDNA clone 239795 3', | P | I | -4,2 | 1,53 |
| subB | RC_N64436_at | za33a09.s1 Homo sapiens cDNA clone 294328 3', | P | I | -3,9 | 1,47 |
| subB | RC_N67583_at | yz42c02.s1 Homo sapiens cDNA clone 285698 3', | P | I | -7,1 | 4,6 |
| subB | RC_R38678_at | yc89d05.s1 Homo sapiens cDNA clone 23443 3', | P | I | -17,3 | 14,43 |
| subB | RC_R56066_s_at | yg91d08.s1 Homo sapiens cDNA clone 40992 3', | P | I | -5,5 | 2,26 |
| subB | RC_R59292_at | yh16a10.s1 Homo sapiens cDNA clone 37689 3', | P | I | -28,4 | 25,16 |
| subB | RC_T24099_at | seq2287 Homo sapiens cDNA clone Cot250Ft-b4H33MA-8 3', | P | I | -29,3 | 24,83 |
| subA | AA150364_at | zl07b03,r1 Soares pregnant uterus NbHPU Homo sapiens cDNA clone 491597 5', | P | I | 3,4 | 1,3 |
| subA | AA174185_at | PTH207 HTCDL1 Homo sapiens cDNA 5'/3', | P | I | 3,1 | 1,16 |
| subA | AA452353_i_at | zx15d05,r1 Soares total fetus Nb2HF8 9w Homo sapiens cDNA clone 786537 5', | P | I | 3,1 | 1,99 |
| subA | AB002316_at | Human mRNA for KIAA0318 gene, partial cds, | P | I | 8,5 | 5,52 |
| subA | H86858_at | ys72d05,r1 Homo sapiens cDNA clone 220329 5', | P | I | 3,5 | 1,09 |
| subA | M93119_s_at | Human zinc-finger DNA-binding motifs (IA-1) mRNA, complete cds | P | I | 21 | 17,52 |
| subA | R72037_at | yj86c09,r1 Homo sapiens cDNA clone 155632 5', | P | I | 3 | 2,1 |
| subA | RC_AA004274_at | similar to contains element MER22 repetitive element ;, | | I | 4,4 | 3,54 |
| subA | RC_AA004415_at | | P | I | 3,5 | 1,01 |
| subA | RC_AA007160_at | | P | I | 3,1 | 1,17 |
| subA | RC_AA053660_at | zl74e07.s1 Stratagene colon (#937204) Homo sapiens cDNA clone 510372 3' similar to ,contains Alu repetitive e:ement; | P | I | 4,7 | 3,63 |
| subA | RC_AA252603_at | zs14a11,s1 NCI_CGAP_GCB1 Homo sapiens cDNA clone IMAGE:685148 3', | | | 3 | 0,78 |
| subA | RC_AA411944_at | zu03h01,s1 Soares testis NHT Homo sapiens cDNA clone 730801 3', | P | I | 17,4 | 13,2 |
| subA | RC_AA412700_at | zu12g03,s1 Soares testis NHT Homo sapiens cDNA clone 731668 3', | | | 3 | 2,1 |
| subA | RC_AA430032_at | zw65f05,s1 Soares testis NHT Homo sapiens cDNA clone 781089 3', | | | 4,4 | 3,63 |
| subA | RC_AA430368_at | zw20f06,s1 Soares ovary tumor NbHOT Homo sapiens cDNA clone 769859 3', | | | 3,2 | 0,83 |

Fig. 17.26

| Chip | Probe Set | Description | Normal Avg Diff | Abs Call |
|---|---|---|---|---|
| Increase in T2 solid | | | | |
| subA | RC_AA434113_at | zw24b11,s1 Soares ovary tumor NbHOT Homo sapiens cDNA clone 770205 3' similar to contains element TAR1 repetitive element ; | 110 | A |
| subA | RC_AA441791_at | zw62c02,s1 Soares total fetus Nb2HF8 9w Homo sapiens cDNA clone 774626 3', | 119 | A |
| subA | RC_AA449419_at | zx05b03,s1 Soares total fetus Nb2HF8 9w Homo sapiens cDNA clone 785549 3', | 51 | P |
| subA | RC_AA449914_at | zx37g02,s1 Soares total fetus Nb2HF8 9w Homo sapiens cDNA clone 788690 3', | 173 | A |
| subA | RC_D59847_at | Human fetal brain cDNA 3'-end GEN-070G07, | 187 | A |
| subA | T95813_f_at | ye45f10,r1 Homo sapiens cDNA clone 120715 5' similar to gb:V00493_rna1 HEMOGLOBIN ALPHA CHAIN (HUMAN);, | 50 | A |
| subA | W80846_at | zd83f05,r1 Soares fetal heart NbHH19W Homo sapiens cDNA clone 347265 5' similar to SW:SYB2_XENLA P47193 SYNAPTOBREVIN 2 ;; | 210 | P |
| subB | RC_AA031360_s_at | zk16f07,s1 Soares pregnant uterus NbHPU Homo sapiens cDNA clone 470725 3', | 90 | P |
| subB | RC_AA063524_at | ze87h05,s1 Soares fetal heart NbHH19W Homo sapiens cDNA clone 366009 3' similar to TR:G300372 G300372 CELL GROWTH REGULATING NUCLEOLAR PROTEIN, ;; | 77 | P |
| subB | RC_AA076238_at | zm19e04,s1 Stratagene pancreas (#937208) Homo sapiens cDNA clone 526110 3' similar to contains Alu repetitive element;, | 196 | A |
| subB | RC_AA076350_at | zm91a02,s1 Stratagene ovarian cancer (#937219) Homo sapiens cDNA clone 545258 3', | 178 | P |
| subB | RC_AA101983_at | zk87c02,s1 Soares pregnant uterus NbHPU Homo sapiens cDNA clone 489794 3', | 192 | P |
| subB | RC_AA151245_at | zl40f12,s1 Soares pregnant uterus NbHPU Homo sapiens cDNA clone 504431 3', | 107 | A |
| subB | RC_AA164252_f_at | | 240 | A |
| subB | RC_AA167006_at | zo86b08,s1 Stratagene ovarian cancer (#937219) Homo sapiens cDNA clone 593751 3', | 187 | A |
| subB | RC_AA206225_at | zq56g08,s1 Stratagene neuroepithelium (#937231) Homo sapiens cDNA clone 645662 3', | 66 | A |
| subB | RC_D62834_at | Human aorta cDNA 3'-end GEN-330D04, | 177 | P |
| subB | RC_D80981_at | Human fetal brain cDNA 3'-end GEN-121E12, | 103 | P |
| subB | RC_H16772_at | ym34g02,s1 Homo sapiens cDNA clone 50227 3', | 109 | A |
| subB | RC_N62522_at | yz74f08,s1 Homo sapiens cDNA clone 288807 3', | 344 | P |
| subB | RC_N68222_at | yz56e12,s1 Homo sapiens cDNA clone 287086 3', | 384 | P |
| subB | RC_T10316_s_at | seq1014 Homo sapiens cDNA clone b4HB3MA-COT8-HAP-F1266 3', | 622 | A |
| subB | RC_W37382_at | | 246 | P |
| subB | RC_W60582_at | zd25e10,s1 Soares fetal heart NbHH19W Homo sapiens cDNA clone-341706 3' similar to gb:M38188 OVARIAN GRANULOSA CELL 13.0 KD PROTEIN HGR74 (HUMAN);, | 158 | A |
| subB | RC_W84768_at | zh53d03,s1 Soares fetal liver spleen 1NFLS S1 Homo sapiens cDNA clone 415781 3' similar to contains L1,b1 L1 repetitive element ;; | 199 | P |

Fig. 17.27

| Chip | Probe Set | Description | Ta Abs Call | Diff Call | Fold Change | Sort Score |
|---|---|---|---|---|---|---|
| Increase in T2 solid | | | | | | |
| subA | RC_AA434113_at | zw24b11.s1 Soares ovary tumor NbHOT Homo sapiens cDNA clone 770205 3' similar, to contains element TAR1 repetitive element ; | A | NC | -1,9 | -0,19 |
| subA | RC_AA441791_at | zw62c02.s1 Soares total fetus Nb2HF8 9w Homo sapiens cDNA clone 774626 3', | A | NC | 1 | 0 |
| subA | RC_AA449419_at | zx05b03.s1 Soares total fetus Nb2HF8 9w Homo sapiens cDNA clone 785549 3'; | P | NC | -1 | 0 |
| subA | RC_AA449914_at | zx37g02.s1 Soares total fetus Nb2HF8 9w Homo sapiens cDNA clone 788690 3', | A | NC | -1,6 | -0,14 |
| subA | RC_D59847_at | Human fetal brain cDNA 3'-end GEN-070G07, | A | NC | 1,5 | 0,21 |
| subA | T95613_f_at | ye45f10.r1 Homo sapiens cDNA clone 120715 5' similar to gb:V00493_ma1 HEMOGLOBIN ALPHA CHAIN (HUMAN);; | P | NC | 11,6 | 7,83 |
| subA | W80846_at | zd83t05.r1 Soares fetal heart NbHH19W Homo sapiens cDNA clone 347265 5' similar to SW:SYB2_XENLA P47193 SYNAPTOBREVIN 2 ; | P | NC | -1,1 | -0,01 |
| subB | RC_AA031360_s_at | zk16t07.s1 Soares pregnant uterus NbHPU Homo sapiens cDNA clone 470725 3', | P | NC | -1,1 | 0 |
| subB | RC_AA063624_at | ze87h05.s1 Soares fetal heart NbHH19W Homo sapiens cDNA clone 366009 3' similar to TR:G300372 G300372 CELL GROWTH REGULATING NUCLEOLAR PROTEIN, ;; | P | NC | 1,1 | 0 |
| subB | RC_AA076238_at | zm19e04.s1 Stratagene pancreas (#937208) Homo sapiens cDNA clone 526110 3' similar to contains Alu repetitive element,; | P | NC | 1,7 | 0,22 |
| subB | RC_AA076350_at | zm91a02.s1 Stratagene ovarian cancer (#937219) Homo sapiens cDNA clone 545258 3', | A | NC | -1,5 | -0,1 |
| subB | RC_AA101983_at | zk87c02.s1 Soares pregnant uterus NbHPU Homo sapiens cDNA clone 489794 3', | P | NC | -1,3 | -0,04 |
| subB | RC_AA151245_at | zl40f12.s1 Soares pregnant uterus NbHPU Homo sapiens cDNA clone 504431 3', | P | NC | -1,0 | 0 |
| subB | RC_AA164252_f_at | zo86b08.s1 Stratagene ovarian cancer (#937231) Homo sapiens cDNA clone 593751 3', | P | NC | 1,6 | 0,14 |
| subB | RC_AA167006_at | | P | NC | -2,3 | -0,4 |
| subB | RC_AA206225_at | zq56g08.s1 Stratagene neuroepithelium (#937231) Homo sapiens cDNA clone 645662 3'; | A | NC | 1,7 | 0,14 |
| subB | RC_D62834_at | Human aorta cDNA 3'-end GEN-330D04, | P | NC | 1,2 | 0,04 |
| subB | RC_D80981_at | Human fetal brain cDNA 3'-end GEN-121E12, | P | NC | -1,4 | -0,05 |
| subB | RC_H16772_at | ym34g02.s1 Homo sapiens cDNA clone 50227 3'; | A | NC | -1,8 | -0,17 |
| subB | RC_N62522_at | yz74f08.s1 Homo sapiens cDNA clone 288807 3', | A | NC | -1,7 | -0,18 |
| subB | RC_N68222_at | yz56e12.s1 Homo sapiens cDNA clone 287086 3' | A | NC | -1,9 | -0,38 |
| subB | RC_T10316_s_at | seq1014 Homo sapiens cDNA clone b4HB3MA-COT8-HAP-Ft266 3', | A | NC | -1,1 | -0,01 |
| subB | RC_W37382_at | zd25e10.s1 Soares fetal heart NbHH19W Homo sapiens cDNA clone 341706 3' similar to gb:M38188 OVARIAN GRANULOSA CELL 13,0 KD PROTEIN HGR74 (HUMAN);. | A | NC | 1,2 | 0,03 |
| subB | RC_W60582_at | | A | NC | 1,3 | 0,04 |
| subB | RC_W84768_at | zh53d03.s1 Soares fetal liver spleen 1NFLS S1 Homo sapiens cDNA clone 415781 3' similar to contains L1.b1 L1 repetitive element ;; | P | NC | 1,5 | 0,11 |

Fig. 17.28

| Chip | Probe Set | Description | T1 Abs Call | Diff Call | Fold Change | Sort Score |
|---|---|---|---|---|---|---|
| Increase in T2 solid | | | | | | |
| subA | RC_AA434113_at | zw24b11.s1 Soares ovary tumor NbHOT Homo sapiens cDNA clone 770205 3' similar ,to contains element TAR1 repetitive element ; | A | NC | -3,2 | -0,67 |
| subA | RC_AA441791_at | zw62c02.s1 Soares total fetus Nb2HF8 9w Homo sapiens cDNA clone 774626 3', | A | NC | -2,6 | 0,11 |
| subA | RC_AA449419_at | zx05b03.s1 Soares total fetus Nb2HF8 9w Homo sapiens cDNA clone 785549 3', | A | NC | -2,8 | -0,34 |
| subA | RC_AA449914_at | zx37g02.s1 Soares total fetus Nb2HF8 9w Homo sapiens cDNA clone 788690 3', | A | NC | 1,1 | 0 |
| subA | RC_D59847_at | Human fetal brain cDNA 3'-end GEN-070G07, | A | NC | 2,4 | 0,77 |
| subA | T95813_f_at | ye45f10.r1 Homo sapiens cDNA clone 120715 5' similar to gb:V00493_rna1 HEMOGLOBIN ALPHA CHAIN (HUMAN);. | A | NC | 15,6 | 11,3 |
| subA | W80846_at | zd83f05.r1 Soares fetal heart NbHH19W Homo sapiens cDNA clone 347265 5' similar to SW:SYB2_XENLA P47193 SYNAPTOBREVIN 2 ;. | P | NC | 1,1 | 0,01 |
| subB | RC_AA031360_s_at | zk16f07.s1 Soares pregnant uterus NbHPU Homo sapiens cDNA clone 470725 3', | A | NC | 1 | 0 |
| subB | RC_AA063624_at | ze87h05.s1 Soares fetal heart NbHH19W Homo sapiens cDNA clone 366009 3' similar to TR:G300372 G300372 CELL GROWTH REGULATING NUCLEOLAR PROTEIN, ;. | P | NC | 1,8 | 0,18 |
| subB | RC_AA076238_at | zm19e04.s1 Stratagene pancreas (#937208) Homo sapiens cDNA clone 526110 3' similar to contains Alu repetitive element;. | A | NC | 2,2 | 0,61 |
| subB | RC_AA076350_at | zm91a02.s1 Stratagene ovarian cancer (#937219) Homo sapiens cDNA clone 545258 3', | A | NC | 1,4 | 0,08 |
| subB | RC_AA101983_at | zk87c02.s1 Soares pregnant uterus NbHPU Homo sapiens cDNA clone 489794 3', | P | NC | 1,9 | 0,36 |
| subB | RC_AA151245_at | zl40f12.s1 Soares pregnant uterus NbHPU Homo sapiens cDNA clone 504431 3', | A | NC | 1,3 | 0,03 |
| subB | RC_AA164252_f_at | | A | NC | 1,8 | 0,24 |
| subB | RC_AA167006_at | zo68b08.s1 Stratagene ovarian cancer (#937219) Homo sapiens cDNA clone 593751 3', | P | NC | -1,9 | -0,23 |
| subB | RC_AA206225_at | zq56g08.s1 Stratagene neuroepithelium (#937231) Homo sapiens cDNA clone 645662 3', | A | NC | -1,8 | -0,1 |
| subB | RC_D62834_at | Human aorta cDNA 3'-end GEN-330D04, | P | NC | 1,7 | 0,21 |
| subB | RC_D80981_at | Human fetal brain cDNA 3'-end GEN-121E12, | P | NC | 1,8 | 0,2 |
| subB | RC_H16772_at | ym34g02.s1 Homo sapiens cDNA clone 50227 3', | P | NC | 1 | 0 |
| subB | RC_N62522_at | yz74f08.s1 Homo sapiens cDNA clone 288807 3', | A | NC | -1,1 | -0,01 |
| subB | RC_N68222_at | yz55e12.s1 Homo sapiens cDNA clone 287086 3', | P | NC | -1,7 | -0,22 |
| subB | RC_T10316_s_at | seq1014 Homo sapiens cDNA clone b4HB3MA-COT8-HAP-Ft266 3', | A | NC | 1,8 | 0,49 |
| subB | RC_W37382_at | | A | NC | 2,1 | 0,6 |
| subB | RC_W60582_at | zd25e10.s1 Soares fetal heart NbHH19W Homo sapiens cDNA clone 341706 3' similar to gb:M38188 OVARIAN GRANULOSA CELL 13,0 KD PROTEIN HGR74 (HUMAN);. | A | NC | 2 | 0,37 |
| subB | RC_W84768_at | zh53d03.s1 Soares fetal liver spleen 1NFLS S1 Homo sapiens cDNA clone 415781 3' similar to contains L1.b1 L1 repetitive element ;. | P | NC | 2,1 | 0,48 |

Fig. 17.29

| Chip | Probe Set | Description | T2 Mix Abs Call | Diff Call | Fold Change | Sort Score |
|---|---|---|---|---|---|---|
| Increase in T2 solid | | | | | | |
| subA | RC_AA434113_at | zw24b11.s1 Soares ovary tumor NbHOT Homo sapiens cDNA clone 770205 3' similar ,to contains element TAR1 repetitive element ; | A | NC | -1 | 0 |
| subA | RC_AA441791_at | zw62c02.s1 Soares total fetus Nb2HF8 9w Homo sapiens cDNA clone 774626 3', | A | NC | 1,1 | 0 |
| subA | RC_AA449419_at | zx05b03.s1 Soares total fetus Nb2HF8 9w Homo sapiens cDNA clone 785549 3', | P | NC | -1,1 | 0 |
| subA | RC_AA449914_at | zx37g02.s1 Soares total fetus Nb2HF8 9w Homo sapiens cDNA clone 788690 3', | A | NC | 1,4 | 0,09 |
| subA | RC_D59847_at | Human fetal brain cDNA 3'-end GEN-070G07, | A | NC | 1,5 | 0,14 |
| subA | T95813_f_at | ye45f10.r1 Homo sapiens cDNA clone 120715 5' similar to gb:V00493_ma1 HEMOGLOBIN ALPHA CHAIN (HUMAN);. | P | NC | 68,9 | 46,5 |
| subA | W80846_at | zd83l05.r1 Soares fetal heart NbHH19W Homo sapiens cDNA clone 347265 5' similar to SW:SYB2_XENLA P47193 SYNAPTOBREVIN 2 ;. | P | NC | 1,3 | 0,04 |
| subB | RC_AA031360_s_at | zk16f07.s1 Soares pregnant uterus NbHPU Homo sapiens cDNA clone 470725 3', | P | NC | 1,1 | 0 |
| subB | RC_AA063624_at | ze87h05.s1 Soares fetal heart NbHH19W Homo sapiens cDNA clone 366009 3' similar to TR:G300372 G300372 CELL GROWTH REGULATING NUCLEOLAR PROTEIN. ;. | P | NC | 1,7 | 0,14 |
| subB | RC_AA076238_at | zm19e04.s1 Stratagene pancreas (#937208) Homo sapiens cDNA clone 526110 3' similar to contains Alu repetitive element;, | P | NC | 2,6 | 0,98 |
| subB | RC_AA076350_at | zm91a02.s1 Stratagene ovarian cancer (#937219) Homo sapiens cDNA clone 545258 3', | P | NC | 1,6 | 0,09 |
| subB | RC_AA101983_at | zk87rc02.s1 Soares pregnant uterus NbHPU Homo sapiens cDNA clone 489794 3', | P | NC | 1,4 | 0,08 |
| subB | RC_AA151245_at | zl40f12.s1 Soares pregnant uterus NbHPU Homo sapiens cDNA clone 504431 3', | A | NC | 1,3 | 0,04 |
| subB | RC_AA164252_f_at | | A | NC | 1,1 | 0 |
| subB | RC_AA167006_at | zo86b08.s1 Stratagene ovarian cancer (#937219) Homo sapiens cDNA clone 593751 3', | A | NC | -1,5 | -0,09 |
| subB | RC_AA206225_at | zq56g08.s1 Stratagene neuroepithelium (#937231) Homo sapiens cDNA clone 645662 3', | A | NC | -1,7 | -0,07 |
| subB | RC_D62834_at | Human aorta cDNA 3'-end GEN-330D04, | P | NC | 2,4 | 0,73 |
| subB | RC_D80981_at | Human fetal brain cDNA 3'-end GEN-121E12, | P | NC | -1 | 0 |
| subB | RC_H16772_at | ym34g02.s1 Homo sapiens cDNA clone 50227 3', | A | NC | -1,6 | -0,11 |
| subB | RC_N62522_at | yz74f08.s1 Homo sapiens cDNA clone 288807 3', | A | NC | 1,1 | 0,01 |
| subB | RC_N68222_at | yz56e12.s1 Homo sapiens cDNA clone 287086 3', | A | NC | -2 | -0,39 |
| subB | RC_T10316_s_at | seq1014 Homo sapiens cDNA clone b4HB3MA-COT8-HAP-F1266 3', | A | NC | 1,4 | 0,13 |
| subB | RC_W37382_at | | P | NC | 2,1 | 0,54 |
| subB | RC_W60582_at | zd25e10.s1 Soares fetal heart NbHH19W Homo sapiens cDNA clone 341706 3' similar to gb:M38188 OVARIAN GRANULOSA CELL 13,0 KD PROTEIN HGR74 (HUMAN);, | A | NC | 1,3 | 0,05 |
| subB | RC_W84768_at | zh53d03.s1 Soares fetal liver spleen 1NFLS S1 Homo sapiens cDNA clone 415781 3' similar to contains L1,b1 L1 repetitive element ;. | P | NC | 3,2 | 1,61 |

Fig. 17.30

| Chip | Probe Set | Description | T2 Solid Abs Call | Diff Call | Fold Change | Sort Score |
|---|---|---|---|---|---|---|
| Increase in T2 solid | | | | | | |
| subA | RC_AA434113_at | zw24b11.s1 Soares ovary tumor NbHOT Homo sapiens cDNA clone 770205 3' similar ,to contains element TAR1 repetitive element ;; | P | | 4,7 | 2,8 |
| subA | RC_AA441791_at | zw62c02.s1 Soares total fetus Nb2HF8 9w Homo sapiens cDNA clone 774626 3'; | P | | 5,2 | 3,24 |
| subA | RC_AA449419_at | zx05b03.s1 Soares total fetus Nb2HF8 9w Homo sapiens cDNA clone 785549 3'; | P | | 3,8 | 1,2 |
| subA | RC_AA449914_at | zx37g02.s1 Soares total fetus Nb2HF8 9w Homo sapiens cDNA clone 788690 3'; | P | | 4,4 | 3,06 |
| subA | RC_D59847_at | Human fetal brain cDNA 3'-end GEN-070G07, | P | | 11,6 | 15,32 |
| subA | T95813_f_at | ye45f10.r1 Homo sapiens cDNA clone 120715 5' similar to gb:V00493_rna1 HEMOGLOBIN ALPHA CHAIN (HUMAN);; | P | | 25 | 18,82 |
| subA | W80846_at | zd83f05.r1 Soares fetal heart NbHH19W Homo sapiens cDNA clone 347265 5' similar to SW:SYB2_XENLA P47193 SYNAPTOBREVIN 2 ;; | P | | 3,1 | 1,55 |
| subB | RC_AA031360_s_at | zk16f07.s1 Soares pregnant uterus NbHPU Homo sapiens cDNA clone 470725 3'; | P | | 13,1 | 12,31 |
| subB | RC_AA063624_at | ze87h05.s1 Soares fetal heart NbHH19W Homo sapiens cDNA clone 366009 3' similar to TR:G300372 G300372 CELL GROWTH REGULATING NUCLEOLAR PROTEIN. ;; | P | | 3,1 | 0,91 |
| subB | RC_AA076238_at | zm19e04.s1 Stratagene pancreas (#937208) Homo sapiens cDNA clone 526110 3' similar to contains Alu repetitive element;; | P | | 3,3 | 1,91 |
| subB | RC_AA076350_at | zm91a02.s1 Stratagene ovarian cancer (#937219) Homo sapiens cDNA clone 545258 3'; | P | | 10,8 | 13,48 |
| subB | RC_AA101983_at | zk87c02.s1 Soares pregnant uterus NbHPU Homo sapiens cDNA clone 489794 3'; | P | | 4,2 | 3,01 |
| subB | RC_AA151245_at | zl40f12.s1 Soares pregnant uterus NbHPU Homo sapiens cDNA clone 504431 3'; | P | | 3,3 | 1,33 |
| subB | RC_AA164252_f_at | | P | | 9,6 | 9,67 |
| subB | RC_AA167006_at | zo86b08.s1 Stratagene ovarian cancer (#937219) Homo sapiens cDNA clone 593751 3'; | P | | 3,2 | 1,54 |
| subB | RC_AA206225_at | zq56g08.s1 Stratagene neuroepithelium (#937231) Homo sapiens cDNA clone 645662 3'; | P | | 3,8 | 2,38 |
| subB | RC_D62834_at | Human aorta cDNA 3'-end GEN-330D04, | P | | 4,2 | 2,79 |
| subB | RC_D80981_at | Human fetal brain cDNA 3'-end GEN-121E12, | P | | 10,6 | 9,69 |
| subB | RC_H16772_at | ym34g02.s1 Homo sapiens cDNA clone 50227 3'; | P | | 3,2 | 1,17 |
| subB | RC_N62522_at | yz74f08.s1 Homo sapiens cDNA clone 288807 3'; | P | | 3,8 | 3,14 |
| subB | RC_N68222_at | yz56e12.s1 Homo sapiens cDNA clone 287086 3'; | P | | 3,2 | 2,29 |
| subB | RC_T10316_s_at | seq1014 Homo sapiens cDNA clone b4HB3MA-COT8-HAP-F1266 3'; | P | | 4,1 | 5,01 |
| subB | RC_W37382_at | zd25e10.s1 Soares fetal heart NbHH19W Homo sapiens cDNA clone 341706 3' similar to gb:M38188 OVARIAN GRANULOSA CELL 13,0 KD PROTEIN HGR74 (HUMAN);; | P | | 5,4 | 5,47 |
| subB | RC_W60582_at | | P | | 8,8 | 9,69 |
| subB | RC_W84768_at | zh53d03.s1 Soares fetal liver spleen 1NFLS S1 Homo sapiens cDNA clone 415781 3' similar to contains L1, b1 L1 repetitive element ;; | P | | 9,4 | 10,78 |

Fig. 17.31

| Chip | Probe Set | Description | Normal Avg Diff | Abs Call |
|---|---|---|---|---|
| Increase in T1+T2 Mix | | | | |
| subA | RC_AA176164_i_at | zp23h11.s1 Stratagene neuroepithelium (#937231) Homo sapiens cDNA clone 610341 3', | -61 | A |
| subA | W52431_at | zc45b12.r1 Soares senescent fibroblasts NbHSF Homo sapiens cDNA clone 325247 5' similar to SW:WDNM_RAT P14730 WDNM1 PROTEIN, [2] PIR:S07807 ;. | 79 | P |
| subB | RC_AA019641_at | contains element L1 repetitive element ;. | 38 | A |
| subB | RC_H13695_at | yj09e04.s1 Homo sapiens cDNA clone 148254 3', | -34 | A |
| subB | RC_N22404_at | yw37h03.s1 Homo sapiens cDNA clone 254453 3', | -10 | A |
| subB | RC_R07501_at | ye97f06.s1 Homo sapiens cDNA clone 125699 3', | 493 | A |
| subA | C14412_s_at | Human fetal brain cDNA 5'-end GEN-055A09, | 564 | P |
| subA | RC_AA236455_s_at | zr75g02.s1 Soares NbHMPu S1 Homo sapiens cDNA clone 669266 3', | 146 | P |
| subA | RC_AA417030_at | zu04e07.s1 Soares testis NHT Homo sapiens cDNA clone 730884 3', | 41 | P |
| subB | RC_F10945_at | H. sapiens partial cDNA sequence; clone c-3mb07, | 125 | P |
| subB | RC_N29319_at | yw84a11.s1 Homo sapiens cDNA clone 258908 3', | 64 | P |
| subB | RC_N68038_f_at | yz53a12.s1 Homo sapiens cDNA clone 286750 3', | 161 | P |
| Increase in T1+T2 Solid | | | | |
| subB | RC_AA417030_at | zu04e07.s1 Soares testis NHT Homo sapiens cDNA clone 730884 3', | 41 | P |
| subA | RC_AA608545_at | ae53d05.s1 Stratagene lung carcinoma 937218 Homo sapiens cDNA clone 950601 3', | -43 | A |
| subA | RC_H09261_at | yl98c12.s1 Homo sapiens cDNA clone 46410 3' similar to contains Alu repetitive element;contains MSR1 repetitive element ;. | -38 | A |
| subB | RC_N68871_at | za23h07.s1 Homo sapiens cDNA clone 293437 3' similar to contains Alu repetitive element,. | 61 | A |
| subA | AA129196_at | zn29d08.r1 Stratagene neuroepithelium NT2RAMI 937234 Homo sapiens cDNA clone 548847 5' similar to SW:NU1M_MOUSE P03888 NADH-UBIQUINONE OXIDOREDUCTASE CHAIN 1 ;. | 45 | A |
| subA | RC_AA620553_s_at | H. sapiens partial cDNA sequence; clone c-3jg08, | 97 | A |
| subB | RC_F10779_at | H. sapiens partial cDNA sequence; clone c-3mb07, | 71 | P |
| subA | RC_F10945_at | yr72d10.s1 Homo sapiens cDNA clone 210835 3', | 125 | P |
| subB | RC_H65650_at | yz53a12.s1 Homo sapiens cDNA clone 286750 3', | 121 | A |
| subB | RC_N68038_f_at | | 161 | P |
| Increase in T1+T2 Mix +T2 solid | | | | |
| subA | RC_AA417030_at | zu04e07.s1 Soares testis NHT Homo sapiens cDNA clone 730884 3', | 41 | P |
| subA | RC_AA608545_at | | -43 | A |
| subB | RC_F10945_at | H. sapiens partial cDNA sequence; clone c-3mb07, | 125 | P |
| subB | RC_N68038_f_at | yz53a12.s1 Homo sapiens cDNA clone 286750 3', | 161 | P |

Fig. 17.32

| Chip | Probe Set | Description | Ta Abs Call | Diff Call | Fold Change | Sort Score |
|---|---|---|---|---|---|---|
| Increase in T1+T2 Mix | | | | | | |
| subA | RC_AA176164_l_at | zp23h11.s1 Stratagene neuroepithelium (#937231) Homo sapiens cDNA clone 610341 3'; | P | NC | -5,7 | 0,31 |
| subA | W52431_at | zc45b12.r1 Soares senescent fibroblasts NbHSF Homo sapiens cDNA clone 325247 5' similar to SW:WDNM_RAT P14730 WDNM1 PROTEIN, [2] PIR:S07807 ;. | P | NC | -1,9 | -0,16 |
| subB | RC_AA019641_at | contains element L1 repetitive element;. | P | NC | -2,6 | 0,25 |
| subB | RC_H13696_at | yj09e04.s1 Homo sapiens cDNA clone 148254 3'; | P | NC | -3,6 | 0,56 |
| subB | RC_N22404_at | yw37h03.s1 Homo sapiens cDNA clone 254453 3'; | A | NC | -1,8 | -0,17 |
| subB | RC_R07501_at | ye97f06.s1 Homo sapiens cDNA clone 125699 3'; | A | NC | -3,6 | 0,29 |
| subA | C14412_s_at | Human fetal brain cDNA 5'-end GEN-055A09; | P | NC | -1,1 | -0,02 |
| subA | RC_AA236455_s_at | zr75g02.s1 Soares NhHMPu S1 Homo sapiens cDNA clone 669286 3'; | P | NC | 2 | 0,34 |
| subA | RC_AA417030_at | zu04e07.s1 Soares testis NHT Homo sapiens cDNA clone 730884 3'; | P | NC | 2,4 | 0,31 |
| subB | RC_F10945_at | H, sapiens partial cDNA sequence; clone c-3mb07; | P | NC | 3,2 | 1,32 |
| subB | RC_N29319_at | yw84a11.s1 Homo sapiens cDNA clone 258908 3'; | P | NC | -1,5 | -0,06 |
| subB | RC_N68038_f_at | yz53a12.s1 Homo sapiens cDNA clone 286750 3'. | P | NC | 1,7 | 0,19 |
| Increase in T1+T2 Solid | | | | | | |
| subA | RC_AA417030_at | zu04e07.s1 Soares testis NHT Homo sapiens cDNA clone 730884 3'; | P | NC | 2,4 | 0,31 |
| subA | RC_AA608545_at | ae53d05.s1 Stratagene lung carcinoma 937218 Homo sapiens cDNA clone 950601 3'. | A | NC | 1,1 | 0 |
| subB | RC_H09261_at | yl98c12.s1 Homo sapiens cDNA clone 464103' similar to contains Alu repetitive element;contains MSR1 repetitive element ;. | A | NC | -1,2 | -0,02 |
| subB | RC_N68871_at | za23h07.s1 Homo sapiens cDNA clone 293437 3' similar to contains Alu repetitive element;. | A | NC | -2,1 | -0,12 |
| subA | AA129196_at | zn29d08.r1 Stratagene neuroepithelium NT2RAMI 937234 Homo sapiens cDNA clone 548847 5' similar to SW:NU1M_MOUSE P03888 NADH-UBIQUINONE OXIDOREDUCTASE CHAIN 1 ;. | P | NC | 1,7 | 0,1 |
| subA | RC_AA620553_s_at | | A | NC | -1,4 | -0,06 |
| subB | RC_F10779_at | H, sapiens partial cDNA sequence; clone c-3ig08; | A | NC | 1,8 | 0,16 |
| subA | RC_F10945_at | H, sapiens partial cDNA sequence; clone c-3mb07; | P | NC | 3,2 | 1,32 |
| subB | RC_H65650_at | yr72d10.s1 Homo sapiens cDNA clone 210835 3'; | M | NC | 2,3 | 0,53 |
| subB | RC_N68038_f_at | yz53a12.s1 Homo sapiens cDNA clone 286750 3'. | P | NC | 1,7 | 0,19 |
| Increase in T1+T2 Mix +T2 solid | | | | | | |
| subA | RC_AA417030_at | zu04e07.s1 Soares testis NHT Homo sapiens cDNA clone 730884 3'; | P | | 2,4 | 0,31 |
| subA | RC_AA608545_at | | A | | 1,1 | 0 |
| subA | RC_F10945_at | H, sapiens partial cDNA sequence; clone c-3mb07, | P | | 3,2 | 1,32 |
| subB | RC_N68038_f_at | yz53a12.s1 Homo sapiens cDNA clone 286750 3'. | P | | 1,7 | 0,19 |

Fig. 17.33

| Chip | Probe Set | Description | T1 Abs Call | Diff Call | Fold Change | Sort Score |
|---|---|---|---|---|---|---|
| Increase in T1+T2 Mix | | | | | | |
| subA | RC_AA176164_i_at | zp23h11,s1 Stratagene neuroepithelium (#937231) Homo sapiens cDNA clone 610341 3'; | P | | -7,4 | 2,56 |
| subA | W52431_at | zc45b12,r1 Soares senescent fibroblasts NbHSF Homo sapiens cDNA clone 325247 5' similar to SW:WDNM_RAT P14730 WDNM1 PROTEIN, [2] PIR:S07807 :; | P | | -21,6 | 10,27 |
| subB | RC_AA019641_ | contains element L1 repetitive element :; | P | | -5,2 | 1,9 |
| subB | RC_H13696_at | yl09e04,s1 Homo sapiens cDNA clone 148254 3'; | P | | -12,4 | 7,14 |
| subB | RC_N22404_at | yw37h03,s1 Homo sapiens cDNA clone 254453 3'; | P | | -19,4 | 13,95 |
| subB | RC_R07501_at | ye97f06,s1 Homo sapiens cDNA clone 125699 3'; | P | | -14,8 | 9,39 |
| subA | C14412_s_at | Human fetal brain cDNA 5'-end GEN-055A09, | P | | 3,1 | 2,56 |
| subA | RC_AA238455_s_at | zr75g02,s1 Soares NhHMPu S1 Homo sapiens cDNA clone 669266 3'; | P | | 7,4 | 7,12 |
| subB | RC_AA417030_at | zu04e07,s1 Soares testis NHT Homo sapiens cDNA clone 730884 3'; | P | | 6,9 | 3,38 |
| subB | RC_F10945_at | H, sapiens partial cDNA sequence; clone c-3mb07; | P | | 3,5 | 1,63 |
| subB | RC_N29319_at | yw84a11,s1 Homo sapiens cDNA clone 258908 3'; | P | | 3,7 | 1,29 |
| subB | RC_N68038_f_at | yz53a12,s1 Homo sapiens cDNA clone 286750 3'; | P | | 4,6 | 3,2 |
| Increase in T1+T2 Solid | | | | | | |
| subA | RC_AA417030_at | zu04e07,s1 Soares testis NHT Homo sapiens cDNA clone 730884 3'; | P | | 6,9 | 3,38 |
| subA | RC_AA608545_at | ae53d05,s1 Stratagene lung carcinoma 937218 Homo sapiens cDNA clone 950601 3'; | P | | -7,0 | 2,41 |
| subB | RC_H09261_at | yl98c12,s1 Homo sapiens cDNA clone 464410 3' similar to contains Alu repetitive element;contains MSR1 repetitive element :; | P | | -4,4 | 1,04 |
| subB | RC_N68871_at | za23h07,s1 Homo sapiens cDNA clone 293437 3' similar to contains Alu repetitive element;; | P | | 2,8 | 0,66 |
| subA | AA129196_at | zn29d08,r1 Stratagene neuroepithelium NT2RAMI 937234 Homo sapiens cDNA clone 548847 5' similar to SW:NU1M_ MOUSE P03888 NADH-UBIQUINONE OXIDOREDUCTASE CHAIN 1 :; | P | | 3,7 | 1,07 |
| subA | RC_AA620553_s_at | H, sapiens partial cDNA sequence; clone c-3jg08; | P | | 3 | 0,98 |
| subB | RC_F10779_at | H, sapiens partial cDNA sequence; clone c-3mb07; | P | | 3 | 0,83 |
| subB | RC_F10945_at | H, sapiens partial cDNA sequence; clone c-3mb07; | P | | 3,5 | 1,63 |
| subB | RC_H65650_at | yr72d10,s1 Homo sapiens cDNA clone 210835 3'; | P | | 3,5 | 1,61 |
| subB | RC_N68038_f_at | yz53a12,s1 Homo sapiens cDNA clone 286750 3'; | P | | 4,6 | 3,2 |
| Increase in T1+T2 Mix +T2 solid | | | | | | |
| subA | RC_AA417030_at | zu04e07,s1 Soares testis NHT Homo sapiens cDNA clone 730884 3'; | P | | 6,9 | 3,38 |
| subA | RC_AA608545_at | | P | | -7,0 | 2,41 |
| subB | RC_F10945_at | H, sapiens partial cDNA sequence; clone c-3mb07; | P | | 3,5 | 1,63 |
| subB | RC_N68038_f_at | yz53a12,s1 Homo sapiens cDNA clone 286750 3'; | P | | 4,6 | 3,2 |

Fig. 17.34

| Chip | Probe Set | Description | T2 Mix Abs Call | Diff Call | Fold Change | Sort Score |
|---|---|---|---|---|---|---|
| Increase in T1+T2 Mix | | | | | | |
| subA | RC_AA176184_i_at | zp23h11.s1 Stratagene neuroepithelium (#937231) Homo sapiens cDNA clone 610341 3'; | P | I | -6,9 | 1,98 |
| subA | W52431_at | zc45b12.r1 Soares senescent fibroblasts NbHSF Homo sapiens cDNA clone 325247 5' similar to SW:WDNM_RAT P14730 WDNM1 PROTEIN, [2] PIR:S07807 ;; | P | I | 28,2 | 26,64 |
| subB | RC_AA019641_at | contains element L1 repetitive element;; | P | I | -6,1 | 3,2 |
| subB | RC_H13696_at | yl09e04.s1 Homo sapiens cDNA clone 148254 3'; | P | I | -29,4 | 23,76 |
| subB | RC_N22404_at | yw37h03.s1 Homo sapiens cDNA clone 254453 3'; | P | I | -43,4 | 34,65 |
| subB | RC_R07501_at | ye97f06.s1 Homo sapiens cDNA clone 125699 3'; | P | I | 3,8 | 2,58 |
| subA | C14412_s_at | Human fetal brain cDNA 5'-end GEN-055A09, | P | I | 3,4 | 3,28 |
| subA | RC_AA236455_s_at | zr75g02.s1 Soares NhHMPu S1 Homo sapiens cDNA clone 669266 3'; | P | I | 6,4 | 5,66 |
| subA | RC_AA417030_at | zu04e07.s1 Soares testis NHT Homo sapiens cDNA clone 730884 3'; | P | I | 5,1 | 1,98 |
| subB | RC_F10945_at | H. sapiens partial cDNA sequence; clone c-3mb07; | P | I | 3,3 | 1,25 |
| subB | RC_N29319_at | yw84a11.s1 Homo sapiens cDNA clone 258908 3'; | P | I | 7,8 | 5,05 |
| subB | RC_N68038_f_at | yz53a12.s1 Homo sapiens cDNA clone 286750 3'; | P | I | 6,9 | 6,69 |
| Increase in T1+ T2 Solid | | | | | | |
| subA | RC_AA417030_at | zu04e07.s1 Soares testis NHT Homo sapiens cDNA clone 730884 3'; | P | I | 5,1 | 1,98 |
| subA | RC_AA608545_at | ae53d05.s1 Stratagene lung carcinoma 937218 Homo sapiens cDNA clone 950601 3'; | P | I | -6,5 | 2,49 |
| subB | RC_H09261_at | yl98c12.s1 Homo sapiens cDNA clone 464410 3' similar to contains Alu repetitive element;contains MSR1 repetitive element ;; | A | NC | -2,8 | 0,26 |
| subB | RC_N68871_at | za23h07.s1 Homo sapiens cDNA clone 293437 3' similar to contains Alu repetitive element;; | A | NC | -2,3 | 0,36 |
| subB | AA129196_at | zn29d08.r1 Stratagene neuroepithelium NT2RAMI 937234 Homo sapiens cDNA clone 548847 5' similar to SW:NU1M_MOUSE P03888 NADH-UBIQUINONE OXIDOREDUCTASE CHAIN 1 ;; | P | MI | 4,1 | 1,39 |
| subA | RC_AA620553_s_at | | P | NC | 3 | 1 |
| subA | RC_F10779_at | H. sapiens partial cDNA sequence; clone c-3lg08, | P | I | 2,7 | 0,64 |
| subB | RC_F10945_at | H. sapiens partial cDNA sequence; clone c-3mb07; | P | I | 3,3 | 1,25 |
| subB | RC_H65650_at | yr72d10.s1 Homo sapiens cDNA clone 210835 3'; | P | I | 2,8 | 0,91 |
| subB | RC_N68038_f_at | yz53a12.s1 Homo sapiens cDNA clone 286750 3'; | P | I | 6,9 | 6,69 |
| Increase in T1+T2 Mix +T2 solid | | | | | | |
| subA | RC_AA417030_at | zu04e07.s1 Soares testis NHT Homo sapiens cDNA clone 730884 3'; | P | I | 5,1 | 1,98 |
| subA | RC_AA608545_at | | P | I | -6,5 | 2,49 |
| subB | RC_F10945_at | H. sapiens partial cDNA sequence; clone c-3mb07; | P | I | 3,3 | 1,25 |
| subB | RC_N68038_f_at | yz53a12.s1 Homo sapiens cDNA clone 286750 3'; | P | I | 0,9 | 6,69 |

Fig. 17.35

| Chip | Probe Set | Description | T2 Solid Abs Call | Diff Call | Fold Change | Sort Score |
|---|---|---|---|---|---|---|
| Increase in T1+T2 Mix | | | | | | |
| subA | RC_AA176164_i_at | zp23h11,s1 Stratagene neuroepithelium (#937231) Homo sapiens cDNA clone 610341 3'; | A | NC | -2,2 | 0,19 |
| subA | W52431_at | zc45b12,r1 Soares senescent fibroblasts NbHSF Homo sapiens cDNA clone 325247 5' similar to SW:WDNM_RAT P14730 WDNM1 PROTEIN, [2] PIR:S07807 ;. | A | D | -1,4 | -0,06 |
| subB | RC_AA019641_at | contains element L1 repetitive element ;. | P | NC | -1,3 | -0,02 |
| subB | RC_H13696_at | yj09e04,s1 Homo sapiens cDNA clone 148254 3'; | A | NC | -1,7 | 0,07 |
| subB | RC_N22404_at | yw37h03,s1 Homo sapiens cDNA clone 254453 3'; | A | NC | -2,4 | -0,18 |
| subB | RC_R07501_at | ye97f06,s1 Homo sapiens cDNA clone 125699 3'; | A | NC | 1,3 | 0,1 |
| subA | C14412_s_at | Human fetal brain cDNA 5'-end GEN-055A09; | P | - | 2,3 | 1,05 |
| subA | RC_AA236455_s_at | zr75g02,s1 Soares NhHMPu S1 Homo sapiens cDNA clone 669266 3'; | P | NC | 2,6 | 0,83 |
| subA | RC_AA417030_at | zu04e07,s1 Soares testis NHT Homo sapiens cDNA clone 730884 3'; | P | 1 | -4,6 | 1,57 |
| subB | RC_F10945_at | H, sapiens partial cDNA sequence; clone c-3mb07; | P | -1 | 3,5 | 1,61 |
| subB | RC_N29319_at | yw84a11,s1 Homo sapiens cDNA clone 258908 3'; | P | NC | -2,1 | 0,29 |
| subB | RC_N68038_f_at | yz53a12,s1 Homo sapiens cDNA clone 286750 3'; | P | 1 | 3,3 | 1,54 |
| Increase in T1+ T2 Solid | | | | | | |
| subA | RC_AA417030_at | zu04e07,s1 Soares testis NHT Homo sapiens cDNA clone 730884 3'; | P | 1 | -4,6 | 1,57 |
| subA | RC_AA608545_at | ae53d05,s1 Stratagene lung carcinoma 937218 Homo sapiens cDNA clone 950601 3'; | P | 1 | -4,7 | 1,54 |
| subB | RC_H09261_at | yl98c12,s1 Homo sapiens cDNA clone 46410 3' similar to contains Alu repetitive element;contains MSR1 repetitive element ;. | P | 1 | -3,7 | 0,83 |
| subB | RC_N68871_at | za23h07,s1 Homo sapiens cDNA clone 293437 3' similar to contains Alu repetitive element;. | P | 1 | -4,9 | 2,35 |
| subA | AA129196_at | zn29d08,r1 Stratagene neuroepithelium NT2RAMI 937234 Homo sapiens cDNA clone 548847 5' similar to SW:NU1M_ MOUSE P03888 NADH-UBIQUINONE OXIDOREDUCTASE CHAIN 1 ;. | P | 1 | 9,5 | 5,74 |
| subA | RC_AA620553_s_at | H, sapiens partial cDNA sequence; clone c-3jg08; | P | 1 | 5,3 | 3,24 |
| subB | RC_F10779_at | H, sapiens partial cDNA sequence; clone c-3mb07; | P | 1 | 3,2 | 0,95 |
| subB | RC_F10945_at | yr72d10,s1 Homo sapiens cDNA clone 210835 3'; | P | 1 | 3,5 | 1,61 |
| subB | RC_H65650_at | yz53a12,s1 Homo sapiens cDNA clone 286750 3'; | P | 1 | 3,6 | 1,66 |
| subB | RC_N68038_f_at | | P | 1 | 3,3 | 1,54 |
| Increase in T1+T2 Mix +T2 solid | | | | | | |
| subA | RC_AA417030_at | zu04e07,s1 Soares testis NHT Homo sapiens cDNA clone 730884 3'; | P | 1 | -4,6 | 1,57 |
| subA | RC_AA608545_at | | P | -1 | -4,7 | 1,54 |
| subB | RC_F10945_at | H, sapiens partial cDNA sequence; clone c-3mb07; | P | 1 | 3,5 | 1,61 |
| subB | RC_N68038_f_at | yz53a12,s1 Homo sapiens cDNA clone 286750 3'; | P | 1 | 3,3 | 1,54 |

Fig. 18
Western blot - polyclonal antibodies
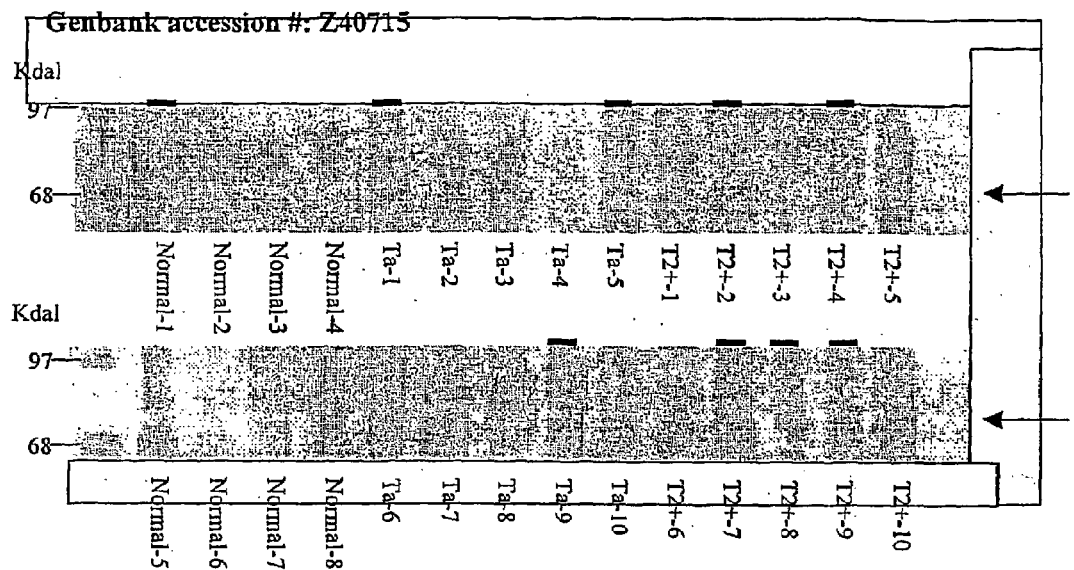
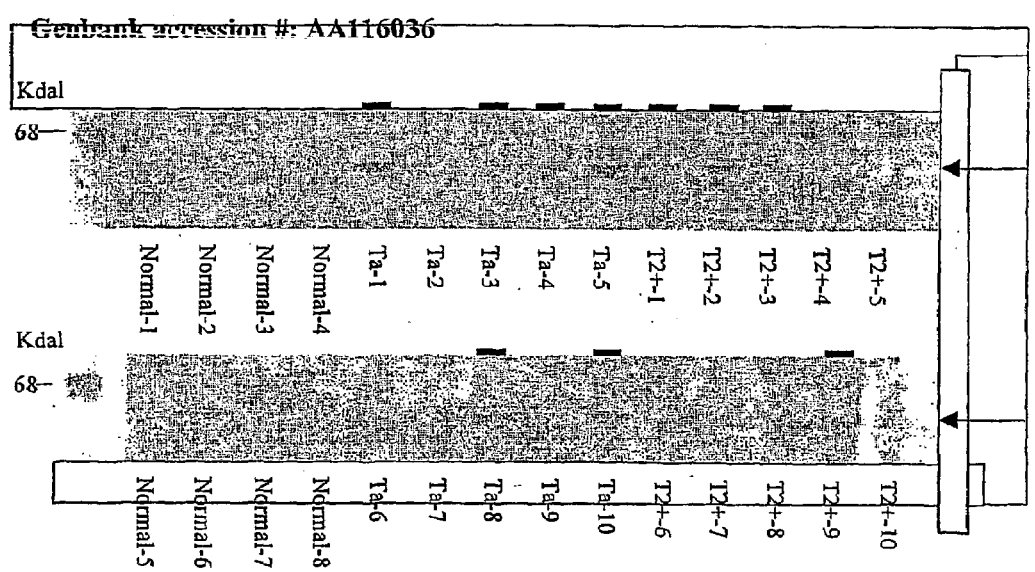

SEQUENCE LISTING

```
<160> NUMBER OF SEQ ID NOS: 2

<210> SEQ ID NO 1
<211> LENGTH: 2004
<212> TYPE: DNA
<213> ORGANISM: Homo sapiens

<400> SEQUENCE: 1
gtcagagaca gaaaactcac tacatatggg ctatagtgca ctagaaataa agagtaaaat      60
gttagcccta gagaaagcag atacctgtat ttacaaccct ttgggtggat cagatcttca     120
gtatacaaat cgggtagata aagtggtaat aaatccatac tttggtctag gagctccaga     180
ctactcaaaa atccaaatac ctaaacagga aaaatggcag agaagcatga gcagtgtcac     240
agaagacaag gaacgacagt gggtagatga ttttcctctc caccgaagcg cctgtgaagg     300
agattcagaa ttactaagcc gtcttctcag tgaaagattt tcagtcaacc agttagatag     360
tgaccactgg gcacccattc attatgcatg ctggtatgga aaagttgagg ccactcgcat     420
attgttagag aaaggaaagt gcaatccaaa cctttaaat ggacaactta gttctcctct     480
```

```
tcattttgct gctggaggag gacatgctga aatagtacag attctcctaa accacccaga    540
aacggataga catataacag accaacaagg aagatctcca ttaaatattt gtgaagaaaa    600
caaacaaaac aactgggaag aagctgcaaa attgttgaag gaagcaatta acaaaccata    660
tgaaaaagtt cgaatataca aatggatgg gtcatatcgt tctgttgaat tgaagcatgg    720
aaataatacc acagtgcagc agataatgga aggaatgcgt ctctctcaag aaactcagca    780
atatttcact atatggattt gttcagaaaa cctcagcctt caactcaaac catatcataa    840
acccttgcaa catgttcgtg actggccaga aatacttgct gaattgacta atctggatcc    900
tcaaagggaa acacctcagc tttttctaag aagagatgtg agacttccct tggaagttga    960
aaaacagatt gaagacccac tagctattct tattctcttt gatgaagcca gatataattt   1020
attgaagggc tttatacag ctcctgatgc taagctgata acattggcaa gtctgctttt   1080
gcaaatagtc tatggaaatt atgagagtaa aaaacacaag caaggtttcc taaatgaaga   1140
aaatctaaaa tccatcgtac ctgttaccaa actgaaaagt aaggcacctc actggacaaa   1200
tcgcatactt catgaataca agaatctcag tacaagtgaa ggtgtcagta agaaatgca    1260 tcaccttcag cgcatgttct tacagaattg ctgggaaatt cctacttatg gagcagcatt   1320
tttcacagga cagatattta caaaggcaag ccccagcaat cataaagtca tccctgtgta   1380
tgtaggagtg aatataaaag gacttcatct cctcaacatg gaaactaagg ctttactcat   1440
cagtcttaag tatggttgtt ttatgtggca attgggagat actgatactt gttttcagat   1500
ccatagcatg gaaaataaaa tgagctttat agtacataca aaacaggctg gtctcgtggt   1560
aaaactgtta atgaagctaa atggacagtt aatggccact gaaagaaatt catgaaagag   1620
aagtaactgt tactcaagcc accacatttt ggtgatgcag agtttccttt ccgcgaaaga   1680
tttcttaaaa tattactttt gggccctagc atggcgggtc aaccctgtaa ttccagcact   1740
ttgggagggt gggggcaggg cgggatcaac tgaagtcaga gttcaagaca gcctgggcaa   1800
catggtgaaa cctgtctcta caaaaataca aaaattaggt gggtgtggtg ggggcgcct    1860 attcatccta gctactaggg gagggcaagg tgggggagat cgcttaaccc caggaggtgg   1920
gggttgttgt gagccaagat tgcaccacgg cacgctagcc tgggtgacac aggaagactc   1980
catctcaaaa aaaaaaaaaa aaaa                                         2004
```

```
<210> SEQ ID NO 2
<211> LENGTH: 462
<212> TYPE: DNA
<213> ORGANISM: Homo sapiens
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
```

```
-continued
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t

<400> SEQUENCE: 2
gctggggctt agctgggagg tggtctgaag cagacaggga atgggagagg nggatgggaa      60
gtagacagtg gctggtatgg ctctgaggct ccctggggcc tgctcaagct cctcctgctc     120
cttgctgttt tctgatgatt tggggggcttg ggagtccctt tgtcctcatc tgagactgaa    180
atgtggggat ccaggatggc cttccttcct cttacccttc ctccctcagc ctgcaacctc    240
tatcctggaa cctgtcctcc ctttctcccc aactatgcat ctgttgtctg ctcctctgca    300
aaggccagcc agcttnggag cagcagagaa ataaacagca tttctgatga aaaaaaaaaa    360
aaaaaaaacc gcggccgaaa gcttattncc ctttaagtaa ggggttaatt tttagcttgg    420
gcactnggcc ntcgttttan aacgtcgtga attnggaaaa cc                        462
```

GENE EXPRESSION IN BIOLOGICAL CONDITIONS

This is a U.S. National Phase Application Under 35 USC 371 and applicant claims the benefit of priority of PCT/DK01/00463 filed 12 Jul. 2001, which was published Under PCT Article 21(2) in English and Danish Application No. PA 2000 01020, filed 30 Jun. 2000.

TECHNICAL FIELD OF THE INVENTION

The present invention relates to a method of determining the presence or absence of a biological condition in animal tissue, wherein the expression of genes in normal tissue and tissue from the biological condition is examined and correlated to standards. The invention further relates to the treatment of the biological condition and an assay for determining the condition.

BACKGROUND

The building of large databases containing human genome sequences is the basis for studies of gene expressions in various tissues during normal physiological and pathological conditions. Constantly (constitutively) expressed sequences as well as sequences whose expression is altered during disease processes are important for our understanding of cellular properties, and for the identification of candidate genes for future therapeutic intervention. As the number of known genes and ESTs build up in the databases, array-based simultaneous screening of thousands of genes is necessary to obtain a profile of transcriptional behaviour, and to identify key genes that either alone or in combination with other genes, control various aspects of cellular life. One cellular behaviour that has been a mystery for many years is the malignant behaviour of cancer cells. It is now known that for example defects in DNA repair can lead to cancer but the cancer-creating mechanism in heterozygous individuals is still largely unknown as is the malignant cell's ability to repeat cell cycles to avoid apoptosis to escape the immune system to invade and metastasize and to escape therapy. There are indications in these areas and excellent progress has been made, buth the myriad of genes interacting with each other in a highly complex multidimensional network is making the road to insight long and contorted.

Similar appearing tumors—morphologically, histochemically, microscopically—can be profoundly different. They can have different invasive and metastasizing properties, as well as respond differently to therapy. There is thus a need in the art for methods which distinguish tumors and tissues on factors different than those currently in clinical use.

The malignant transformation from normal tissue to cancer is believed to be a multistep process, in which tumorsuppressor genes, that normally repress cancer growth show reduced gene expression and in which other genes that encode tumor promoting proteins (oncogenes) show an increased expression level. Several tumor suppressor genes have been identified up till now, as e.g. p16, Rb, p53 (Nesrin Özören and Wafik S. El-Deiry, Introduction to cancer genes and growth control, In: DNA alterations in cancer, genetic and epigenetic changes, Eaton publishing, Melanie Ehrlich (ed) p. 1-43, 2000.; and references therein). They are usually identified by their lack of expression or their mutation in cancer tissue.

Other examinations have shown this downregulation of transcripts to be partly due to loss of genomic material (loss of heterozygosity), partly to methylation of promo-torregions, and partly due to unknown factors (Nesrin Özören and Wafik S. El-Deiry, Introduction to cancer genes and growth control, In: DNA alterations in cancer, genetic and epigenetic changes, Eaton publishing, Melanie Ehrlich (ed) p. 1-43, 2000.; and references therein).

Several oncogenes are known, e.g. cyclinD1/PRAD1/BCL1, FGFs, c-MYC, BCL-2 all of which are genes that are amplified in cancer showing an increased level of transcript (Nesrin Özören and Wafik S. El-Deiry, Introduction to cancer genes and growth control, In: DNA alterations in cancer, genetic and epigenetic changes, Eaton publishing, Melanie Ehrlich (ed) p. 1-43, 2000.; and references therein). Many of these genes are related to cell growth and directs the tumor cells to uninhibited growth. Others may be related to tissue degradation as they e.g. encode enzymes that break down the surrounding connective tissue.

SUMMARY OF THE INVENTION

In one aspect the present invention relates to a method of determining the presence or absence of a biological condition in animal tissue comprising
  collecting a sample comprising cells from the tissue and/or expression products from the cells,
  assaying a first expression level of at least one gene from a first gene group, wherein the gene from the first gene group is selected from genes expressed in normal tissue cells in an amount higher than expression in biological condition cells, and/or
  assaying a second expression level of at least one gene from a second gene group, wherein the second gene group is selected from genes expressed in normal tissue cells in an amount lower than expression in biological condition cells,
  correlating the first expression level to a standard expression level for normal tissue, and/or the second expression level to a standard expression level for biological condition cells to determine the presence or absence of a biological condition in the animal tissue.

Animal tissue may be tissue from any animal, preferably from a mammal, such as a horse, a cow, a dog, a cat, and more preferably the tissue is human tissue. The biological condition may be any condition exhibiting gene expression different from normal tissue. In particular the biological condition relates to a malignant or premalignant condition, such as a tumor or cancer.

Furthermore, the invention relates to a method of determining the stage of a biological condition in animal tissue,
  comprising collecting a sample comprising cells from the tissue,
  assaying the expression of at least a first stage gene from a first stage gene group and at least a second stage gene from a second stage gene group, wherein at least one of said genes is expressed in said first stage of the condition in a higher amount than in said second stage, and the other gene is expressed in said first stage of the condition in a lower amount than in said second stage of the condition,
  correlating the expression level of the at least two genes to a standard level of expression determining the stage of the condition.

Thereby, it is possible to determine the biological condition in more details, such as determination of a stage and/or a grade of a tumor.

The methods above may be used for determining single gene expressions, however the invention also relates to a method of determining an expression pattern of a cell sample, comprising:

collecting sample comprising bladder cells and/or expression products from bladder cells, determining the expression level of at least one gene in the sample, wherein at least one gene belongs to a first group of genes, said gene from the first gene group being expressed in a higher amount in normal tissue than in biological condition cells, and wherein at least one other gene belongs to a second group of genes, said gene from the second gene group being expressed in a lower amount in normal tissue than in biological condition cells, and the difference between the expression level of the first gene group in normal cells and biological condition cells being at least two-fold, obtaining an expression pattern of the bladder cell sample.

Gene expression patterns may rely on one or a few genes, but more preferred gene expression patterns relies on expression from multiple genes, whereby a combined information from several genes is obtained.

Further, the invention relates to a method of determining an expression pattern of a bladder cell sample independent of the proportion of submucosal, muscle, or connective tissue cells present, comprising:

determining the expression of one or more genes in a sample comprising cells, wherein the one or more genes exclude genes which are expressed in the submucosal, muscle, or connective tissue, whereby a pattern of expression is formed for the sample which is independent of the proportion of submucosal, muscle, or connective tissue cells in the sample.

The expression pattern may be used in a method according to this information, and accordingly, the invention also relates to a method of determining the presence or absence of a biological condition in human bladder tissue comprising, collecting a sample comprising cells from the tissue, determining an expression pattern of the cells as defined above, correlating the determined expression pattern to a standard pattern, determining the presence or absence of the biological condition in said tissue.

as well as a method for determining the stage of a biological condition in animal tissue, comprising collecting a sample comprising cells from the tissue, determining an expression pattern of the cells as defined above, correlating the determined expression, pattern to a standard pattern, determining the stage of the biological condition is said tissue.

The invention further relates to a method for reducing cell tumorigenicity or malignancy of a cell, said method comprising contacting a tumor cell with at least one peptide expressed by at least one gene selected from genes being expressed in an amount at least two-fold higher in normal cells than the amount expressed in said tumor cell, or comprising obtaining at least one gene selected from genes being expressed in an amount at least two-fold higher in normal cells than the amount expressed in said tumor cell, introducing said at least one gene into the tumor cell in a manner allowing expression of said gene(s), or obtaining at least one nucleotide probe capable of hybridising with at least one gene of a tumor cell, said at least one gene being selected from genes being expressed in an amount one-fold lower in normal cells than the amount expressed in said tumor cell, and introducing said at least one nucleotide probe into the tumor cell in a manner allowing the probe to hybridise to the at least one gene, thereby inhibiting expression of said at least one gene.

In a further aspect the invention relates to a method for producing antibodies against an expression product of a cell from a biological tissue, said method comprising the steps of obtaining expression product(s) from at least one gene said gene being expressed as defined above, immunising a mammal with said expression product(s) obtaining antibodies against the expression product.

The antibodies produced may be used for producing a pharmaceutical composition. Further, the invention relates to a vaccine capable of eliciting an immune response against at least one expression product from at least one gene said gene being expressed as defined above.

The invention furthermore relates to the use of any of the methods discussed above for producing an assay for diagnosing a biological condition in animal tissue.

Also, the invention relates to the use of a peptide as defined above as an expression product and/or the use of a gene as defined above and/or the use of a probe as defined above for preparation of a pharmaceutical composition for the treatment of a biological condition in animal tissue.

In yet a further aspect the invention relates to an assay for determining the presence or absence of a biological condition in animal tissue, comprising at least one first marker capable of detecting a first expression level of at least one gene from a first gene group, wherein the gene from the first gene group is selected from genes expressed in normal tissue cells in an amount higher than expression in biological condition cells, and/or at least one second marker capable of detecting a second expression level of at least one gene from a second gene group, wherein the second gene group is selected from genes expressed in normal tissue cells in an amount lower than expression in biological condition cells.

In another aspect the invention relates to an assay for determining an expression pattern of a bladder cell, comprising at least a first marker and and/or a second marker, wherein the first marker is capable of detecting a gene from a first gene group as defined above, and the second marker is capable of detecting a gene from a second gene group as defined above.

DRAWINGS

FIGS. 1-4. Describes genes that were only present (P) in normal urothelium and absent (A) from the other four samples (samples 1, 2, 3, 4, 5 scored as P, A, A, A, A), genes that were present in normal and superficial tumors and absent from the others (PP,AAA) etcetera. These genes could for example encode tumor inhibitors, or stage specific genes.

FIG. 5. Genes that are decreased (D) in tumors compared with normal urothelium (P,D,D,D,D). These could encode tumor inhibitors.

FIG. 6. Genes that are increased >3 fold in all tumor compared to normal. Encode Tumor associated proteins.

FIG. 7. Genes that are scored as PPPPA but decreased in all tumors and finally absent in the most malignant solid tumor.

FIG. 8. Genes that lose expression in the muscle invasive tumors, PPPAA.

FIG. 9. Genes that re lost in slightly invasive tumors, PPAAA

FIG. 10. Genes that are increased in expression level in all tumors, APPPP. Tumor specific genes.

FIG. 11. Genes that are turned on in all invasive tumors, AAPPP.

FIG. 12. Genes that are associated with muscle invasive tumors. AAAPP.

FIG. 13. Genes that identify solid tumors only AAAAP.

FIG. 14. Genes that identify mixed tumors solid/papillom of invasive type. AAAPA.

FIG. 15. Genes that identify T1 tumors. AAPAA

FIG. 16. Genes that identoify superficial tumors APAAA

FIG. 17 shows the absolute level (called average difference) of appr. 18,000 Expressed Sequence Tags.

FIG. 18 shows western blots based on antibodies raised against synthetic peptides selected from the EST sequence.

DETAILED DESCRIPTION OF THE INVENTION

Samples

The samples according to the present invention may be any tissue sample, it is however often preferred to conduct the methods according to the invention on epithelial tissue, such as epithelial tissue from the bladder. In particular the epithelial tissue may be mucosa.

The sample may be obtained by any suitable manner known to the man skilled in the art, such as a biopsy of the tissue, or a superficial sample scraped from the tissue. The sample may be prepared by forming a cell suspension made from the tissue, or by obtaining an extract from the tissue.

In one embodiment it is preferred that the sample comprises substantially only cells from said tissue, such as substantially only cells from mucosa of the bladder.

Biological Condition

The methods according to the invention may be used for determining any biological condition, wherein said condition leads to a change in the expression of at least one gene, and preferably a change in a variety of genes.

Thus, the biological condition may be any malignant or premalignant condition, in particular in bladder, such as a tumor or an adenocarcinoma, a carcinoma, a teratoma, a sarcoma, and/or a lymphoma, and/or carcinoma-in-situ, and/or dysplasia-in-situ.

Single Gene Expression Contra Expression Pattern

The expression level may be determined as single gene approaches, i.e. wherein the determination of expression from one or two or a few genes is conducted. It is preferred that expression from at least one gene from a first (normal) group is determined, said first gene group representing genes being expressed at a higher level in normal tissue, i.e. so-called suppressors, in combination with determination of expression of at least one gene from a second group, said second group representing genes being expressed at a higher level in tissue from the biological condition than in normal tissue, i.e. so-called oncogenes. However, determination of the expression of a single gene whether belonging to the first group or second group is within the scope of the present invention. In this case it is preferred that the single gene is selected among genes having a high change in expression level from normal cells to biological condition cells.

Another approach is determination of an expression pattern from a variety of genes, wherein the determination of the biological condition in the tissue relies on information from a variety of gene expression, i.e. rather on the combination of expressed genes than on the information from single genes.

Bladder Tumors

The following data presented herein relates to bladder tumors, and therefore the description has focused on the gene expression level as one way of identifying genes that lose or gain function in cancer tissue. Genes showing a remarkable downregulation (or complete loss) or upregulation (gene expression gained de novo) of the expression level—measured as the mRNA transcript, during the malignant progression in bladder from normal mucosa through Ta superficial tumors to T1, slightly invasive tumors, to T2, T3 and T4 which have spread to muscle or even further into lymph nodes or other organs are within the scope of the invention, as well as genes gaining importance during the differentiation from normal towards malignancy.

Gene Groups

The present invention relates to a variety of genes identified either by an EST identification number and/or by a gene identification number. Both type of identification numbers relates to identification numbers of UniGene database, NCBI, build 18.

The various genes have been identified using Affymetrix arrays of the following product numbers:

HU35K SubA 900 184

HU35K SubB 900 185

First Gene Group

The first gene group relates to at least one, such as at least two, for example at least three, such as at least four, such as at least five, such as more than six genes being expressed in normal tissue cells in an amount higher than expression in biological condition cells. The term "normal tissue cells" relates to cells from the same type of tissue that is examined with respect to the biological condition in question. Thus, with respect to bladder tumors, the normal tissue relates to bladder tissue, in particular to normal bladder mucosa.

The first gene group therefore relates to genes being downregulated in tumors, such genes being expected to serve as tumor suppressor genes, and they are of importance as predictive markers for the disease as loss of one or more of these may signal a poor outcome or an aggressive disease course. Furthermore, they may be important targets for therapy as restoring their expression level, e.g. by gene therapy, or substitution with those peptide products or small molecules with a similar biological effect may suppress the malignant growth.

For a bladder tissue sample a gene from the first gene group is preferably selected individually from genes comprising a sequence as identified below by EST

| | |
|---|---|
| AA131127_at | zo16a05.r1 Stratagene colon (#937204) *Homo sapiens* cDNA clone 587024 5' similar to SW: CATX_BOVIN P05689 CATHEPSIN;. |
| AA372630_s_at | EST84548 Colon adenocarcinoma IV *Homo sapiens* cDNA 5' end. |
| AA434329_at | zw24g07.r1 Soares ovary tumor NbHOT *Homo sapiens* cDNA clone 770268 5' similar to contains element TAR1 repetitive element;. |

-continued

| | |
|---|---|
| C01409_s_at | HUMGS0008391, Human Gene Signature, 3'-directed cDNA sequence. |
| RC_AA256485_at | zr81e12.s1 Soares NhHMPu S1 *Homo sapiens* cDNA clone 682126 3'. |
| RC_AA290679_at | zt19f03.s1 Soares ovary tumor NbHOT *Homo sapiens* cDNA clone 713597 3' similar to TR: E92665 E92665 AP56;. |
| RC_AA429655_at | zw71d04.s1 Soares testis NHT *Homo sapiens* cDNA clone 781639 3'. |
| RC_AA452410_at | zx31f03.s1 Soares total fetus Nb2HF8 9w *Homo sapiens* cDNA clone 788093 3'. |
| RC_AA461174_at | zx70c04.s1 Soares total fetus Nb2HF8 9w *Homo sapiens* cDNA clone 796806 3'. |
| RC_AA491463_at | ab01d12.s1 Stratagene fetal retina 937202 *Homo sapiens* cDNA clone 839543 3'. |
| RC_AA025434_at | ze84f10.s1 Soares fetal heart NbHH19W *Homo sapiens* cDNA clone 365707 3'. |
| RC_AA026030_at | ze84d01.s1 Soares fetal heart NbHH19W *Homo sapiens* cDNA clone 365665 3' similar to PIR: A48764 A48764 calpain;. |
| RC_AA054321_s_at | zl68c01.s1 Stratagene colon (#937204) *Homo sapiens* cDNA clone 509760 3'. |
| RC_AA099820_at | zk87c05.s1 Soares pregnant uterus NbHPU *Homo sapiens* cDNA clone 489800 3'. |
| RC_AA161043_at | zo74g11.s1 Stratagene pancreas (#937208) *Homo sapiens* cDNA clone 592676 3'. |
| RC_AA215379_at | zr97c07.s1 NCI_CGAP_GCB1 *Homo sapiens* cDNA clone IMAGE: 683628 3'. |
| RC_H09281_at | yl98f11.s1 *Homo sapiens* cDNA clone 46316 3'. |
| RC_H18836_at | ym45d10.s1 *Homo sapiens* cDNA clone 51262 3'. |
| RC_H52937_at | yq76e12.s1 *Homo sapiens* cDNA clone 201742 3' similar to gb: J02982 GLYCOPHORIN B PRECURSOR (HUMAN);. |
| RC_H69547_at | yr89e02.s1 *Homo sapiens* cDNA clone 212474 3'. |
| RC_H95039_at | yv20a05.s1 *Homo sapiens* cDNA clone 243248 3'. |
| RC_N21687_at | yx63h03.s1 Soares melanocyte 2NbHM *Homo sapiens* cDNA clone 266453 3'. |
| RC_N54841_at | yv73b09.s1 Soares fetal liver spleen 1NFLS *Homo sapiens* cDNA clone 248345 3'. |
| RC_N59622_at | yv74b06.s1 Soares fetal liver spleen 1NFLS *Homo sapiens* cDNA clone 248435 3'. |
| RC_N66312_at | yz38a06.s1 *Homo sapiens* cDNA clone 285298 3'. |
| RC_N90717_at | za90a10.s1 Soares fetal lung NbHL19W *Homo sapiens* cDNA clone 299802 3'. |
| RC_R22189_at | yh26a02.s1 *Homo sapiens* cDNA clone 130826 3'. |
| RC_R53457_at | yg83e10.s1 *Homo sapiens* cDNA clone 39835 3'. |
| RC_T53389_s_at | ya88f04.s1 *Homo sapiens* cDNA clone 68767 3'. |
| RC_W86375_s_at | zh55a02.s1 Soares fetal liver spleen 1NFLS S1 *Homo sapiens* cDNA clone 415946 3'. |
| RC_Z38289_at | *H. sapiens* partial cDNA sequence; clone c-05e04. | or a sequence as identified below

| | |
|---|---|
| RC_AA621122_at | af34f04.s1 Soares total fetus Nb2HF8 9w *Homo sapiens* cDNA clone 1033567 3'. |
| RC_AA129216_at | zn84b03.s1 Stratagene lung carcinoma 937218 *Homo sapiens* cDNA clone 564845 3'. |
| RC_AA133214_s_at | zk97h05.s1 Soares pregnant uterus NbHPU *Homo sapiens* cDNA clone 490809 3'. |
| RC_H99675_at | yx35c02.s1 *Homo sapiens* cDNA clone 263714 3'. |
| RC_R87160_at | yq31h10.s1 *Homo sapiens* cDNA clone 197443 3'. | or a sequence as identified below

| | |
|---|---|
| RC_AA429904_at | zw66d03.s1 Soares testis NHT *Homo sapiens* cDNA clone 781157 3'. | or a sequence as identified below

| | |
|---|---|
| RC_AA460273_at | zx67f05.s1 Soares total fetus Nb2HF8 9w *Homo sapiens* cDNA clone 796545 3'. |
| RC_AA490930_at | aa46e04.s1 NCI_CGAP_GCB1 *Homo sapiens* cDNA clone IMAGE: 823998 3'. |
| RC_AA418072_at | zv97g08.s1 Soares NhHMPu S1 *Homo sapiens* cDNA clone 767774 3'. |
| RC_H61476_s_at | yr17e08.s1 *Homo sapiens* cDNA clone 205574 3'. |
| RC_H16209_at | yl28d11.s1 *Homo sapiens* cDNA clone 159573 3'. |

-continued

| | |
|---|---|
| RC_N93816_at | zb63f11.s1 Soares fetal lung NbHL19W *Homo sapiens* cDNA clone 308301 3'. |
| RC_H17550_at | ym41h05.s1 *Homo sapiens* cDNA clone 50842 3'. |
| RC_N36835_at | yy35f02.s1 *Homo sapiens* cDNA clone 273243 3'. |
| RC_T35289_at | EST82492 *Homo sapiens* cDNA 3' end similar to None. |
| RC_AA447977_s_at | zw82e09.s1 Soares testis NHT *Homo sapiens* cDNA clone 782728 3'. |
| RC_AA160879_at | zo62h06.s1 Stratagene pancreas (#937208) *Homo sapiens* cDNA clone 591515 3'. |
| RC_W45051_at | zc21g08.s1 Soares senescent fibroblasts NbHSF *Homo sapiens* cDNA clone 323006 3'. |
| RC_AA040699_at | zk48g04.s1 Soares pregnant uterus NbHPU *Homo sapiens* cDNA clone 486102 3'. |
| RC_R63734_at | yi15g05.s1 *Homo sapiens* cDNA clone 139352 3'. |
| RC_T61475_at | yc06h08.s1 *Homo sapiens* cDNA clone 79935 3'. |
| H23847_at | yn71d04.r1 *Homo sapiens* cDNA clone 173863 5'. |
| RC_AA482014_at | zu98d05.s1 NCI_CGAP_GCB1 *Homo sapiens* cDNA clone IMAGE: 746025 3' similar to TR: G414993 G414993 CENTRIN.;. |
| RC_AA143323_s_at | zo37d04.s1 Stratagene endothelial cell 937223 *Homo sapiens* cDNA clone 589063 3' similar to gb: M60483_rna1 PROTEIN PHOSPHATASE PP2A-ALPHA, CATALYTIC SUBUNIT (HUMAN);. |
| R55902_at | yg92d05.r1 *Homo sapiens* cDNA clone 41017 5'. |
| RC_AA035638_at | zk28a05.s1 Soares pregnant uterus NbHPU *Homo sapiens* cDNA clone 471824 3'. |
| AA263146_at | PMY0511 KG1a Lambda Zap Express cDNA Library *Homo sapiens* cDNA 5'. |
| RC_W19222_at | zb89h05.s1 Soares senescent fibroblasts NbHSF *Homo sapiens* cDNA clone 310809 3' similar to contains Alu repetitive element; contains element L1 repetitive element;. |
| RC_AA262276_at | zs25f07.s1 NCI_CGAP_GCB1 *Homo sapiens* cDNA clone IMAGE: 686245 3'. |
| H61361_s_at | yu41b03.r1 *Homo sapiens* cDNA clone 236333 5'. |
| RC_R10657_s_at | yf31e11.s1 *Homo sapiens* cDNA clone 128492 3'. |
| RC_AA227261_at | zr22h04.s1 Stratagene NT2 neuronal precursor 937230 *Homo sapiens* cDNA clone 664183 3'. |
| RC_AA477641_at | zu37b12.s1 Soares ovary tumor NbHOT *Homo sapiens* cDNA clone 740159 3'. |
| RC_T70596_at | yd15f10.s1 *Homo sapiens* cDNA clone 108331 3'. |
| R31641_at | yh69e02.r1 *Homo sapiens* cDNA clone 135002 5'. |
| RC_N62855_at | yz83c04.s1 *Homo sapiens* cDNA clone 289638 3'. |
| RC_AA279695_at | zs92d10.s1 NCI_CGAP_GCB1 *Homo sapiens* cDNA clone IMAGE: 704947 3'. |
| RC_H95071_s_at | yv20f02.s1 Soares fetal liver spleen 1NFLS *Homo sapiens* cDNA clone 243291 3'. |
| RC_N54385_at | yv39f05.s1 Soares fetal liver spleen 1NFLS *Homo sapiens* cDNA clone 245121 3'. |
| H15314_at | ym28c02.r1 *Homo sapiens* cDNA clone 49413 5'. |
| RC_AA151435_at | zl43h11.s1 Soares pregnant uterus NbHPU *Homo sapiens* cDNA clone 504741 3'. |
| RC_F01568_at | *H. sapiens* partial cDNA sequence; clone c-06g08. | or a sequence as identified below

| | |
|---|---|
| RC_AA451685_at | zx44c03.s1 Soares total fetus Nb2HF8 9w *Homo sapiens* cDNA clone 789316 3'. |
| RC_W44745_at | zb98a11.s1 Soares parathyroid tumor NbHPA *Homo sapiens* cDNA clone 320828 3'. |
| AA482319_f_at | ab15c03.r1 Stratagene lung (#937210) *Homo sapiens* cDNA clone 840868 5'. |
| RC_AA155820_at | zo47a08.s1 Stratagene endothelial cell 937223 *Homo sapiens* cDNA clone 590006 3'. |
| H51340_at | yo30c06.r1 *Homo sapiens* cDNA clone 179434 5'. |
| RC_H09594_at | yl97b11.s1 *Homo sapiens* cDNA clone 46276 3'. |
| RC_N29764_at | yw91b09.s1 *Homo sapiens* cDNA clone 259577 3'. |
| R80048_at | yi91e08.r1 *Homo sapiens* cDNA clone 146630 5'. |
| AC000115_cds1_at | WUGSC: H_GS188P18.1a gene extracted from Human BAC clone GS188P18 |
| AA203222_at | zx56e01.r1 Soares fetal liver spleen 1NFLS S1 *Homo sapiens* cDNA clone 446520 5' similar to contains element MER17 repetitive element;. |
| RC_AA100437_at | zn59e02.s1 Stratagene muscle 937209 *Homo sapiens* cDNA clone 562490 3'. |
| RC_T51990_at | yb29e01.s1 *Homo sapiens* cDNA clone 72600 3'. |

-continued

| | |
|---|---|
| AA491114_at | aa46e04.r1 NCI_CGAP_GCB1 *Homo sapiens* cDNA clone IMAGE: 823998 5'. |
| RC_R39869_at | yf63b06.s1 *Homo sapiens* cDNA clone 26725 3'. |
| RC_AA394071_at | zt52g01.s1 Soares ovary tumor NbHOT *Homo sapiens* cDNA clone 726000 3' similar to SW: ADG_MOUSE P22892 GAMMA-ADAPTIN;. |
| RC_AA196790_at | zq60b06.s1 Stratagene neuroepithelium (#937231) *Homo sapiens* cDNA clone 645971 3'. |
| AA465000_s_at | zx80b07.r1 Soares ovary tumor NbHOT *Homo sapiens* cDNA clone 810037 5'. |
| RC_R39923_at | yf51d10.s1 *Homo sapiens* cDNA clone 25662 3'. |
| RC_R91819_at | yp99c05.s1 *Homo sapiens* cDNA clone 195560 3' similar to contains MER1 repetitive element;. |
| AA484982_at | aa39b02.r1 NCI_CGAP_GCB1 *Homo sapiens* cDNA clone IMAGE: 815595 5'. |
| AA036900_at | zk29e11.r1 Soares pregnant uterus NbHPU *Homo sapiens* cDNA clone 471980 5'. |
| RC_AA449951_at | zx38a10.s1 Soares total fetus Nb2HF8 9w *Homo sapiens* cDNA clone 788730 3'. |
| RC_Z40233_at | *H. sapiens* partial cDNA sequence; clone c-1wg05. |
| RC_AA166810_at | zo87a05.s1 Stratagene ovarian cancer (#937219) *Homo sapiens* cDNA clone 593840 3'. |
| RC_H06746_at | yl83h08.s1 *Homo sapiens* cDNA clone 44847 3'. |
| AA046674_at | zf12d12.r1 Soares fetal heart NbHH19W *Homo sapiens* cDNA clone 376727 5'. |
| RC_AA450118_at | zx42e09.s1 Soares total fetus Nb2HF8 9w *Homo sapiens* cDNA clone 789160 3'. |
| RC_AA486410_at | ab36b12.s1 Stratagene HeLa cell s3 937216 *Homo sapiens* cDNA clone 842879 3'. |
| RC_AA026417_at | ze92g08.s1 Soares fetal heart NbHH19W *Homo sapiens* cDNA clone 366494 3'. |
| RC_AA125808_at | zl29e12.s1 Soares pregnant uterus NbHPU *Homo sapiens* cDNA clone 503374 3'. |
| RC_AA243721_at | zr68f11.s1 Soares NhHMPu S1 *Homo sapiens* cDNA clone 668589 3'. |
| RC_AA452131_at | zx15d06.s1 Soares total fetus Nb2HF8 9w *Homo sapiens* cDNA clone 786539 3'. |
| RC_N29345_at | yw85c10.s1 *Homo sapiens* cDNA clone 259026 3'. |
| RC_Z39191_at | *H. sapiens* partial cDNA sequence; clone c-13c12. |
| RC_AA156187_at | zo47c04.s1 Stratagene endothelial cell 937223 *Homo sapiens* cDNA clone 590022 3' similar to contains Alu repetitive element;. |
| RC_AA157340_at | zo42h04.s1 Stratagene endothelial cell 937223 *Homo sapiens* cDNA clone 589591 3'. |
| RC_AA343514_at | EST49299 Gall bladder I *Homo sapiens* cDNA 3' end. |
| RC_AA482224_f_at | ab15c03.s1 Stratagene lung (#937210) *Homo sapiens* cDNA clone 840868 3'. |
| RC_AA053021_at | zl72f02.s1 Stratagene colon (#937204) *Homo sapiens* cDNA clone 510171 3'. |
| RC_AA279420_at | zs85d09.s1 NCI_CGAP_GCB1 *Homo sapiens* cDNA clone IMAGE: 704273 3' similar to TR: G974805 G974805 T08A11.2;. |
| RC_AA477252_at | zu29h10.s1 Soares ovary tumor NbHOT *Homo sapiens* cDNA clone 739459 3'. |
| RC_N31597_s_at | yy20b11.s1 *Homo sapiens* cDNA clone 271773 3'. |
| U31875_at | Human Hep27 protein mRNA, complete cds. |
| RC_F04611_at | *H. sapiens* partial cDNA sequence; clone c-zse11. |
| AA263032_s_at | PMY0335 KG1a Lambda Zap Express cDNA Library *Homo sapiens* cDNA 5'. |
| AA447052_at | zw86b06.r1 Soares total fetus Nb2HF8 9w *Homo sapiens* cDNA clone 783827 5' similar to TR: G595950 G595950 PROTEIN N-TERMINAL ASPARAGINE AMIDOHYDROLASE.; |
| RC_AA056247_at | zf62c02.s1 Soares retina N2b4HR *Homo sapiens* cDNA clone 381506 3' similar to contains Alu repetitive element;. |
| RC_AA156532_at | zo34b05.s1 Stratagene colon (#937204) *Homo sapiens* cDNA clone 588753 3'. |
| RC_AA456039_at | aa03d01.s1 Soares NhHMPu S1 *Homo sapiens* cDNA clone 812161 3'. |
| RC_AA461444_at | zx68b01.s1 Soares total fetus Nb2HF8 9w *Homo sapiens* cDNA clone 796585 3'. |
| RC_AA033974_at | zi05c10.s1 Soares fetal liver spleen 1NFLS S1 *Homo sapiens* cDNA clone 429906 3'. |
| RC_AA034365_at | zf02b10.s1 Soares fetal heart NbHH19W *Homo sapiens* cDNA clone 375739 3' similar to gb: J05096_rna1 SODIUM/POTASSIUM-TRANSPORTING ATPASE ALPHA-1 CHAIN (HUMAN); contains Alu repetitive element;. |
| RC_N22115_s_at | yw32a09.s1 *Homo sapiens* cDNA clone 253912 3'. |
| RC_W04698_at | zb94b05.s1 Soares parathyroid tumor NbHPA *Homo sapiens* cDNA clone 320433 3'. |
| AA126592_at | zl17g05.r1 Soares pregnant uterus NbHPU *Homo sapiens* cDNA clone 502232 5'. |

-continued

| | |
|---|---|
| AA428172_f_at | zw32b06.r1 Soares ovary tumor NbHOT *Homo sapiens* cDNA clone 770963 5'. |
| C01790_at | HUMGS0003746, Human Gene Signature, 3'-directed cDNA sequence. |
| RC_AA017146_at | ze41a07.s1 Soares retina N2b4HR *Homo sapiens* cDNA clone 361524 3' similar to contains element PTR7 repetitive element;. |
| RC_AA236037_at | zs05g08.s1 NCI_CGAP_GCB1 *Homo sapiens* cDNA clone IMAGE: 684350 3'. |
| RC_AA026270_at | ze97f07.s1 Soares fetal heart NbHH19W *Homo sapiens* cDNA clone 366949 3'. |
| RC_AA233837_at | zr47f06.s1 Soares NhHMPu S1 *Homo sapiens* cDNA clone 666563 3'. |
| RC_H60595_s_at | yr41h02.s1 *Homo sapiens* cDNA clone 207891 3'. |
| RC_N66388_at | yz39f01.s1 *Homo sapiens* cDNA clone 285433 3'. |
| RC_N91023_at | zb41a09.s1 Soares parathyroid tumor NbHPA *Homo sapiens* cDNA clone 306136 3'. |
| RC_W80354_at | zh49a02.s1 Soares fetal liver spleen 1NFLS S1 *Homo sapiens* cDNA clone 415370 3'. |
| RC_T51995_at | yb29e09.s1 *Homo sapiens* cDNA clone 72616 3'. |
| RC_AA463637_at | zx98h04.s1 Soares NhHMPu S1 *Homo sapiens* cDNA clone 811831 3'. |
| RC_AA161085_at | zo62h09.s1 Stratagene pancreas (#937208) *Homo sapiens* cDNA clone 591521 3' similar to SW: PPAP_RAT P20646 PROSTATIC ACID PHOSPHATASE PRECURSOR;. |
| RC_AA489101_at | aa56h11.s1 NCI_CGAP_GCB1 *Homo sapiens* cDNA clone IMAGE: 824997 3'. |
| RC_AA255464_at | zr83b02.s1 Soares NhHMPu S1 *Homo sapiens* cDNA clone 682251 3'. |
| RC_AA609614_at | af15f12.s1 Soares testis NHT *Homo sapiens* cDNA clone 1031759 3'. |
| L32832_s_at | *Homo sapiens* zinc finger homeodomain protein (ATBF1-A) mRNA, complete cds. |
| AA464051_s_at | zx86d04.r1 Soares ovary tumor NbHOT *Homo sapiens* cDNA clone 810631 5'. |
| RC_Z39652_at | *H. sapiens* partial cDNA sequence; clone c-1fg03. |
| AB002321_at | Human mRNA for KIAA0323 gene, partial cds. |
| RC_D59981_s_at | Human fetal brain cDNA 3'-end GEN-079C04. |
| RC_AA027954_at | zk05c12.s1 Soares pregnant uterus NbHPU *Homo sapiens* cDNA clone 469654 3'. |
| RC_AA115559_at | zl07b12.s1 Soares pregnant uterus NbHPU *Homo sapiens* cDNA clone 491615 3'. |
| L02547_at | *Homo sapiens* (clone pZ50-19) cleavage stimulation factor 50 kDa subunit, complete cds |
| RC_AA256996_at | zr81h11.s1 Soares NhHMPu S1 *Homo sapiens* cDNA clone 682149 3'. |
| RC_AA450373_at | zx05h06.s1 Soares total fetus Nb2HF8 9w *Homo sapiens* cDNA clone 785627 3'. |
| RC_N71875_at | yz34f07.s1 *Homo sapiens* cDNA clone 284965 3'. |
| AA431505_at | zw76e03.r1 Soares testis NHT *Homo sapiens* cDNA clone 782140 5'. |
| U77942_at | Human syntaxin 7 mRNA, complete cds. |
| RC_AA393876_s_at | zv64h10.s1 Soares total fetus Nb2HF8 9w *Homo sapiens* cDNA clone 758467 3'. |
| W16686_at | zb08f12.r1 Soares fetal lung NbHL19W *Homo sapiens* cDNA clone 301487 5'. |
| RC_AA287388_at | zs50f04.s1 NCI_CGAP_GCB1 *Homo sapiens* cDNA clone IMAGE: 700927 3'. |
| RC_F02397_s_at | *H. sapiens* partial cDNA sequence; clone c-0xh11. |
| AA247679_at | hfe0045.seq.F Human fetal heart, Lambda ZAP Express *Homo sapiens* cDNA 5'. |
| RC_AA282791_at | zs91c05.s1 NCI_CGAP_GCB1 *Homo sapiens* cDNA clone IMAGE: 704840 3'. |
| AA504744_at | aa63f03.r1 NCI_CGAP_GCB1 *Homo sapiens* cDNA clone IMAGE: 825629 5'. |
| RC_AA149987_at | zo03d03.s1 Stratagene colon (#937204) *Homo sapiens* cDNA clone 566597 3'. |
| RC_AA262485_at | zs17h07.s1 NCI_CGAP_GCB1 *Homo sapiens* cDNA clone IMAGE: 685501 3'. |
| AA436536_at | zv08g07.r1 Soares NhHMPu S1 *Homo sapiens* cDNA clone 753084 5'. |
| RC_AA037828_at | zf03g09.s1 Soares fetal heart NbHH19W *Homo sapiens* cDNA clone 375904 3'. |
| RC_AA255628_at | zs31g06.s1 NCI_CGAP_GCB1 *Homo sapiens* cDNA clone IMAGE: 686842 3'. |
| AA418098_at | zv94b04.r1 Soares NhHMPu S1 *Homo sapiens* cDNA clone 767407 5'. |
| RC_N21380_at | yx54c04.s1 *Homo sapiens* cDNA clone 265542 3'. |
| AA459542_s_at | zx89d08.r1 Soares ovary tumor NbHOT *Homo sapiens* cDNA clone 810927 5' similar to TR: G608025 G608025 ANKYRIN G.;. |

-continued

| | |
|---|---|
| RC_AA464180_at | zx83f04.s1 Soares ovary tumor NbHOT *Homo sapiens* cDNA clone 810367 3' similar to gb: M38188 OVARIAN GRANULOSA CELL 13.0 KD PROTEIN HGR74 (HUMAN);. |
| RC_AA143726_at | zo67g06.s1 Stratagene pancreas (#937208) *Homo sapiens* cDNA clone 591994 3' similar to TR: G530823 G530823 EPIDERMAL GROWTH FACTOR RECEPTOR KINASE SUBSTRATE.;. |
| RC_N38930_at | yy43e04.s1 *Homo sapiens* cDNA clone 274014 3'. |
| H27242_at | yl63h11.r1 *Homo sapiens* cDNA clone 162981 5' similar to SP: GCN5_YEAST Q03330 TRANSCRIPTIONAL ACTIVATOR;. |
| RC_AA002088_at | zh85g03.s1 Soares fetal liver spleen 1NFLS S1 *Homo sapiens* cDNA clone 428116 3'. |
| D31313_s_at | Human fetal-lung cDNA 5'-end sequence. |
| RC_R40702_at | yf73f10.s1 *Homo sapiens* cDNA clone 27969 3'. |
| RC_AA405543_at | zw39c01.s1 Soares total fetus Nb2HF8 9w *Homo sapiens* cDNA clone 772416 3'. |
| RC_AA284143_at | zs47c07.s1 NCI_CGAP_GCB1 *Homo sapiens* cDNA clone IMAGE: 700620 3'. |
| RC_AA158234_at | zo76b01.s1 Stratagene pancreas (#937208) *Homo sapiens* cDNA clone 592777 3'. |
| R66920_at | yi25f09.r1 *Homo sapiens* cDNA clone 140297 5' similar to contains Alu repetitive element;. |
| RC_AA034189_at | zi06h12.s1 Soares fetal liver spleen 1NFLS S1 *Homo sapiens* cDNA clone 430055 3'. |
| AA147510_s_at | zl50c12.r1 Soares pregnant uterus NbHPU *Homo sapiens* cDNA clone 505366 5'. |
| RC_N48715_at | yy75h02.s1 *Homo sapiens* cDNA clone 279411 3'. |
| AA489299_at | ab35g04.r1 Stratagene HeLa cell s3 937216 *Homo sapiens* cDNA clone 842838 5'. |
| RC_AA242799_at | zr65f06.s1 Soares NhHMPu S1 *Homo sapiens* cDNA clone 668291 3' similar to SW: SPO8_YEAST P41833 TRANSCRIPTIONAL REGULATOR SPO8. [1];. |
| AA091412_s_at | ll2053.seq.F Fetal heart, Lambda ZAP Express *Homo sapiens* cDNA 5'. |
| RC_H70554_at | yr91a03.s1 *Homo sapiens* cDNA clone 212620 3'. |
| RC_AA256208_at | zr80a08.s1 Soares NhHMPu S1 *Homo sapiens* cDNA clone 681974 3'. |
| RC_R64660_at | yi22a10.s1 *Homo sapiens* cDNA clone 139962 3'. |
| RC_AA135185_at | zo27a05.s1 Stratagene colon (#937204) *Homo sapiens* cDNA clone 588080 3'. |
| AA442428_at | zv70f08.r1 Soares total fetus Nb2HF8 9w *Homo sapiens* cDNA clone 759015 5' similar to SW: YB72_YEAST P38137 HYPOTHETICAL 60.5 KD PROTEIN IN PDB1-ABD1 INTERGENIC REGION.;. |
| RC_AA293719_at | zt55h03.s1 Soares ovary tumor NbHOT *Homo sapiens* cDNA clone 726293 3'. |
| RC_AA287131_at | zt20g02.s1 Soares ovary tumor NbHOT *Homo sapiens* cDNA clone 713714 3' similar to TR: E124071 E124071 NAD+– ISOCITRATE DEHYDROGENASE;. |
| AB002387_at | Human mRNA for KIAA0389 gene, complete cds. |
| RC_N50550_at | yy89f05.s1 *Homo sapiens* cDNA clone 280737 3'. | or a sequence as identified below

| | |
|---|---|
| RC_AA599501_at | ag23g12.s1 Jia bone marrow stroma *Homo sapiens* cDNA clone 1071238 3'. |
| RC_AA443923_at | zv51a02.s1 Soares testis NHT *Homo sapiens* cDNA clone 757130 3'. |
| R82598_s_at | yj19b12.r1 *Homo sapiens* cDNA clone 149183 5'. | or a sequence as identified below

| | |
|---|---|
| RC_AA402000_at | zu55b03.s1 Soares ovary tumor NbHOT *Homo sapiens* cDNA clone 741869 3' similar to TR: G452270 G452270 2-19 PROTEIN PRECURSOR.;. | or a sequence as identified below

| | |
|---|---|
| RC_T40767_at | ya11a06.s1 *Homo sapiens* cDNA clone 61138 3'. |
| RC_AA426454_s_at | zv61f08.s1 Soares testis NHT *Homo sapiens* cDNA clone 758151 3' similar to contains element TAR1 repetitive element;. |
| RC_AA057620_at | zf15h06.s1 Soares fetal heart NbHH19W *Homo sapiens* cDNA clone 377051 3'. |
| RC_AA398197_at | zt59a08.s1 Soares testis NHT *Homo sapiens* cDNA clone 726614 3'. |
| RC_N63332_at | yz33d11.s1 *Homo sapiens* cDNA clone 284853 3' similar to contains Alu repetitive element;. |
| RC_H58692_s_at | yr20g08.s1 *Homo sapiens* cDNA clone 205886 3' similar to SP: FTDH_RAT P28037 FORMYLTETRAHYDROFOLATE DEHYDROGENASE;. | or a sequence as identified below

| | |
|---|---|
| zo76b01.s1 Stratagene pancreas (#937208) *Homo sapiens* cDNA clone 592777 3'. | RC_AA158234_at |
| yo61a11.s1 *Homo sapiens* cDNA clone 182396 3'. | RC_H42123_at |
| *H. sapiens* partial cDNA sequence; clone c-13f02. | RC_Z39200_at |
| yx63h03.s1 Soares melanocyte 2NbHM *Homo sapiens* cDNA clone 266453 3'. | RC_N21687_at |
| *Homo sapiens* mRNA for uroplakin II. | Y13645_at |
| zb86b03.s1 Soares senescent fibroblasts NbHSF *Homo sapiens* cDNA clone 310445 3'. | RC_N98461_at |
| zd99d10.s1 Soares fetal heart NbHH19W *Homo sapiens* cDNA clone 357619 3'. | RC_W92449_at |
| *H. sapiens* partial cDNA sequence; clone c-13c12. | RC_Z39191_at |
| zl29e12.s1 Soares pregnant uterus NbHPU *Homo sapiens* cDNA clone 503374 3'. | RC_AA125808_at |
| ya11a06.s1 *Homo sapiens* cDNA clone 61138 3'. | RC_T40767_at |
| yb29c05.s1 *Homo sapiens* cDNA clone 72584 3'. | RC_T51972_at |
| zs58b06.s1 NCI_CGAP_GCB1 *Homo sapiens* cDNA clone IMAGE: 701651 3'. | RC_AA286862_at |
| yw91b09.s1 *Homo sapiens* cDNA clone 259577 3'. | RC_N29764_at |
| zw32b06.r1 Soares ovary tumor NbHOT *Homo sapiens* cDNA clone 770963 5'. | AA428172_f_at |
| yj35d05.s1 *Homo sapiens* cDNA clone 150729 3'. | RC_H02265_at |
| zb98a11.s1 Soares parathyroid tumor NbHPA *Homo sapiens* cDNA clone 320828 3'. | RC_W44745_at |
| yp99c05.s1 *Homo sapiens* cDNA clone 195560 3' similar to contains MER1 repetitive element;. | RC_R91819_at |
| zx84d05.r1 Soares ovary tumor NbHOT *Homo sapiens* cDNA clone 810441 5'. | AA464468_at |
| zp78e01.s1 Stratagene HeLa cell s3 937216 *Homo sapiens* cDNA clone 626328 3' similar to TR: G998813 G998813 TIF1.[1];. | RC_AA188647_at |
| zu57g11.s1 Soares ovary tumor NbHOT *Homo sapiens* cDNA clone 742148 3' similar to TR: G780241 G780241 AU-BINDING PROTEIN/ENOYL-COA HYDRATASE.;. | RC_AA405832_at |
| zc13b12.s1 Soares parathyroid tumor NbHPA *Homo sapiens* cDNA clone 322175 3' similar to contains LTR2.t3 LTR2 repetitive element;. | RC_W37778_f_at |
| *Homo sapiens* breast cancer-specific protein 1 (BCSG1) mRNA, complete cds. | AF010126_at |
| yx83a05.r1 *Homo sapiens* cDNA clone 268304 5'. | N36432_at |
| zr74c04.s1 Soares NhHMPu S1 *Homo sapiens* cDNA clone 669126 3' similar to gb: S69002 ECOTROPIC VIRUS INTEGRATION 1 SITE PROTEIN (HUMAN);. | RC_AA236533_s_at |
| zt55e05.s1 Soares ovary tumor NbHOT *Homo sapiens* cDNA clone 726272 3'. | RC_AA293163_at |
| zq60b06.s1 Stratagene neuroepithelium (#937231) *Homo sapiens* cDNA clone 645971 3'. | RC_AA196790_at |
| zr53g12.s1 Soares NhHMPu S1 *Homo sapiens* cDNA clone 667174 3'. | RC_AA253220_at |
| zn59e02.s1 Stratagene muscle 937209 *Homo sapiens* cDNA clone 562490 3'. | RC_AA100437_at |
| zt28d03.s1 Soares ovary tumor NbHOT *Homo sapiens* cDNA clone 714437 3'. | RC_AA293300_s_at |
| *H. sapiens* partial cDNA sequence; clone c-1fg03. | RC_Z39652_at |
| Human glutathione transferase M2 (GSTM2) mRNA, complete cds | M63509_s_at |
| *H. sapiens* partial cDNA sequence; clone c-1ke11. | RC_Z39842_at |
| yx78e10.s1 *Homo sapiens* cDNA clone 267882 3'. | RC_N23319_at |
| zs78d11.s1 NCI_CGAP_GCB1 *Homo sapiens* cDNA clone IMAGE: 703605 3'. | RC_AA278817_at |
| *Homo sapiens* mRNA in the region near the btk gene involved in a-gamma-globulinemia | L20773_at |
| yi44h05.s1 Soares placenta Nb2HP *Homo sapiens* cDNA clone 142137 3'. | RC_R69276_at |
| *H. sapiens* partial cDNA sequence; clone c-15d02. | RC_F02641_at |
| zw03a04.s1 Soares NhHMPu S1 *Homo sapiens* cDNA clone 768174 3' similar to contains Alu repetitive element;. | RC_AA424791_at |
| yf63b06.s1 *Homo sapiens* cDNA clone 26725 3'. | RC_R39869_at |
| ab15c03.s1 Stratagene lung (#937210) *Homo sapiens* cDNA clone 840868 3'. | RC_AA482224_f_at |
| ze76f02.s1 Soares fetal heart NbHH19W *Homo sapiens* cDNA clone 364923 3' similar to contains Alu repetitive element; contains element LTR4 repetitive element;. | RC_AA025277_at |
| ab15c03.r1 Stratagene lung (#937210) *Homo sapiens* cDNA clone 840868 5'. | AA482319_f_at |
| ze47b04.s1 Soares retina N2b4HR *Homo sapiens* cDNA clone 362095 3'. | RC_AA001045_at |

-continued

| | |
|---|---|
| zo10f03.s1 Stratagene neuroepithelium NT2RAMI 937234 *Homo sapiens* cDNA clone 567293 3' similar to SW: NI2M_BOVIN Q02369 NADH-UBIQUINONE OXIDORE-DUCTASE B22 SUBUNIT;. | RC_AA130645_s_at |
| zt37c02.s1 Soares ovary tumor NbHOT *Homo sapiens* cDNA clone 724514 3'. | RC_AA291659_at |
| zk72d02.r1 Soares pregnant uterus NbHPU *Homo sapiens* cDNA clone 488355 5'. | AA046768_at |
| yl81e01.r1 *Homo sapiens* cDNA clone 44466 5'. | H07011_at |
| zt54g04.s1 Soares ovary tumor NbHOT *Homo sapiens* cDNA clone 726198 3' similar to gb: J05158 CARBOXYPEPTIDASE N 83 KD CHAIN (HUMAN);. | RC_AA293533_i_at |
| zn63g10.s1 Stratagene HeLa cell s3 937216 *Homo sapiens* cDNA clone 562914 3' similar to SW: LCFA_ECOLI P29212 LONG-CHAIN-FATTY-ACID-COA LIGASE;. | RC_AA100649_at |
| ze41a07.s1 Soares retina N2b4HR *Homo sapiens* cDNA clone 361524 3' similar to contains element PTR7 repetitive element;. | RC_AA017146_at |
| zp40g07.s1 Stratagene muscle 937209 *Homo sapiens* cDNA clone 611964 3'. | RC_AA180054_at |
| PMY0335 KG1a Lambda Zap Express cDNA Library *Homo sapiens* cDNA 5'. | AA263032_s_at |
| zd46f07.r1 Soares fetal heart NbHH19W *Homo sapiens* cDNA clone 343717 5'. | W69310_at |
| zr05e02.s1 Stratagene NT2 neuronal precursor 937230 *Homo sapiens* cDNA clone 650618 3'. | RC_AA219653_at |
| aa91c07.s1 Stratagene fetal retina 937202 *Homo sapiens* cDNA clone 838668 3'. | RC_AA457235_at |
| aa16h10.s1 Soares NhHMPu S1 *Homo sapiens* cDNA clone 813475 3'. | RC_AA455967_at |
| yx51a09.r1 *Homo sapiens* cDNA clone 265240 5'. | N27670_at |
| za65e02.s1 *Homo sapiens* cDNA clone 297434 3'. | RC_N80152_at |
| yi22a10.s1 *Homo sapiens* cDNA clone 139962 3'. | RC_R64660_at |
| zo64g03.s1 Stratagene pancreas (#937208) *Homo sapiens* cDNA clone 591700 3'. | RC_AA147218_s_at |
| HUMGS0007818, Human Gene Signature, 3'-directed cDNA sequence. | C01139_at |
| PMY0691 KG1a Lambda Zap Express cDNA Library *Homo sapiens* cDNA 5'. | AA285284_at |
| zx44c03.s1 Soares total fetus Nb2HF8 9w *Homo sapiens* cDNA clone 789316 3'. | RC_AA451685_at |
| zx56e01.r1 Soares fetal liver spleen 1NFLS S1 *Homo sapiens* cDNA clone 446520 5' similar to contains element MER17 repetitive element;. | AA203222_at |
| zt52g01.s1 Soares ovary tumor NbHOT *Homo sapiens* cDNA clone 726000 3' similar to SW: ADG_MOUSE P22892 GAMMA-ADAPTIN;. | RC_AA394071_at |
| zv17e07.s1 Soares NhHMPu S1 *Homo sapiens* cDNA clone 753924 3'. | RC_AA479096_at |
| zo34b05.s1 Stratagene colon (#937204) *Homo sapiens* cDNA clone 588753 3'. | RC_AA156532_at |
| *H. sapiens* partial cDNA sequence; clone c-1wg05. | RC_Z40233_at |
| seq2490 *Homo sapiens* cDNA clone 3HFLSK20-87 3'. | RC_T03927_at |
| EST186294 Colon carcinoma (HCC) cell line II *Homo sapiens* cDNA 5' end. | AA314457_at |
| yy89f05.s1 *Homo sapiens* cDNA clone 280737 3'. | RC_N50550_at |
| zp88f04.s1 Stratagene HeLa cell s3 937216 *Homo sapiens* cDNA clone 627295 3'. | RC_AA191524_at |
| yw90b12.s1 *Homo sapiens* cDNA clone 259487 3'. | RC_N29740_at |
| yy75h02.s1 *Homo sapiens* cDNA clone 279411 3'. | RC_N48715_at |
| zx98h04.s1 Soares NhHMPu S1 *Homo sapiens* cDNA clone 811831 3'. | RC_AA463637_at |
| zw38a06.s1 Soares total fetus Nb2HF8 9w *Homo sapiens* cDNA clone 772306 3'. | RC_AA404487_at |
| ym26a10.s1 *Homo sapiens* cDNA clone 49155 3'. | RC_H16666_at |
| zv24d11.s1 Soares NhHMPu S1 *Homo sapiens* cDNA clone 754581 3'. | RC_AA406197_at |
| yl97b11.s1 *Homo sapiens* cDNA clone 46276 3'. | RC_H09594_at |
| zo62h09.s1 Stratagene pancreas (#937208) *Homo sapiens* cDNA clone 591521 3' similar to SW: PPAP_RAT P20646 PROSTATIC ACID PHOSPHATASE PRECURSOR;. | RC_AA161085_at |
| zx15d06.s1 Soares total fetus Nb2HF8 9w *Homo sapiens* cDNA clone 786539 3'. | RC_AA452131_at |
| zt54g04.s1 Soares ovary tumor NbHOT *Homo sapiens* cDNA clone 726198 3' similar to gb: J05158 CARBOXYPEPTIDASE N 83 KD CHAIN (HUMAN);. | RC_AA293533_f_at |
| zt59a08.s1 Soares testis NHT *Homo sapiens* cDNA clone 726614 3'. | RC_AA398197_at |

-continued

| | |
|---|---|
| zx86d04.r1 Soares ovary tumor NbHOT *Homo sapiens* cDNA clone 810631 5'. | AA464051_s_at |
| yb29e01.s1 *Homo sapiens* cDNA clone 72600 3'. | RC_T51990_at |
| zr54a11.s1 Soares NhHMPu S1 *Homo sapiens* cDNA clone 667196 3'. | RC_AA236356_at |
| zd92a04.r1 Soares fetal heart NbHH19W *Homo sapiens* cDNA clone 356910 5' similar to contains element LTR3 repetitive element;. | W92678_at |
| yz33d11.s1 *Homo sapiens* cDNA clone 284853 3' similar to contains Alu repetitive element;. | RC_N63332_at |
| Human aorta cDNA 5'-end GEN-259H09. | C16281_s_at |
| zu29h10.s1 Soares ovary tumor NbHOT *Homo sapiens* cDNA clone 739459 3'. | RC_AA477252_at |
| yw20e07.r1 *Homo sapiens* cDNA clone 252804 5'. | H88035_s_at |
| Human mRNA for KIAA0389 gene, complete cds. | AB002387_at |
| yg45h12.s1 *Homo sapiens* cDNA clone 35838 3'. | RC_R45698_at |
| zr75g11.s1 Soares NhHMPu S1 *Homo sapiens* cDNA clone 669284 3'. | RC_AA236542_at |
| EST89388 Small intestine I *Homo sapiens* cDNA 5' end similar to monoamine oxidase A. | AA376875_at |
| yg15g06.s1 *Homo sapiens* cDNA clone 32365 3'. | RC_R43365_at |
| yl83h08.s1 *Homo sapiens* cDNA clone 44847 3'. | RC_H06746_at |
| zr47f06.s1 Soares NhHMPu S1 *Homo sapiens* cDNA clone 666563 3'. | RC_AA233837_at |
| zf15h06.s1 Soares fetal heart NbHH19W *Homo sapiens* cDNA clone 377051 3'. | RC_AA057620_at |
| zx42e09.s1 Soares total fetus Nb2HF8 9w *Homo sapiens* cDNA clone 789160 3'. | RC_AA450118_at |
| ae37b10.s1 Gessler Wilms tumor *Homo sapiens* cDNA clone 897979 3'. | RC_AA598872_at |
| zl52g06.s1 Soares pregnant uterus NbHPU *Homo sapiens* cDNA clone 505594 3'. | RC_AA147646_s_at |
| zb94b05.s1 Soares parathyroid tumor NbHPA *Homo sapiens* cDNA clone 320433 3'. | RC_W04698_at |
| yv39c06.s1 *Homo sapiens* cDNA clone 245098 3'. | RC_N54365_at |
| zr80a08.s1 Soares NhHMPu S1 *Homo sapiens* cDNA clone 681974 3'. | RC_AA256208_at |
| zk62g01.r1 Soares pregnant uterus NbHPU *Homo sapiens* cDNA clone 487440 5'. | AA046593_at |
| zh85g03.s1 Soares fetal liver spleen 1NFLS S1 *Homo sapiens* cDNA clone 428116 3'. | RC_AA002088_at |
| zr81c12.s1 Soares NhHMPu S1 *Homo sapiens* cDNA clone 682102 3'. | RC_AA256273_at |
| aa46e04.r1 NCI_CGAP_GCB1 *Homo sapiens* cDNA clone IMAGE: 823998 5'. | AA491114_at |
| zt55h03.s1 Soares ovary tumor NbHOT *Homo sapiens* cDNA clone 726293 3'. | RC_AA293719_at |
| zl84c04.s1 Stratagene colon (#937204) *Homo sapiens* cDNA clone 511302 3'. | RC_AA086005_at |
| zw44a07.s1 Soares total fetus Nb2HF8 9w *Homo sapiens* cDNA clone 772884 3'. | RC_AA479885_at |
| zv70f08.r1 Soares total fetus Nb2HF8 9w *Homo sapiens* cDNA clone 759015 5' similar to SW: YB72_YEAST P38137 HYPOTHETICAL 60.5 KD PROTEIN IN PDB1-ABD1 INTERGENIC REGION.;. | AA442428_at |
| ab36c12.s1 Stratagene HeLa cell s3 937216 *Homo sapiens* cDNA clone 842879 3'. | RC_AA486410_at |
| yf89f02.r1 *Homo sapiens* cDNA clone 29665 5'. | R15268_at |
| zw86a10.s1 Soares total fetus Nb2HF8 9w *Homo sapiens* cDNA clone 783834 3' similar to TR: G438639 G438639 LAMIN B RECEPTOR. [1];. | RC_AA443658_at |
| ym39b01.s1 *Homo sapiens* cDNA clone 50559 3'. | RC_H16790_at |
| zx80b07.r1 Soares ovary tumor NbHOT *Homo sapiens* cDNA clone 810037 5'. | AA465000_s_at |
| yy43e04.s1 *Homo sapiens* cDNA clone 274014 3'. | RC_N38930_at |
| Human mRNA for KIAA0323 gene, partial cds. | AB002321_at |
| *H. sapiens* partial cDNA sequence; clone c-0qb09. | RC_Z38810_at |
| WUGSC: H_GS188P18.1a gene extracted from Human BAC clone GS188P18 | AC000115_cds1_at |
| zr83b02.s1 Soares NhHMPu S1 *Homo sapiens* cDNA clone 682251 3'. | RC_AA255464_at |
| zs31g06.s1 NCI_CGAP_GCB1 *Homo sapiens* cDNA clone IMAGE: 686842 3'. | RC_AA255628_at |
| yr91a03.s1 *Homo sapiens* cDNA clone 212620 3'. | RC_H70554_at |
| EST180743 Jurkat T-cells V *Homo sapiens* cDNA 5' end. | AA309880_at |
| yg21a08.s1 *Homo sapiens* cDNA clone 32940 3'. | RC_R43812_at |
| zv47a04.s1 Soares ovary tumor NbHOT *Homo sapiens* cDNA clone 756750 3'. | RC_AA425636_at |
| yz39f01.s1 *Homo sapiens* cDNA clone 285433 3'. | RC_N66388_at |

-continued

| | |
|---|---|
| zs85d09.s1 NCI_CGAP_GCB1 *Homo sapiens* cDNA clone IMAGE: 704273 3' similar to TR: G974805 G974805 T08A11.2;. | RC_AA279420_at |
| zi05c10.s1 Soares fetal liver spleen 1NFLS S1 *Homo sapiens* cDNA clone 429906 3'. | RC_AA033974_at |
| *Homo sapiens* sodium bicarbonate cotransporter (HNBC1) mRNA, complete cds. | AF007216_at |
| aa56h11.s1 NCI_CGAP_GCB1 *Homo sapiens* cDNA clone IMAGE: 824997 3'. | RC_AA489101_at |
| Human aorta cDNA 5'-end GEN-286G10. | D79601_f_at |
| yw70f05.s1 *Homo sapiens* cDNA clone 257601 3'. | RC_N30856_at |
| *Homo sapiens* clk2 mRNA, complete cds | L29218_s_at |
| zo67g06.s1 Stratagene pancreas (#937208) *Homo sapiens* cDNA clone 591994 3' similar to TR: G530823 G530823 EPIDERMAL GROWTH FACTOR RECEPTOR KINASE SUBSTRATE.;. | RC_AA143726_at |
| zl17g05.r1 Soares pregnant uterus NbHPU *Homo sapiens* cDNA clone 502232 5'. | AA126592_at |
| *H. sapiens* partial cDNA sequence; clone c-0xh11. | RC_F02397_s_at |
| zs27d03.s1 NCI_CGAP_GCB1 *Homo sapiens* cDNA clone IMAGE: 686405 3'. | RC_AA252765_at |
| zc36a04.s1 Soares senescent fibroblasts NbHSF *Homo sapiens* cDNA clone 324366 3'. | RC_W46846_at |
| zo27a05.s1 Stratagene colon (#937204) *Homo sapiens* cDNA clone 588080 3'. | RC_AA135185_at |
| yf73f10.s1 *Homo sapiens* cDNA clone 27969 3'. | RC_R40702_at |
| yv36d12.s1 *Homo sapiens* cDNA clone 244823 3'. | RC_N52565_at |
| zc06a02.s1 Soares parathyroid tumor NbHPA *Homo sapiens* cDNA clone 321482 3'. | RC_W32506_s_at |
| zr85c04.s1 Soares NhHMPu S1 *Homo sapiens* cDNA clone 682470 3'. | RC_AA255539_at |
| zx38a10.s1 Soares total fetus Nb2HF8 9w *Homo sapiens* cDNA clone 788730 3'. | RC_AA449951_at |
| cchn2404.seq.F Fetal heart, Lambda ZAP Express *Homo sapiens* cDNA 5'. | AA091278_at |
| zs05g08.s1 NCI_CGAP_GCB1 *Homo sapiens* cDNA clone IMAGE: 684350 3'. | RC_AA236037_at |
| Il2053.seq.F Fetal heart, Lambda ZAP Express *Homo sapiens* cDNA 5'. | AA091412_s_at |
| zf12b09.r1 Soares fetal heart NbHH19W *Homo sapiens* cDNA clone 376697 5'. | AA046865_at |
| EST27743 Cerebellum II *Homo sapiens* cDNA 5' end. | AA324825_at |
| zx79d09.s1 Soares ovary tumor NbHOT *Homo sapiens* cDNA clone 809969 3'. | RC_AA454840_s_at |
| zh49a02.s1 Soares fetal liver spleen 1NFLS S1 *Homo sapiens* cDNA clone 415370 3'. | RC_W80354_at |
| zt65c03.s1 Soares testis NHT *Homo sapiens* cDNA clone 727204 3'. | RC_AA402484_at |
| 15h10 Human retina cDNA randomly primed sublibrary *Homo sapiens* cDNA. | W26883_at |
| zs17h07.s1 NCI_CGAP_GCB1 *Homo sapiens* cDNA clone IMAGE: 685501 3'. | RC_AA262485_at |
| zw39c01.s1 Soares total fetus Nb2HF8 9w *Homo sapiens* cDNA clone 772416 3'. | RC_AA405543_at |
| yx54c04.s1 *Homo sapiens* cDNA clone 265542 3'. | RC_N21380_at |
| zn77a05.s1 Stratagene NT2 neuronal precursor 937230 *Homo sapiens* cDNA clone 564176 3'. | RC_AA121360_s_at |
| *Homo sapiens* zinc finger homeodomain protein (ATBF1-A) mRNA, complete cds. | L32832_s_at |
| Human fetal-lung cDNA 5'-end sequence. | D31313_s_at |
| ym45b05.r1 *Homo sapiens* cDNA clone 51043 5' similar to contains Alu repetitive element;. | H18718_at |
| zf03g09.s1 Soares fetal heart NbHH19W *Homo sapiens* cDNA clone 375904 3'. | RC_AA037828_at |
| yi04c10.s1 *Homo sapiens* cDNA clone 138258 3'. | RC_R67996_at |
| ze92g08.s1 Soares fetal heart NbHH19W *Homo sapiens* cDNA clone 366494 3'. | RC_AA026417_at |
| *H. sapiens* partial cDNA sequence; clone c-33a10. | RC_F11115_at |
| yf21e07.s1 *Homo sapiens* cDNA clone 127524 3'. | RC_R08871_at |
| zr12e05.s1 Stratagene hNT neuron (#937233) *Homo sapiens* cDNA clone 648608 3'. | RC_AA224324_at |
| zt50c01.s1 Soares ovary tumor NbHOT *Homo sapiens* cDNA clone 725760 3'. | RC_AA399226_at |
| yi25f09.r1 *Homo sapiens* cDNA clone 140297 5' similar to contains Alu repetitive element;. | R66920_at |
| zx81a05.s1 Soares ovary tumor NbHOT *Homo sapiens* cDNA clone 810128 3'. | RC_AA464240_s_at |
| zv08g07.r1 Soares NhHMPu S1 *Homo sapiens* cDNA clone 753084 5'. | AA436536_at |
| yz34f07.s1 *Homo sapiens* cDNA clone 284965 3'. | RC_N71875_at |

-continued

| | |
|---|---|
| zk10b03.s1 Soares pregnant uterus NbHPU *Homo sapiens* cDNA clone 470093 3' similar to PIR: H45193 H45193 zinc finger protein ZNF65;. | RC_AA029288_at |
| yl63h11.r1 *Homo sapiens* cDNA clone 162981 5' similar to SP: GCN5_YEAST Q03330 TRANSCRIPTIONAL ACTIVATOR;. | H27242_at |
| Human cytochrome P450 PCN3 gene, complete cds | J04813_s_at |
| aa32h08.s1 NCI_CGAP_GCB1 *Homo sapiens* cDNA clone IMAGE: 815007 3'. | RC_AA465093_at |
| zs91c05.s1 NCI_CGAP_GCB1 *Homo sapiens* cDNA clone IMAGE: 704840 3'. | RC_AA282791_at |
| zx83f04.s1 Soares ovary tumor NbHOT *Homo sapiens* cDNA clone 810367 3' similar to gb: M38188 OVARIAN GRANULOSA CELL 13.0 KD PROTEIN HGR74 (HUMAN);. | RC_AA464180_at |
| zo03d03.s1 Stratagene colon (#937204) *Homo sapiens* cDNA clone 566597 3'. | RC_AA149987_at |
| zr82h09.s1 Soares NhHMPu S1 *Homo sapiens* cDNA clone 682241 3'. | RC_AA256680_at |
| zl50c12.r1 Soares pregnant uterus NbHPU *Homo sapiens* cDNA clone 505366 5'. | AA147510_s_at |
| yi80c10.r1 *Homo sapiens* cDNA clone 145554 5'. | R78119_at |
| *H. sapiens* partial cDNA sequence; clone c-0ac03. | RC_Z38407_s_at |
| zs58f12.s1 NCI_CGAP_GCB1 *Homo sapiens* cDNA clone IMAGE: 701711 3'. | RC_AA287107_s_at |
| zs57e07.s1 NCI_CGAP_GCB1 *Homo sapiens* cDNA clone IMAGE: 701604 3'. | RC_AA287042_at |
| ab35g04.r1 Stratagene HeLa cell s3 937216 *Homo sapiens* cDNA clone 842838 5'. | AA489299_at |
| aa63f03.r1 NCI_CGAP_GCB1 *Homo sapiens* cDNA clone IMAGE: 825629 5'. | AA504744_at |
| zu47g07.s1 Soares ovary tumor NbHOT *Homo sapiens* cDNA clone 741180 3'. | RC_AA402622_at |
| zw55e10.s1 Soares total fetus Nb2HF8 9w *Homo sapiens* cDNA clone 773994 3'. | RC_AA436628_at |
| zt02a10.s1 NCI_CGAP_GCB1 *Homo sapiens* cDNA clone IMAGE: 711930 3'. | RC_AA282138_at |
| zk75a04.r1 Soares pregnant uterus NbHPU *Homo sapiens* cDNA clone 488622 5'. | AA045870_at |
| zv94b04.s1 Soares NhHMPu S1 *Homo sapiens* cDNA clone 767407 5'. | AA418098_at |
| zr65f06.s1 Soares NhHMPu S1 *Homo sapiens* cDNA clone 668291 3' similar to SW: SPO8_YEAST P41833 TRANSCRIPTIONAL REGULATOR SPO8.[1];. | RC_AA242799_at |
| af12f04.s1 Soares testis NHT *Homo sapiens* cDNA clone 1031455 3'. | RC_AA609210_at |
| zo13e11.s1 Stratagene colon (#937204) *Homo sapiens* cDNA clone 586796 3'. | RC_AA133469_at |
| yh25b11.r1 *Homo sapiens* cDNA clone 130749 5'. | R22139_at |
| EST176117 Colon carcinoma (Caco-2) cell line II *Homo sapiens* cDNA 5' end. | AA305116_at |
| zk05c12.s1 Soares pregnant uterus NbHPU *Homo sapiens* cDNA clone 469654 3'. | RC_AA027954_at |
| zk29e11.r1 Soares pregnant uterus NbHPU *Homo sapiens* cDNA clone 471980 5'. | AA036900_at |
| ze92d07.s1 Soares fetal heart NbHH19W *Homo sapiens* cDNA clone 366445 3'. | RC_AA026397_at |
| Human fetal brain cDNA 3'-end GEN-079C04. | RC_D59981_s_at |
| zs47c07.s1 NCI_CGAP_GCB1 *Homo sapiens* cDNA clone IMAGE: 700620 3'. | RC_AA284143_at |
| zb08f12.r1 Soares fetal lung NbHL19W *Homo sapiens* cDNA clone 301487 5'. | W16686_at |
| yw28c11.r1 *Homo sapiens* cDNA clone 253556 5'. | H89575_s_at |
| zs07g11.s1 NCI_CGAP_GCB1 *Homo sapiens* cDNA clone IMAGE: 684548 3'. | RC_AA251003_at |
| zs84h09.s1 NCI_CGAP_GCB1 *Homo sapiens* cDNA clone IMAGE: 704225 3'. | RC_AA279408_at |
| zt07g10.s1 NCI_CGAP_GCB1 *Homo sapiens* cDNA clone IMAGE: 712482 3' similar to TR: G808826 G808826 HYPOTHETICAL 25.7 KD PROTEIN.;. | RC_AA281760_at |
| Human mRNA for KIAA0383 gene, partial cds. | AB002381_at |
| zx89d08.r1 Soares ovary tumor NbHOT *Homo sapiens* cDNA clone 810927 5' similar to TR: G608025 G608025 ANKYRING.;. | AA459542_s_at |
| zl07b12.s1 Soares pregnant uterus NbHPU *Homo sapiens* cDNA clone 491615 3'. | RC_AA115559_at |
| ye36a05.r1 *Homo sapiens* cDNA clone 119792 5'. | T94506_at |
| Human fetal brain cDNA 5'-end GEN-404F02. | D55869_s_at |
| *Homo sapiens* (clone pZ50-19) cleavage stimulation factor 50 kDa subunit, complete cds | L02547_at |
| Human syntaxin 7 mRNA, complete cds. | U77942_at |

| | |
|---|---|
| zw76e03.r1 Soares testis NHT *Homo sapiens* cDNA clone 782140 5'. | AA431505_at |
| zr38c08.s1 Soares NhHMPu S1 *Homo sapiens* cDNA clone 665678 3'. | RC_AA194045_at |
| ze78f05.s1 Soares fetal heart NbHH19W *Homo sapiens* cDNA clone 365121 3'. | RC_AA025104_at |
| zr65e09.s1 Soares NhHMPu S1 *Homo sapiens* cDNA clone 668296 3'. | RC_AA242822_at |
| zs50f04.s1 NCI_CGAP_GCB1 *Homo sapiens* cDNA clone IMAGE: 700927 3'. | RC_AA287388_at |
| hfe0045.seq.F Human fetal heart, Lambda ZAP Express *Homo sapiens* cDNA 5'. | AA247679_at |
| ab41e08.s1 Stratagene HeLa cell s3 937216 *Homo sapiens* cDNA clone 843398 3'. | RC_AA489383_at |
| zu81a08.s1 Soares testis NHT *Homo sapiens* cDNA clone 744374 3'. | RC_AA621188_at |
| ab35a01.s1 Stratagene HeLa cell s3 937216 *Homo sapiens* cDNA clone 842760 3'. | RC_AA486182_at |
| zv64h01.s1 Soares total fetus Nb2HF8 9w *Homo sapiens* cDNA clone 758467 3'. | RC_AA393876_s_at |
| zi06h12.s1 Soares fetal liver spleen 1NFLS S1 *Homo sapiens* cDNA clone 430055 3'. | RC_AA034189_at |
| ze79b09.s1 Soares fetal heart NbHH19W *Homo sapiens* cDNA clone 365177 3'. | RC_AA024866_at |
| zx05h06.s1 Soares total fetus Nb2HF8 9w *Homo sapiens* cDNA clone 785627 3'. | RC_AA450373_at |
| yz78d07.r1 *Homo sapiens* cDNA clone 289165 5'. | N78483_at |
| zs94d07.s1 NCI_CGAP_GCB1 *Homo sapiens* cDNA clone IMAGE: 705133 3'. | RC_AA281245_at |
| zc45b12.r1 Soares senescent fibroblasts NbHSF *Homo sapiens* cDNA clone 325247 5' similar to SW: WDNM_RAT P14730 WDNM1 PROTEIN. [2] PIR: S07807;. | W52431_at |
| zw84f01.s1 Soares total fetus Nb2HF8 9w *Homo sapiens* cDNA clone 783673 3'. | RC_AA446597_at |
| zr81h11.s1 Soares NhHMPu S1 *Homo sapiens* cDNA clone 682149 3'. | RC_AA256996_at |
| *H. sapiens* gene for cytokeratin 20 | X73501_at |
| zt20g02.s1 Soares ovary tumor NbHOT *Homo sapiens* cDNA clone 713714 3' similar to TR: E124071 E124071 NAD+-ISOCITRATE DEHYDROGENASE;. | RC_AA287131_at |

In a preferred embodiment genes from the first gene group is preferably selected individually from genes comprising a sequence as identified below by EST

| | |
|---|---|
| RC_N23319_at | yx78e10.s1 *Homo sapiens* cDNA clone 267882 3'. |
| RC_R43812_at | yg21a08.s1 *Homo sapiens* cDNA clone 32940 3'. |
| RC_W37778_f_at | zc13b12.s1 Soares parathyroid tumor NbHPA *Homo sapiens* cDNA clone 322175 3' similar to contains LTR2.t3 LTR2 repetitive element;. |
| RC_AA001045_at | ze47b04.s1 Soares retina N2b4HR *Homo sapiens* cDNA clone 362095 3'. |
| RC_AA086005_at | zl84c04.s1 Stratagene colon (#937204) *Homo sapiens* cDNA clone 511302 3'. |
| RC_AA191524_at | zp88f04.s1 Stratagene HeLa cell s3 937216 *Homo sapiens* cDNA clone 627295 3'. |
| RC_AA219653_at | zr05e02.s1 Stratagene NT2 neuronal precursor 937230 *Homo sapiens* cDNA clone 650618 3'. |
| RC_AA252765_at | zs27d03.s1 NCI_CGAP_GCB1 *Homo sapiens* cDNA clone IMAGE: 686405 3'. |
| RC_AA293300_s_at | zt28d03.s1 Soares ovary tumor NbHOT *Homo sapiens* cDNA clone 714437 3'. |
| RC_AA405832_at | zu57g11.s1 Soares ovary tumor NbHOT *Homo sapiens* cDNA clone 742148 3' similar to TR: G780241 G780241 AU-BINDING PROTEIN/ENOYL-COA HYDRATASE.;. |
| X73501_at | *H. sapiens* gene for cytokeratin 20 |
| AA046768_at | zk72d02.r1 Soares pregnant uterus NbHPU *Homo sapiens* cDNA clone 488355 5'. |
| AA314457_at | EST186294 Colon carcinoma (HCC) cell line II *Homo sapiens* cDNA 5' end. |
| AA324825_at | EST27743 Cerebellum II *Homo sapiens* cDNA 5' end. |

In another embodiment a gene from the first gene group is selected individually from genes comprising a sequence as identified below by EST

| | |
|---|---|
| Human mRNA for KIAA0372 gene, complete cds. | AB002370_at |
| *Homo sapiens* purinergic receptor P2Y5 mRNA, complete cds. | AF000546_at |
| yo70c03.r1 *Homo sapiens* cDNA clone 183268 5'. | H43922_at |
| yp17b05.r1 *Homo sapiens* cDNA clone 187665 5' similar to contains Alu repetitive element;. | H44269_at |
| yw23e08.r1 *Homo sapiens* cDNA clone 253094 5'. | H88706_s_at |
| *Homo sapiens* epoxide hydrolase (EPHX) gene, complete cds | L25880_s_at |
| yw36d01.r1 *Homo sapiens* cDNA clone 254305 5'. | N81162_at |
| *H. sapiens* partial cDNA sequence; clone c-3ec07. | RC_F10381_s_at |
| EST00018 HE6W *Homo sapiens* cDNA clone HE6WCR108 3'. | RC_H54558_at |
| yr20g08.s1 *Homo sapiens* cDNA clone 205886 3' similar to SP: FTDH_RAT P28037 FORMYLTETRAHYDROFOLATE DEHYDROGENASE;. | RC_H58692_s_at |
| yx28d06.s1 *Homo sapiens* cDNA clone 263051 3'. | RC_N20047_at |
| yv28e04.s1 *Homo sapiens* cDNA clone 244062 3'. | RC_N38810_at |
| yg51h01.s1 *Homo sapiens* cDNA clone 36305 3'. | RC_R46497_at |
| yj76a08.s1 *Homo sapiens* cDNA clone 154646 3'. | RC_R55001_at |
| EST10130 *Homo sapiens* cDNA 3' end similar to None. | RC_T29986_s_at |
| EST12901 *Homo sapiens* cDNA 3' end similar to None. | RC_T30214_at |
| ya01c07.s2 *Homo sapiens* cDNA clone 60204 3'. | RC_T40438_at |
| zc37f06.s1 Soares senescent fibroblasts NbHSF *Homo sapiens* cDNA clone 324515 3'. | RC_W51910_at |
| zd71f09.s1 Soares fetal heart NbHH19W *Homo sapiens* cDNA clone 346121 3'. | RC_W73949_at |
| zh55a02.s1 Soares fetal liver spleen 1NFLS S1 *Homo sapiens* cDNA clone 415946 3'. | RC_W86375_s_at |
| *H. sapiens* partial cDNA sequence; clone c-05e04. | RC_Z38289_at |
| *H. sapiens* partial cDNA sequence; clone c-0qb04. | RC_Z38807_s_at |
| *H. sapiens* partial cDNA sequence; clone c-1ed10. | RC_Z39599_at |
| ze74h03.s1 Soares fetal heart NbHH19W *Homo sapiens* cDNA clone 364757 3' similar to contains OFR.t1 OFR repetitive element;. | RC_AA025351_at |
| zl01f04.s1 Soares pregnant uterus NbHPU *Homo sapiens* cDNA clone 491071 3'. | RC_AA136474_at |
| zk99b02.s1 Soares pregnant uterus NbHPU *Homo sapiens* cDNA clone 490923 3'. | RC_AA136611_at |
| zr48f07.s1 Soares NhHMPu S1 *Homo sapiens* cDNA clone 666661 3'. | RC_AA233375_at |
| zt36c05.s1 Soares ovary tumor NbHOT *Homo sapiens* cDNA clone 724424 3'. | RC_AA235621_s_at |
| zr72g02.s1 Soares NhHMPu S1 *Homo sapiens* cDNA clone 668978 3'. | RC_AA253331_at |
| zv64a10.s1 Soares total fetus Nb2HF8 9w *Homo sapiens* cDNA clone 758394 3'. | RC_AA393793_at |
| zv04a05.s1 Soares NhHMPu S1 *Homo sapiens* cDNA clone 752624 3'. | RC_AA419547_at |
| zu27d11.s1 Soares ovary tumor NbHOT *Homo sapiens* cDNA clone 739221 3'. | RC_AA421100_at |
| zw87f06.s1 Soares total fetus Nb2HF8 9w *Homo sapiens* cDNA clone 783971 3'. | RC_AA443277_at |
| zw84c05.s1 Soares total fetus Nb2HF8 9w *Homo sapiens* cDNA clone 783656 3'. | RC_AA446570_at |
| zw93c01.s1 Soares total fetus Nb2HF8 9w *Homo sapiens* cDNA clone 784512 3'. | RC_AA447123_at |
| zx06g09.s1 Soares total fetus Nb2HF8 9w *Homo sapiens* cDNA clone 785728 3'. | RC_AA449343_at |
| aa03a08.s1 Soares NhHMPu S1 *Homo sapiens* cDNA clone 812150 3'. | RC_AA456016_at |
| zv21f04.s1 Soares NhHMPu S1 *Homo sapiens* cDNA clone 754303 3'. | RC_AA479299_at |
| zv17d09.s1 Soares NhHMPu S1 *Homo sapiens* cDNA clone 753905 3' similar to contains element TAR1 TAR1 repetitive element;. | RC_AA479350_at |
| Human leukemogenic homolog protein (MEIS1) mRNA, complete cds | U85707_at |
| Human multispanning membrane protein mRNA, complete cds. /gb = U94831 /ntype = RNA | U94831_at |
| 38c8 Human retina cDNA randomly primed sublibrary *Homo sapiens* cDNA. | W27827_at |
| zd85a12.r1 Soares fetal heart NbHH19W *Homo sapiens* cDNA clone 347422 5'. | W81301_at |

| | |
|---|---|
| *H. sapiens* mRNA for putative progesterone binding protein | Y12711_at |
| zm15c08.r1 Stratagene pancreas (#937208) *Homo sapiens* cDNA clone 525710 5'. | AA074407_at |
| yy1646.seq.F Fetal heart, Lambda ZAP Express *Homo sapiens* cDNA 5'. | AA091017_at |
| l7134.seq.F Fetal heart, Lambda ZAP Express *Homo sapiens* cDNA 5'. | AA104023_at |
| zo95d05.r1 Stratagene ovarian cancer (#937219) *Homo sapiens* cDNA clone 594633 5'. | AA171913_at |
| zr32h05.r1 Soares NhHMPu S1 *Homo sapiens* cDNA clone 665145 5'. | AA195678_at |
| zr55e05.r1 Soares NhHMPu S1 *Homo sapiens* cDNA clone 667328 5'. | AA227678_at |
| csg0306.seq.F Human fetal heart, Lambda ZAP Express *Homo sapiens* cDNA 5'. | AA247204_at |
| zv18b05.r1 Soares NhHMPu S1 *Homo sapiens* cDNA clone 753969 5'. | AA479995_at |

In one preferred embodiment a gene from the first gene group is selected individually from genes comprising a sequence as identified below by EST

| | |
|---|---|
| AF000546_at | *Homo sapiens* purinergic receptor P2Y5 mRNA, complete cds. |
| L25880_s_at | *Homo sapiens* epoxide hydrolase (EPHX) gene, complete cds |
| RC_N20047_at | yx28d06.s1 *Homo sapiens* cDNA clone 263051 3'. |
| RC_W51910_at | zc37f06.s1 Soares senescent fibroblasts NbHSF *Homo sapiens* cDNA clone 324515 3'. |
| RC_W86375_s_at | zh55a02.s1 Soares fetal liver spleen 1NFLS S1 *Homo sapiens* cDNA clone 415946 3'. |
| RC_Z38289_at | *H. sapiens* partial cDNA sequence; clone c-05e04. |
| RC_Z38807_s_at | *H. sapiens* partial cDNA sequence; clone c-0qb04. |
| RC_AA393793_at | zv64a10.s1 Soares total fetus Nb2HF8 9w *Homo sapiens* cDNA clone 758394 3'. |
| RC_AA446570_at | zw84c05.s1 Soares total fetus Nb2HF8 9w *Homo sapiens* cDNA clone 783656 3'. |
| RC_AA456016_at | aa03a08.s1 Soares NhHMPu S1 *Homo sapiens* cDNA clone 812150 3'. |
| RC_AA479350_at | zv17d09.s1 Soares NhHMPu S1 *Homo sapiens* cDNA clone 753905 3' similar to contains element TAR1 TAR1 repetitive element;. |

In yet another embodiment a gene from the first gene group is selected individually from genes comprising a sequence as identified below by EST

| | |
|---|---|
| yl26e06.s1 *Homo sapiens* cDNA clone 159394 3'. | RC_H14633_at |
| yz74d02.s1 *Homo sapiens* cDNA clone 288771 3'. | RC_N62506_at |
| za74g10.s1 *Homo sapiens* cDNA clone 298338 3'. | RC_N70481_at |
| za57b06.s1 *Homo sapiens* cDNA clone 296627 3'. | RC_N73988_at |
| ya88g06.s1 *Homo sapiens* cDNA clone 68794 3'. | RC_T53404_at |
| *H. sapiens* partial cDNA sequence; clone c-01a09. | RC_Z38149_at |
| *H. sapiens* partial cDNA sequence; clone c-0rb11. | RC_Z38849_at |
| zc03h03.s1 Soares parathyroid tumor NbHPA *Homo sapiens* cDNA clone 321269 3'. | RC_AA037409_at |
| zn18b04.s1 Stratagene neuroepithelium NT2RAMI 937234 *Homo sapiens* cDNA clone 547759 3'. | RC_AA084318_at |
| zk94d04.s1 Soares pregnant uterus NbHPU *Homo sapiens* cDNA clone 490471 3'. | RC_AA126419_at |
| zm24d04.s1 Stratagene pancreas (#937208) *Homo sapiens* cDNA clone 526567 3'. | RC_AA128407_at |
| zp02e08.s1 Stratagene ovarian cancer (#937219) *Homo sapiens* cDNA clone 595238 3'. | RC_AA173430_at |
| zt58d03.s1 Soares testis NHT *Homo sapiens* cDNA clone 726533 3'. | RC_AA398104_at |
| zt50e07.s1 Soares ovary tumor NbHOT *Homo sapiens* cDNA clone 725796 3'. | RC_AA399414_at |
| zw72f05.s1 Soares testis NHT *Homo sapiens* cDNA clone 781761 3'. | RC_AA431479_at |
| zv08e05.s1 Soares NhHMPu S1 *Homo sapiens* cDNA clone 753056 3'. | RC_AA436471_at |
| zx05e10.s1 Soares total fetus Nb2HF8 9w *Homo sapiens* cDNA clone 785610 3' similar to contains Alu repetitive element;. | RC_AA449455_at |
| zx88d07.s1 Soares ovary tumor NbHOT *Homo sapiens* cDNA clone 810829 3'. | RC_AA458899_at |
| zx98g09.s1 Soares NhHMPu S1 *Homo sapiens* cDNA clone 811840 3'. | RC_AA463630_s_at |
| aa54d11.s1 NCI_CGAP_GCB1 *Homo sapiens* cDNA clone IMAGE: 824757 3'. | RC_AA489009_at |

| | |
|---|---|
| zc11f08.r1 Soares parathyroid tumor NbHPA *Homo sapiens* cDNA clone 322023 5'. | W37319_at |

In a preferred embodiment a gene from the first gene group is selected individually from genes comprising a sequence as identified below by EST

| | |
|---|---|
| N75611_s_at | yw37b04.r1 *Homo sapiens* cDNA clone 254383 5'. |
| RC_H20769_at | yn64a06.s1 *Homo sapiens* cDNA clone 173170 3'. |
| RC_R54822_at | yg87f06.s1 *Homo sapiens* cDNA clone 40364 3'. |
| RC_AA058357_s_at | zl67e01.s1 Stratagene colon (#937204) *Homo sapiens* cDNA clone 509688 3' similar to TR: G189087 G189087 NONSPECIFIC CROSSREACTING ANTIGEN.;. |
| RC_AA086487_at | zn53a05.s1 Stratagene muscle 937209 *Homo sapiens* cDNA clone 561872 3' similar to contains Alu repetitive element;. |
| RC_AA456289_at | aa13e06.s1 Soares NhHMPu S1 *Homo sapiens* cDNA clone 813154 3'. |
| RC_AA609539_at | af14g11.s1 Soares testis NHT *Homo sapiens* cDNA clone 1031684 3'. |

In another embodiment a gene from the first gene group is selected individually from genes comprising a sequence as identified below by EST

| | |
|---|---|
| N24990_s_at | yx16e10.r1 *Homo sapiens* cDNA clone 261930 5'. |
| R11267_at | yf41e08.r1 *Homo sapiens* cDNA clone 129446 5' similar to SP: A46661 A46661 LEUKOTRIENE B4 OMEGA-HYDROXYLASE, P-450LTB OMEGA = CYTOCHROME P-450 SUPERFAMILY MEMBER-;. |
| RC_H52937_at | yq76e12.s1 *Homo sapiens* cDNA clone 201742 3' similar to gb: J02982 GLYCOPHORIN B PRECURSOR (HUMAN);. |
| RC_H69547_at | yr89e02.s1 *Homo sapiens* cDNA clone 212474 3'. |
| RC_H70047_at | yu73c12.s1 *Homo sapiens* cDNA clone 239446 3'. |
| RC_N24879_at | yx99c11.s1 *Homo sapiens* cDNA clone 269876 3'. |
| RC_N66312_at | yz38a06.s1 *Homo sapiens* cDNA clone 285298 3'. |
| RC_R22189_at | yh26a02.s1 *Homo sapiens* cDNA clone 130826 3'. |
| RC_R45582_at | yg44f05.s1 *Homo sapiens* cDNA clone 35270 3'. |
| RC_R53457_at | yg83e10.s1 *Homo sapiens* cDNA clone 39835 3'. |
| RC_R70903_at | yi49g10.s1 *Homo sapiens* cDNA clone 142626 3'. |
| RC_AA054321_s_at | zl68c01.s1 Stratagene colon (#937204) *Homo sapiens* cDNA clone 509760 3'. |
| RC_AA099820_at | zk87c05.s1 Soares pregnant uterus NbHPU *Homo sapiens* cDNA clone 489800 3'. |
| RC_AA127238_at | zl17g05.s1 Soares pregnant uterus NbHPU *Homo sapiens* cDNA clone 502232 3'. |
| RC_AA147224_at | zo64h02.s1 Stratagene pancreas (#937208) *Homo sapiens* cDNA clone 591699 3'. |
| RC_AA192765_at | zq12e02.s1 Stratagene muscle 937209 *Homo sapiens* cDNA clone 629498 3'. |
| RC_AA195718_at | zr33d07.s1 Soares NhHMPu S1 *Homo sapiens* cDNA clone 665197 3'. |
| RC_AA232114_s_at | zr28b08.s1 Stratagene NT2 neuronal precursor 937230 *Homo sapiens* cDNA clone 664695 3' similar to gb: L05779 SOLUBLE EPOXIDE HYDROLASE (HUMAN);. |
| RC_AA281770_at | zt07h12.s1 NCI_CGAP_GCB1 *Homo sapiens* cDNA clone IMAGE: 712487 3'. |
| RC_AA430209_at | zw59e03.s1 Soares total fetus Nb2HF8 9w *Homo sapiens* cDNA clone 774364 3' similar to TR: G1199667 G1199667 PROTEIN KINASE C-BINDING PROTEIN ENIGMA;. |
| RC_AA452410_at | zx31f03.s1 Soares total fetus Nb2HF8 9w *Homo sapiens* cDNA clone 788093 3'. |
| RC_AA485115_at | aa39g12.s1 NCI_CGAP_GCB1 *Homo sapiens* cDNA clone IMAGE: 815686 3'. |
| AA099391_s_at | zk85e12.r1 Soares pregnant uterus NbHPU *Homo sapiens* cDNA clone 489646 5'. |
| AA131127_at | zo16a05.r1 Stratagene colon (#937204) *Homo sapiens* cDNA clone 587024 5' similar to SW: CATX_BOVIN P05689 CATHEPSIN;. |

-continued

| | |
|---|---|
| AA173505_at | zp02c06.r1 Stratagene ovarian cancer (#937219) *Homo sapiens* cDNA clone 595210 5' similar to SW: QRI2_YEAST P43124 HYPOTHETICAL 46.1 KD PROTEIN IN PHO2-POL3 INTERGENIC REGION. [1];. |
| AA291786_s_at | zt39b07.r1 Soares ovary tumor NbHOT *Homo sapiens* cDNA clone 724693 5'. |
| AA402971_s_at | zu53f10.r1 Soares ovary tumor NbHOT *Homo sapiens* cDNA clone 741739 5'. |

In yet another embodiment a gene from the first gene group is selected individually from genes comprising a sequence as identified below by EST

| | |
|---|---|
| D84239_at | Human mRNA for IgG Fc binding protein, complete cds |
| RC_N54841_at | yv73b09.s1 Soares fetal liver spleen 1NFLS *Homo sapiens* cDNA clone 248345 3'. |
| RC_T53389_s_at | ya88f04.s1 *Homo sapiens* cDNA clone 68767 3'. |
| RC_T98227_at | ye30d12.s1 *Homo sapiens* cDNA clone 119255 3'. |
| RC_AA215379_at | zr97c07.s1 NCI_CGAP_GCB1 *Homo sapiens* cDNA clone IMAGE: 683628 3'. |
| RC_AA256485_at | zr81e12.s1 Soares NhHMPu S1 *Homo sapiens* cDNA clone 682126 3'. |
| RC_AA290679_at | zt19f03.s1 Soares ovary tumor NbHOT *Homo sapiens* cDNA clone 713597 3' similar to TR: E92665 E92665 AP56;. |
| RC_AA425309_at | zw46c01.s1 Soares total fetus Nb2HF8 9w *Homo sapiens* cDNA clone 773088 3'. |
| RC_AA429655_at | zw71d04.s1 Soares testis NHT *Homo sapiens* cDNA clone 781639 3'. |
| RC_AA456981_at | aa90h11.s1 Stratagene fetal retina 937202 *Homo sapiens* cDNA clone 838629 3' similar to contains Alu repetitive element;. |
| RC_AA461174_at | zx70c04.s1 Soares total fetus Nb2HF8 9w *Homo sapiens* cDNA clone 796806 3'. |
| W61377_at | zd27g09.r1 Soares fetal heart NbHH19W *Homo sapiens* cDNA clone 341920 5'. |

Second Gene Group

Genes that are up-regulated (or gained de novo) during the malignant progression of bladder cancer from normal tissue through Ta, T1, T2, T3 and T4 is also within the scope of the invention. These genes are potential oncogenes and may be those genes that create or enhance the malignant growth of the cells. The expression level of these genes may serve as predictive markers for the disease course and treatment response, as a high level may signal an aggressive disease course, and they may serve as targets for therapy, as blocking these genes by e.g. anti-sense therapy, or by biochemical means could inhibit, or slow the tumor growth. Such upregulated (or gained de novo) genes, oncogenes, may be classified according to the present invention as genes belonging to second genes group.

With respect to bladder tumors genes belonging to the second gene group at least one, such as at least two, for example at least three, such as at least four, such as at least five, such as more than six genes are being expressed and are preferably selected individually from genes comprising a sequence as identified below by EST

| | |
|---|---|
| RC_AA116036_at | zm79a11.s1 Stratagene neuroepithelium (#937231) *Homo sapiens* cDNA clone 531836 3'. |
| RC_AA101562_at | zn76c11.s1 Stratagene NT2 neuronal precursor 937230 *Homo sapiens* cDNA clone 564116 3' similar to contains Alu repetitive element;. |
| RC_H20269_at | yn53b04.s1 *Homo sapiens* cDNA clone 172111 3'. |
| RC_Z40715_at | *H. sapiens* partial cDNA sequence; clone c-2ea12. | or a sequence as described below

| | |
|---|---|
| AA402119_at | zu55d04.r1 Soares ovary tumor NbHOT *Homo sapiens* cDNA clone 741895 5' similar to TR: G397579 G397579 LL5 MRNA. ;. |
| RC_AA102581_at | zn42d02.s1 Stratagene endothelial cell 937223 *Homo sapiens* cDNA clone 550083 3'. |
| RC_H14089_at | ym62c07.s1 *Homo sapiens* cDNA clone 163500 3'. |
| RC_R46079_f_at | yg49c02.s1 *Homo sapiens* cDNA clone 36133 3'. |
| RC_R67918_at | yi25g01.s1 *Homo sapiens* cDNA clone 140304 3'. |
| RC_W15360_at | zc17d10.s1 Soares parathyroid tumor NbHPA *Homo sapiens* cDNA clone 322579 3' similar to PIR: S39983 S39983 eps8 protein - mouse;. |

-continued

| | |
|---|---|
| AA082171_at | zn42g07.r1 Stratagene endothelial cell 937223 *Homo sapiens* cDNA clone 550140 5'. |
| AA425593_at | zw48f02.r1 Soares total fetus Nb2HF8 9w *Homo sapiens* cDNA clone 773307 5'. |
| F15201_at | *H. sapiens* partial cDNA sequence. |
| H15219_at | ym30f02.r1 *Homo sapiens* cDNA clone 49693 5'. |
| R60368_at | yh04b02.r1 *Homo sapiens* cDNA clone 42052 5'. |
| R86859_at | ym86a02.r1 *Homo sapiens* cDNA clone 165770 5'. |
| RC_AA045342_at | zk59g01.s1 Soares pregnant uterus NbHPU *Homo sapiens* cDNA clone 487152 3'. |
| RC_AA171985_at | zo98g05.s1 Stratagene ovarian cancer (#937219) *Homo sapiens* cDNA clone 594968 3'. |
| T63174_s_at | yc04e08.r1 *Homo sapiens* cDNA clone 79718 5' similar to contains Alu repetitive element;. |
| U90268_at | Human Krit1 mRNA, complete cds. |
| X14787_at | Human mRNA for thrombospondin |
| RC_AA196991_s_at | zq10a10.s1 Stratagene muscle 937209 *Homo sapiens* cDNA clone 629274 3' similar to TR: G1049074 G1049074 VASOPRESSIN-ACTIVATED CALCIUM-MOBILIZING PROTEIN. ;. |
| RC_F02470_at | *H. sapiens* partial cDNA sequence; clone c-10c01. |
| RC_F08899_at | *H. sapiens* partial cDNA sequence; clone c-2uc10. |
| RC_H15259_at | ym30c10.s1 *Homo sapiens* cDNA clone 49795 3'. |
| RC_H52133_at | yo44d04.s1 *Homo sapiens* cDNA clone 180775 3'. |
| RC_R17059_at | yf45a10.s2 *Homo sapiens* cDNA clone 129786 3'. |
| RC_R45292_at | yg46b01.s1 *Homo sapiens* cDNA clone 35626 3'. | or a sequence as described below

| | |
|---|---|
| C01360_at | HUMGS0008341, Human Gene Signature, 3'-directed cDNA sequence. |
| D80002_at | Human mRNA for KIAA0180 gene, partial cds |
| RC_AA149586_at | zl39e03.s1 Soares pregnant uterus NbHPU *Homo sapiens* cDNA clone 504316 3'. |
| RC_H68772_at | yr83f01.s1 *Homo sapiens* cDNA clone 211897 3'. |
| RC_N30806_at | yw65f02.s1 *Homo sapiens* cDNA clone 257115 3'. |
| RC_N63143_at | yz37c12.s1 *Homo sapiens* cDNA clone 285238 3'. |
| RC_R33146_at | yh81f02.s1 *Homo sapiens* cDNA clone 136155 3' similar to contains Alu repetitive element;. |
| RC_R46206_at | yj53d08.s1 *Homo sapiens* cDNA clone 152463 3'. |
| RC_R49731_s_at | yg71e10.s1 *Homo sapiens* cDNA clone 38554 3'. |
| AA043223_at | zk55g12.r1 Soares pregnant uterus NbHPU *Homo sapiens* cDNA clone 486790 5'. |
| AB002346_at | Human mRNA for KIAA0348 gene, complete cds. |
| D81608_at | Human fetal brain cDNA 5'-end GEN-177B09. |
| M83670_s_at | Human carbonic anhydrase IV mRNA, complete cds |
| N28843_at | yx59d10.r1 *Homo sapiens* cDNA clone 266035 5'. |
| RC_AA149044_at | zl45d09.s1 Soares pregnant uterus NbHPU *Homo sapiens* cDNA clone 504881 3'. |
| RC_AA258130_at | zs35f03.s1 NCI_CGAP_GCB1 *Homo sapiens* cDNA clone IMAGE: 687197 3'. |
| RC_AA281743_r_at | zt06h05.s1 NCI_CGAP_GCB1 *Homo sapiens* cDNA clone IMAGE: 712377 3'. |
| RC_AA406338_at | zv10f06.s1 Soares NhHMPu S1 *Homo sapiens* cDNA clone 753251 3'. |
| RC_AA424524_at | zv90g02.s1 Soares NhHMPu S1 *Homo sapiens* cDNA clone 767090 3'. |
| RC_AA435840_at | zt80b08.s1 Soares testis NHT *Homo sapiens* cDNA clone 728631 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA135406_at | zo28e08.s1 Stratagene colon (#937204) *Homo sapiens* cDNA clone 588230 3'. |
| RC_AA148923_at | zl27g11.s1 Soares pregnant uterus NbHPU *Homo sapiens* cDNA clone 503204 3'. |
| RC_H98653_at | yx12h06.s1 *Homo sapiens* cDNA clone 261563 3'. |
| RC_N30077_at | yw81g11.s1 *Homo sapiens* cDNA clone 258692 3'. |
| RC_R40166_at | yf70a09.s1 *Homo sapiens* cDNA clone 27448 3'. |
| RC_T90374_at | yd43e03.s1 *Homo sapiens* cDNA clone 111004 3' similar to SP: POL2_MOUSE P11369 RETROVIRUS-RELATED POL POLYPROTEIN;. |
| RC_Z38182_at | *H. sapiens* partial cDNA sequence; clone c-02a08. | or a sequence as described below

| | |
|---|---|
| RC_AA054726_at | Zk68e06.s1 Soares pregnant uterus NbHPU *Homo sapiens* cDNA clone 488002 3'. |
| RC_AA206042_at | Zq77f02.s1 Stratagene hNT neuron (#937233) *Homo sapiens* cDNA clone 647643 3' similar to contains element MSR1 repetitive element;. |
| RC_R98735_at | Yr31g12.s1 *Homo sapiens* cDNA clone 206950 3'. |
| AA115572_s_at | Zl05d11.r1 Soares pregnant uterus NbHPU *Homo sapiens* cDNA clone 491445 5' similar to TR: G895845 G895845 PUTATIVE P64 CLCP PROTEIN. ;. |
| AA430979_at | PMY0789 KG1a Lambda Zap Express cDNA Library *Homo sapiens* cDNA 5'. |
| AA489287_at | ab36e04.r1 Stratagene HeLa cell s3 937216 *Homo sapiens* cDNA clone 842910 5'. |
| D82226_s_at | similar to TAT-binding protein-2. |
| H49499_s_at | yq20g10.r1 Soares fetal liver spleen 1NFLS *Homo sapiens* cDNA clone 274386 5'. |
| M11844_at | Human prealbumin gene, complete cds. |
| RC_AA026388_at | ze92c03.s1 Soares fetal heart NbHH19W *Homo sapiens* cDNA clone 366436 3'. |
| RC_AA044601_at | zk55d05.s1 Soares pregnant uterus NbHPU *Homo sapiens* cDNA clone 486729 3'. |
| RC_AA182030_at | zp57a03.s1 Stratagene endothelial cell 937223 *Homo sapiens* cDNA clone 624268 3'. |
| RC_AA233451_at | zr30b02.s1 Stratagene NT2 neuronal precursor 937230 *Homo sapiens* cDNA clone 664875 3'. |
| RC_AA236493_at | zr75c10.s1 Soares NhHMPu S1 *Homo sapiens* cDNA clone 669234 3'. |
| RC_AA401098_f_at | zu50g01.s1 Soares ovary tumor NbHOT *Homo sapiens* cDNA clone 741456 3' similar to contains Alu repetitive element; contains element THR repetitive element;. |
| RC_AA441818_at | zw62f01.s1 Soares total fetus Nb2HF8 9w *Homo sapiens* cDNA clone 774649 3'. |
| RC_AA478109_at | zt89d04.s1 Soares testis NHT *Homo sapiens* cDNA clone 729511 3'. |
| RC_AA481430_at | zv06g11.s1 Soares NhHMPu S1 *Homo sapiens* cDNA clone 752900 3'. |
| RC_AA488878_at | aa55f02.s1 NCI_CGAP_GCB1 *Homo sapiens* cDNA clone IMAGE: 824859 3'. |
| RC_AA599032_at | ae41h03.s1 Gessler Wilms tumor *Homo sapiens* cDNA clone 898421 3'. |
| S73288_at | small proline-rich protein SPRK [human, odontogenic keratocysts, mRNA Partial, 317 nt]. |
| U87459_at | Human autoimmunogenic cancer/testis antigen NY-ESO-1 mRNA, complete cds |
| U88047_at | Human DNA binding protein homolog (DRX) mRNA, partial cds |
| RC_AA063574_at | ze25f03.s1 Soares fetal heart NbHH19W *Homo sapiens* cDNA clone 360029 3' similar to gb: X52104 P68 PROTEIN (HUMAN);. |
| RC_AA132524_at | zo20c04.s1 Stratagene colon (#937204) *Homo sapiens* cDNA clone 587430 3' similar to contains Alu repetitive element;. |
| RC_F09317_at | *H. sapiens* partial cDNA sequence; clone c-2zh11. |
| RC_H12863_at | yj14b12.s1 *Homo sapiens* cDNA clone 148703 3'. |
| RC_N33927_s_at | yv25e09.s1 *Homo sapiens* cDNA clone 243784 3'. |
| RC_R08189_at | yf18f03.s1 *Homo sapiens* cDNA clone 127229 3'. |
| RC_R39191_s_at | yc89c12.s1 *Homo sapiens* cDNA clone 23345 3'. |
| RC_T82323_at | AS322 *Homo sapiens* cDNA clone AS322 3'. |
| RC_T90746_at | yd41f10.s1 *Homo sapiens* cDNA clone 110827 3'. |
| RC_Z39338_at | *H. sapiens* partial cDNA sequence; clone c-17f11. | or a sequence as described below

| | |
|---|---|
| AA011479_at | zi01b10.r1 Soares fetal liver spleen 1NFLS S1 *Homo sapiens* cDNA clone 429499 5'. |
| AA314779_at | EST186601 Colon carcinoma (HCC) cell line II *Homo sapiens* cDNA 5' end, |
| RC_AA084640_at | zn20d05.s1 Stratagene neuroepithelium NT2RAMI 937234 *Homo sapiens* cDNA clone 547977 3'. |
| RC_AA121534_at | zk89d11.s1 Soares pregnant uterus NbHPU *Homo sapiens* cDNA clone 490005 3' similar to gb: X79535 TUBULIN BETA-2 CHAIN (HUMAN);. |
| RC_AA131047_s_at | zo16f05.s1 Stratagene colon (#937204) *Homo sapiens* cDNA clone 587073 3'. |

| | |
|---|---|
| RC_AA461549_at | zx62b09.s1 Soares total fetus Nb2HF8 9w *Homo sapiens* cDNA clone 796025 3'. |
| RC_AA491465_at | ab04a05.s1 Stratagene fetal retina 937202 *Homo sapiens* cDNA clone 839792 3'. |
| RC_AA496936_at | ae32d03.s1 Gessler Wilms tumor *Homo sapiens* cDNA clone 897509 3'. |
| RC_AA598689_at | ae49a08.s1 Stratagene lung carcinoma 937218 *Homo sapiens* cDNA clone 950198 3'. |
| W26392_at | 30g3 Human retina cDNA randomly primed sublibrary *Homo sapiens* cDNA, |
| RC_AA004887_at | zh90g01.s1 Soares fetal liver spleen 1NFLS S1 *Homo sapiens* cDNA clone 428592 3'. |
| RC_AA135153_at | zo24g02.s1 Stratagene colon (#937204) *Homo sapiens* cDNA clone 587858 3'. |
| RC_AA197311_s_at | zq50e09.s1 Stratagene neuroepithelium (#937231) *Homo sapiens* cDNA clone 645064 3' similar to gb: M24283 INTERCELLULAR ADHESION MOLECULE-1 PRECURSOR (HUMAN);. |
| RC_H80622_at | yu77b06.s1 *Homo sapiens* cDNA clone 239795 3'. |
| RC_N64436_at | za33a09.s1 *Homo sapiens* cDNA clone 294328 3'. |
| RC_N67583_at | yz42c02.s1 *Homo sapiens* cDNA clone 285698 3'. |
| RC_R38678_at | yc89d05.s1 *Homo sapiens* cDNA clone 23443 3'. |
| RC_R56066_s_at | yg91d08.s1 *Homo sapiens* cDNA clone 40992 3'. |
| RC_R59292_at | yh16a10.s1 *Homo sapiens* cDNA clone 37689 3'. |
| RC_T24099_at | seq2287 *Homo sapiens* cDNA clone Cot250Ft-b4HB3MA-8 3'. |
| AA150364_at | zl07b03.r1 Soares pregnant uterus NbHPU *Homo sapiens* cDNA clone 491597 5'. |
| AA174185_at | PTH207 HTCDL1 *Homo sapiens* cDNA 5'/3'. |
| AA452353_i_at | zx15d05.r1 Soares total fetus Nb2HF8 9w *Homo sapiens* cDNA clone 786537 5'. |
| AB002316_at | Human mRNA for KIAA0318 gene, partial cds, |
| H86858_at | ys72d05.r1 *Homo sapiens* cDNA clone 220329 5'. |
| M93119_s_at | Human zinc-finger DNA-binding motifs (IA-1) mRNA, complete cds |
| R72037_at | yj86c09.r1 *Homo sapiens* cDNA clone 155632 5'. |
| RC_AA004274_at | zh97f02.s1 Soares fetal liver spleen 1NFLS S1 *Homo sapiens* cDNA clone 429243 3' similar to contains element MER22 repetitive element;. |
| RC_AA004415_at | zh89b04.s1 Soares fetal liver spleen 1NFLS S1 *Homo sapiens* cDNA clone 428431 3'. |
| RC_AA007160_at | 13cDNA30A-3, seq Soares infant brain 1NIB *Homo sapiens* cDNA clone HY18-3 3'. |
| RC_AA053660_at | zl74e07.s1 Stratagene colon (#937204) *Homo sapiens* cDNA clone 510372 3' similar to contains Alu repetitive element;. |
| RC_AA252603_at | zs14a11.s1 NCI_CGAP_GCB1 *Homo sapiens* cDNA clone IMAGE: 685148 3'. |
| RC_AA411944_at | zu03h01.s1 Soares testis NHT *Homo sapiens* cDNA clone 730801 3'. |
| RC_AA412700_at | zu12g03.s1 Soares testis NHT *Homo sapiens* cDNA clone 731668 3'. |
| RC_AA430032_at | zw65f05.s1 Soares testis NHT *Homo sapiens* cDNA clone 781089 3'. |
| RC_AA430368_at | zw20f06.s1 Soares ovary tumor NbHOT *Homo sapiens* cDNA clone 769859 3'. |
| RC_AA434113_at | zw24b11.s1 Soares ovary tumor NbHOT *Homo sapiens* cDNA clone 770205 3' similar to contains element TAR1 repetitive element;. |
| RC_AA441791_at | zw62c02.s1 Soares total fetus Nb2HF8 9w *Homo sapiens* cDNA clone 774626 3'. |
| RC_AA449419_at | zx05b03.s1 Soares total fetus Nb2HF8 9w *Homo sapiens* cDNA clone 785549 3'. |
| RC_AA449914_at | zx37g02.s1 Soares total fetus Nb2HF8 9w *Homo sapiens* cDNA clone 788690 3'. |
| RC_D59847_at | Human fetal brain cDNA 3'-end GEN-070G07, |
| T95813_f_at | ye45f10.r1 *Homo sapiens* cDNA clone 120715 5' similar to gb: V00493_rna1 HEMOGLOBIN ALPHA CHAIN (HUMAN);. |
| W80846_at | zd83f05.r1 Soares fetal heart NbHH19W *Homo sapiens* cDNA clone 347265 5' similar to SW: SYB2_XENLA P47193 SYNAPTOBREVIN 2;. |
| RC_AA031360_s_at | zk16f07.s1 Soares pregnant uterus NbHPU *Homo sapiens* cDNA clone 470725 3'. |
| RC_AA063624_at | ze87h05.s1 Soares fetal heart NbHH19W *Homo sapiens* cDNA clone 366009 3' similar to TR: G300372 G300372 CELL GROWTH REGULATING NUCLEOLAR PROTEIN,;; |
| RC_AA076238_at | zm19e04.s1 Stratagene pancreas (#937208) *Homo sapiens* cDNA clone 526110 3' similar to contains Alu repetitive element;. |
| RC_AA076350_at | zm91a02.s1 Stratagene ovarian cancer (#937219) *Homo sapiens* cDNA clone 545258 3'. |
| RC_AA101983_at | zk87c02.s1 Soares pregnant uterus NbHPU *Homo sapiens* cDNA clone 489794 3'. |

| | |
|---|---|
| RC_AA151245_at | zl40f12.s1 Soares pregnant uterus NbHPU *Homo sapiens* cDNA clone 504431 3'. |
| RC_AA164252_f_at | zq46f06.s1 Stratagene hNT neuron (#937233) *Homo sapiens* cDNA clone 632771 3'. |
| RC_AA167006_at | zo86b08.s1 Stratagene ovarian cancer (#937219) *Homo sapiens* cDNA clone 593751 3'. |
| RC_AA206225_at | zq56g08.s1 Stratagene neuroepithelium (#937231) *Homo sapiens* cDNA clone 645662 3'. |
| RC_D62834_at | Human aorta cDNA 3'-end GEN-330D04, |
| RC_D80981_at | Human fetal brain cDNA 3'-end GEN-121E12, |
| RC_H16772_at | ym34g02.s1 *Homo sapiens* cDNA clone 50227 3'. |
| RC_N62522_at | yz74f08.s1 *Homo sapiens* cDNA clone 288807 3'. |
| RC_N68222_at | yz56e12.s1 *Homo sapiens* cDNA clone 287086 3'. |
| RC_T10316_s_at | seq1014 *Homo sapiens* cDNA clone b4HB3MA-COT8-HAP-Ft266 3'. |
| RC_W37382_at | zc12c07.s1 Soares parathyroid tumor NbHPA *Homo sapiens* cDNA clone 322092 3'. |
| RC_W60582_at | zd25e10.s1 Soares fetal heart NbHH19W *Homo sapiens* cDNA clone 341706 3' similar to gb: M38188 OVARIAN GRANULOSA CELL 13.0 KD PROTEIN HGR74 (HUMAN);. |
| RC_W84768_at | zh53d03.s1 Soares fetal liver spleen 1NFLS S1 *Homo sapiens* cDNA clone 415781 3' similar to contains L1, b1 L1 repetitive element;. | or a sequence as described below

| | |
|---|---|
| RC_AA176164_i_at | zp23h11.s1 Stratagene neuroepithelium (#937231) *Homo sapiens* cDNA clone 610341 3'. |
| W52431_at | zc45b12.r1 Soares senescent fibroblasts NbHSF *Homo sapiens* cDNA clone 325247 5' similar to SW: WDNM_RAT P14730 WDNM1 PROTEIN, [2] PIR: S07807;. |
| RC_AA019641_at | ze62g03.s1 Soares retina N2b4HR *Homo sapiens* cDNA clone 363604 3' similar to contains element L1 repetitive element;. |
| RC_H13696_at | yj09e04.s1 *Homo sapiens* cDNA clone 148254 3'. |
| RC_N22404_at | yw37h03.s1 *Homo sapiens* cDNA clone 254453 3'. |
| RC_R07501_at | ye97f06.s1 *Homo sapiens* cDNA clone 125699 3'. |
| C14412_s_at | Human fetal brain cDNA 5'-end GEN-055A09, |
| RC_AA236455_s_at | zr75g02.s1 Soares NhHMPu S1 *Homo sapiens* cDNA clone 669266 3'. |
| RC_AA417030_at | zu04e07.s1 Soares testis NHT *Homo sapiens* cDNA clone 730884 3'. |
| RC_F10945_at | *H. sapiens* partial cDNA sequence; clone c-3mb07, |
| RC_N29319_at | yw84a11.s1 *Homo sapiens* cDNA clone 258908 3'. |
| RC_N68038_f_at | yz53a12.s1 *Homo sapiens* cDNA clone 286750 3'. | or a sequence as described below

| | |
|---|---|
| RC_AA417030_at | zu04e07.s1 Soares testis NHT *Homo sapiens* cDNA clone 730884 3'. |
| RC_AA608545_at | ae53d05.s1 Stratagene lung carcinoma 937218 *Homo sapiens* cDNA clone 950601 3'. |
| RC_H09261_at | y198c12.s1 *Homo sapiens* cDNA clone 46410 3' similar to contains Alu repetitive element; contains MSR1 repetitive element;. |
| RC_N68871_at | za23h07.s1 *Homo sapiens* cDNA clone 293437 3' similar to contains Alu repetitive element;. |
| AA129196_at | zn29d08.r1 Stratagene neuroepithelium NT2RAMI 937234 *Homo sapiens* cDNA clone 548847 5' similar to SW: NU1M_MOUSE P03888 NADH-UBIQUINONE OXIDOREDUCTASE CHAIN 1;. |
| RC_AA620553_s_at | ae58g12.s1 Stratagene lung carcinoma 937218 *Homo sapiens* cDNA clone 951142 3'. |
| RC_F10779_at | *H. sapiens* partial cDNA sequence; clone c-3jg08. |
| RC_F10945_at | *H. sapiens* partial cDNA sequence; clone c-3mb07. |
| RC_H65650_at | yr72d10.s1 *Homo sapiens* cDNA clone 210835 3'. |
| RC_N68038_f_at | yz53a12.s1 *Homo sapiens* cDNA clone 286750 3'. | or a sequence as described below

| | |
|---|---|
| RC_AA417030_at | zu04e07.s1 Soares testis NHT *Homo sapiens* cDNA clone 730884 3'. |
| RC_AA608545_at | ae53d05.s1 Stratagene lung carcinoma 937218 *Homo sapiens* cDNA clone 950601 3'. |
| RC_F10945_at | *H. sapiens* partial cDNA sequence; clone c-3mb07. |
| RC_N68038_f_at | yz53a12.s1 *Homo sapiens* cDNA clone 286750 3'. |

In one embodiment the genes belonging to the second gene group are preferably selected individually from genes comprising sequences as identified below by EST

| | |
|---|---|
| AB000221_at | *Homo sapiens* mRNA for CC chemokine, complete cds. |
| RC_D60296_at | Human fetal brain cDNA 3'-end GEN-097D06. |
| RC_D60813_at | Human fetal brain cDNA 3'-end GEN-132E11. |
| RC_R49708_s_at | Yg71a11.s1 *Homo sapiens* cDNA clone 38542 3'. |
| RC_Z38182_at | *H. sapiens* partial cDNA sequence; clone c-02a08. |
| RC_AA456821_at | Aa38e07.s1 NCI_CGAP_GCB1 *Homo sapiens* cDNA clone IMAGE: 815556 3'. |
| RC_AA608545_at | ae53d05.s1 Stratagene lung carcinoma 937218 *Homo sapiens* cDNA clone 950601 3'. |
| RC_AA620553_s_at | ae58g12.s1 Stratagene lung carcinoma 937218 *Homo sapiens* cDNA clone 951142 3'. |
| AA095119_at | cp3087.seq.F Fetal heart, Lambda ZAP Express *Homo sapiens* cDNA 5'. |

In another embodiment genes from the second gene group are selected individually from genes comprising sequences as identified below by EST

| | |
|---|---|
| M63180_at | Human threonyl-tRNA synthetase mRNA, complete cds |
| N89563_s_at | HFBEST-40 Human fetal brain QBoqin2 *Homo sapiens* cDNA. |
| RC_D80198_at | Human fetal brain cDNA 3'-end GEN-045C11. |
| RC_F01986_f_at | *H. sapiens* partial cDNA sequence; clone c-0kf11. |
| RC_H18997_at | yn51g07.s1 *Homo sapiens* cDNA clone 171996 3'. |
| RC_AA101562_at | zn76c11.s1 Stratagene NT2 neuronal precursor 937230 *Homo sapiens* cDNA clone 564116 3' similar to contains Alu repetitive element;. |

In yet another embodiment genes from the second gene group are selected individually from genes comprising sequences as identified below by EST.

| | |
|---|---|
| RC_H20269_at | yn53b04.s1 *Homo sapiens* cDNA clone 172111 3'. |
| RC_Z40715_at | *H. sapiens* partial cDNA sequence; clone c-2ea12. |
| RC_AA116036_at | zm79a11.s1 Stratagene neuroepithelium (#937231) *Homo sapiens* cDNA clone 531836 3'. |
| RC_AA133250_at | zn92a08.s1 Stratagene lung carcinoma 937218 *Homo sapiens* cDNA clone 565622 3'. |

In a further embodiment genes from the second gene group are selected individually from genes comprising sequences as identified below by EST.

| | |
|---|---|
| RC_R00083_at | ye73c08.s1 *Homo sapiens* cDNA clone 123374 3'. |
| RC_R71391_at | yj80e01.s1 *Homo sapiens* cDNA clone 155064 3'. |
| RC_T23991_at | seq2147 *Homo sapiens* cDNA clone NHB3MK-9 3'. |
| RC_T79196_at | yd70f06.s1 *Homo sapiens* cDNA clone 113603 3' similar to contains Alu repetitive element;. |
| RC_AA130596_at | zo26a09.s1 Stratagene colon (#937204) *Homo sapiens* cDNA clone 587992 3'. |
| RC_AA459310_r_at | zx89d06.s1 Soares ovary tumor NbHOT *Homo sapiens* cDNA clone 810923 3'. |
| RC_AA490965_at | aa48f12.s1 NCI_CGAP_GCB1 *Homo sapiens* cDNA clone IMAGE: 824207 3'. |
| U88047_at | Human DNA binding protein homolog (DRX) mRNA, partial cds |
| X56807_at | Human DSC2 mRNA for desmocollins type 2a and 2b |
| AA011479_at | zi01b10.r1 Soares fetal liver spleen 1NFLS S1 *Homo sapiens* cDNA clone 429499 5'. |
| AA296821_at | EST112387 Aorta endothelial cells *Homo sapiens* cDNA 5' end. |

In a preferred embodiment genes from the second gene group are selected individually from genes comprising sequences as identified below by EST.

| | |
|---|---|
| RC_AA054726_at | zk68e06.s1 Soares pregnant uterus NbHPU *Homo sapiens* cDNA clone 488002 3'. |
| RC_AA206042_at | zq77f02.s1 Stratagene hNT neuron (#937233) *Homo sapiens* cDNA clone 647643 3' similar to contains element MSR1 repetitive element;. |
| RC_R98735_at | yr31g12.s1 *Homo sapiens* cDNA clone 206950 3'. |
| AA115572_s_at | zl05d11.r1 Soares pregnant uterus NbHPU *Homo sapiens* cDNA clone 491445 5' similar to TR: G895845 G895845 PUTATIVE P64 CLCP PROTEIN, ;. |
| AA430979_at | PMY0789 KG1a Lambda Zap Express cDNA Library *Homo sapiens* cDNA 5'. |
| AA489287_at | ab36e04.r1 Stratagene HeLa cell s3 937216 *Homo sapiens* cDNA clone 842910 5'. |
| D82226_s_at | similar to TAT-binding protein-2. |
| H49499_s_at | yq20g10.r1 Soares fetal liver spleen 1NFLS *Homo sapiens* cDNA clone 274386 5'. |
| M11844_at | Human prealbumin gene, complete cds. |
| RC_AA026388_at | ze92c03.s1 Soares fetal heart NbHH19W *Homo sapiens* cDNA clone 366436 3'. |
| RC_AA044601_at | zk55d05.s1 Soares pregnant uterus NbHPU *Homo sapiens* cDNA clone 486729 3'. |
| RC_AA182030_at | zp57a03.s1 Stratagene endothelial cell 937223 *Homo sapiens* cDNA clone 624268 3'. |
| RC_AA233451_at | zr30b02.s1 Stratagene NT2 neuronal precursor 937230 *Homo sapiens* cDNA clone 664875 3'. |
| RC_AA236493_at | zr75c10.s1 Soares NhHMPu S1 *Homo sapiens* cDNA clone 669234 3'. |
| RC_AA401098_f_at | zu50g01.s1 Soares ovary tumor NbHOT *Homo sapiens* cDNA clone 741456 3' similar to contains Alu repetitive element; contains element THR repetitive element;. |
| RC_AA441818_at | zw62f01.s1 Soares total fetus Nb2HF8 9w *Homo sapiens* cDNA clone 774649 3'. |
| RC_AA478109_at | zt89d04.s1 Soares testis NHT *Homo sapiens* cDNA clone 729511 3'. |
| RC_AA481430_at | zv06g11.s1 Soares NhHMPu S1 *Homo sapiens* cDNA clone 752900 3'. |
| RC_AA488878_at | aa55f02.s1 NCI_CGAP_GCB1 *Homo sapiens* cDNA clone IMAGE: 824859 3'. |
| RC_AA599032_at | ae41h03.s1 Gessler Wilms tumor *Homo sapiens* cDNA clone 898421 3'. |
| S73288_at | small proline-rich protein SPRK [human, odontogenic keratocysts. mRNA Partial, 317 nt]. |
| U87459_at | Human autoimmunogenic cancer/testis antigen NY-ESO-1 mRNA, complete cds |
| U88047_at | Human DNA binding protein homolog (DRX) mRNA, partial cds |
| RC_AA063574_at | ze25f03.s1 Soares fetal heart NbHH19W *Homo sapiens* cDNA clone 360029 3' similar to gb: X52104 P68 PROTEIN (HUMAN);. |
| RC_AA132524_at | zo20c04.s1 Stratagene colon (#937204) *Homo sapiens* cDNA clone 587430 3' similar to contains Alu repetitive element;. |
| RC_F09317_at | *H. sapiens* partial cDNA sequence; clone c-2zh11. |
| RC_H12863_at | yj14b12.s1 *Homo sapiens* cDNA clone 148703 3'. |
| RC_N33927_s_at | yv25e09.s1 *Homo sapiens* cDNA clone 243784 3'. |
| RC_R08189_at | yf18f03.s1 *Homo sapiens* cDNA clone 127229 3'. |
| RC_R39191_s_at | yc89c12.s1 *Homo sapiens* cDNA clone 23345 3'. |
| RC_T82323_at | AS322 *Homo sapiens* cDNA clone AS322 3'. |
| RC_T90746_at | yd41f10.s1 *Homo sapiens* cDNA clone 110827 3'. |
| RC_Z39338_at | *H. sapiens* partial cDNA sequence; clone c-17f11. |
| AA011479_at | zi01b10.r1 Soares fetal liver spleen 1NFLS S1 *Homo sapiens* cDNA clone 429499 5'. |
| AA314779_at | EST186601 Colon carcinoma (HCC) cell line II *Homo sapiens* cDNA 5' end. |
| RC_AA084640_at | zn20d05.s1 Stratagene neuroepithelium NT2RAMI 937234 *Homo sapiens* cDNA clone 547977 3'. |
| RC_AA121534_at | zk89d11.s1 Soares pregnant uterus NbHPU *Homo sapiens* cDNA clone 490005 3' similar to gb: X79535 TUBULIN BETA-2 CHAIN (HUMAN);. |
| RC_AA131047_s_at | zo16f05.s1 Stratagene colon (#937204) *Homo sapiens* cDNA clone 587073 3'. |
| RC_AA461549_at | zx62b09.s1 Soares total fetus Nb2HF8 9w *Homo sapiens* cDNA clone 796025 3'. |
| RC_AA491465_at | ab04a05.s1 Stratagene fetal retina 937202 *Homo sapiens* cDNA clone 839792 3'. |
| RC_AA496936_at | ae32d03.s1 Gessler Wilms tumor *Homo sapiens* cDNA clone 897509 3'. |

-continued

| | |
|---|---|
| RC_AA598689_at | ae49a08.s1 Stratagene lung carcinoma 937218 *Homo sapiens* cDNA clone 950198 3'. |
| W26392_at | 30g3 Human retina cDNA randomly primed sublibrary *Homo sapiens* cDNA. |
| RC_AA004887_at | zh90g01.s1 Soares fetal liver spleen 1NFLS S1 *Homo sapiens* cDNA clone 428592 3'. |
| RC_AA135153_at | zo24g02.s1 Stratagene colon (#937204) *Homo sapiens* cDNA clone 587858 3'. |
| RC_AA197311_s_at | zq50e09.s1 Stratagene neuroepithelium (#937231) *Homo sapiens* cDNA clone 645064 3' similar to gb: M24283 INTERCELLULAR ADHESION MOLECULE-1 PRECURSOR (HUMAN);. |
| RC_H80622_at | yu77b06.s1 *Homo sapiens* cDNA clone 239795 3'. |
| RC_N64436_at | za33a09.s1 *Homo sapiens* cDNA clone 294328 3'. |
| RC_N67583_at | yz42c02.s1 *Homo sapiens* cDNA clone 285698 3'. |
| RC_R38678_at | yc89d05.s1 *Homo sapiens* cDNA clone 23443 3'. |
| RC_R56066_s_at | yg91d08.s1 *Homo sapiens* cDNA clone 40992 3'. |
| RC_R59292_at | yh16a10.s1 *Homo sapiens* cDNA clone 37689 3'. |
| RC_T24099_at | seq2287 *Homo sapiens* cDNA clone Cot250Ft-b4HB3MA-8 3'. |
| AA150364_at | zl07b03.r1 Soares pregnant uterus NbHPU *Homo sapiens* cDNA clone 491597 5'. |
| AA174185_at | PTH207 HTCDL1 *Homo sapiens* cDNA 5'/3'. |
| AA452353_i_at | zx15d05.r1 Soares total fetus Nb2HF8 9w *Homo sapiens* cDNA clone 786537 5'. |
| AB002316_at | Human mRNA for KIAA0318 gene, partial cds. |
| H86858_at | ys72d05.r1 *Homo sapiens* cDNA clone 220329 5'. |
| M93119_s_at | Human zinc-finger DNA-binding motifs (IA-1) mRNA, complete cds |
| R72037_at | yj86c09.r1 *Homo sapiens* cDNA clone 155632 5'. |
| RC_AA004274_at | zh97f02.s1 Soares fetal liver spleen 1NFLS S1 *Homo sapiens* cDNA clone 429243 3' similar to contains element MER22 repetitive element;. |
| RC_AA004415_at | zh89b04.s1 Soares fetal liver spleen 1NFLS S1 *Homo sapiens* cDNA clone 428431 3'. |
| RC_AA007160_at | l3cDNA30A-3, seq Soares infant brain 1NIB *Homo sapiens* cDNA clone HY18-3 3'. |
| RC_AA053660_at | zl74e07.s1 Stratagene colon (#937204) *Homo sapiens* cDNA clone 510372 3' similar to contains Alu repetitive element;. |
| RC_AA252603_at | zs14a11.s1 NCI_CGAP_GCB1 *Homo sapiens* cDNA clone IMAGE: 685148 3'. |
| RC_AA411944_at | zu03h01.s1 Soares testis NHT *Homo sapiens* cDNA clone 730801 3'. |
| RC_AA412700_at | zu12g03.s1 Soares testis NHT *Homo sapiens* cDNA clone 731668 3'. |
| RC_AA430032_at | zw65f05.s1 Soares testis NHT *Homo sapiens* cDNA clone 781089 3'. |
| RC_AA430368_at | zw20f06.s1 Soares ovary tumor NbHOT *Homo sapiens* cDNA clone 769859 3'. |
| RC_AA434113_at | zw24b11.s1 Soares ovary tumor NbHOT *Homo sapiens* cDNA clone 770205 3' similar to contains element TAR1 repetitive element;. |
| RC_AA441791_at | zw62c02.s1 Soares total fetus Nb2HF8 9w *Homo sapiens* cDNA clone 774626 3'. |
| RC_AA449419_at | zx05b03.s1 Soares total fetus Nb2HF8 9w *Homo sapiens* cDNA clone 785549 3'. |
| RC_AA449914_at | zx37g02.s1 Soares total fetus Nb2HF8 9w *Homo sapiens* cDNA clone 788690 3'. |
| RC_D59847_at | Human fetal brain cDNA 3'-end GEN-070G07. |
| T95813_f_at | ye45f10.r1 *Homo sapiens* cDNA clone 120715 5' similar to gb: V00493_rna1 HEMOGLOBIN ALPHA CHAIN (HUMAN);. |
| W80846_at | zd83f05.r1 Soares fetal heart NbHH19W *Homo sapiens* cDNA clone 347265 5' similar to SW: SYB2_XENLA P47193 SYNAPTOBREVIN 2;. |
| RC_AA031360_s_at | zk16f07.s1 Soares pregnant uterus NbHPU *Homo sapiens* cDNA clone 470725 3'. |
| RC_AA063624_at | ze87h05.s1 Soares fetal heart NbHH19W *Homo sapiens* cDNA clone 366009 3' similar to TR: G300372 G300372 CELL GROWTH REGULATING NUCLEOLAR PROTEIN,;. |
| RC_AA076238_at | zm19e04.s1 Stratagene pancreas (#937208) *Homo sapiens* cDNA clone 526110 3' similar to contains Alu repetitive element;. |
| RC_AA076350_at | zm91a02.s1 Stratagene ovarian cancer (#937219) *Homo sapiens* cDNA clone 545258 3'. |
| RC_AA101983_at | zk87c02.s1 Soares pregnant uterus NbHPU *Homo sapiens* cDNA clone 489794 3'. |
| RC_AA151245_at | zl40f12.s1 Soares pregnant uterus NbHPU *Homo sapiens* cDNA clone 504431 3'. |
| RC_AA164252_f_at | zq46f06.s1 Stratagene hNT neuron (#937233) *Homo sapiens* cDNA clone 632771 3'. |
| RC_AA167006_at | zo86b08.s1 Stratagene ovarian cancer (#937219) *Homo sapiens* cDNA clone 593751 3'. |

| | |
|---|---|
| RC_AA206225_at | zq56g08.s1 Stratagene neuroepithelium (#937231) *Homo sapiens* cDNA clone 645662 3'. |
| RC_D62834_at | Human aorta cDNA 3'-end GEN-330D04. |
| RC_D80981_at | Human fetal brain cDNA 3'-end GEN-121E12. |
| RC_H16772_at | ym34g02.s1 *Homo sapiens* cDNA clone 50227 3'. |
| RC_N62522_at | yz74f08.s1 *Homo sapiens* cDNA clone 288807 3'. |
| RC_N68222_at | yz56e12.s1 *Homo sapiens* cDNA clone 287086 3'. |
| RC_T10316_s_at | seq1014 *Homo sapiens* cDNA clone b4HB3MA-COT8-HAP-Ft266 3'. |
| RC_W37382_at | zc12c07.s1 Soares parathyroid tumor NbHPA *Homo sapiens* cDNA clone 322092 3'. |
| RC_W60582_at | zd25e10.s1 Soares fetal heart NbHH19W *Homo sapiens* cDNA clone 341706 3' similar to gb: M38188 OVARIAN GRANULOSA CELL 13,0 KD PROTEIN HGR74 (HUMAN);. |
| RC_W84768_at | zh53d03.s1 Soares fetal liver spleen 1NFLS S1 *Homo sapiens* cDNA clone 415781 3' similar to contains L1, b1 L1 repetitive element |

In a preferred embodiment genes from the second gene group are selected individually from genes comprising sequences as identified below by EST.

| | |
|---|---|
| AA011479_at | zi01b10.r1 Soares fetal liver spleen 1NFLS S1 *Homo sapiens* cDNA clone 429499 5'. |
| AA314779_at | EST186601 Colon carcinoma (HCC) cell line II *Homo sapiens* cDNA 5' end. |
| RC_AA084640_at | zn20d05.s1 Stratagene neuroepithelium NT2RAMI 937234 *Homo sapiens* cDNA clone 547977 3'. |
| RC_AA121534_at | zk89d11.s1 Soares pregnant uterus NbHPU *Homo sapiens* cDNA clone 490005 3' similar to gb: X79535 TUBULIN BETA-2 CHAIN (HUMAN);. |
| RC_AA131047_s_at | zo16f05.s1 Stratagene colon (#937204) *Homo sapiens* cDNA clone 587073 3'. |
| RC_AA461549_at | zx62b09.s1 Soares total fetus Nb2HF8 9w *Homo sapiens* cDNA clone 796025 3'. |
| RC_AA491465_at | ab04a05.s1 Stratagene fetal retina 937202 *Homo sapiens* cDNA clone 839792 3'. |
| RC_AA496936_at | ae32d03.s1 Gessler Wilms tumor *Homo sapiens* cDNA clone 897509 3'. |
| RC_AA598689_at | ae49a08.s1 Stratagene lung carcinoma 937218 *Homo sapiens* cDNA clone 950198 3'. |
| W26392_at | 30g3 Human retina cDNA randomly primed sublibrary *Homo sapiens* cDNA. |
| RC_AA004887_at | zh90g01.s1 Soares fetal liver spleen 1NFLS S1 *Homo sapiens* cDNA clone 428592 3'. |
| RC_AA135153_at | zo24g02.s1 Stratagene colon (#937204) *Homo sapiens* cDNA clone 587858 3'. |
| RC_AA197311_s_at | zq50e09.s1 Stratagene neuroepithelium (#937231) *Homo sapiens* cDNA clone 645064 3' similar to gb: M24283 INTERCELLULAR ADHESION MOLECULE-1 PRECURSOR (HUMAN);. |
| RC_H80622_at | yu77b06.s1 *Homo sapiens* cDNA clone 239795 3'. |
| RC_N64436_at | za33a09.s1 *Homo sapiens* cDNA clone 294328 3'. |
| RC_N67583_at | yz42c02.s1 *Homo sapiens* cDNA clone 285698 3'. |
| RC_R38678_at | yc89d05.s1 *Homo sapiens* cDNA clone 23443 3'. |
| RC_R56066_s_at | yg91d08.s1 *Homo sapiens* cDNA clone 40992 3'. |
| RC_R59292_at | yh16a10.s1 *Homo sapiens* cDNA clone 37689 3'. |
| RC_T24099_at | seq2287 *Homo sapiens* cDNA clone Cot250Ft-b4HB3MA-8 3'. |
| AA150364_at | zl07b03.r1 Soares pregnant uterus NbHPU *Homo sapiens* cDNA clone 491597 5'. |
| AA174185_at | PTH207 HTCDL1 *Homo sapiens* cDNA 5'/3'. |
| AA452353_i_at | zx15d05.r1 Soares total fetus Nb2HF8 9w *Homo sapiens* cDNA clone 786537 5'. |
| AB002316_at | Human mRNA for KIAA0318 gene, partial cds. |
| H86858_at | ys72d05.r1 *Homo sapiens* cDNA clone 220329 5'. |
| M93119_s_at | Human zinc-finger DNA-binding motifs (IA-1) mRNA, complete cds |
| R72037_at | yj86c09.r1 *Homo sapiens* cDNA clone 155632 5'. |
| RC_AA004274_at | zh97f02.s1 Soares fetal liver spleen 1NFLS S1 *Homo sapiens* cDNA clone 429243 3' similar to contains element MER22 repetitive element;. |
| RC_AA004415_at | zh89b04.s1 Soares fetal liver spleen 1NFLS S1 *Homo sapiens* cDNA clone 428431 3'. |

-continued

| | |
|---|---|
| RC_AA007160_at | l3cDNA30A-3,seq Soares infant brain 1NIB *Homo sapiens* cDNA clone HY18-3 3'. |
| RC_AA053660_at | zl74e07.s1 Stratagene colon (#937204) *Homo sapiens* cDNA clone 510372 3' similar to contains Alu repetitive element;. |
| RC_AA252603_at | zs14a11.s1 NCI_CGAP_GCB1 *Homo sapiens* cDNA clone IMAGE: 685148 3'. |
| RC_AA411944_at | zu03h01.s1 Soares testis NHT *Homo sapiens* cDNA clone 730801 3'. |
| RC_AA412700_at | zu12g03.s1 Soares testis NHT *Homo sapiens* cDNA clone 731668 3'. |
| RC_AA430032_at | zw65f05.s1 Soares testis NHT *Homo sapiens* cDNA clone 781089 3'. |
| RC_AA430368_at | zw20f06.s1 Soares ovary tumor NbHOT *Homo sapiens* cDNA clone 769859 3'. |
| RC_AA434113_at | zw24b11.s1 Soares ovary tumor NbHOT *Homo sapiens* cDNA clone 770205 3' similar to contains element TAR1 repetitive element;. |
| RC_AA441791_at | zw62c02.s1 Soares total fetus Nb2HF8 9w *Homo sapiens* cDNA clone 774626 3'. |
| RC_AA449419_at | zx05b03.s1 Soares total fetus Nb2HF8 9w *Homo sapiens* cDNA clone 785549 3'. |
| RC_AA449914_at | zx37g02.s1 Soares total fetus Nb2HF8 9w *Homo sapiens* cDNA clone 788690 3'. |
| RC_D59847_at | Human fetal brain cDNA 3'-end GEN-070G07. |
| T95813_f_at | ye45f10.r1 *Homo sapiens* cDNA clone 120715 5' similar to gb: V00493_rna1 HEMOGLOBIN ALPHA CHAIN (HUMAN);. |
| W80846_at | zd83f05.r1 Soares fetal heart NbHH19W *Homo sapiens* cDNA clone 347265 5' similar to SW: SYB2_XENLA P47193 SYNAPTOBREVIN 2;. |
| RC_AA031360_s_at | zk16f07.s1 Soares pregnant uterus NbHPU *Homo sapiens* cDNA clone 470725 3'. |
| RC_AA063624_at | ze87h05.s1 Soares fetal heart NbHH19W *Homo sapiens* cDNA clone 366009 3' similar to TR: G300372 G300372 CELL GROWTH REGULATING NUCLEOLAR PROTEIN, ;. |
| RC_AA076238_at | zm19e04.s1 Stratagene pancreas (#937208) *Homo sapiens* cDNA clone 526110 3' similar to contains Alu repetitive element;. |
| RC_AA076350_at | zm91a02.s1 Stratagene ovarian cancer (#937219) *Homo sapiens* cDNA clone 545258 3'. |
| RC_AA101983_at | zk87c02.s1 Soares pregnant uterus NbHPU *Homo sapiens* cDNA clone 489794 3'. |
| RC_AA151245_at | zl40f12.s1 Soares pregnant uterus NbHPU *Homo sapiens* cDNA clone 504431 3'. |
| RC_AA164252_f_at | zq46f06.s1 Stratagene hNT neuron (#937233) *Homo sapiens* cDNA clone 632771 3'. |
| RC_AA167006_at | zo86b08.s1 Stratagene ovarian cancer (#937219) *Homo sapiens* cDNA clone 593751 3'. |
| RC_AA206225_at | zq56g08.s1 Stratagene neuroepithelium (#937231) *Homo sapiens* cDNA clone 645662 3'. |
| RC_D62834_at | Human aorta cDNA 3'-end GEN-330D04. |
| RC_D80981_at | Human fetal brain cDNA 3'-end GEN-121E12. |
| RC_H16772_at | ym34g02.s1 *Homo sapiens* cDNA clone 50227 3'. |
| RC_N62522_at | yz74f08.s1 *Homo sapiens* cDNA clone 288807 3'. |
| RC_N68222_at | yz56e12.s1 *Homo sapiens* cDNA clone 287086 3'. |
| RC_T10316_s_at | seq1014 *Homo sapiens* cDNA clone b4HB3MA-COT8-HAP-Ft266 3'. |
| RC_W37382_at | zc12c07.s1 Soares parathyroid tumor NbHPA *Homo sapiens* cDNA clone 322092 3'. |
| RC_W60582_at | zd25e10.s1 Soares fetal heart NbHH19W *Homo sapiens* cDNA clone 341706 3' similar to gb: M38188 OVARIAN GRANULOSA CELL 13.0 KD PROTEIN HGR74 (HUMAN);. |
| RC_W84768_at | zh53d03.s1 Soares fetal liver spleen 1NFLS S1 *Homo sapiens* cDNA clone 415781 3' similar to contains L1, b1 L1 repetitive element;. |

In a preferred embodiment genes from the second gene group are selected individually from genes comprising sequences as identified below by EST.

| | |
|---|---|
| AA203639_at | zx58c10.r1 Soares fetal liver spleen 1NFLS S1 *Homo sapiens* cDNA clone 446706 5' similar to contains Alu repetitive element;. |
| M11844_at | Human prealbumin gene, complete cds. |
| RC_AA206042_at | zq77f02.s1 Stratagene hNT neuron (#937233) *Homo sapiens* cDNA clone 647643 3' similar to contains element MSR1 repetitive element;. |

-continued

| | |
|---|---|
| RC_N51097_at | yz03e04.s1 *Homo sapiens* cDNA clone 281982 3'. |
| RC_H05527_at | yl70f08.s1 Soares infant brain 1NIB *Homo sapiens* cDNA clone 43327 3'. |
| AA115572_s_at | zl05d11.r1 Soares pregnant uterus NbHPU *Homo sapiens* cDNA clone 491445 5' similar to TR: G895845 G895845 PUTATIVE P64 CLCP PROTEIN.;. |
| RC_H12863_at | yj14b12.s1 *Homo sapiens* cDNA clone 148703 3'. |
| AA489287_at | ab36e04.r1 Stratagene HeLa cell s3 937216 *Homo sapiens* cDNA clone 842910 5'. |
| RC_T96383_at | ye49h07.s1 *Homo sapiens* cDNA clone 121117 3'. |
| RC_H56453_at | yq98g12.s1 *Homo sapiens* cDNA clone 203878 3'. |
| RC_AA152194_at | zl03h01.s1 Soares pregnant uterus NbHPU *Homo sapiens* cDNA clone 491281 3'. |
| RC_Z38520_at | *H. sapiens* partial cDNA sequence; clone c-0ed05. |
| RC_R38944_at | yd06g09.s1 *Homo sapiens* cDNA clone 25061 3' similar to contains Alu repetitive element;. |
| RC_AA133926_at | zo16e11.s1 Stratagene colon (#937204) *Homo sapiens* cDNA clone 587084 3'. |
| RC_N69908_f_at | za68f06.s1 *Homo sapiens* cDNA clone 297731 3' similar to gb: X59244 ZINC FINGER PROTEIN 43 (HUMAN);. |
| RC_AA151945_at | zo02c02.s1 Stratagene colon (#937204) *Homo sapiens* cDNA clone 566498 3' similar to contains Alu repetitive element;. |
| S83308_at | SOX5 = Sry-related HMG box gene {alternatively spliced} [human. testis, mRNA, 1473 nt] |
| RC_AA406570_at | zv11b06.s1 Soares NhHMPu S1 *Homo sapiens* cDNA clone 753299 3'. |
| RC_AA058314_at | zl67g04.s1 Stratagene colon (#937204) *Homo sapiens* cDNA clone 509718 3' similar to contains Alu repetitive element; contains element PTR5 repetitive element;. |
| RC_R98735_at | yr31g12.s1 *Homo sapiens* cDNA clone 206950 3'. |

In a preferred embodiment genes from the second gene group are selected individually from genes comprising sequences as identified below by EST.

| | |
|---|---|
| RC_AA054726_at | zk68e06.s1 Soares pregnant uterus NbHPU *Homo sapiens* cDNA clone 488002 3'. |
| RC_AA206042_at | zq77f02.s1 Stratagene hNT neuron (#937233) *Homo sapiens* cDNA clone 647643 3' similar to contains element MSR1 repetitive element;. |
| RC_R98735_at | yr31g12.s1 *Homo sapiens* cDNA clone 206950 3'. |
| AA115572_s_at | zl05d11.r1 Soares pregnant uterus NbHPU *Homo sapiens* cDNA clone 491445 5' similar to TR: G895845 G895845 PUTATIVE P64 CLCP PROTEIN,;. |
| AA430979_at | PMY0789 KG1a Lambda Zap Express cDNA Library *Homo sapiens* cDNA 5'. |
| AA489287_at | ab36e04.r1 Stratagene HeLa cell s3 937216 *Homo sapiens* cDNA clone 842910 5'. |
| D82226_s_at | similar to TAT-binding protein-2. |
| H49499_s_at | yq20g10.r1 Soares fetal liver spleen 1NFLS *Homo sapiens* cDNA clone 274386 5'. |
| M11844_at | Human prealbumin gene, complete cds. |
| RC_AA026388_at | ze92c03.s1 Soares fetal heart NbHH19W *Homo sapiens* cDNA clone 366436 3'. |
| RC_AA044601_at | zk55d05.s1 Soares pregnant uterus NbHPU *Homo sapiens* cDNA clone 486729 3'. |
| RC_AA182030_at | zp57a03.s1 Stratagene endothelial cell 937223 *Homo sapiens* cDNA clone 624268 3'. |
| RC_AA233451_at | zr30b02.s1 Stratagene NT2 neuronal precursor 937230 *Homo sapiens* cDNA clone 664875 3'. |
| RC_AA236493_at | zr75c10.s1 Soares NhHMPu S1 *Homo sapiens* cDNA clone 669234 3'. |
| RC_AA401098_f_at | zu50g01.s1 Soares ovary tumor NbHOT *Homo sapiens* cDNA clone 741456 3' similar to contains Alu repetitive element; contains element THR repetitive element;. |
| RC_AA441818_at | zw62f01.s1 Soares total fetus Nb2HF8 9w *Homo sapiens* cDNA clone 774649 3'. |
| RC_AA478109_at | zt89d04.s1 Soares testis NHT *Homo sapiens* cDNA clone 729511 3'. |
| RC_AA481430_at | zv06g11.s1 Soares NhHMPu S1 *Homo sapiens* cDNA clone 752900 3'. |
| RC_AA488878_at | aa55f02.s1 NCI_CGAP_GCB1 *Homo sapiens* cDNA clone IMAGE: 824859 3'. |

-continued

| | |
|---|---|
| RC_AA599032_at | ae41h03.s1 Gessler Wilms tumor *Homo sapiens* cDNA clone 898421 3'. |
| S73288_at | small proline-rich protein SPRK [human, odontogenic kerato-cysts, mRNA Partial, 317 nt]. |
| U87459_at | Human autoimmunogenic cancer/testis antigen NY-ESO-1 mRNA, complete cds |
| U88047_at | Human DNA binding protein homolog (DRX) mRNA, partial cds |
| RC_AA063574_at | ze25f03.s1 Soares fetal heart NbHH19W *Homo sapiens* cDNA clone 360029 3' similar to gb: X52104 P68 PROTEIN (HUMAN);. |
| RC_AA132524_at | zo20c04.s1 Stratagene colon (#937204) *Homo sapiens* cDNA clone 587430 3' similar to contains Alu repetitive element;. |
| RC_F09317_at | *H. sapiens* partial cDNA sequence; clone c-2zh11. |
| RC_H12863_at | yj14b12.s1 *Homo sapiens* cDNA clone 148703 3'. |
| RC_N33927_s_at | yv25e09.s1 *Homo sapiens* cDNA clone 243784 3'. |
| RC_R08189_at | yf18f03.s1 *Homo sapiens* cDNA clone 127229 3'. |
| RC_R39191_s_at | yc89c12.s1 *Homo sapiens* cDNA clone 23345 3'. |
| RC_T82323_at | AS322 *Homo sapiens* cDNA clone AS322 3'. |
| RC_T90746_at | yd41f10.s1 *Homo sapiens* cDNA clone 110827 3'. |
| RC_Z39338_at | *H. sapiens* partial cDNA sequence; clone c-17f11. |

In one embodiment genes from the second gene group are selected individually from genes comprising sequences as identified below by EST.

| | |
|---|---|
| D80002_at | Human mRNA for KIAA0180 gene, partial cds |
| D82418_at | similar to none. |
| N28843_at | yx59d10.r1 *Homo sapiens* cDNA clone 266035 5'. |
| RC_F02541_at | *H. sapiens* partial cDNA sequence; clone c-12c11. |
| RC_N30806_at | yw65f02.s1 *Homo sapiens* cDNA clone 257115 3'. |
| RC_R33146_at | yh81f02.s1 *Homo sapiens* cDNA clone 136155 3' similar to contains Alu repetitive element;. |
| RC_R40166_at | yf70a09.s1 *Homo sapiens* cDNA clone 27448 3'. |
| RC_R65998_at | yi23g09.s1 *Homo sapiens* cDNA clone 140128 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA223902_at | zr13a10.s1 Stratagene hNT neuron (#937233) *Homo sapiens* cDNA clone 648666 3'. |
| RC_AA424524_at | zv90g02.s1 Soares NhHMPu S1 *Homo sapiens* cDNA clone 767090 3'. |
| RC_AA505136_at | aa65d11.s1 NCI_CGAP_GCB1 *Homo sapiens* cDNA clone IMAGE: 825813 3'. |
| AA043223_at | zk55g12.r1 Soares pregnant uterus NbHPU *Homo sapiens* cDNA clone 486790 5'. |

In a preferred embodiment genes from the second gene group are selected individually from genes comprising sequences as identified below by EST

| | |
|---|---|
| C01360_at | HUMGS0008341, Human Gene Signature, 3'-directed cDNA sequence. |
| D80002_at | Human mRNA for KIAA0180 gene, partial cds |
| RC_AA149586_at | zl39e03.s1 Soares pregnant uterus NbHPU *Homo sapiens* cDNA clone 504316 3'. |
| RC_H68772_at | yr83f01.s1 *Homo sapiens* cDNA clone 211897 3'. |
| RC_N30806_at | yw65f02.s1 *Homo sapiens* cDNA clone 257115 3'. |
| RC_N63143_at | yz37c12.s1 *Homo sapiens* cDNA clone 285238 3'. |
| RC_R33146_at | yh81f02.s1 *Homo sapiens* cDNA clone 136155 3' similar to contains Alu repetitive element;. |
| RC_R46206_at | yj53d08.s1 *Homo sapiens* cDNA clone 152463 3'. |
| RC_R49731_s_at | yg71e10.s1 *Homo sapiens* cDNA clone 38554 3'. |
| AA043223_at | zk55g12.r1 Soares pregnant uterus NbHPU *Homo sapiens* cDNA clone 486790 5'. |
| AB002346_at | Human mRNA for KIAA0348 gene, complete cds. |
| D81608_at | Human fetal brain cDNA 5'-end GEN-177B09. |
| M83670_s_at | Human carbonic anhydrase IV mRNA, complete cds |

-continued

| | |
|---|---|
| N28843_at | yx59d10.r1 *Homo sapiens* cDNA clone 266035 5'. |
| RC_AA149044_at | zl45d09.s1 Soares pregnant uterus NbHPU *Homo sapiens* cDNA clone 504881 3'. |
| RC_AA258130_at | zs35f03.s1 NCI_CGAP_GCB1 *Homo sapiens* cDNA clone IMAGE: 687197 3'. |
| RC_AA281743_r_at | zt06h05.s1 NCI_CGAP_GCB1 *Homo sapiens* cDNA clone IMAGE: 712377 3'. |
| RC_AA406338_at | zv10f06.s1 Soares NhHMPu S1 *Homo sapiens* cDNA clone 753251 3'. |
| RC_AA424524_at | zv90g02.s1 Soares NhHMPu S1 *Homo sapiens* cDNA clone 767090 3'. |
| RC_AA435840_at | zt80b08.s1 Soares testis NHT *Homo sapiens* cDNA clone 728631 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA135406_at | zo28e08.s1 Stratagene colon (#937204) *Homo sapiens* cDNA clone 588230 3'. |
| RC_AA148923_at | zl27g11.s1 Soares pregnant uterus NbHPU *Homo sapiens* cDNA clone 503204 3'. |
| RC_H98653_at | yx12h06.s1 *Homo sapiens* cDNA clone 261563 3'. |
| RC_N30077_at | yw81g11.s1 *Homo sapiens* cDNA clone 258692 3'. |
| RC_R40166_at | yf70a09.s1 *Homo sapiens* cDNA clone 27448 3'. |
| RC_T90374_at | yd43e03.s1 *Homo sapiens* cDNA clone 111004 3'similar to SP: POL2_MOUSE P11369 RETROVIRUS-RELATED POL POLYPROTEIN;. |
| RC_Z38182_at | *H. sapiens* partial cDNA sequence; clone c-02a08. |

In another embodiment genes from the second gene group are selected individually from genes comprising sequences as identified below by EST.

| | |
|---|---|
| RC_F03192_at | *H. sapiens* partial cDNA sequence; clone c-1pb12. |
| RC_W81552_at | zd87g10.s1 Soares fetal heart NbHH19W *Homo sapiens* cDNA clone 347682 3'. |
| RC_F02470_at | *H. sapiens* partial cDNA sequence; clone c-10c01. |
| RC_W44927_at | zc20b06.s1 Scares senescent fibroblasts NbHSF *Homo sapiens* cDNA clone 322835 3' similar to PIR: S44218 S44218 testin — mouse [1];. |
| RC_R45292_at | yg46b01.s1 *Homo sapiens* cDNA clone 35626 3'. |
| RC_H62159_at | yr47b09.s1 *Homo sapiens* cDNA clone 208409 3' similar to contains Alu repetitive element; contains MER15 repetitive element;. |
| RC_R17059_at | yf45a10.s2 *Homo sapiens* cDNA clone 129786 3'. |
| RC_H15259_at | ym30c10.s1 *Homo sapiens* cDNA clone 49795 3'. |
| W26376_at | 29a6 Human retina cDNA randomly primed sublibrary Homo sapiens cDNA. |
| Y09616_at | *H. sapiens* mRNA for putative carboxylesterase |
| AA425593_at | zw48f02.r1 Soares total fetus Nb2HF8 9w *Homo sapiens* cDNA clone 773307 5'. |
| RC_AA279980_at | zt08e05.s1 NCI_CGAP_GCB1 *Homo sapiens* cDNA clone IMAGE: 712544 3'. |
| RC_H14089_at | ym62c07.s1 *Homo sapiens* cDNA clone 163500 3'. |
| RC_R46079_f_at | yg49c02.s1 *Homo sapiens* cDNA clone 36133 3'. |
| RC_W15360_at | zc17d10.s1 Soares parathyroid tumor NbHPA *Homo sapiens* cDNA clone 322579 3' similar to PIR: S39983 S39983 eps8 protein — mouse;. |
| X52773_at | Human mRNA for retinoic acid receptor-like protein |
| RC_AA053886_s_at | ze75b05.s1 Soares fetal heart NbHH19W *Homo sapiens* cDNA clone 364785 3' similar to TR: G451330 G451330 STEROL REGULATORY ELEMENT BINDING PROTEIN-2.;. |
| RC_AA143493_at | zo31a10.s1 Stratagene colon (#937204) *Homo sapiens* cDNA clone 588474 3'. |
| RC_Z98492_at | *Homo sapiens* mRNA; expressed sequence tag; clone DKFZphsnu1_1b13, 3' read. |
| F15201_at | *H. sapiens* partial cDNA sequence. |
| RC_R61883_at | yh10f08.s1 *Homo sapiens* cDNA clone 42872 3'. |
| W26505_at | 30e12 Human retina cDNA randomly primed sublibrary *Homo sapiens* cDNA. |
| RC_AA085676_at | zn53e03.s1 Stratagene muscle 937209 *Homo sapiens* cDNA clone 561916 3'. |
| AA018804_at | ze55c07.r1 Soares retina N2b4HR *Homo sapiens* cDNA clone 362892 5' similar to SW: RB14_RAT P35287 RAS-RELATED PROTEIN RAB-14. [1];. |

-continued

| | |
|---|---|
| U22963_at | Human class I histocompatibility antigen-like protein mRNA. complete cds. |
| RC_R09230_at | yf26d08.s1 *Homo sapiens* cDNA clone 127983 3'. |
| RC_R67918_at | yi25g01.s1 *Homo sapiens* cDNA clone 140304 3'. |
| AA402119_at | zu55d04.r1 Soares ovary tumor NbHOT *Homo sapiens* cDNA clone 741895 5' similar to TR: G397579 G397579 LL5 MRNA,;. |
| AA082171_at | zn42g07.r1 Stratagene endothelial cell 937223 *Homo sapiens* cDNA clone 550140 5'. |
| R79750_at | yi89d09.r1 *Homo sapiens* cDNA clone 146417 5'. |
| RC_AA431773_at | zw80d04.s1 Soares testis NHT *Homo sapiens* cDNA clone 782503 3'. |
| RC_AA280670_at | zs97a07.s1 NCI_CGAP_GCB1 *Homo sapiens* cDNA clone IMAGE: 711540 3'. |
| AA303711_at | EST16378 Aorta endothelial cells, TNF alpha-treated *Homo sapiens* cDNA 5' end. |
| AA400361_at | zu64g03.r1 Soares testis NHT *Homo sapiens* cDNA clone 742804 5'. |
| AF007111_at | *Homo sapiens* MDM2-like p53-binding protein (MDMX) mRNA. complete cds. |
| AA504384_at | aa59c02.r1 NCI_CGAP_GCB1 *Homo sapiens* cDNA clone IMAGE: 825218 5' similar to contains element MIR repetitive element;. |
| N88108_at | K1565F Fetal heart, Lambda ZAP Express *Homo sapiens* cDNA clone K1565 5' similar to EST(YD54C09.R1). |
| RC_AA447769_at | aa20e01.s1 Soares NhHMPu S1 *Homo sapiens* cDNA clone 813816 3'. |

In yet another preferred embodiment genes from the second gene group are selected individually from genes comprising sequences as identified below by EST.

| | |
|---|---|
| AA402119_at | zu55d04.r1 Soares ovary tumor NbHOT *Homo sapiens* cDNA clone 741895 5' similar to TR: G397579 G397579 LL5 MRNA,;, |
| RC_AA102581_at | zn42d02.s1 Stratagene endothelial cell 937223 *Homo sapiens* cDNA clone 550083 3', |
| RC_H14089_at | ym62c07.s1 *Homo sapiens* cDNA clone 163500 3', |
| RC_R46079_f_at | yg49c02.s1 *Homo sapiens* cDNA clone 36133 3', |
| RC_R67918_at | yi25g01.s1 *Homo sapiens* cDNA clone 140304 3', |
| RC_W15360_at | zc17d10.s1 Soares parathyroid tumor NbHPA *Homo sapiens* cDNA clone 322579 3' similar to PIR: S39983 S39983 eps8 protein — mouse;, |
| AA082171_at | zn42g07.r1 Stratagene endothelial cell 937223 *Homo sapiens* cDNA clone 550140 5', |
| AA425593_at | zw48f02.r1 Soares total fetus Nb2HF8 9w *Homo sapiens* cDNA clone 773307 5', |
| F15201_at | *H. sapiens* partial cDNA sequence, |
| H15219_at | ym30f02.r1 *Homo sapiens* cDNA clone 49693 5', |
| R60368_at | yh04b02.r1 *Homo sapiens* cDNA clone 42052 5', |
| R86859_at | ym86a02.r1 *Homo sapiens* cDNA clone 165770 5', |
| RC_AA045342_at | zk59g01.s1 Soares pregnant uterus NbHPU *Homo sapiens* cDNA clone 487152 3', |
| RC_AA171985_at | zo98g05.s1 Stratagene ovarian cancer (#937219) *Homo sapiens* cDNA clone 594968 3', |
| T63174_s_at | yc04e08.r1 *Homo sapiens* cDNA clone 79718 5' similar to contains Alu repetitive element;, |
| U90268_at | Human Krit1 mRNA, complete cds, |
| X14787_at | Human mRNA for thrombospondin |
| RC_AA196991_s_at | zq10a10.s1 Stratagene muscle 937209 *Homo sapiens* cDNA clone 629274 3' similar to TR: G1049074 G1049074 VASOPRESSIN-ACTIVATED CALCIUM-MOBILIZING PROTEIN,;, |
| RC_F02470_at | *H. sapiens* partial cDNA sequence; clone c-10c01, |
| RC_F08899_at | *H. sapiens* partial cDNA sequence; clone c-2uc10, |
| RC_H15259_at | ym30c10.s1 *Homo sapiens* cDNA clone 49795 3', |
| RC_H52133_at | yo44d04.s1 *Homo sapiens* cDNA clone 180775 3', |
| RC_R17059_at | yf45a10.s2 *Homo sapiens* cDNA clone 129786 3', |
| RC_R45292_at | yg46b01.s1 *Homo sapiens* cDNA clone 35626 3', |

The genes from the second gene group discussed above are preferably genes being expressed in all stages of the biological condition, such as all stages of a bladder tumor, to be used for determining the biological condition.

Particularly, the genes from the second gene group are selected individually from genes comprising sequences as identified below by EST, and which are associated with muscle invasive tumors.

| | |
|---|---|
| RC_R00083_at | ye73c08.s1 Homo sapiens cDNA clone 123374 3'. |
| RC_R71391_at | yj80e01.s1 Homo sapiens cDNA clone 155064 3'. |
| RC_T23991_at | seq2147 Homo sapiens cDNA clone NHB3MK-9 3'. |
| RC_T79196_at | yd70f06.s1 Homo sapiens cDNA clone 113603 3' similar to contains Alu repetitive element;. |
| RC_AA130596_at | zo26a09.s1 Stratagene colon (#937204) Homo sapiens cDNA clone 587992 3'. |
| RC_AA459310_r_at | zx89d06.s1 Soares ovary tumor NbHOT Homo sapiens cDNA clone 810923 3'. |
| RC_AA490965_at | aa48f12.s1 NCI_CGAP_GCB1 Homo sapiens cDNA clone IMAGE: 824207 3'. |
| U88047_at | Human DNA binding protein homolog (DRX) mRNA, partial cds |
| X56807_at | Human DSC2 mRNA for desmocollins type 2a and 2b |
| AA011479_at | zi01b10.r1 Soares fetal liver spleen 1NFLS S1 Homo sapiens cDNA clone 429499 5'. |
| AA296821_at | EST112387 Aorta endothelial cells Homo sapiens cDNA 5' end. |

Further, the genes from the second gene group are selected individually from genes comprising sequences as identified below by EST, and which are associated with solid tumors only.

| | |
|---|---|
| RC_AA026418_at | ze92h01.s1 Soares fetal heart NbHH19W Homo sapiens cDNA clone 366481 3'. |
| RC_D59847_at | Human fetal brain cDNA 3'-end GEN-070G07. |
| RC_T24099_at | seq2287 Homo sapiens cDNA clone Cot250Ft-b4HB3MA-8 3'. |
| RC_R59292_at | yh16a10.s1 Homo sapiens cDNA clone 37689 3'. |
| RC_W60582_at | zd25e10.s1 Soares fetal heart NbHH19W Homo sapiens cDNA clone 341706 3' similar to gb: M38188 OVARIAN GRANULOSA CELL 13.0 KD PROTEIN HGR74 (HUMAN);. |
| M63262_at | Human 5-lipoxygenase activating protein (FLAP) gene |
| RC_R38678_at | yc89d05.s1 Homo sapiens cDNA clone 23443 3'. |
| W60268_at | zd29g01.r1 Soares fetal heart NbHH19W Homo sapiens cDNA clone 342096 5'. |
| AA465016_at | zx80d02.r1 Soares ovary tumor NbHOT Homo sapiens cDNA clone 810051 5' similar to TR: G1020091 G1020091 NEUROPSIN.; contains element LTR3 repetitive element;. |
| RC_T79842_at | yd83f04.s1 Homo sapiens cDNA clone 114847 3'. |
| RC_AA206225_at | zq56g08.s1 Stratagene neuroepithelium (#937231) Homo sapiens cDNA clone 645662 3'. |
| RC_AA449914_at | zx37g02.s1 Soares total fetus Nb2HF8 9w Homo sapiens cDNA clone 788690 3'. |
| RC_F10211_at | H. sapiens partial cDNA sequence; clone c-3bh08. |
| RC_AA480109_r_at | zv41f05.s1 Soares ovary tumor NbHOT Homo sapiens cDNA clone 756225 3' similar to TR: G498729 G498729 ZINC FINGER PROTEIN;. |
| RC_AA053102_s_at | zl72a06.s1 Stratagene colon (#937204) Homo sapiens cDNA clone 5101303 3'. |
| RC_AA434113_at | zw24b11.s1 Soares ovary tumor NbHOT Homo sapiens cDNA clone 770205 3' similar to contains element TAR1 repetitive element;. |
| RC_AA441791_at | zw62c02.s1 Soares total fetus Nb2HF8 9w Homo sapiens cDNA clone 774626 3'. |
| RC_N67583_at | yz42c02.s1 Homo sapiens cDNA clone 285698 3'. |
| RC_T96077_at | ye47b12.s1 Homo sapiens cDNA clone 120863 3'. |
| AB002316_at | Human mRNA for KIAA0318 gene, partial cds. |
| RC_W96222_at | ze10g07.s1 Soares fetal heart NbHH19W Homo sapiens cDNA clone 358620 3'. |
| M16591_s_at | Human hemopoietic cell protein-tyrosine kinase (HCK) gene, complete cds, clone lambda-a2/1a |
| RC_N59808_at | yz76b12.s1 Homo sapiens cDNA clone 288959 3'. |
| RC_F10040_at | H. sapiens partial cDNA sequence; clone c-39g09. |
| RC_AA461549_at | zx62b09.s1 Soares total fetus Nb2HF8 9w Homo sapiens cDNA clone 796025 3'. |
| RC_W68683_at | zd35d04.s1 Soares fetal heart NbHH19W Homo sapiens cDNA clone 342631 3'. |
| RC_AA084640_at | zn20d05.s1 Stratagene neuroepithelium NT2RAMI 937234 Homo sapiens cDNA clone 547977 3'. |
| C01169_at | HUMGS0007858, Human Gene Signature, 3'-directed cDNA sequence. |
| RC_AA491465_at | ab04a05.s1 Stratagene fetal retina 937202 Homo sapiens cDNA clone 839792 3'. |
| RC_W67564_s_at | zd41c07.s1 Soares fetal heart NbHH19W Homo sapiens cDNA clone 343212 3'. |
| J03019_s_at | Human beta-1-adrenergic receptor mRNA, complete cds. |

-continued

| | |
|---|---|
| RC_H80622_at | yu77b06.s1 *Homo sapiens* cDNA clone 239795 3'. |
| RC_N34686_at | yy15h06.s1 *Homo sapiens* cDNA clone 271355 3'. |
| RC_R56066_s_at | yg91d08.s1 *Homo sapiens* cDNA clone 40992 3'. |
| RC_T34611_at | EST71577 *Homo sapiens* cDNA 3' end similar to None. |
| RC_AA031373_s_at | zk15e12.s1 Soares pregnant uterus NbHPU *Homo sapiens* cDNA clone 470638 3'. |
| X52056_at | Human mRNA for spi-1 proto-oncogene |
| N77564_at | yz89g12.r1 *Homo sapiens* cDNA clone 290278 5'. |
| C01765_at | HUMGS0003713, Human Gene Signature, 3'-directed cDNA sequence. |
| RC_AA496936_at | ae32d03.s1 Gessler Wilms tumor *Homo sapiens* cDNA clone 897509 3'. |
| RC_AA027103_at | zk04e03.s1 Soares pregnant uterus NbHPU *Homo sapiens* cDNA clone 469564 3'. |
| RC_R44131_at | yg32c11.s1 *Homo sapiens* cDNA clone 34089 3'. |
| RC_N67227_at | yz48f04.s1 *Homo sapiens* cDNA clone 286303 3'. |
| RC_T96677_at | ye52f03.s1 *Homo sapiens* cDNA clone 121373 3'. |
| RC_AA134965_i_at | zo23g05.s1 Stratagene colon (#937204) *Homo sapiens* cDNA clone 587768 3'. |
| RC_T86600_at | yd87d10.s1 *Homo sapiens* cDNA clone 115219 3'. |
| RC_AA054087_at | zf51f03.s1 Soares retina N2b4HR *Homo sapiens* cDNA clone 380477 3'. |
| AA444374_at | zv76b10.r1 Soares total fetus Nb2HF8 9w *Homo sapiens* cDNA 5'. |
| RC_H72357_at | ys04f01.s1 *Homo sapiens* cDNA clone 213817 3' similar to gb: J04970 CARBOXYPEPTIDASE M PRECURSOR (HUMAN); contains Alu repetitive element;. |
| RC_AA017045_at | ze37d11.s1 Soares retina N2b4HR *Homo sapiens* cDNA clone 361173 3'. |
| AA010324_at | zi09c03.r1 Soares fetal liver spleen 1NFLS S1 *Homo sapiens* cDNA clone 430276 5'. |
| RC_AA234743_at | zs38b09.s1 Soares NhHMPu S1 *Homo sapiens* cDNA clone 687449 3'. |
| RC_AA055892_at | zf20d06.s1 Soares fetal heart NbHH19W *Homo sapiens* cDNA clone 377483 3'. |
| RC_AA446650_at | zw89g02.s1 Soares total fetus Nb2HF8 9w *Homo sapiens* cDNA clone 784178 3'. |
| H91747_s_at | ys80e03.r1 *Homo sapiens* cDNA clone 221116 5'. |
| AA401510_s_at | zu63c08.r1 Soares testis NHT *Homo sapiens* cDNA clone 742670 5'. |
| RC_W61239_at | zd31d10.s1 Soares fetal heart NbHH19W *Homo sapiens* cDNA clone 342259 3'. |

In another embodiment the genes from the second gene group are selected individually from genes comprising sequences as identified below by EST, and which are associated with mixed tumors comprising both solid and papilloma elements of invasive type.

| | |
|---|---|
| AA203639_at | zx58c10.r1 Soares fetal liver spleen 1NFLS S1 *Homo sapiens* cDNA clone 446706 5' similar to contains Alu repetitive element;. |
| M11844_at | Human prealbumin gene, complete cds. |
| RC_AA206042_at | zq77f02.s1 Stratagene hNT neuron (#937233) *Homo sapiens* cDNA clone 647643 3' similar to contains element MSR1 repetitive element;. |
| RC_N51097_at | yz03e04.s1 *Homo sapiens* cDNA clone 281982 3'. |
| RC_H05527_at | yl70f08.s1 Soares infant brain 1NIB *Homo sapiens* cDNA clone 43327 3'. |
| AA115572_s_at | zl05d11.r1 Soares pregnant uterus NbHPU *Homo sapiens* cDNA clone 491445 5' similar to TR: G895845 G895845 PUTATIVE P64 CLCP PROTEIN.;. |
| RC_H12863_at | yj14b12.s1 *Homo sapiens* cDNA clone 148703 3'. |
| AA489287_at | ab36e04.r1 Stratagene HeLa cell s3 937216 *Homo sapiens* cDNA clone 842910 5'. |
| RC_T96383_at | ye49h07.s1 *Homo sapiens* cDNA clone 121117 3'. |
| RC_H56453_at | yq98g12.s1 *Homo sapiens* cDNA clone 203878 3'. |
| RC_AA152194_at | zl03h01.s1 Soares pregnant uterus NbHPU *Homo sapiens* cDNA clone 491281 3'. |
| RC_Z38520_at | *H. sapiens* partial cDNA sequence; clone c-0ed05. |
| RC_R38944_at | yd06g09.s1 *Homo sapiens* cDNA clone 25061 3' similar to contains Alu repetitive element;. |

-continued

| | |
|---|---|
| RC_AA133926_at | zo16e11.s1 Stratagene colon (#937204) *Homo sapiens* cDNA clone 587084 3'. |
| RC_N69908_f_at | za68f06.s1 *Homo sapiens* cDNA clone 297731 3' similar to gb: X59244 ZINC FINGER PROTEIN 43 (HUMAN);. |
| RC_AA151945_at | zo02c02.s1 Stratagene colon (#937204) *Homo sapiens* cDNA clone 566498 3' similar to contains Alu repetitive element;. |
| S83308_at | SOX5 = Sry-related HMG box gene {alternatively spliced} [human, testis, mRNA, 1473 nt] |
| RC_AA406570_at | zv11b06.s1 Soares NhHMPu S1 *Homo sapiens* cDNA clone 753299 3'. |
| RC_AA058314_at | zl67g04.s1 Stratagene colon (#937204) *Homo sapiens* cDNA clone 509718 3' similar to contains Alu repetitive element; contains element PTR5 repetitive element;. |
| RC_R98735_at | yr31g12.s1 *Homo sapiens* cDNA clone 206950 3'. |

More particularly the genes from the second gene group are selected individually from genes comprising sequences as identified below by EST, and which are associated with T1 tumors (mucosa invasive tumor)

| | |
|---|---|
| D80002_at | Human mRNA for KIAA0180 gene, partial cds |
| D82418_at | similar to none. |
| N28843_at | yx59d10.r1 *Homo sapiens* cDNA clone 266035 5'. |
| RC_F02541_at | *H. sapiens* partial cDNA sequence; clone c-12c11. |
| RC_N30806_at | yw65f02.s1 *Homo sapiens* cDNA clone 257115 3'. |
| RC_R33146_at | yh81f02.s1 *Homo sapiens* cDNA clone 136155 3' similar to contains Alu repetitive element;. |
| RC_R40166_at | yf70a09.s1 *Homo sapiens* cDNA clone 27448 3'. |
| RC_R65998_at | yi23g09.s1 *Homo sapiens* cDNA clone 140128 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA223902_at | zr13a10.s1 Stratagene hNT neuron (#937233) *Homo sapiens* cDNA clone 648666 3'. |
| RC_AA424524_at | zv90g02.s1 Soares NhHMPu S1 *Homo sapiens* cDNA clone 767090 3'. |
| RC_AA505136_at | aa65d11.s1 NCI_CGAP_GCB1 *Homo sapiens* cDNA clone IMAGE: 825813 3'. |
| AA043223_at | zk55g12.r1 Soares pregnant uterus NbHPU *Homo sapiens* cDNA clone 486790 5'. |

Even more particularly the genes from the second gene group are selected individually from genes comprising sequences as identified below by EST, and which are associated with superficial Ta tumors.

| | |
|---|---|
| RC_F03192_at | *H. sapiens* partial cDNA sequence; clone c-1pb12. |
| RC_W81552_at | zd87g10.s1 Soares fetal heart NbHH19W *Homo sapiens* cDNA clone 347682 3'. |
| RC_F02470_at | *H. sapiens* partial cDNA sequence; clone c-10c01. |
| RC_W44927_at | zc20b06.s1 Soares senescent fibroblasts NbHSF *Homo sapiens* cDNA clone 322835 3' similar to PIR: S44218 S44218 testin - mouse [1];. |
| RC_R45292_at | yg46b01.s1 *Homo sapiens* cDNA clone 35626 3'. |
| RC_H62159_at | yr47b09.s1 *Homo sapiens* cDNA clone 208409 3' similar to contains Alu repetitive element; contains MER15 repetitive element;. |
| RC_R17059_at | yf45a10.s2 *Homo sapiens* cDNA clone 129786 3'. |
| RC_H15259_at | ym30c10.s1 *Homo sapiens* cDNA clone 49795 3'. |
| W26376_at | 29a6 Human retina cDNA randomly primed sublibrary *Homo sapiens* cDNA. |
| Y09616_at | *H. sapiens* mRNA for putative carboxylesterase |
| AA425593_at | zw48f02.r1 Soares total fetus Nb2HF8 9w *Homo sapiens* cDNA clone 773307 5'. |

-continued

| | |
|---|---|
| RC_AA279980_at | zt08e05.s1 NCI_CGAP_GCB1 *Homo sapiens* cDNA clone IMAGE: 712544 3'. |
| RC_H14089_at | ym62c07.s1 *Homo sapiens* cDNA clone 163500 3'. |
| RC_R46079_f_at | yg49c02.s1 *Homo sapiens* cDNA clone 36133 3'. |
| RC_W15360_at | zc17d10.s1 Soares parathyroid tumor NbHPA *Homo sapiens* cDNA clone 322579 3' similar to PIR: S39983 S39983 eps8 protein - mouse;. |
| X52773_at | Human mRNA for retinoic acid receptor-like protein |
| RC_AA053886_s_at | ze75b05.s1 Soares fetal heart NbHH19W *Homo sapiens* cDNA clone 364785 3' similar to TR: G451330 G451330 STEROL REGULATORY ELEMENT BINDING PROTEIN-2.;. |
| RC_AA143493_at | zo31a10.s1 Stratagene colon (#937204) *Homo sapiens* cDNA clone 588474 3'. |
| RC_Z98492_at | *Homo sapiens* mRNA; expressed sequence tag; clone DKFZphsnu1_1b13, 3' read. |
| F15201_at | *H. sapiens* partial cDNA sequence. |
| RC_R61883_at | yh10f08.s1 *Homo sapiens* cDNA clone 42872 3'. |
| W26505_at | 30e12 Human retina cDNA randomly primed sublibrary *Homo sapiens* cDNA. |
| RC_AA085676_at | zn53e03.s1 Stratagene muscle 937209 *Homo sapiens* cDNA clone 561916 3'. |
| AA018804_at | ze55c07.r1 Soares retina N2b4HR *Homo sapiens* cDNA clone 362892 5' similar to SW: RB14_RAT P35287 RAS-RELATED PROTEIN RAB-14. [1];. |
| U22963_at | Human class I histocompatibility antigen-like protein mRNA, complete cds. |
| RC_R09230_at | yf26d08.s1 *Homo sapiens* cDNA clone 127983 3'. |
| RC_R67918_at | yi25g01.s1 *Homo sapiens* cDNA clone 140304 3'. |
| AA402119_at | zu55d04.r1 Soares ovary tumor NbHOT *Homo sapiens* cDNA clone 741895 5' similar to TR: G397579 G397579 LL5 MRNA.;. |
| AA082171_at | zn42g07.r1 Stratagene endothelial cell 937223 *Homo sapiens* cDNA clone 550140 5'. |
| R79750_at | yi89d09.r1 *Homo sapiens* cDNA clone 146417 5'. |
| RC_AA431773_at | zw80d04.s1 Soares testis NHT *Homo sapiens* cDNA clone 782503 3'. |
| RC_AA280670_at | zs97a07.s1 NCI_CGAP_GCB1 *Homo sapiens* cDNA clone IMAGE: 711540 3'. |
| AA303711_at | EST16378 Aorta endothelial cells, TNF alpha-treated *Homo sapiens* cDNA 5' end. |
| AA400361_at | zu64g03.r1 Soares testis NHT *Homo sapiens* cDNA clone 742804 5'. |
| AF007111_at | *Homo sapiens* MDM2-like p53-binding protein (MDMX) mRNA, complete cds. |
| AA504384_at | aa59c02.r1 NCI_CGAP_GCB1 *Homo sapiens* cDNA clone IMAGE: 825218 5' similar to contains element MIR repetitive element;. |
| N88108_at | K1565F Fetal heart, Lambda ZAP Express *Homo sapiens* cDNA clone K1565 5' similar to EST(YD54C09.R1). |
| RC_AA447769_at | aa20e01.s1 Soares NhHMPu S1 *Homo sapiens* cDNA clone 813816 3'. |

More particularly the genes from the second gene group are selected individually from genes comprising sequences as identified below by EST, and which are associated with T1 tumors (mucosa invasive tumor).

| | |
|---|---|
| D80002_at | Human mRNA for KIAA0180 gene, partial cds |
| D82418_at | similar to none. |
| N28843_at | yx59d10.r1 *Homo sapiens* cDNA clone 266035 5'. |
| RC_F02541_at | *H. sapiens* partial cDNA sequence; clone c-12c11. |
| RC_N30806_at | yw65f02.s1 *Homo sapiens* cDNA clone 257115 3'. |
| RC_R33146_at | yh81f02.s1 *Homo sapiens* cDNA clone 136155 3' similar to contains Alu repetitive element;. |
| RC_R40166_at | yf70a09.s1 *Homo sapiens* cDNA clone 27448 3'. |
| RC_R65998_at | yi23g09.s1 *Homo sapiens* cDNA clone 140128 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA223902_at | zr13a10.s1 Stratagene hNT neuron (#937233) *Homo sapiens* cDNA clone 648666 3'. |

-continued

| | |
|---|---|
| RC_AA424524_at | zv90g02.s1 Soares NhHMPu S1 *Homo sapiens* cDNA clone 767090 3'. |
| RC_AA505136_at | aa65d11.s1 NCI_CGAP_GCB1 *Homo sapiens* cDNA clone IMAGE: 825813 3'. |
| AA043223_at | zk55g12.r1 Soares pregnant uterus NbHPU *Homo sapiens* cDNA clone 486790 5'. |

Number of Genes

As discussed above, it is possible to use a single gene approach determining the expression of one of the genes only, in order to determine the biological condition of the tissue. It is however preferred that expression from at least one gene from the first group, such as at least two, for example at least three, such as at least four, such as at least five, such as more than six genes are determined as well as expression from at least one gene from the second group, such as at least two, for example at least three, such as at least four, such as at least five, such as more than six genes are determined to obtain a more statistically significant result, that is more independent of the expression level of the individual gene.

In one embodiment expression from more genes from both groups are determined, such as determination of expression from at least two genes from either of the gene groups, such as determination of expression from at least three genes from either of the gene groups, such as determination of expression from at least four genes from either of the gene groups, such as determination of expression from at least five genes from either of the gene groups, such as determination of expression from at least six genes from either of the gene groups, such as determination of expression from at least seven genes from either of the gene groups.

A pattern of characteristic expression of one gene can be useful in characterizing a cell type source or a stage of disease. However, more genes may be usefully analyzed. Useful patterns include expression of at least one, two, three, five, ten, fifteen, twenty, twenty-five, fifty, seventy-five, one hundred or several hundred informative genes.

Expression Level

Using the results provided in the accompanying figures, a gene is indicated as being expressed if an intensity value of greater than or equal to 20 or scored as P=present by the software is shown. Conversely, an intensity value of less than 20 or scored as A=absent indicates that the gene is not expressed above background levels. Comparison of an expression pattern to another may score a change from expressed to non-expressed, or the reverse. Alternatively, changes in intensity of expression may be scored, either increases or decreases. Any significant change can be used. Typical changes which are more than 2-fold are suitable. Changes which are greater than 5-fold are highly suitable.

The present invention in particular relates to methods using genes wherein the ratio of the expression level in normal tissue to biological condition tissue for suppressor genes or vice versa of the expression level in biological condition tissue to normal tissue for condition genes is as high as possible, such as at least a two-fold change in expression, such as at least a three-fold change, for example at least a four fold change, such as at least a five fold change, for example at least a six fold change, such as at least a ten fold change, for example at least a fifteen fold change, such as at least a twenty fold change.

Stages and Grades

Stage of a bladder tumor indicates how deep the tumor has penetrated. Superficial tumors are termed Ta, T1, T2, T3 and T4 are used to describe increasing degrees of penetration into the muscle. The grade of a bladder tumor is expressed on a scale of I-IV (1-4) according to Bergkvist, A.; Ijungquist, A.; Moberger, B. "Classification of bladder tumours basedf on the cellular pattern. Preliminary report of a clinical-pathological study of 300 cases with a minimum follow-up of eight years", Acta Chir Scand., 1965, 130(4):371-8). The grade reflects the cytological appearance of the cells. Grade I cells are almost normal. Grade II cells are slightly deviant. Grade III cells are clearly abnormal. And Grade IV cells are highly abnormal. A special form of bladder malignancy is carcinoma-in-situ or dyplasia-in-situ in which the altered cells are located in-situ.

It is important to classify the stage of a cancer disease, as superficial tumors may require a less intensive treatment than invasive tumors. According to the invention the expression level of genes may be used to identify genes whose expression can be used to identify a certain stage of the disease. These "Classifiers" are divided into those which can be used to identify Ta, T2, T3, and T4 stages. In one aspect of the invention measuring the transcript level of one or more of these genes may lead to a classifier that can add supplementary information to the information obtained from the pathological T2 classification. For example gene expression levels that signify a T2 will be unfavourable to detect in a Ta tumor, as they may signal that the Ta tumor has the potential to become a T2 tumor. The opposite is probably also true, that an expression level that signify Ta will be favorable to have in a T2 tumor. In that way independent information may be obtained from T2-T4 pathological classification and a classification based on gene expression levels is made.

The method of determining the stage of a tumor may be combined with determination of the biological condition or may be an independent method as such. The difference in expression level of a gene from one stage to the expression level of the gene in another group is preferably at least two-fold, such as at least three-fold.

Thus, the invention relates to a method of determining the stage of a bladder tumor, wherein the stage is selected from bladder cancer stages Ta, T1; T2, T3 and T4 comprising assaying at least the expression of Ta stage gene from a Ta stage gene group, at least one expression of T1 stage gene from a T1 stage gene group, at least the expression of T2 stage gene from a T2 stage gene group, at least the expression of T3 stage gene from a T3 stage gene group, at least the expression of T4 stage gene from a T4 stage gene group wherein at least one gene from each gene group is expressed in a significantly different amount in that stage than in one of the other stages.

Preferably, the genes selected may be a gene from each gene group being expressed in a significantly higher amount in that stage than in one of the other stages, such as:

a Ta stage gene selected individually from any gene comprising a sequence as identified below as EST

| | |
|---|---|
| RC_F03192_at | *H. sapiens* partial cDNA sequence; clone c-1pb12. |
| RC_W81552_at | zd87g10.s1 Soares fetal heart NbHH19W *Homo sapiens* cDNA clone 347682 3'. |
| RC_F02470_at | *H. sapiens* partial cDNA sequence; clone c-10c01. |
| RC_W44927_at | zc20b06.s1 Soares senescent fibroblasts NbHSF *Homo sapiens* cDNA clone 322835 3' similar to PIR: S44218 S44218 testin - mouse [1];. |
| RC_R45292_at | yg46b01.s1 *Homo sapiens* cDNA clone 35626 3'. |
| RC_H62159_at | yr47b09.s1 *Homo sapiens* cDNA clone 208409 3' similar to contains Alu repetitive element; contains MER15 repetitive element;. |
| RC_R17059_at | yf45a10.s2 *Homo sapiens* cDNA clone 129786 3'. |
| RC_H15259_at | ym30c10.s1 *Homo sapiens* cDNA clone 49795 3'. |
| W26376_at | 29a6 Human retina cDNA randomly primed sublibrary *Homo sapiens* cDNA. |
| Y09616_at | *H. sapiens* mRNA for putative carboxylesterase |
| AA425593_at | zw48f02.r1 Soares total fetus Nb2HF8 9w *Homo sapiens* cDNA clone 773307 5'. |
| RC_AA279980_at | zt08e05.s1 NCI_CGAP_GCB1 *Homo sapiens* cDNA clone IMAGE: 712544 3'. |
| RC_H14089_at | ym62c07.s1 *Homo sapiens* cDNA clone 163500 3'. |
| RC_R46079_f_at | yg49c02.s1 *Homo sapiens* cDNA clone 36133 3'. |
| RC_W15360_at | zc17d10.s1 Soares parathyroid tumor NbHPA *Homo sapiens* cDNA clone 322579 3' similar to PIR: S39983 S39983 eps8 protein - mouse;. |
| X52773_at | Human mRNA for retinoic acid receptor-like protein |
| RC_AA053886_s_at | ze75b05.s1 Soares fetal heart NbHH19W *Homo sapiens* cDNA clone 364785 3' similar to TR: G451330 G451330 STEROL REGULATORY ELEMENT BINDING PROTEIN-2.;. |
| RC_AA143493_at | zo31a10.s1 Stratagene colon (#937204) *Homo sapiens* cDNA clone 588474 3'. |
| RC_Z98492_at | *Homo sapiens* mRNA; expressed sequence tag; clone DKFZphsnu1_1b13 3' read. |
| F15201_at | *H. sapiens* partial cDNA sequence. |
| RC_R61883_at | yh10f08.s1 *Homo sapiens* cDNA clone 42872 3'. |
| W26505_at | 30e12 Human retina cDNA randomly primed sublibrary *Homo sapiens* cDNA. |
| RC_AA085676_at | zn53e03.s1 Stratagene muscle 937209 *Homo sapiens* cDNA clone 561916 3'. |
| AA018804_at | ze55c07.r1 Soares retina N2b4HR *Homo sapiens* cDNA clone 362892 5' similar to SW: RB14_RAT P35287 RAS-RELATED PROTEIN RAB-14. [1];. |
| U22963_at | Human class I histocompatibility antigen-like protein mRNA, complete cds. |
| RC_R09230_at | yf26d08.s1 *Homo sapiens* cDNA clone 127983 3'. |
| RC_R67918_at | yi25g01.s1 *Homo sapiens* cDNA clone 140304 3'. |
| AA402119_at | zu55d04.r1 Soares ovary tumor NbHOT *Homo sapiens* cDNA clone 741895 5' similar to TR: G397579 G397579 LL5 MRNA.;. |
| AA082171_at | zn42g07.r1 Stratagene endothelial cell 937223 *Homo sapiens* cDNA clone 550140 5'. |
| R79750_at | yi89d09.r1 *Homo sapiens* cDNA clone 146417 5'. |
| RC_AA431773_at | zw80d04.s1 Soares testis NHT *Homo sapiens* cDNA clone 782503 3'. |
| RC_AA280670_at | zs97a07.s1 NCI_CGAP_GCB1 *Homo sapiens* cDNA clone IMAGE: 711540 3'. |
| AA303711_at | EST16378 Aorta endothelial cells, TNF alpha-treated *Homo sapiens* cDNA 5' end. |
| AA400361_at | zu64g03.r1 Soares testis NHT *Homo sapiens* cDNA clone 742804 5'. |
| AF007111_at | *Homo sapiens* MDM2-like p53-binding protein (MDMX) mRNA, complete cds. |
| AA504384_at | aa59c02.r1 NCI_CGAP_GCB1 *Homo sapiens* cDNA clone IMAGE: 825218 5' similar to contains element MIR repetitive element;. |
| N88108_at | K1565F Fetal heart, Lambda ZAP Express *Homo sapiens* cDNA clone K1565 5' similar to EST(YD54C09.R1). |
| RC_AA447769_at | aa20e01.s1 Soares NhHMPu S1 *Homo sapiens* cDNA clone 813816 3'. | or a sequence as identified below

| UniGene number | Homologous to |
| --- | --- |
| AA402119_at | Zu55d04.r1 Soares ovary tumor NbHOT *Homo sapiens* cDNA clone 741895 5' similar to TR: G397579 G397579 LL5 MRNA.;, |
| RC_AA102581_at | Zn42d02.s1 Stratagene endothelial cell 937223 *Homo sapiens* cDNA clone 550083 3', |
| RC_H14089_at | Ym62c07.s1 *Homo sapiens* cDNA clone 163500 3', |
| RC_R46079_f_at | Yg49c02.s1 *Homo sapiens* cDNA clone 36133 3', |
| RC_R67918_at | Yi25g01.s1 *Homo sapiens* cDNA clone 140304 3', |
| RC_W15360_at | Zc17d10.s1 Soares parathyroid tumor NbHPA *Homo sapiens* cDNA clone 322579 3' similar to PIR: S39983 S39983 eps8 protein - mouse;, |
| AA082171_at | Zn42g07.r1 Stratagene endothelial cell 937223 *Homo sapiens* cDNA clone 550140 5', |
| AA425593_at | Zw48f02.r1 Soares total fetus Nb2HF8 9w *Homo sapiens* cDNA clone 773307 5', |
| F15201_at | *H. sapiens* partial cDNA sequence, |
| H15219_at | Ym30f02.r1 *Homo sapiens* cDNA clone 49693 5', |
| R60368_at | Yh04b02.r1 *Homo sapiens* cDNA clone 42052 5', |
| R86859_at | Ym86a02.r1 *Homo sapiens* cDNA clone 165770 5', |
| RC_AA045342_at | Zk59g01.s1 Soares pregnant uterus NbHPU *Homo sapiens* cDNA clone 487152 3', |
| RC_AA171985_at | Zo98g05.s1 Stratagene ovarian cancer (#937219) *Homo sapiens* cDNA clone 594968 3', |
| T63174_s_at | Yc04e08.r1 *Homo sapiens* cDNA clone 79718 5' similar to contains Alu repetitive element;, |
| U90268_at | Human Krit1 mRNA, complete cds, |
| X14787_at | Human mRNA for thrombospondin |
| RC_AA196991_s_at | Zq10a10.s1 Stratagene muscle 937209 *Homo sapiens* cDNA clone 629274 3' similar to TR: G1049074 G1049074 VASOPRESSIN-ACTIVATED CALCIUM-MOBILIZING PROTEIN.;, |
| RC_F02470_at | *H. sapiens* partial cDNA sequence; clone c-10c01, |
| RC_F08899_at | *H. sapiens* partial cDNA sequence; clone c-2uc10, |
| RC_H15259_at | Ym30c10.s1 *Homo sapiens* cDNA clone 49795 3', |
| RC_H52133_at | Yo44d04.s1 *Homo sapiens* cDNA clone 180775 3', |
| RC_R17059_at | Yf45a10.s2 *Homo sapiens* cDNA clone 129786 3', |
| RC_R45292_at | Yg46b01.s1 *Homo sapiens* cDNA clone 35626 3', |

More preferably, a T1 stage gene is selected individually from any gene comprising a sequence as identified below

| | |
| --- | --- |
| D80002_at | Human mRNA for KIAA0180 gene, partial cds |
| D82418_at | similar to none. |
| N28843_at | yx59d10.r1 *Homo sapiens* cDNA clone 266035 5'. |
| RC_F02541_at | *H. sapiens* partial cDNA sequence; clone c-12c11. |
| RC_N30806_at | yw65f02.s1 *Homo sapiens* cDNA clone 257115 3'. |
| RC_R33146_at | yh81f02.s1 *Homo sapiens* cDNA clone 136155 3' similar to contains Alu repetitive element;. |
| RC_R40166_at | yf70a09.s1 *Homo sapiens* cDNA clone 27448 3'. |
| RC_R65998_at | yi23g09.s1 *Homo sapiens* cDNA clone 140128 3'. |
| RC_AA027823_at | zk05c04.s1 Soares pregnant uterus NbHPU *Homo sapiens* cDNA clone 469638 3'. |
| RC_AA084138_at | zn17a03.s1 Stratagene neuroepithelium NT2RAMI 937234 *Homo sapiens* cDNA clone 547660 3'. |
| RC_AA223902_at | zr13a10.s1 Stratagene hNT neuron (#937233) *Homo sapiens* cDNA clone 648666 3'. |
| RC_AA424524_at | zv90g02.s1 Soares NhHMPu S1 *Homo sapiens* cDNA clone 767090 3'. |
| RC_AA505136_at | aa65d11.s1 NCI_CGAP_GCB1 *Homo sapiens* cDNA clone IMAGE: 825813 3'. |
| AA043223_at | zk55g12.r1 Soares pregnant uterus NbHPU *Homo sapiens* cDNA clone 486790 5'. | or a sequence as identified below

| UniGene number | Homologous to |
|---|---|
| C01360_at | HUMGS0008341, Human Gene Signature, 3'-directed cDNA sequence, |
| D80002_at | Human mRNA for KIAA0180 gene, partial cds |
| RC_AA149586_at | Zl39e03.s1 Soares pregnant uterus NbHPU *Homo sapiens* cDNA clone 504316 3', |
| RC_H68772_at | Yr83f01.s1 *Homo sapiens* cDNA clone 211897 3', |
| RC_N30806_at | Yw65f02.s1 *Homo sapiens* cDNA clone 257115 3', |
| RC_N63143_at | Yz37c12.s1 *Homo sapiens* cDNA clone 285238 3', |
| RC_R33146_at | Yh81f02.s1 *Homo sapiens* cDNA clone 136155 3' similar to contains Alu repetitive element;, |
| RC_R46206_at | Yj53d08.s1 *Homo sapiens* cDNA clone 152463 3', |
| RC_R49731_s_at | Yg71e10.s1 *Homo sapiens* cDNA clone 38554 3', |
| AA043223_at | Zk55g12.r1 Soares pregnant uterus NbHPU *Homo sapiens* cDNA clone 486790 5', |
| AB002346_at | Human mRNA for KIAA0348 gene, complete cds, |
| D81608_at | Human fetal brain cDNA 5'-end GEN-177B09, |
| M83670_s_at | Human carbonic anhydrase IV mRNA, complete cds |
| N28843_at | Yx59d10.r1 *Homo sapiens* cDNA clone 266035 5', |
| RC_AA149044_at | Zl45d09.s1 Soares pregnant uterus NbHPU *Homo sapiens* cDNA clone 504881 3', |
| RC_AA258130_at | Zs35f03.s1 NCI_CGAP_GCB1 *Homo sapiens* cDNA clone IMAGE: 687197 3', |
| RC_AA281743_r_at | Zt06h05.s1 NCI_CGAP_GCB1 *Homo sapiens* cDNA clone IMAGE: 712377 3', |
| RC_AA406338_at | Zv10f06.s1 Soares NhHMPu S1 *Homo sapiens* cDNA clone 753251 3', |
| RC_AA424524_at | Zv90g02.s1 Soares NhHMPu S1 *Homo sapiens* cDNA clone 767090 3', |
| RC_AA435840_at | Zt80b08.s1 Soares testis NHT *Homo sapiens* cDNA clone 728631 3', |
| RC_AA027823_at | Zk05c04.s1 Soares pregnant uterus NbHPU *Homo sapiens* cDNA clone 469638 3', |
| RC_AA084138_at | Zn17a03.s1 Stratagene neuroepithelium NT2RAMI 937234 *Homo sapiens* cDNA clone 547660 3', |
| RC_AA135406_at | Zo28e08.s1 Stratagene colon (#937204) *Homo sapiens* cDNA clone 588230 3', |
| RC_AA148923_at | Zl27g11.s1 Soares pregnant uterus NbHPU *Homo sapiens* cDNA clone 503204 3', |
| RC_H98653_at | Yx12h06.s1 *Homo sapiens* cDNA clone 261563 3', |
| RC_N30077_at | Yw81g11.s1 *Homo sapiens* cDNA clone 258692 3', |
| RC_R40166_at | Yf70a09.s1 *Homo sapiens* cDNA clone 27448 3', |
| RC_T90374_at | Yd43e03.s1 *Homo sapiens* cDNA clone 111004 3' similar to SP: POL2_MOUSE P11369 RETROVIRUS-RELATED POL POLYPROTEIN;, |
| RC_Z38182_at | *H. sapiens* partial cDNA sequence; clone c-02a08, |

In yet another preferred embodiment a T2-T4 stage gene is selected individually from any gene comprising a sequence as identified below

| UniGene number | Homologous to |
|---|---|
| RC_R00083_at | ye73c08.s1 *Homo sapiens* cDNA clone 123374 3'. |
| RC_R71391_at | yj80e01.s1 *Homo sapiens* cDNA clone 155064 3'. |
| RC_T23991_at | seq2147 *Homo sapiens* cDNA clone NHB3MK-9 3'. |
| RC_T79196_at | yd70f06.s1 *Homo sapiens* cDNA clone 113603 3' similar to contains Alu repetitive element;. |
| RC_AA130596_at | zo26a09.s1 Stratagene colon (#937204) *Homo sapiens* cDNA clone 587992 3'. |
| RC_AA459310_r_at | zx89d06.s1 Soares ovary tumor NbHOT *Homo sapiens* cDNA clone 810923 3'. |
| RC_AA490965_at | aa48f12.s1 NCI_CGAP_GCB1 *Homo sapiens* cDNA clone IMAGE: 824207 3'. |
| U88047_at | Human DNA binding protein homolog (DRX) mRNA, partial cds |
| X56807_at | Human DSC2 mRNA for desmocollins type 2a and 2b |
| AA011479_at | zi01b10.r1 Soares fetal liver spleen 1NFLS S1 *Homo sapiens* cDNA clone 429499 5'. |
| AA296821_at | EST112387 Aorta endothelial cells *Homo sapiens* cDNA 5' end. | or a sequence as identified below

| | |
|---|---|
| RC_AA054726_at | Zk68e06.s1 Soares pregnant uterus NbHPU *Homo sapiens* cDNA clone 488002 3', |
| RC_AA206042_at | Zq77f02.s1 Stratagene hNT neuron (#937233) *Homo sapiens* cDNA clone 647643 3' similar to contains element MSR1 repetitive element;, |
| RC_R98735_at | Yr31g12.s1 *Homo sapiens* cDNA clone 206950 3', |
| AA115572_s_at | Zl05d11.r1 Soares pregnant uterus NbHPU *Homo sapiens* cDNA clone 491445 5' similar to TR: G895845 G895845 PUTATIVE P64 CLCP PROTEIN,;, |
| AA430979_at | PMY0789 KG1a Lambda Zap Express cDNA Library *Homo sapiens* cDNA 5', |
| AA489287_at | ab36e04.r1 Stratagene HeLa cell s3 937216 *Homo sapiens* cDNA clone 842910 5', |
| D82226_s_at | similar to TAT-binding protein-2, |
| H49499_s_at | yq20g10.r1 Soares fetal liver spleen 1NFLS *Homo sapiens* cDNA clone 274386 5', |
| M11844_at | Human prealbumin gene, complete cds, |
| RC_AA026388_at | ze92c03.s1 Soares fetal heart NbHH19W *Homo sapiens* cDNA clone 366436 3', |
| RC_AA044601_at | zk55d05.s1 Soares pregnant uterus NbHPU *Homo sapiens* cDNA clone 486729 3', |
| RC_AA182030_at | zp57a03.s1 Stratagene endothelial cell 937223 *Homo sapiens* cDNA clone 624268 3', |
| RC_AA233451_at | zr30b02.s1 Stratagene NT2 neuronal precursor 937230 *Homo sapiens* cDNA clone 664875 3', |
| RC_AA236493_at | zr75c10.s1 Soares NhHMPu S1 *Homo sapiens* cDNA clone 669234 3', |
| RC_AA401098_f_at | zu50g01.s1 Soares ovary tumor NbHOT *Homo sapiens* cDNA clone 741456 3' similar to contains Alu repetitive element; contains element THR repetitive element;, |
| RC_AA441818_at | zw62f01.s1 Soares total fetus Nb2HF8 9w *Homo sapiens* cDNA clone 774649 3', |
| RC_AA478109_at | zt89d04.s1 Soares testis NHT *Homo sapiens* cDNA clone 729511 3', |
| RC_AA481430_at | zv06g11.s1 Soares NhHMPu S1 *Homo sapiens* cDNA clone 752900 3', |
| RC_AA488878_at | aa55f02.s1 NCI_CGAP_GCB1 *Homo sapiens* cDNA clone IMAGE: 824859 3', |
| RC_AA599032_at | ae41h03.s1 Gessler Wilms tumor *Homo sapiens* cDNA clone 898421 3', |
| S73288_at | small proline-rich protein SPRK [human, odontogenic keratocysts, mRNA Partial, 317 nt], |
| U87459_at | Human autoimmunogenic cancer/testis antigen NY-ESO-1 mRNA, complete cds |
| U88047_at | Human DNA binding protein homolog (DRX) mRNA, partial cds |
| RC_AA063574_at | ze25f03.s1 Soares fetal heart NbHH19W *Homo sapiens* cDNA clone 360029 3' similar to gb: X52104 P68 PROTEIN (HUMAN);, |
| RC_AA132524_at | zo20c04.s1 Stratagene colon (#937204) *Homo sapiens* cDNA clone 587430 3' similar to contains Alu repetitive element;, |
| RC_F09317_at | *H. sapiens* partial cDNA sequence; clone c-2zh11, |
| RC_H12863_at | yj14b12.s1 *Homo sapiens* cDNA clone 148703 3', |
| RC_N33927_s_at | yv25e09.s1 *Homo sapiens* cDNA clone 243784 3', |
| RC_R08189_at | yf18f03.s1 *Homo sapiens* cDNA clone 127229 3', |
| RC_R39191_s_at | yc89c12.s1 *Homo sapiens* cDNA clone 23345 3', |
| RC_T82323_at | AS322 *Homo sapiens* cDNA clone AS322 3', |
| RC_T90746_at | yd41f10.s1 *Homo sapiens* cDNA clone 110827 3', |
| RC_Z39338_at | *H. sapiens* partial cDNA sequence; clone c-17f11, | or preferably any gene comprising a sequence as identified below

| | |
|---|---|
| AA011479_at | zi01b10.r1 Soares fetal liver spleen 1NFLS S1 *Homo sapiens* cDNA clone 429499 5', |
| AA314779_at | EST186601 Colon carcinoma (HCC) cell line II *Homo sapiens* cDNA 5' end, |
| RC_AA084640_at | zn20d05.s1 Stratagene neuroepithelium NT2RAMI 937234 *Homo sapiens* cDNA clone 547977 3', |
| RC_AA121534_at | zk89d11.s1 Soares pregnant uterus NbHPU *Homo sapiens* cDNA clone 490005 3' similar to gb: X79535 TUBULIN BETA-2 CHAIN (HUMAN);, |

-continued

| | |
|---|---|
| RC_AA131047_s_at | zo16f05.s1 Stratagene colon (#937204) *Homo sapiens* cDNA clone 587073 3', |
| RC_AA461549_at | zx62b09.s1 Soares total fetus Nb2HF8 9w *Homo sapiens* cDNA clone 796025 3', |
| RC_AA491465_at | ab04a05.s1 Stratagene fetal retina 937202 *Homo sapiens* cDNA clone 839792 3', |
| RC_AA496936_at | ae32d03.s1 Gessler Wilms tumor *Homo sapiens* cDNA clone 897509 3', |
| RC_AA598689_at | ae49a08.s1 Stratagene lung carcinoma 937218 *Homo sapiens* cDNA clone 950198 3', |
| W26392_at | 30g3 Human retina cDNA randomly primed sublibrary *Homo sapiens* cDNA, |
| RC_AA004887_at | zh90g01.s1 Soares fetal liver spleen 1NFLS S1 *Homo sapiens* cDNA clone 428592 3', |
| RC_AA135153_at | zo24g02.s1 Stratagene colon (#937204) *Homo sapiens* cDNA clone 587858 3', |
| RC_AA197311_s_at | zq50e09.s1 Stratagene neuroepithelium (#937231) *Homo sapiens* cDNA clone 645064 3' similar to gb: M24283 INTERCELLULAR ADHESION MOLECULE-1 PRECURSOR (HUMAN);, |
| RC_H80622_at | yu77b06.s1 *Homo sapiens* cDNA clone 239795 3', |
| RC_N64436_at | za33a09.s1 *Homo sapiens* cDNA clone 294328 3', |
| RC_N67583_at | yz42c02.s1 *Homo sapiens* cDNA clone 285698 3', |
| RC_R38678_at | yc89d05.s1 *Homo sapiens* cDNA clone 23443 3', |
| RC_R56066_s_at | yg91d08.s1 *Homo sapiens* cDNA clone 40992 3', |
| RC_R59292_at | yh16a10.s1 *Homo sapiens* cDNA clone 37689 3', |
| RC_T24099_at | seq2287 *Homo sapiens* cDNA clone Cot250Ft-b4HB3MA-8 3', |
| AA150364_at | zl07b03.r1 Soares pregnant uterus NbHPU *Homo sapiens* cDNA clone 491597 5', |
| AA174185_at | PTH207 HTCDL1 *Homo sapiens* cDNA 5'/3', |
| AA452353_i_at | zx15d05.r1 Soares total fetus Nb2HF8 9w *Homo sapiens* cDNA clone 786537 5', |
| AB002316_at | Human mRNA for KIAA0318 gene, partial cds, |
| H86858_at | ys72d05.r1 *Homo sapiens* cDNA clone 220329 5', |
| M93119_s_at | Human zinc-finger DNA-binding motifs (IA-1) mRNA, complete cds |
| R72037_at | yj86c09.r1 *Homo sapiens* cDNA clone 155632 5', |
| RC_AA004274_at | zh97f02.s1 Soares fetal liver spleen 1NFLS S1 *Homo sapiens* cDNA clone 429243 3' similar to contains element MER22 repetitive element;, |
| RC_AA004415_at | zh89b04.s1 Soares fetal liver spleen 1NFLS S1 *Homo sapiens* cDNA clone 428431 3', |
| RC_AA007160_at | 13cDNA30A-3,seq Soares infant brain 1NIB *Homo sapiens* cDNA clone HY18-3 3', |
| RC_AA053660_at | zl74e07.s1 Stratagene colon (#937204) *Homo sapiens* cDNA clone 510372 3' similar to contains Alu repetitive element;, |
| RC_AA252603_at | zs14a11.s1 NCI_CGAP_GCB1 *Homo sapiens* cDNA clone IMAGE: 685148 3', |
| RC_AA411944_at | zu03h01.s1 Soares testis NHT *Homo sapiens* cDNA clone 730801 3', |
| RC_AA412700_at | zu12g03.s1 Soares testis NHT *Homo sapiens* cDNA clone 731668 3', |
| RC_AA430032_at | zw65f05.s1 Soares testis NHT *Homo sapiens* cDNA clone 781089 3', |
| RC_AA430368_at | zw20f06.s1 Soares ovary tumor NbHOT *Homo sapiens* cDNA clone 769859 3', |
| RC_AA434113_at | zw24b11.s1 Soares ovary tumor NbHOT *Homo sapiens* cDNA clone 770205 3' similar to contains element TAR1 repetitive element;, |
| RC_AA441791_at | zw62c02.s1 Soares total fetus Nb2HF8 9w *Homo sapiens* cDNA clone 774626 3', |
| RC_AA449419_at | zx05b03.s1 Soares total fetus Nb2HF8 9w *Homo sapiens* cDNA clone 785549 3', |
| RC_AA449914_at | zx37g02.s1 Soares total fetus Nb2HF8 9w *Homo sapiens* cDNA clone 788690 3', |
| RC_D59847_at | Human fetal brain cDNA 3'-end GEN-070G07, |
| T95813_f_at | ye45f10.r1 *Homo sapiens* cDNA clone 120715 5' similar to gb: V00493_rna1 HEMOGLOBIN ALPHA CHAIN (HUMAN);, |
| W80846_at | zd83f05.r1 Soares fetal heart NbHH19W *Homo sapiens* cDNA clone 347265 5' similar to SW: SYB2_XENLA P47193 SYNAPTOBREVIN 2;, |
| RC_AA031360_s_at | zk16f07.s1 Soares pregnant uterus NbHPU *Homo sapiens* cDNA clone 470725 3', |
| RC_AA063624_at | ze87h05.s1 Soares fetal heart NbHH19W *Homo sapiens* cDNA clone 366009 3' similar to TR: G300372 G300372 CELL GROWTH REGULATING NUCLEOLAR PROTEIN,;, |
| RC_AA076238_at | zm19e04.s1 Stratagene pancreas (#937208) *Homo sapiens* cDNA clone 526110 3' similar to contains Alu repetitive element;, |
| RC_AA076350_at | zm91a02.s1 Stratagene ovarian cancer (#937219) *Homo sapiens* cDNA clone 545258 3', |

-continued

| | |
|---|---|
| RC_AA101983_at | zk87c02.s1 Soares pregnant uterus NbHPU *Homo sapiens* cDNA clone 489794 3', |
| RC_AA151245_at | zl40f12.s1 Soares pregnant uterus NbHPU *Homo sapiens* cDNA clone 504431 3', |
| RC_AA164252_f_at | zq46f06.s1 Stratagene hNT neuron (#937233) *Homo sapiens* cDNA clone 632771 3', |
| RC_AA167006_at | zo86b08.s1 Stratagene ovarian cancer (#937219) *Homo sapiens* cDNA clone 593751 3', |
| RC_AA206225_at | zq56g08.s1 Stratagene neuroepithelium (#937231) *Homo sapiens* cDNA clone 645662 3', |
| RC_D62834_at | Human aorta cDNA 3'-end GEN-330D04, |
| RC_D80981_at | Human fetal brain cDNA 3'-end GEN-121E12, |
| RC_H16772_at | ym34g02.s1 *Homo sapiens* cDNA clone 50227 3', |
| RC_N62522_at | yz74f08.s1 *Homo sapiens* cDNA clone 288807 3', |
| RC_N68222_at | yz56e12.s1 *Homo sapiens* cDNA clone 287086 3', |
| RC_T10316_s_at | seq1014 *Homo sapiens* cDNA clone b4HB3MA-COT8-HAP-Ft266 3', |
| RC_W37382_at | zc12c07.s1 Soares parathyroid tumor NbHPA *Homo sapiens* cDNA clone 322092 3', |
| RC_W60582_at | zd25e10.s1 Soares fetal heart NbHH19W *Homo sapiens* cDNA clone 341706 3' similar to gb: M38188 OVARIAN GRANULOSA CELL 13,0 KD PROTEIN HGR74 (HUMAN);, |
| RC_W84768_at | zh53d03.s1 Soares fetal liver spleen 1NFLS S1 *Homo sapiens* cDNA clone 415781 3' similar to contains L1,b1 L1 repetitive element;, |

25 or a sequence as identified below expressed in solid tumors

| | |
|---|---|
| RC_AA026418_at | ze92h01.s1 Soares fetal heart NbHH19W *Homo sapiens* cDNA clone 366481 3'. |
| RC_D59847_at | Human fetal brain cDNA 3'-end GEN-070G07. |
| RC_T24099_at | seq2287 *Homo sapiens* cDNA clone Cot250Ft-b4HB3MA-8 3'. |
| RC_R59292_at | yh16a10.s1 *Homo sapiens* cDNA clone 37689 3'. |
| RC_W60582_at | zd25e10.s1 Soares fetal heart NbHH19W *Homo sapiens* cDNA clone 341706 3' similar to gb: M38188 OVARIAN GRANULOSA CELL 13.0 KD PROTEIN HGR74 (HUMAN);. |
| M63262_at | Human 5-lipoxygenase activating protein (FLAP) gene |
| RC_R38678_at | yc89d05.s1 *Homo sapiens* cDNA clone 23443 3'. |
| W60268_at | zd29g01.r1 Soares fetal heart NbHH19W *Homo sapiens* cDNA clone 342096 5'. |
| AA465016_at | zx80d02.r1 Soares ovary tumor NbHOT *Homo sapiens* cDNA clone 810051 5' similar to TR: G1020091 G1020091 NEUROPSIN.; contains element LTR3 repetitive element;. |
| RC_T79842_at | yd83f04.s1 *Homo sapiens* cDNA clone 114847 3'. |
| RC_AA206225_at | zq56g08.s1 Stratagene neuroepithelium (#937231) *Homo sapiens* cDNA clone 645662 3'. |
| RC_AA449914_at | zx37g02.s1 Soares total fetus Nb2HF8 9w *Homo sapiens* cDNA clone 788690 3'. |
| RC_F10211_at | *H. sapiens* partial cDNA sequence; clone c-3bh08. |
| RC_AA480109_r_at | zv41f05.s1 Soares ovary tumor NbHOT *Homo sapiens* cDNA clone 756225 3' similar to TR: G498729 G498729 ZINC FINGER PROTEIN;. |
| RC_AA053102_s_at | zl72a06.s1 Stratagene colon (#937204) *Homo sapiens* cDNA clone 510130 3'. |
| RC_AA434113_at | zw24b11.s1 Soares ovary tumor NbHOT *Homo sapiens* cDNA clone 770205 3' similar to contains element TAR1 repetitive element;. |
| RC_AA441791_at | zw62c02.s1 Soares total fetus Nb2HF8 9w *Homo sapiens* cDNA clone 774626 3'. |
| RC_N67583_at | yz42c02.s1 *Homo sapiens* cDNA clone 285698 3'. |
| RC_T96077_at | ye47b12.s1 *Homo sapiens* cDNA clone 120863 3'. |
| AB002316_at | Human mRNA for KIAA0318 gene, partial cds. |
| RC_W96222_at | ze10g07.s1 Soares fetal heart NbHH19W *Homo sapiens* cDNA clone 358620 3'. |
| M16591_s_at | Human hemopoietic cell protein-tyrosine kinase (HCK) gene. complete cds, clone lambda-a2/1a |
| RC_N59808_at | yz76b12.s1 *Homo sapiens* cDNA clone 288959 3'. |
| RC_F10040_at | *H. sapiens* partial cDNA sequence; clone c-39g09. |
| RC_AA461549_at | zx62b09.s1 Soares total fetus Nb2HF8 9w *Homo sapiens* cDNA clone 796025 3'. |
| RC_W68683_at | zd35d04.s1 Soares fetal heart NbHH19W *Homo sapiens* cDNA clone 342631 3'. |
| RC_AA084640_at | zn20d05.s1 Stratagene neuroepithelium NT2RAMl 937234 *Homo sapiens* cDNA clone 547977 3'. |

-continued

| | |
|---|---|
| C01169_at | HUMGS0007858, Human Gene Signature, 3'-directed cDNA sequence. |
| RC_AA491465_at | ab04a05.s1 Stratagene fetal retina 937202 *Homo sapiens* cDNA clone 839792 3'. |
| RC_W67564_s_at | zd41c07.s1 Soares fetal heart NbHH19W *Homo sapiens* cDNA clone 343212 3'. |
| J03019_s_at | Human beta-1-adrenergic receptor mRNA, complete cds. |
| RC_H80622_at | yu77b06.s1 *Homo sapiens* cDNA clone 239795 3'. |
| RC_N34686_at | yy15h06.s1 *Homo sapiens* cDNA clone 271355 3'. |
| RC_R56066_s_at | yg91d08.s1 *Homo sapiens* cDNA clone 40992 3'. |
| RC_T34611_at | EST71577 *Homo sapiens* cDNA 3' end similar to None. |
| RC_AA031373_s_at | zk15e12.s1 Soares pregnant uterus NbHPU *Homo sapiens* cDNA clone 470638 3'. |
| X52056_at | Human mRNA for spi-1 proto-oncogene |
| N77564_at | yz89g12.r1 *Homo sapiens* cDNA clone 290278 5'. |
| C01765_at | HUMGS0003713, Human Gene Signature, 3'-directed cDNA sequence. |
| RC_AA496936_at | ae32d03.s1 Gessler Wilms tumor *Homo sapiens* cDNA clone 897509 3'. |
| RC_AA027103_at | zk04e03.s1 Soares pregnant uterus NbHPU *Homo sapiens* cDNA clone 469564 3'. |
| RC_R44131_at | yg32c11.s1 *Homo sapiens* cDNA clone 34089 3'. |
| RC_N67227_at | yz48f04.s1 *Homo sapiens* cDNA clone 286303 3'. |
| RC_T96677_at | ye52f03.s1 *Homo sapiens* cDNA clone 121373 3'. |
| RC_AA134965_i_at | zo23g05.s1 Stratagene colon (#937204) *Homo sapiens* cDNA clone 587768 3'. |
| RC_T86600_at | yd87d10.s1 *Homo sapiens* cDNA clone 115219 3'. |
| RC_AA054087_at | zf51f03.s1 Soares retina N2bHR *Homo sapiens* cDNA clone 380477 3'. |
| AA444374_at | zv76b10.r1 Soares total fetus Nb2HF8 9w *Homo sapiens* cDNA 5'. |
| RC_H72357_at | ys04f01.s1 *Homo sapiens* cDNA clone 213817 3' similar to gb: J04970 CARBOXYPEPTIDASE M PRECURSOR (HUMAN); contains Alu repetitive element;. |
| RC_AA017045_at | ze37d11.s1 Soares retina N2b4HR *Homo sapiens* cDNA clone 361173 3'. |
| AA010324_at | zi09c03.r1 Soares fetal liver spleen 1NFLS S1 *Homo sapiens* cDNA clone 430276 5'. |
| RC_AA234743_at | zs38b09.s1 Soares NhHMPu S1 *Homo sapiens* cDNA clone 687449 3'. |
| RC_AA055892_at | zf20d06.s1 Soares fetal heart NbHH19W *Homo sapiens* cDNA clone 377483 3'. |
| RC_AA446650_at | zw89g02.s1 Soares total fetus Nb2HF8 9w *Homo sapiens* cDNA clone 784178 3'. |
| H91747_s_at | ys80e03.r1 *Homo sapiens* cDNA clone 221116 5'. |
| AA401510_s_at | zu63c08.r1 Soares testis NHT *Homo sapiens* cDNA clone 742670 5'. |
| RC_W61239_at | zd31d10.s1 Soares fetal heart NbHH19W *Homo sapiens* cDNA clone 342259 3'. | or a sequence as identified below expressed in mixed tumors

| | |
|---|---|
| AA203639_at | zx58c10.r1 Soares fetal liver spleen 1NFLS S1 *Homo sapiens* cDNA clone 446706 5' similar to contains Alu repetitive element;. |
| M11844_at | Human prealbumin gene, complete cds. |
| RC_AA206042_at | zq77f02.s1 Stratagene hNT neuron (#937233) *Homo sapiens* cDNA clone 647643 3' similar to contains element MSR1 repetitive element;. |
| RC_N51097_at | yz03e04.s1 *Homo sapiens* cDNA clone 281982 3'. |
| RC_H05527_at | yl70f08.s1 Soares infant brain 1NIB *Homo sapiens* cDNA clone 43327 3'. |
| AA115572_s_at | zl05d11.r1 Soares pregnant uterus NbHPU *Homo sapiens* cDNA clone 491445 5' similar to TR: G895845 G895845 PUTATIVE P64 CLCP PROTEIN.;. |
| RC_H12863_at | yj14b12.s1 *Homo sapiens* cDNA clone 148703 3'. |
| AA489287_at | ab36e04.r1 Stratagene HeLa cell s3 937216 *Homo sapiens* cDNA clone 842910 5'. |
| RC_T96383_at | ye49h07.s1 *Homo sapiens* cDNA clone 121117 3'. |
| RC_H56453_at | yq98g12.s1 *Homo sapiens* cDNA clone 203878 3'. |
| RC_AA152194_at | zl03h01.s1 Soares pregnant uterus NbHPU *Homo sapiens* cDNA clone 491281 3'. |
| RC_Z38520_at | *H. sapiens* partial cDNA sequence; clone c-0ed05. |

-continued

| | |
|---|---|
| RC_R38944_at | yd06g09.s1 Homo sapiens cDNA clone 25061 3' similar to contains Alu repetitive element;. |
| RC_AA133926_at | zo16e11.s1 Stratagene colon (#937204) Homo sapiens cDNA clone 587084 3'. |
| RC_N69908_f_at | za68f06.s1 Homo sapiens cDNA clone 297731 3' similar to gb: X59244 ZINC FINGER PROTEIN 43 (HUMAN);. |
| RC_AA151945_at | zo02c02.s1 Stratagene colon (#937204) Homo sapiens cDNA clone 566498 3' similar to contains Alu repetitive element;. |
| S83308_at | SOX5 = Sry-related HMG box gene {alternatively spliced} [human, testis, mRNA, 1473 nt] |
| RC_AA406570_at | zv11b06.s1 Soares NhHMPu S1 Homo sapiens cDNA clone 753299 3'. |
| RC_AA058314_at | zl67g04.s1 Stratagene colon (#937204) Homo sapiens cDNA clone 509718 3' similar to contains Alu repetitive element; contains element PTR5 repetitive element;. |
| RC_R98735_at | yr31g12.s1 Homo sapiens cDNA clone 206950 3'. |

The genes selected may be a gene from each gene group being expressed in a significantly lower amount in that stage than in one of the other stages.

Expression Patterns

The objects of the invention are achieved by providing one or more of the embodiments described below. In one embodiment a method is provided for determining an expression pattern of a cell sample preferably independent of the proportion of submucosal, muscle and connective tissue cells present. Expression is determined of one or more genes in a sample comprising cells, said genes being selected from the same genes as discussed above and shown in the tables.

It is an object of the present invention that characteristic patterns of expression of genes can be used to characterize different types of tissue. Thus, for example gene expression patterns can be used to characterize stages and grades of bladder tumors. Similarly, gene expression patterns can be used to distinguish cells having a bladder origin from other cells. Moreover, gene expression of cells which routinely contaminate bladder tumor biopsies has been identified, and such gene expression can be removed or subtracted from patterns obtained from bladder biopsies. Further, the gene expression patterns of single-cell solutions of bladder tumor cells have been found to be substantially without interfering expression of contaminating muscle, submucosal, and connective tissue cells than biopsy samples.

The one or more genes exclude genes which are expressed in the submucosal, muscle, and connective tissue. A pattern of expression is formed for the sample which is independent of the proportion of submucosal, muscle, and connective tissue cells in the sample.

In another aspect of the invention a method of determining an expression pattern of a cell sample is provided. Expression is determined of one or more genes in a sample comprising cells. A first pattern of expression is thereby formed for the sample. Genes which are expressed in submucosal, muscle, and connective tissue cells are removed from the first pattern of expression, forming a second pattern of expression which is independent of the proportion of submucosal, muscle, and connective tissue cells in the sample.

Another embodiment of the invention provides a method for determining an expression pattern of a bladder mucosa or bladder cancer cell. Expression is determined of one or more genes in a sample comprising bladder mucosa or bladder cancer cells; the expression determined forms a first pattern of expression. A second pattern of expression which was formed using the one or more genes and a sample comprising predominantly submucosal, muscle, and connective tissue cells, is subtracted from the first pattern of expression, forming a third pattern of expression. The third pattern of expression reflects expression of the bladder mucosa or bladder cancer cells independent of the proportion of submucosal, muscle, and connective tissue cells present in the sample.

Diagnosing

In another embodiment of the invention a method is provided for detecting an invasive tumor in a patient. A marker is detected in a sample of a body fluid. The body fluid is selected from the group consisting of blood, plasma, serum, faeces, mucus, sputum, cerebrospinal fluid and/or urine. The marker is an mRNA or protein expression product of a gene which is more prevalent in submucosal, muscle, and connective tissue than in the body fluid. An increased amount of the marker in the body fluid indicates a tumor which has become invasive in the patient.

In another aspect of the invention a method is provided for diagnosing a bladder cancer. A first pattern of expression is determined of one or more genes in a sample from bladder tissue suspected of being neoplastic. The first pattern of expression is compared to a second and third reference pattern of expression. The second pattern is of the one or more genes in normal bladder mucosa and the third pattern is of the one or more genes in bladder cancer. A first pattern of expression which is found to be more similar to the third pattern than the second indicates neopiasia of the bladder tissue sample.

According to yet another aspect of the invention a method is provided for predicting the outcome, or prescribing a treatment of a bladder tumor. A first pattern of expression is determined of one or more genes in a bladder tumor sample. The first pattern is compared to one or more reference patterns of expression determined for bladder tumors at a grade between I and IV. The reference pattern which shares maximum similarity with the first pattern is identified. The outcome or treatment appropriate for the grade of tumor of the reference pattern with the maximum similarity is assigned to the bladder tumor sample.

In another embodiment of the invention a method is provided for determining the grade of a bladder tumor. A first pattern of expression is determined of one or more genes in a bladder tumor sample. The first pattern is compared to one or more reference patterns of expression determined for bladder tumors at a grade between I and IV. The grade of the reference pattern with the maximum similarity is assigned to the bladder tumor sample.

Yet another embodiment of the invention provides a method to determine the stage of a bladder tumor as described above. A first pattern of expression is determined of one or more genes in a bladder tumor sample. The first pattern is compared to one or more reference patterns of expression determined for bladder tumors at different stages. The reference pattern which shares maximum similarity with the first pattern is identified. The stage of the reference pattern with the maximum similarity is assigned to the bladder tumor sample.

In still another embodiment of the invention a method is provided for identifying a tissue sample as being from bladder. A first pattern of expression is determined for one or more genes in a tissue sample. The first pattern is compared to a second pattern of expression determined, obtained for normal mucosa cells. Similarities between the first and the second patterns suggest that the tissue sample is mucosa in its origin. This method being particularly useful when diagnosing metastasis possibly distant from its origin.

Another aspect of the invention is a method to aid in diagnosing, predicting the outcome, or prescribing treatment of bladder cancer. A first pattern of expression is determined for one or more genes in a first bladder tissue sample. And a second pattern of expression is determined for the one or more genes in a second bladder tissue sample. The first bladder tissue sample is a normal bladder mucosa sample or an earlier stage or lover grade of bladder tumor than the second bladder tissue sample. The first pattern of expression is compared to the second pattern of expression to identify a first set of genes which are increased in the second bladder tissue sample relative to the first bladder tissue sample, and a second set of genes which are decreased in the second bladder tissue sample relative to the first bladder tissue sample. Those genes which are expressed in submucosal, muscle or connective tissue are removed from the first set of genes. Those genes which are not expressed in submucosal, muscle, or connective tissue are removed from the second set of genes.

Independence of Submucosal, Muscle and Conn Ctive Tissue

Since a biopsy of the tissue often contains more tissue material such as connective tissue than the tissue to be examined, when the tissue to be examined is epithelial or mucosa, the invention also relates to methods, wherein the expression pattern of the tissue is independent of the amount of connective tissue in the sample.

Biopsies contain epithelial cells that most often are the targets for the studies, and in addition many other cells that contaminate the epithelial cell fraction to a varying extent. The contaminants include histiocytes, endothelial cells, leukocytes, nerve cells, muscle cells etc. Micro dissection is the method of choice for DNA examination, but in the case of expression studies this procedure is difficult due to RNA degradation during the procedure. The epithelium may be gently removed and the expression in the remaining submucosa and underlying connective tissue (the bladder wall) monitored. Genes expressed at high or low levels in the bladder wall should be interrogated when performing expression monitoring of the mucosa and tumors. A similar approach could be used for studies of epithelia in other organs.

In one embodiment of the invention normal mucosa lining the bladder lumen from bladders for cancer is scraped off. Then biopsies is taken from the denuded submucosa and connective tissue, reaching approximately 5 mm into the bladder wall, and immediately disintegrated in guanidinium isothiocyanate. Total RNA may be extracted, pooled, and poly(A)$^+$ mRNA may be prepared from the pool followed by conversion to double-stranded cDNA and in vitro transcription into cDNA containing biotin-labeled CTP and UTP.

Genes that are expressed and genes that are not expressed in bladder wall can both interfere with the interpretation of the expression in a biopsy, and should be considered when interpreting expression intensities in tumor biopsies, as the bladder wall component of a biopsy varies in amount from biopsy to biopsy.

When having determined the pattern of genes expressed in bladder wall components said pattern may be subtracted from a pattern obtained from the sample resulting in a third pattern related to the mucosa (epithelial) cells.

In another aspect of the invention a method is provided for determining an expression pattern of a bladder tissue sample independent of the proportion of submucosal, muscle and connective tissue cells present. A single-cell suspension of disaggregated bladder tumor cells is isolated from a bladder tissue sample comprising bladder tumor cells is isolated from a bladder tissue sample comprising bladder cells, submucosal cells, muscle cells, and connective tissue cells. A pattern of expression is thus formed for the sample which is independent of the proportion of submucosal, muscle, and connective tissue cells in the bladder tissue sample.

Yet another method relates to the elimination of mRNA from bladder wall components before determining the pattern, e.g. by filtration and/or affinity chromatography to remove mRNA related to the bladder wall.

Detection

Working with human tumor material requires biopsies, and working with RNA requires freshly frozen or immediately processed biopsies, or chemical pretreatment of the biopsy. Apart from the cancer tissue, biopsies do inevitably contain many different cell types, such as cells present in the blood, connective and muscle tissue, endothelium etc. In the case of DNA studies, microdissection or laser capture are methods of choice, however the time-dependent degradation of RNA makes it difficult to perform manipulation of the tissue for more than a few minutes. Furthermore, studies of expressed sequences may be difficult on the few cells obtained via microdissection or laser capture, as these cells may have an expression pattern that deviates from the predominant pattern in a tumor due to large intratumoral heterogeneity.

In the present context high density expression arrays may be used to evaluate the impact of bladder wall components in bladder tumor biopsies, and tested preparation of single cell solutions as a means of eliminating the contaminants. The results of these evaluations permit for the design of methods of evaluating bladder samples without the interfering background noise caused by ubiquitous contaminating submucosal, muscle, and connective tissue cells. The evaluating assays of the invention may be of any type.

While high density expression arrays can be used, other techniques are also contemplated. These include other techniques for assaying for specific mRNA species, including RT-PCR and Northern Blotting, as well as techniques for assaying for particular protein products, such as ELISA, Western blotting, and enzyme assays. Gene expression patterns according to the present invention are determined by measuring any gene product of a particular gene, including mRNA and protein. A pattern may be for one or more genes.

RNA or protein can be isolated and assayed from a test sample using any techniques known in the art. They can for example be isolated from a fresh or frozen biopsy, from formalin-fixed tissue, from body fluids, such as blood, plasma, serum, urine, or sputum.

Detection of Expression

Expression of genes may in general be detected by either detecting mRNA from the cells and/or detecting expression products, such as peptides and proteins.

mRNA Detection

The detection of mRNA of the invention may be a tool for determining the developmental stage of a cell type which may be definable by its pattern of expression of messenger RNA. For example, in particular stages of cells, high levels of ribosomal RNA are found whereas relatively low levels of other types of messenger RNAs may be found. Where a pattern is shown to be characteristic of a stage, said stage may be defined by that particular pattern of messenger RNA expression. The mRNA population is a good determinant of a developmental stage, and maybe correlated with other structural features of the cell. In this manner, cells at specific developmental stages will be characterized by the intracellular environment, as well as the extracellular environment. The present invention also allows the combination of definitions based in part upon antigens and in part upon mRNA expression. In one embodiment, the two may be combined in a single incubation step. A particular incubation condition may be found which is compatible with both hybridization recognition and non-hybridization recognition molecules. Thus, e.g. an incubation condition may be selected which allows both specificity of antibody binding and specificity of nucleic acid hybridization. This allows simultaneous performance of both types of interactions on a single matrix. Again, where developmental mRNA patterns are correlated with structural features, or with probes which are able to hybridize to intracellular mRNA populations, a cell sorter may be used to sort specifically those cells having desired mRNA population patterns.

It is within the general scope of the present invention to provide methods for the detection of mRNA. Such methods often involve sample extraction, PCR amplification, nucleic acid fragmentation and labeling, extension reactions, and transcription reactions.

Sample Preparation

The nucleic acid (either genomic DNA or mRNA) may be isolated from the sample according to any of a number of methods well known to those of skill in the art. One of skill will appreciate that where alterations in the copy number of a gene are to be detected genomic DNA is preferably isolated. Conversely; where expression levels of a gene or genes are to be detected, preferably RNA (mRNA) is isolated.

Methods of isolating total mRNA are well known to those of skill in the art. In one embodiment, the total nucleic acid is isolated from a given sample using, for example, an acid guanidinium-phenol-chloroform extraction method and polyA.sup. and mRNA is isolated by oligo dT column chromatography or by using (dT)n magnetic beads (see, e.g., Sambrook et al., Molecular Cloning: A Laboratory Manual (2nd.ed.), Vols. 1-3, Cold Spring Harbor Laboratory, (1989), or Current Protocols in Molecular Biology, F. Ausubel et al., ed. Greene Publishing and Wiley-Interscience, New York (1987)).

The sample may be from tissue and/or body fluids, as defined elsewhere herein. Before analyzing the sample, e.g., on an oligonucleotide array, it will often be desirable to perform one or more sample preparation operations upon the sample. Typically, these sample preparation operations will include such manipulations as extraction of intracellular material, e.g., nucleic acids from whole cell samples, viruses, amplification of nucleic acids, fragmentation, transcription, labeling and/or extension reactions. One or more of these various operations may be readily incorporated into the device of the present invention.

DNA Extraction

DNA extraction may be relevant under circumstances where possible mutations in the genes are to be determined in addition to the determination of expression of the genes.

For those embodiments where whole cells, or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat etc. into a crude extract followed by additional treatments to prepare the sample for subsequent operations, such as denaturation of contaminating (DNA binding) proteins, purification, filtration and desalting.

Liberation of nucleic acids from the sample cells, and denaturation of DNA binding proteins may generally be performed by physical or chemical methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins.

Alternatively, physical methods may be used to extract the nucleic acids and denature DNA binding proteins, such as physical protrusions within microchannels or sharp edged particles piercing cell membranes and extract their contents. Combinations of such structures with piezoelectric elements for agitation can provide suitable shear forces for lysis.

More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. Subjecting cells to ultrasonic agitation, or forcing cells through microgeometry apertures, thereby subjecting the cells to high shear stress resulting in rupture are also possible extraction methods.

Filtration

Following extraction, it will often be desirable to separate the nucleic acids from other elements of the crude extract, e.g. denatured proteins, cell membrane particles and salts. Removal of particulate matter is generally, accomplished by filtration or flocculation. Further, where chemical denaturing methods are used, it may be desirable to desalt the sample prior to proceeding to the next step. Desalting of the sample and isolation of the nucleic acid may generally be carried out in a single step, e.g. by binding the nucleic acids to a solid phase and washing away the contaminating salts, or performing gel filtration chromatography on the sample passing salts through dialysis membranes. Suitable solid supports for nucleic acid binding include e.g. diatomaceous earth or silica (i.e., glass wool). Suitable gel exclusion media also well known in the art may be readily incorporated into the devices of the present invention and is commercially available from, e.g., Pharmacia and Sigma Chemical.

Alternatively, desalting methods may generally take advantage of the high electrophoretic mobility and negativity of DNA compared to other elements.

Electrophoretic methods may also be utilized in the purification of nucleic acids from other cell contaminants and debris. Upon application of an appropriate electric field, the nucleic acids present in, the sample will migrate toward the positive electrode and become trapped on the capture membrane. Sample impurities remaining free of the membrane are then washed away by applying an appropriate fluid flow. Upon reversal of the voltage, the nucleic acids are released from the membrane in a substantially purer form. Further, coarse filters may also be overlaid on the barriers to avoid any fouling of the barriers by particulate matter, proteins or nucleic acids, thereby permitting repeated use.

Separation of Contaminants by Chromatography

In a similar aspect, the high electrophoretic mobility of nucleic acids with their negative charges, may be utilized to separate nucleic acids from contaminants by utilizing a short column of a gel or other appropriate matrices or gels which will slow or retard the flow of other contaminants while allowing the faster nucleic acids to pass.

This invention provides nucleic acid affinity matrices that bear a large number of different nucleic acid affinity ligands allowing the simultaneous selection and removal of a large number of preselected nucleic acids from the sample. Methods of producing such affinity matrices are also provided. In general the methods involve the steps of a) providing a nucleic acid amplification template array comprising a surface to which are attached at least 50 oligonucleotides having different nucleic acid sequences, and wherein each different oligonucleotide is localized in a predetermined region of said surface, the density of said oligonucleotides is greater than about 60 different oligonucleotides per 1 cm.sup.2, and all of said different oligonucleotides have an identical terminal 3' nucleic acid sequence and an identical terminal 5' nucleic acid sequence b) amplifying said multiplicity of oligonucleotides to provide a pool of amplified nucleic acids; and c) attaching the pool of nucleic acids to a solid support.

For example, nucleic acid affinity chromatography is based on the tendency of complementary, single-stranded nucleic acids to form a double-stranded or duplex structure through complementary base pairing. A nucleic acid (either DNA or RNA) can easily be attached to a solid substrate (matrix) where it acts as an immobilized ligand that interacts with and forms duplexes with complementary nucleic acids present in a solution contacted to the immobilized ligand. Unbound components can be washed away from the bound complex to either provide a solution lacking the target molecules bound to the affinity column, or to provide the isolated target molecules themselves. The nucleic acids captured in a hybrid duplex can be separated and released from the affinity matrix by denaturation either through heat, adjustment of salt concentration, or the use of a destabilizing agent such as formamide, TWEEN.TM.-20 denaturing agent, or sodium dodecyl sulfate (SDS).

Affinity columns (matrices) are typically used either to isolate a single nucleic acid typically by providing a single species of affinity ligand. Alternatively, affinity columns bearing a single affinity ligand (e.g. oligo dt columns) have been used to isolate a multiplicity of nucleic acids where the nucleic acids all share a common sequence (e.g. a polyA).

Affinity Matrices

The type of affinity matrix used depends on the purpose of the analysis. For example, where it is desired to analyze mRNA expression levels of particular genes in a complex nucleic acid sample (e.g., total mRNA) it is often desirable to eliminate nucleic acids produced by genes that are constitutively overexpressed and thereby tend to mask gene products expressed at characteristically lower levels. Thus, in one embodiment, the affinity matrix can be used to remove a number of preselected gene products (e.g., actin, GAPDH, etc.). This is accomplished by providing an affinity matrix bearing nucleic acid affinity ligands complementary to the gene products (e.g., mRNAs or nucleic acids derived therefrom) or to subsequences thereof. Hybridization of the nucleic acid sample to the affinity matrix will result in duplex formation between the affinity ligands and their target nucleic acids. Upon elution of the sample from the affinity matrix, the matrix will retain the duplexes nucleic acids leaving a sample depleted of the overexpressed target nucleic acids.

The affinity matrix can also be used to identify unknown mRNAs or cDNAs in a sample. Where the affinity matrix contains nucleic acids complementary to every known gene (e.g., in a cDNA library, DNA reverse transcribed from an mRNA, mRNA used directly or amplified, or polymerized from a DNA template) in a sample, capture of the known nucleic acids by the affinity matrix leaves a sample enriched for those nucleic acid sequences that are unknown. In effect, the affinity matrix is used to perform a subtractive hybridization to isolate unknown nucleic acid sequences. The remaining "unknown" sequences can then be purified and sequenced according to standard methods.

The affinity matrix can also be used to capture (isolate) and thereby purify unknown nucleic acid sequences. For example, an affinity matrix can be prepared that contains nucleic acid. (affinity ligands) that are complementary to sequences not previously identified, or not previously known to be expressed in a particular nucleic acid sample. The sample is then hybridized to the affinity matrix and those sequences that are retained on the affinity matrix are "unknown" nucleic acids. The retained nucleic acids can be eluted from the matrix (e.g. at increased temperature, increased destabilizing agent concentration, or decreased salt) and the nucleic acids can then be sequenced according to standard methods.

Similarly, the affinity matrix can be used to efficiently capture (isolate) a number of known nucleic acid sequences. Again, the matrix is prepared bearing nucleic acids complementary to those nucleic acids it is desired to isolate. The sample is contacted to the matrix under conditions where the complementary nucleic acid sequences hybridize to the affinity ligands in the matrix. The non-hybridized material is washed off the matrix leaving the desired sequences bound. The hybrid duplexes are then denatured providing a pool of the isolated nucleic acids. The different nucleic acids in the pool can be subsequently separated according to standard methods (e.g. gel electrophoresis).

As indicated above the affinity matrices can be used to selectively remove nucleic acids from virtually any sample containing nucleic acids (e.g. in a cDNA library, DNA reverse transcribed from an mRNA, mRNA used directly or amplified, or polymerized from a DNA template, and so forth). The nucleic acids adhering to the column can be removed by washing with a low salt concentration buffer, a buffer containing a destabilizing agent such as formamide, or by elevating the column temperature.

In one particularly preferred embodiment, the affinity matrix can be used in a method to enrich a sample for unknown RNA sequences (e.g. expressed sequence tags (ESTs)). The method involves first providing an affinity matrix bearing a library of oligonucleotide probes specific to known RNA (e.g., EST) sequences. Then, RNA from undifferentiated and/or unactivated cells and RNA from differentiated or activated or pathological, (e.g., transformed) or otherwise having a different metabolic state are separately hybridized against the affinity matrices to provide two pools of RNAs lacking the known RNA sequences.

In a preferred embodiment, the affinity matrix is packed into a columnar casing. The sample is then applied to the affinity matrix (e.g. injected onto a column or applied to a column by a pump such as a sampling pump driven by an autosampler). The affinity matrix (e.g. affinity column) bearing the sample is subjected to conditions under which the nucleic acid probes comprising the affinity matrix hybridize specifically with complementary target nucleic acids. Such conditions are accomplished by maintaining appropriate pH, salt and temperature conditions to facilitate hybridization as discussed above.

For a number of applications, it may be desirable to extract and separate messenger RNA from cells, cellular debris, and other contaminants. As such, the device of the present invention may, in some cases, include a mRNA purification chamber or channel. In general, such purification takes advantage of the poly-A tails on mRNA. In particular and as noted above, poly-T oligonucleotides may be immobilized within a chamber or channel of the device to serve as affinity ligands for mRNA. Poly-T oligonucleotides may be immobilized upon a solid support incorporated within the chamber or channel, or alternatively, may be immobilized upon the surface(s) of the chamber or channel itself. Immobilization of oligonucleotides on the surface of the chambers or channels may be carried out by methods described herein including, e.g., oxidation and silanation of the surface followed by standard DMT synthesis of the oligonucleotides.

In operation, the lysed sample is introduced to a high salt solution to increase the ionic strength for hybridization, whereupon the mRNA will hybridize to the immobilized poly-T. The mRNA bound to the immobilized poly-T oligonucleotides is then washed free in a low ionic strength buffer. The poly-T oligonucleotides may be immobiliized upon poroussurfaces, e.g., porous silicon, zeolites silica xerogels, scintered particles, or other solid supports.

Hybridization

Following sample preparation, the sample can be subjected to one or more different analysis operations. A variety of analysis operations may generally be performed, including size based analysis using, e.g., microcapillary electrophoresis, and/or sequence based analysis using, e.g., hybridization to an oligonucleotide array.

In the latter case, the nucleic acid sample may be probed using an array of oligonucleotide probes. Oligonucleotide arrays generally include a substrate having a large number of positionally distinct oligonucleotide probes attached to the substrate. These arrays may be produced using mechanical or light directed synthesis methods which incorporate a combination of photolithographic methods and solid phase oligonucleotide synthesis methods.

Light Directed Synthesis of Oligonucleotide Arrays

The basic strategy for light directed synthesis of oligonucleotide arrays is as follows. The surface of a solid support, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Since photolithography is used the process can be readily miniaturized to generate high density arrays of oligonucleotide probes. Furthermore, the sequence of the oligonucleotides at each site is known. See Pease et al. Mechanical synthesis methods are similar to the light directed methods except involving mechanical direction of fluids for deprotection and addition in the synthesis steps.

For some embodiments, oligonucleotide arrays may be prepared having all possible probes of a given length. The hybridization pattern of the target sequence on the array may be used to reconstruct the target DNA sequence. Hybridization analysis of large numbers of probes can be used to sequence long stretches of DNA or provide an oligonucleotide array which is specific and complementary to a particular nucleic acid sequence. For example, in particularly preferred aspects, the oligonucleotide array will contain oligonucleotide probes which are complementary to specific target sequences, and individual or multiple mutations of these. Such arrays are particularly useful in the diagnosis of specific disorders which are characterized by the presence of a particular nucleic acid sequence.

Following sample collection and nucleic acid extraction, the nucleic acid portion of the sample is typically subjected to one or more preparative reactions. These preparative reactions include in vitro transcription, labeling, fragmentation, amplification and other reactions. Nucleic acid amplification increases the number of copies of the target nucleic acid sequence of interest. A variety of amplification methods are suitable for use in the methods and device of the present invention, including for example, the polymerase chain reaction method or (PCR), the ligase chain reaction (LCR), self sustained sequence replication (3SR), and nucleic acid based sequence amplification (NASBA).

The latter two amplification methods involve isothermal reactions based on isothermal transcription, which produce both single stranded RNA (ssRNA) and double stranded DNA (dsDNA) as the amplification products in a ratio of approximately 30 or 100 to 1, respectively. As a result, where these latter methods are employed, sequence analysis may be carried out using either type of substrate, i.e. complementary to either DNA or RNA.

Frequently, it is desirable to amplify the nucleic acid sample prior to hybridization. One of skill in the art will appreciate that whatever amplification method is used, if a quantitative result is desired, care must be taken to use a method that maintains or controls for the relative frequencies of the amplified nucleic acids.

PCR

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid.

Thus, in one embodiment, this invention provides-for a method of optimizing a probe set for detection of a particular gene. Generally, this method involves providing a high density array containing a multiplicity of probes of one or more particular length(s) that are complementary to subsequences of the mRNA transcribed by the target gene. In one embodiment the high density array may contain every probe of a particular length that is complementary to a particular mRNA. The probes of the high density array are then hybridized with their target nucleic acid alone and then hybridized with a high complexity, high concentration nucleic acid sample that does not contain the targets complementary to the probes. Thus, for example, where the target nucleic acid is an RNA, the probes are first hybridized with their target nucleic acid alone and then hybridized with RNA made from a cDNA library (e.g., reverse transcribed polyA.sup.+mRNA) where the sense of the hybridized RNA is opposite that of the target nucleic acid (to insure that the high complexity sample does not contain targets for the probes). Those probes that show a strong hybridization signal with their target and little or no cross-hybridization with the high complexity sample are preferred probes for use in the high density arrays of this invention.

PCR amplification generally involves the use of one strand of the target nucleic acid sequence as a template for producing a large number of complements to that sequence. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In PCR methods, strand separation is normally achieved by heating the reaction to a sufficiently high temperature for a sufficient time to cause the denaturation of the duplex but not to cause an irreversible denaturation of the polymerase. Typical heat denaturation involves temperatures ranging from about 80.degree. C. to 105.degree. C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity.

In addition to PCR and IVT reactions, the methods and devices of the present invention are also applicable to a number of other reaction types, e.g., reverse transcription, nick translation, and the like.

Labelling Before Hybridization

The nucleic acids in a sample will generally be labeled to facilitate detection in subsequent steps. Labeling may be carried out during the amplification, in vitro transcription or nick translation processes. In particular, amplification, in vitro transcription or nick translation may incorporate a label into the amplified or transcribed sequence, either through the use of labeled primers or the incorporation of labeled dNTPs into the amplified sequence.

Hybridization between the sample nucleic acid and the oligonucleotide probes upon the array is then detected, using, e.g., epifluorescence confocal microscopy. Typically, sample is mixed during hybridization to enhance hybridization of nucleic acids in the sample to nucleoc acid probes on the array.

Labelling After Hybridization

In some cases, hybridized oligonucleotides may be labeled following hybridization. For example, where biotin labeled dNTPs are used in, e.g. amplification or transcription, streptavidin linked-reporter groups may be used to label hybridized complexes. Such operations are readily integratable into the systems of the present invention. Alternatively, the nucleic acids in the sample may be labeled following amplification. Post amplification labeling typically involves the covalent, attachment of a particular detectable group upon the amplified sequences. Suitable labels or detectable groups include a variety of fluorescent or radioactive labeling groups well known in the art. These labels may also be coupled to the sequences using methods that are well known in the art.

Methods for detection depend upon the label selected. A fluorescent label is preferred because of its extreme sensitivity and simplicity. Standard labeling procedures are used to determine the positions where interactions between a sequence and a reagent take place. For example, if a target sequence is labeled and exposed to a matrix of different probes, only those locations where probes do interact with the target will exhibit any signal. Alternatively, other methods may be used to scan the matrix to determine where interaction takes place. Of course, the spectrum of interactions may be determined in a temporal manner by repeated scans of interactions which occur at each of a multiplicity of conditions. However, instead of testing each individual interaction separately, a multiplicity of sequence interactions may be simultaneously determined on a matrix.

Means of detecting labeled target (sample) nucleic acids hybridized to the probes of the high density array are known to those of skill in the art. Thus, for example, where a colorimetric label is used, simple visualization of the label is sufficient. Where a radioactive labeled probe is used, detection of the radiation (e.g with photographic film or a solid state detector) is sufficient.

In a preferred embodiment, however, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In a particularly preferred embodiment, the excitation light source is a laser appropriate for the excitation of the fluorescent label.

The target polynucleotide may be labeled by any of a number of convenient detectable markers. A fluorescent label is preferred because it provides a very strong signal with low background. It is also optically detectable at high resolution and sensitivity through a quick scanning procedure. Other potential labeling moieties include, radioisotopes, chemiluminescent compounds, labeled, binding proteins, heavy metal atoms, spectroscopic markers, magnetic labels, and linked enzymes. Another method for labeling may bypass any label of the target sequence. The target may be exposed to the probes, and a double strand hybrid is formed at those positions only. Addition of a double strand specific reagent will detect where hybridization takes place. An intercalative dye such as ethidium bromide may be used as long as the probes themselves do not fold back on themselves to a significant extent forming hairpin loops. However, the length of the hairpin loops in short oligonucleotide probes would typically be insufficient to form a stable duplex.

Suitable chromogens will include molecules and compounds which absorb light in a distinctive range of wavelengths so that a color may be observed, or emit light when irradiated with radiation of a particular wave length or wave length range, e.g., fluorescers. Biliproteins, e.g., phycoerythrin, may also serve as labels.

A wide variety of suitable dyes are available, being primarily chosen to provide an intense color with minimal absorption by their surroundings. Illustrative dye types include quinoline dyes, triarylmethane dyes, acridine dyes, alizarine dyes, phthaleins, insect dyes, azo dyes, anthraquinoid dyes, cyanine dyes, phenazathionium dyes, and phenazoxonium dyes.

A wide variety of fluorescers may be employed either by themselves or in conjunction with quencher molecules. Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-hydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 0.4-acetamido-4-isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; auromine-0,2-(9'-anthroyl)palmitate; dansyl phosphatidylethanolamine; N,N'-dioctadecyl oxacarbocyanine; N,N'-dihexyl oxacarbocyanine; merocyanine, 4-(3'-pyrenyl)butyrate; d-3-aminodesoxy-equilenin; 1,2-(9'-anthroyl)stearate; 2-methylanthracene; 9-vinylanthracene; 2,2'-(vinylene-p-phenylene) bisbenzoxazole; p-bis)2-(4-methyl-5-phenyl-oxazolyl) benzene; 6-dimethylamino-1,2-benzophenazin; retinol; bis (3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-)p-(2-benzimidazolyl)-phenyl!maleimide; N-(4-fluoranthyl) maleimide; bis(homovanillic acid); resazarin; 4-chloro-7-nitro-2,1,3-benzooxadiazole; merocyanine 540; resorufin; rose bengal; and 2,4-diphenyl-3(2H)-furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye; Therefore, when referring to the various wavelength ranges and characteristics of the dyes, it is intended to indicate the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events.

Detectable signal may also be provided by chemiluminescent and bioluminescent sources. Chemiluminescent sources include a compound which becomes electronically excited by a chemical reaction and may then emit light which serves as the detectible signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino<calbenz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and—methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence.

Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals.

Fragmentation

In addition, amplified sequences may be subjected to other post amplification treatments. For example, in some cases, it may be desirable to fragment the sequence prior to hybridization with an oligonucleotide array, in order to provide segments which are more readily accessible to the probes, which avoid looping and/or hybridization to multiple probes. Fragmentation of the nucleic acids may generally be carried out by physical, chemical or enzymatic methods that are known in the art.

Sample Analysis

Following the various sample preparation operations, the sample will generally be subjected to one or more analysis operations. Particularly preferred analysis operations include, e.g. sequence based analyses using an oligonucleotide array and/or size based analyses using, e.g. microcapillary array electrophoresis.

Capillary Electrophoresis

In some embodiments it may be desirable to provide an additional, or alternative means for analyzing the nucleic acids from the sample Microcapillary array electrophoresis generally involves the use of a thin capillary or channel which may, or may not be filled with a particular separation medium. Electrophoresis of a sample through the capillary provides a size based separation profile for the sample. Microcapillary array electrophoresis generally provides a rapid method for size based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods these methods provide sensitivity in the range of attomoles, which is comparable to the sensitivity of radioactive sequencing methods.

In many capillary electrophoresis methods, the capillaries e.g. fused silica capillaries or channels etched, machined or molded into planar substrates, are filled with an appropriate separation/sieving matrix. Typically, a variety of sieving matrices are known in the art may be used in the microcapillary arrays. Examples of such matrices include, e.g. hydroxyethyl cellulose, polyacrylamide and agarose. Gel matrices may be introduced and polymerized within the capillary channel. However, in some cases this may result in entrapment of bubbles within the channels which can interfere with sample separations. Accordingly, it is often desirable to place a preformed separation matrix within the capillary channel(s), prior to mating the planar elements of the capillary portion. Fixing the two parts, e.g. through sonic welding, permanently fixes the matrix within the channel. Polymerization outside of the channels helps to ensure that no bubbles are formed. Further, the pressure of the welding process helps to ensure a void-free system.

In addition to its use in nucleic acid "fingerprinting" and other sized based analyses the capillary arrays may also be used in sequencing applications. In particular, gel based sequencing techniques may be readily adapted for capillary array electrophoresis.

Expression Products

In addition to detection of mRNA or as the sole detection method expression products from the genes discussed above may be detected as indications of the biological condition of the tissue. Expression products may be detected in either the tissue sample as such, or in a body fluid sample, such as blood, serum, plasma, faeces, mucus, sputum, cerebrospinal fluid, and/or urine of the individual.

The expression products, peptides and proteins, may be detected by any suitable technique known to the person skilled in the art.

In a preferred embodiment the expression products are detected by means of specific antibodies directed to the various expression products, such as immunofluorescent and/or immunohistochemical staining of the tissue.

Immunohistochemical localization of expressed proteins may be carried out by immunostaining of tissue sections from the single tumors to determine which cells expressed the protein encoded by the transcript in question. The transcript levels may be used to select a group of proteins supposed to show variation from sample to sample making a rough correlation between the level of protein detected and the intensity of the transcript on the microarray possible.

For example sections may be cut from paraffin-embedded tissue blocks, mounted, and deparaffinized by incubation at 80 C° for 10 min. followed by immersion in heated oil at 60° C. for 10 min. (Estisol 312, Estichem A/Si Denmark) and rehydration. Antigen retrieval is achieved in TEG (TrisEDTA-Glycerol) buffer using microwaves at 900 W. The tissue sections may be cooled in the buffer for 15 min before a brief rinse in tap water. Endogenous peroxidase activity is blocked by incubating the sections with 1% $H_2O_2$ for 20 min. followed by three rinses in tap water, 1 min each. The sections may then be soaked in PBS buffer for 2 min. The next steps can be modified from the descriptions given by Oncogene Science Inc., in the Mouse Immunohistochemistry Detection System, XHCO1 (UniTect, Uniondale, N.Y., USA). Briefly, the tissue sections are incubated overnight at 4° C. with primary antibody (against beta-2 microglobulin (Dako), cytokeratin 8, cystatin-C (both from Europa, US), junB, CD59, E-cadherin, apo-E, cathepsin E, vimentin, IGFII (all from Santa Cruz), followed by three rinses in PBS buffer for 5 min each. Afterwards, the sections are incubated with biotinylated secondary antibody for 30 min, rinsed three times with PBS buffer and subsequently incubated with ABC (avidin-biotinlylated horseradish peroxidase complex) for 30 min. followed by three rinses in PBS buffer.

Staining may be performed by incubation with AEC (3-amino-ethylcarbazole) for 10 min. The tissue sections are counter stained with Mayers hematoxylin, washed in tap water for 5 min. and mounted with glycerol-gelatin. Positive and negative controls may be included in each staining round with all antibodies.

In yet another embodiment the expression products may be detected by means of conventional enzyme assays, such as ELISA methods.

Furthermore, the expression products may be detected by means of peptide/protein chips capable of specifically binding the peptides and/or proteins assessed. Thereby an expression pattern may be obtained.

Assay

Thus, in a further aspect the invention relates to an assay for determining an expression pattern of a bladder cell, comprising at least a first marker and/or a second marker, wherein the first marker is capable of detecting a gene from a first gene group as defined above, and/or the second marker is capable of detecting a gene from a second gene group as defined above, correlating the first expression level and/or the second expression level to a standard level of the assessed genes to determine the presence or absence of a biological condition in the animal tissue. The marker(s) are preferably specifically detecting a gene as identified herein.

In another embodiment the assay comprises at least two markers for each gene group.

As discussed above the marker may be any nucleotide probe, such as a DNA, RNA, PNA, or LNA probe capable of hybridising to mRNA indicative of the expression level. The hybridisation conditions are preferably as described below for probes. In another embodiment the marker is an antibody capable of specifically binding the expression product in question.

Detection

Patterns can be compared manually by a person or by a computer or other machine. An algorithm can be used to detect similarities and differences. The algorithm may score and compare, for example, the genes which are expressed and the genes which are not expressed. Alternatively, the algorithm may look for changes in intensity of expression of a particular gene and score changes in intensity between two samples. Similarities may be determined on the basis of genes which are expressed in both samples and genes which are not expressed in both samples or on the basis of genes whose intensity of expression are numerically similar.

Generally, the detection operation will be performed using a reader device external to the diagnostic device. However, it may be desirable in some cases to incorporate the data gathering operation into the diagnostic device itself.

The detection apparatus may be a fluorescence detector, or a spectroscopic detector, or another detector.

Although hybridization is one type of specific interaction which is clearly useful for use in this mapping embodiment antibody reagents may also be very useful.

Data Gathering and Analysis

Gathering data from the various analysis operations, e.g. oligonucleotide and/or microcapillary arrays will typically be carried out using methods known in the art. For example, the arrays may be scanned using lasers to excite fluorescently labeled targets that have hybridized to regions of probe arrays mentioned above, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like.

It is an object of the present invention to provide a biological sample which may be classified or characterized by analyzing the pattern of specific interactions mentioned above. This may be applicable to a cell or tissue type, to the messenger RNA population expressed by a cell to the genetic content of a cell, or to virtually any sample which can be classified and/or identified by its combination of specific molecular properties.

Pharmaceutical Composition

The invention also relates to a pharmaceutical composition for treating a biological condition, such as bladder tumors.

In one embodiment the pharmaceutical composition comprises one or more of the peptides being expression products as defined above. In a preferred embodiment, the peptides are bound to carriers. The peptides may suitably be coupled to a polymer carrier, for example a protein carrier, such as BSA. Such formulations are well-known to the person skilled in the art.

The peptides may be suppressor peptides normally lost or decreased in tumor tissue administered in order to stabilise tumors towards a less malignant stage. In another embodiment the peptides are onco-peptides capable of eliciting an immune response towards the tumor cells.

In another embodiment the pharmaceutical composition comprises genetic material, either genetic material for substitution therapy, or for suppressing therapy as discussed below.

In a third embodiment the pharmaceutical composition comprises at least one anti-body produced as described above.

In the present context the term pharmaceutical composition is used synonymously with the, term medicament. The medicament of the invention comprises an effective amount of one or more of the compounds as defined above, or a composition as defined above in combination with pharmaceutically acceptable additives. Such medicament may suitably be formulated for oral, percutaneous, intramuscular, intravenous, intracranial, intrathecal, intracerebroventricular, intranasal or pulmonal administration. For most indications a localised or substantially localised application is preferred.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either: as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules and nanoparticles.

The preparation may suitably be administered by injection, optionally at the site, where the active ingredient is to exert its effect. Additional formulations which are suitable for other modes of administration include suppositories, and in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium, saccharine, cellulose, magnesium carbonate, and the like. These compositions take the form of solutions, suspensions, tablets, pills, capsules, sustained release formations or powders and generally contain 10-95% of the active ingredient(s), preferably 25-70%.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are of the order of several hundred µg active ingredient per administration with a preferred range of from about 0.1 µg to 1000 µg, such as in the range of from about 1 µg to 300 µg, and especially in the range of from about 10 µg to 50 µg. Administration may be performed once or may be followed by subsequent administrations. The dosage will also depend on the route of administration and will vary with the age and weight of the subject to be treated. A preferred dosis would be in the interval 30 mg to 70 mg per 70 kg body weight.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc.

Vaccines

In a further embodiment the present invention relates to a vaccine for the prophylaxis or treatment of a biological condition comprising at least one expression product from at least one gene said gene being expressed as defined above.

The term vaccines is used with its normal meaning, i.e preparations of immunogenic material for administration to induce in the recipient an immunity to infection or intoxication by a given infecting agent. Vaccines may be administered by intravenous injection or through oral, nasal and/or mucosal administration. Vaccines may be either simple vaccines prepared from one species of expression products, such as proteins or peptides, or a variety of expression products, or they may be mixed vaccines containing two or more simple vaccines. They are prepared in such a manner as not to destroy the immunogenic material, although the methods of preparation vary, depending on the vaccine.

The enhanced immune response achieved according to the invention can be attributable to e.g. an enhanced increase in the level of immunoglobulins or in the level of T-cells including cytotoxic T-cells will result in immunisation of at least 50% of individuals exposed to said immunogenic composition or vaccine, such as at least 55%, for example at least 60%, such as at least 65%, for example at least 70%, for example at least 75%, such as at least 80%, for example at least 85%, such as at least 90%, for example at least 92%, such as at least 94%, for example at least 96%, such as at least 97%, for example at least 98%, such as at least 98.5%, for example at least 99%, for example at least 99.5% of the individuals exposed to said immunogenic composition or vaccine are immunised.

Compositions according to the invention may also comprise any carrier and/or adjuvant known in the art including functional equivalents thereof. Functionally equivalent carriers are capable of presenting the same immunogenic determinant in essentially the same steric conformation when used under similar conditions. Functionally equivalent adjuvants are capable of providing similar increases in the efficacy of the composition when used under similar conditions.

Therapy

The invention further relates to a method of treating individuals suffering from the biological condition in question, in particular for treating a bladder tumor.

In one embodiment the invention relates to a method of substitution therapy, ie. administration of genetic material generally expressed in normal cells, but lost or decreased in biological condition cells (tumor suppressors). Thus, the invention relates to a method for reducing cell tumorigenicity or malignancy of a cell, said method comprising obtaining at least one gene selected from genes being expressed in an amount two-fold higher in normal cells than the amount expressed in said tumor cell (tumor suppressors), introducing said at least one gene into the tumor cell in a manner allowing expression of said gene(s).

The at least one gene is preferably selected individually from genes comprising a sequence as identified below

| | |
|---|---|
| RC_AA158234_at | zo76b01.s1 Stratagene pancreas (#937208) *Homo sapiens* cDNA clone 592777 3'. |
| RC_H42123_at | yo61a11.s1 *Homo sapiens* cDNA clone 182396 3'. |
| RC_Z39200_at | *H. sapiens* partial cDNA sequence; clone c-13f02. |
| RC_N21687_at | yx63h03.s1 Soares melanocyte 2NbHM *Homo sapiens* cDNA clone 266453 3'. |
| Y13645_at | *Homo sapiens* mRNA for uroplakin II. |
| RC_N98461_at | zb86b03.s1 Soares senescent fibroblasts NbHSF *Homo sapiens* cDNA clone 310445 3'. |
| RC_W92449_at | zd99d10.s1 Soares fetal heart NbHH19W *Homo sapiens* cDNA clone 357619 3'. |
| RC_Z39191_at | *H. sapiens* partial cDNA sequence; clone c-13c12. |
| RC_AA125808_at | zl29e12.s1 Soares pregnant uterus NbHPU *Homo sapiens* cDNA clone 503374 3'. |
| RC_T40767_at | ya11a06.s1 *Homo sapiens* cDNA clone 61138 3'. |
| RC_T51972_at | yb29c05.s1 *Homo sapiens* cDNA clone 72584 3'. |
| RC_AA286862_at | zs58b06.s1 NCI_CGAP_GCB1 *Homo sapiens* cDNA clone IMAGE: 701651 3'. |
| RC_N29764_at | yw91b09.s1 *Homo sapiens* cDNA clone 259577 3'. |
| AA428172_f_at | zw32b06.r1 Soares ovary tumor NbHOT *Homo sapiens* cDNA clone 770963 5'. |
| RC_H02265_at | yj35d05.s1 *Homo sapiens* cDNA clone 150729 3'. |
| RC_W44745_at | zb98a11.s1 Soares parathyroid tumor NbHPA *Homo sapiens* cDNA clone 320828 3'. |
| RC_R91819_at | yp99c05.s1 *Homo sapiens* cDNA clone 195560 3' similar to contains MER1 repetitive element;. |
| AA464468_at | zx84d05.r1 Soares ovary tumor NbHOT *Homo sapiens* cDNA clone 810441 5'. |
| RC_AA188647_at | zp78e01.s1 Stratagene HeLa cell s3 937216 *Homo sapiens* cDNA clone 626328 3' similar to TR: G998813 G998813 TIF1. [1];. |
| RC_AA405832_at | zu57g11.s1 Soares ovary tumor NbHOT *Homo sapiens* cDNA clone 742148 3' similar to TR: G780241 G780241 AU-BINDING PROTEIN/ENOYL-COA HYDRATASE.;. |
| RC_W37778_f_at | zc13b12.s1 Soares parathyroid tumor NbHPA *Homo sapiens* cDNA clone 322175 3' similar to contains LTR2.t3 LTR2 repetitive element;. |
| AF010126_at | *Homo sapiens* breast cancer-specific protein 1 (BCSG1) mRNA, complete cds. |
| N36432_at | yx83a05.r1 *Homo sapiens* cDNA clone 268304 5'. |
| RC_AA236533_s_at | zr74c04.s1 Soares NhHMPu S1 *Homo sapiens* cDNA clone 669126 3' similar to gb: S69002 ECOTROPIC VIRUS INTEGRATION 1 SITE PROTEIN (HUMAN);. |
| RC_AA293163_at | zt55e05.s1 Soares ovary tumor NbHOT *Homo sapiens* cDNA clone 726272 3'. |
| RC_AA196790_at | zq60b06.s1 Stratagene neuroepithelium (#937231) *Homo sapiens* cDNA clone 645971 3'. |
| RC_AA253220_at | zr53g12.s1 Soares NhHMPu S1 *Homo sapiens* cDNA clone 667174 3'. |
| RC_AA100437_at | zn59e02.s1 Stratagene muscle 937209 *Homo sapiens* cDNA clone 562490 3'. |

-continued

| | |
|---|---|
| RC_AA293300_s_at | zt28d03.s1 Soares ovary tumor NbHOT *Homo sapiens* cDNA clone 714437 3'. |
| RC_Z39652_at | *H. sapiens* partial cDNA sequence; clone c-1fg03. |
| M63509_s_at | Human glutathione transferase M2 (GSTM2) mRNA, complete cds |
| RC_Z39842_at | *H. sapiens* partial cDNA sequence; clone c-1ke11. |
| RC_N23319_at | yx78e10.s1 *Homo sapiens* cDNA clone 267882 3'. |
| RC_AA278817_at | zs78d11.s1 NCI_CGAP_GCB1 *Homo sapiens* cDNA clone IMAGE: 703605 3'. |
| L20773_at | *Homo sapiens* mRNA in the region near the btk gene involved in a-gamma-globulinemia |
| RC_R69276_at | yi44h05.s1 Soares placenta Nb2HP *Homo sapiens* cDNA clone 142137 3'. |
| RC_F02641_at | *H. sapiens* partial cDNA sequence; clone c-15d02. |
| RC_AA424791_at | zw03a04.s1 Soares NhHMPu S1 *Homo sapiens* cDNA clone 768174 3' similar to contains Alu repetitive element;. |
| RC_R39869_at | yf63b06.s1 *Homo sapiens* cDNA clone 26725 3'. |
| RC_AA482224_f_at | ab15c03.s1 Stratagene lung (#937210) *Homo sapiens* cDNA clone 840868 3'. |
| RC_AA025277_at | ze76f02.s1 Soares fetal heart NbHH19W *Homo sapiens* cDNA clone 364923 3' similar to contains Alu repetitive element; contains element LTR4 repetitive element;. |
| AA482319_f_at | ab15c03.r1 Stratagene lung (#937210) *Homo sapiens* cDNA clone 840868 5'. |
| RC_AA001045_at | ze47b04.s1 Soares retina N2b4HR *Homo sapiens* cDNA clone 362095 3'. |
| RC_AA130645_s_at | zo10f03.s1 Stratagene neuroepithelium NT2RAMI 937234 *Homo sapiens* cDNA clone 567293 3' similar to SW: NI2M_BOVIN Q02369 NADH-UBIQUINONE OXIDOREDUCTASE B22 SUBUNIT;. |
| RC_AA291659_at | zt37c02.s1 Soares ovary tumor NbHOT *Homo sapiens* cDNA clone 724514 3'. |
| AA046768_at | zk72d02.r1 Soares pregnant uterus NbHPU *Homo sapiens* cDNA clone 488355 5'. |
| H07011_at | yl81e01.r1 *Homo sapiens* cDNA clone 44466 5'. |
| RC_AA293533_i_at | zt54g04.s1 Soares ovary tumor NbHOT *Homo sapiens* cDNA clone 726198 3' similar to gb: J05158 CARBOXYPEPTIDASE N 83 KD CHAIN (HUMAN);. |
| RC_AA100649_at | zn63g10.s1 Stratagene HeLa cell s3 937216 *Homo sapiens* cDNA clone 562914 3' similar to SW: LCFA_ECOLI P29212 LONG-CHAIN-FATTY-ACID—COA LIGASE;. |
| RC_AA017146_at | ze41a07.s1 Soares retina N2b4HR *Homo sapiens* cDNA clone 361524 3' similar to contains element PTR7 repetitive element;. |
| RC_AA180054_at | zp40g07.s1 Stratagene muscle 937209 *Homo sapiens* cDNA clone 611964 3'. |
| AA263032_s_at | PMY0335 KG1a Lambda Zap Express cDNA Library *Homo sapiens* cDNA 5'. |
| W69310_at | zd46f07.r1 Soares fetal heart NbHH19W *Homo sapiens* cDNA clone 343717 5'. |
| RC_AA219653_at | zr05e02.s1 Stratagene NT2 neuronal precursor 937230 *Homo sapiens* cDNA clone 650618 3'. |
| RC_AA457235_at | aa91c07.s1 Stratagene fetal retina 937202 *Homo sapiens* cDNA clone 838668 3'. |
| RC_AA455967_at | aa16h10.s1 Soares NhHMPu S1 *Homo sapiens* cDNA clone 813475 3'. |
| N27670_at | yx51a09.r1 *Homo sapiens* cDNA clone 265240 5'. |
| RC_N80152_at | za65e02.s1 *Homo sapiens* cDNA clone 297434 3'. |
| RC_R64660_at | yi22a10.s1 *Homo sapiens* cDNA clone 139962 3'. |
| RC_AA147218_s_at | zo64g03.s1 Stratagene pancreas (#937208) *Homo sapiens* cDNA clone 591700 3'. |
| C01139_at | HUMGS0007818, Human Gene Signature, 3'-directed cDNA sequence. |
| AA285284_at | PMY0691 KG1a Lambda Zap Express cDNA Library *Homo sapiens* cDNA 5'. |
| RC_AA451685_at | zx44c03.s1 Soares total fetus Nb2HF8 9w *Homo sapiens* cDNA clone 789316 3'. |
| AA203222_at | zx56e01.r1 Soares fetal liver spleen 1NFLS S1 *Homo sapiens* cDNA clone 446520 5' similar to contains element MER17 repetitive element;. |
| RC_AA394071_at | zt52g01.s1 Soares ovary tumor NbHOT *Homo sapiens* cDNA clone 726000 3' similar to SW: ADG_MOUSE P22892 GAMMAADAPTIN;. |
| RC_AA479096_at | zv17e07.s1 Soares NhHMPu S1 *Homo sapiens* cDNA clone 753924 3'. |
| RC_AA156532_at | zo34b05.s1 Stratagene colon (#937204) *Homo sapiens* cDNA clone 588753 3'. |
| RC_Z40233_at | *H. sapiens* partial cDNA sequence; clone c-1wg05. |
| RC_T03927_at | seq2490 *Homo sapiens* cDNA clone 3HFLSK20-87 3'. |
| AA314457_at | EST186294 Colon carcinoma (HCC) cell line II *Homo sapiens* cDNA 5' end. |

-continued

| | |
|---|---|
| RC_N50550_at | yy89f05.s1 *Homo sapiens* cDNA clone 280737 3'. |
| RC_AA191524_at | zp88f04.s1 Stratagene HeLa cell s3 937216 *Homo sapiens* cDNA clone 627295 3'. |
| RC_N29740_at | yw90b12.s1 *Homo sapiens* cDNA clone 259487 3'. |
| RC_N48715_at | yy75h02.s1 *Homo sapiens* cDNA clone 279411 3'. |
| RC_AA463637_at | zx98h04.s1 Soares NhHMPu S1 *Homo sapiens* cDNA clone 811831 3'. |
| RC_AA404487_at | zw38a06.s1 Soares total fetus Nb2HF8 9w *Homo sapiens* cDNA clone 772306 3'. |
| RC_H16666_at | ym26a10.s1 *Homo sapiens* cDNA clone 49155 3'. |
| RC_AA406197_at | zv24d11.s1 Soares NhHMPu S1 *Homo sapiens* cDNA clone 754581 3'. |
| RC_H09594_at | yl97b11.s1 *Homo sapiens* cDNA clone 46276 3'. |
| RC_AA161085_at | zo62h09.s1 Stratagene pancreas (#937208) *Homo sapiens* cDNA clone 591521 3' similar to SW:PPAP_RAT P20646 PROSTATIC ACID PHOSPHATASE PRECURSOR;. |
| RC_AA452131_at | zx15d06.s1 Soares total fetus Nb2HF8 9w *Homo sapiens* cDNA clone 786539 3'. |
| RC_AA293533_f_at | zt54g04.s1 Soares ovary tumor NbHOT *Homo sapiens* cDNA clone 726198 3' similar to gb:J05158 CARBOXYPEPTIDASE N 83 KD CHAIN (HUMAN);. |
| RC_AA398197_at | zt59a08.s1 Soares testis NHT *Homo sapiens* cDNA clone 726614 3'. |
| AA464051_s_at | zx86d04.r1 Soares ovary tumor NbHOT *Homo sapiens* cDNA clone 810631 5'. |
| RC_T51990_at | yb29e01.s1 *Homo sapiens* cDNA clone 72600 3'. |
| RC_AA236356_at | zr54a11.s1 Soares NhHMPu S1 *Homo sapiens* cDNA clone 667196 3'. |
| W92678_at | zd92a04.r1 Soares fetal heart NbHH19W *Homo sapiens* cDNA clone 356910 5' similar to contains element LTR3 repetitive element;. |
| RC_N63332_at | yz33d11.s1 *Homo sapiens* cDNA clone 284853 3' similar to contains Alu repetitive element;. |
| C16281_s_at | Human aorta cDNA 5'-end GEN-259H09. |
| RC_AA477252_at | zu29h10.s1 Soares ovary tumor NbHOT *Homo sapiens* cDNA clone 739459 3'. |
| H88035_s_at | yw20e07.r1 *Homo sapiens* cDNA clone 252804 5'. |
| AB002387_at | Human mRNA for KIAA0389 gene, complete cds. |
| RC_R45698_at | yg45h12.s1 *Homo sapiens* cDNA clone 35838 3'. |
| RC_AA236542_at | zr75g11.s1 Soares NhHMPu S1 *Homo sapiens* cDNA clone 669284 3'. |
| AA376875_at | EST89388 Small intestine I *Homo sapiens* cDNA 5' end similar to monoamine oxidase A. |
| RC_R43365_at | yg15g06.s1 *Homo sapiens* cDNA clone 32365 3'. |
| RC_H06746_at | yl83h08.s1 *Homo sapiens* cDNA clone 44847 3'. |
| RC_AA233837_at | zr47f06.s1 Soares NhHMPu S1 *Homo sapiens* cDNA clone 666563 3'. |
| RC_AA057620_at | zf15h06.s1 Soares fetal heart NbHH19W *Homo sapiens* cDNA clone 377051 3'. |
| RC_AA450118_at | zx42e09.s1 Soares total fetus Nb2HF8 9w *Homo sapiens* cDNA clone 789160 3'. |
| RC_AA598872_at | ae37b10.s1 Gessler Wilms tumor *Homo sapiens* cDNA clone 897979 3'. |
| RC_AA147646_s_at | zl52g06.s1 Soares pregnant uterus NbHPU *Homo sapiens* cDNA clone 505594 3'. |
| RC_W04698_at | zb94b05.s1 Soares parathyroid tumor NbHPA *Homo sapiens* cDNA clone 320433 3'. |
| RC_N54365_at | yv39c06.s1 *Homo sapiens* cDNA clone 245098 3'. |
| RC_AA256208_at | zr80a08.s1 Soares NhHMPu S1 *Homo sapiens* cDNA clone 681974 3'. |
| AA046593_at | zk62g01.r1 Soares pregnant uterus NbHPU *Homo sapiens* cDNA clone 487440 5'. |
| RC_AA002088_at | zh85g03.s1 Soares fetal liver spleen 1NFLS S1 *Homo sapiens* cDNA clone 428116 3'. |
| RC_AA256273_at | zr81c12.s1 Soares NhHMPu S1 *Homo sapiens* cDNA clone 682102 3'. |
| AA491114_at | aa46e04.r1 NCI_CGAP_GCB1 *Homo sapiens* cDNA clone IMAGE:823998 5'. |
| RC_AA293719_at | zt55h03.s1 Soares ovary tumor NbHOT *Homo sapiens* cDNA clone 726293 3'. |
| RC_AA086005_at | zl84c04.s1 Stratagene colon (#937204) *Homo sapiens* cDNA clone 511302 3'. |
| RC_AA479885_at | zw44a07.s1 Soares total fetus Nb2HF8 9w *Homo sapiens* cDNA clone 772884 3'. |
| AA442428_at | zv70f08.r1 Soares total fetus Nb2HF8 9w *Homo sapiens* cDNA clone 759015 5' similar to SW:YB72_YEAST P38137 HYPOTHETICAL 60.5 KD PROTEIN IN PDB1-ABD1 INTERGENIC REGION. ;. |
| RC_AA486410_at | ab36b12.s1 Stratagene HeLa cell s3 937216 *Homo sapiens* cDNA clone 842879 3'. |

| | -continued |
|---|---|
| R15268_at | yf89f02.r1 *Homo sapiens* cDNA clone 29665 5'. |
| RC_AA443658_at | zw86a10.s1 Soares total fetus Nb2HF8 9w *Homo sapiens* cDNA clone 783834 3' similar to TR: G438639 G438639 LAMIN B RECEPTOR. [1];. |
| RC_H16790_at | ym39b01.s1 *Homo sapiens* cDNA clone 50559 3'. |
| AA465000_s_at | zx80b07.r1 Soares ovary tumor NbHOT *Homo sapiens* cDNA clone 810037 5'. |
| RC_N38930_at | yy43e04.s1 *Homo sapiens* cDNA clone 274014 3'. |
| AB002321_at | Human mRNA for KIAA0323 gene, partial cds. |
| RC_Z38810_at | *H. sapiens* partial cDNA sequence; clone c-0qb09. |
| AC000115_cds1_at | WUGSC: H_GS188P18.1a gene extracted from Human BAC clone GS188P18 |
| RC_AA255464_at | zr83b02.s1 Soares NhHMPu S1 *Homo sapiens* cDNA clone 682251 3'. |
| RC_AA255628_at | zs31g06.s1 NCI_CGAP_GCB1 *Homo sapiens* cDNA clone IMAGE: 686842 3'. |
| RC_H70554_at | yr91a03.s1 *Homo sapiens* cDNA clone 212620 3'. |
| AA309880_at | EST180743 Jurkat T-cells V *Homo sapiens* cDNA 5' end. |
| RC_R43812_at | yg21a08.s1 *Homo sapiens* cDNA clone 32940 3'. |
| RC_AA425636_at | zv47a04.s1 Soares ovary tumor NbHOT *Homo sapiens* cDNA clone 756750 3'. |
| RC_N66388_at | yz39f01.s1 *Homo sapiens* cDNA clone 285433 3'. |
| RC_AA279420_at | zs85d09.s1 NCI_CGAP_GCB1 *Homo sapiens* cDNA clone IMAGE: 704273 3' similar to TR: G974805 G974805 T08A11.2;. |
| RC_AA033974_at | zi05c10.s1 Soares fetal liver spleen 1NFLS S1 *Homo sapiens* cDNA clone 429906 3'. |
| AF007216_at | *Homo sapiens* sodium bicarbonate cotransporter (HNBC1) mRNA, complete cds. |
| RC_AA489101_at | aa56h11.s1 NCI_CGAP_GCB1 *Homo sapiens* cDNA clone IMAGE: 824997 3'. |
| D79601_f_at | Human aorta cDNA 5'-end GEN-286G10. |
| RC_N30856_at | yw70f05.s1 *Homo sapiens* cDNA clone 257601 3'. |
| L29218_s_at | *Homo sapiens* clk2 mRNA, complete cds |
| RC_AA143726_at | zo67g06.s1 Stratagene pancreas (#937208) *Homo sapiens* cDNA clone 591994 3' similar to TR: G530823 G530823 EPIDERMAL GROWTH FACTOR RECEPTOR KINASE SUBSTRATE. ;. |
| AA126592_at | zl17g05.r1 Soares pregnant uterus NbHPU *Homo sapiens* cDNA clone 502232 5'. |
| RC_F02397_s_at | *H. sapiens* partial cDNA sequence; clone c-0xh11. |
| RC_AA252765_at | zs27d03.s1 NCI_CGAP_GCB1 *Homo sapiens* cDNA clone IMAGE: 686405 3'. |
| RC_W46846_at | zc36a04.s1 Soares senescent fibroblasts NbHSF *Homo sapiens* cDNA clone 324366 3'. |
| RC_AA135185_at | zo27a05.s1 Stratagene colon (#937204) *Homo sapiens* cDNA clone 588080 3'. |
| RC_R40702_at | yf73f10.s1 *Homo sapiens* cDNA clone 27969 3'. |
| RC_N52565_at | yv36d12.s1 *Homo sapiens* cDNA clone 244823 3'. |
| RC_W32506_s_at | zc06a02.s1 Soares parathyroid tumor NbHPA *Homo sapiens* cDNA clone 321482 3'. |
| RC_AA255539_at | zr85c04.s1 Soares NhHMPu S1 *Homo sapiens* cDNA clone 682470 3'. |
| RC_AA449951_at | zx38a10.s1 Soares total fetus Nb2HF8 9w *Homo sapiens* cDNA clone 788730 3'. |
| AA091278_at | cchn2404.seq.F Fetal heart, Lambda ZAP Express *Homo sapiens* cDNA 5'. |
| RC_AA236037_at | zs05g08.s1 NCI_CGAP_GCB1 *Homo sapiens* cDNA clone IMAGE: 684350 3'. |
| AA091412_s_at | ll2053.seq.F Fetal heart, Lambda ZAP Express *Homo sapiens* cDNA 5'. |
| AA046865_at | zf12b09.r1 Soares fetal heart NbHH19W *Homo sapiens* cDNA clone 376697 5'. |
| AA324825_at | EST27743 Cerebellum II *Homo sapiens* cDNA 5' end. |
| RC_AA454840_s_at | zx79d09.s1 Soares ovary tumor NbHOT *Homo sapiens* cDNA clone 809969 3'. |
| RC_W80354_at | zh49a02.s1 Soares fetal liver spleen 1NFLS S1 *Homo sapiens* cDNA clone 415370 3'. |
| RC_AA402484_at | zt65c03.s1 Soares testis NHT *Homo sapiens* cDNA clone 727204 3'. |
| W26883_at | 15h10 Human retina cDNA randomly primed sublibrary *Homo sapiens* cDNA. |
| RC_AA262485_at | zs17h07.s1 NCI_CGAP_GCB1 *Homo sapiens* cDNA clone IMAGE: 685501 3'. |
| RC_AA405543_at | zw39c01.s1 Soares total fetus Nb2HF8 9w *Homo sapiens* cDNA clone 772416 3'. |
| RC_N21380_at | yx54c04.s1 *Homo sapiens* cDNA clone 265542 3'. |
| RC_AA121360_s_at | zn77a05.s1 Stratagene NT2 neuronal precursor 937230 *Homo sapiens* cDNA clone 564176 3'. |
| L32832_s_at | *Homo sapiens* zinc finger homeodomain protein (ATBF1-A) mRNA, complete cds. |

-continued

| | |
|---|---|
| D31313_s_at | Human fetal-lung cDNA 5'-end sequence. |
| H18718_at | ym45b05.r1 *Homo sapiens* cDNA clone 51043 5' similar to contains Alu repetitive element;. |
| RC_AA037828_at | zf03g09.s1 Soares fetal heart NbHH19W *Homo sapiens* cDNA clone 375904 3'. |
| RC_R67996_at | yi04c10.s1 *Homo sapiens* cDNA clone 138258 3'. |
| RC_AA026417_at | ze92g08.s1 Soares fetal heart NbHHI9W *Homo sapiens* cDNA clone 366494 3'. |
| RC_F11115_at | *H. sapiens* partial cDNA sequence; clone c-33a10. |
| RC_R08871_at | yf21e07.s1 *Homo sapiens* cDNA clone 127524 3'. |
| RC_AA224324_at | zr12e05.s1 Stratagene hNT neuron (#937233) *Homo sapiens* cDNA clone 648608 3'. |
| RC_AA399226_at | zt50c01.s1 Soares ovary tumor NbHOT *Homo sapiens* cDNA clone 725760 3'. |
| R66920_at | yi25f09.r1 *Homo sapiens* cDNA clone 140297 5' similar to contains Alu repetitive element;. |
| RC_AA464240_s_at | zx81a05.s1 Soares ovary tumor NbHOT *Homo sapiens* cDNA clone 810128 3'. |
| AA436536_at | zv08g07.r1 Soares NhHMPu S1 *Homo sapiens* cDNA clone 753084 5'. |
| RC_N71875_at | yz34f07.s1 *Homo sapiens* cDNA clone 284965 3'. |
| RC_AA029288_at | zk10b03.s1 Soares pregnant uterus NbHPU *Homo sapiens* cDNA clone 470093 3' similar to PIR: H45193 H45193 zinc finger protein ZNF65;. |
| H27242_at | yl63h11.r1 *Homo sapiens* cDNA clone 162981 5' similar to SP: GCN5_YEAST Q03330 TRANSCRIPTIONAL ACTIVATOR;. |
| J04813_s_at | Human cytochrome P450 PCN3 gene, complete cds |
| RC_AA465093_at | aa32h08.s1 NCI_CGAP_GCB1 *Homo sapiens* cDNA clone IMAGE: 815007 3'. |
| RC_AA282791_at | zs91c05.s1 NCI_CGAP_GCB1 *Homo sapiens* cDNA clone IMAGE: 704840 3'. |
| RC_AA464180_at | zx83f04.s1 Soares ovary tumor NbHOT *Homo sapiens* cDNA clone 810367 3' similar to gb: M38188 OVARIAN GRANULOSA CELL 13.0 KD PROTEIN HGR74 (HUMAN);. |
| RC_AA149987_at | zo03d03.s1 Stratagene colon (#937204) *Homo sapiens* cDNA clone 566597 3'. |
| RC_AA256680_at | zr82h09.s1 Soares NhHMPu S1 *Homo sapiens* cDNA clone 682241 3'. |
| AA147510_s_at | zl50c12.r1 Soares pregnant uterus NbHPU *Homo sapiens* cDNA clone 505366 5'. |
| R78119_at | yi80c10.r1 *Homo sapiens* cDNA clone 145554 5'. |
| RC_Z38407_s_at | *H. sapiens* partial cDNA sequence; clone c-0ac03. |
| RC_AA287107_s_at | zs58f12.s1 NCI_CGAP_GCB1 *Homo sapiens* cDNA clone IMAGE: 701711 3'. |
| RC_AA287042_at | zs57e07.s1 NCI_CGAP_GCB1 *Homo sapiens* cDNA clone IMAGE: 701604 3'. |
| AA489299_at | ab35g04.r1 Stratagene HeLa cell s3 937216 *Homo sapiens* cDNA clone 842838 5'. |
| AA504744_at | aa63f03.r1 NCI_CGAP_GCB1 *Homo sapiens* cDNA clone IMAGE: 825629 5'. |
| RC_AA402622_at | zu47g07.s1 Soares ovary tumor NbHOT *Homo sapiens* cDNA clone 741180 3'. |
| RC_AA436628_at | zw55e10.s1 Soares total fetus Nb2HF8 9w *Homo sapiens* cDNA clone 773994 3'. |
| RC_AA282138_at | zt02a10.s1 NCI_CGAP_GCB1 *Homo sapiens* cDNA clone IMAGE: 711930 3'. |
| AA045870_at | zk75a04.r1 Soares pregnant uterus NbHPU *Homo sapiens* cDNA clone 488622 5'. |
| AA418098_at | zv94b04.r1 Soares NhHMPu S1 *Homo sapiens* cDNA clone 767407 5'. |
| RC_AA242799_at | zr65f06.s1 Soares NhHMPu S1 *Homo sapiens* cDNA clone 668291 3' similar to SW: SPO8_YEAST P41833 TRANSCRIPTIONAL REGULATOR SPO8. [1];. |
| RC_AA609210_at | af12f04.s1 Soares testis NHT *Homo sapiens* cDNA clone 1031455 3'. |
| RC_AA133469_at | zo13e11.s1 Stratagene colon (#937204) *Homo sapiens* cDNA clone 586796 3'. |
| R22139_at | yh25b11.r1 *Homo sapiens* cDNA clone 130749 5'. |
| AA305116_at | EST176117 Colon carcinoma (Caco-2) cell line II *Homo sapiens* cDNA 5' end. |
| RC_AA027954_at | zk05c12.s1 Soares pregnant uterus NbHPU *Homo sapiens* cDNA clone 469654 3'. |
| AA036900_at | zk29e11.r1 Soares pregnant uterus NbHPU *Homo sapiens* cDNA clone 471980 5'. |
| RC_AA026397_at | ze92d07.s1 Soares fetal heart NbHH19W *Homo sapiens* cDNA clone 366445 3'. |
| RC_D59981_s_at | Human fetal brain cDNA 3'-end GEN-079C04. |
| RC_AA284143_at | zs47c07.s1 NCI_CGAP_GCB1 *Homo sapiens* cDNA clone IMAGE: 700620 3'. |

-continued

| | |
|---|---|
| W16686_at | zb08f12.r1 Soares fetal lung NbHL19W *Homo sapiens* cDNA clone 301487 5'. |
| H89575_s_at | yw28c11.r1 *Homo sapiens* cDNA clone 253556 5'. |
| RC_AA251003_at | zs07g11.s1 NCI_CGAP_GCB1 *Homo sapiens* cDNA clone IMAGE: 684548 3'. |
| RC_AA279408_at | zs84h09.s1 NCI_CGAP_GCB1 *Homo sapiens* cDNA clone IMAGE: 704225 3'. |
| RC_AA281760_at | zt07g10.s1 NCI_CGAP_GCB1 *Homo sapiens* cDNA clone IMAGE: 712482 3' similar to TR: G808826 G808826 HYPOTHETICAL 25.7 KD PROTEIN.;. |
| AB002381_at | Human mRNA for KIAA0383 gene, partial cds. |
| AA459542_s_at | zx89d08.r1 Soares ovary tumor NbHOT *Homo sapiens* cDNA clone 810927 5' similar to TR: G608025 G608025 ANKYRING.;. |
| RC_AA115559_at | zl07b12.s1 Soares pregnant uterus NbHPU *Homo sapiens* cDNA clone 491615 3'. |
| T94506_at | ye36a05.r1 *Homo sapiens* cDNA clone 119792 5'. |
| D55869_s_at | Human fetal brain cDNA 5'-end GEN-404F02. |
| L02547_at | *Homo sapiens* (clone pZ50-19) cleavage stimulation factor 50 kDa subunit, complete cds |
| U77942_at | Human syntaxin 7 mRNA, complete cds. |
| AA431505_at | zw76e03.r1 Soares testis NHT *Homo sapiens* cDNA clone 782140 5'. |
| RC_AA194045_at | zr38c08.s1 Soares NhHMPu S1 *Homo sapiens* cDNA clone 665678 3'. |
| RC_AA025104_at | ze78f05.s1 Soares fetal heart NbHH19W *Homo sapiens* cDNA clone 365121 3'. |
| RC_AA242822_at | zr65e09.s1 Soares NhHMPu S1 *Homo sapiens* cDNA clone 668296 3'. |
| RC_AA287388_at | zs50f04.s1 NCI_CGAP_GCB1 *Homo sapiens* cDNA clone IMAGE: 700927 3'. |
| AA247679_at | hfe0045.seq.F Human fetal heart, Lambda ZAP Express *Homo sapiens* cDNA 5'. |
| RC_AA489383_at | ab41e08.s1 Stratagene HeLa cell s3 937216 *Homo sapiens* cDNA clone 843398 3'. |
| RC_AA621188_at | zu81a08.s1 Soares testis NHT *Homo sapiens* cDNA clone 744374 3'. |
| RC_AA486182_at | ab35a01.s1 Stratagene HeLa cell s3 937216 *Homo sapiens* cDNA clone 842760 3'. |
| RC_AA393876_s_at | zv64h10.s1 Soares total fetus Nb2HF8 9w *Homo sapiens* cDNA clone 758467 3'. |
| RC_AA034189_at | zi06h12.s1 Soares fetal liver spleen 1NFLS S1 *Homo sapiens* cDNA clone 430055 3'. |
| RC_AA024866_at | ze79b09.s1 Soares fetal heart NbHH19W *Homo sapiens* cDNA clone 365177 3'. |
| RC_AA450373_at | zx05h06.s1 Soares total fetus Nb2HF8 9w *Homo sapiens* cDNA clone 785627 3'. |
| N78483_at | yz78d07.r1 *Homo sapiens* cDNA clone 289165 5'. |
| RC_AA281245_at | zs94d07.s1 NCI_CGAP_GCB1 *Homo sapiens* cDNA clone IMAGE: 705133 3'. |
| W52431_at | zc45b12.r1 Soares senescent fibroblasts NbHSF *Homo sapiens* cDNA clone 325247 5' similar to SW: WDNM_RAT P14730 WDNM1 PROTEIN. [2] PIR: S07807;. |
| RC_AA446597_at | zw84f01.s1 Soares total fetus Nb2HF8 9w *Homo sapiens* cDNA clone 783673 3'. |
| RC_AA256996_at | zr81h11.s1 Soares NhHMPu S1 *Homo sapiens* cDNA clone 682149 3'. |
| X73501_at | *H. sapiens* gene for cytokeratin 20 |
| RC_AA287131_at | zt20g02.s1 Soares ovary tumor NbHOT *Homo sapiens* cDNA clone 713714 3' similar to TR: E124071 E124071 NAD +− ISOCITRATE DEHYDROGENASE;. | or from a sequence as identified below

| | |
|---|---|
| AB002370_at | Human mRNA for KIAA0372 gene, complete cds. |
| AF000546_at | *Homo sapiens* purinergic receptor P2Y5 mRNA, complete cds. |
| H43922_at | yo70c03.r1 *Homo sapiens* cDNA clone 183268 5'. |
| H44269_at | yp17b05.r1 *Homo sapiens* cDNA clone 187665 5' similar to contains Alu repetitive element;. |
| H88706_s_at | yw23e08.r1 *Homo sapiens* cDNA clone 253094 5'. |
| L25880_s_at | *Homo sapiens* epoxide hydrolase (EPHX) gene, complete cds |
| N81162_at | yw36d01.r1 *Homo sapiens* cDNA clone 254305 5'. |
| RC_F10381_s_at | *H. sapiens* partial cDNA sequence; clone c-3ec07. |
| RC_H54558_at | EST00018 HE6W *Homo sapiens* cDNA clone HE6WCR108 3'. |

-continued

| | |
|---|---|
| RC_H58692_s_at | yr20g08.s1 *Homo sapiens* cDNA clone 205886 3' similar to SP: FTDH_RAT P28037 FORMYLTETRAHYDROFOLATE DEHYDROGENASE;. |
| RC_N20047_at | yx28d06.s1 *Homo sapiens* cDNA clone 263051 3'. |
| RC_N38810_at | yv28e04.s1 *Homo sapiens* cDNA clone 244062 3'. |
| RC_R46497_at | yg51h01.s1 *Homo sapiens* cDNA clone 36305 3'. |
| RC_R55001_at | yj76a08.s1 *Homo sapiens* cDNA clone 154646 3'. |
| RC_T29986_s_at | EST10130 *Homo sapiens* cDNA 3' end similar to None. |
| RC_T30214_at | EST12901 *Homo sapiens* cDNA 3' end similar to None. |
| RC_T40438_at | ya01c07.s2 *Homo sapiens* cDNA clone 60204 3'. |
| RC_W51910_at | zc37f06.s1 Soares senescent fibroblasts NbHSF *Homo sapiens* cDNA clone 324515 3'. |
| RC_W73949_at | zd71f09.s1 Soares fetal heart NbHH19W *Homo sapiens* cDNA clone 346121 3'. |
| RC_W86375_s_at | zh55a02.s1 Soares fetal liver spleen 1NFLS S1 *Homo sapiens* cDNA clone 415946 3'. |
| RC_Z38289_at | *H. sapiens* partial cDNA sequence; clone c-05e04. |
| RC_Z38807_s_at | *H. sapiens* partial cDNA sequence; clone c-0qb04. |
| RC_Z39599_at | *H. sapiens* partial cDNA sequence; clone c-1ed10. |
| RC_AA025351_at | ze74h03.s1 Soares fetal heart NbHH19W *Homo sapiens* cDNA clone 364757 3' similar to contains OFR.t1 OFR repetitive element;. |
| RC_AA136474_at | zl01f04.s1 Soares pregnant uterus NbHPU *Homo sapiens* cDNA clone 491071 3'. |
| RC_AA136611_at | zk99b02.s1 Soares pregnant uterus NbHPU *Homo sapiens* cDNA clone 490923 3'. |
| RC_AA233375_at | zr48f07.s1 Soares NhHMPu S1 *Homo sapiens* cDNA clone 666661 3'. |
| RC_AA235621_s_at | zt36c05.s1 Soares ovary tumor NbHOT *Homo sapiens* cDNA clone 724424 3'. |
| RC_AA253331_at | zr72g02.s1 Soares NhHMPu S1 *Homo sapiens* cDNA clone 668978 3'. |
| RC_AA393793_at | zv64a10.s1 Soares total fetus Nb2HF8 9w *Homo sapiens* cDNA clone 758394 3'. |
| RC_AA419547_at | zv04a05.s1 Soares NhHMPu S1 *Homo sapiens* cDNA clone 752624 3'. |
| RC_AA421100_at | zu27d11.s1 Soares ovary tumor NbHOT *Homo sapiens* cDNA clone 739221 3'. |
| RC_AA443277_at | zw87f06.s1 Soares total fetus Nb2HF8 9w *Homo sapiens* cDNA clone 783971 3'. |
| RC_AA446570_at | zw84c05.s1 Soares total fetus Nb2HF8 9w *Homo sapiens* cDNA clone 783656 3'. |
| RC_AA447123_at | zw93c01.s1 Soares total fetus Nb2HF8 9w *Homo sapiens* cDNA clone 784512 3'. |
| RC_AA449343_at | zx06g09.s1 Soares total fetus Nb2HF8 9w *Homo sapiens* cDNA clone 785728 3'. |
| RC_AA456016_at | aa03a08.s1 Soares NhHMPu S1 *Homo sapiens* cDNA clone 812150 3'. |
| RC_AA479299_at | zv21f04.s1 Soares NhHMPu S1 *Homo sapiens* cDNA clone 754303 3'. |
| RC_AA479350_at | zv17d09.s1 Soares NhHMPu S1 *Homo sapiens* cDNA clone 753905 3' similar to contains element TAR1 TAR1 repetitive element;. |
| U85707_at | Human leukemogenic homolog protein (MEIS1) mRNA, complete cds |
| U94831_at | Human multispanning membrane protein mRNA, complete cds./ gb = U94831/ntype = RNA |
| W27827_at | 38c8 Human retina cDNA randomly primed sublibrary *Homo sapiens* cDNA. |
| W81301_at | zd85a12.r1 Soares fetal heart NbHH19W *Homo sapiens* cDNA clone 347422 5'. |
| Y12711_at | *H. sapiens* mRNA for putative progesterone binding protein |
| AA074407_at | zm15c08.r1 Stratagene pancreas (#937208) *Homo sapiens* cDNA clone 525710 5'. |
| AA091017_at | yy1646.seq.F Fetal heart, Lambda ZAP Express *Homo sapiens* cDNA 5'. |
| AA104023_at | l7134.seq.F Fetal heart, Lambda ZAP Express *Homo sapiens* cDNA 5'. |
| AA171913_at | zo95d05.r1 Stratagene ovarian cancer (#937219) *Homo sapiens* cDNA clone 594633 5'. |
| AA195678_at | zr32h05.r1 Soares NhHMPu S1 *Homo sapiens* cDNA clone 665145 5'. |
| AA227678_at | zr55e05.r1 Soares NhHMPu S1 *Homo sapiens* cDNA clone 667328 5'. |
| AA247204_at | csg0306.seq.F Human fetal heart, Lambda ZAP Express *Homo sapiens* cDNA 5'. |
| AA479995_at | zv18b05.r1 Soares NhHMPu S1 *Homo sapiens* cDNA clone 753969 5'. | or from a sequence as identified below

| | |
|---|---|
| RC_H14633_at | yl26e06.s1 *Homo sapiens* cDNA clone 159394 3'. |
| RC_N62506_at | yz74d02.s1 *Homo sapiens* cDNA clone 288771 3'. |
| RC_N70481_at | za74g10.s1 *Homo sapiens* cDNA clone 298338 3'. |
| RC_N73988_at | za57b06.s1 *Homo sapiens* cDNA clone 296627 3'. |
| RC_T53404_at | ya88g06.s1 *Homo sapiens* cDNA clone 68794 3'. |
| RC_Z38149_at | *H. sapiens* partial cDNA sequence; clone c-01a09. |
| RC_Z38849_at | *H. sapiens* partial cDNA sequence; clone c-0rb11. |
| RC_AA037409_at | zc03h03.s1 Soares parathyroid tumor NbHPA *Homo sapiens* cDNA clone 321269 3'. |
| RC_AA084318_at | zn18b04.s1 Stratagene neuroepithelium NT2RAMI 937234 *Homo sapiens* cDNA clone 547759 3'. |
| RC_AA126419_at | zk94d04.s1 Soares pregnant uterus NbHPU *Homo sapiens* cDNA clone 490471 3'. |
| RC_AA128407_at | zm24d04.s1 Stratagene pancreas (#937208) *Homo sapiens* cDNA clone 526567 3'. |
| RC_AA173430_at | zp02e08.s1 Stratagene ovarian cancer (#937219) *Homo sapiens* cDNA clone 595238 3'. |
| RC_AA398104_at | zt58d03.s1 Soares testis NHT *Homo sapiens* cDNA clone 726533 3'. |
| RC_AA399414_at | zt50e07.s1 Soares ovary tumor NbHOT *Homo sapiens* cDNA clone 725796 3'. |
| RC_AA431479_at | zw72f05.s1 Soares testis NHT *Homo sapiens* cDNA clone 781761 3'. |
| RC_AA436471_at | zv08e05.s1 Soares NhHMPu S1 *Homo sapiens* cDNA clone 753056 3'. |
| RC_AA449455_at | zx05e10.s1 Soares total fetus Nb2HF8 9w *Homo sapiens* cDNA clone 785610 3' similar to contains Alu repetitive element;. |
| RC_AA458899_at | zx88d07.s1 Soares ovary tumor NbHOT *Homo sapiens* cDNA clone 810829 3'. |
| RC_AA463630_s_at | zx98g09.s1 Soares NhHMPu S1 *Homo sapiens* cDNA clone 811840 3'. |
| RC_AA489009_at | aa54d11.s1 NCI_CGAP_GCB1 *Homo sapiens* cDNA clone IMAGE: 824757 3'. |
| W37319_at | zc11f08.r1 Soares parathyroid tumor NbHPA *Homo sapiens* cDNA clone 322023 5'. | or from a sequence as identified below

| | |
|---|---|
| yx16e10.r1 *Homo sapiens* cDNA clone 261930 5'. | N24990_s_at |
| yf41e08.r1 *Homo sapiens* cDNA clone 129446 5' similar to SP: A46661 A46661 LEUKOTRIENE B4 OMEGA-HYDROXYLASE, P-450LTB OMEGA = CYTOCHROME P-450 SUPERFAMILY MEMBER-;. | R11267_at |
| yq76e12.s1 *Homo sapiens* cDNA clone 201742 3' similar to gb: J02982 GLYCOPHORIN B PRECURSOR (HUMAN);. | RC_H52937_at |
| yr89e02.s1 *Homo sapiens* cDNA clone 212474 3'. | RC_H69547_at |
| yu73c12.s1 *Homo sapiens* cDNA clone 239446 3'. | RC_H70047_at |
| yx99c11.s1 *Homo sapiens* cDNA clone 269876 3'. | RC_N24879_at |
| yz38a06.s1 *Homo sapiens* cDNA clone 285298 3'. | RC_N66312_at |
| yh26a02.s1 *Homo sapiens* cDNA clone 130826 3'. | RC_R22189_at |
| yg44f05.s1 *Homo sapiens* cDNA clone 35270 3'. | RC_R45582_at |
| yg83e10.s1 *Homo sapiens* cDNA clone 39835 3'. | RC_R53457_at |
| yi49g10.s1 *Homo sapiens* cDNA clone 142626 3'. | RC_R70903_at |
| zl68c01.s1 Stratagene colon (#937204) *Homo sapiens* cDNA clone 509760 3'. | RC_AA054321_s_at |
| zk87c05.s1 Soares pregnant uterus NbHPU *Homo sapiens* cDNA clone 489800 3'. | RC_AA099820_at |
| zl17g05.s1 Soares pregnant uterus NbHPU *Homo sapiens* cDNA clone 502232 3'. | RC_AA127238_at |
| zo64h02.s1 Stratagene pancreas (#937208) *Homo sapiens* cDNA clone 591699 3'. | RC_AA147224_at |
| zq12e02.s1 Stratagene muscle 937209 *Homo sapiens* cDNA clone 629498 3'. | RC_AA192765_at |
| zr33d07.s1 Soares NhHMPu S1 *Homo sapiens* cDNA clone 665197 3'. | RC_AA195718_at |
| zr28b08.s1 Stratagene NT2 neuronal precursor 937230 *Homo sapiens* cDNA clone 664695 3' similar to gb: L05779 SOLUBLE EPOXIDE HYDROLASE (HUMAN);. | RC_AA232114_s_at |
| zt07h12.s1 NCI_CGAP_GCB1 *Homo sapiens* cDNA clone IMAGE: 712487 3'. | RC_AA281770_at |

-continued

| | |
|---|---|
| zw59e03.s1 Soares total fetus Nb2HF8 9w *Homo sapiens* cDNA clone 774364 3' similar to TR: G1199667 G1199667 PROTEIN KINASE C-BINDING PROTEIN ENIGMA;. | RC__AA430209__at |
| zx31f03.s1 Soares total fetus Nb2HF8 9w *Homo sapiens* cDNA clone 788093 3'. | RC__AA452410__at |
| aa39g12.s1 NCI_CGAP_GCB1 *Homo sapiens* cDNA clone IMAGE: 815686 3'. | RC__AA485115__at |
| zk85e12.r1 Soares pregnant uterus NbHPU *Homo sapiens* cDNA clone 489646 5'. | AA099391__s__at |
| zo16a05.r1 Stratagene colon (#937204) *Homo sapiens* cDNA clone 587024 5' similar to SW: CATX_BOVIN P05689 CATHEPSIN;. | AA131127__at |
| zp02c06.r1 Stratagene ovarian cancer (#937219) *Homo sapiens* cDNA clone 595210 5' similar to SW: QRI2_YEAST P43124 HYPOTHETICAL 46.1 KD PROTEIN IN PHO2-POL3 INTERGENIC REGION. [1];. | AA173505__at |
| zt39b07.r1 Soares ovary tumor NbHOT *Homo sapiens* cDNA clone 724693 5'. | AA291786__s__at |
| zu53f10.r1 Soares ovary tumor NbHOT *Homo sapiens* cDNA clone 741739 5'. | AA402971__s__at | or from a sequence as identified below

| | |
|---|---|
| Human mRNA for IgG Fc binding protein, complete cds | D84239__at |
| yv73b09.s1 Soares fetal liver spleen 1NFLS *Homo sapiens* cDNA clone 248345 3'. | RC__N54841__at |
| ya88f04.s1 Home sapiens cDNA clone 68767 3'. | RC__T53389__s__at |
| ye30d12.s1 *Homo sapiens* cDNA clone 119255 3'. | RC__T98227__at |
| zr97c07.s1 NCI_CGAP_GCB1 *Homo sapiens* cDNA clone IMAGE: 683628 3'. | RC__AA215379__at |
| zr81e12.s1 Soares NhHMPu S1 Home sapiens cDNA clone 682126 3'. | RC__AA256485__at |
| zt19f03.s1 Soares ovary tumor NbHOT Home sapiens cDNA clone 713597 3' similar to TR: E92665 E92665 AP56;. | RC__AA290679__at |
| zw46c01.s1 Soares total fetus Nb2HF8 9w Home sapiens cDNA clone 773088 3'. | RC__AA425309__at |
| zw71d04.s1 Soares testis NHT *Homo sapiens* cDNA clone 781639 3'. | RC__AA429655__at |
| aa90h11.s1 Stratagene fetal retina 937202 *Homo sapiens* cDNA clone 838629 3' similar to contains Alu repetitive element;. | RC__AA456981__at |
| zx70c04.s1 Soares total fetus Nb2HF8 9w *Homo sapiens* cDNA clone 796806 3'. | RC__AA461174__at |
| zd27g09.r1 Soares fetal heart NbHH19W *Homo sapiens* cDNA clone 341920 5'. | W61377__at |

In one embodiment at least one gene is introduced into the tumor cell. In another embodiment at least two genes are introduced into the tumor cell.

In one aspect of the invention small molecules that either inhibit increased gene expression or their effects or substitute decreased gene expression or their effects, are introduced to the cellular environment or the cells. Application of small molecules to tumor cells may be performed by e.g. local application or intravenous injection or by oral ingestion. Small molecules have the ability to restore function of reduced gene expression in tumor or cancer tissue.

In another aspect the invention relates to a therapy whereby genes (increase and/or decrease) generally are correlated to disease are inhibited by one or more of the following methods:

A method for reducing cell tumorigenicity or malignancy of a cell, said method comprising obtaining at least one nucleotide probe capable of hybridising with at least one gene of a tumor cell, said at least one gene being selected from genes being expressed in an amount at least one-fold lower in normal cells than the amount expressed in said tumor cell, and introducing said at least one nucleotide probe into the tumor cell in a manner allowing the probe to hybridise to the at least one gene, thereby inhibiting expression of said at least one gene. This method is preferably based on anti-sense technology, whereby the hybridisation of said probe to the gene leads to a downregulation of said gene.

The down-regulation may of course also be based on a probe capable of hybridising to regulatory components of the genes in question, such as promoters.

The probes are preferably selected from probes capable of hybridising to a nucleotide sequence comprising a sequence as identified below

| | |
|---|---|
| *Homo sapiens* mRNA for CC chemokine, complete cds. | AB000221__at |
| Human fetal brain cDNA 3'-end GEN-097D06. | RC__D60296__at |

-continued

| | |
|---|---|
| Human fetal brain cDNA 3'-end GEN-132E11. | RC_D60813_at |
| yg71a11.s1 *Homo sapiens* cDNA clone 38542 3'. | RC_R49708_s_at |
| *H. sapiens* partial cDNA sequence; clone c-02a08. | RC_Z38182_at |
| aa38e07.s1 NCI_CGAP_GCB1 *Homo sapiens* cDNA clone IMAGE: 815556 3'; | RC_AA456821_at |
| ae53d05.s1 Stratagene lung carcinoma 937218 *Homo sapiens* cDNA clone 950601 3'. | RC_AA608545_at |
| ae58g12.s1 Stratagene lung carcinoma 937218 *Homo sapiens* cDNA clone 951142 3'. | RC_AA620553_s_at |
| cp3087.seq.F Fetal heart, Lambda ZAP Express *Homo sapiens* cDNA 5'. | AA095119_at | or from

| | |
|---|---|
| yn53b04.s1 *Homo sapiens* cDNA clone 172111 3'. | RC_H20269_at |
| *H. sapiens* partial cDNA sequence; clone c-2ea12. | RC_Z40715_at |
| zm79a11.s1 Stratagene neuroepithelium (#937231) *Homo sapiens* cDNA clone 531836 3'. | RC_AA116036_at |
| zn92a08.s1 Stratagene lung carcinoma 937218 *Homo sapiens* cDNA clone 565622 3'. | RC_AA133250_at |

25 or from a sequence as identified below

| | |
|---|---|
| Human threonyl-tRNA synthetase mRNA, complete cds | M63180_at |
| HFBEST-40 Human fetal brain QBoqin2 *Homo sapiens* cDNA. | N89563_s_at |
| Human fetal brain cDNA 3'-end GEN-045C11. | RC_D80198_at |
| *H. sapiens* partial cDNA sequence; clone c-0kf11. | RC_F01986_f_at |
| yn51g07.s1 *Homo sapiens* cDNA clone 171996 3'. | RC_H18997_at |
| zn76c11.s1 Stratagene NT2 neuronal precursor 937230 *Homo sapiens* cDNA clone 564116 3' similar to contains Alu repetitive. element;. | RC_AA101562_at | or from a sequence as identified below

| | |
|---|---|
| Ye73c08.s1 *Homo sapiens* cDNA clone 123374 3'. | RC_R00083_at |
| yj80e01.s1 *Homo sapiens* cDNA clone 155064 3'. | RC_R71391_at |
| Seq2147 *Homo sapiens* cDNA clone NHB3MK-9 3'. | RC_T23991_at |
| Yd70f06.s1 *Homo sapiens* cDNA clone 113603 3' similar to contains Alu repetitive element;. | RC_T79196_at |
| Zo26a09.s1 Stratagene colon (#937204) *Homo sapiens* cDNA clone 587992 3'. | RC_AA130596_at |
| Zx89d06.s1 Soares ovary tumor NbHOT *Homo sapiens* cDNA clone 810923 3'. | RC_AA459310_r_at |
| aa48f12.s1 NCI_CGAP_GCB1 *Homo sapiens* cDNA clone IMAGE: 824207 3'. | RC_AA490965_at |
| Human DNA binding protein homolog (DRX) mRNA, partial cds | U88047_at |
| Human DSC2 mRNA for desmocollins type 2a and 2b | X56807_at |
| zi01b10.r1 Soares fetal liver spleen 1NFLS S1 *Homo sapiens* cDNA clone 429499 5'. | AA011479_at |
| EST112387 Aorta endothelial cells *Homo sapiens* cDNA 5' end. | AA296821_at | or from a sequence as identified below

| | |
|---|---|
| zx58c10.r1 Soares fetal liver spleen 1NFLS S1 *Homo sapiens* cDNA clone 446706 5' similar to contains Alu repetitive element;. | AA203639_at |
| Human prealbumin gene, complete cds. | M11844_at |

-continued

| | |
|---|---|
| zq77f02.s1 Stratagene hNT neuron (#937233) *Homo sapiens* cDNA clone 647643 3' similar to contains element MSR1 repetitive element;. | RC_AA206042_at |
| yz03e04.s1 *Homo sapiens* cDNA clone 281982 3'. | RC_N51097_at |
| yl70f08.s1 Soares infant brain 1NIB *Homo sapiens* cDNA clone 43327 3'. | RC_H05527_at |
| zl05d11.r1 Soares pregnant uterus NbHPU *Homo sapiens* cDNA clone 491445 5' similar to TR: G895845 G895845 PUTATIVE P64 CLCP PROTEIN.;. | AA115572_s_at |
| yj14b12.s1 *Homo sapiens* cDNA clone 148703 3'. | RC_H12863_at |
| ab36e04.r1 Stratagene HeLa cell s3 937216 *Homo sapiens* cDNA clone 842910 5'. | AA489287_at |
| ye49h07.s1 *Homo sapiens* cDNA clone 121117 3'. | RC_T96383_at |
| yq98g12.s1 *Homo sapiens* cDNA clone 203878 3'. | RC_H56453_at |
| zl03h01.s1 Soares pregnant uterus-NbHPU *Homo sapiens* cDNA clone 491281 3'. | RC_AA152194_at |
| *H. sapiens* partial cDNA sequence; clone c-0ed05. | RC_Z38520_at |
| yd06g09.s1 *Homo sapiens* cDNA clone 25061 3' similar to contains Alu repetitive element;. | RC_R38944_at |
| zo16e11.s1 Stratagene colon (#937204) *Homo sapiens* cDNA clone 587084 3'. | RC_AA133926_at |
| za68f06.s1 *Homo sapiens* cDNA clone 297731 3' similar to gb: X59244 ZINC FINGER PROTEIN 43 (HUMAN);. | RC_N69908_f_at |
| zo02c02.s1 Stratagene colon (#937204) *Homo sapiens* cDNA clone 566498 3' similar to contains Alu repetitive element;. | RC_AA151945_at |
| SOX5 = Sry-related HMG box gene {alternatively spliced} [human, testis, mRNA, 1473 nt] | S83308_at |
| zv11b06.s1 Soares NhHMPu S1 *Homo sapiens* cDNA clone 753299 3'. | RC_AA406570_at |
| zl67g04.s1 Stratagene colon (#937204) *Homo sapiens* cDNA clone 509718 3' similar to contains Alu repetitive element; contains element PTR5 repetitive element;. | RC_AA058314_at |
| yr31g12.s1 *Homo sapiens* cDNA clone 206950 3'. | RC_R98735_at | or from a sequence as identified below

| | |
|---|---|
| Human mRNA for KIAA0180 gene, partial cds | D80002_at |
| Similar to none. | D82418_at |
| Yx59d10.r1 *Homo sapiens* cDNA clone 266035 5'. | N28843_at |
| *H. sapiens* partial cDNA sequence; clone c-12c11. | RC_F02541_at |
| Yw65f02.s1 *Homo sapiens* cDNA clone 257115 3'. | RC_N30806_at |
| Yh81f02.s1 *Homo sapiens* cDNA clone 136155 3' similar to contains Alu repetitive element;. | RC_R33146_at |
| Yf70a09.s1 *Homo sapiens* cDNA clone 27448 3'. | RC_R40166_at |
| Yi23g09.s1 *Homo sapiens* cDNA clone 140128 3'. | RC_R65998_at |
| Zk05c04.s1 Soares pregnant uterus NbHP *Homo sapiens* cDNA clone 469638 3'. | RC_AA027823_at |

-continued

| | |
|---|---|
| Zn17a03.s1 Stratagene neuroepithelium NT2RAMI 937234 *Homo sapiens* cDNA clone 547660 3'. | RC_AA084138_at |
| Zr13a10.s1 Stratagene hNT neuron (#937233) *Homo sapiens* cDNA clone 648666 3'. | RC_AA223902_at |
| Zv90g02.s1 Soares NhHMPu S1 *Homo sapiens* cDNA clone 767090 3'. | RC_AA424524_at |
| Aa65d11.s1 NCI_CGAP_GCB1 *Homo sapiens* cDNA clone IMAGE: 825813 3'. | RC_AA505136_at |
| Zk55g12.r1 Soares pregnant uterus NbHPU *Homo sapiens* cDNA clone 486790 5'. | AA043223_at | or from a sequence as identified below

| | |
|---|---|
| *H. sapiens* partial cDNA sequence; clone c-1pb12. | RC_F03192_at |
| Zd87g10.s1 Soares fetal heart NbHH19W *Homo sapiens* cDNA clone 347682 3'. | RC_W81552_at |
| *H. sapiens* partial cDNA sequence; clone c-10c01. | RC_F02470_at |
| zc20b06.s1 Soares senescent fibroblasts NbHSF *Homo sapiens* cDNA clone 322835 3' similar to PIR: S44218 S44218 testin - mouse [1];. | RC_W44927_at |
| yg46b01.s1 *Homo sapiens* cDNA clone 35626 3'. | RC_R45292_at |
| yr47b09.s1 *Homo sapiens* cDNA clone 208409 3' similar to contains Alu repetitive element; contains MER15 repetitive element;. | RC_H62159_at |
| yf45a10.s2 *Homo sapiens* cDNA clone 129786 3'. | RC_R17059_at |
| ym30c10.s1 *Homo sapiens* cDNA clone 49795 3'. | RC_H15259_at |
| 29a6 Human retina cDNA randomly primed sublibrary *Homo sapiens* cDNA. | W26376_at |
| *H. sapiens* mRNA for putative carboxylesterase | Y09616_at |
| zw48f02.r1 Soares total fetus Nb2HF8 9w *Homo sapiens* cDNA clone 773307 5'. | AA425593_at |
| zt08e05.s1 NCI_CGAP_GCB1 *Homo sapiens* cDNA clone IMAGE: 712544 3'. | RC_AA279980_at |
| ym62c07.s1 *Homo sapiens* cDNA clone 163500 3'. | RC_H14089_at |

-continued

| | |
|---|---|
| yg49c02.s1 Homo sapiens cDNA clone 36133 3'. | RC_R46079_f_at |
| zc17d10.s1 Soares parathyroid tumor NbHPA Homo sapiens cDNA clone 322579 3' similar to PIR: S39983 S39983 eps8 protein - mouse;. | RC_W15360_at |
| Human mRNA for retinoic acid receptor-like protein | X52773_at |
| ze75b05.s1 Soares fetal heart NbHH19W Homo sapiens cDNA clone 364785 3' similar to TR: G451330 G451330 STEROL REGULATORY ELEMENT BINDING PROTEIN-2.;. | RC_AA053886_s_at |
| zo31a10.s1 Stratagene colon (#937204) Homo sapiens cDNA clone 588474 3'. | RC_AA143493_at |
| Homo sapiens mRNA; expressed sequence tag; clone DKFZphsnu1_1b13, 3' read. | RC_Z98492_at |
| H. sapiens partial cDNA sequence. | F15201_at |
| yh10f08.s1 Homo sapiens cDNA clone 42872 3'. | RC_R61883_at |
| 30e12 Human retina cDNA randomly primed sublibrary Homo sapiens cDNA. | W26505_at |
| zn53e03.s1 Stratagene muscle 937209 Homo sapiens cDNA clone 561916 3'. | RC_AA085676_at |
| ze55c07.r1 Soares retina N2b4HR Homo sapiens cDNA clone 362892 5' similar to SW: RB14_RAT P35287 RAS-RELATED PROTEIN RAB-14. [1];. | AA018804_at |
| Human class I histocompatibility antigen-like protein mRNA, complete cds. | U22963_at |
| yf26d08.s1 Homo sapiens cDNA clone 127983 3'. | RC_R09230_at |
| yi25g01.s1 Homo sapiens cDNA clone 140304 3'. | RC_R67918_at |
| zu55d04.r1 Soares ovary tumor NbHOT Homo sapiens cDNA clone 741895 5' similar to TR: G397579 G397579 LL5 MRNA. | AA402119_at |
| zn42g07.r1 Stratagene endothelial cell 937223 Homo sapiens cDNA clone 550140 5'. | AA082171_at |
| yi89d09.r1 Homo sapiens cDNA clone 146417 5'. | R79750_at |
| zw80d04.s1 Soares testis NHT Homo sapiens cDNA clone 782503 3'. | RC_AA431773_at |
| zs97a07.s1 NCI_CGAP_GCB1 Homo sapiens cDNA clone IMAGE: 711540 3'. | RC_AA280670_at |
| EST16378 Aorta endothelial cells, TNF alpha-treated Homo sapiens cDNA 5' end. | AA303711_at |
| zu64g03.r1 Soares testis NHT Homo sapiens cDNA clone 742804 5'. | AA400361_at |
| Homo sapiens MDM2-like p53-binding protein (MDMX) mRNA, complete cds. | AF007111_at |
| aa59c02.r1 NCI_CGAP_GCB1 Homo sapiens cDNA clone IMAGE: 825218 5' similar to contains element MIR repetitive element | AA504384_at |
| K1565F Fetal heart, Lambda ZAP Express Homo sapiens cDNA clone K1565 5' similar to EST(YD54C09.R1). | N88108_at |
| aa20e01.s1 Soares NhHMPu S1 Homo sapiens cDNA clone 813816 3'. | RC_AA447769_at | or from a sequence as identified below

| | |
|---|---|
| Ze92h01.s1 Soares fetal heart NbHH19W Homo sapiens cDNA clone 366481 3'. | RC_AA026418_at |
| Human fetal brain cDNA 3'-end GEN-070G07. | RC_D59847_at |
| Seq2287 Homo sapiens cDNA clone Cot250Ft-b4HB3MA-8 3'. | RC_T24099_at |
| Yh16a10.s1 Homo sapiens cDNA clone 37689 3'. | RC_R59292_at |
| Zd25e10.s1 Soares fetal heart NbHH19W Homo sapiens cDNA clone 341706 3' similar to gb: M38188 OVARIAN GRANULOSA CELL 13.0 KD PROTEIN HGR74 (HUMAN);. | RC_W60582_at |
| Human 5-lipoxygenase activating protein (FLAP) gene | M63262_at |
| Yc89d05.s1 Homo sapiens cDNA clone 23443 3'. | RC_R38678_at |
| Zd29g01.r1 Soares fetal heart NbHH19W Homo sapiens cDNA clone 342096 5'. | W60268_at |
| Zx80d02.r1 Soares ovary tumor NbHOT Homo sapiens cDNA clone 810051 5' similar to TR: G1020091 G1020091 NEUROPSIN.; contains element LTR3 repetitive element;. | AA465016_at |
| Yd83f04.s1 Homo sapiens cDNA clone 114847 3'. | RC_T79842_at |
| Zq56g08.s1 Stratagene neuroepithelium (#937231) Homo sapiens cDNA clone 645662 3'. | RC_AA206225_at |
| Zx37g02.s1 Soares total fetus Nb2HF8 9w Homo sapiens cDNA clone 788690 3'. | RC_AA449914_at |
| H. sapiens partial cDNA sequence; clone c-3bh08. | RC_F10211_at |

-continued

| | |
|---|---|
| zv41f05.s1 Soares ovary tumor NbHOT *Homo sapiens* cDNA clone 756225 3' similar to TR: G498729 G498729 ZINC FINGER PROTEIN;. | RC__AA480109__r__at |
| zl72a06.s1 Stratagene colon (#937204) *Homo sapiens* cDNA clone 510130 3'. | RC__AA053102__s__at |
| zw24b11.s1 Soares ovary tumor NbHOT *Homo sapiens* cDNA clone 770205 3' similar to contains element TAR1 repetitive element;. | RC__AA434113__at |
| zw62c02.s1 Soares total fetus Nb2HF8 9w *Homo sapiens* cDNA clone 774626 3'. | RC__AA441791__at |
| yz42c02.s1 *Homo sapiens* cDNA clone 285698 3'. | RC__N67583__at |
| ye47b12.s1 *Homo sapiens* cDNA clone 120863 3'. | RC__T96077__at |
| Human mRNA for KIAA0318 gene, partial cds. | AB002316__at |
| ze10g07.s1 Soares fetal heart NbHH19W *Homo sapiens* cDNA clone 358620 3'. | RC__W96222__at |
| Human hemopoietic cell protein-tyrosine kinase (HCK) gene, complete cds, clone lambda-a2/1a | M16591__s__at |
| yz76b12.s1 *Homo sapiens* cDNA clone 288959 3'. | RC__N59808__at |
| *H. sapiens* partial cDNA sequence; clone c-39g09. | RC__F10040__at |
| zx62b09.s1 Soares total fetus Nb2HF8 9w *Homo sapiens* cDNA clone 796025 3'. | RC__AA461549__at |
| zd35d04.s1 Soares fetal heart NbHH19W *Homo sapiens* cDNA clone 342631 3'. | RC__W68683__at |
| zn20d05.s1 Stratagene neuroepithelium NT2RAMI 937234 *Homo sapiens* cDNA clone 547977 3'. | RC__AA084640__at |
| HUMGS0007858, Human Gene Signature, 3'-directed cDNA sequence. | C01169__at |
| ab04a05.s1 Stratagene fetal retina 937202 *Homo sapiens* cDNA clone 839792 3'. | RC__AA491465__at |
| zd41c07.s1 Soares fetal heart NbHH19W *Homo sapiens* cDNA clone 343212 3'. | RC__W67564__s__at |
| Human beta-1-adrenergic receptor mRNA, complete cds. | J03019__s__at |
| yu77b06.s1 *Homo sapiens* cDNA clone 239795 3'. | RC__H80622__at |
| yy15h06.s1 *Homo sapiens* cDNA clone 271355 3'. | RC__N34686__at |
| yg91d08.s1 *Homo sapiens* cDNA clone 40992 3'. | RC__R56066__s__at |
| EST71577 *Homo sapiens* cDNA 3' end similar to None. | RC__T34611__at |
| zk15e12.s1 Soares pregnant uterus NbHPU *Homo sapiens* cDNA clone 470638 3'. | RC__AA031373__s__at |
| Human mRNA for spi-1 proto-oncogene | X52056__at |
| yz89g12.r1 *Homo sapiens* cDNA clone 290278 5'. | N77564__at |
| HUMGS0003713, Human Gene Signature, 3'-directed cDNA sequence. | C01765__at |
| ae32d03.s1 Gessler Wilms tumor *Homo sapiens* cDNA clone 897509 3'. | RC__AA496936__at |
| zk04e03.s1 Soares pregnant uterus NbHPU *Homo sapiens* cDNA clone 469564 3'. | RC__AA027103__at |
| yg32c11.s1 *Homo sapiens* cDNA clone 34089 3'. | RC__R44131__at |
| yz48f04.s1 *Homo sapiens* cDNA clone 286303 3'. | RC__N67227__at |
| ye52f03.s1 *Homo sapiens* cDNA clone 121373 3'. | RC__T96677__at |
| zo23g05.s1 Stratagene colon (#937204) *Homo sapiens* cDNA clone 587768 3'. | RC__AA134965__i__at |
| yd87d10.s1 *Homo sapiens* cDNA clone 115219 3'. | RC__T86600__at |
| zf51f03.s1 Soares retina N2b4HR *Homo sapiens* cDNA clone 380477 3'. | RC__AA054087__at |
| zv76b10.r1 Soares total fetus Nb2HF8 9w *Homo sapiens* cDNA 5'. | AA444374__at |
| ys04f01.s1 *Homo sapiens* cDNA clone 213817 3' similar to gb: J04970 CARBOXYPEPTIDASE M PRECURSOR (HUMAN); contains Alu repetitive element;. | RC__H72357__at |
| ze37d11.s1 Soares retina N2b4HR *Homo sapiens* cDNA clone 361173 3'. | RC__AA017045__at |
| zi09c03.r1 Soares fetal liver spleen 1NFLS S1 *Homo sapiens* cDNA clone 430276 5'. | AA010324__at |
| zs38b09.s1 Soares NhHMPu S1 *Homo sapiens* cDNA clone 687449 3'. | RC__AA234743__at |
| zf20d06.s1 Soares fetal heart NbHH19W *Homo sapiens* cDNA clone 377483 3'. | RC__AA055892__at |
| zw89g02.s1 Soares total fetus Nb2HF8 9w *Homo sapiens* cDNA clone 784178 3'. | RC__AA446650__at |
| ys80e03.r1 *Homo sapiens* cDNA clone 221116 5'. | H91747__s__at |
| zu63c08.r1 Soares testis NHT *Homo sapiens* cDNA clone 742670 5'. | AA401510__s__at |
| zd31d10.s1 Soares fetal heart NbHH19W *Homo sapiens* cDNA clone 342259 3'. | RC__W61239__at |

In another embodiment the probes consists of the sequences identified above.

The hybridization may be tested in vitro at conditions corresponding to in vivo conditions. Typically, hybridization conditions are of low to moderate stringency. These conditions favour specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10-15 minutes each in the order listed above). Any or all of the washes can be repeated. As mentioned above, optimal conditions will vary and can be determined empirically.

In another aspect a method of reducing tumoregeneicity relates to the use of antibodies against an expression product of a cell from the biological tissue. The antibodies may be produced by any suitable method, such as a method comprising the steps of obtaining expression product(s) from at least one gene said gene being expressed as defined above for oncogenes,
immunising a mammal with said expression product(s)
obtaining antibodies against the expression product.

Use

The methods described above may be used for producing an assay for diagnosing a biological condition in animal tissue, or for identification of the origin of a piece of tissue. Further, the methods of the invention may be used for prediction of a disease course and treatment response.

Furthermore, the invention relates to the use of a peptide as defined above for preparation of a pharmaceutical composition for the treatment of a biological condition in animal tissue.

Furthermore, the invention relates to the use of a gene as defined above for preparation of a pharmaceutical composition for the treatment of a biological condition in animal tissue.

Also, the invention relates to the use of a probe as defined above for preparation of a pharmaceutical composition for the treatment of a biological condition in animal tissue.

Gene Delivery Therapy

The genetic material discussed above for may be any of the described genes or functional parts thereof. The constructs may be introduced as a single DNA molecule encoding all of the genes, or different DNA molecules having one or more genes. The constructs may be introduced simultaneously or consecutively, each with the same or different markers.

The gene may be linked to the complex as such or protected by any suitable system normally used for transfection such as viral vectors or artificial viral envelope, liposomes or micellas, wherein the system is linked to the complex.

Numerous techniques for introducing DNA into eukaryotic cells are known to the skilled artisan. Often this is done by means of vectors, and often in the form of nucleic acid encapsidated by a (frequently virus-like) proteinaceous coat. Gene delivery systems may be applied to a wide range of clinical as well as experimental applications.

Vectors containing useful elements such as selectable and/or amplifiable markers, promoter/enhancer elements for expression in mammalian, particularly human, cells, and which may be used to prepare stocks of construct DNAs and for carrying out transfections are well known in the art. Many are commercially available.

Various techniques have been developed for modification of target tissue and cells in vivo. A number of virus vectors, discussed below, are known which allow transfection and random integration of the virus into the host. See, for example, Dubensky et al. (1984) Proc. Natl. Acad. Sci. USA 81:7529-7533; Kaneda et al., (1989) Science 243:375-378; Hiebert et al. (1989) Proc. Natl. Acad. Sci. USA 86:3594-3598; Hatzoglu et al., (1990) J. Biol. Chem. 265:17285-17293; Ferry et al. (1991) Proc. Natl. Acad. Sci. USA 88:8377-8381. Routes and modes of administering the vector include injection, e.g intravascularly or intramuscularly, inhalation, or other parenteral administration.

Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms.

Another vector which can express the DNA molecule of the present invention, and is useful in gene therapy, particularly in humans, is vaccinia virus, which can be rendered non-replicating (U.S. Pat. Nos. 5,225,336; 5,204,243; 5,155,020; 4,769,330).

Based on the concept of viral mimicry, artificial viral envelopes (AVE) are designed based on the structure and composition of a viral membrane, such as HIV-1 or RSV and used to deliver genes into cells in vitro and in vivo. See, for example, U.S. Pat. No. 5,252,348, Schreier H. et al., J. Mol. Recognit., 1995, 8:59-62; Schreier H et al., J. Biol. Chem., 1994, 269: 9090-9098; Schreier, H., Pharm. Acta Helv. 1994, 68:145-159; Chander, R et al. Life Sci., 1992, 50:481-489, which references are hereby incorporated by reference in their entirety. The envelope is preferably produced in a two-step dialysis procedure where the "naked" envelope is formed initially, followed by unidirectional insertion of the viral surface glycoprotein of interest. This process and the physical characteristics of the resulting AVE are described in detail by Chander et al., (supra). Examples of AVE systems are (a) an AVE containing the HIV-1 surface glycoprotein gp160 (Chander et al., supra; Schreier et al., 1995, supra) or glycosyl phosphatidylinositol (GPI)-linked gp120 (Schreier et al., 1994, supra), respectively, and (b) an AVE containing the respiratory syncytial virus (RSV) attachment (G) and fusion (F) glycoproteins (Stecenko, A. A. et al., Pharm. Pharmacol. Left. 1:127-129 (1992)). Thus, vesicles are constructed which mimic the natural membranes of enveloped viruses in their ability to bind to and deliver materials to cells bearing corresponding surface receptors.

AVEs are used to deliver genes both by intravenous injection and by instillation in the lungs. For example, AVEs are manufactured to mimic RSV, exhibiting the RSV F surface glycoprotein which provides selective entry into epithelial cells. F-AVE are loaded with a plasmid coding for the gene of interest, (or a reporter gene such as CAT not present in mammalian tissue).

The AVE system described herein in physically and chemically essentially identical to the natural virus yet is entirely "artificial", as it is constructed from phospholipids, cholesterol, and recombinant viral surface glycoproteins. Hence, there is no carry-over of viral genetic information and no danger of inadvertant viral infection. Construction of the AVEs in two independent steps allows for bulk production of the plain lipid envelopes which, in a separate second step, can then be marked with the desired viral glycoprotein, also allowing for the preparation of protein cocktail formulations if desired.

Another delivery vehicle for use in the present invention are based on the recent description of attenuated Shigella as a DNA delivery system (Sizemore, D. R. et al., Science 270: 299-302 (1995), which reference is incorporated by reference in its entirety). This approach exploits the ability of Shigellae to enter epithelial cells and escape the phagocytic vacuole as a method for delivering the gene construct into the cytoplasm of the target cell. Invasion with as few as one to five bacteria can result in expression of the foreign plasmid DNA delivered by these bacteria.

A preferred type of mediator of nonviral transfection in vitro and in vivo is cationic (ammonium derivatized) lipids. These positively charged lipids form complexes with negatively charged DNA, resulting in DNA charged neutralization and compaction. The complexes endocytosed upon association with the cell membrane, and the DNA somehow escapes the endosome, gaining access to the cytoplasm. Cationic lipid:DNA complexes appear highly stable under normal conditions. Studies of the cationic lipid DOTAP suggest the complex dissociates when the inner layer of the cell membrane is destabilized and anionic lipids from the inner layer displace DNA from the cationic lipid. Several cationic lipids are available commercially. Two of these, DMRI and DC-cholesterol, have been used in human clinical trials. First generation cationic lipids are less efficient than viral vectors. For delivery to lung, any inflammatory responses accompanying the liposome administration are reduced by changing the delivery mode to aerosol administration which distributes the dose more evenly.

Drug Screening

Genes identified as changing in various stages of bladder cancer can be used as markers for drug screening. Thus by treating bladder cancer cells with test compounds or extracts, and monitoring the expression of genes identified as changing in the progression of bladder cancers, one can identify compounds or extracts which change expression of genes to a pattern which is of an earlier stage or even of normal bladder mucosa.

It is also within the scope of the invention to use small molecules in drug screening.

The following are non-limiting examples illustrating the present invention.

Experimentals

Affymetrix GeneChip Expression Analysis cRNA Preparation

10 μg total RNA was used as starting material for the cDNA preparation. The first and second strand cDNA synthesis was performed using the SuperScript Choice System (Life Technologies) according to the manufacturers instructions except using a oligo-dT primer containing a T7 RNA polymerase promoter site. Labeled cRNA was prepared using the BioArray High Yield RNA Transcript Labeling Kit (ENZO). Biotin labeled CTP and UTP (Enzo) were used in the reaction together with unlabeled NTP's. Following the IVT reaction, the unincorporated nucleotides were removed using RNeasy columns (Qiagen).

Array Hybridization and Scanning

Fifteen μg of cRNA was fragmented at 94° C. for 35 min in a fragmentation buffer containing 40 mM Tris-acetate pH 8.1, 100 mM KOAc, 30 mM MgOAc. Prior to hybridization, the fragmented cRNA in a 6×SSPE-T hybridization buffer (1 M NaCl, 10 mM Tris pH 7.6, 0.005% Triton), was heated to 95° C. for 5 min and subsequently to 40° C. for 5 min before loading onto the Affymetrix probe array cartridge. The probe array was then incubated for 16 h at 45° C. at constant rotation (60 rpm). The washing and staining procedure was performed in the Affymetrix Fluidics Station. The probe array was exposed to 10 washes in 6×SSPE-T at 25° C. followed by 4 washes in 0.5×SSPE-T at 50° C. The biotinylated cRNA was stained with a streptavidin-phycoerythrin conjugate, final concentration 2 μg/μl (Molecular Probes, Eugene, Oreg.) in 6×SSPE-T for 30 min at 25° C. followed by 10 washes in 6×SSPE-T at 25° C. An antibody amplification step was added using normal goat IgG final concentration 0.1 mg/ml (Sigma) and Anti-streptavidin antibody (goat) biotinylated final concentration 3 μg/ml. (Vector Laboratories). This was followed by a staining step with a streptavidin-phycoerythrin conjugate, final concentration 2 μg/μl (Molecular Probes, Eugene, Oreg.) in 6×SSPE-T for 30 min at 25° C. and 10 washes in 6×SSPE-T at 25° C.

The probe arrays were scanned at 560 nm using a confocal laser-scanning microscope with an argon ion laser as the excitation source, (Hewlett Packard GeneArray Scanner G2500A). The readings from the quantitative scanning were analysed by the Affymetrix Gene Expression Analysis Software. For comparison from array to array, these were scaled to a global intensity of 150, as previously published (Zhu, H., Cong, J. P., Mamtora, G., Gingeras, T., and Shenk, T. Cellular gene expression altered by human cytomegalovirus: Global monitoring with oligonucleotide arrays. Proc. Natl Acad USA, 95:14470-75,1998).

A spreadsheet approach using the fold change of gene level and the scoring of presence or absence of genes was used to sort genes in the different categories.

Western Blotting Analysis

Ten μl diluted protein marker (ECL protein molecular marker, Amersham) were used. The samples were electrophoresed at 200 V for 50 min in an X-CELL system (Novex). Then the proteins were transferred to a PVDF membrane at 30 V for 1 hour followed by blocking for 1 hour. The membrane was subsequently washed in 3×10 min in PBS buffer pH 7.4+0.1% Tween 20. The membrane was incubated with polyclonal antibodies, against peptides derived from two genes with accession numbers Z40715 and AA116036, overnight at 4° C. The membrane was then washed 3×10 min in PBS buffer pH 7.4+0.1% Tween 20, followed by incubation for 1 hour with a biotinylated streptavidin horseradish peroxidase complex. The detection reagent (ECL+Western blotting detection system, Amersham) was applied for 5 min. Finally, the membrane was wrapped in plastic, sealed, and scanned in a Phosphorimager, STORM 840 (Molecular Dynamics, Amersham Pharmacia, Sweden).

Quantitative PCR Analysis Using Light Cycler (Roche™).

Quantitative PCR analysis was performed as described in the manufacturers instructions and as described in (Morrison et al (1998) Biotechniques 24 (6):954-962.). The quantitation was in all cases related to GAPDH. Ten samples was used in the quantitation experiment: Four T2-4 bladder tumor samples, four Ta bladder tumor samples, and two normal bladder samples.

For verification of expression levels by another method quantitative PCR based on a light cycler was made on three genes using Normal, Ta and T2 biopsy material. RNA was amplified and the data shown in the table below (Table XX) were obtained. It shows that a similar finding as made with the arrays were made using the light cycler. Genes that varied between normal and tumor samples and between tumor samples were reproduced by this independent method, showing the validity of the data. Due to the high number of genes only a few were selected for this reproducibility study, as a proof of principle.

Quantitative PCR analysis

| | Category GeneChip: | | |
|---|---|---|---|
| | Upregulated in tumor | Upregulated in Invasive tumors | Upregulated in tumor |
| | Accession #: | | |
| RNA samples | AA101562 Relative expression | AA417030 Relative expression | H20264 Relative expression |
| T2-4 #1 | 5.3 | 24.8 | 0 |
| T2-4 #2 | 12.0 | 30.5 | 5.8 |
| T2-4 #3 | 1.0 | 63.8 | 0.8 |
| T2-4 #4 | 12.1 | 6.8 | 4.8 |
| Ta #1 | 4.8 | 14.2 | 6.8 |
| Ta #2 | 6.1 | 21.7 | 5.4 |
| Ta #3 | 7.7 | 2.2 | 0.9 |
| Ta #4 | 9.8 | 9.0 | 2.4 |
| Normal #1 | Absent | Absent | Absent |
| Normal #2 | Absent | Absent | Absent |
| Average T2-4 | 7.6 | 31.5 | 2.9 |
| Average Ta | 7.1 | 11.7 | 3.9 |
| Average Normal | Absent | Absent | Absent |

To correlate between RNA levels and protein levels western blots based on antibodies raised against synthetic peptides selected from the EST sequence was a performed (see FIG. 18). This was done with two EST's and the resulting two antibodies were used for western blotting of solubilized Normal, stage Ta and stage T2 bladder tumors. The experiment showed that similar findings were made using this protein apporoach. The level of proteins was much higher and more consistent in the tumor tissue than in the normal tissue, often being absent from normal tissue. Due to the high number of EST's only two were selected for this antibody based verification of the proteins (see FIG. 18). It should be regarded as a proof of principle.

The invention claimed is;

1. A method of classifying the disease course of a human bladder cancer tissue, comprising collecting a sample comprising cells from the cancer tissue,
   assaying the expression of at least one Ta stage gene from a Ta stage gene group, wherein said Ta gene is characterized by being up-regulated in Ta stage tissue compared to T2 stage tissue, and
   assaying at least one T2 stage gene from a T2 stage gene group, wherein said T2 gene is characterized by being up-regulated in T2 stage tissue compared to Ta stage tissue, wherein said Ta stage gene is SEQ ID NO: 1 and wherein said T2 stage gene is SEQ ID NO: 2,
   (i) correlating the expression level of the assessed Ta stage gene to a standard level of the Ta gene expression level in T2 stage tissue and
   (ii) correlating the expression level of the assessed T2 stage gene to a standard level of the T2 gene expression level in Ta stage tissue,
   wherein up-regulation of the expression level of said Ta stage gene and down-regulation of said T2 stage gene classifies said bladder cancer disease course as non-muscle invasive
   and
   wherein up-regulation of the expression level of said T2 stage gene and down-regulation of said Ta stage gene classifies said bladder cancer disease course as muscle invasive.

2. A method of classifying the disease course of a human bladder cancer tissue, comprising collecting a sample comprising cells from the cancer tissue,
   assaying the expression of at least one Ta stage gene from a Ta stage gene group, wherein said Ta gene is characterized by being up-regulated in Ta stage tissue compared to T2 stage tissue, and
   assaying at least one T2 stage gene from a T2 stage gene group, wherein said T2 gene is characterized by being up-regulated in T2 stage tissue compared to Ta stage tissue, wherein said Ta stage gene comprises the sequence of SEQ ID NO: 1 and wherein said T2 gene comprises the sequence of SEQ ID NO: 2,
   (i) correlating the expression level of the assessed Ta stage gene to a standard level of the Ta gene expression level in T2 stage tissue and
   (ii) correlating the expression level of the assessed T2 stage gene to a standard level of the T2 gene expression level in Ta stage tissue,
   wherein up-regulation of the expression level of said Ta stage gene and down-regulation of said T2 stage gene classifies said bladder cancer disease course as non-muscle invasive and
   wherein up-regulation of the expression level of said T2 stage gene and down-regulation of said Ta stage gene classifies said bladder cancer disease course as muscle invasive.

* * * * *